US012016932B2

(12) United States Patent
Brooks

(10) Patent No.: US 12,016,932 B2
(45) Date of Patent: Jun. 25, 2024

(54) GENE EDITING FOR HEMOPHILIA A WITH IMPROVED FACTOR VIII EXPRESSION

(71) Applicants: CRISPR THERAPEUTICS AG, Zug (CH); BAYER HEALTHCARE LLC, Whippany, NJ (US)

(72) Inventor: Alan Richard Brooks, Cambridge, MA (US)

(73) Assignees: CRISPR THERAPEUTICS AG, Zug (CH); BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 18/055,823

(22) Filed: Nov. 15, 2022

(65) Prior Publication Data

US 2023/0285597 A1 Sep. 14, 2023

Related U.S. Application Data

(63) Continuation of application No. 16/849,796, filed on Apr. 15, 2020, now Pat. No. 11,529,427.

(60) Provisional application No. 62/857,782, filed on Jun. 5, 2019, provisional application No. 62/806,702, filed on Feb. 15, 2019.

(51) Int. Cl.

*C07H 21/02* (2006.01)
*A61K 48/00* (2006.01)
*C12N 15/113* (2010.01)

(52) U.S. Cl.

CPC ...... *A61K 48/0058* (2013.01); *A61K 48/0066* (2013.01); *A61K 48/0075* (2013.01); *C12N 15/113* (2013.01); *C12N 2310/141* (2013.01)

(58) Field of Classification Search

CPC .......................... C12N 15/111; C12N 2310/20
See application file for complete search history.

(56) References Cited

U.S. PATENT DOCUMENTS

| | | | |
|---|---|---|---|
| 7,041,635 | B2 | 5/2006 | Kim et al. |
| 10,124,041 | B2 | 11/2018 | Nathwani et al. |
| 10,143,760 | B2 | 12/2018 | Riley et al. |
| 10,189,888 | B2 | 1/2019 | Falkner et al. |
| 10,189,889 | B2 | 1/2019 | Falkner et al. |
| 10,272,163 | B2 | 4/2019 | Laterza et al. |
| 10,407,476 | B2 | 9/2019 | Miller |
| 10,421,798 | B2 | 9/2019 | Schellenberger et al. |
| 10,442,850 | B2 | 10/2019 | Arruda et al. |
| 10,463,718 | B2 | 11/2019 | Colosi et al. |
| 10,512,675 | B2 | 12/2019 | Bunting et al. |
| 10,654,910 | B2 | 5/2020 | Spencer et al. |
| 10,709,796 | B2 | 7/2020 | Nathwani et al. |
| 2004/0147436 | A1 | 7/2004 | Kim et al. |
| 2017/0216408 | A1 | 8/2017 | Anguela |
| 2017/0233455 | A1 | 8/2017 | Falkner |
| 2020/0237930 | A1 | 7/2020 | Anguela |

FOREIGN PATENT DOCUMENTS

| | | |
|---|---|---|
| JP | 2015-521465 | 7/2015 |
| JP | 2016-521975 | 7/2016 |
| JP | 2018-538003 | 12/2018 |
| JP | 2018537087 | 12/2018 |
| WO | 2013/186563 | 12/2013 |
| WO | WO 2013/186563 A2 | 12/2013 |
| WO | WO 2015/191899 A1 | 12/2015 |
| WO | 2017/109039 | 6/2017 |
| WO | WO 2017/112895 A1 | 6/2017 |
| WO | 2018/064681 | 4/2018 |
| WO | 2019/079527 | 4/2019 |

OTHER PUBLICATIONS

Mcintosh et al., Therapeutic levels of FVIII following a single peripheral vein administration of rAAV vector encoding a novel human factor VIII variant. Blood. Apr. 25, 2013;121(17):3335-44. Epub Feb. 20, 2013.

Rouet et al., Engineering CRISPR-Cas9 RNA-Protein Complexes for Improved Function and Delivery. Crispr J. Dec. 2018;1(6):367-378.

Sandberg et al., Structural and functional characterization of B-domain deleted recombinant factor VIII. Semin Hematol. Apr. 2001;38(2 Suppl 4):4-12.

Suzuki et al., In vivo genome editing via CRISPR/Cas9 mediated homology-independent targeted integration. Nature. Dec. 1, 2016;540(7631):144-149. Epub Nov. 16, 2016.

*Primary Examiner* — Amy Rose Hudson

(74) *Attorney, Agent, or Firm* — Casimir Jones, S.C.; J. Mitchell Jones

(57) ABSTRACT

Provided herein, in some embodiments, are materials and methods for treating hemophilia A in a subject ex vivo or in vivo. Also provided herein, in some embodiments, are materials and methods for knocking in a coding sequence encoding a synthetic FVIII having a B domain substitute into a genome.

13 Claims, 9 Drawing Sheets

Specification includes a Sequence Listing.

| Code | Codon Optimization | Number of N-glycans | FVII plasmid |
|---|---|---|---|
| co1-7 | 1 | 7 | pCB1008 |
| co1-6 | 1 | 6 | pCB077 |
| co1-6 | 1 | 6 | pCB076 |
| co1-6(StoT) | 1 | 6 (with Ser to Thr change) | pCB1006 |
| co1-5 | 1 | 5 | pCB1007 |
| co1-5 | 1 | 5 | pCB1007 |
| co1-3 | 1 | 3 | pCB1018 |
| co1-2 | 1 | 2 | pCB1029 |
| co1-1 | 1 | 1 | pCB1030 |
| co2-5 | 2 | 5 | pCB1019 |
| co3-5 | 3 | 5 | pCB1020 |
| co1-0 | 1 | 0 | pCB100 |

SEQUENCE LISTING

```
Sequence total quantity: 373
SEQ ID NO: 1            moltype = DNA  length = 20
FEATURE                 Location/Qualifiers
misc_feature            1..20
                        note = Synthetic polynucleotide
misc_feature            1..20
                        note = Transferrin_T12 gRNA spacer
source                  1..20
                        mol_type = other DNA
                        organism = synthetic construct
SEQUENCE: 1
aaggaagcgg tgccatcgag                                             20

SEQ ID NO: 2            moltype = DNA  length = 20
FEATURE                 Location/Qualifiers
misc_feature            1..20
                        note = Synthetic polynucleotide
misc_feature            1..20
                        note = Transferrin_T168 gRNA spacer
source                  1..20
                        mol_type = other DNA
                        organism = synthetic construct
SEQUENCE: 2
aacttctgcc tgccattcat                                             20

SEQ ID NO: 3            moltype = DNA  length = 20
FEATURE                 Location/Qualifiers
misc_feature            1..20
                        note = Synthetic polynucleotide
misc_feature            1..20
                        note = Transferrin_T73 gRNA spacer
source                  1..20
                        mol_type = other DNA
                        organism = synthetic construct
SEQUENCE: 3
agcaaagggt tttgataacc                                             20

SEQ ID NO: 4            moltype = DNA  length = 20
FEATURE                 Location/Qualifiers
misc_feature            1..20
```

```
                        note = Synthetic polynucleotide
misc_feature            1..20
                        note = Transferrin_T99 gRNA spacer
source                  1..20
                        mol_type = other DNA
                        organism = synthetic construct
SEQUENCE: 4
ttgcctggga gggtcaaatg                                          20

SEQ ID NO: 5            moltype = DNA  length = 20
FEATURE                 Location/Qualifiers
misc_feature            1..20
                        note = Synthetic polynucleotide
misc_feature            1..20
                        note = Transferrin_T26 gRNA spacer
source                  1..20
                        mol_type = other DNA
                        organism = synthetic construct
SEQUENCE: 5
ggcttggcca acgacaagca                                          20

SEQ ID NO: 6            moltype = DNA  length = 20
FEATURE                 Location/Qualifiers
misc_feature            1..20
                        note = Synthetic polynucleotide
misc_feature            1..20
                        note = Transferrin_T111 gRNA spacer
source                  1..20
                        mol_type = other DNA
                        organism = synthetic construct
SEQUENCE: 6
ccttgtgggc caccacagca                                          20

SEQ ID NO: 7            moltype = DNA  length = 20
FEATURE                 Location/Qualifiers
misc_feature            1..20
                        note = Synthetic polynucleotide
misc_feature            1..20
                        note = Transferrin_T76 gRNA spacer
source                  1..20
                        mol_type = other DNA
                        organism = synthetic construct
SEQUENCE: 7
gggcccactc cctatgctga                                          20

SEQ ID NO: 8            moltype = DNA  length = 20
FEATURE                 Location/Qualifiers
misc_feature            1..20
                        note = Synthetic polynucleotide
misc_feature            1..20
                        note = Transferrin_T128 gRNA spacer
source                  1..20
                        mol_type = other DNA
                        organism = synthetic construct
SEQUENCE: 8
tctgagtctg agccaataga                                          20

SEQ ID NO: 9            moltype = DNA  length = 20
FEATURE                 Location/Qualifiers
misc_feature            1..20
                        note = Synthetic polynucleotide
misc_feature            1..20
                        note = Transferrin_T188 gRNA spacer
source                  1..20
                        mol_type = other DNA
                        organism = synthetic construct
SEQUENCE: 9
cctgcctcca gagttcccat                                          20

SEQ ID NO: 10           moltype = DNA  length = 20
FEATURE                 Location/Qualifiers
misc_feature            1..20
                        note = Synthetic polynucleotide
misc_feature            1..20
                        note = Transferrin_T151 gRNA spacer
source                  1..20
                        mol_type = other DNA
                        organism = synthetic construct
SEQUENCE: 10
```

```
acagctctcc aggatgcatg                                              20

SEQ ID NO: 11          moltype = DNA  length = 20
FEATURE                Location/Qualifiers
misc_feature           1..20
                       note = Synthetic polynucleotide
misc_feature           1..20
                       note = Transferrin_T67 gRNA spacer
source                 1..20
                       mol_type = other DNA
                       organism = synthetic construct
SEQUENCE: 11
ggcccatggg aaatcctagg                                              20

SEQ ID NO: 12          moltype = DNA  length = 20
FEATURE                Location/Qualifiers
misc_feature           1..20
                       note = Synthetic polynucleotide
misc_feature           1..20
                       note = Transferrin_T138 gRNA spacer
source                 1..20
                       mol_type = other DNA
                       organism = synthetic construct
SEQUENCE: 12
agggtggtca gtaggaaact                                              20

SEQ ID NO: 13          moltype = DNA  length = 20
FEATURE                Location/Qualifiers
misc_feature           1..20
                       note = Synthetic polynucleotide
misc_feature           1..20
                       note = Transferrin_T115 gRNA spacer
source                 1..20
                       mol_type = other DNA
                       organism = synthetic construct
SEQUENCE: 13
ccttgctgtg gtggcccaca                                              20

SEQ ID NO: 14          moltype = DNA  length = 20
FEATURE                Location/Qualifiers
misc_feature           1..20
                       note = Synthetic polynucleotide
misc_feature           1..20
                       note = Transferrin_T45 gRNA spacer
source                 1..20
                       mol_type = other DNA
                       organism = synthetic construct
SEQUENCE: 14
ggtagcaagc caatgtgttg                                              20

SEQ ID NO: 15          moltype = DNA  length = 20
FEATURE                Location/Qualifiers
misc_feature           1..20
                       note = Synthetic polynucleotide
misc_feature           1..20
                       note = Transferrin_T180 gRNA spacer
source                 1..20
                       mol_type = other DNA
                       organism = synthetic construct
SEQUENCE: 15
gcagattgtc atctccagct                                              20

SEQ ID NO: 16          moltype = DNA  length = 20
FEATURE                Location/Qualifiers
misc_feature           1..20
                       note = Synthetic polynucleotide
misc_feature           1..20
                       note = Transferrin_T148 gRNA spacer
source                 1..20
                       mol_type = other DNA
                       organism = synthetic construct
SEQUENCE: 16
ccacagcaag gctgactcac                                              20

SEQ ID NO: 17          moltype = DNA  length = 20
FEATURE                Location/Qualifiers
misc_feature           1..20
                       note = Synthetic polynucleotide
misc_feature           1..20
```

```
                        note = Transferrin_T100 gRNA spacer
source                  1..20
                        mol_type = other DNA
                        organism = synthetic construct
SEQUENCE: 17
actgaggctt atgttccatg                                              20

SEQ ID NO: 18           moltype = DNA  length = 20
FEATURE                 Location/Qualifiers
misc_feature            1..20
                        note = Synthetic polynucleotide
misc_feature            1..20
                        note = Transferrin_T66 gRNA spacer
source                  1..20
                        mol_type = other DNA
                        organism = synthetic construct
SEQUENCE: 18
gggcaaaagc tcatgtgata                                              20

SEQ ID NO: 19           moltype = DNA  length = 20
FEATURE                 Location/Qualifiers
misc_feature            1..20
                        note = Synthetic polynucleotide
misc_feature            1..20
                        note = Transferrin_T162 gRNA spacer
source                  1..20
                        mol_type = other DNA
                        organism = synthetic construct
SEQUENCE: 19
atactgaggc ttatgttcca                                              20

SEQ ID NO: 20           moltype = DNA  length = 20
FEATURE                 Location/Qualifiers
misc_feature            1..20
                        note = Synthetic polynucleotide
misc_feature            1..20
                        note = Transferrin_T175 gRNA spacer
source                  1..20
                        mol_type = other DNA
                        organism = synthetic construct
SEQUENCE: 20
ccagtgagtc agccttgctg                                              20

SEQ ID NO: 21           moltype = DNA  length = 20
FEATURE                 Location/Qualifiers
misc_feature            1..20
                        note = Synthetic polynucleotide
misc_feature            1..20
                        note = Transferrin_T172 gRNA spacer
source                  1..20
                        mol_type = other DNA
                        organism = synthetic construct
SEQUENCE: 21
ggatttccca tgggccaaga                                              20

SEQ ID NO: 22           moltype = DNA  length = 20
FEATURE                 Location/Qualifiers
misc_feature            1..20
                        note = Synthetic polynucleotide
misc_feature            1..20
                        note = Transferrin_T104 gRNA spacer
source                  1..20
                        mol_type = other DNA
                        organism = synthetic construct
SEQUENCE: 22
gggtcaaatg agggtcagcg                                              20

SEQ ID NO: 23           moltype = DNA  length = 20
FEATURE                 Location/Qualifiers
misc_feature            1..20
                        note = Synthetic polynucleotide
misc_feature            1..20
                        note = Transferrin_T19 gRNA spacer
source                  1..20
                        mol_type = other DNA
                        organism = synthetic construct
SEQUENCE: 23
tcaactatgg aaaaccagcg                                              20
```

```
SEQ ID NO: 24           moltype = DNA  length = 20
FEATURE                 Location/Qualifiers
misc_feature            1..20
                        note = Synthetic polynucleotide
misc_feature            1..20
                        note = Transferrin_T77 gRNA spacer
source                  1..20
                        mol_type = other DNA
                        organism = synthetic construct
SEQUENCE: 24
cataagcctc agtatgcaca                                              20

SEQ ID NO: 25           moltype = DNA  length = 20
FEATURE                 Location/Qualifiers
misc_feature            1..20
                        note = Synthetic polynucleotide
misc_feature            1..20
                        note = Transferrin_T62 gRNA spacer
source                  1..20
                        mol_type = other DNA
                        organism = synthetic construct
SEQUENCE: 25
tatgttccat gggggccag                                               20

SEQ ID NO: 26           moltype = DNA  length = 20
FEATURE                 Location/Qualifiers
misc_feature            1..20
                        note = Synthetic polynucleotide
misc_feature            1..20
                        note = Transferrin_T106 gRNA spacer
source                  1..20
                        mol_type = other DNA
                        organism = synthetic construct
SEQUENCE: 26
agggcccact ccctatgctg                                              20

SEQ ID NO: 27           moltype = DNA  length = 20
FEATURE                 Location/Qualifiers
misc_feature            1..20
                        note = Synthetic polynucleotide
misc_feature            1..20
                        note = Transferrin_T163 gRNA spacer
source                  1..20
                        mol_type = other DNA
                        organism = synthetic construct
SEQUENCE: 27
gctgtgggcc tcctctccac                                              20

SEQ ID NO: 28           moltype = DNA  length = 20
FEATURE                 Location/Qualifiers
misc_feature            1..20
                        note = Synthetic polynucleotide
misc_feature            1..20
                        note = Transferrin_T134 gRNA spacer
source                  1..20
                        mol_type = other DNA
                        organism = synthetic construct
SEQUENCE: 28
acaaatgccc catgaatggc                                              20

SEQ ID NO: 29           moltype = DNA  length = 20
FEATURE                 Location/Qualifiers
misc_feature            1..20
                        note = Synthetic polynucleotide
misc_feature            1..20
                        note = Transferrin_T167 gRNA spacer
source                  1..20
                        mol_type = other DNA
                        organism = synthetic construct
SEQUENCE: 29
gtggctgtca aggcctttct                                              20

SEQ ID NO: 30           moltype = DNA  length = 20
FEATURE                 Location/Qualifiers
misc_feature            1..20
                        note = Synthetic polynucleotide
misc_feature            1..20
                        note = Transferrin_T61 gRNA spacer
source                  1..20
```

-continued

```
                         mol_type = other DNA
                         organism = synthetic construct
SEQUENCE: 30
tcctgtccat gaacactaca                                                20

SEQ ID NO: 31            moltype = DNA  length = 20
FEATURE                  Location/Qualifiers
misc_feature             1..20
                         note = Synthetic polynucleotide
misc_feature             1..20
                         note = Transferrin_T6 gRNA spacer
source                   1..20
                         mol_type = other DNA
                         organism = synthetic construct
SEQUENCE: 31
agacagcatc gcccctagaa                                                20

SEQ ID NO: 32            moltype = DNA  length = 20
FEATURE                  Location/Qualifiers
misc_feature             1..20
                         note = Synthetic polynucleotide
misc_feature             1..20
                         note = Transferrin_T44 gRNA spacer
source                   1..20
                         mol_type = other DNA
                         organism = synthetic construct
SEQUENCE: 32
ccttcttggc cagtagttga                                                20

SEQ ID NO: 33            moltype = DNA  length = 20
FEATURE                  Location/Qualifiers
misc_feature             1..20
                         note = Synthetic polynucleotide
misc_feature             1..20
                         note = Transferrin_T3 gRNA spacer
source                   1..20
                         mol_type = other DNA
                         organism = synthetic construct
SEQUENCE: 33
aaggtcaccc tgcttgtcgt                                                20

SEQ ID NO: 34            moltype = DNA  length = 20
FEATURE                  Location/Qualifiers
misc_feature             1..20
                         note = Synthetic polynucleotide
misc_feature             1..20
                         note = Transferrin_T68 gRNA spacer
source                   1..20
                         mol_type = other DNA
                         organism = synthetic construct
SEQUENCE: 34
gagggaaaat gggggtcgct                                                20

SEQ ID NO: 35            moltype = DNA  length = 20
FEATURE                  Location/Qualifiers
misc_feature             1..20
                         note = Synthetic polynucleotide
misc_feature             1..20
                         note = Transferrin_T103 gRNA spacer
source                   1..20
                         mol_type = other DNA
                         organism = synthetic construct
SEQUENCE: 35
taggaggcaa cataagcctg                                                20

SEQ ID NO: 36            moltype = DNA  length = 20
FEATURE                  Location/Qualifiers
misc_feature             1..20
                         note = Synthetic polynucleotide
misc_feature             1..20
                         note = Transferrin_T81 gRNA spacer
source                   1..20
                         mol_type = other DNA
                         organism = synthetic construct
SEQUENCE: 36
aaaacgccct gtgcatactg                                                20

SEQ ID NO: 37            moltype = DNA  length = 20
FEATURE                  Location/Qualifiers
```

```
misc_feature          1..20
                      note = Synthetic polynucleotide
misc_feature          1..20
                      note = Transferrin_T146 gRNA spacer
source                1..20
                      mol_type = other DNA
                      organism = synthetic construct
SEQUENCE: 37
gtgagtcagc cttgctgtgg                                              20

SEQ ID NO: 38         moltype = DNA  length = 20
FEATURE               Location/Qualifiers
misc_feature          1..20
                      note = Synthetic polynucleotide
misc_feature          1..20
                      note = Transferrin_T63 gRNA spacer
source                1..20
                      mol_type = other DNA
                      organism = synthetic construct
SEQUENCE: 38
ggctgtcaag gcctttctag                                              20

SEQ ID NO: 39         moltype = DNA  length = 20
FEATURE               Location/Qualifiers
misc_feature          1..20
                      note = Synthetic polynucleotide
misc_feature          1..20
                      note = Transferrin_T87 gRNA spacer
source                1..20
                      mol_type = other DNA
                      organism = synthetic construct
SEQUENCE: 39
aggtagcaag ccaatgtgtt                                              20

SEQ ID NO: 40         moltype = DNA  length = 20
FEATURE               Location/Qualifiers
misc_feature          1..20
                      note = Synthetic polynucleotide
misc_feature          1..20
                      note = Transferrin_T184 gRNA spacer
source                1..20
                      mol_type = other DNA
                      organism = synthetic construct
SEQUENCE: 40
gattgtcatc tccagctggg                                              20

SEQ ID NO: 41         moltype = DNA  length = 20
FEATURE               Location/Qualifiers
misc_feature          1..20
                      note = Synthetic polynucleotide
misc_feature          1..20
                      note = Transferrin_T116 gRNA spacer
source                1..20
                      mol_type = other DNA
                      organism = synthetic construct
SEQUENCE: 41
tcctggccgg ctcctcacca                                              20

SEQ ID NO: 42         moltype = DNA  length = 20
FEATURE               Location/Qualifiers
misc_feature          1..20
                      note = Synthetic polynucleotide
misc_feature          1..20
                      note = Transferrin_T24 gRNA spacer
source                1..20
                      mol_type = other DNA
                      organism = synthetic construct
SEQUENCE: 42
attctcgcct atgggaactc                                              20

SEQ ID NO: 43         moltype = DNA  length = 20
FEATURE               Location/Qualifiers
misc_feature          1..20
                      note = Synthetic polynucleotide
misc_feature          1..20
                      note = Transferrin_T21 gRNA spacer
source                1..20
                      mol_type = other DNA
                      organism = synthetic construct
```

```
SEQUENCE: 43
tggcttggcc aacgacaagc                                           20

SEQ ID NO: 44           moltype = DNA  length = 20
FEATURE                 Location/Qualifiers
misc_feature            1..20
                        note = Synthetic polynucleotide
misc_feature            1..20
                        note = Transferrin_T41 gRNA spacer
source                  1..20
                        mol_type = other DNA
                        organism = synthetic construct
SEQUENCE: 44
ttggcttgct acctcaacta                                           20

SEQ ID NO: 45           moltype = DNA  length = 20
FEATURE                 Location/Qualifiers
misc_feature            1..20
                        note = Synthetic polynucleotide
misc_feature            1..20
                        note = Transferrin_T55 gRNA spacer
source                  1..20
                        mol_type = other DNA
                        organism = synthetic construct
SEQUENCE: 45
gaggtagcaa gccaatgtgt                                           20

SEQ ID NO: 46           moltype = DNA  length = 20
FEATURE                 Location/Qualifiers
misc_feature            1..20
                        note = Synthetic polynucleotide
misc_feature            1..20
                        note = Transferrin_T90 gRNA spacer
source                  1..20
                        mol_type = other DNA
                        organism = synthetic construct
SEQUENCE: 46
aggagacaag gcggatacag                                           20

SEQ ID NO: 47           moltype = DNA  length = 20
FEATURE                 Location/Qualifiers
misc_feature            1..20
                        note = Synthetic polynucleotide
misc_feature            1..20
                        note = Transferrin_T101 gRNA spacer
source                  1..20
                        mol_type = other DNA
                        organism = synthetic construct
SEQUENCE: 47
gactctgggt ctgctactca                                           20

SEQ ID NO: 48           moltype = DNA  length = 20
FEATURE                 Location/Qualifiers
misc_feature            1..20
                        note = Synthetic polynucleotide
misc_feature            1..20
                        note = Transferrin_T39 gRNA spacer
source                  1..20
                        mol_type = other DNA
                        organism = synthetic construct
SEQUENCE: 48
ccgctggttt tccatagttg                                           20

SEQ ID NO: 49           moltype = DNA  length = 20
FEATURE                 Location/Qualifiers
misc_feature            1..20
                        note = Synthetic polynucleotide
misc_feature            1..20
                        note = Transferrin_T150 gRNA spacer
source                  1..20
                        mol_type = other DNA
                        organism = synthetic construct
SEQUENCE: 49
cctcaactat ggaaaaccag                                           20

SEQ ID NO: 50           moltype = DNA  length = 20
FEATURE                 Location/Qualifiers
misc_feature            1..20
                        note = Synthetic polynucleotide
```

```
misc_feature            1..20
                        note = Transferrin_T156 gRNA spacer
source                  1..20
                        mol_type = other DNA
                        organism = synthetic construct
SEQUENCE: 50
tggattttaa tagttaccca                                            20

SEQ ID NO: 51           moltype = DNA  length = 20
FEATURE                 Location/Qualifiers
misc_feature            1..20
                        note = Synthetic polynucleotide
misc_feature            1..20
                        note = Transferrin_T40 gRNA spacer
source                  1..20
                        mol_type = other DNA
                        organism = synthetic construct
SEQUENCE: 51
ggggataaag gcaagtaacg                                            20

SEQ ID NO: 52           moltype = DNA  length = 20
FEATURE                 Location/Qualifiers
misc_feature            1..20
                        note = Synthetic polynucleotide
misc_feature            1..20
                        note = Transferrin_T8 gRNA spacer
source                  1..20
                        mol_type = other DNA
                        organism = synthetic construct
SEQUENCE: 52
ccgggttgca gggaacgcgc                                            20

SEQ ID NO: 53           moltype = DNA  length = 20
FEATURE                 Location/Qualifiers
misc_feature            1..20
                        note = Synthetic polynucleotide
misc_feature            1..20
                        note = Transferrin_T53 gRNA spacer
source                  1..20
                        mol_type = other DNA
                        organism = synthetic construct
SEQUENCE: 53
cgcgcgggcc agcgactctg                                            20

SEQ ID NO: 54           moltype = DNA  length = 20
FEATURE                 Location/Qualifiers
misc_feature            1..20
                        note = Synthetic polynucleotide
misc_feature            1..20
                        note = Transferrin_T117 gRNA spacer
source                  1..20
                        mol_type = other DNA
                        organism = synthetic construct
SEQUENCE: 54
ctgaggctta tgttccatgg                                            20

SEQ ID NO: 55           moltype = DNA  length = 20
FEATURE                 Location/Qualifiers
misc_feature            1..20
                        note = Synthetic polynucleotide
misc_feature            1..20
                        note = Transferrin_T49 gRNA spacer
source                  1..20
                        mol_type = other DNA
                        organism = synthetic construct
SEQUENCE: 55
cggagtgcat gcaggctgcg                                            20

SEQ ID NO: 56           moltype = DNA  length = 20
FEATURE                 Location/Qualifiers
misc_feature            1..20
                        note = Synthetic polynucleotide
misc_feature            1..20
                        note = Transferrin_T83 gRNA spacer
source                  1..20
                        mol_type = other DNA
                        organism = synthetic construct
SEQUENCE: 56
acaggcttat gttgcctcct                                            20
```

```
SEQ ID NO: 57          moltype = DNA  length = 20
FEATURE                Location/Qualifiers
misc_feature           1..20
                       note = Synthetic polynucleotide
misc_feature           1..20
                       note = Transferrin_T64 gRNA spacer
source                 1..20
                       mol_type = other DNA
                       organism = synthetic construct
SEQUENCE: 57
gggcatttgt cacactgttg                                                  20

SEQ ID NO: 58          moltype = DNA  length = 20
FEATURE                Location/Qualifiers
misc_feature           1..20
                       note = Synthetic polynucleotide
misc_feature           1..20
                       note = Transferrin_T120 gRNA spacer
source                 1..20
                       mol_type = other DNA
                       organism = synthetic construct
SEQUENCE: 58
tggcccctcc tcatgcatcc                                                  20

SEQ ID NO: 59          moltype = DNA  length = 20
FEATURE                Location/Qualifiers
misc_feature           1..20
                       note = Synthetic polynucleotide
misc_feature           1..20
                       note = Transferrin_T161 gRNA spacer
source                 1..20
                       mol_type = other DNA
                       organism = synthetic construct
SEQUENCE: 59
aaaatggagg gatagttcag                                                  20

SEQ ID NO: 60          moltype = DNA  length = 20
FEATURE                Location/Qualifiers
misc_feature           1..20
                       note = Synthetic polynucleotide
misc_feature           1..20
                       note = Transferrin_T183 gRNA spacer
source                 1..20
                       mol_type = other DNA
                       organism = synthetic construct
SEQUENCE: 60
tgtgacaaat gccccatgaa                                                  20

SEQ ID NO: 61          moltype = DNA  length = 20
FEATURE                Location/Qualifiers
misc_feature           1..20
                       note = Synthetic polynucleotide
misc_feature           1..20
                       note = Transferrin_T182 gRNA spacer
source                 1..20
                       mol_type = other DNA
                       organism = synthetic construct
SEQUENCE: 61
gtggtcagta ggaaactggg                                                  20

SEQ ID NO: 62          moltype = DNA  length = 20
FEATURE                Location/Qualifiers
misc_feature           1..20
                       note = Synthetic polynucleotide
misc_feature           1..20
                       note = Transferrin_T119 gRNA spacer
source                 1..20
                       mol_type = other DNA
                       organism = synthetic construct
SEQUENCE: 62
tgaggcttat gttccatggg                                                  20

SEQ ID NO: 63          moltype = DNA  length = 20
FEATURE                Location/Qualifiers
misc_feature           1..20
                       note = Synthetic polynucleotide
misc_feature           1..20
                       note = Transferrin_T18 gRNA spacer
```

```
source                  1..20
                        mol_type = other DNA
                        organism = synthetic construct
SEQUENCE: 63
gggataaagg caagtaacgt                                              20

SEQ ID NO: 64           moltype = DNA  length = 20
FEATURE                 Location/Qualifiers
misc_feature            1..20
                        note = Synthetic polynucleotide
misc_feature            1..20
                        note = Transferrin_T107 gRNA spacer
source                  1..20
                        mol_type = other DNA
                        organism = synthetic construct
SEQUENCE: 64
agggcaaaag ctcatgtgat                                              20

SEQ ID NO: 65           moltype = DNA  length = 20
FEATURE                 Location/Qualifiers
misc_feature            1..20
                        note = Synthetic polynucleotide
misc_feature            1..20
                        note = Transferrin_T20 gRNA spacer
source                  1..20
                        mol_type = other DNA
                        organism = synthetic construct
SEQUENCE: 65
gccatcgagc ggtcagagca                                              20

SEQ ID NO: 66           moltype = DNA  length = 20
FEATURE                 Location/Qualifiers
misc_feature            1..20
                        note = Synthetic polynucleotide
misc_feature            1..20
                        note = Transferrin_T80 gRNA spacer
source                  1..20
                        mol_type = other DNA
                        organism = synthetic construct
SEQUENCE: 66
ccctcaacta ctggccaaga                                              20

SEQ ID NO: 67           moltype = DNA  length = 20
FEATURE                 Location/Qualifiers
misc_feature            1..20
                        note = Synthetic polynucleotide
misc_feature            1..20
                        note = Transferrin_T133 gRNA spacer
source                  1..20
                        mol_type = other DNA
                        organism = synthetic construct
SEQUENCE: 67
cctcaactac tggccaagaa                                              20

SEQ ID NO: 68           moltype = DNA  length = 20
FEATURE                 Location/Qualifiers
misc_feature            1..20
                        note = Synthetic polynucleotide
misc_feature            1..20
                        note = Transferrin_T84 gRNA spacer
source                  1..20
                        mol_type = other DNA
                        organism = synthetic construct
SEQUENCE: 68
gagggtggtc agtaggaaac                                              20

SEQ ID NO: 69           moltype = DNA  length = 20
FEATURE                 Location/Qualifiers
misc_feature            1..20
                        note = Synthetic polynucleotide
misc_feature            1..20
                        note = Transferrin_T85 gRNA spacer
source                  1..20
                        mol_type = other DNA
                        organism = synthetic construct
SEQUENCE: 69
gtcgctgggg tggccatccc                                              20

SEQ ID NO: 70           moltype = DNA  length = 20
```

-continued

```
FEATURE                Location/Qualifiers
misc_feature           1..20
                       note = Synthetic polynucleotide
misc_feature           1..20
                       note = Transferrin_T143 gRNA spacer
source                 1..20
                       mol_type = other DNA
                       organism = synthetic construct
SEQUENCE: 70
tggggagaga aaactaaacg                                              20

SEQ ID NO: 71          moltype = DNA  length = 20
FEATURE                Location/Qualifiers
misc_feature           1..20
                       note = Synthetic polynucleotide
misc_feature           1..20
                       note = Transferrin_T15 gRNA spacer
source                 1..20
                       mol_type = other DNA
                       organism = synthetic construct
SEQUENCE: 71
cctgagcgcg gagtgcatgc                                              20

SEQ ID NO: 72          moltype = DNA  length = 20
FEATURE                Location/Qualifiers
misc_feature           1..20
                       note = Synthetic polynucleotide
misc_feature           1..20
                       note = Transferrin_T96 gRNA spacer
source                 1..20
                       mol_type = other DNA
                       organism = synthetic construct
SEQUENCE: 72
gcgaccccca ttttccctct                                              20

SEQ ID NO: 73          moltype = DNA  length = 20
FEATURE                Location/Qualifiers
misc_feature           1..20
                       note = Synthetic polynucleotide
misc_feature           1..20
                       note = Transferrin_T118 gRNA spacer
source                 1..20
                       mol_type = other DNA
                       organism = synthetic construct
SEQUENCE: 73
ctcaactatg gaaaaccagc                                              20

SEQ ID NO: 74          moltype = DNA  length = 20
FEATURE                Location/Qualifiers
misc_feature           1..20
                       note = Synthetic polynucleotide
misc_feature           1..20
                       note = Transferrin_T152 gRNA spacer
source                 1..20
                       mol_type = other DNA
                       organism = synthetic construct
SEQUENCE: 74
gatccacaaa gcctgtggag                                              20

SEQ ID NO: 75          moltype = DNA  length = 20
FEATURE                Location/Qualifiers
misc_feature           1..20
                       note = Synthetic polynucleotide
misc_feature           1..20
                       note = Transferrin_T38 gRNA spacer
source                 1..20
                       mol_type = other DNA
                       organism = synthetic construct
SEQUENCE: 75
ccccgcacag agcacttcac                                              20

SEQ ID NO: 76          moltype = DNA  length = 20
FEATURE                Location/Qualifiers
misc_feature           1..20
                       note = Synthetic polynucleotide
misc_feature           1..20
                       note = Transferrin_T132 gRNA spacer
source                 1..20
                       mol_type = other DNA
```

```
                        organism = synthetic construct
SEQUENCE: 76
tgcaaggtaa tgctccactg                                                  20

SEQ ID NO: 77           moltype = DNA  length = 20
FEATURE                 Location/Qualifiers
misc_feature            1..20
                        note = Synthetic polynucleotide
misc_feature            1..20
                        note = Transferrin_T149 gRNA spacer
source                  1..20
                        mol_type = other DNA
                        organism = synthetic construct
SEQUENCE: 77
aggggacgtc agcctctgaa                                                  20

SEQ ID NO: 78           moltype = DNA  length = 20
FEATURE                 Location/Qualifiers
misc_feature            1..20
                        note = Synthetic polynucleotide
misc_feature            1..20
                        note = Transferrin_T171 gRNA spacer
source                  1..20
                        mol_type = other DNA
                        organism = synthetic construct
SEQUENCE: 78
agggaaaatg ggggtcgctg                                                  20

SEQ ID NO: 79           moltype = DNA  length = 20
FEATURE                 Location/Qualifiers
misc_feature            1..20
                        note = Synthetic polynucleotide
misc_feature            1..20
                        note = Transferrin_T30 gRNA spacer
source                  1..20
                        mol_type = other DNA
                        organism = synthetic construct
SEQUENCE: 79
tgaggacaca ttctcgccta                                                  20

SEQ ID NO: 80           moltype = DNA  length = 20
FEATURE                 Location/Qualifiers
misc_feature            1..20
                        note = Synthetic polynucleotide
misc_feature            1..20
                        note = Transferrin_T71 gRNA spacer
source                  1..20
                        mol_type = other DNA
                        organism = synthetic construct
SEQUENCE: 80
tgcctcctag gatttcccat                                                  20

SEQ ID NO: 81           moltype = DNA  length = 20
FEATURE                 Location/Qualifiers
misc_feature            1..20
                        note = Synthetic polynucleotide
misc_feature            1..20
                        note = Transferrin_T158 gRNA spacer
source                  1..20
                        mol_type = other DNA
                        organism = synthetic construct
SEQUENCE: 81
cttggcccat gggaaatcct                                                  20

SEQ ID NO: 82           moltype = DNA  length = 20
FEATURE                 Location/Qualifiers
misc_feature            1..20
                        note = Synthetic polynucleotide
misc_feature            1..20
                        note = Transferrin_T36 gRNA spacer
source                  1..20
                        mol_type = other DNA
                        organism = synthetic construct
SEQUENCE: 82
aggagttcgg acttgacaag                                                  20

SEQ ID NO: 83           moltype = DNA  length = 20
FEATURE                 Location/Qualifiers
misc_feature            1..20
```

-continued

```
                        note = Synthetic polynucleotide
misc_feature            1..20
                        note = Transferrin_T27 gRNA spacer
source                  1..20
                        mol_type = other DNA
                        organism = synthetic construct
SEQUENCE: 83
acataagcct cagtatgcac                                                      20

SEQ ID NO: 84           moltype = DNA  length = 20
FEATURE                 Location/Qualifiers
misc_feature            1..20
                        note = Synthetic polynucleotide
misc_feature            1..20
                        note = Transferrin_T130 gRNA spacer
source                  1..20
                        mol_type = other DNA
                        organism = synthetic construct
SEQUENCE: 84
caggacatct acagctccca                                                      20

SEQ ID NO: 85           moltype = DNA  length = 20
FEATURE                 Location/Qualifiers
misc_feature            1..20
                        note = Synthetic polynucleotide
misc_feature            1..20
                        note = Transferrin_T124 gRNA spacer
source                  1..20
                        mol_type = other DNA
                        organism = synthetic construct
SEQUENCE: 85
gggccccacc tcaggaggtc                                                      20

SEQ ID NO: 86           moltype = DNA  length = 20
FEATURE                 Location/Qualifiers
misc_feature            1..20
                        note = Synthetic polynucleotide
misc_feature            1..20
                        note = Transferrin_T185 gRNA spacer
source                  1..20
                        mol_type = other DNA
                        organism = synthetic construct
SEQUENCE: 86
aacgacaagc agggtgacct                                                      20

SEQ ID NO: 87           moltype = DNA  length = 20
FEATURE                 Location/Qualifiers
misc_feature            1..20
                        note = Synthetic polynucleotide
misc_feature            1..20
                        note = Transferrin_T79 gRNA spacer
source                  1..20
                        mol_type = other DNA
                        organism = synthetic construct
SEQUENCE: 87
gcaggacatc tacagctccc                                                      20

SEQ ID NO: 88           moltype = DNA  length = 20
FEATURE                 Location/Qualifiers
misc_feature            1..20
                        note = Synthetic polynucleotide
misc_feature            1..20
                        note = Transferrin_T72 gRNA spacer
source                  1..20
                        mol_type = other DNA
                        organism = synthetic construct
SEQUENCE: 88
cctgtgaagt gctctgtgcg                                                      20

SEQ ID NO: 89           moltype = DNA  length = 20
FEATURE                 Location/Qualifiers
misc_feature            1..20
                        note = Synthetic polynucleotide
misc_feature            1..20
                        note = Transferrin_T179 gRNA spacer
source                  1..20
                        mol_type = other DNA
                        organism = synthetic construct
SEQUENCE: 89
```

```
tgcctgggag ggtcaaatga                                                20

SEQ ID NO: 90           moltype = DNA  length = 20
FEATURE                 Location/Qualifiers
misc_feature            1..20
                        note = Synthetic polynucleotide
misc_feature            1..20
                        note = Transferrin_T170 gRNA spacer
source                  1..20
                        mol_type = other DNA
                        organism = synthetic construct
SEQUENCE: 90
tggccatgcc tgcacccctc                                                20

SEQ ID NO: 91           moltype = DNA  length = 20
FEATURE                 Location/Qualifiers
misc_feature            1..20
                        note = Synthetic polynucleotide
misc_feature            1..20
                        note = Transferrin_T181 gRNA spacer
source                  1..20
                        mol_type = other DNA
                        organism = synthetic construct
SEQUENCE: 91
gccagcagag ggtggtcagt                                                20

SEQ ID NO: 92           moltype = DNA  length = 20
FEATURE                 Location/Qualifiers
misc_feature            1..20
                        note = Synthetic polynucleotide
misc_feature            1..20
                        note = Transferrin_T42 gRNA spacer
source                  1..20
                        mol_type = other DNA
                        organism = synthetic construct
SEQUENCE: 92
ctcctgtcca tgaacactac                                                20

SEQ ID NO: 93           moltype = DNA  length = 20
FEATURE                 Location/Qualifiers
misc_feature            1..20
                        note = Synthetic polynucleotide
misc_feature            1..20
                        note = Transferrin_T114 gRNA spacer
source                  1..20
                        mol_type = other DNA
                        organism = synthetic construct
SEQUENCE: 93
ggagtgggcc cttccacctc                                                20

SEQ ID NO: 94           moltype = DNA  length = 20
FEATURE                 Location/Qualifiers
misc_feature            1..20
                        note = Synthetic polynucleotide
misc_feature            1..20
                        note = Transferrin_T23 gRNA spacer
source                  1..20
                        mol_type = other DNA
                        organism = synthetic construct
SEQUENCE: 94
caactatgga aaaccagcgg                                                20

SEQ ID NO: 95           moltype = DNA  length = 20
FEATURE                 Location/Qualifiers
misc_feature            1..20
                        note = Synthetic polynucleotide
misc_feature            1..20
                        note = Transferrin_T144 gRNA spacer
source                  1..20
                        mol_type = other DNA
                        organism = synthetic construct
SEQUENCE: 95
tactgaggct tatgttccat                                                20

SEQ ID NO: 96           moltype = DNA  length = 20
FEATURE                 Location/Qualifiers
misc_feature            1..20
                        note = Synthetic polynucleotide
misc_feature            1..20
```

```
                         note = Transferrin_T1 gRNA spacer
source                   1..20
                         mol_type = other DNA
                         organism = synthetic construct
SEQUENCE: 96
cccatgctct gaccgctcga                                              20

SEQ ID NO: 97            moltype = DNA  length = 20
FEATURE                  Location/Qualifiers
misc_feature             1..20
                         note = Synthetic polynucleotide
misc_feature             1..20
                         note = Transferrin_T186 gRNA spacer
source                   1..20
                         mol_type = other DNA
                         organism = synthetic construct
SEQUENCE: 97
ctccccgacc tcctgaggtg                                              20

SEQ ID NO: 98            moltype = DNA  length = 20
FEATURE                  Location/Qualifiers
misc_feature             1..20
                         note = Synthetic polynucleotide
misc_feature             1..20
                         note = Transferrin_T58 gRNA spacer
source                   1..20
                         mol_type = other DNA
                         organism = synthetic construct
SEQUENCE: 98
ggggaatggt cagacccggg                                              20

SEQ ID NO: 99            moltype = DNA  length = 20
FEATURE                  Location/Qualifiers
misc_feature             1..20
                         note = Synthetic polynucleotide
misc_feature             1..20
                         note = Transferrin_T113 gRNA spacer
source                   1..20
                         mol_type = other DNA
                         organism = synthetic construct
SEQUENCE: 99
cttgtgccct gtagtgttca                                              20

SEQ ID NO: 100           moltype = DNA  length = 20
FEATURE                  Location/Qualifiers
misc_feature             1..20
                         note = Synthetic polynucleotide
misc_feature             1..20
                         note = Transferrin_T29 gRNA spacer
source                   1..20
                         mol_type = other DNA
                         organism = synthetic construct
SEQUENCE: 100
cccgcgcgtt ccctgcaacc                                              20

SEQ ID NO: 101           moltype = DNA  length = 20
FEATURE                  Location/Qualifiers
misc_feature             1..20
                         note = Synthetic polynucleotide
misc_feature             1..20
                         note = Transferrin_T2 gRNA spacer
source                   1..20
                         mol_type = other DNA
                         organism = synthetic construct
SEQUENCE: 101
ccatcgagcg gtcagagcat                                              20

SEQ ID NO: 102           moltype = DNA  length = 20
FEATURE                  Location/Qualifiers
misc_feature             1..20
                         note = Synthetic polynucleotide
misc_feature             1..20
                         note = Transferrin_T48 gRNA spacer
source                   1..20
                         mol_type = other DNA
                         organism = synthetic construct
SEQUENCE: 102
gccctgtagt gttcatggac                                              20
```

```
SEQ ID NO: 103          moltype = DNA  length = 20
FEATURE                 Location/Qualifiers
misc_feature            1..20
                        note = Synthetic polynucleotide
misc_feature            1..20
                        note = Transferrin_T17 gRNA spacer
source                  1..20
                        mol_type = other DNA
                        organism = synthetic construct
SEQUENCE: 103
aaatcagagc acgtctaacc                                               20

SEQ ID NO: 104          moltype = DNA  length = 20
FEATURE                 Location/Qualifiers
misc_feature            1..20
                        note = Synthetic polynucleotide
misc_feature            1..20
                        note = Transferrin_T153 gRNA spacer
source                  1..20
                        mol_type = other DNA
                        organism = synthetic construct
SEQUENCE: 104
gcctgtgaag tgctctgtgc                                               20

SEQ ID NO: 105          moltype = DNA  length = 20
FEATURE                 Location/Qualifiers
misc_feature            1..20
                        note = Synthetic polynucleotide
misc_feature            1..20
                        note = Transferrin_T60 gRNA spacer
source                  1..20
                        mol_type = other DNA
                        organism = synthetic construct
SEQUENCE: 105
ctcgcctatg ggaactctgg                                               20

SEQ ID NO: 106          moltype = DNA  length = 20
FEATURE                 Location/Qualifiers
misc_feature            1..20
                        note = Synthetic polynucleotide
misc_feature            1..20
                        note = Transferrin_T164 gRNA spacer
source                  1..20
                        mol_type = other DNA
                        organism = synthetic construct
SEQUENCE: 106
ggccccacct caggaggtcg                                               20

SEQ ID NO: 107          moltype = DNA  length = 20
FEATURE                 Location/Qualifiers
misc_feature            1..20
                        note = Synthetic polynucleotide
misc_feature            1..20
                        note = Transferrin_T47 gRNA spacer
source                  1..20
                        mol_type = other DNA
                        organism = synthetic construct
SEQUENCE: 107
ccgcgcgttc cctgcaaccc                                               20

SEQ ID NO: 108          moltype = DNA  length = 20
FEATURE                 Location/Qualifiers
misc_feature            1..20
                        note = Synthetic polynucleotide
misc_feature            1..20
                        note = Transferrin_T110 gRNA spacer
source                  1..20
                        mol_type = other DNA
                        organism = synthetic construct
SEQUENCE: 108
tggctgtcaa ggcctttcta                                               20

SEQ ID NO: 109          moltype = DNA  length = 20
FEATURE                 Location/Qualifiers
misc_feature            1..20
                        note = Synthetic polynucleotide
misc_feature            1..20
                        note = Transferrin_T177 gRNA spacer
source                  1..20
```

```
                        mol_type = other DNA
                        organism = synthetic construct
SEQUENCE: 109
tggcagatgc tgagtaccag                                            20

SEQ ID NO: 110          moltype = DNA  length = 20
FEATURE                 Location/Qualifiers
misc_feature            1..20
                        note = Synthetic polynucleotide
misc_feature            1..20
                        note = Transferrin_T13 gRNA spacer
source                  1..20
                        mol_type = other DNA
                        organism = synthetic construct
SEQUENCE: 110
gttaatttac cctcaactac                                            20

SEQ ID NO: 111          moltype = DNA  length = 20
FEATURE                 Location/Qualifiers
misc_feature            1..20
                        note = Synthetic polynucleotide
misc_feature            1..20
                        note = Transferrin_T7 gRNA spacer
source                  1..20
                        mol_type = other DNA
                        organism = synthetic construct
SEQUENCE: 111
cctgcatgca ctccgcgctc                                            20

SEQ ID NO: 112          moltype = DNA  length = 20
FEATURE                 Location/Qualifiers
misc_feature            1..20
                        note = Synthetic polynucleotide
misc_feature            1..20
                        note = Transferrin_T89 gRNA spacer
source                  1..20
                        mol_type = other DNA
                        organism = synthetic construct
SEQUENCE: 112
gaccctcatt tgaccctccc                                            20

SEQ ID NO: 113          moltype = DNA  length = 20
FEATURE                 Location/Qualifiers
misc_feature            1..20
                        note = Synthetic polynucleotide
misc_feature            1..20
                        note = Transferrin_T16 gRNA spacer
source                  1..20
                        mol_type = other DNA
                        organism = synthetic construct
SEQUENCE: 113
ccattagggc aaccttctat                                            20

SEQ ID NO: 114          moltype = DNA  length = 20
FEATURE                 Location/Qualifiers
misc_feature            1..20
                        note = Synthetic polynucleotide
misc_feature            1..20
                        note = Transferrin_T155 gRNA spacer
source                  1..20
                        mol_type = other DNA
                        organism = synthetic construct
SEQUENCE: 114
atgcatgagg aggggccacc                                            20

SEQ ID NO: 115          moltype = DNA  length = 20
FEATURE                 Location/Qualifiers
misc_feature            1..20
                        note = Synthetic polynucleotide
misc_feature            1..20
                        note = Transferrin_T108 gRNA spacer
source                  1..20
                        mol_type = other DNA
                        organism = synthetic construct
SEQUENCE: 115
gtcagccact gccccatagc                                            20

SEQ ID NO: 116          moltype = DNA  length = 20
FEATURE                 Location/Qualifiers
```

```
misc_feature          1..20
                      note = Synthetic polynucleotide
misc_feature          1..20
                      note = Transferrin_T160 gRNA spacer
source                1..20
                      mol_type = other DNA
                      organism = synthetic construct
SEQUENCE: 116
cctatgggaa ctctggaggc                                              20

SEQ ID NO: 117        moltype = DNA  length = 20
FEATURE               Location/Qualifiers
misc_feature          1..20
                      note = Synthetic polynucleotide
misc_feature          1..20
                      note = Transferrin_T139 gRNA spacer
source                1..20
                      mol_type = other DNA
                      organism = synthetic construct
SEQUENCE: 117
acttctgcct gccattcatg                                              20

SEQ ID NO: 118        moltype = DNA  length = 20
FEATURE               Location/Qualifiers
misc_feature          1..20
                      note = Synthetic polynucleotide
misc_feature          1..20
                      note = Transferrin_T11 gRNA spacer
source                1..20
                      mol_type = other DNA
                      organism = synthetic construct
SEQUENCE: 118
cggtggccgc ccgggttgca                                              20

SEQ ID NO: 119        moltype = DNA  length = 20
FEATURE               Location/Qualifiers
misc_feature          1..20
                      note = Synthetic polynucleotide
misc_feature          1..20
                      note = Transferrin_T169 gRNA spacer
source                1..20
                      mol_type = other DNA
                      organism = synthetic construct
SEQUENCE: 119
ggggacgtca gcctctgaaa                                              20

SEQ ID NO: 120        moltype = DNA  length = 20
FEATURE               Location/Qualifiers
misc_feature          1..20
                      note = Synthetic polynucleotide
misc_feature          1..20
                      note = Transferrin_T5 gRNA spacer
source                1..20
                      mol_type = other DNA
                      organism = synthetic construct
SEQUENCE: 120
gaggacacat tctcgcctat                                              20

SEQ ID NO: 121        moltype = DNA  length = 20
FEATURE               Location/Qualifiers
misc_feature          1..20
                      note = Synthetic polynucleotide
misc_feature          1..20
                      note = Transferrin_T131 gRNA spacer
source                1..20
                      mol_type = other DNA
                      organism = synthetic construct
SEQUENCE: 121
gcatggcatt caaggcctcc                                              20

SEQ ID NO: 122        moltype = DNA  length = 20
FEATURE               Location/Qualifiers
misc_feature          1..20
                      note = Synthetic polynucleotide
misc_feature          1..20
                      note = Transferrin_T22 gRNA spacer
source                1..20
                      mol_type = other DNA
                      organism = synthetic construct
```

```
SEQUENCE: 122
catcgagcgg tcagagcatg                                          20

SEQ ID NO: 123          moltype = DNA  length = 20
FEATURE                 Location/Qualifiers
misc_feature            1..20
                        note = Synthetic polynucleotide
misc_feature            1..20
                        note = Transferrin_T126 gRNA spacer
source                  1..20
                        mol_type = other DNA
                        organism = synthetic construct
SEQUENCE: 123
ctcaactact ggccaagaag                                          20

SEQ ID NO: 124          moltype = DNA  length = 20
FEATURE                 Location/Qualifiers
misc_feature            1..20
                        note = Synthetic polynucleotide
misc_feature            1..20
                        note = Transferrin_T145 gRNA spacer
source                  1..20
                        mol_type = other DNA
                        organism = synthetic construct
SEQUENCE: 124
ctgtggtggc ccacaaggag                                          20

SEQ ID NO: 125          moltype = DNA  length = 20
FEATURE                 Location/Qualifiers
misc_feature            1..20
                        note = Synthetic polynucleotide
misc_feature            1..20
                        note = Transferrin_T187 gRNA spacer
source                  1..20
                        mol_type = other DNA
                        organism = synthetic construct
SEQUENCE: 125
tctgctggcc agaggggtgc                                          20

SEQ ID NO: 126          moltype = DNA  length = 20
FEATURE                 Location/Qualifiers
misc_feature            1..20
                        note = Synthetic polynucleotide
misc_feature            1..20
                        note = Transferrin_T112 gRNA spacer
source                  1..20
                        mol_type = other DNA
                        organism = synthetic construct
SEQUENCE: 126
aggcgagaat gtgtcctcag                                          20

SEQ ID NO: 127          moltype = DNA  length = 20
FEATURE                 Location/Qualifiers
misc_feature            1..20
                        note = Synthetic polynucleotide
misc_feature            1..20
                        note = Transferrin_T14 gRNA spacer
source                  1..20
                        mol_type = other DNA
                        organism = synthetic construct
SEQUENCE: 127
gctcgatggc accgcttcct                                          20

SEQ ID NO: 128          moltype = DNA  length = 20
FEATURE                 Location/Qualifiers
misc_feature            1..20
                        note = Synthetic polynucleotide
misc_feature            1..20
                        note = Transferrin_T70 gRNA spacer
source                  1..20
                        mol_type = other DNA
                        organism = synthetic construct
SEQUENCE: 128
gtcctggccg gctcctcacc                                          20

SEQ ID NO: 129          moltype = DNA  length = 20
FEATURE                 Location/Qualifiers
misc_feature            1..20
                        note = Synthetic polynucleotide
```

```
misc_feature          1..20
                      note = Transferrin_T57 gRNA spacer
source                1..20
                      mol_type = other DNA
                      organism = synthetic construct
SEQUENCE: 129
tttcagctac cccaacacat                                        20

SEQ ID NO: 130        moltype = DNA  length = 20
FEATURE               Location/Qualifiers
misc_feature          1..20
                      note = Synthetic polynucleotide
misc_feature          1..20
                      note = Transferrin_T4 gRNA spacer
source                1..20
                      mol_type = other DNA
                      organism = synthetic construct
SEQUENCE: 130
gggtagcacc gcagagtcgc                                        20

SEQ ID NO: 131        moltype = DNA  length = 20
FEATURE               Location/Qualifiers
misc_feature          1..20
                      note = Synthetic polynucleotide
misc_feature          1..20
                      note = Transferrin_T92 gRNA spacer
source                1..20
                      mol_type = other DNA
                      organism = synthetic construct
SEQUENCE: 131
cccttcttgg ccagtagttg                                        20

SEQ ID NO: 132        moltype = DNA  length = 20
FEATURE               Location/Qualifiers
misc_feature          1..20
                      note = Synthetic polynucleotide
misc_feature          1..20
                      note = Transferrin_T102 gRNA spacer
source                1..20
                      mol_type = other DNA
                      organism = synthetic construct
SEQUENCE: 132
aaaggggaat ggtcagaccc                                        20

SEQ ID NO: 133        moltype = DNA  length = 20
FEATURE               Location/Qualifiers
misc_feature          1..20
                      note = Synthetic polynucleotide
misc_feature          1..20
                      note = Transferrin_T159 gRNA spacer
source                1..20
                      mol_type = other DNA
                      organism = synthetic construct
SEQUENCE: 133
agctagcaat tccttgagag                                        20

SEQ ID NO: 134        moltype = DNA  length = 20
FEATURE               Location/Qualifiers
misc_feature          1..20
                      note = Synthetic polynucleotide
misc_feature          1..20
                      note = Transferrin_T10 gRNA spacer
source                1..20
                      mol_type = other DNA
                      organism = synthetic construct
SEQUENCE: 134
catgcactcc gcgctcaggc                                        20

SEQ ID NO: 135        moltype = DNA  length = 20
FEATURE               Location/Qualifiers
misc_feature          1..20
                      note = Synthetic polynucleotide
misc_feature          1..20
                      note = Transferrin_T157 gRNA spacer
source                1..20
                      mol_type = other DNA
                      organism = synthetic construct
SEQUENCE: 135
ttgcctccta ggatttccca                                        20
```

```
SEQ ID NO: 136          moltype = DNA  length = 20
FEATURE                 Location/Qualifiers
misc_feature            1..20
                        note = Synthetic polynucleotide
misc_feature            1..20
                        note = Transferrin_T173 gRNA spacer
source                  1..20
                        mol_type = other DNA
                        organism = synthetic construct
SEQUENCE: 136
catcacagca cttgcctggg                                              20

SEQ ID NO: 137          moltype = DNA  length = 20
FEATURE                 Location/Qualifiers
misc_feature            1..20
                        note = Synthetic polynucleotide
misc_feature            1..20
                        note = Transferrin_T121 gRNA spacer
source                  1..20
                        mol_type = other DNA
                        organism = synthetic construct
SEQUENCE: 137
tgatgacccc ctccctggtg                                              20

SEQ ID NO: 138          moltype = DNA  length = 20
FEATURE                 Location/Qualifiers
misc_feature            1..20
                        note = Synthetic polynucleotide
misc_feature            1..20
                        note = Transferrin_T137 gRNA spacer
source                  1..20
                        mol_type = other DNA
                        organism = synthetic construct
SEQUENCE: 138
agcagattgt catctccagc                                              20

SEQ ID NO: 139          moltype = DNA  length = 20
FEATURE                 Location/Qualifiers
misc_feature            1..20
                        note = Synthetic polynucleotide
misc_feature            1..20
                        note = Transferrin_T98 gRNA spacer
source                  1..20
                        mol_type = other DNA
                        organism = synthetic construct
SEQUENCE: 139
tcaaatgagg gtcagcgagg                                              20

SEQ ID NO: 140          moltype = DNA  length = 20
FEATURE                 Location/Qualifiers
misc_feature            1..20
                        note = Synthetic polynucleotide
misc_feature            1..20
                        note = Transferrin_T141 gRNA spacer
source                  1..20
                        mol_type = other DNA
                        organism = synthetic construct
SEQUENCE: 140
tggccggctc ctcaccaggg                                              20

SEQ ID NO: 141          moltype = DNA  length = 20
FEATURE                 Location/Qualifiers
misc_feature            1..20
                        note = Synthetic polynucleotide
misc_feature            1..20
                        note = Transferrin_T50 gRNA spacer
source                  1..20
                        mol_type = other DNA
                        organism = synthetic construct
SEQUENCE: 141
gatggcaatt cctcccccgc                                              20

SEQ ID NO: 142          moltype = DNA  length = 20
FEATURE                 Location/Qualifiers
misc_feature            1..20
                        note = Synthetic polynucleotide
misc_feature            1..20
                        note = Transferrin_T94 gRNA spacer
```

```
source                  1..20
                        mol_type = other DNA
                        organism = synthetic construct
SEQUENCE: 142
caaggaattg ctagcttatg                                              20

SEQ ID NO: 143          moltype = DNA  length = 20
FEATURE                 Location/Qualifiers
misc_feature            1..20
                        note = Synthetic polynucleotide
misc_feature            1..20
                        note = Transferrin_T86 gRNA spacer
source                  1..20
                        mol_type = other DNA
                        organism = synthetic construct
SEQUENCE: 143
taacgtgggg tcctctctca                                              20

SEQ ID NO: 144          moltype = DNA  length = 20
FEATURE                 Location/Qualifiers
misc_feature            1..20
                        note = Synthetic polynucleotide
misc_feature            1..20
                        note = Transferrin_T35 gRNA spacer
source                  1..20
                        mol_type = other DNA
                        organism = synthetic construct
SEQUENCE: 144
agtgctctgt gcggggataa                                              20

SEQ ID NO: 145          moltype = DNA  length = 20
FEATURE                 Location/Qualifiers
misc_feature            1..20
                        note = Synthetic polynucleotide
misc_feature            1..20
                        note = Transferrin_T174 gRNA spacer
source                  1..20
                        mol_type = other DNA
                        organism = synthetic construct
SEQUENCE: 145
cattttccct cttggcccat                                              20

SEQ ID NO: 146          moltype = DNA  length = 20
FEATURE                 Location/Qualifiers
misc_feature            1..20
                        note = Synthetic polynucleotide
misc_feature            1..20
                        note = Transferrin_T97 gRNA spacer
source                  1..20
                        mol_type = other DNA
                        organism = synthetic construct
SEQUENCE: 146
ttcactgctg caagatttac                                              20

SEQ ID NO: 147          moltype = DNA  length = 20
FEATURE                 Location/Qualifiers
misc_feature            1..20
                        note = Synthetic polynucleotide
misc_feature            1..20
                        note = Transferrin_T127 gRNA spacer
source                  1..20
                        mol_type = other DNA
                        organism = synthetic construct
SEQUENCE: 147
gtgaggagcc ggccaggact                                              20

SEQ ID NO: 148          moltype = DNA  length = 20
FEATURE                 Location/Qualifiers
misc_feature            1..20
                        note = Synthetic polynucleotide
misc_feature            1..20
                        note = Transferrin_T56 gRNA spacer
source                  1..20
                        mol_type = other DNA
                        organism = synthetic construct
SEQUENCE: 148
atgttgcaca catcctgcta                                              20

SEQ ID NO: 149          moltype = DNA  length = 20
```

```
FEATURE                    Location/Qualifiers
misc_feature               1..20
                           note = Synthetic polynucleotide
misc_feature               1..20
                           note = Transferrin_T65 gRNA spacer
source                     1..20
                           mol_type = other DNA
                           organism = synthetic construct
SEQUENCE: 149
tcaaggaatt gctagcttat                                                   20

SEQ ID NO: 150             moltype = DNA   length = 20
FEATURE                    Location/Qualifiers
misc_feature               1..20
                           note = Synthetic polynucleotide
misc_feature               1..20
                           note = Transferrin_T123 gRNA spacer
source                     1..20
                           mol_type = other DNA
                           organism = synthetic construct
SEQUENCE: 150
tcttggatcc aagtcctggc                                                   20

SEQ ID NO: 151             moltype = DNA   length = 20
FEATURE                    Location/Qualifiers
misc_feature               1..20
                           note = Synthetic polynucleotide
misc_feature               1..20
                           note = Transferrin_T59 gRNA spacer
source                     1..20
                           mol_type = other DNA
                           organism = synthetic construct
SEQUENCE: 151
ttctgagtta caccccttct                                                   20

SEQ ID NO: 152             moltype = DNA   length = 20
FEATURE                    Location/Qualifiers
misc_feature               1..20
                           note = Synthetic polynucleotide
misc_feature               1..20
                           note = Transferrin_T129 gRNA spacer
source                     1..20
                           mol_type = other DNA
                           organism = synthetic construct
SEQUENCE: 152
ttcagaggct gacgtcccct                                                   20

SEQ ID NO: 153             moltype = DNA   length = 20
FEATURE                    Location/Qualifiers
misc_feature               1..20
                           note = Synthetic polynucleotide
misc_feature               1..20
                           note = Transferrin_T9 gRNA spacer
source                     1..20
                           mol_type = other DNA
                           organism = synthetic construct
SEQUENCE: 153
ccaatagaag gttgccctaa                                                   20

SEQ ID NO: 154             moltype = DNA   length = 20
FEATURE                    Location/Qualifiers
misc_feature               1..20
                           note = Synthetic polynucleotide
misc_feature               1..20
                           note = Transferrin_T122 gRNA spacer
source                     1..20
                           mol_type = other DNA
                           organism = synthetic construct
SEQUENCE: 154
cactccccga cctcctgagg                                                   20

SEQ ID NO: 155             moltype = DNA   length = 20
FEATURE                    Location/Qualifiers
misc_feature               1..20
                           note = Synthetic polynucleotide
misc_feature               1..20
                           note = Transferrin_T31 gRNA spacer
source                     1..20
                           mol_type = other DNA
```

```
                        organism = synthetic construct
SEQUENCE: 155
cgcgttccct gcaacccggg                                                   20

SEQ ID NO: 156          moltype = DNA  length = 20
FEATURE                 Location/Qualifiers
misc_feature            1..20
                        note = Synthetic polynucleotide
misc_feature            1..20
                        note = Transferrin_T28 gRNA spacer
source                  1..20
                        mol_type = other DNA
                        organism = synthetic construct
SEQUENCE: 156
gatggcaccg cttccttggc                                                   20

SEQ ID NO: 157          moltype = DNA  length = 20
FEATURE                 Location/Qualifiers
misc_feature            1..20
                        note = Synthetic polynucleotide
misc_feature            1..20
                        note = Transferrin_T43 gRNA spacer
source                  1..20
                        mol_type = other DNA
                        organism = synthetic construct
SEQUENCE: 157
tatgaagggg gccccacctc                                                   20

SEQ ID NO: 158          moltype = DNA  length = 20
FEATURE                 Location/Qualifiers
misc_feature            1..20
                        note = Synthetic polynucleotide
misc_feature            1..20
                        note = Transferrin_T125 gRNA spacer
source                  1..20
                        mol_type = other DNA
                        organism = synthetic construct
SEQUENCE: 158
tgctgtgatg accccctccc                                                   20

SEQ ID NO: 159          moltype = DNA  length = 20
FEATURE                 Location/Qualifiers
misc_feature            1..20
                        note = Synthetic polynucleotide
misc_feature            1..20
                        note = Transferrin_T165 gRNA spacer
source                  1..20
                        mol_type = other DNA
                        organism = synthetic construct
SEQUENCE: 159
cacatcctgc tatggggcag                                                   20

SEQ ID NO: 160          moltype = DNA  length = 20
FEATURE                 Location/Qualifiers
misc_feature            1..20
                        note = Synthetic polynucleotide
misc_feature            1..20
                        note = Transferrin_T82 gRNA spacer
source                  1..20
                        mol_type = other DNA
                        organism = synthetic construct
SEQUENCE: 160
aggctgcgcg gtggccgccc                                                   20

SEQ ID NO: 161          moltype = DNA  length = 20
FEATURE                 Location/Qualifiers
misc_feature            1..20
                        note = Synthetic polynucleotide
misc_feature            1..20
                        note = Transferrin_T109 gRNA spacer
source                  1..20
                        mol_type = other DNA
                        organism = synthetic construct
SEQUENCE: 161
tggggcattt gtcacactgt                                                   20

SEQ ID NO: 162          moltype = DNA  length = 20
FEATURE                 Location/Qualifiers
misc_feature            1..20
```

```
                        note = Synthetic polynucleotide
misc_feature            1..20
                        note = Transferrin_T52 gRNA spacer
source                  1..20
                        mol_type = other DNA
                        organism = synthetic construct
SEQUENCE: 162
ctcaaggaat tgctagctta                                                20

SEQ ID NO: 163          moltype = DNA  length = 20
FEATURE                 Location/Qualifiers
misc_feature            1..20
                        note = Synthetic polynucleotide
misc_feature            1..20
                        note = Transferrin_T34 gRNA spacer
source                  1..20
                        mol_type = other DNA
                        organism = synthetic construct
SEQUENCE: 163
ctatggaaaa ccagcggggg                                                20

SEQ ID NO: 164          moltype = DNA  length = 20
FEATURE                 Location/Qualifiers
misc_feature            1..20
                        note = Synthetic polynucleotide
misc_feature            1..20
                        note = Transferrin_T88 gRNA spacer
source                  1..20
                        mol_type = other DNA
                        organism = synthetic construct
SEQUENCE: 164
tgttgcacac atcctgctat                                                20

SEQ ID NO: 165          moltype = DNA  length = 20
FEATURE                 Location/Qualifiers
misc_feature            1..20
                        note = Synthetic polynucleotide
misc_feature            1..20
                        note = Transferrin_T51 gRNA spacer
source                  1..20
                        mol_type = other DNA
                        organism = synthetic construct
SEQUENCE: 165
agagggaaaa tgggggtcgc                                                20

SEQ ID NO: 166          moltype = DNA  length = 20
FEATURE                 Location/Qualifiers
misc_feature            1..20
                        note = Synthetic polynucleotide
misc_feature            1..20
                        note = Transferrin_T46 gRNA spacer
source                  1..20
                        mol_type = other DNA
                        organism = synthetic construct
SEQUENCE: 166
cttatgttcc atggggggcc                                                20

SEQ ID NO: 167          moltype = DNA  length = 20
FEATURE                 Location/Qualifiers
misc_feature            1..20
                        note = Synthetic polynucleotide
misc_feature            1..20
                        note = Transferrin_T178 gRNA spacer
source                  1..20
                        mol_type = other DNA
                        organism = synthetic construct
SEQUENCE: 167
tctgaccatt cccctttcag                                                20

SEQ ID NO: 168          moltype = DNA  length = 20
FEATURE                 Location/Qualifiers
misc_feature            1..20
                        note = Synthetic polynucleotide
misc_feature            1..20
                        note = Transferrin_T74 gRNA spacer
source                  1..20
                        mol_type = other DNA
                        organism = synthetic construct
SEQUENCE: 168
```

```
ggggcatttg tcacactgtt                                              20

SEQ ID NO: 169          moltype = DNA  length = 20
FEATURE                 Location/Qualifiers
misc_feature            1..20
                        note = Synthetic polynucleotide
misc_feature            1..20
                        note = Transferrin_T176 gRNA spacer
source                  1..20
                        mol_type = other DNA
                        organism = synthetic construct
SEQUENCE: 169
ccgcgctcag gctggaagcc                                              20

SEQ ID NO: 170          moltype = DNA  length = 20
FEATURE                 Location/Qualifiers
misc_feature            1..20
                        note = Synthetic polynucleotide
misc_feature            1..20
                        note = Transferrin_T54 gRNA spacer
source                  1..20
                        mol_type = other DNA
                        organism = synthetic construct
SEQUENCE: 170
gcggtggccg cccgggttgc                                              20

SEQ ID NO: 171          moltype = DNA  length = 20
FEATURE                 Location/Qualifiers
misc_feature            1..20
                        note = Synthetic polynucleotide
misc_feature            1..20
                        note = Transferrin_T32 gRNA spacer
source                  1..20
                        mol_type = other DNA
                        organism = synthetic construct
SEQUENCE: 171
tgcttgtcgt tggccaagcc                                              20

SEQ ID NO: 172          moltype = DNA  length = 20
FEATURE                 Location/Qualifiers
misc_feature            1..20
                        note = Synthetic polynucleotide
misc_feature            1..20
                        note = Transferrin_T136 gRNA spacer
source                  1..20
                        mol_type = other DNA
                        organism = synthetic construct
SEQUENCE: 172
tccctggtga ggagccggcc                                              20

SEQ ID NO: 173          moltype = DNA  length = 20
FEATURE                 Location/Qualifiers
misc_feature            1..20
                        note = Synthetic polynucleotide
misc_feature            1..20
                        note = Transferrin_T78 gRNA spacer
source                  1..20
                        mol_type = other DNA
                        organism = synthetic construct
SEQUENCE: 173
ttatgttcca tggggggcca                                              20

SEQ ID NO: 174          moltype = DNA  length = 20
FEATURE                 Location/Qualifiers
misc_feature            1..20
                        note = Synthetic polynucleotide
misc_feature            1..20
                        note = Transferrin_T154 gRNA spacer
source                  1..20
                        mol_type = other DNA
                        organism = synthetic construct
SEQUENCE: 174
ttttaatagt tacccatggc                                              20

SEQ ID NO: 175          moltype = DNA  length = 20
FEATURE                 Location/Qualifiers
misc_feature            1..20
                        note = Synthetic polynucleotide
misc_feature            1..20
```

```
                        note = Transferrin_T140 gRNA spacer
source                  1..20
                        mol_type = other DNA
                        organism = synthetic construct
SEQUENCE: 175
ccaggcttcc agcctgagcg                                              20

SEQ ID NO: 176          moltype = DNA  length = 20
FEATURE                 Location/Qualifiers
misc_feature            1..20
                        note = Synthetic polynucleotide
misc_feature            1..20
                        note = Transferrin_T93 gRNA spacer
source                  1..20
                        mol_type = other DNA
                        organism = synthetic construct
SEQUENCE: 176
caggctgcgc ggtggccgcc                                              20

SEQ ID NO: 177          moltype = DNA  length = 20
FEATURE                 Location/Qualifiers
misc_feature            1..20
                        note = Synthetic polynucleotide
misc_feature            1..20
                        note = Transferrin_T95 gRNA spacer
source                  1..20
                        mol_type = other DNA
                        organism = synthetic construct
SEQUENCE: 177
atgtgtgcaa catctgccac                                              20

SEQ ID NO: 178          moltype = DNA  length = 20
FEATURE                 Location/Qualifiers
misc_feature            1..20
                        note = Synthetic polynucleotide
misc_feature            1..20
                        note = Transferrin_T37 gRNA spacer
source                  1..20
                        mol_type = other DNA
                        organism = synthetic construct
SEQUENCE: 178
agtgcatgca ggctgcgcgg                                              20

SEQ ID NO: 179          moltype = DNA  length = 20
FEATURE                 Location/Qualifiers
misc_feature            1..20
                        note = Synthetic polynucleotide
misc_feature            1..20
                        note = Transferrin_T91 gRNA spacer
source                  1..20
                        mol_type = other DNA
                        organism = synthetic construct
SEQUENCE: 179
actccccgac ctcctgaggt                                              20

SEQ ID NO: 180          moltype = DNA  length = 20
FEATURE                 Location/Qualifiers
misc_feature            1..20
                        note = Synthetic polynucleotide
misc_feature            1..20
                        note = Transferrin_T166 gRNA spacer
source                  1..20
                        mol_type = other DNA
                        organism = synthetic construct
SEQUENCE: 180
gaaaggggaa tggtcagacc                                              20

SEQ ID NO: 181          moltype = DNA  length = 20
FEATURE                 Location/Qualifiers
misc_feature            1..20
                        note = Synthetic polynucleotide
misc_feature            1..20
                        note = Transferrin_T105 gRNA spacer
source                  1..20
                        mol_type = other DNA
                        organism = synthetic construct
SEQUENCE: 181
cgcgctcagg ctggaagcct                                              20
```

```
SEQ ID NO: 182          moltype = DNA  length = 20
FEATURE                 Location/Qualifiers
misc_feature            1..20
                        note = Synthetic polynucleotide
misc_feature            1..20
                        note = Transferrin_T142 gRNA spacer
source                  1..20
                        mol_type = other DNA
                        organism = synthetic construct
SEQUENCE: 182
gtgtctagaa gcccaagcaa                                              20

SEQ ID NO: 183          moltype = DNA  length = 20
FEATURE                 Location/Qualifiers
misc_feature            1..20
                        note = Synthetic polynucleotide
misc_feature            1..20
                        note = Transferrin_T25 gRNA spacer
source                  1..20
                        mol_type = other DNA
                        organism = synthetic construct
SEQUENCE: 183
cccgggttgc agggaacgcg                                              20

SEQ ID NO: 184          moltype = DNA  length = 20
FEATURE                 Location/Qualifiers
misc_feature            1..20
                        note = Synthetic polynucleotide
misc_feature            1..20
                        note = Transferrin_T135 gRNA spacer
source                  1..20
                        mol_type = other DNA
                        organism = synthetic construct
SEQUENCE: 184
tttcagaggc tgacgtcccc                                              20

SEQ ID NO: 185          moltype = DNA  length = 20
FEATURE                 Location/Qualifiers
misc_feature            1..20
                        note = Synthetic polynucleotide
misc_feature            1..20
                        note = Transferrin_T69 gRNA spacer
source                  1..20
                        mol_type = other DNA
                        organism = synthetic construct
SEQUENCE: 185
gagctgtaga tgtcctgcca                                              20

SEQ ID NO: 186          moltype = DNA  length = 20
FEATURE                 Location/Qualifiers
misc_feature            1..20
                        note = Synthetic polynucleotide
misc_feature            1..20
                        note = Transferrin_T147 gRNA spacer
source                  1..20
                        mol_type = other DNA
                        organism = synthetic construct
SEQUENCE: 186
gggtcatcac agcacttgcc                                              20

SEQ ID NO: 187          moltype = DNA  length = 20
FEATURE                 Location/Qualifiers
misc_feature            1..20
                        note = Synthetic polynucleotide
misc_feature            1..20
                        note = Transferrin_T33 gRNA spacer
source                  1..20
                        mol_type = other DNA
                        organism = synthetic construct
SEQUENCE: 187
ggataaaggc aagtaacgtg                                              20

SEQ ID NO: 188          moltype = DNA  length = 20
FEATURE                 Location/Qualifiers
misc_feature            1..20
                        note = Synthetic polynucleotide
misc_feature            1..20
                        note = Transferrin_T75 gRNA spacer
source                  1..20
```

```
                         mol_type = other DNA
                         organism = synthetic construct
SEQUENCE: 188
tctccctcag catagggagt                                                20

SEQ ID NO: 189           moltype = DNA  length = 20
FEATURE                  Location/Qualifiers
misc_feature             1..20
                         note = Synthetic polynucleotide
misc_feature             1..20
                         note = mTF-T1 gRNA spacer
source                   1..20
                         mol_type = other DNA
                         organism = synthetic construct
SEQUENCE: 189
taacaagcaa gacccgtcgc                                                20

SEQ ID NO: 190           moltype = DNA  length = 20
FEATURE                  Location/Qualifiers
misc_feature             1..20
                         note = Synthetic polynucleotide
misc_feature             1..20
                         note = mTF-T2 gRNA spacer
source                   1..20
                         mol_type = other DNA
                         organism = synthetic construct
SEQUENCE: 190
gagaacgcac cactttacga                                                20

SEQ ID NO: 191           moltype =   length =
SEQUENCE: 191
000

SEQ ID NO: 192           moltype = DNA  length = 20
FEATURE                  Location/Qualifiers
misc_feature             1..20
                         note = Synthetic polynucleotide
misc_feature             1..20
                         note = FGA Intron 1_T61 gRNA spacer
source                   1..20
                         mol_type = other DNA
                         organism = synthetic construct
SEQUENCE: 192
gattaaggag agcagacaca                                                20

SEQ ID NO: 193           moltype = DNA  length = 20
FEATURE                  Location/Qualifiers
misc_feature             1..20
                         note = Synthetic polynucleotide
misc_feature             1..20
                         note = FGA Intron 1_T30 gRNA spacer
source                   1..20
                         mol_type = other DNA
                         organism = synthetic construct
SEQUENCE: 193
gagagtgtac aaactcacaa                                                20

SEQ ID NO: 194           moltype = DNA  length = 20
FEATURE                  Location/Qualifiers
misc_feature             1..20
                         note = Synthetic polynucleotide
misc_feature             1..20
                         note = FGA Intron 1_T57 gRNA spacer
source                   1..20
                         mol_type = other DNA
                         organism = synthetic construct
SEQUENCE: 194
tatcttcaaa tggaaatcct                                                20

SEQ ID NO: 195           moltype = DNA  length = 20
FEATURE                  Location/Qualifiers
misc_feature             1..20
                         note = Synthetic polynucleotide
misc_feature             1..20
                         note = FGA Intron 1_T11 gRNA spacer
source                   1..20
                         mol_type = other DNA
                         organism = synthetic construct
SEQUENCE: 195
```

```
accaaggctt tataggtaca                                              20

SEQ ID NO: 196         moltype = DNA  length = 20
FEATURE                Location/Qualifiers
misc_feature           1..20
                       note = Synthetic polynucleotide
misc_feature           1..20
                       note = FGA Intron 1_T26 gRNA spacer
source                 1..20
                       mol_type = other DNA
                       organism = synthetic construct
SEQUENCE: 196
ggcctgggag gaaatttcct                                              20

SEQ ID NO: 197         moltype = DNA  length = 20
FEATURE                Location/Qualifiers
misc_feature           1..20
                       note = Synthetic polynucleotide
misc_feature           1..20
                       note = FGA Intron 1_T33 gRNA spacer
source                 1..20
                       mol_type = other DNA
                       organism = synthetic construct
SEQUENCE: 197
ttattccaca aagagcctgg                                              20

SEQ ID NO: 198         moltype = DNA  length = 20
FEATURE                Location/Qualifiers
misc_feature           1..20
                       note = Synthetic polynucleotide
misc_feature           1..20
                       note = FGA Intron 1_T20 gRNA spacer
source                 1..20
                       mol_type = other DNA
                       organism = synthetic construct
SEQUENCE: 198
cttgacacct caagaataca                                              20

SEQ ID NO: 199         moltype = DNA  length = 20
FEATURE                Location/Qualifiers
misc_feature           1..20
                       note = Synthetic polynucleotide
misc_feature           1..20
                       note = FGA Intron 1_T24 gRNA spacer
source                 1..20
                       mol_type = other DNA
                       organism = synthetic construct
SEQUENCE: 199
atctcttcct ggggacttgt                                              20

SEQ ID NO: 200         moltype = DNA  length = 20
FEATURE                Location/Qualifiers
misc_feature           1..20
                       note = Synthetic polynucleotide
misc_feature           1..20
                       note = FGA Intron 1_T27 gRNA spacer
source                 1..20
                       mol_type = other DNA
                       organism = synthetic construct
SEQUENCE: 200
cacccaggaa atttcctccc                                              20

SEQ ID NO: 201         moltype = DNA  length = 20
FEATURE                Location/Qualifiers
misc_feature           1..20
                       note = Synthetic polynucleotide
misc_feature           1..20
                       note = FGA Intron 1_T48 gRNA spacer
source                 1..20
                       mol_type = other DNA
                       organism = synthetic construct
SEQUENCE: 201
aggcctggga ggaaatttcc                                              20

SEQ ID NO: 202         moltype = DNA  length = 20
FEATURE                Location/Qualifiers
misc_feature           1..20
                       note = Synthetic polynucleotide
misc_feature           1..20
```

```
                        note = FGA Intron 1_T8 gRNA spacer
source                  1..20
                        mol_type = other DNA
                        organism = synthetic construct
SEQUENCE: 202
actagcatta taatgcacca                                                20

SEQ ID NO: 203          moltype = DNA  length = 20
FEATURE                 Location/Qualifiers
misc_feature            1..20
                        note = Synthetic polynucleotide
misc_feature            1..20
                        note = FGA Intron 1_T56 gRNA spacer
source                  1..20
                        mol_type = other DNA
                        organism = synthetic construct
SEQUENCE: 203
tacaagtccc caggaagaga                                                20

SEQ ID NO: 204          moltype = DNA  length = 20
FEATURE                 Location/Qualifiers
misc_feature            1..20
                        note = Synthetic polynucleotide
misc_feature            1..20
                        note = FGA Intron 1_T19 gRNA spacer
source                  1..20
                        mol_type = other DNA
                        organism = synthetic construct
SEQUENCE: 204
tggcactctc acagagatta                                                20

SEQ ID NO: 205          moltype = DNA  length = 20
FEATURE                 Location/Qualifiers
misc_feature            1..20
                        note = Synthetic polynucleotide
misc_feature            1..20
                        note = FGA Intron 1_T67 gRNA spacer
source                  1..20
                        mol_type = other DNA
                        organism = synthetic construct
SEQUENCE: 205
ttagccagaa gaggagacag                                                20

SEQ ID NO: 206          moltype = DNA  length = 20
FEATURE                 Location/Qualifiers
misc_feature            1..20
                        note = Synthetic polynucleotide
misc_feature            1..20
                        note = FGA Intron 1_T41 gRNA spacer
source                  1..20
                        mol_type = other DNA
                        organism = synthetic construct
SEQUENCE: 206
gagagtgcca tctcttcctg                                                20

SEQ ID NO: 207          moltype = DNA  length = 20
FEATURE                 Location/Qualifiers
misc_feature            1..20
                        note = Synthetic polynucleotide
misc_feature            1..20
                        note = FGA Intron 1_T18 gRNA spacer
source                  1..20
                        mol_type = other DNA
                        organism = synthetic construct
SEQUENCE: 207
gtgagagtgc catctcttcc                                                20

SEQ ID NO: 208          moltype = DNA  length = 20
FEATURE                 Location/Qualifiers
misc_feature            1..20
                        note = Synthetic polynucleotide
misc_feature            1..20
                        note = FGA Intron 1_T45 gRNA spacer
source                  1..20
                        mol_type = other DNA
                        organism = synthetic construct
SEQUENCE: 208
agattaagga gagcagacac                                                20
```

```
SEQ ID NO: 209          moltype = DNA  length = 20
FEATURE                 Location/Qualifiers
misc_feature            1..20
                        note = Synthetic polynucleotide
misc_feature            1..20
                        note = FGA Intron 1_T66 gRNA spacer
source                  1..20
                        mol_type = other DNA
                        organism = synthetic construct
SEQUENCE: 209
ggagttgtta tgagaattaa                                              20

SEQ ID NO: 210          moltype = DNA  length = 20
FEATURE                 Location/Qualifiers
misc_feature            1..20
                        note = Synthetic polynucleotide
misc_feature            1..20
                        note = FGA Intron 1_T4 gRNA spacer
source                  1..20
                        mol_type = other DNA
                        organism = synthetic construct
SEQUENCE: 210
tggcatgcct acaagtcccc                                              20

SEQ ID NO: 211          moltype = DNA  length = 20
FEATURE                 Location/Qualifiers
misc_feature            1..20
                        note = Synthetic polynucleotide
misc_feature            1..20
                        note = FGA Intron 1_T5 gRNA spacer
source                  1..20
                        mol_type = other DNA
                        organism = synthetic construct
SEQUENCE: 211
ttgaggtgtc aagcccaccc                                              20

SEQ ID NO: 212          moltype = DNA  length = 20
FEATURE                 Location/Qualifiers
misc_feature            1..20
                        note = Synthetic polynucleotide
misc_feature            1..20
                        note = FGA Intron 1_T69 gRNA spacer
source                  1..20
                        mol_type = other DNA
                        organism = synthetic construct
SEQUENCE: 212
tatgagaatt aaaggagaca                                              20

SEQ ID NO: 213          moltype = DNA  length = 20
FEATURE                 Location/Qualifiers
misc_feature            1..20
                        note = Synthetic polynucleotide
misc_feature            1..20
                        note = FGA Intron 1_T54 gRNA spacer
source                  1..20
                        mol_type = other DNA
                        organism = synthetic construct
SEQUENCE: 213
ggagagcaga cacagggctt                                              20

SEQ ID NO: 214          moltype = DNA  length = 20
FEATURE                 Location/Qualifiers
misc_feature            1..20
                        note = Synthetic polynucleotide
misc_feature            1..20
                        note = FGA Intron 1_T42 gRNA spacer
source                  1..20
                        mol_type = other DNA
                        organism = synthetic construct
SEQUENCE: 214
tctgacctcc aggctctttg                                              20

SEQ ID NO: 215          moltype = DNA  length = 20
FEATURE                 Location/Qualifiers
misc_feature            1..20
                        note = Synthetic polynucleotide
misc_feature            1..20
                        note = FGA Intron 1_T23 gRNA spacer
source                  1..20
```

```
                          mol_type = other DNA
                          organism = synthetic construct
SEQUENCE: 215
gcaggtagac tctgacctcc                                                    20

SEQ ID NO: 216            moltype = DNA  length = 20
FEATURE                   Location/Qualifiers
misc_feature              1..20
                          note = Synthetic polynucleotide
misc_feature              1..20
                          note = FGA Intron 1_T29 gRNA spacer
source                    1..20
                          mol_type = other DNA
                          organism = synthetic construct
SEQUENCE: 216
accaagagga agatcttaga                                                    20

SEQ ID NO: 217            moltype = DNA  length = 20
FEATURE                   Location/Qualifiers
misc_feature              1..20
                          note = Synthetic polynucleotide
misc_feature              1..20
                          note = FGA Intron 1_T13 gRNA spacer
source                    1..20
                          mol_type = other DNA
                          organism = synthetic construct
SEQUENCE: 217
tctactgaag cagcaattac                                                    20

SEQ ID NO: 218            moltype = DNA  length = 20
FEATURE                   Location/Qualifiers
misc_feature              1..20
                          note = Synthetic polynucleotide
misc_feature              1..20
                          note = FGA Intron 1_T25 gRNA spacer
source                    1..20
                          mol_type = other DNA
                          organism = synthetic construct
SEQUENCE: 218
tgagagtgcc atctcttcct                                                    20

SEQ ID NO: 219            moltype = DNA  length = 20
FEATURE                   Location/Qualifiers
misc_feature              1..20
                          note = Synthetic polynucleotide
misc_feature              1..20
                          note = FGA Intron 1_T16 gRNA spacer
source                    1..20
                          mol_type = other DNA
                          organism = synthetic construct
SEQUENCE: 219
tcagaagaga ttagttagta                                                    20

SEQ ID NO: 220            moltype = DNA  length = 20
FEATURE                   Location/Qualifiers
misc_feature              1..20
                          note = Synthetic polynucleotide
misc_feature              1..20
                          note = FGA Intron 1_T22 gRNA spacer
source                    1..20
                          mol_type = other DNA
                          organism = synthetic construct
SEQUENCE: 220
agtgtgtcag gacatagagc                                                    20

SEQ ID NO: 221            moltype = DNA  length = 20
FEATURE                   Location/Qualifiers
misc_feature              1..20
                          note = Synthetic polynucleotide
misc_feature              1..20
                          note = FGA Intron 1_T44 gRNA spacer
source                    1..20
                          mol_type = other DNA
                          organism = synthetic construct
SEQUENCE: 221
acagcaatgt tagccagaag                                                    20

SEQ ID NO: 222            moltype = DNA  length = 20
FEATURE                   Location/Qualifiers
```

```
misc_feature          1..20
                      note = Synthetic polynucleotide
misc_feature          1..20
                      note = FGA Intron 1_T14 gRNA spacer
source                1..20
                      mol_type = other DNA
                      organism = synthetic construct
SEQUENCE: 222
aggctttata ggtacaagga                                             20

SEQ ID NO: 223        moltype = DNA  length = 20
FEATURE               Location/Qualifiers
misc_feature          1..20
                      note = Synthetic polynucleotide
misc_feature          1..20
                      note = FGA Intron 1_T28 gRNA spacer
source                1..20
                      mol_type = other DNA
                      organism = synthetic construct
SEQUENCE: 223
cagggtaata tgacaccaag                                             20

SEQ ID NO: 224        moltype = DNA  length = 20
FEATURE               Location/Qualifiers
misc_feature          1..20
                      note = Synthetic polynucleotide
misc_feature          1..20
                      note = FGA Intron 1_T7 gRNA spacer
source                1..20
                      mol_type = other DNA
                      organism = synthetic construct
SEQUENCE: 224
ataatgcacc aaggctttat                                             20

SEQ ID NO: 225        moltype = DNA  length = 20
FEATURE               Location/Qualifiers
misc_feature          1..20
                      note = Synthetic polynucleotide
misc_feature          1..20
                      note = FGA Intron 1_T40 gRNA spacer
source                1..20
                      mol_type = other DNA
                      organism = synthetic construct
SEQUENCE: 225
tccatctaag atcttcctct                                             20

SEQ ID NO: 226        moltype = DNA  length = 20
FEATURE               Location/Qualifiers
misc_feature          1..20
                      note = Synthetic polynucleotide
misc_feature          1..20
                      note = FGA Intron 1_T36 gRNA spacer
source                1..20
                      mol_type = other DNA
                      organism = synthetic construct
SEQUENCE: 226
aaatcctagg acccatttta                                             20

SEQ ID NO: 227        moltype = DNA  length = 20
FEATURE               Location/Qualifiers
misc_feature          1..20
                      note = Synthetic polynucleotide
misc_feature          1..20
                      note = FGA Intron 1_T15 gRNA spacer
source                1..20
                      mol_type = other DNA
                      organism = synthetic construct
SEQUENCE: 227
acattcagtt aagatagtct                                             20

SEQ ID NO: 228        moltype = DNA  length = 20
FEATURE               Location/Qualifiers
misc_feature          1..20
                      note = Synthetic polynucleotide
misc_feature          1..20
                      note = FGA Intron 1_T58 gRNA spacer
source                1..20
                      mol_type = other DNA
                      organism = synthetic construct
```

```
SEQUENCE: 228
catgccactg tctcctcttc                                              20

SEQ ID NO: 229          moltype = DNA  length = 20
FEATURE                 Location/Qualifiers
misc_feature            1..20
                        note = Synthetic polynucleotide
misc_feature            1..20
                        note = FGA Intron 1_T63 gRNA spacer
source                  1..20
                        mol_type = other DNA
                        organism = synthetic construct
SEQUENCE: 229
tcataacaac tccataaaat                                              20

SEQ ID NO: 230          moltype = DNA  length = 20
FEATURE                 Location/Qualifiers
misc_feature            1..20
                        note = Synthetic polynucleotide
misc_feature            1..20
                        note = FGA Intron 1_T55 gRNA spacer
source                  1..20
                        mol_type = other DNA
                        organism = synthetic construct
SEQUENCE: 230
ttctatgtaa cctttagaga                                              20

SEQ ID NO: 231          moltype = DNA  length = 20
FEATURE                 Location/Qualifiers
misc_feature            1..20
                        note = Synthetic polynucleotide
misc_feature            1..20
                        note = FGA Intron 1_T50 gRNA spacer
source                  1..20
                        mol_type = other DNA
                        organism = synthetic construct
SEQUENCE: 231
ttaaaagaat accattactg                                              20

SEQ ID NO: 232          moltype = DNA  length = 20
FEATURE                 Location/Qualifiers
misc_feature            1..20
                        note = Synthetic polynucleotide
misc_feature            1..20
                        note = FGA Intron 1_T21 gRNA spacer
source                  1..20
                        mol_type = other DNA
                        organism = synthetic construct
SEQUENCE: 232
catattaccc tgtattcttg                                              20

SEQ ID NO: 233          moltype = DNA  length = 20
FEATURE                 Location/Qualifiers
misc_feature            1..20
                        note = Synthetic polynucleotide
misc_feature            1..20
                        note = FGA Intron 1_T2 gRNA spacer
source                  1..20
                        mol_type = other DNA
                        organism = synthetic construct
SEQUENCE: 233
gcttgacacc tcaagaatac                                              20

SEQ ID NO: 234          moltype = DNA  length = 20
FEATURE                 Location/Qualifiers
misc_feature            1..20
                        note = Synthetic polynucleotide
misc_feature            1..20
                        note = FGA Intron 1_T60 gRNA spacer
source                  1..20
                        mol_type = other DNA
                        organism = synthetic construct
SEQUENCE: 234
aaggttacat agaaacttga                                              20

SEQ ID NO: 235          moltype = DNA  length = 20
FEATURE                 Location/Qualifiers
misc_feature            1..20
                        note = Synthetic polynucleotide
```

```
misc_feature          1..20
                      note = FGA Intron 1_T77 gRNA spacer
source                1..20
                      mol_type = other DNA
                      organism = synthetic construct
SEQUENCE: 235
gcaagaagaa aaaatgaaaa                                              20

SEQ ID NO: 236        moltype = DNA  length = 20
FEATURE               Location/Qualifiers
misc_feature          1..20
                      note = Synthetic polynucleotide
misc_feature          1..20
                      note = FGA Intron 1_T10 gRNA spacer
source                1..20
                      mol_type = other DNA
                      organism = synthetic construct
SEQUENCE: 236
actcttagct ttatgacccc                                              20

SEQ ID NO: 237        moltype = DNA  length = 20
FEATURE               Location/Qualifiers
misc_feature          1..20
                      note = Synthetic polynucleotide
misc_feature          1..20
                      note = FGA Intron 1_T64 gRNA spacer
source                1..20
                      mol_type = other DNA
                      organism = synthetic construct
SEQUENCE: 237
ctcataacaa ctccataaaa                                              20

SEQ ID NO: 238        moltype = DNA  length = 20
FEATURE               Location/Qualifiers
misc_feature          1..20
                      note = Synthetic polynucleotide
misc_feature          1..20
                      note = FGA Intron 1_T3 gRNA spacer
source                1..20
                      mol_type = other DNA
                      organism = synthetic construct
SEQUENCE: 238
aatacgcttt tccgcagtaa                                              20

SEQ ID NO: 239        moltype = DNA  length = 20
FEATURE               Location/Qualifiers
misc_feature          1..20
                      note = Synthetic polynucleotide
misc_feature          1..20
                      note = FGA Intron 1_T49 gRNA spacer
source                1..20
                      mol_type = other DNA
                      organism = synthetic construct
SEQUENCE: 239
gaaatttcct cccaggcctg                                              20

SEQ ID NO: 240        moltype = DNA  length = 20
FEATURE               Location/Qualifiers
misc_feature          1..20
                      note = Synthetic polynucleotide
misc_feature          1..20
                      note = FGA Intron 1_T46 gRNA spacer
source                1..20
                      mol_type = other DNA
                      organism = synthetic construct
SEQUENCE: 240
ctgggaggaa atttcctggg                                              20

SEQ ID NO: 241        moltype = DNA  length = 20
FEATURE               Location/Qualifiers
misc_feature          1..20
                      note = Synthetic polynucleotide
misc_feature          1..20
                      note = FGA Intron 1_T1 gRNA spacer
source                1..20
                      mol_type = other DNA
                      organism = synthetic construct
SEQUENCE: 241
acagggcttc ggcaagcttc                                              20
```

```
SEQ ID NO: 242          moltype = DNA  length = 20
FEATURE                 Location/Qualifiers
misc_feature            1..20
                        note = Synthetic polynucleotide
misc_feature            1..20
                        note = FGA Intron 1_T6 gRNA spacer
source                  1..20
                        mol_type = other DNA
                        organism = synthetic construct
SEQUENCE: 242
tccttgtacc tataaagcct                                             20

SEQ ID NO: 243          moltype = DNA  length = 20
FEATURE                 Location/Qualifiers
misc_feature            1..20
                        note = Synthetic polynucleotide
misc_feature            1..20
                        note = FGA Intron 1_T37 gRNA spacer
source                  1..20
                        mol_type = other DNA
                        organism = synthetic construct
SEQUENCE: 243
tgggaggaaa tttcctgggt                                             20

SEQ ID NO: 244          moltype = DNA  length = 20
FEATURE                 Location/Qualifiers
misc_feature            1..20
                        note = Synthetic polynucleotide
misc_feature            1..20
                        note = FGA Intron 1_T52 gRNA spacer
source                  1..20
                        mol_type = other DNA
                        organism = synthetic construct
SEQUENCE: 244
actaaaagtt ctgcttatta                                             20

SEQ ID NO: 245          moltype = DNA  length = 20
FEATURE                 Location/Qualifiers
misc_feature            1..20
                        note = Synthetic polynucleotide
misc_feature            1..20
                        note = FGA Intron 1_T71 gRNA spacer
source                  1..20
                        mol_type = other DNA
                        organism = synthetic construct
SEQUENCE: 245
ataagcattt gataaatatt                                             20

SEQ ID NO: 246          moltype = DNA  length = 20
FEATURE                 Location/Qualifiers
misc_feature            1..20
                        note = Synthetic polynucleotide
misc_feature            1..20
                        note = FGA Intron 1_T12 gRNA spacer
source                  1..20
                        mol_type = other DNA
                        organism = synthetic construct
SEQUENCE: 246
aactccataa aatgggtcct                                             20

SEQ ID NO: 247          moltype = DNA  length = 20
FEATURE                 Location/Qualifiers
misc_feature            1..20
                        note = Synthetic polynucleotide
misc_feature            1..20
                        note = FGA Intron 1_T47 gRNA spacer
source                  1..20
                        mol_type = other DNA
                        organism = synthetic construct
SEQUENCE: 247
aattatgaat ccatctctaa                                             20

SEQ ID NO: 248          moltype = DNA  length = 20
FEATURE                 Location/Qualifiers
misc_feature            1..20
                        note = Synthetic polynucleotide
misc_feature            1..20
                        note = FGA Intron 1_T43 gRNA spacer
```

```
source                  1..20
                        mol_type = other DNA
                        organism = synthetic construct
SEQUENCE: 248
gttagtacag ttttgctgaa                                                 20

SEQ ID NO: 249          moltype = DNA  length = 20
FEATURE                 Location/Qualifiers
misc_feature            1..20
                        note = Synthetic polynucleotide
misc_feature            1..20
                        note = FGA Intron 1_T39 gRNA spacer
source                  1..20
                        mol_type = other DNA
                        organism = synthetic construct
SEQUENCE: 249
tgagagtgta caaactcaca                                                 20

SEQ ID NO: 250          moltype = DNA  length = 20
FEATURE                 Location/Qualifiers
misc_feature            1..20
                        note = Synthetic polynucleotide
misc_feature            1..20
                        note = FGA Intron 1_T76 gRNA spacer
source                  1..20
                        mol_type = other DNA
                        organism = synthetic construct
SEQUENCE: 250
aaacaaaaca aaacaaaatg                                                 20

SEQ ID NO: 251          moltype = DNA  length = 20
FEATURE                 Location/Qualifiers
misc_feature            1..20
                        note = Synthetic polynucleotide
misc_feature            1..20
                        note = FGA Intron 1_T17 gRNA spacer
source                  1..20
                        mol_type = other DNA
                        organism = synthetic construct
SEQUENCE: 251
tagctttatg accccaggcc                                                 20

SEQ ID NO: 252          moltype = DNA  length = 20
FEATURE                 Location/Qualifiers
misc_feature            1..20
                        note = Synthetic polynucleotide
misc_feature            1..20
                        note = FGA Intron 1_T38 gRNA spacer
source                  1..20
                        mol_type = other DNA
                        organism = synthetic construct
SEQUENCE: 252
tttatgaccc caggcctggg                                                 20

SEQ ID NO: 253          moltype = DNA  length = 20
FEATURE                 Location/Qualifiers
misc_feature            1..20
                        note = Synthetic polynucleotide
misc_feature            1..20
                        note = FGA Intron 1_T51 gRNA spacer
source                  1..20
                        mol_type = other DNA
                        organism = synthetic construct
SEQUENCE: 253
aaaagcaaac gaattatctt                                                 20

SEQ ID NO: 254          moltype = DNA  length = 20
FEATURE                 Location/Qualifiers
misc_feature            1..20
                        note = Synthetic polynucleotide
misc_feature            1..20
                        note = FGA Intron 1_T9 gRNA spacer
source                  1..20
                        mol_type = other DNA
                        organism = synthetic construct
SEQUENCE: 254
cataaagcta agagtgtgtc                                                 20

SEQ ID NO: 255          moltype = DNA  length = 20
```

```
FEATURE                Location/Qualifiers
misc_feature           1..20
                       note = Synthetic polynucleotide
misc_feature           1..20
                       note = FGA Intron 1_T62 gRNA spacer
source                 1..20
                       mol_type = other DNA
                       organism = synthetic construct
SEQUENCE: 255
catagaaact tgaaggagag                                                   20

SEQ ID NO: 256         moltype = DNA  length = 20
FEATURE                Location/Qualifiers
misc_feature           1..20
                       note = Synthetic polynucleotide
misc_feature           1..20
                       note = FGA Intron 1_T74 gRNA spacer
source                 1..20
                       mol_type = other DNA
                       organism = synthetic construct
SEQUENCE: 256
attcaaataa ttttcctttt                                                   20

SEQ ID NO: 257         moltype = DNA  length = 20
FEATURE                Location/Qualifiers
misc_feature           1..20
                       note = Synthetic polynucleotide
misc_feature           1..20
                       note = FGA Intron 1_T34 gRNA spacer
source                 1..20
                       mol_type = other DNA
                       organism = synthetic construct
SEQUENCE: 257
tgcattataa tgctagttaa                                                   20

SEQ ID NO: 258         moltype = DNA  length = 20
FEATURE                Location/Qualifiers
misc_feature           1..20
                       note = Synthetic polynucleotide
misc_feature           1..20
                       note = FGA Intron 1_T70 gRNA spacer
source                 1..20
                       mol_type = other DNA
                       organism = synthetic construct
SEQUENCE: 258
agtcattagt aaaaatgaaa                                                   20

SEQ ID NO: 259         moltype = DNA  length = 20
FEATURE                Location/Qualifiers
misc_feature           1..20
                       note = Synthetic polynucleotide
misc_feature           1..20
                       note = FGA Intron 1_T31 gRNA spacer
source                 1..20
                       mol_type = other DNA
                       organism = synthetic construct
SEQUENCE: 259
tgtttattcc acaaagagcc                                                   20

SEQ ID NO: 260         moltype = DNA  length = 20
FEATURE                Location/Qualifiers
misc_feature           1..20
                       note = Synthetic polynucleotide
misc_feature           1..20
                       note = FGA Intron 1_T59 gRNA spacer
source                 1..20
                       mol_type = other DNA
                       organism = synthetic construct
SEQUENCE: 260
tttaaagaat ccatcctaaa                                                   20

SEQ ID NO: 261         moltype = DNA  length = 20
FEATURE                Location/Qualifiers
misc_feature           1..20
                       note = Synthetic polynucleotide
misc_feature           1..20
                       note = FGA Intron 1_T72 gRNA spacer
source                 1..20
                       mol_type = other DNA
```

```
                        organism = synthetic construct
SEQUENCE: 261
taatggaata aaacatttta                                                20

SEQ ID NO: 262          moltype = DNA  length = 20
FEATURE                 Location/Qualifiers
misc_feature            1..20
                        note = Synthetic polynucleotide
misc_feature            1..20
                        note = FGA Intron 1_T65 gRNA spacer
source                  1..20
                        mol_type = other DNA
                        organism = synthetic construct
SEQUENCE: 262
aaataatttt ccttttagga                                                20

SEQ ID NO: 263          moltype = DNA  length = 20
FEATURE                 Location/Qualifiers
misc_feature            1..20
                        note = Synthetic polynucleotide
misc_feature            1..20
                        note = FGA Intron 1_T79 gRNA spacer
source                  1..20
                        mol_type = other DNA
                        organism = synthetic construct
SEQUENCE: 263
gttttgtttt gttttaaaaa                                                20

SEQ ID NO: 264          moltype = DNA  length = 20
FEATURE                 Location/Qualifiers
misc_feature            1..20
                        note = Synthetic polynucleotide
misc_feature            1..20
                        note = FGA Intron 1_T32 gRNA spacer
source                  1..20
                        mol_type = other DNA
                        organism = synthetic construct
SEQUENCE: 264
agctttatga ccccaggcct                                                20

SEQ ID NO: 265          moltype = DNA  length = 20
FEATURE                 Location/Qualifiers
misc_feature            1..20
                        note = Synthetic polynucleotide
misc_feature            1..20
                        note = FGA Intron 1_T68 gRNA spacer
source                  1..20
                        mol_type = other DNA
                        organism = synthetic construct
SEQUENCE: 265
tcaggtttct tatcttcaaa                                                20

SEQ ID NO: 266          moltype = DNA  length = 20
FEATURE                 Location/Qualifiers
misc_feature            1..20
                        note = Synthetic polynucleotide
misc_feature            1..20
                        note = FGA Intron 1_T75 gRNA spacer
source                  1..20
                        mol_type = other DNA
                        organism = synthetic construct
SEQUENCE: 266
agcaagaaga aaaaatgaaa                                                20

SEQ ID NO: 267          moltype = DNA  length = 20
FEATURE                 Location/Qualifiers
misc_feature            1..20
                        note = Synthetic polynucleotide
misc_feature            1..20
                        note = FGA Intron 1_T78 gRNA spacer
source                  1..20
                        mol_type = other DNA
                        organism = synthetic construct
SEQUENCE: 267
tgttttgttt tgttttaaaa                                                20

SEQ ID NO: 268          moltype = DNA  length = 20
FEATURE                 Location/Qualifiers
misc_feature            1..20
```

```
                        note = Synthetic polynucleotide
misc_feature            1..20
                        note = FGA Intron 1_T35 gRNA spacer
source                  1..20
                        mol_type = other DNA
                        organism = synthetic construct
SEQUENCE: 268
ggaaatttcc tcccaggcct                                              20

SEQ ID NO: 269          moltype = DNA  length = 20
FEATURE                 Location/Qualifiers
misc_feature            1..20
                        note = Synthetic polynucleotide
misc_feature            1..20
                        note = FGA Intron 1_T53 gRNA spacer
source                  1..20
                        mol_type = other DNA
                        organism = synthetic construct
SEQUENCE: 269
aggaaatttc ctcccaggcc                                              20

SEQ ID NO: 270          moltype = DNA  length = 20
FEATURE                 Location/Qualifiers
misc_feature            1..20
                        note = Synthetic polynucleotide
misc_feature            1..20
                        note = FGA Intron 1_T73 gRNA spacer
source                  1..20
                        mol_type = other DNA
                        organism = synthetic construct
SEQUENCE: 270
ttttcttctt gctttctctc                                              20

SEQ ID NO: 271          moltype = DNA  length = 23
FEATURE                 Location/Qualifiers
misc_feature            1..23
                        note = Synthetic polynucleotide
misc_feature            1..23
                        note = Human Albumin Intron-1_T1
source                  1..23
                        mol_type = other DNA
                        organism = synthetic construct
SEQUENCE: 271
taattttctt ttgcgcacta agg                                          23

SEQ ID NO: 272          moltype = DNA  length = 23
FEATURE                 Location/Qualifiers
misc_feature            1..23
                        note = Synthetic polynucleotide
misc_feature            1..23
                        note = Human Albumin Intron-1_T2
source                  1..23
                        mol_type = other DNA
                        organism = synthetic construct
SEQUENCE: 272
tagtgcaatg gataggtctt tgg                                          23

SEQ ID NO: 273          moltype = DNA  length = 23
FEATURE                 Location/Qualifiers
misc_feature            1..23
                        note = Synthetic polynucleotide
misc_feature            1..23
                        note = Human Albumin Intron-1_T3
source                  1..23
                        mol_type = other DNA
                        organism = synthetic construct
SEQUENCE: 273
agtgcaatgg ataggtcttt ggg                                          23

SEQ ID NO: 274          moltype = DNA  length = 23
FEATURE                 Location/Qualifiers
misc_feature            1..23
                        note = Synthetic polynucleotide
misc_feature            1..23
                        note = Human Albumin Intron-1_T4
source                  1..23
                        mol_type = other DNA
                        organism = synthetic construct
SEQUENCE: 274
```

```
taaagcatag tgcaatggat agg                                            23

SEQ ID NO: 275          moltype = DNA  length = 23
FEATURE                 Location/Qualifiers
misc_feature            1..23
                        note = Synthetic polynucleotide
misc_feature            1..23
                        note = Human Albumin Intron-1_T5
source                  1..23
                        mol_type = other DNA
                        organism = synthetic construct
SEQUENCE: 275
atttatgaga tcaacagcac agg                                            23

SEQ ID NO: 276          moltype = DNA  length = 23
FEATURE                 Location/Qualifiers
misc_feature            1..23
                        note = Synthetic polynucleotide
misc_feature            1..23
                        note = Human Albumin Intron-1_T6
source                  1..23
                        mol_type = other DNA
                        organism = synthetic construct
SEQUENCE: 276
tgattcctac agaaaaactc agg                                            23

SEQ ID NO: 277          moltype = DNA  length = 23
FEATURE                 Location/Qualifiers
misc_feature            1..23
                        note = Synthetic polynucleotide
misc_feature            1..23
                        note = Human Albumin Intron-1_T7
source                  1..23
                        mol_type = other DNA
                        organism = synthetic construct
SEQUENCE: 277
tgtatttgtg aagtcttaca agg                                            23

SEQ ID NO: 278          moltype = DNA  length = 23
FEATURE                 Location/Qualifiers
misc_feature            1..23
                        note = Synthetic polynucleotide
misc_feature            1..23
                        note = Human Albumin Intron-1_T8
source                  1..23
                        mol_type = other DNA
                        organism = synthetic construct
SEQUENCE: 278
gactgaaact tcacagaata ggg                                            23

SEQ ID NO: 279          moltype = DNA  length = 23
FEATURE                 Location/Qualifiers
misc_feature            1..23
                        note = Synthetic polynucleotide
misc_feature            1..23
                        note = Human Albumin Intron-1_T9
source                  1..23
                        mol_type = other DNA
                        organism = synthetic construct
SEQUENCE: 279
aatgcataat ctaagtcaaa tgg                                            23

SEQ ID NO: 280          moltype = DNA  length = 23
FEATURE                 Location/Qualifiers
misc_feature            1..23
                        note = Synthetic polynucleotide
misc_feature            1..23
                        note = Human Albumin Intron-1_T10
source                  1..23
                        mol_type = other DNA
                        organism = synthetic construct
SEQUENCE: 280
tgactgaaac ttcacagaat agg                                            23

SEQ ID NO: 281          moltype = DNA  length = 23
FEATURE                 Location/Qualifiers
misc_feature            1..23
                        note = Synthetic polynucleotide
misc_feature            1..23
```

```
                        note = Human Albumin Intron-1_T11
source                  1..23
                        mol_type = other DNA
                        organism = synthetic construct
SEQUENCE: 281
ttaaataaag catagtgcaa tgg                                              23

SEQ ID NO: 282          moltype = DNA  length = 23
FEATURE                 Location/Qualifiers
misc_feature            1..23
                        note = Synthetic polynucleotide
misc_feature            1..23
                        note = Human Albumin Intron-1_T12
source                  1..23
                        mol_type = other DNA
                        organism = synthetic construct
SEQUENCE: 282
gatcaacagc acaggttttg tgg                                              23

SEQ ID NO: 283          moltype = DNA  length = 23
FEATURE                 Location/Qualifiers
misc_feature            1..23
                        note = Synthetic polynucleotide
misc_feature            1..23
                        note = Human Albumin Intron-1_T13
source                  1..23
                        mol_type = other DNA
                        organism = synthetic construct
SEQUENCE: 283
taataaaatt caaacatcct agg                                              23

SEQ ID NO: 284          moltype = DNA  length = 23
FEATURE                 Location/Qualifiers
misc_feature            1..23
                        note = Synthetic polynucleotide
misc_feature            1..23
                        note = Human Albumin Intron-1_T14
source                  1..23
                        mol_type = other DNA
                        organism = synthetic construct
SEQUENCE: 284
ttcattttag tctgtcttct tgg                                              23

SEQ ID NO: 285          moltype = DNA  length = 23
FEATURE                 Location/Qualifiers
misc_feature            1..23
                        note = Synthetic polynucleotide
misc_feature            1..23
                        note = Human Albumin Intron-1_T15
source                  1..23
                        mol_type = other DNA
                        organism = synthetic construct
SEQUENCE: 285
attatctaag tttgaatata agg                                              23

SEQ ID NO: 286          moltype = DNA  length = 23
FEATURE                 Location/Qualifiers
misc_feature            1..23
                        note = Synthetic polynucleotide
misc_feature            1..23
                        note = Human Albumin Intron-1_T16
source                  1..23
                        mol_type = other DNA
                        organism = synthetic construct
SEQUENCE: 286
atcatcctga gtttttctgt agg                                              23

SEQ ID NO: 287          moltype = DNA  length = 23
FEATURE                 Location/Qualifiers
misc_feature            1..23
                        note = Synthetic polynucleotide
misc_feature            1..23
                        note = Human Albumin Intron-1_T17
source                  1..23
                        mol_type = other DNA
                        organism = synthetic construct
SEQUENCE: 287
gcatctttaa agaattattt tgg                                              23
```

```
SEQ ID NO: 288         moltype = DNA  length = 23
FEATURE                Location/Qualifiers
misc_feature           1..23
                       note = Synthetic polynucleotide
misc_feature           1..23
                       note = Human Albumin Intron-1_T18
source                 1..23
                       mol_type = other DNA
                       organism = synthetic construct
SEQUENCE: 288
tactaaaact ttattttact ggg                                          23

SEQ ID NO: 289         moltype = DNA  length = 23
FEATURE                Location/Qualifiers
misc_feature           1..23
                       note = Synthetic polynucleotide
misc_feature           1..23
                       note = Human Albumin Intron-1_T19
source                 1..23
                       mol_type = other DNA
                       organism = synthetic construct
SEQUENCE: 289
tgaattattc ttctgtttaa agg                                          23

SEQ ID NO: 290         moltype = DNA  length = 23
FEATURE                Location/Qualifiers
misc_feature           1..23
                       note = Synthetic polynucleotide
misc_feature           1..23
                       note = Human Albumin Intron-1_T20
source                 1..23
                       mol_type = other DNA
                       organism = synthetic construct
SEQUENCE: 290
aatttttaaa atagtattct tgg                                          23

SEQ ID NO: 291         moltype = DNA  length = 23
FEATURE                Location/Qualifiers
misc_feature           1..23
                       note = Synthetic polynucleotide
misc_feature           1..23
                       note = Human Albumin Intron-1_T21
source                 1..23
                       mol_type = other DNA
                       organism = synthetic construct
SEQUENCE: 291
atgcatttgt ttcaaaatat tgg                                          23

SEQ ID NO: 292         moltype = DNA  length = 23
FEATURE                Location/Qualifiers
misc_feature           1..23
                       note = Synthetic polynucleotide
misc_feature           1..23
                       note = Human Albumin Intron-1_T22
source                 1..23
                       mol_type = other DNA
                       organism = synthetic construct
SEQUENCE: 292
tttggcattt atttctaaaa tgg                                          23

SEQ ID NO: 293         moltype = DNA  length = 23
FEATURE                Location/Qualifiers
misc_feature           1..23
                       note = Synthetic polynucleotide
misc_feature           1..23
                       note = Human Albumin Intron-1_T23
source                 1..23
                       mol_type = other DNA
                       organism = synthetic construct
SEQUENCE: 293
aaagttgaac aatagaaaaa tgg                                          23

SEQ ID NO: 294         moltype = DNA  length = 23
FEATURE                Location/Qualifiers
misc_feature           1..23
                       note = Synthetic polynucleotide
misc_feature           1..23
                       note = Human Albumin Intron-1_T24
source                 1..23
```

```
                         mol_type = other DNA
                         organism = synthetic construct
SEQUENCE: 294
ttactaaaac tttattttac tgg                                               23

SEQ ID NO: 295           moltype = DNA  length = 23
FEATURE                  Location/Qualifiers
misc_feature             1..23
                         note = Synthetic polynucleotide
misc_feature             1..23
                         note = Human Albumin Intron-1_T26
source                   1..23
                         mol_type = other DNA
                         organism = synthetic construct
SEQUENCE: 295
tgcatttgtt tcaaaatatt ggg                                               23

SEQ ID NO: 296           moltype = DNA  length = 23
FEATURE                  Location/Qualifiers
misc_feature             1..23
                         note = Synthetic polynucleotide
misc_feature             1..23
                         note = Human Albumin Intron-1_T27
source                   1..23
                         mol_type = other DNA
                         organism = synthetic construct
SEQUENCE: 296
tgggcaaggg aagaaaaaaa agg                                               23

SEQ ID NO: 297           moltype = DNA  length = 23
FEATURE                  Location/Qualifiers
misc_feature             1..23
                         note = Synthetic polynucleotide
misc_feature             1..23
                         note = Human Albumin Intron-1_T28
source                   1..23
                         mol_type = other DNA
                         organism = synthetic construct
SEQUENCE: 297
tcctaggtaa aaaaaaaaaa agg                                               23

SEQ ID NO: 298           moltype = DNA  length = 23
FEATURE                  Location/Qualifiers
misc_feature             1..23
                         note = Synthetic polynucleotide
misc_feature             1..23
                         note = Human Albumin Intron-1_T25
source                   1..23
                         mol_type = other DNA
                         organism = synthetic construct
SEQUENCE: 298
acctttttttt tttttacct agg                                               23

SEQ ID NO: 299           moltype = RNA  length = 20
FEATURE                  Location/Qualifiers
misc_feature             1..20
                         note = Synthetic polynucleotide
misc_feature             1..20
                         note = Exemplary gRNA spacer
source                   1..20
                         mol_type = other RNA
                         organism = synthetic construct
SEQUENCE: 299
taattttctt ttgcgcacta                                                   20

SEQ ID NO: 300           moltype = AA  length = 9
FEATURE                  Location/Qualifiers
REGION                   1..9
                         note = Synthetic polypeptide
REGION                   1..9
                         note = MISC_FEATURE - N-terminal sequence
source                   1..9
                         mol_type = protein
                         organism = synthetic construct
SEQUENCE: 300
DAHATRRYY                                                               9

SEQ ID NO: 301           moltype = DNA  length = 4402
FEATURE                  Location/Qualifiers
```

```
misc_feature          1..4402
                      note = Synthetic polynucleotide
misc_feature          1..4402
                      note = MAB8A
source                1..4402
                      mol_type = other DNA
                      organism = synthetic construct
SEQUENCE: 301
aattgctgac ctcttctctt cctcccacag tggccaccag aagatactac ctcggagccg  60
tcgaattgag ctgggattac atgcaatccg acctgggaga actgcccgtg gatgccaggt  120
ttcctcctcg ggtccccaag tccttcccgt tcaacacctc agtcgtctac aagaaaaccc  180
tcttcgtgga gttcaccgac catctgttca acatcgccaa gccaagaccc ccgtggatgg  240
gactcctcgg tccgaccatc caagccgaag tgtacgacac tgtggtcatt accctgaaga  300
acatggcctc ccatcctgtg tccctgcatg cagtgggcgt gtcctactgg aaggcttccg  360
aaggggccga gtacgacgat caaaccagcc agcgggaaaa ggaggatgac aaagtgttcc  420
cgggtggttc gcacacctac gtgtggcaag tgctcaagga gaacggtcct atggcctctg  480
atcccctgtg tctgacctac tcctacctgt cccatgtcga cctcgtgaag gatctgaaca  540
gcgggctgat tggcgccctg ctcgtgtgcc gggaaggctc cctggccaag gaaaagaccc  600
agacactgca caagttcatc ttgctgttcg ccgtgtttga tgagggaaag tcctggcata  660
gcgagactaa gaactccctt atgcaagacc gggatgctgc ctccgctagg gcttggccta  720
agatgcatac tgtgaacgga tacgtgaaca gatccctgcc tggccttatc ggttgccacc  780
ggaagtccgt gtattggcat gtgatcggca tgggaaccac tccagaggtg cactccattt  840
tcttggaggg gcataccttc ttggtgcgca accacagaca ggcctccctg gaaatttctc  900
cgatcacttt cctgactgcc cagaccctcc ttatggacct gggtcagttc ctgctgttct  960
gccacatttc gtcccaccaa cacgatggca tggaagccta cgtgaaagtg gactcgtgcc  1020
cggaagaacc acagctgcgg atgaagaaca acgaagaggc agaggactac gatgatgatc  1080
ttaccgattc ggaaatggat gtggtccgat tcgacgacga taatagccca tccttcatcc  1140
aaattaggag cgtggccaag aagcacccca aaacttgggt gcattacatt gcggccgagg  1200
aagaggattg ggactacgca cccctcgtgc ttgcacccga tgatcggtcc tacaagtccc  1260
aatacctgaa caacggcccg cagaggatcg gtcggaagta taagaaagtg cgcttcatgg  1320
cctacaccga cgagactttc aagaccagag aggccattca gcacgaaagc ggcattctgg  1380
ggccgctgtt gtacggggag gtcggagata cactgctcat cattttcaag aaccaggcgt  1440
ccagacccta caacatctac ccgcacggaa tcactgacgt ccgcccccctg tactcccgga  1500
gactcccgaa gggagtcaag cacttgaaag acttccccat cctgcctggg gaaatcttca  1560
agtacaagtg gaccgtgacc gtcgaggatg ggccgaccaa gtccgatcca agatgcctca  1620
ctagatacta ctcatccttc gtcaacatgg aacgggacct ggcctcagga ctgattggcc  1680
ccctgctcat ctgctacaag gagtccgtgg atcagcgcgg aaaccagatc atgtcggaca  1740
aacgcaacgt catcctcttc tccgtctttg acgagaaccg ctcatggtac cttacggaga  1800
acatccagcg gttcctcccc aaccctgccg gagtgcagct cgaggacccg gaattccagg  1860
catcaaacat tatgcactcc atcaacggtt acgtgttcga cagcctccag cttagcgtgt  1920
gcctccatga agtcgcatat tggtacatcc tgtccattgg agcacaaacc gactttctct  1980
ccgtgttctt ctccggatat accttcaagc acaagatggt gtacgaggat accctgaccc  2040
tcttcccctt ctccggagag actgtgttta tgtcgatgga aaacccaggc ctgtggattt  2100
tggggtgcca caactcggat ttccgaaacc ggggcatgac tgccttgctc aaggtgtcct  2160
cctgtgacaa gaacacggga gactactacg aggactccta cgaggatatt tccgcctacc  2220
tcctgtccaa gaacaacgcc atcgaaccca ggtccttcag ccagaaccct cctgtcctca  2280
agcgccatca gagagaaatc acccgcacga ccctgcagtc cgaccaggaa gagatcgatt  2340
acgacgacac tatctccgtc gaaatgaaga aggaggactt tgacatctac gacgaagatg  2400
aaaatcagtc ccctcgctcg ttccaaaaga aaacgagaca ctacttcatc gctgctgtgg  2460
agcggctctg ggactacggc atgtcctcat cgccccacgt gcttaggaac cgggctcaat  2520
ccgggagcgt ccctcagttc aagaaagtgg tgtttcaaga attcaccgat ggaagcttca  2580
cgcagccgtt gtacaggggc gaactgaacg agcaccttgg cctgctggga ccttacatca  2640
gagcagaggt cgaggacaac atcatggtga ccttccggaa ccaagcctcc cggccatatt  2700
cattctactc gagccttatc tcatacgagg aggatcagag acaggggggct gaacctcgga  2760
agaacttcgt caagccgaac gagacaaaga cctacttttg gaaggtgcag caccacatgg  2820
ccccgaccaa ggatgagttc gactgcaagg cctgggcgta cttctccgac gtggatctcg  2880
aaaaggacgt gcattccggg ctgatcggac cgctgctcgt ctgccacact aacaccctca  2940
atcctgctca cggcagacaa gtgaccgtgc aggagttcgc cctgttcttc accatcttcg  3000
acgaaactaa gtcatggtac tttaccgaga acatggagcg gaattgtcgg gccccatgta  3060
acatccagat ggaggacccg acattcaagg agaactaccg gttccacgcc attaacggat  3120
acattatgga cactcttccg ggactcgtga tggcacagga ccaacgcatc agatggtatc  3180
ttctgtcgat ggggagcaac gaaaacatcc attcgatcca ctttagcggt cacgtgttca  3240
cagtgcgcaa gaaggaagag tacaagatgg cgctgtacaa cctgtaccct ggggtgttcg  3300
agactgtgga aatgctgccg tccaaggccg gaatttggcg cgtggaatgt ctgatcggtg  3360
aacatctgca tgccggaatg tccaccctgt tcctggtgta ctccaacaag tgccaaaccc  3420
cactgggaat ggcatcagga cacattagag acttccagat taccgcgagc ggacagtacg  3480
gacaatgggc ccccaagttg gccaggctgc actactctgg aagcattaac gcctggagca  3540
ccaaggagcc gttcagctgg atcaaggtgg accttctggc gccaatgatc atccacggaa  3600
ttaagactca gggagcccgc cagaagttct catcgctcta catctcccag tttatcatca  3660
tgtactcact ggatgggaag aagtggcaga cttaccgggg aaattccacc ggtactctga  3720
tggtgttctt cggaaacgtg gacagctccg gcatcaagca caatatcttt aacccgccta  3780
tcatcgcccg atacatccgg ctccacccga ctcactactc catccggtcg actctgcgga  3840
tggaactcat gggttgcgac ctcaactcct gctcaatgcc actgggcatg gagtccaagg  3900
ctatctcgga cgctcagatt actgcatcgt cgtactttac caacatgttc gctacctggt  3960
ccccgtccaa agcccggctg catctccaag gcagatcaaa cgcgtggagg cctcaggtca  4020
acaacccgaa ggaatggctt caggtcgact tccaaaagac catgaaagtc accggagtga  4080
ccacccaggg cgtgaaatcg ctgctgacct ctatgtacgt gaaggaattc ctgatctcat  4140
caagccagga cggccaccag tggacactgt tcttccaaaa tggaaaggtc aaggtctttc  4200
agggaaatca agactccttc acccccgtgg tgaactccct ggacccccct ctgcttaccc  4260
```

```
gctacttgcg cattcatccg caatcctggg tgcaccagat cgccctgcga atggaagtgc  4320
tgggctgtga agcgcaggac ctgtactaaa ataaaagatc tttattttca ttagatctgt  4380
gtgttggttt tttgtgtgcc gc                                           4402

SEQ ID NO: 302         moltype =   length =
SEQUENCE: 302
000

SEQ ID NO: 303         moltype = DNA  length = 25
FEATURE                Location/Qualifiers
misc_feature           1..25
                       note = Synthetic polynucleotide
misc_feature           1..25
                       note = synthetic splice acceptor
source                 1..25
                       mol_type = other DNA
                       organism = synthetic construct
SEQUENCE: 303
ctgacctctt ctcttcctcc cacag                                        25

SEQ ID NO: 304         moltype = DNA  length = 32
FEATURE                Location/Qualifiers
misc_feature           1..32
                       note = Synthetic polynucleotide
misc_feature           1..32
                       note = native albumin intron 1/exon 2 splice acceptor, human
source                 1..32
                       mol_type = other DNA
                       organism = synthetic construct
SEQUENCE: 304
ttaacaatcc ttttttttct tcccttgccc ag                                32

SEQ ID NO: 305         moltype = DNA  length = 40
FEATURE                Location/Qualifiers
misc_feature           1..40
                       note = Synthetic polynucleotide
misc_feature           1..40
                       note = native albumin intron 1/exon 2 splice acceptor, mouse
source                 1..40
                       mol_type = other DNA
                       organism = synthetic construct
SEQUENCE: 305
ttaaatatgt tgtgtggttt ttctctccct gtttccacag                        40

SEQ ID NO: 306         moltype = DNA  length = 49
FEATURE                Location/Qualifiers
misc_feature           1..49
                       note = Synthetic polynucleotide
misc_feature           1..49
                       note = consensus synthetic poly A signal
source                 1..49
                       mol_type = other DNA
                       organism = synthetic construct
SEQUENCE: 306
aataaaagat ctttattttc attagatctg tgtgttggtt ttttgtgtg              49

SEQ ID NO: 307         moltype = DNA  length = 28
FEATURE                Location/Qualifiers
misc_feature           1..28
                       note = Synthetic polynucleotide
misc_feature           1..28
                       note = Native splice acceptor sequence from human Factor IX
                        gene intron 1/exon 2 boundary
source                 1..28
                       mol_type = other DNA
                       organism = synthetic construct
SEQUENCE: 307
actaaagaat tattctttta catttcag                                     28

SEQ ID NO: 308         moltype = DNA  length = 4502
FEATURE                Location/Qualifiers
misc_feature           1..4502
                       note = Synthetic polynucleotide
misc_feature           1..4502
                       note = MAB8B
source                 1..4502
                       mol_type = other DNA
                       organism = synthetic construct
SEQUENCE: 308
```

```
aattgaactt tgagtgtagc agagaggaac cattgccacc ttcagatttt aatgtctgac  60
ctcttctctt cctcccacag tggccaccag aagatactac ctcggagccg tcgaattgag  120
ctgggattac atgcaatccg acctgggaga actgcccgtg gatgccaggt ttcctcctcg  180
ggtccccaag tccttcccgt tcaacacctc agtcgtctac aagaaaaccc tcttcgtgga  240
gttcaccgac catctgttca acatcgccaa gccaagaccc ccgtggatgg gactcctcgg  300
tccgaccatc caagccgaag tgtacgacac tgtggtcatt accctgaaga acatggcctc  360
ccatcctgtg tccctgcatg cagtgggcgt gtcctactgg aaggcttccg aaggggccga  420
gtacgacgat caaaccagcc agcgggaaaa ggaggatgac aaagtgttcc cgggtggttc  480
gcacacctac gtgtggcaag tgctcaagga gaacggtcct atggcctctg atcccctgtg  540
tctgacctac tcctacctgt cccatgtcga cctcgtgaag gatctgaaca gcgggctgat  600
tggcgccctg ctcgtgtgcc gggaaggctc cctggccaag gaaaagaccc agacactgca  660
caagttcatc ttgctgttcg ccgtgtttga tgagggaaag tcctggcata gcgagactaa  720
gaactccctt atgcaagacc gggatgctgc ctccgctagg gcttggccta agatgcatac  780
tgtgaacgga tacgtgaaca gatccctgcc tggccttatc ggttgccacc ggaagtccgt  840
gtattggcat gtgatcggca tgggaaccac tccagaggtg cactccattt tcttggaggg  900
gcataccttc ttggtgcgca accacagaca ggcctccctg gaaatttctc cgatcacttt  960
cctgactgcc cagaccctcc ttatggacct gggtcagttc ctgctgttct gccacatttc  1020
gtcccaccaa cacgatggca tggaagccta cgtgaaagtg gactcgtgcc cggaagaacc  1080
acagctgcgg atgaagaaca acgaagaggc agaggactac gatgatgatc ttaccgattc  1140
ggaaatggat gtggtccgat tcgacgacga taatagccca tccttcatcc aaattaggag  1200
cgtggccaag aagcacccca aaacttgggt gcattacatt gcggccgagg aagaggattg  1260
ggactacgca cccctcgtgc ttgcacccga tgatcggtcc tacaagtccc aatacctgaa  1320
caacggcccg cagaggatcg gtcggaagta taagaaagtg cgcttcatgg cctacaccga  1380
cgagactttc aagaccagag aggccattca gcacgaaagc ggcattctgg ggccgctgtt  1440
gtacggggag gtcggagata cactgctcat catttcaag aaccaggcgt ccagacccta  1500
caacatctac ccgcacggaa tcactgacgt ccgccccctg tactcccgga gactcccgaa  1560
gggagtcaag cacttgaaag acttccccat cctgcctggg gaaatcttca agtacaagtg  1620
gaccgtgacc gtcgaggatg ggccgaccaa gtccgatcca agatgcctca ctagatacta  1680
ctcatccttc gtcaacatgg aacgggacct ggcctcagga ctgattggcc ccctgctcat  1740
ctgctacaag gagtccgtgg atcagcgcgg aaaccagatc atgtcggaca aacgcaacgt  1800
catcctcttc tccgtctttg acgagaaccg ctcatggtac cttacggaga acatccagcg  1860
gttcctcccc aaccctgccg gagtgcagct cgaggacccg gaattccagg catcaaacat  1920
tatgcactcc atcaacggtt acgtgttcga cagcctccag cttagcgtgt gcctccatga  1980
agtcgcatat tggtacatcc tgtccattgg agcacaaacc gactttctct ccgtgttctt  2040
ctccggatat accttcaagc acaagatggt gtacgaggat accctgaccc tcttcccctt  2100
ctccggagag actgtgttta tgtcgatgga aaacccaggc ctgtggattt tggggtgcca  2160
caactcggat ttccgaaacc ggggcatgac tgccttgctc aaggtgtcct cctgtgacaa  2220
gaacacggga gactactacg aggactccta cgaggatatt tccgcctacc tcctgtccaa  2280
gaacaacgcc atcgaaccca ggtccttcag ccagaaccct cctgtcctca agcgccatca  2340
gagagaaatc acccgcacga ccctgcagtc cgaccaggaa gagatcgatt acgacgacac  2400
tatctccgtc gaaatgaaga aggaggactt tgacatctac gacgaagatg aaaatcagtc  2460
ccctcgctcg ttccaaaaga aaacgagaca ctacttcatc gctgctgtgg agcggctctg  2520
ggactacggc atgtcctcat cgccccacgt gcttaggaac cggggctcaat ccgggagcgt  2580
ccctcagttc aagaaagtgg tgtttcaaga attcaccgat ggaagcttca cgcagccgtt  2640
gtacaggggc gaactgaacg agcaccttgg cctgctggga ccttacatca gagcagaggt  2700
cgaggacaac atcatggtga ccttccggaa ccaagcctcc cggccatatt cattctactc  2760
gagccttatc tcatacgagg aggatcagag acagggggct gaacctcgga agaacttcgt  2820
caagccgaac gagacaaaga cctacttttg gaaggtgcag caccacatgg ccccgaccaa  2880
ggatgagttc gactgcaagg cctgggcgta cttctccgac gtggatctcg aaaaggacgt  2940
gcattccggg ctgatcggac cgctgctcgt ctgccacact aacaccctca atcctgctca  3000
cggcagacaa gtgaccgtgc aggagttcgc cctgttcttc accatcttcg acgaaactaa  3060
gtcatggtac tttaccgaga acatggagcg gaattgtcgg gccccatgta acatccagat  3120
ggaggacccg acattcaagg agaactaccg gttccacgcc attaacggat acattatgga  3180
cactcttccg ggactcgtga tggcacagga ccaacgcatc agatggtatc ttctgtcgat  3240
ggggagcaac gaaaacatcc attcgatcca ctttagcggt cacgtgttca cagtgcgcaa  3300
gaaggaagag tacaagatgg cgctgtacaa cctgtaccct ggggtgttcg agactgtgga  3360
aatgctgccg tccaaggccg gaatttggcg cgtggaatgt ctgatcggtg aacatctgca  3420
tgccggaatg tccaccctgt tcctggtgta ctccaacaag tgccaaaccc cactgggaat  3480
ggcatcagga cacattagag acttccagat taccgcgagc ggacagtacg gacaatgggc  3540
ccccaagttg gccaggctgc actactctgg aagcattaac gcctggagca ccaaggagcc  3600
gttcagctgg atcaaggtgg accttctggc gccaatgatc atccacggaa ttaagactca  3660
gggagcccgc cagaagttct catcgctcta catctcccag tttatcatca tgtactcact  3720
ggatgggaag aagtggcaga cttaccgggg aaattccacc ggtactctga tggtgttctt  3780
cggaaacgtg gacagctccg gcatcaagca caatatcttt aacccgccta tcatcgcccg  3840
atacatccgg ctccacccga ctcactactc catccggtcg actctgcgga tggaactcat  3900
gggttgcgac ctcaactcct gctcaatgcc actgggcatg gagtccaagg ctatctcgga  3960
cgctcagatt actgcatcgt cgtactttac caacatgttc gctacctggt ccccgtccaa  4020
agcccggctg catctccaag gcagatcaaa cgcgtggagg cctcaggtca acaacccgaa  4080
ggaatggctt caggtcgact tccaaaagac catgaaagtc accggagtga ccacccaggg  4140
cgtgaaatcg ctgctgacct ctatgtacgt gaaggaattc ctgatctcat caagccagga  4200
cggccaccag tggacactgt tcttccaaaa tggaaaggtc aaggtctttc agggaaatca  4260
agactccttc acccccgtgg tgaactccct ggaccccccct ctgcttaccc gctacttgcg  4320
cattcatccg caatcctggg tgcaccagat cgccctgcga atggaagtgc tgggctgtga  4380
agcgcaggac ctgtactaaa ataaaagatc tttattttca ttagatctgt gtgttggttt  4440
tttgtgtgcg atcgggaact ggcatcttca gggagtagct taggtcagtg aagagaagcc  4500
gc                                                                4502
```

```
SEQ ID NO: 309          moltype = DNA  length = 4567
FEATURE                 Location/Qualifiers
```

```
misc_feature           1..4567
                       note = Synthetic polynucleotide
misc_feature           1..4567
                       note = MAB8C
source                 1..4567
                       mol_type = other DNA
                       organism = synthetic construct
SEQUENCE: 309
gcggcctaag gcaattgtgc cagttcccga tcgttacagg aactttgagt gtagcagaga  60
ggaaccattg ccaccttcag attttaatgt ctgacctctt ctcttcctcc cacagtggcc  120
accagaagat actacctcgg agccgtcgaa ttgagctggg attacatgca atccgacctg  180
ggagaactgc ccgtggatgc caggtttcct cctcgggtcc ccaagtcctt cccgttcaac  240
acctcagtcg tctacaagaa aaccctcttc gtggagttca ccgaccatct gttcaacatc  300
gccaagccaa gacccccgtg gatgggactc ctcggtccga ccatccaagc cgaagtgtac  360
gacactgtgg tcattaccct gaagaacatg gcctcccatc ctgtgtccct gcatgcagtg  420
ggcgtgtcct actggaaggc ttccgaaggg gccgagtacg acgatcaaac cagccagcgg  480
gaaaaggagg atgacaaagt gttcccgggt ggttcgcaca cctacgtgtg gcaagtgctc  540
aaggagaacg gtcctatggc ctctgatccc ctgtgtctga cctactccta cctgtcccat  600
gtcgacctcg tgaaggatct gaacagcggg ctgattggcg ccctgctcgt gtgccgggaa  660
ggctccctgg ccaaggaaaa gacccagaca ctgcacaagt tcatcttgct gttcgccgtg  720
tttgatgagg gaaagtcctg gcatagcgag actaagaact cccttatgca agaccgggat  780
gctgcctccg ctagggcttg gcctaagatg catactgtga acggatacgt gaacagatcc  840
ctgcctggcc ttatcggttg ccaccggaag tccgtgtatt ggcatgtgat cggcatggga  900
accactccag aggtgcactc cattttcttg gaggggcata ccttcttggt gcgcaaccac  960
agacaggcct ccctggaaat ttctccgatc actttcctga ctgcccagac cctccttatg  1020
gacctgggtc agttcctgct gttctgccac atttcgtccc accaacacga tggcatggaa  1080
gcctacgtga aagtggactc gtgcccggaa gaaccacagc tgcggatgaa gaacaacgaa  1140
gaggcagagg actacgatga tgatcttacc gattcggaaa tggatgtggt ccgattcgac  1200
gacgataata gcccatcctt catccaaatt aggagcgtgg ccaagaagca ccccaaaact  1260
tgggtgcatt acattgcggc cgaggaagag gattgggact acgcacccct cgtgcttgca  1320
cccgatgatc ggtcctacaa gtcccaatac ctgaacaacg gcccgcagag gatcggtcgg  1380
aagtataaga aagtgcgctt catggcctac accgacgaga ctttcaagac cagagaggcc  1440
attcagcacg aaagcggcat tctggggccg ctgttgtacg gggaggtcgg agatacactg  1500
ctcatcattt tcaagaacca ggcgtccaga ccctacaaca tctacccgca cggaatcact  1560
gacgtccgcc ccctgtactc ccggagactc ccgaagggag tcaagcactt gaaagacttc  1620
cccatcctgc ctggggaaat cttcaagtac aagtggaccg tgaccgtcga ggatgggccg  1680
accaagtccg atccaagatg cctcactaga tactactcat ccttcgtcaa catggaacgg  1740
gacctggcct caggactgat tggcccccctg ctcatctgct acaaggagtc cgtggatcag  1800
cgcggaaacc agatcatgtc ggacaaacgc aacgtcatcc tcttctccgt ctttgacgag  1860
aaccgctcat ggtaccttac ggagaacatc cagcggttcc tccccaaccc tgccggagtg  1920
cagctcgagg acccggaatt ccaggcatca aacattatgc actccatcaa cggttacgtg  1980
ttcgacagcc tccagcttag cgtgtgcctc catgaagtcg catattggta catcctgtcc  2040
attggagcac aaaccgactt tctctccgtg ttcttctccg gatatacctt caagcacaag  2100
atggtgtacg aggataccct gaccctcttc cccttctccg gagagactgt gtttatgtcg  2160
atggaaaacc caggcctgtg gattttgggg tgccacaact cggatttccg aaaccggggc  2220
atgactgcct tgctcaaggt gtcctcctgt gacaagaaca cgggagacta ctacgaggac  2280
tcctacgagg atatttccgc ctacctcctg tccaagaaca acgccatcga acccaggtcc  2340
ttcagccaga accctcctgt cctcaagcgc catcagagag aaatcacccg cacgaccctg  2400
cagtccgacc aggaagagat cgattacgac gacactatct ccgtcgaaat gaagaaggag  2460
gactttgaca tctacgacga agatgaaaat cagtcccctc gctcgttcca aaagaaaacg  2520
agacactact tcatcgctgc tgtggagcgg ctctgggact acggcatgtc ctcatcgccc  2580
cacgtgctta ggaaccgggc tcaatccggg agcgtccctc agttcaagaa agtggtgttt  2640
caagaattca ccgatggaag cttcacgcag ccgttgtaca ggggcgaact gaacgagcac  2700
cttggcctgc tgggacctta catcagagca gaggtcgagg acaacatcat ggtgaccttc  2760
cggaaccaag cctcccggcc atattcattc tactcgagcc ttatctcata cgaggaggat  2820
cagagacagg ggctgaaccc tcggaagaac ttcgtcaagc cgaacgagac aaagacctac  2880
ttttggaagg tgcagcacca catggccccg accaaggatg agttcgactg caaggcctgg  2940
gcgtacttct ccgacgtgga tctcgaaaag gacgtgcatt ccgggctgat cggaccgctg  3000
ctcgtctgcc acactaacac cctcaatcct gctcacggca gacaagtgac cgtgcaggag  3060
ttcgccctgt tcttcaccat cttcgacgaa actaagtcat ggtactttac cgagaacatg  3120
gagcggaatt gtcgggcccc atgtaacatc cagatggagg acccgacatt caaggagaac  3180
taccggttcc acgccattaa cggatacatt atggacactc ttccgggact cgtgatggca  3240
caggaccaac gcatcagatg gtatcttctg tcgatgggga gcaacgaaaa catccattcg  3300
atccacttta gcggtcacgt gttcacagtg cgcaagaagg aagagtacaa gatggcgctg  3360
tacaacctgt accctggggt gttcgagact gtggaaatgc tgccgtccaa ggccggaatt  3420
tggcgcgtgg aatgtctgat cggtgaacat ctgcatgccg gaatgtccac cctgttcctg  3480
gtgtactcca acaagtgcca aaccccactg ggaatggcat caggacacat tagagacttc  3540
cagattaccg cgagcggaca gtacggacaa tgggccccca agttggccag gctgcactac  3600
tctggaagca ttaacgcctg gagcaccaag gagccgttca gctggatcaa ggtggacctt  3660
ctggcgccaa tgatcatcca cggaattaag actcagggag cccgccagaa gttctcatcg  3720
ctctacatct cccagtttat catcatgtac tcactggatg ggaagaagtg gcagacttac  3780
cggggaaatt ccaccggtac tctgatggtg ttcttcggaa acgtggacag ctccggcatc  3840
aagcacaata tctttaaccc gcctatcatc gcccgataca tccggctcca cccgactcac  3900
tactccatcc ggtcgactct gcggatggaa ctcatgggtt gcgacctcaa ctcctgctca  3960
atgccactgg gcatggagtc caaggctatc tcggacgctc agattactgc atcgtcgtac  4020
tttaccaaca tgttcgctac ctggtccccg tccaaagccc ggctgcatct ccaaggcaga  4080
tcaaacgcgt ggaggcctca ggtcaacaac ccgaaggaat ggcttcaggt cgacttccaa  4140
aagaccatga aagtcaccgg agtgaccacc cagggcgtga aatcgctgct gacctctatg  4200
tacgtgaagg aattcctgat ctcatcaagc caggacggcc accagtggac actgttcttc  4260
```

```
caaaatggaa aggtcaaggt ctttcaggga aatcaagact ccttcacccc cgtggtgaac  4320
tccctggacc cccctctgct tacccgctac ttgcgcattc atccgcaatc ctgggtgcac  4380
cagatcgccc tgcgaatgga agtgctgggc tgtgaagcgc aggacctgta ctaaaataaa  4440
agatctttat tttcattaga tctgtgtgtt ggttttttgt gtgcgatcgg gaactggcat  4500
cttcagggag tagcttaggt cagtgaagag aagtgccagt tcccgatcgt tacaggccgc  4560
gggccgc                                                            4567

SEQ ID NO: 310          moltype = DNA  length = 4838
FEATURE                 Location/Qualifiers
misc_feature            1..4838
                        note = Synthetic polynucleotide
misc_feature            1..4838
                        note = pCB1009 (FVIII donor for integration intro
                         Transferrin intron 1)
source                  1..4838
                        mol_type = other DNA
                        organism = synthetic construct
SEQUENCE: 310
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcccgc gggagaacgc accactttac gaaggcggta  180
ctcctcaaag cgtactaaag aattattctt ttacatttca gggctgtgtc tggctgccac  240
caggagatac tacctggggg ctgtggagct gagctgggac tacatgcagt ctgacctggg  300
ggagctgcct gtggatgcca ggttcccccc cagagtgccc aagagcttcc ccttcaacac  360
ctctgtggtg tacaagaaga ccctgtttgt ggagttcact gaccacctgt tcaacattgc  420
caagcccagg ccccccctgga tgggcctgct gggccccacc atccaggctg aggtgtatga  480
cactgtggtg atcaccctga agaacatggc cagccaccct gtgagcctgc atgctgtggg  540
ggtgagctac tggaaggcct ctgagggggc tgagtatgat gaccagacca gccagaggga  600
gaaggaggat gacaaggtgt tccctggggg cagccacacc tatgtgtggc aggtgctgaa  660
ggagaatggc cccatggcct ctgacccccct gtgcctgacc tacagctacc tgagccatgt  720
ggacctggtg aaggacctga actctggcct gattggggcc ctgctggtgt gcagggaggg  780
cagcctggcc aaggagaaga cccagaccct gcacaagttc atcctgctgt ttgctgtgtt  840
tgatgagggc aagagctggc actctgaaac caagaacagc ctgatgcagg acagggatgc  900
tgcctctgcc agggcctggc ccaagatgca cactgtgaat ggctatgtga acaggagcct  960
gcctggcctg attggctgcc acaggaagtc tgtgtactgg catgtgattg gcatgggcac  1020
cacccctgag gtgcacagca tcttcctgga gggccacacc ttcctggtca ggaaccacag  1080
gcaggccagc ctggagatca gccccatcac cttcctgact gcccagaccc tgctgatgga  1140
cctgggccag ttcctgctgt tctgccacat cagcagccac cagcatgatg gcatggaggc  1200
ctatgtgaag gtggacagct gccctgagga gccccagctg aggatgaaga acaatgagga  1260
ggctgaggac tatgatgatg acctgactga ctctgagatg gatgtggtga ggtttgatga  1320
tgacaacagc cccagcttca tccagatcag gtctgtggcc aagaagcacc ccaagacctg  1380
ggtgcactac attgctgctg aggaggagga ctgggactat gccccccctgg tgctggcccc  1440
tgatgacagg agctacaaga gccagtacct gaacaatggc ccccagagga ttggcaggaa  1500
gtacaagaag gtcaggttca tggcctacac tgatgaaacc ttcaagacca gggaggccat  1560
ccagcatgag tctggcatcc tgggcccccct gctgtatggg gaggtggggg acaccctgct  1620
gatcatcttc aagaaccagg ccagcaggcc ctacaacatc tacccccatg gcatcactga  1680
tgtgaggccc ctgtacagca ggaggctgcc caagggggtg aagcacctga aggacttccc  1740
catcctgcct ggggagatct tcaagtacaa gtggactgtg actgtggagg atggccccac  1800
caagtctgac cccaggtgcc tgaccagata ctacagcagc tttgtgaaca tggagaggga  1860
cctggcctct ggcctgattg gccccctgct gatctgctac aaggagtctg tggaccagag  1920
gggcaaccag atcatgtctg acaagaggaa tgtgatcctg ttctctgtgt ttgatgagaa  1980
caggagctgg tacctgactg agaacatcca gaggttcctg cccaaccctg ctggggtgca  2040
gctggaggac cctgagttcc aggccagcaa catcatgcac agcatcaatg gctatgtgtt  2100
tgacagcctg cagctgtctg tgtgcctgca tgaggtggcc tactggtaca tcctgagcat  2160
tggggcccag actgacttcc tgtctgtgtt cttctctggc tacaccttca agcacaagat  2220
ggtgtatgag gacaccctga ccctgttccc cttctctggg gagactgtgt tcatgagcat  2280
ggagaaccct ggcctgtgga ttctgggctg ccacaactct gacttcagga acaggggcat  2340
gactgccctg ctgaaagtct ccagctgtga caagaacact ggggactact atgaggacag  2400
ctatgaggac atctctgcct acctgctgag caagaacaat gccattgagc ccaggagctt  2460
cagccagaat gccactaatg tgtctaacaa cagcaacacc agcaatgaca gcaatgtgtc  2520
tcccccagtg ctgaagaggc accagaggga gatcaccagg accaccctgc agtctgacca  2580
ggaggagatt gactatgatg acaccatctc tgtggagatg aagaaggagg actttgacat  2640
ctacgacgag gacgagaacc agagccccag gagcttccag aagaagacca ggcactactt  2700
cattgctgct gtggagaggc tgtgggacta tggcatgagc agcagccccc atgtgctgag  2760
gaacagggcc cagtctggct ctgtgcccca gttcaagaag gtggtgttcc aggagttcac  2820
tgatggcagc ttcacccagc ccctgtacag aggggagctg aatgagcacc tgggcctgct  2880
gggcccctac atcagggctg aggtggagga caacatcatg gtgaccttca ggaaccaggc  2940
cagcaggccc tacagcttct acagcagcct gatcagctat gaggaggacc agaggcaggg  3000
ggctgaagcc aggaagaact ttgtgaagcc caatgaaacc aagacctact tctggaaggt  3060
gcagcaccac atggccccca ccaaggatga gtttgactgc aaggcctggg cctacttctc  3120
tgatgtggac ctggagaagg atgtgcactc tggcctgatt ggccccctgc tggtgtgcca  3180
caccaacacc ctgaaccctg cccatggcag gcaggtgact gtgcaggagt ttgccctgtt  3240
cttcaccatc tttgatgaaa ccaagagctg gtacttcact gagaacatgg agaggaactg  3300
cagggccccc tgcaacatcc agatggagga ccccaccttc aaggagaact acaggttcca  3360
tgccatcaat ggctacatca tggacaccct gcctggcctg gtgatggccc aggaccagag  3420
gatcaggtgg tacctgctga gcatgggcag caatgagaac atccacagca tccacttctc  3480
tggccatgtg ttcactgtga ggaagaagga ggagtacaag atggccctgt acaacctgta  3540
ccctggggtg tttgagactg tggagatgct gcccagcaag gctggcatct ggagggtgga  3600
gtgcctgatt ggggagcacc tgcatgctgg catgagcacc ctgttcctgg tgtacagcaa  3660
```

```
caagtgccag accccccctgg gcatggcctc tggccacatc agggacttcc agatcactgc  3720
ctctggccag tatggccagt gggcccccaa gctggccagg ctgcactact ctggcagcat  3780
caatgcctgg agcaccaagg agcccttcag ctggatcaag gtggacctgc tggcccccat  3840
gatcatccat ggcatcaaga cccagggggc caggcagaag ttcagcagcc tgtacatcag  3900
ccagttcatc atcatgtaca gcctggatgg caagaagtgg cagacctaca ggggcaacag  3960
cactggcacc ctgatggtgt tctttggcaa tgtggacagc tctggcatca agcacaacat  4020
cttcaacccc cccatcattg ccagatacat caggctgcac cccacccact acagcatcag  4080
gagcaccctg aggatggagc tgatgggctg tgacctgaac agctgcagca tgcccctggg  4140
catggagagc aaggccatct ctgatgccca gatcactgcc agcagctact tcaccaacat  4200
gtttgccacc tggagcccca gcaaggccag gctgcacctg cagggcagga gcaatgcctg  4260
gaggccccag gtcaacaacc ccaaggagtg gctgcaggtg gacttccaga agaccatgaa  4320
ggtgactggg gtgaccaccc agggggtgaa gagcctgctg accagcatgt atgtgaagga  4380
gttcctgatc agcagcagcc aggatggcca ccagtggacc ctgttcttcc agaatggcaa  4440
ggtgaaggtg ttccagggca accaggacag cttcacccct gtggtgaaca gcctggaccc  4500
cccccctgctg accagatacc tgaggattca cccccagagc tgggtgcacc agattgccct  4560
gaggatggag gtgctgggct gtgaggccca ggacctgtac tgatcgcgaa taaaagatct  4620
ttattttcat tagatctgtg tgttggtttt ttgtgtggag aacgcaccac tttacgaagg  4680
caattgcctt aggccgcagg aacccctagt gatggagttg gccactccct ctctgcgcgc  4740
tcgctcgctc actgaggccg ggcgaccaaa ggtcgcccga cgcccgggct ttgcccgggc  4800
ggcctcagtg agcgagcgag cgcgcagctg cctgcagg                         4838
```

```
SEQ ID NO: 311         moltype = DNA  length = 4830
FEATURE                Location/Qualifiers
misc_feature           1..4830
                       note = Synthetic polynucleotide
misc_feature           1..4830
                       note = pCB099 (FVIII donor for integration into albumin
                        intron 1)
source                 1..4830
                       mol_type = other DNA
                       organism = synthetic construct
SEQUENCE: 311
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcctaa ggcaattgcc tgtaacgatc gggaactggc  180
agatccacac aaaaaaccaa cacacagatc taatgaaaat aaagatcttt tattcgcgat  240
cagtacaggt cctgggcctc acagcccagc acctccatcc tcagggcaat ctggtgcacc  300
cagctctggg ggtgaatcct caggtatctg gtcagcaggg gggggtccag gctgttcacc  360
acaggggtga agctgtcctg gttgccctgg aacaccttca ccttgccatt ctggaagaac  420
agggtccact ggtggccatc ctggctgctg ctgatcagga actccttcac atacatgctg  480
gtcagcaggc tcttcacccc ctgggtggtc accccagtca ccttcatggt cttctggaag  540
tccacctgca gccactcctt ggggttgttg acctggggcc tccaggcatt gctcctgccc  600
tgcaggtgca gcctggcctt gctggggctc caggtggcaa acatgttggt gaagtagctg  660
ctggcagtga tctgggcatc agagatggcc ttgctctcca tgcccagggg catgctgcag  720
ctgttcaggt cacagcccat cagctccatc ctcagggtgc tcctgatgct gtagtgggtg  780
gggtgcagcc tgatgtatct ggcaatgatg gggggttga agatgttgtg cttgatgcca  840
gagctgtcca cattgccaaa gaacaccatc agggtgccag tgctgttgcc cctgtaggtc  900
tgccacttct tgccatccag gctgtacatg atgatgaact ggctgatgta caggctgctg  960
aacttctgcc tggcccccctg ggtcttgatg ccatggatga tcatgggggc cagcaggtcc  1020
accttgatcc agctgaaggg ctccttggtg ctccaggcat tgatgctgcc agagtagtgc  1080
agcctggcca gcttgggggc ccactggcca tactggccag aggcagtgat ctggaagtcc  1140
ctgatgtggc cagaggccat gcccaggggg gtctggcact tgttgctgta caccaggaac  1200
agggtgctca tgccagcatg caggtgctcc ccaatcaggc actccaccct ccagatgcca  1260
gccttgctgg gcagcatctc cacagtctca aacaccccag ggtacaggtt gtacagggcc  1320
atcttgtact cctccttctt cctcacagtg aacacatggc cagagaagtg gatgctgtgg  1380
atgttctcat tgctgcccat gctcagcagg taccacctga tcctctggtc ctgggccatc  1440
accaggccag gcagggtgtc catgatgtag ccattgatgg catggaacct gtagttctcc  1500
ttgaaggtgg ggtcctccat ctggatgttg cagggggccc tgcagttcct ctccatgttc  1560
tcagtgaagt accagctctt ggtttcatca aagatggtga agaacagggc aaactcctgc  1620
acagtcacct gcctgccatg ggcagggttc agggtgttgg tgtggcacac cagcaggggg  1680
ccaatcaggc cagagtgcac atccttctcc aggtccacat cagagaagta ggcccaggcc  1740
ttgcagtcaa actcatcctt ggtgggggcc atgtggtgct gcaccttcca gaagtaggtc  1800
ttggtttcat tgggcttcac aaagttcttc ctgggctcag ccccctgcct ctggtcctcc  1860
tcatagctga tcaggctgct gtagaagctg tagggcctgc tggcctggtt cctgaaggtc  1920
accatgatgt tgtcctccac ctcagccctg atgtaggggc ccagcaggcc caggtgctca  1980
ttcagctccc ctctgtacag ggctgggtg aagctgccat cagtgaactc ctggaacacc  2040
accttcttga actggggcac agagccagac tgggccctgt tcctcagcac atgggggctg  2100
ctgctcatgc catagtccca cagcctctcc acagcagcaa tgaagtagtg cctggtcttc  2160
ttctggaagc tcctggggct ctggttctcg tcctcgtcgt agatgtcaaa gtcctccttc  2220
ttcatctcca cagagatggt gtcatcatag tcaatctcct cctggtcaga ctgcagggtg  2280
gtcctggtga tctccctctg gtgcctcttc agcactgggg gagacacatt gctgtcattg  2340
ctggtgttgc tgttgttaga cacattagtg gcattctggc tgaagctcct gggctcaatg  2400
gcattgttct tgctcagcag gtaggcagag atgtcctcat agctgtcctc atagtagtcc  2460
ccagtgttct tgtcacagct ggagactttc agcagggcag tcatgcccct gttcctgaag  2520
tcagagttgt ggcagcccag aatccacagg ccagggttct ccatgctcat gaacacagtc  2580
tccccagaga aggggaacag ggtcagggtg tcctcataca ccatcttgtg cttgaaggtg  2640
tagccagaga agaacacaga caggaagtca gtctgggccc caatgctcag gatgtaccag  2700
taggccacct catgcaggca cacagacagc tgcaggctgt caaacacata gccattgatg  2760
ctgtgcatga tgttgctggc ctggaactca gggtcctcca gctgcacccc agcagggttg  2820
```

```
ggcaggaacc tctggatgtt ctcagtcagg taccagctcc tgttctcatc aaacacagag  2880
aacaggatca cattcctctt gtcagacatg atctggttgc cctctggtc cacagactcc  2940
ttgtagcaga tcagcagggg gccaatcagg ccagaggcca ggtccctctc catgttcaca  3000
aagctgctgt agtatctggt caggcacctg ggtcagact tggtggggcc atcctccaca  3060
gtcacagtcc acttgtactt gaagatctcc ccaggcagga tggggaagtc cttcaggtgc  3120
ttcacccccct tgggcagcct cctgctgtac aggggcctca catcagtgat gccatggggg  3180
tagatgttgt agggcctgct ggcctggttc ttgaagatga tcagcagggt gtcccccacc  3240
tccccataca gcagggggcc caggatgcca gactcatgct ggatggcctc cctggtcttg  3300
aaggtttcat cagtgtaggc catgaacctg accttcttgt acttcctgcc aatcctctgg  3360
gggccattgt tcaggtactg gctcttgtag ctcctgtcat caggggccag caccaggggg  3420
gcatagtccc agtcctcctc ctcagcagca atgtagtgca cccaggtctt ggggtgcttc  3480
ttggccacag acctgatctg gatgaagctg gggctgttgt catcatcaaa cctcaccaca  3540
tccatctcag agtcagtcag gtcatcatca tagtcctcag cctcctcatt gttcttcatc  3600
ctcagctggg gctcctcagg gcagctgtcc accttcacat aggcctccat gccatcatgc  3660
tggtggctgc tgatgtggca gaacagcagg aactggccca ggtccatcag cagggtctgg  3720
gcagtcagga aggtgatggg gctgatctcc aggctggcct gcctgtggtt cctgaccagg  3780
aaggtgtggc cctccaggaa gatgctgtgc acctcagggg tggtgcccat gccaatcaca  3840
tgccagtaca cagacttcct gtggcagcca atcaggccag gcaggctcct gttcacatag  3900
ccattcacag tgtgcatctt gggccaggcc ctggcagagg cagcatccct gtcctgcatc  3960
aggctgttct tggtttcaga gtgccagctc ttgccctcat caaacacagc aaacagcagg  4020
atgaacttgt gcagggtctg ggtcttctcc ttggccaggc tgccctccct gcacaccagc  4080
agggccccaa tcaggccaga gttcaggtcc ttcaccaggt ccacatggct caggtagctg  4140
taggtcaggc acagggggtc agaggccatg gggccattct ccttcagcac ctgccacaca  4200
taggtgtggc tgcccccagg gaacaccttg tcatcctcct tctccctctg gctggtctgg  4260
tcatcatact cagccccctc agaggccttc cagtagctca cccccacagc atgcaggctc  4320
acagggtggc tggccatgtt cttcagggtg atcaccacag tgtcatacac ctcagcctgg  4380
atggtggggc ccagcaggcc catccagggg ggcctgggct tggcaatgtt gaacaggtgg  4440
tcagtgaact ccacaaacag ggtcttcttg tacaccacag aggtgttgaa ggggaagctc  4500
ttgggcactc tgggggggaa cctggcatcc acaggcagct cccccaggtc agactgcatg  4560
tagtcccagc tcagctccac agcccccagg tagtatctcc tggtggccac tgaaatgtaa  4620
aagaataatt ctttagtacg ctttgaggag taccgcctgt aacgatcggg aactggcacc  4680
gcgggccgca ggaacccta gtgatggagt tggccactcc ctctctgcgc gctcgctcgc  4740
tcactgaggc cgggcgacca aaggtcgccc gacgcccggg ctttgcccgg gcggcctcag  4800
tgagcgagcg agcgcgcagc tgcctgcagg                                  4830
```

SEQ ID NO: 312 moltype = length =
SEQUENCE: 312
000

SEQ ID NO: 313 moltype = length =
SEQUENCE: 313
000

SEQ ID NO: 314 moltype = length =
SEQUENCE: 314
000

SEQ ID NO: 315 moltype = AA length = 9
FEATURE Location/Qualifiers
REGION 1..9
note = Synthetic polypeptide
REGION 1..9
note = MISC_FEATURE - Structural classification for homing endonuclease (HE)
source 1..9
mol_type = protein
organism = synthetic construct
SEQUENCE: 315
LAGLIDADG 9

SEQ ID NO: 316 moltype = DNA length = 4488
FEATURE Location/Qualifiers
misc_feature 1..4488
note = Synthetic polynucleotide
misc_feature 1..4488
note = pCB076
source 1..4488
mol_type = other DNA
organism = synthetic construct
SEQUENCE: 316

```
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga ccccctgtgc ctgacctaca  540
```

```
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag ggggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagca  2340
atgacagcaa tgtgtctccc ccagtgctga agaggcacca gagggagatc accaggacca  2400
ccctgcagtc tgaccaggag gagattgact atgatgacac catctctgtg gagatgaaga  2460
aggaggactt tgacatctac gacgaggacg agaaccagag ccccaggagc ttccagaaga  2520
agaccaggca ctacttcatt gctgctgtgg agaggctgtg ggactatggc atgagcagca  2580
gcccccatgt gctgaggaac agggcccagt ctggctctgt gccccagttc aagaaggtgg  2640
tgttccagga gttcactgat ggcagcttca cccagcccct gtacagaggg gagctgaatg  2700
agcacctggg cctgctgggc ccctacatca gggctgaggt ggaggacaac atcatggtga  2760
ccttcaggaa ccaggccagc aggccctaca gcttctacag cagcctgatc agctatgagg  2820
aggaccagag gcaggggggct gagcccagga agaactttgt gaagcccaat gaaaccaaga  2880
cctacttctg gaaggtgcag caccacatgg cccccaccaa ggatgagttt gactgcaagg  2940
cctgggccta cttctctgat gtggacctgg agaaggatgt gcactctggc ctgattggcc  3000
ccctgctggt gtgccacacc aacaccctga accctgccca tggcaggcag gtgactgtgc  3060
aggagtttgc cctgttcttc accatctttg atgaaaccaa gagctggtac ttcactgaga  3120
acatggagag gaactgcagg gccccctgca acatccagat ggaggacccc accttcaagg  3180
agaactacag gttccatgcc atcaatggct acatcatgga caccctgcct ggcctggtga  3240
tggcccagga ccagaggatc aggtggtacc tgctgagcat gggcagcaat gagaacatcc  3300
acagcatcca cttctctggc catgtgttca ctgtgaggaa gaaggaggag tacaagatgg  3360
ccctgtacaa cctgtaccct ggggtgtttg agactgtgga gatgctgccc agcaaggctg  3420
gcatctggag ggtggagtgc ctgattgggg agcacctgca tgctggcatg agcaccctgt  3480
tcctggtgta cagcaacaag tgccagaccc ccctgggcat ggcctctggc cacatcaggg  3540
acttccagat cactgcctct ggccagtatg gccagtgggc cccccaagctg gccaggctgc  3600
actactctgg cagcatcaat gcctggagca ccaaggagcc cttcagctgg atcaaggtgg  3660
acctgctggc ccccatgatc atccatggca tcaagaccca gggggccagg cagaagttca  3720
gcagcctgta catcagccag ttcatcatca tgtacagcct ggatggcaag aagtggcaga  3780
cctacagggg caacagcact ggcaccctga tggtgttctt tggcaatgtg gacagctctg  3840
gcatcaagca caacatcttc aacccccccca tcattgccag atacatcagg ctgcacccca  3900
cccactacag catcaggagc accctgagga tggagctgat gggctgtgac ctgaacagct  3960
gcagcatgcc cctgggcatg gagagcaagg ccatctctga tgcccagatc actgccagca  4020
gctacttcac caacatgttt gccacctgga gccccagcaa ggccaggctg cacctgcagg  4080
gcaggagcaa tgcctggagg ccccaggtca acaaccccaa ggagtggctg caggtggact  4140
tccagaagac catgaaggtg actggggtga ccacccaggg ggtgaagagc ctgctgacca  4200
gcatgtatgt gaaggagttc ctgatcagca gcagccagga tggccaccag tggaccctgt  4260
tcttccagaa tggcaaggtg aaggtgttcc agggcaacca ggacagcttc accccctgtgg  4320
tgaacagcct ggacccccccc ctgctgacca gatacctgag gattcacccc cagagctggg  4380
tgcaccagat tgccctgagg atggaggtgc tgggctgtga ggcccaggac ctgtactgaa  4440
ataaaagatc tttattttca ttagatctgt gtgttggttt tttgtgtg              4488
```

SEQ ID NO: 317 moltype = DNA length = 4493
FEATURE Location/Qualifiers
misc_feature 1..4493
note = Synthetic polynucleotide
misc_feature 1..4493
note = pCB077
source 1..4493
mol_type = other DNA
organism = synthetic construct
SEQUENCE: 317

```
tgccagttcc cgatcgttac aggcggtact cctcaaagcg tactaaagaa ttattctttt  60
acatttcagt ggccaccagg agatactacc tgggggctgt ggagctgagc tgggactaca  120
```

```
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc ccccaccatcc 300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga cccccctgtgc ctgacctaca 540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg ccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggggtgaagc 1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagca  2340
atgacagcaa tgtgtctccc ccagtgctga agaggcacca gagggagatc accaggacca  2400
ccctgcagtc tgaccaggag gagattgact atgatgacac catctctgtg gagatgaaga  2460
aggaggactt tgacatctac gacgaggacg agaaccagag ccccaggagc ttccagaaga  2520
agaccaggca ctacttcatt gctgctgtgg agaggctgtg ggactatggc atgagcagca  2580
gcccccatgt gctgaggaac agggcccagt ctggctctgt gccccagttc aagaaggtgg  2640
tgttccagga gttcactgat ggcagcttca cccagcccct gtacagaggg gagctgaatg  2700
agcacctggg cctgctgggc ccctacatca gggctgaggt ggaggacaac atcatggtga  2760
ccttcaggaa ccaggccagc aggccctaca gcttctacag cagcctgatc agctatgagg  2820
aggaccagag gcagggggct gagcccagga agaactttgt gaagcccaat gaaaccaaga  2880
cctacttctg gaaggtgcag caccacatgg cccccaccaa ggatgagttt gactgcaagg  2940
cctgggccta cttctctgat gtggacctgg agaaggatgt gcactctggc ctgattggcc  3000
ccctgctggt gtgccacacc aacaccctga accctgccca tggcaggcag gtgactgtgc  3060
aggagtttgc cctgttcttc accatctttg atgaaaccaa gagctggtac ttcactgaga  3120
acatggagag gaactgcagg gccccctgca acatccagat ggaggacccc accttcaagg  3180
agaactacag gttccatgcc atcaatggct acatcatgga caccctgcct ggcctggtga  3240
tggcccagga ccagaggatc aggtggtacc tgctgagcat gggcagcaat gagaacatcc  3300
acagcatcca cttctctggc catgtgttca ctgtgaggaa gaaggaggag tacaagatgg  3360
ccctgtacaa cctgtaccct ggggtgtttg agactgtgga gatgctgccc agcaaggctg  3420
gcatctggag ggtggagtgc ctgattgggg agcacctgca tgctggcatg agcaccctgt  3480
tcctggtgta cagcaacaag tgccagaccc ccctgggcat ggcctctggc cacatcaggg  3540
acttccagat cactgcctct ggccagtatg gccagtgggc ccccaagctg gccaggctgc  3600
actactctgg cagcatcaat gcctggagca ccaaggagcc cttcagctgg atcaaggtgg  3660
acctgctggc ccccatgatc atccatggca tcaagaccca gggggccagg cagaagttca  3720
gcagcctgta catcagccag ttcatcatca tgtacagcct ggatggcaag aagtggcaga  3780
cctacagggg caacagcact ggcaccctga tggtgttctt tggcaatgtg gacagctctg  3840
gcatcaagca caacatcttc aacccccccca tcattgccag atacatcagg ctgcacccca 3900
cccactacag catcaggagc accctgagga tggagctgat gggctgtgac ctgaacagct  3960
gcagcatgcc cctgggcatg gagagcaagg ccatctctga tgcccagatc actgccagca  4020
gctacttcac caacatgttt gccacctgga gccccagcaa ggccaggctg cacctgcagg  4080
gcaggagcaa tgcctggagg ccccaggtca acaaccccaa ggagtggctg caggtggact  4140
tccagaagac catgaaggtg actggggtga ccacccaggg ggtgaagagc ctgctgacca  4200
gcatgtatgt gaaggagttc ctgatcagca gcagccagga tggccaccag tggaccctgt  4260
tcttccagaa tggcaaggtg aaggtgttcc agggcaacca ggacagcttc acccctgtgg  4320
tgaacagcct ggacccccccc ctgctgacca gatacctgag gattcacccc cagagctggg 4380
tgcaccagat tgccctgagg atggaggtgc tgggctgtga ggcccaggac ctgtactgat  4440
cgcgaataaa agatctttat tttcattaga tctgtgtgtt ggttttttgt gtg         4493
```

```
SEQ ID NO: 318          moltype = DNA  length = 4437
FEATURE                 Location/Qualifiers
misc_feature            1..4437
                        note = Synthetic polynucleotide
misc_feature            1..4437
```

```
                        note = pCB080
source                  1..4437
                        mol_type = other DNA
                        organism = synthetic construct
SEQUENCE: 318
tgccagttcc cgatcgttac aggcggtact cctcaaagcg tactaaagaa ttattctttt  60
acatttcagt ggccaccaga aggtactacc tgggagctgt ggaactgagc tgggactaca  120
tgcagtctga cctgggagag ctgcctgtgg atgctagatt tcctccaaga gtgcccaaga  180
gcttcccctt caacacctct gtggtgtaca agaaaaccct gtttgtggaa ttcacagacc  240
acctgttcaa tattgccaag cctagacctc cttggatggg cctgctgggc cctacaattc  300
aggctgaggt gtatgacaca gtggtcatca ccctgaagaa catggccagc catcctgtgt  360
ctctgcatgc tgtgggagtg tcttactgga aggcttctga gggggctgag tatgatgacc  420
agacaagcca gagagagaaa gaggatgaca aggttttccc tgggggcagc cacacctatg  480
tctggcaggt cctgaaagaa aatggcccta tggcctctga tcctctgtgc ctgacataca  540
gctacctgag ccatgtggac ctggtcaagg acctgaactc tggcctgatt ggggctctgc  600
tggtgtgtag agaaggcagc ctggccaaag aaaagaccca gacactgcac aagttcatcc  660
tgctgtttgc tgtgtttgat gagggcaaga gctggcactc tgagacaaag aacagcctga  720
tgcaggacag agatgctgcc tctgctagag cttggcccaa gatgcacaca gtgaatggct  780
atgtgaacag aagcctgcct ggactgattg gatgccacag aaagtctgtg tactggcatg  840
tgattggcat gggcaccaca cctgaggtgc acagcatctt tctggaagga cacaccttcc  900
tggtgaggaa ccacagacag gccagcctgg aaatcagccc tatcaccttc ctgacagctc  960
agaccctgct gatggatctg ggccagtttc tgctgttctg ccacatcagc agccaccagc  1020
atgatggcat ggaagcctat gtgaaggtgg acagctgccc tgaagaaccc cagctgagaa  1080
tgaagaacaa tgaggaagct gaggactatg atgatgacct gacagactct gagatggatg  1140
tggtcagatt tgatgatgat aacagcccca gcttcatcca gatcagatct gtggccaaga  1200
agcaccccaa gacctgggtg cactatattg ctgctgagga agaggactgg gattatgctc  1260
ctctggtgct ggcccctgat gacagaagct acaagagcca gtacctgaac aatggccctc  1320
agagaattgg caggaagtat aagaaagtga ggttcatggc ctacacagat gagacattca  1380
agaccagaga ggctatccag catgagtctg gcattctggg acctctgctg tatggggaag  1440
tgggggacac actgctgatc atcttcaaga accaggccag cagaccctac aacatctacc  1500
ctcatggcat cacagatgtg aggcctctgt actctagaag gctgcccaag gggggtgaagc  1560
acctgaagga cttccctatc ctgcctgggg agatcttcaa gtacaagtgg acagtgacag  1620
tggaggatgg ccctaccaag tctgatccta gatgcctgac aaggtactac agcagctttg  1680
tgaacatgga aagggacctg gcctctggcc tgattggtcc tctgctgatc tgctacaaag  1740
aatctgtgga ccagaggggc aaccagatca tgagtgacaa gagaaatgtg atcctgttct  1800
ctgtctttga tgagaacagg tcctggtatc tgacagagaa catccagagg tttctgccca  1860
atcctgctgg ggtgcagctg gaagatcctg agttccaggc ctccaacatc atgcactcca  1920
tcaatggcta tgtgtttgac agcctgcagc tgtctgtgtg cctgcatgaa gtggcctact  1980
ggtacatcct gtctattggg gcccagacag acttcctgtc tgtgttcttt tctggctaca  2040
ccttcaagca caagatggtg tatgaggata ccctgacact gttcccattc tctgggggaga  2100
cagtgttcat gagcatggaa aaccctggcc tgtggatcct gggctgtcac aacagtgact  2160
tcagaaacag aggcatgaca gccctgctga aggtgtccag ctgtgacaag aacactgggg  2220
actactatga ggactcttat gaggacatct ctgcctacct gctgagcaag aacaatgcca  2280
ttgagcctag gagcttctct cagaaccctc ctgtgctgaa gagacaccag agggagatca  2340
ccagaaccac actgcagtct gaccaagagg aaattgatta tgatgacacc atctctgtgg  2400
agatgaagaa agaagatttt gacatctatg atgaggatga gaatcagagc cccagatctt  2460
tccagaagaa aacaaggcac tacttcattg ctgctgtgga aagactgtgg gactatggca  2520
tgagcagcag cccccatgtg ctgagaaaca gggcccagtc tggaagtgtg ccccagttca  2580
agaaagtggt gttccaagag ttcacagatg gcagcttcac ccagcctctg tatagagggg  2640
agctgaatga gcacctggga ctgctgggac cttacatcag agctgaggtg gaggataaca  2700
tcatggtcac ctttagaaac caggcctcta ggccctactc cttctacagc tccctgatca  2760
gctatgaaga ggaccagaga caggggggctg agcccagaaa gaactttgtg aagcccaatg  2820
agactaagac ctacttttgg aaggtgcagc accacatggc cctacaaag gatgagtttg  2880
actgcaaggc ctgggcctac ttctctgatg tggacctgga gaaggatgtg cactctggac  2940
tcattggacc cctgcttgtg tgccacacca acacactgaa tcctgctcat ggcaggcaag  3000
tgacagtgca agagtttgcc ctgttcttca ccatctttga tgagacaaag tcctggtact  3060
tcacagaaaa catggaaaga aactgcaggg ccccttgcaa catccagatg gaagatccca  3120
ccttcaaaga gaactacagg ttccatgcca tcaatggcta catcatggac actctgcctg  3180
gcctggttat ggcacaggat cagaggatca gatggtatct gctgtccatg ggctccaatg  3240
agaatatcca cagcatccac ttctctggcc atgtgttcac agtgaggaaa aaagaagagt  3300
acaagatggc cctgtacaat ctgtaccctg ggtgtgttga gactgtggaa atgctgccta  3360
gcaaggctgg aatctggagg gtggaatgtc tgattggaga gcatctgcat gctggaatgt  3420
ctaccctgtt cctggtgtac agcaacaagt gtcagacccc tctgggcatg gcctctggac  3480
acatcagaga cttccagatc acagcctctg gccagtatgg acagtgggct cctaaactgg  3540
ctagactgca ctactctggc agcatcaatg cctggtccac caaagagccc ttcagctgga  3600
tcaaggtgga cctgctggct cccatgatca tccatggaat caagacccag gggccagac  3660
agaagttcag cagcctgtac atcagccagt tcatcatcat gtacagcctg gatggcaaga  3720
agtggcagac ctacagaggc aacagcacag gcacactcat ggtgttcttt ggcaatgtgg  3780
actcttctgg cattaagcac aacatcttca accctccaat cattgccagg tacatcaggc  3840
tgcaccccac acactacagc atcagatcta ccctgaggat ggaactgatg ggctgtgacc  3900
tgaacagctg ctctatgccc ctgggaatgg aaagcaaggc catctctgat gcccagatca  3960
cagccagcag ctacttcacc aacatgtttg ccacatggtc cccatctaag gccaggctgc  4020
atctgcaggg cagatctaat gcttggaggc cccaagtgaa caaccccaaa gagtggctgc  4080
aggtggactt tcagaaaacc atgaaagtga caggagtgac cacacagggg gtcaagtctc  4140
tgctgacctc tatgtatgtg aaagagttcc tgatctccag cagccaggat ggccaccagt  4200
ggaccctgtt tttccagaat ggcaaagtca aggtgttcca gggaaaccag gacagcttca  4260
cacctgtggt caactccctg gatcctccac tgctgaccag atacctgaga attcaccctc  4320
agtcttgggt gcaccagatt gctctgagaa tggaagtgct gggatgtgaa gctcaggacc  4380
tctactaaaa taaaagatct ttattttcat tagatctgtg tgttggtttt ttgtgtg     4437
```

```
SEQ ID NO: 319          moltype = DNA  length = 4437
FEATURE                 Location/Qualifiers
misc_feature            1..4437
                        note = Synthetic polynucleotide
misc_feature            1..4437
                        note = pCB085
source                  1..4437
                        mol_type = other DNA
                        organism = synthetic construct
SEQUENCE: 319
tgccagttcc cgatcgttac aggcggtact cctcaaagcg tactaaagaa ttattctttt  60
acatttcagt ggccaccaga aggtactacc taggagccgt ggaactgagc tgggactaca  120
tgcagtctga cctgggagag ctgcccgtgg acgctagatt tcctccaaga gtgcccaaga  180
gcttcccctt caacacctcc gtggtgtaca agaaaaccct gttcgtggaa ttcaccgacc  240
acctgttcaa tatcgccaag cctagacctc cttggatggg cctgctgggc cctacaattc  300
aggccgaggt gtacgacacc gtggtcatca ccctgaagaa catggccagc catcctgtgt  360
ctctgcacgc cgtgggagtg tcttactgga aggcttctga gggcgccgag tacgacgacc  420
agacaagcca gagagagaaa gaggacgaca aggttttccc tggcggcagc cacacctatg  480
tctggcaggt cctgaaagaa aacggcccta tggcctccga tcctctgtgc ctgacataca  540
gctacctgag ccatgtggac ctggtcaagg acctgaactc tggcctgatc ggcgctctgc  600
tcgtgtgtag agaaggcagc ctggccaaag aaaagaccca gacactgcac aagttcatcc  660
tgctgttcgc cgtgttcgac gagggcaaga gctggcacag cgagacaaag aacagcctga  720
tgcaggacag agatgccgcc tctgctagag cttggcccaa gatgcacacc gtgaacggct  780
acgtgaacag aagcctgcct ggactgatcg gatgccacag aaagtccgtg tactggcatg  840
tgatcggcat gggcaccaca cctgaggtgc acagcatctt tctggaagga cacaccttcc  900
tcgtgcggaa ccacagacag gccagcctgg aaatcagccc tatcaccttc ctgaccgctc  960
agaccctgct gatggatctg ggccagtttc tgctgttctg ccacatcagc agccaccagc  1020
acgatggcat ggaagcctac gtgaaggtgg acagctgccc cgaagaaccc cagctgagaa  1080
tgaagaacaa cgaggaagcc gaggactacg acgacgacct gaccgactct gagatggacg  1140
tcgtcagatt cgacgacgat aacagcccca gcttcatcca gatcagaagc gtggccaaga  1200
agcaccccaa gacctgggtg cactatatcg ccgccgagga agaggactgg gattacgctc  1260
ctctggtgct ggcccctgac gacagaagct acaagagcca gtacctgaac aacggccctc  1320
agagaatcgg ccggaagtat aagaaagtgc ggttcatggc ctacaccgac gagacattca  1380
agaccagaga ggctatccag cacgagagcg gcattctggg acctctgctg tatggcgaag  1440
tgggcgacac actgctgatc atcttcaaga accaggccag cagaccctac aacatctacc  1500
ctcacggcat caccgatgtg cggcctctgt actctagaag gctgcccaag ggcgtgaagc  1560
acctgaagga cttccctatc ctgcctggcg agatcttcaa gtacaagtgg accgtgaccg  1620
tcgaggacgg ccctaccaag agcgatccta gatgcctgac acggtactac agcagcttcg  1680
tgaacatgga acgcgacctg gccagcggcc tgattggtcc tctgctgatc tgctacaaag  1740
aaagcgtgga ccagaggggc aaccagatca tgagcgacaa gagaaacgtg atcctgttct  1800
ccgtctttga cgagaacagg tcctggtatc tgaccgagaa catccagcgg tttctgccca  1860
atcctgctgg cgtgcagctg gaagatcctg agttccaggc ctccaacatc atgcactcca  1920
tcaacggcta tgtgttcgac agcctgcagc tgagcgtgtg cctgcacgaa gtggcctact  1980
ggtacatcct gtctatcggc gcccagaccg acttcctgtc cgtgttcttt agcggctaca  2040
ccttcaagca caagatggtg tacgaggata ccctgacact gttcccattc agcggcgaga  2100
cagtgttcat gagcatggaa aaccccggcc tgtggatcct gggctgtcac aacagcgact  2160
tcagaaacag aggcatgaca gccctgctga aggtgtccag ctgcgacaag aacaccggcg  2220
actactacga ggactcttac gaggacatca gcgcctacct gctgagcaag aacaatgcca  2280
tcgagcctcg gagcttctct cagaaccctc ctgtgctgaa gagacaccag cgcgagatca  2340
ccagaaccac actgcagagc gaccaagagg aaatcgatta cgacgacacc atcagcgtcg  2400
agatgaagaa agaagatttc gacatctacg acgaggacga gaatcagagc cccagatctt  2460
tccagaagaa aacgcggcac tacttcattg ccgccgtgga aagactgtgg gactacggca  2520
tgagcagcag cccacatgtg ctgagaaaca gggcccagag cggaagcgtg ccccagttca  2580
agaaagtggt gttccaagag ttcaccgacg gcagcttcac ccagcctctg tatagaggcg  2640
agctgaacga gcacctggga ctgctgggac cttacatcag agctgaggtc gaggataaca  2700
tcatggtcac ctttagaaac caggcctcta ggccctactc cttctacagc tccctgatca  2760
gctacgaaga ggaccagaga cagggcgctg agcccagaaa gaacttcgtg aagcccaacg  2820
agactaagac ctacttttgg aaggtgcagc accacatggc ccctacaaag gacgagttcg  2880
actgcaaggc ctgggcctac ttctctgacg tggacctcga gaaggatgtg cacagcggac  2940
tcatcggacc cctgcttgtg tgccacacca acacactgaa tcccgctcac ggcaggcaag  3000
tgaccgtgca agagttcgcc ctgttcttca ccatcttcga tgagacaaag tcctggtact  3060
tcaccgaaaa catggaaaga aactgcaggg cccccttgcaa catccagatg gaagatccca  3120
ccttcaaaga gaactaccgg ttccacgcca tcaatggcta catcatggac actctgcccg  3180
gcctggttat ggcacaggat cagaggatca gatggtatct gctgtccatg ggctccaacg  3240
agaatatcca cagcatccac ttcagcggcc atgtgttcac cgtgcggaaa aaagaagagt  3300
acaagatggc cctgtacaat ctgtaccccg gcgtgttcga gactgtggaa atgctgccta  3360
gcaaggccgg aatctggcgc gtggaatgtc tgatcggaga gcatctgcat gccggaatgt  3420
ctaccctgtt cctggtgtac agcaacaagt gtcagacccc tctcggcatg gcctctggac  3480
acatcagaga cttccagatc accgcctctg gccagtacgg acagtgggct cctaaactgg  3540
ctagactgca ctacagcggc agcatcaacg cctggtccac caaagagccc ttcagctgga  3600
tcaaggtgga cctgctggct cccatgatca tccacggaat caagacccag ggcgccagac  3660
agaagttcag cagcctgtac atcagccagt tcatcatcat gtacagcctg gacggcaaga  3720
agtggcagac ctacagaggc aacagcaccg gcacactcat ggtgttcttc ggcaacgtgg  3780
actccagcgg cattaagcac aacatcttca accctccaat cattgcccgg tacatccggc  3840
tgcaccccac acactacagc atcagatcta ccctgaggat ggaactgatg ggctgcgacc  3900
tgaacagctg ctctatgccc ctcggaatgg aaagcaaggc catcagcgac gcccagatca  3960
cagccagcag ctacttcacc aacatgttcg ccacatggtc cccatctaag gcccggctgc  4020
atctgcaggg cagatctaac gcttggaggc cccaagtgaa caaccccaaa gagtggctgc  4080
```

```
aggtcgactt tcagaaaacc atgaaagtga ccggcgtgac cacacagggc gtcaagtctc  4140
tgctgacctc tatgtacgtg aaagagttcc tgatctccag cagccaggac ggccaccagt  4200
ggaccctgtt tttccagaac ggcaaagtca aggtgttcca gggaaaccag gacagcttca  4260
cacccgtggt caactccctg gatcctccac tgctgaccag atacctgaga attcaccctc  4320
agtcttgggt gcaccagatc gctctgagaa tggaagtgct gggatgtgaa gctcaggacc  4380
tctactaaaa taaaagatct ttattttcat tagatctgtg tgttggtttt ttgtgtg     4437

SEQ ID NO: 320          moltype = DNA  length = 4437
FEATURE                 Location/Qualifiers
misc_feature            1..4437
                        note = Synthetic polynucleotide
misc_feature            1..4437
                        note = pCB100
source                  1..4437
                        mol_type = other DNA
                        organism = synthetic construct
SEQUENCE: 320
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc ccccaccatcc 300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga cccccctgtgc ctgacctaca 540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg ccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggtgaagc   1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatcccc cagtgctgaa gaggcaccag agggagatca  2340
ccaggaccac cctgcagtct gaccaggagg agattgacta tgatgacacc atctctgtgg  2400
agatgaagaa ggaggacttt gacatctacg acgaggacga gaaccagagc cccaggagct  2460
tccagaagaa gaccaggcac tacttcattg ctgctgtgga gaggctgtgg gactatggca  2520
tgagcagcag cccccatgtg ctgaggaaca gggcccagtc tggctctgtg ccccagttca  2580
agaaggtggt gttccaggag ttcactgatg gcagcttcac ccagcccctg tacagagggg  2640
agctgaatga gcacctgggc ctgctgggcc cctacatcag ggctgaggtg gaggacaaca  2700
tcatggtgac cttcaggaac caggccagca ggccctacag cttctacagc agcctgatca  2760
gctatgagga ggaccagagg cagggggctg agcccaggaa gaactttgtg aagcccaatg  2820
aaaccaagac ctacttctgg aaggtgcagc accacatggc cccccaccaag gatgagtttg 2880
actgcaaggc ctgggcctac ttctctgatg tggacctgga gaaggatgtg cactctggcc  2940
tgattggccc cctgctggtg tgccacacca acaccctgaa ccctgcccat ggcaggcagg  3000
tgactgtgca ggagtttgcc ctgttcttca ccatctttga tgaaaccaag agctggtact  3060
tcactgagaa catggagagg aactgcaggg ccccctgcaa catccagatg gaggacccca  3120
ccttcaagga gaactacagg ttccatgcca tcaatggcta catcatggac accctgcctg  3180
gcctggtgat ggcccaggac cagaggatca ggtggtacct gctgagcatg ggcagcaatg  3240
agaacatcca cagcatccac ttctctggcc atgtgttcac tgtgaggaag aaggaggagt  3300
acaagatggc cctgtacaac ctgtaccctg ggtgtttga gactgtggag atgctgccca   3360
gcaaggctgg catctggagg gtggagtgcc tgattgggga gcacctgcat gctggcatga  3420
gcaccctgtt cctggtgtac agcaacaagt gccagacccc cctgggcatg gcctctggcc  3480
acatcaggga cttccagatc actgcctctg gccagtatgg ccagtgggcc cccaagctgg  3540
ccaggctgca ctactctggc agcatcaatg cctggagcac caaggagccc ttcagctgga  3600
tcaaggtgga cctgctggcc cccatgatca tccatggcat caagacccag gggccaggc   3660
agaagttcag cagcctgtac atcagccagt tcatcatcat gtacagcctg gatggcaaga  3720
```

```
agtggcagac ctacaggggc aacagcactg gcaccctgat ggtgttcttt ggcaatgtgg  3780
acagctctgg catcaagcac aacatcttca acccccccat cattgccaga tacatcaggc  3840
tgcaccccac ccactacagc atcaggagca ccctgaggat ggagctgatg ggctgtgacc  3900
tgaacagctg cagcatgccc ctgggcatgg agagcaaggc catctctgat gcccagatca  3960
ctgccagcag ctacttcacc aacatgtttg ccacctggag ccccagcaag gccaggctgc  4020
acctgcaggg caggagcaat gcctggaggc cccaggtcaa caaccccaag gagtggctgc  4080
aggtggactt ccagaagacc atgaaggtga ctggggtgac cacccagggg gtgaagagcc  4140
tgctgaccag catgtatgtg aaggagttcc tgatcagcag cagccaggat ggccaccagt  4200
ggaccctgtt cttccagaat ggcaaggtga aggtgttcca gggcaaccag gacagcttca  4260
cccctgtggt gaacagcctg gacccccccc tgctgaccag atacctgagg attcaccccc  4320
agagctgggt gcaccagatt gccctgagga tggaggtgct gggctgtgag gcccaggacc  4380
tgtactgaaa taaaagatct ttattttcat tagatctgtg tgttggtttt ttgtgtg     4437
```

```
SEQ ID NO: 321          moltype = DNA  length = 4775
FEATURE                 Location/Qualifiers
misc_feature            1..4775
                        note = Synthetic polynucleotide
misc_feature            1..4775
                        note = pCB1000
source                  1..4775
                        mol_type = other DNA
                        organism = synthetic construct
SEQUENCE: 321
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcctaa ggcaattgtg ccagttcccg atcgttacag  180
gcggtactcc tcaaagcgta ctaaagaatt attcttttac atttcagtgg ccaccagaag  240
gtactacctg ggagctgtgg aactgagctg ggactacatg cagtctgacc tgggagagct  300
gcctgtggat gctagatttc ctccaagagt gcccaagagc ttccccttca acacctctgt  360
ggtgtacaag aaaaccctgt ttgtggaatt cacagaccac ctgttcaata ttgccaagcc  420
tagacctcct tggatgggcc tgctgggccc tacaattcag gctgaggtgt atgacacagt  480
ggtcatcacc ctgaagaaca tggccagcca tcctgtgtct ctgcatgctg tgggagtgtc  540
ttactggaag gcttctgagg gggctgagta tgatgaccag acaagccaga gagagaaaga  600
ggatgacaag gttttccctg gggcagccca cacctatgtc tggcaggtcc tgaaagaaaa  660
tggccctatg gcctctgatc ctctgtgcct gacatacagc tacctgagcc atgtggacct  720
ggtcaaggac ctgaactctg gcctgattgg ggctctgctg gtgtgtagag aaggcagcct  780
ggccaaagaa aagacccaga cactgcacaa gttcatcctg ctgtttgctg tgtttgatga  840
gggcaagagc tggcactctg agacaaagaa cagcctgatg caggacagag atgctgcctc  900
tgctagagct tggcccaaga tgcacacagt gaatggctat gtgaacagaa gcctgcctgg  960
actgattgga tgccacagaa agtctgtgta ctggcatgtg attggcatgg gcaccacacc  1020
tgaggtgcac agcatctttc tggaaggaca caccttcctg gtgaggaacc acagacaggc  1080
cagcctggaa atcagcccta tcaccttcct gacagctcag accctgctga tggatctggg  1140
ccagtttctg ctgttctgcc acatcagcag ccaccagcat gatggcatgg aagcctatgt  1200
gaaggtggac agctgccctg aagaacccca gctgagaatg aagaacaatg aggaagctga  1260
ggactatgat gatgacctga cagactctga gatggatgtg gtcagatttg atgatgataa  1320
cagccccagc ttcatccaga tcagatctgt ggccaagaag caccccaaga cctgggtgca  1380
ctatattgct gctgaggaag aggactggga ttatgctcct ctggtgctgg cccctgatga  1440
cagaagctac aagagccagt acctgaacaa tggccctcag agaattggca ggaagtataa  1500
gaaagtgagg ttcatggcct acacagatga gacattcaag accagagagg ctatccagca  1560
tgagtctggc attctgggac ctctgctgta tggggaagtg ggggacacac tgctgatcat  1620
cttcaagaac caggccagca gaccctacaa catctaccct catggcatca cagatgtgag  1680
gcctctgtac tctagaaggc tgcccaaggg ggtgaagcac ctgaaggact tccctatcct  1740
gcctggggag atcttcaagt acaagtggac agtgacagtg gaggatggcc ctaccaagtc  1800
tgatcctaga tgcctgacaa ggtactacag cagctttgtg aacatggaaa gggacctggc  1860
ctctggcctg attggtcctc tgctgatctg ctacaaagaa tctgtggacc agaggggcaa  1920
ccagatcatg agtgacaaga gaaatgtgat cctgttctct gtctttgatg agaacaggtc  1980
ctggtatctg acagagaaca tccagaggtt tctgcccaat cctgctgggg tgcagctgga  2040
agatcctgag ttccaggcct ccaacatcat gcactccatc aatggctatg tgtttgacag  2100
cctgcagctg tctgtgtgcc tgcatgaagt ggcctactgg tacatcctgt ctattggggc  2160
ccagacagac ttcctgtctg tgttcttttc tggctacacc ttcaagcaca agatggtgta  2220
tgaggatacc ctgacactgt tcccattctc tggggagaca gtgttcatga gcatggaaaa  2280
ccctggcctg tggatcctgg gctgtcacaa cagtgacttc agaaacagag gcatgacagc  2340
cctgctgaag gtgtccagct gtgacaagaa cactggggac tactatgagg actcttatga  2400
ggacatctct gcctacctgc tgagcaagaa caatgccatt gagcctagga gcttctctca  2460
gaaccctcct gtgctgaaga gacaccagag ggagatcacc agaaccacac tgcagtctga  2520
ccaagaggaa attgattatg atgacaccat ctctgtggag atgaagaaag aagattttga  2580
catctatgat gaggatgaga atcagagccc cagatctttc cagaagaaaa caaggcacta  2640
cttcattgct gctgtggaaa gactgtggga ctatggcatg agcagcagcc cccatgtgct  2700
gagaaacagg gcccagtctg gaagtgtgcc ccagttcaag aaagtggtgt tccaagagtt  2760
cacagatggc agcttcaccc agcctctgta tagaggggag ctgaatgagc acctgggact  2820
gctgggacct tacatcagag ctgaggtgga ggataacatc atggtcacct ttagaaacca  2880
ggcctctagg ccctactcct tctacagctc cctgatcagc tatgaagagg accagagaca  2940
gggggctgag cccagaaaga actttgtgaa gcccaatgag actaagacct acttttggaa  3000
ggtgcagcac cacatggccc ctacaaagga tgagtttgac tgcaaggcct gggcctactt  3060
ctctgatgtg gacctggaga aggatgtgca ctctggactc attggacccc tgcttgtgtg  3120
ccacaccaac acactgaatc ctgctcatgg caggcaagtg acagtgcaag agtttgccct  3180
gttcttcacc atctttgatg agacaaagtc ctggtacttc acagaaaaca tggaaagaaa  3240
ctgcagggcc ccttgcaaca tccagatgga agatcccacc ttcaaagaga actacaggtt  3300
ccatgccatc aatggctaca tcatggacac tctgcctggc ctggttatgg cacaggatca  3360
```

```
gaggatcaga tggtatctgc tgtccatggg ctccaatgag aatatccaca gcatccactt  3420
ctctggccat gtgttcacag tgaggaaaaa agaagagtac aagatggccc tgtacaatct  3480
gtaccctggg gtgtttgaga ctgtggaaat gctgcctagc aaggctggaa tctggagggt  3540
ggaatgtctg attggagagc atctgcatgc tggaatgtct accctgttcc tggtgtacag  3600
caacaagtgt cagacccctc tgggcatggc ctctggacac atcagagact tccagatcac  3660
agcctctggc cagtatggac agtgggctcc taaactggct agactgcact actctggcag  3720
catcaatgcc tggtccacca aagagccctt cagctggatc aaggtggacc tgctggctcc  3780
catgatcatc catggaatca agacccaggg ggccagacag aagttcagca gcctgtacat  3840
cagccagttc atcatcatgt acagcctgga tggcaagaag tggcagacct acagaggcaa  3900
cagcacaggc acactcatgg tgttctttgg caatgtggac tcttctggca ttaagcacaa  3960
catcttcaac cctccaatca ttgccaggta catcaggctg caccccacac actacagcat  4020
cagatctacc ctgaggatgg aactgatggg ctgtgacctg aacagctgct ctatgcccct  4080
gggaatggaa agcaaggcca tctctgatgc ccagatcaca gccagcagct acttcaccaa  4140
catgtttgcc acatggtccc catctaaggc caggctgcat ctgcagggca gatctaatgc  4200
ttggaggccc caagtgaaca accccaaaga gtggctgcag gtggactttc agaaaaccat  4260
gaaagtgaca ggagtgacca cacagggggt caagtctctg ctgacctcta tgtatgtgaa  4320
agagttcctg atctccagca gccaggatgg ccaccagtgg accctgtttt tccagaatgg  4380
caaagtcaag gtgttccagg gaaaccagga cagcttcaca cctgtggtca actccctgga  4440
tcctccactg ctgaccagat acctgagaat tcaccctcag tcttgggtgc accagattgc  4500
tctgagaatg gaagtgctgg gatgtgaagc tcaggacctc tactgatcgc gaataaaaga  4560
tctttatttt cattagatct gtgtgttggt tttttgtgtg tgccagttcc cgatcgttac  4620
aggccgcggg ccgcaggaac ccctagtgat ggagttggcc actccctctc tgcgcgctcg  4680
ctcgctcact gaggccgggc gaccaaaggt cgcccgacgc ccgggctttg cccgggcggc  4740
ctcagtgagc gagcgagcgc gcagctgcct gcagg                            4775
```

```
SEQ ID NO: 322          moltype = DNA  length = 4775
FEATURE                 Location/Qualifiers
misc_feature            1..4775
                        note = Synthetic polynucleotide
misc_feature            1..4775
                        note = pCB1001
source                  1..4775
                        mol_type = other DNA
                        organism = synthetic construct
SEQUENCE: 322
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcctaa ggcaattgtg ccagttcccg atcgttacag  180
gcggtactcc tcaaagcgta ctaaagaatt attcttttac atttcagtgg ccaccagaag  240
gtactaccta ggagccgtgg aactgagctg ggactacatg cagtctgacc tgggagagct  300
gcccgtggac gctagatttc ctccaagagt gcccaagagc ttccccttca acacctccgt  360
ggtgtacaag aaaaccctgt tcgtggaatt caccgaccac ctgttcaata tcgccaagcc  420
tagacctcct tggatgggcc tgctgggccc tacaattcag gccgaggtgt acgacaccgt  480
ggtcatcacc ctgaagaaca tggccagcca tcctgtgtct ctgcacgccg tgggagtgtc  540
ttactggaag gcttctgagg gcgccgagta cgacgaccag acaagccaga gagagaaaga  600
ggacgacaag gttttccctg gcggcagcca cacctatgtc tggcaggtcc tgaaagaaaa  660
cggccctatg gcctccgatc ctctgtgcct gacatacagc tacctgagcc atgtggacct  720
ggtcaaggac ctgaactctg gcctgatcgg cgctctgctc gtgtgtagag aaggcagcct  780
ggccaaagaa aagacccaga cactgcacaa gttcatcctg ctgttcgccg tgttcgacga  840
gggcaagagc tggcacagcg agacaaagaa cagcctgatg caggacagag atgccgcctc  900
tgctagagct tggcccaaga tgcacaccgt gaacggctac gtgaacagaa gcctgcctgg  960
actgatcgga tgccacagaa agtccgtgta ctggcatgtg atcggcatgg gcaccacacc  1020
tgaggtgcac agcatctttc tggaaggaca caccttcctc gtgcggaacc acagacaggc  1080
cagcctggaa atcagcccta tcaccttcct gaccgctcag accctgctga tggatctggg  1140
ccagtttctg ctgttctgcc acatcagcag ccaccagcac gatggcatgg aagcctacgt  1200
gaaggtggac agctgccccg aagaacccca gctgagaatg aagaacaacg aggaagccga  1260
ggactacgac gacgacctga ccgactctga gatggacgtc gtcagattcg acgacgataa  1320
cagccccagc ttcatccaga tcagaagcgt ggccaagaag caccccaaga cctgggtgca  1380
ctatatcgcc gccgaggaag aggactggga ttacgctcct ctggtgctgg cccctgacga  1440
cagaagctac aagagccagt acctgaacaa cggccctcag agaatcggcc ggaagtataa  1500
gaaagtgcgg ttcatggcct acaccgacga gacattcaag accagagagg ctatccagca  1560
cgagagcggc attctgggac ctctgctgta tggcgaagtg ggcgacacac tgctgatcat  1620
cttcaagaac caggccagca gaccctacaa catctaccct cacggcatca ccgatgtgcg  1680
gcctctgtac tctagaaggc tgcccaaggg cgtgaagcac ctgaaggact tccctatcct  1740
gcctggcgag atcttcaagt acaagtggac cgtgaccgtc gaggacggcc ctaccaagag  1800
cgatcctaga tgcctgacac ggtactacag cagcttcgtg aacatggaac gcgacctggc  1860
cagcggcctg attggtcctc tgctgatctg ctacaaagaa agcgtggacc agaggggcaa  1920
ccagatcatg agcgacaaga gaaacgtgat cctgttctcc gtctttgacg agaacaggtc  1980
ctggtatctg accgagaaca tccagcggtt tctgcccaat cctgctggcg tgcagctgga  2040
agatcctgag ttccaggcct ccaacatcat gcactccatc aacggctatg tgttcgacag  2100
cctgcagctg agcgtgtgcc tgcacgaagt ggcctactgg tacatcctgt ctatcggcgc  2160
ccagaccgac ttcctgtccg tgttctttag cggctacacc ttcaagcaca agatggtgta  2220
cgaggatacc ctgacactgt tcccattcag cggcgagaca gtgttcatga gcatggaaaa  2280
ccccggcctg tggatcctgg gctgtcacaa cagcgacttc agaaacagag gcatgacagc  2340
cctgctgaag gtgtccagct gcgacaagaa caccggcgac tactacgagg actcttacga  2400
ggacatcagc gcctacctgc tgagcaagaa caatgccatc gagcctcgga gcttctctca  2460
gaaccctcct gtgctgaaga gacaccagcg cgagatcacc agaaccacac tgcagagcga  2520
ccaagaggaa atcgattacg acgacaccat cagcgtcgag atgaagaaag aagatttcga  2580
catctacgac gaggacgaga atcagagccc cagatctttc cagaagaaaa cgcggcacta  2640
```

```
cttcattgcc gccgtggaaa gactgtggga ctacggcatg agcagcagcc cacatgtgct  2700
gagaaacagg gcccagagcg gaagcgtgcc ccagttcaag aaagtggtgt tccaagagtt  2760
caccgacggc agcttcaccc agcctctgta tagaggcgag ctgaacgagc acctgggact  2820
gctgggacct tacatcagag ctgaggtcga ggataacatc atggtcacct ttagaaacca  2880
ggcctctagg ccctactcct tctacagctc cctgatcagc tacgaagagg accagagaca  2940
gggcgctgag cccagaaaga acttcgtgaa gcccaacgag actaagacct acttttggaa  3000
ggtgcagcac cacatggccc ctacaaagga cgagttcgac tgcaaggcct gggcctactt  3060
ctctgacgtg gacctcgaga aggatgtgca cagcggactc atcggacccc tgcttgtgtg  3120
ccacaccaac acactgaatc ccgctcacgg caggcaagtg accgtgcaag agttcgccct  3180
gttcttcacc atcttcgatg agacaaagtc ctggtacttc accgaaaaca tggaaagaaa  3240
ctgcagggcc ccttgcaaca tccagatgga agatcccacc ttcaaagaga actaccggtt  3300
ccacgccatc aatggctaca tcatggacac tctgcccggc ctggttatgg cacaggatca  3360
gaggatcaga tggtatctgc tgtccatggg ctccaacgag aatatccaca gcatccactt  3420
cagcggccat gtgttcaccg tgcggaaaaa agaagagtac aagatggccc tgtacaatct  3480
gtaccccggc gtgttcgaga ctgtggaaat gctgcctagc aaggccggaa tctggcgcgt  3540
ggaatgtctg atcggagagc atctgcatgc cggaatgtct accctgttcc tggtgtacag  3600
caacaagtgt cagacccctc tcggcatggc ctctggacac atcagagact tccagatcac  3660
cgcctctggc cagtacggac agtgggctcc taaactggct agactgcact acagcggcag  3720
catcaacgcc tggtccacca aagagccctt cagctggatc aaggtggacc tgctggctcc  3780
catgatcatc cacggaatca agacccaggg cgccagacag aagttcagca gcctgtacat  3840
cagccagttc atcatcatgt acagcctgga cggcaagaag tggcagacct acagaggcaa  3900
cagcaccggc acactcatgg tgttcttcgg caacgtggac tccagcggca ttaagcacaa  3960
catcttcaac cctccaatca ttgcccggta catccggctg caccccacac actacagcat  4020
cagatctacc ctgaggatgg aactgatggg ctgcgacctg aacagctgct ctatgcccct  4080
cggaatggaa agcaaggcca tcagcgacgc ccagatcaca gccagcagct acttcaccaa  4140
catgttcgcc acatggtccc catctaaggc ccggctgcat ctgcagggca gatctaacgc  4200
ttggaggccc caagtgaaca accccaaaga gtggctgcag gtcgactttc agaaaaccat  4260
gaaagtgacc ggcgtgacca cacagggcgt caagtctctg ctgacctcta tgtacgtgaa  4320
agagttcctg atctccagca gccaggacgg ccaccagtgg accctgtttt tccagaacgg  4380
caaagtcaag gtgttccagg gaaaccagga cagcttcaca cccgtggtca actccctgga  4440
tcctccactg ctgaccagat acctgagaat tcaccctcag tcttgggtgc accagatcgc  4500
tctgagaatg gaagtgctgg gatgtgaagc tcaggacctc tactgatcgc gaataaaaga  4560
tctttatttt cattagatct gtgtgttggt tttttgtgtg tgccagttcc cgatcgttac  4620
aggccgcggg ccgcaggaac ccctagtgat ggagttggcc actccctctc tgcgcgctcg  4680
ctcgctcact gaggccgggc gaccaaaggt cgcccgacgc ccgggctttg cccgggcggc  4740
ctcagtgagc gagcgagcgc gcagctgcct gcagg                            4775

SEQ ID NO: 323         moltype = DNA  length = 4780
FEATURE                Location/Qualifiers
misc_feature           1..4780
                       note = Synthetic polynucleotide
misc_feature           1..4780
                       note = pCB1002
source                 1..4780
                       mol_type = other DNA
                       organism = synthetic construct
SEQUENCE: 323
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggccctc gagtgccagt tcccgatcgt tacaggcggt  180
actcctcaaa gcgtactaaa gaattattct tttacatttc agtggctacc agaagatact  240
acctgggagc cgtcgaactg agctgggatt acatgcagtc tgacctggga gagctgcccg  300
tggacgctag attcccacct agagtcccta agtccttccc cttcaacacc agcgtggtct  360
acaagaaaac cctgttcgtg gagtttaccg accacctgtt caacatcgct aagcctagac  420
caccatggat gggactgctg ggaccaacca tccaggccga ggtgtacgac accgtggtca  480
tcaccctgaa aaacatggct tctcaccccg tgtccctgca tgctgtgggc gtctcctact  540
ggaaggccag cgaaggggct gagtatgacg atcagaccag ccagcgggaa aaagaggacg  600
ataaggtgtt ccctggcggg tcccatacct acgtgtggca ggtcctgaag gagaatggac  660
caatggcttc cgaccctctg tgcctgacct actcttatct gtcccacgtg gacctggtca  720
aggatctgaa cagcggcctg atcggggctc tgctggtgtg tcgcgaaggg tccctggcca  780
aggagaaaac ccagaccctg cataagttca tcctgctgtt cgccgtgttt gacgaaggaa  840
aaagctggca ctctgagacc aagaactctc tgatgcagga cagggatgcc gcttccgcca  900
gagcttggcc caagatgcac accgtgaacg gctacgtcaa taggagcctg cctggactga  960
tcggctgcca cagaaagtcc gtgtattggc atgtcatcgg aatgggcacc acccctgaag  1020
tgcacagcat cttcctggag gggcatacct ttctggtccg caaccaccgg caggctagcc  1080
tggagatctc tccaatcacc ttcctgaccg cccagaccct gctgatggac ctgggacagt  1140
tcctgctgtt ttgccacatc tccagccacc agcatgatgg catggaggct tacgtgaaag  1200
tcgactcctg tcccgaggaa cctcagctga ggatgaagaa caatgaggaa gccgaagact  1260
atgacgatga cctgaccgac agcgagatgg atgtggtccg cttcgatgac gataactctc  1320
cctcctttat ccagatccgg tccgtggcca agaaacaccc taagacctgg gtccattaca  1380
tcgccgctga ggaagaggac tgggattatg ctccactggt gctggccccc gacgatagat  1440
cctacaaaag ccagtatctg aacaatggac cccagaggat cggcagaaag tacaagaaag  1500
tgaggttcat ggcttatacc gatgagacct ttaagaccag agaagccatc cagcacgagt  1560
ccgggatcct gggacctctg ctgtacggcg aagtggggga caccctgctg atcatcttca  1620
agaaccaggc cagcaggcct tacaatatct atccacatgg catcaccgat gtgagacctc  1680
tgtactcccg ccggctgcca aagggcgtga aacacctgaa ggacttccca atcctgcccg  1740
gggaaatctt taagtataaa tggaccgtca ccgtcgagga tgggcccacc aagagcgacc  1800
ctaggtgcct gaccagatac tattcttcct tcgtgaatat ggagagagac ctggcttccg  1860
gactgatcgg acccctgctg atctgttaca aagagagcgt ggatcagcgc ggcaaccaga  1920
```

-continued

```
tcatgtctga caagcggaat gtgatcctgt tcagcgtctt tgacgaaaac cgctcttggt  1980
acctgaccga gaacatccag cggttcctgc ctaatccagc tggagtgcag ctggaagatc  2040
ccgagttcca ggcctctaac atcatgcatt ccatcaatgg ctacgtgttc gactccctgc  2100
agctgagcgt gtgcctgcac gaggtcgctt actggtatat cctgagcatc ggagcccaga  2160
ccgatttcct gtctgtgttc ttttccggct acacctttaa gcataaaatg gtgtatgagg  2220
acaccctgac cctgttccca ttttccggcg aaaccgtgtt catgagcatg gagaatcccg  2280
ggctgtggat cctgggatgc cacaactccg atttcaggaa tagagggatg accgccctgc  2340
tgaaagtgag ctcttgtgac aagaacaccg gagactacta tgaagatagc tacgaggaca  2400
tctctgctta tctgctgtcc aaaaacaatg ccatcgagcc caggagcttc tctcagaacc  2460
ctccagtgct gaagcgccac cagcgggaga tcaccagaac caccctgcag agcgatcagg  2520
aagagatcga ctacgacgat accatctccg tggaaatgaa gaaagaggac ttcgatatct  2580
atgacgaaga tgagaaccag tctcccaggt ccttccagaa gaaaaccaga cattacttta  2640
tcgccgctgt ggagcggctg tgggactatg gcatgtccag ctctcctcac gtgctgagaa  2700
atagagctca gtccggaagc gtcccacagt tcaagaaagt ggtcttccag gagtttaccg  2760
acggaagctt tacccagcca ctgtaccgcg gcgaactgaa cgagcacctg gggctgctgg  2820
gaccctatat ccgggctgaa gtggaggata acatcatggt caccttcagg aatcaggcca  2880
gcagaccccta ctctttttat tccagcctga tctcctacga agaggaccag agacagggag  2940
ctgaaccaag aaaaaacttc gtgaagccta atgagaccaa aacctacttt tggaaggtgc  3000
agcaccatat ggcccctacc aaagacgagt tcgattgcaa ggcctgggct tattttagcg  3060
acgtggatct ggagaaggac gtccactccg gcctgatcgg gccactgctg gtgtgtcata  3120
ccaacaccct gaatccagct cacggaaggc aggtgaccgt ccaggaattc gccctgttct  3180
ttaccatctt tgatgagacc aagagctggt acttcaccga aaacatggag aggaattgca  3240
gagccccatg taacatccag atggaagacc ccaccttcaa ggagaactac agatttcatg  3300
ctatcaatgg gtatatcatg gataccctgc caggactggt catggctcag gaccagagga  3360
tcagatggta cctgctgagc atggggtcta acgagaatat ccactccatc catttcagcg  3420
gacacgtgtt taccgtccgc aagaaagaag agtacaagat ggccctgtac aacctgtatc  3480
ccggcgtgtt cgaaaccgtc gagatgctgc cttccaaggc tgggatctgg cgggtggaat  3540
gcctgatcgg ggagcacctg catgccggaa tgtctaccct gttcctggtg tactccaata  3600
agtgtcagac ccccctgggg atggctagcg gacatatccg cgacttccag atcaccgctt  3660
ccggacagta cggacagtgg gctcctaagc tggctagact gcactattct ggctccatca  3720
acgcttggtc taccaaagag cctttctcct ggatcaaggt ggacctgctg gctccaatga  3780
tcatccatgg catcaaaacc caggggggcca ggcagaagtt ctcttccctg tacatcagcc  3840
agtttatcat catgtattct ctggatggga agaaatggca gacctacaga ggcaattcca  3900
ccgggaccct gatggtgttc tttggcaacg tcgacagctc tgggatcaag cacaacatct  3960
tcaatccccc tatcatcgcc cgctacatcc ggctgcaccc aacccattat tccatccgca  4020
gcaccctgcg gatggagctg atggggtgcg atctgaacag ctgttctatg cccctgggaa  4080
tggagtctaa ggccatctcc gacgctcaga tcaccgcctc cagctacttc accaatatgt  4140
ttgctacctg gtccccaagc aaggctagac tgcatctgca gggaagaagc aacgcttgga  4200
gaccacaggt gaacaatccc aaggagtggc tgcaggtcga cttccagaaa accatgaagg  4260
tgaccggagt caccacccag ggcgtgaaaa gcctgctgac ctctatgtac gtcaaggagt  4320
tcctgatctc ttccagccag gacgggcacc agtggaccct gttctttcag aacggaaagg  4380
tgaaagtctt ccagggcaat caggattcct ttaccccctgt ggtcaacagc ctggacccac  4440
ccctgctgac caggtacctg agaatccacc cacagtcctg ggtgcatcag atcgctctga  4500
ggatggaagt cctgggctgc gaggcccagg acctgtattg atcgcgaata aaagatcttt  4560
attttcatta gatctgtgtg ttggtttttt gtgtggatct gccagttccc gatcgttaca  4620
ggcaattgcc ttaggccgca ggaaccccta gtgatggagt tggccactcc ctctctgcgc  4680
gctcgctcgc tcactgaggc cgggcgacca aaggtcgccc gacgcccggg ctttgcccgg  4740
gcggcctcag tgagcgagcg agcgcgcagc tgcctgcagg                        4780
```

```
SEQ ID NO: 324          moltype = DNA  length = 4442
FEATURE                 Location/Qualifiers
misc_feature            1..4442
                        note = Synthetic polynucleotide
misc_feature            1..4442
                        note = pCB1003
source                  1..4442
                        mol_type = other DNA
                        organism = synthetic construct
SEQUENCE: 324
tgccagttcc cgatcgttac aggcggtact cctcaaagcg tactaaagaa ttattctttt  60
acatttcagt ggctaccaga agatactacc tgggagccgt cgaactgagc tgggattaca  120
tgcagtctga cctgggagag ctgcccgtgg acgctagatt cccacctaga gtccctaagt  180
ccttcccctt caacaccagc gtggtctaca agaaaaccct gttcgtggag tttaccgacc  240
acctgttcaa catcgctaag cctagaccac catggatggg actgctggga ccaaccatcc  300
aggccgaggt gtacgacacc gtggtcatca ccctgaaaaa catggcttct caccccgtgt  360
ccctgcatgc tgtgggcgtc tcctactgga aggccagcga aggggctgag tatgacgatc  420
agaccagcca gcgggaaaaa gaggacgata aggtgttccc tggcgggtcc catacctacg  480
tgtggcaggt cctgaaggag aatggaccaa tggcttccga ccctctgtgc ctgacctact  540
cttatctgtc ccacgtggac ctggtcaagg atctgaacag cggcctgatc ggggctctgc  600
tggtgtgtcg cgaagggtcc ctggccaagg agaaaaccca gaccctgcat aagttcatcc  660
tgctgttcgc cgtgtttgac gaaggaaaaa gctggcactc tgagaccaag aactctctga  720
tgcaggacag ggatgccgct tccgccagag cttggcccaa gatgcacacc gtgaacggct  780
acgtcaatag gagcctgcct ggactgatcg gctgccacag aaagtccgtg tattggcatg  840
tcatcggaat gggcaccacc cctgaagtgc acagcatctt cctggagggg catacctttc  900
tggtccgcaa ccaccggcag gctagcctgg agatctctcc aatcaccttc ctgaccgccc  960
agaccctgct gatggacctg ggacagttcc tgctgttttg ccacatctcc agccaccagc  1020
atgatggcat ggaggcttac gtgaaagtcg actcctgtcc cgaggaacct cagctgagga  1080
tgaagaacaa tgaggaagcc gaagactatg acgatgacct gaccgacagc gagatggatg  1140
tggtccgctt cgatgacgat aactctccct cctttatcca gatccggtcc gtggccaaga  1200
```

```
aacaccctaa gacctgggtc cattacatcg ccgctgagga agaggactgg gattatgctc  1260
cactggtgct ggcccccgac gatagatcct acaaaagcca gtatctgaac aatggacccc  1320
agaggatcgg cagaaagtac aagaaagtga ggttcatggc ttataccgat gagacccttta  1380
agaccagaga agccatccag cacgagtccg ggatcctggg acctctgctg tacggcgaag  1440
tgggggacac cctgctgatc atcttcaaga accaggccag caggccttac aatatctatc  1500
cacatggcat caccgatgtg agacctctgt actcccgccg gctgccaaag ggcgtgaaac  1560
acctgaagga cttcccaatc ctgcccgggg aaatctttaa gtataaatgg accgtcaccg  1620
tcgaggatgg gcccaccaag agcgacccta ggtgcctgac cagatactat tcttccttcg  1680
tgaatatgga gagagacctg gcttccggac tgatcggacc cctgctgatc tgttacaaag  1740
agagcgtgga tcagcgcggc aaccagatca tgtctgacaa gcggaatgtg atcctgttca  1800
gcgtctttga cgaaaaccgc tcttggtacc tgaccgagaa catccagcgg ttcctgccta  1860
atccagctgg agtgcagctg gaagatcccg agttccaggc ctctaacatc atgcattcca  1920
tcaatggcta cgtgttcgac tccctgcagc tgagcgtgtg cctgcacgag gtcgcttact  1980
ggtatatcct gagcatcgga gcccagaccg atttcctgtc tgtgttcttt tccggctaca  2040
cctttaagca taaaatggtg tatgaggaca ccctgaccct gttcccattt tccggcgaaa  2100
ccgtgttcat gagcatggag aatcccgggc tgtggatcct gggatgccac aactccgatt  2160
tcaggaatag agggatgacc gccctgctga aagtgagctc ttgtgacaag aacaccggag  2220
actactatga agatagctac gaggacatct ctgcttatct gctgtccaaa aacaatgcca  2280
tcgagcccag gagcttctct cagaaccctc cagtgctgaa gcgccaccag cgggagatca  2340
ccagaaccac cctgcagagc gatcaggaag agatcgacta cgacgatacc atctccgtgg  2400
aaatgaagaa agaggacttc gatatctatg acgaagatga gaaccagtct cccaggtcct  2460
tccagaagaa aaccagacat tactttatcg ccgctgtgga gcggctgtgg gactatggca  2520
tgtccagctc tcctcacgtg ctgagaaata gagctcagtc cggaagcgtc ccacagttca  2580
agaaagtggt cttccaggag tttaccgacg gaagctttac ccagccactg taccgcggcg  2640
aactgaacga gcacctgggg ctgctgggac cctatatccg ggctgaagtg gaggataaca  2700
tcatggtcac cttcaggaat caggccagca gaccctactc tttttattcc agcctgatct  2760
cctacgaaga ggaccagaga cagggagctg aaccaagaaa aaacttcgtg aagcctaatg  2820
agaccaaaac ctacttttgg aaggtgcagc accatatggc ccctaccaaa gacgagttcg  2880
attgcaaggc ctgggcttat tttagcgacg tggatctgga gaaggacgtc cactccggcc  2940
tgatcgggcc actgctggtg tgtcatacca acaccctgaa tccagctcac ggaaggcagg  3000
tgaccgtcca ggaattcgcc ctgttcttta ccatctttga tgagaccaag agctggtact  3060
tcaccgaaaa catggagagg aattgcagag ccccatgtaa catccagatg gaagacccca  3120
ccttcaagga gaactacaga tttcatgcta tcaatgggta tatcatggat accctgccag  3180
gactggtcat ggctcaggac cagaggatca gatggtacct gctgagcatg ggtctaacg  3240
agaatatcca ctccatccat ttcagcggac acgtgtttac cgtccgcaag aaagaagagt  3300
acaagatggc cctgtacaac ctgtatcccg gcgtgttcga aaccgtcgag atgctgcctt  3360
ccaaggctgg gatctggcgg gtggaatgcc tgatcgggga gcacctgcat gccggaatgt  3420
ctaccctgtt cctggtgtac tccaataagt gtcagacccc cctggggatg gctagcggac  3480
atatccgcga cttccagatc accgcttccg gacagtacgg acagtgggct cctaagctgg  3540
ctagactgca ctattctggc tccatcaacg cttggtctac caaagagcct ttctcctgga  3600
tcaaggtgga cctgctggct ccaatgatca tccatggcat caaaacccag gggccaggc  3660
agaagttctc ttccctgtac atcagccagt ttatcatcat gtattctctg gatgggaaga  3720
aatggcagac ctacagaggc aattccaccg ggaccctgat ggtgttcttt ggcaacgtcg  3780
acagctctgg gatcaagcac aacatcttca atccccctat catcgcccgc tacatccggc  3840
tgcacccaac ccattattcc atccgcagca ccctgcggat ggagctgatg ggtgcgatc  3900
tgaacagctg ttctatgccc ctgggaatgg agtctaaggc catctccgac gctcagatca  3960
ccgcctccag ctacttcacc aatatgtttg ctacctggtc cccaagcaag gctagactgc  4020
atctgcaggg aagaagcaac gcttggagac cacaggtgaa caatcccaag gagtggctgc  4080
aggtcgactt ccagaaaacc atgaaggtga ccggagtcac caccccagggc gtgaaaagcc  4140
tgctgacctc tatgtacgtc aaggagttcc tgatctcttc cagccaggac gggcaccagt  4200
ggaccctgtt ctttcagaac ggaaaggtga aagtcttcca gggcaatcag gattccttta  4260
cccctgtggt caacagcctg gacccacccc tgctgaccag gtacctgaga atccacccac  4320
agtcctgggt gcatcagatc gctctgagga tggaagtcct gggctgcgag gcccaggacc  4380
tgtattgatc gcgaataaaa gatctttatt ttcattagat ctgtgtgttg gtttttttgtg  4440
tg                                                                 4442
```

```
SEQ ID NO: 325         moltype = DNA  length = 4493
FEATURE                Location/Qualifiers
misc_feature           1..4493
                       note = Synthetic polynucleotide
misc_feature           1..4493
                       note = pCB1006
source                 1..4493
                       mol_type = other DNA
                       organism = synthetic construct
SEQUENCE: 325
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga cccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
```

-continued

```
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag ggggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagca  2340
atgacaccaa tgtgtctccc ccagtgctga agaggcacca gagggagatc accaggacca  2400
ccctgcagtc tgaccaggag gagattgact atgatgacac catctctgtg gagatgaaga  2460
aggaggactt tgacatctac gacgaggacg agaaccagag ccccaggagc ttccagaaga  2520
agaccaggca ctacttcatt gctgctgtgg agaggctgtg ggactatggc atgagcagca  2580
gcccccatgt gctgaggaac agggcccagt ctggctctgt gccccagttc aagaaggtgg  2640
tgttccagga gttcactgat ggcagcttca cccagcccct gtacagaggg gagctgaatg  2700
agcacctggg cctgctgggc ccctacatca gggctgaggt ggaggacaac atcatggtga  2760
ccttcaggaa ccaggccagc aggccctaca gcttctacag cagcctgatc agctatgagg  2820
aggaccagag gcaggggggct gagcccagga agaactttgt gaagcccaat gaaaccaaga  2880
cctacttctg gaaggtgcag caccacatgg cccccaccaa ggatgagttt gactgcaagg  2940
cctgggccta cttctctgat gtggacctgg agaaggatgt gcactctggc ctgattggcc  3000
ccctgctggt gtgccacacc aacaccctga accctgccca tggcaggcag gtgactgtgc  3060
aggagtttgc cctgttcttc accatctttg atgaaaccaa gagctggtac ttcactgaga  3120
acatggagag gaactgcagg gcccccctgca acatccagat ggaggacccc accttcaagg  3180
agaactacag gttccatgcc atcaatggct acatcatgga caccctgcct ggcctggtga  3240
tggcccagga ccagaggatc aggtggtacc tgctgagcat gggcagcaat gagaacatcc  3300
acagcatcca cttctctggc catgtgttca ctgtgaggaa gaaggaggag tacaagatgg  3360
ccctgtacaa cctgtaccct ggggtgtttg agactgtgga gatgctgccc agcaaggctg  3420
gcatctggag ggtggagtgc ctgattgggg agcacctgca tgctggcatg agcaccctgt  3480
tcctggtgta cagcaacaag tgccagaccc ccctgggcat ggcctctggc cacatcaggg  3540
acttccagat cactgcctct ggccagtatg gccagtgggc cccccaagctg gccaggctgc  3600
actactctgg cagcatcaat gcctggagca ccaaggagcc cttcagctgg atcaaggtgg  3660
acctgctggc ccccatgatc atccatggca tcaagaccca gggggccagg cagaagttca  3720
gcagcctgta catcagccag ttcatcatca tgtacagcct ggatggcaag aagtggcaga  3780
cctacagggg caacagcact ggcaccctga tggtgttctt tggcaatgtg gacagctctg  3840
gcatcaagca caacatcttc aacccccccca tcattgccag atacatcagg ctgcacccca  3900
cccactacag catcaggagc accctgagga tggagctgat gggctgtgac ctgaacagct  3960
gcagcatgcc cctgggcatg gagagcaagg ccatctctga tgcccagatc actgccagca  4020
gctacttcac caacatgttt gccacctgga gccccagcaa ggccaggctg cacctgcagg  4080
gcaggagcaa tgcctggagg ccccaggtca acaaccccaa ggagtggctg caggtggact  4140
tccagaagac catgaaggtg actggggtga ccacccaggg ggtgaagagc ctgctgacca  4200
gcatgtatgt gaaggagttc ctgatcagca gcagccagga tggccaccag tggaccctgt  4260
tcttccagaa tggcaaggtg aaggtgttcc agggcaacca ggacagcttc acccctgtgg  4320
tgaacagcct ggacccccccc ctgctgacca gatacctgag gattcacccc cagagctggg  4380
tgcaccagat tgccctgagg atggaggtgc tgggctgtga ggcccaggac ctgtactgat  4440
cgcgaataaa agatctttat tttcattaga tctgtgtgtt ggttttttgt gtg         4493
```

```
SEQ ID NO: 326          moltype = DNA  length = 4484
FEATURE                 Location/Qualifiers
misc_feature            1..4484
                        note = Synthetic polynucleotide
misc_feature            1..4484
                        note = pCB1007
source                  1..4484
                        mol_type = other DNA
                        organism = synthetic construct
SEQUENCE: 326
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
```

```
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga cccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagca  2340
atgacagccc cccagtgctg aagaggcacc agagggagat caccaggacc accctgcagt  2400
ctgaccagga ggagattgac tatgatgaca ccatctctgt ggagatgaag aaggaggact  2460
ttgacatcta cgacgaggac gagaaccaga gccccaggag cttccagaag aagaccaggc  2520
actacttcat tgctgctgtg gagaggctgt gggactatgg catgagcagc agcccccatg  2580
tgctgaggaa cagggcccag tctggctctg tgccccagtt caagaaggtg gtgttccagg  2640
agttcactga tggcagcttc acccagcccc tgtacagagg ggagctgaat gagcacctgg  2700
gcctgctggg cccctacatc agggctgagg tggaggacaa catcatggtg accttcagga  2760
accaggccag caggccctac agcttctaca gcagcctgat cagctatgag gaggaccaga  2820
ggcaggggc tgagcccagg aagaactttg tgaagcccaa tgaaaccaag acctacttct  2880
ggaaggtgca gcaccacatg gcccccacca aggatgagtt tgactgcaag gcctgggcct  2940
acttctctga tgtggacctg gagaaggatg tgcactctgg cctgattggc cccctgctgg  3000
tgtgccacac caacaccctg aaccctgccc atggcaggca ggtgactgtg caggagtttg  3060
ccctgttctt caccatcttt gatgaaacca agagctggta cttcactgag aacatggaga  3120
ggaactgcag ggcccccctgc aacatccaga tggaggaccc caccttcaag gagaactaca  3180
ggttccatgc catcaatggc tacatcatgg acaccctgcc tggcctggtg atggcccagg  3240
accagaggat caggtggtac ctgctgagca tgggcagcaa tgagaacatc cacagcatcc  3300
acttctctgg ccatgtgttc actgtgagga agaaggagga gtacaagatg gccctgtaca  3360
acctgtaccc tggggtgttt gagactgtgg agatgctgcc cagcaaggct ggcatctgga  3420
gggtggagtg cctgattggg gagcacctgc atgctggcat gagcaccctg ttcctggtgt  3480
acagcaacaa gtgccagacc cccctgggca tggcctctgg ccacatcagg gacttccaga  3540
tcactgcctc tggccagtat ggccagtggg cccccaagct ggccaggctg cactactctg  3600
gcagcatcaa tgcctggagc accaaggagc ccttcagctg gatcaaggtg gacctgctgg  3660
cccccatgat catccatggc atcaagaccc agggggccag gcagaagttc agcagcctgt  3720
acatcagcca gttcatcatc atgtacagcc tggatggcaa gaagtggcag acctacaggg  3780
gcaacagcac tggcaccctg atggtgttct ttggcaatgt ggacagctct ggcatcaagc  3840
acaacatctt caacccccc atcattgcca gatacatcag gctgcacccc acccactaca  3900
gcatcaggag caccctgagg atggagctga tgggctgtga cctgaacagc tgcagcatgc  3960
ccctgggcat ggagagcaag gccatctctg atgcccagat cactgccagc agctacttca  4020
ccaacatgtt tgccacctgg agccccagca aggccaggct gcacctgcag ggcaggagca  4080
atgcctggag gccccaggtc aacaacccca aggagtggct gcaggtggac ttccagaaga  4140
ccatgaaggt gactggggtg accacccagg gggtgaagag cctgctgacc agcatgtatg  4200
tgaaggagtt cctgatcagc agcagccagg atggccacca gtggaccctg ttcttccaga  4260
atggcaaggt gaaggtgttc cagggcaacc aggacagctt caccccctgtg gtgaacagcc  4320
tggacccccc cctgctgacc agatacctga ggattcaccc ccagagctgg gtgcaccaga  4380
ttgccctgag gatggaggtg ctgggctgtg aggcccagga cctgtactga tcgcgaataa  4440
aagatcttta ttttcattag atctgtgtgt tggttttttg tgtg                   4484
```

```
SEQ ID NO: 327          moltype = DNA  length = 4502
FEATURE                 Location/Qualifiers
misc_feature            1..4502
                        note = Synthetic polynucleotide
misc_feature            1..4502
                        note = pCB1008
source                  1..4502
                        mol_type = other DNA
                        organism = synthetic construct
```

```
SEQUENCE: 327
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc ccccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga ccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagca  2340
atgacagcaa tgtgtctaac aagactcccc cagtgctgaa gaggcaccag agggagatca  2400
ccaggaccac cctgcagtct gaccaggagg agattgacta tgatgacacc atctctgtgg  2460
agatgaagaa ggaggacttt gacatctacg acgaggacga gaaccagagc cccaggagct  2520
tccagaagaa gaccaggcac tacttcattg ctgctgtgga gaggctgtgg gactatggca  2580
tgagcagcag cccccatgtg ctgaggaaca gggcccagtc tggctctgtg ccccagttca  2640
agaaggtggt gttccaggag ttcactgatg gcagcttcac ccagcccctg tacagagggg  2700
agctgaatga gcacctgggc ctgctgggcc cctacatcag ggctgaggtg gaggacaaca  2760
tcatggtgac cttcaggaac caggccagca ggccctacag cttctacagc agcctgatca  2820
gctatgagga ggaccagagg caggggggctg agcccaggaa gaactttgtg aagcccaatg  2880
aaaccaagac ctacttctgg aaggtgcagc accacatggc cccccaccaag gatgagtttg  2940
actgcaaggc ctgggcctac ttctctgatg tggacctgga gaaggatgtg cactctggcc  3000
tgattggccc cctgctggtg tgccacacca acaccctgaa ccctgcccat ggcaggcagg  3060
tgactgtgca ggagtttgcc ctgttcttca ccatctttga tgaaaccaag agctggtact  3120
tcactgagaa catggagagg aactgcaggg cccccctgcaa catccagatg gaggacccca  3180
ccttcaagga gaactacagg ttccatgcca tcaatggcta catcatggac accctgcctg  3240
gcctggtgat ggcccaggac cagaggatca ggtggtacct gctgagcatg ggcagcaatg  3300
agaacatcca cagcatccac ttctctggcc atgtgttcac tgtgaggaag aaggaggagt  3360
acaagatggc cctgtacaac ctgtaccctg ggggtgtttga gactgtggag atgctgccca  3420
gcaaggctgg catctggagg gtggagtgcc tgattgggga gcacctgcat gctggcatga  3480
gcaccctgtt cctggtgtac agcaacaagt gccagacccc cctgggcatg gcctctggcc  3540
acatcaggga cttccagatc actgcctctg gccagtatgg ccagtgggcc cccaagctgg  3600
ccaggctgca ctactctggc agcatcaatg cctggagcac caaggagccc ttcagctgga  3660
tcaaggtgga cctgctggcc cccatgatca tccatggcat caagacccag gggccaggc  3720
agaagttcag cagcctgtac atcagccagt tcatcatcat gtacagcctg gatggcaaga  3780
agtggcagac ctacaggggc aacagcactg gcaccctgat ggtgttcttt ggcaatgtgg  3840
acagctctgg catcaagcac aacatcttca accccccccat cattgccaga tacatcaggc  3900
tgcaccccac ccactacagc atcaggagca ccctgaggat ggagctgatg ggctgtgacc  3960
tgaacagctg cagcatgccc ctgggcatgg agagcaaggc catctctgat gcccagatca  4020
ctgccagcag ctacttcacc aacatgtttg ccacctggag ccccagcaag gccaggctgc  4080
acctgcaggg caggagcaat gcctggaggc cccaggtcaa caaccccaag gagtggctgc  4140
aggtggactt ccagaagacc atgaaggtga ctggggtgac cacccagggg gtgaagagcc  4200
tgctgaccag catgtatgtg aaggagttcc tgatcagcag cagccaggat ggccaccagt  4260
ggaccctgtt cttccagaat ggcaaggtga aggtgttcca gggcaaccag gacagcttca  4320
cccctgtggt gaacagcctg gacccccccc tgctgaccag atacctgagg attcaccccc  4380
agagctgggt gcaccagatt gccctgagga tggaggtgct gggctgtgag gcccaggacc  4440
tgtactgatc gcgaataaaa gatctttatt ttcattagat ctgtgtgttg gtttttgtg  4500
tg                                                                  4502

SEQ ID NO: 328         moltype = DNA  length = 4511
```

```
FEATURE                Location/Qualifiers
misc_feature           1..4511
                       note = Synthetic polynucleotide
misc_feature           1..4511
                       note = pCB1015
source                 1..4511
                       mol_type = other DNA
                       organism = synthetic construct
SEQUENCE: 328
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga ccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagca  2340
atgacagcaa tgtgtctaac aagactaaca atagcccccc agtgctgaag aggcaccaga  2400
gggagatcac caggaccacc ctgcagtctg accaggagga gattgactat gatgacacca  2460
tctctgtgga gatgaagaag gaggactttg acatctacga cgaggacgag aaccagagcc  2520
ccaggagctt ccagaagaag accaggcact acttcattgc tgctgtggag aggctgtggg  2580
actatggcat gagcagcagc ccccatgtgc tgaggaacag ggcccagtct ggctctgtgc  2640
cccagttcaa gaaggtggtg ttccaggagt tcactgatgg cagcttcacc cagcccctgt  2700
acagagggga gctgaatgag cacctgggcc tgctgggccc ctacatcagg gctgaggtgg  2760
aggacaacat catggtgacc ttcaggaacc aggccagcag gccctacagc ttctacagca  2820
gcctgatcag ctatgaggag gaccagaggc agggggctga gcccaggaag aactttgtga  2880
agcccaatga aaccaagacc tacttctgga aggtgcagca ccacatggcc cccaccaagg  2940
atgagtttga ctgcaaggcc tgggcctact tctctgatgt ggacctggag aaggatgtgc  3000
actctggcct gattggcccc ctgctggtgt gccacaccaa caccctgaac cctgcccatg  3060
gcaggcaggt gactgtgcag gagtttgccc tgttcttcac catctttgat gaaaccaaga  3120
gctggtactt cactgagaac atggagagga actgcagggc cccctgcaac atccagatgg  3180
aggaccccac cttcaaggag aactacaggt tccatgccat caatggctac atcatggaca  3240
ccctgcctgg cctggtgatg gcccaggacc agaggatcag gtggtacctg ctgagcatgg  3300
gcagcaatga gaacatccac agcatccact tctctggcca tgtgttcact gtgaggaaga  3360
aggaggagta caagatggcc ctgtacaacc tgtaccctgg ggtgtttgag actgtggaga  3420
tgctgcccag caaggctggc atctggaggg tggagtgcct gattggggag cacctgcatg  3480
ctggcatgag caccctgttc ctggtgtaca gcaacaagtg ccagaccccc ctgggcatgg  3540
cctctggcca catcagggac ttccagatca ctgcctctgg ccagtatggc cagtgggccc  3600
ccaagctggc caggctgcac tactctggca gcatcaatgc ctggagcacc aaggagccct  3660
tcagctggat caaggtggac ctgctggccc ccatgatcat ccatggcatc aagacccagg  3720
gggccaggca gaagttcagc agcctgtaca tcagccagtt catcatcatg tacagcctgg  3780
atggcaagaa gtggcagacc tacaggggca acagcactgg caccctgatg gtgttctttg  3840
gcaatgtgga cagctctggc atcaagcaca acatcttcaa cccccccatc attgccagat  3900
acatcaggct gcaccccacc cactacagca tcaggagcac cctgaggatg gagctgatgg  3960
gctgtgacct gaacagctgc agcatgcccc tgggcatgga gagcaaggcc atctctgatg  4020
cccagatcac tgccagcagc tacttcacca acatgtttgc cacctggagc cccagcaagg  4080
ccaggctgca cctgcagggc aggagcaatg cctggaggcc ccaggtcaac aaccccaagg  4140
agtggctgca ggtggacttc cagaagacca tgaaggtgac tggggtgacc acccaggggg  4200
```

```
tgaagagcct gctgaccagc atgtatgtga aggagttcct gatcagcagc agccaggatg  4260
gccaccagtg gaccctgttc ttccagaatg gcaaggtgaa ggtgttccag ggcaaccagg  4320
acagcttcac ccctgtggtg aacagcctgg acccccccct gctgaccaga tacctgagga  4380
ttcaccccca gagctgggtg caccagattg ccctgaggat ggaggtgctg ggctgtgagg  4440
cccaggacct gtactgatcg cgaataaaag atctttattt tcattagatc tgtgtgttgg  4500
tttttgtgt g                                                        4511

SEQ ID NO: 329          moltype = DNA  length = 4520
FEATURE                 Location/Qualifiers
misc_feature            1..4520
                        note = Synthetic polynucleotide
misc_feature            1..4520
                        note = pCB1016
source                  1..4520
                        mol_type = other DNA
                        organism = synthetic construct
SEQUENCE: 329
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga cccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatgggggagg  1440
tgggggacac cctgctgatc atcttcaaga accaggccag caggccctac aacatctacc  1500
cccatggcat cactgatgtg aggcccctgt acagcaggag gctgcccaag gggggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagca  2340
atgacagcaa tgtgtctaac aagactaaca atagcaatgc caccccccca gtgctgaaga  2400
ggcaccagag ggagatcacc aggaccaccc tgcagtctga ccaggaggag attgactatg  2460
atgacaccat ctctgtggag atgaagaagg aggactttga catctacgac gaggacgaga  2520
accagagccc caggagcttc cagaagaaga ccaggcacta cttcattgct gctgtggaga  2580
ggctgtggga ctatggcatg agcagcagcc cccatgtgct gaggaacagg gcccagtctg  2640
gctctgtgcc ccagttcaag aaggtggtgt tccaggagtt cactgatggc agcttcaccc  2700
agcccctgta cagaggggag ctgaatgagc acctgggcct gctgggcccc tacatcaggg  2760
ctgaggtgga ggacaacatc atggtgacct tcaggaacca ggccagcagg ccctacagct  2820
tctacagcag cctgatcagc tatgaggagg accagaggca gggggctgag cccaggaaga  2880
actttgtgaa gcccaatgaa accaagacct acttctggaa ggtgcagcac cacatggccc  2940
ccaccaagga tgagtttgac tgcaaggcct gggcctactt ctctgatgtg gacctggaga  3000
aggatgtgca ctctggcctg attggccccc tgctggtgtg ccacaccaac accctgaacc  3060
ctgcccatgg caggcaggtg actgtgcagg agtttgccct gttcttcacc atctttgatg  3120
aaaccaagag ctggtacttc actgagaaca tggagaggaa ctgcagggcc ccctgcaaca  3180
tccagatgga ggacccccacc ttcaaggaga actacaggtt ccatgccatc aatggctaca  3240
tcatggacac cctgcctggc ctggtgatgg cccaggacca gaggatcagg tggtacctgc  3300
tgagcatggg cagcaatgag aacatccaca gcatccactt ctctggccat gtgttcactg  3360
tgaggaagaa ggaggagtac aagatggccc tgtacaacct gtaccctggg gtgtttgaga  3420
ctgtggagat gctgcccagc aaggctggca tctggagggt ggagtgcctg attggggagc  3480
acctgcatgc tggcatgagc accctgttcc tggtgtacag caacaagtgc cagacccccc  3540
tgggcatggc ctctggccac atcagggact tccagatcac tgcctctggc cagtatggcc  3600
agtgggcccc caagctggcc aggctgcact actctggcag catcaatgcc tggagcacca  3660
aggagccctt cagctggatc aaggtggacc tgctggcccc catgatcatc catggcatca  3720
```

```
agacccaggg ggccaggcag aagttcagca gcctgtacat cagccagttc atcatcatgt  3780
acagcctgga tggcaagaag tggcagacct acaggggcaa cagcactggc accctgatgg  3840
tgttctttgg caatgtggac agctctggca tcaagcacaa catcttcaac ccccccatca  3900
ttgccagata catcaggctg caccccaccc actacagcat caggagcacc ctgaggatgg  3960
agctgatggg ctgtgacctg aacagctgca gcatgcccct gggcatggag agcaaggcca  4020
tctctgatgc ccagatcact gccagcagct acttcaccaa catgtttgcc acctggagcc  4080
ccagcaaggc caggctgcac ctgcagggca ggagcaatgc ctggaggccc caggtcaaca  4140
accccaagga gtggctgcag gtggacttcc agaagaccat gaaggtgact ggggtgacca  4200
cccaggggt gaagagcctg ctgaccagca tgtatgtgaa ggagttcctg atcagcagca  4260
gccaggatgg ccaccagtgg accctgttct tccagaatgg caaggtgaag gtgttccagg  4320
gcaaccagga cagcttcacc cctgtggtga acagcctgga ccccccccctg ctgaccagat  4380
acctgaggat tcacccccag agctgggtgc accagattgc cctgaggatg gaggtgctgg  4440
gctgtgaggc ccaggacctg tactgatcgc gaataaaaga tctttatttt cattagatct  4500
gtgtgttggt tttttgtgtg                                             4520
```

```
SEQ ID NO: 330          moltype = DNA  length = 4475
FEATURE                 Location/Qualifiers
misc_feature            1..4475
                        note = Synthetic polynucleotide
misc_feature            1..4475
                        note = pCB1017
source                  1..4475
                        mol_type = other DNA
                        organism = synthetic construct
SEQUENCE: 330
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga cccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg ccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc aacaccagcc  2340
ccccagtgct gaagaggcac cagagggaga tcaccaggac caccctgcag tctgaccagg  2400
aggagattga ctatgatgac accatctctg tggagatgaa gaaggaggac tttgacatct  2460
acgacgagga cgagaaccag agccccagga gcttccagaa gaagaccagg cactacttca  2520
ttgctgctgt ggagaggctg tgggactatg gcatgagcag cagcccccat gtgctgagga  2580
acagggccca gtctggctct gtgccccagt tcaagaaggt ggtgttccag gagttcactg  2640
atggcagctt cacccagccc ctgtacagag gggagctgaa tgagcacctg ggcctgctgg  2700
gcccctacat cagggctgag gtggaggaca acatcatggt gaccttcagg aaccaggcca  2760
gcaggcccta cagcttctac agcagcctga tcagctatga ggaggaccag aggcaggggg  2820
ctgagcccag gaagaacttt gtgaagccca atgaaaccaa gacctacttc tggaaggtgc  2880
agcaccacat ggcccccacc aaggatgagt ttgactgcaa ggcctgggcc tacttctctg  2940
atgtggacct ggagaaggat gtgcactctg gcctgattgg cccccctgctg gtgtgccaca  3000
ccaacaccct gaaccctgcc catggcaggc aggtgactgt gcaggagttt gccctgttct  3060
tcaccatctt tgatgaaacc aagagctggt acttcactga gaacatggag aggaactgca  3120
gggcccccctg caacatccag atggaggacc ccaccttcaa ggagaactac aggttccatg  3180
ccatcaatgg ctacatcatg gacaccctgc ctggcctggt gatggcccag gaccagagga  3240
```

```
tcaggtggta cctgctgagc atgggcagca atgagaacat ccacagcatc cacttctctg  3300
gccatgtgtt cactgtgagg aagaaggagg agtacaagat ggccctgtac aacctgtacc  3360
ctggggtgtt tgagactgtg gagatgctgc ccagcaaggc tggcatctgg agggtggagt  3420
gcctgattgg ggagcacctg catgctggca tgagcaccct gttcctggtg tacagcaaca  3480
agtgccagac ccccctgggc atggcctctg gccacatcag ggacttccag atcactgcct  3540
ctggccagta tggccagtgg gcccccaagc tggccaggct gcactactct ggcagcatca  3600
atgcctggag caccaaggag cccttcagct ggatcaaggt ggacctgctg gcccccatga  3660
tcatccatgg catcaagacc caggggggcca ggcagaagtt cagcagcctg tacatcagcc  3720
agttcatcat catgtacagc ctggatggca agaagtggca gacctacagg ggcaacagca  3780
ctggcaccct gatggtgttc tttggcaatg tggacagctc tggcatcaag cacaacatct  3840
tcaacccccc catcattgcc agatacatca ggctgcaccc cacccactac agcatcagga  3900
gcaccctgag gatggagctg atgggctgtg acctgaacag ctgcagcatg cccctgggca  3960
tggagagcaa ggccatctct gatgcccaga tcactgccag cagctacttc accaacatgt  4020
ttgccacctg gagccccagc aaggccaggc tgcacctgca gggcaggagc aatgcctgga  4080
ggccccaggt caacaacccc aaggagtggc tgcaggtgga cttccagaag accatgaagg  4140
tgactggggt gaccacccag ggggtgaaga gcctgctgac cagcatgtat gtgaaggagt  4200
tcctgatcag cagcagccag gatggccacc agtggaccct gttcttccag aatggcaagg  4260
tgaaggtgtt ccagggcaac caggacagct tcacccctgt ggtgaacagc ctggaccccc  4320
ccctgctgac cagatacctg aggattcacc cccagagctg ggtgcaccag attgccctga  4380
ggatggaggt gctgggctgt gaggcccagg acctgtactg atcgcgaata aaagatcttt  4440
attttcatta gatctgtgtg ttggtttttt gtgtg                             4475
```

```
SEQ ID NO: 331          moltype = DNA  length = 4466
FEATURE                 Location/Qualifiers
misc_feature            1..4466
                        note = Synthetic polynucleotide
misc_feature            1..4466
                        note = pCB1018
source                  1..4466
                        mol_type = other DNA
                        organism = synthetic construct
SEQUENCE: 331
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc ccccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga ccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc taacaacagc cccccagtgc  2340
tgaagaggca ccagagggag atcaccagga ccaccctgca gtctgaccag gaggagattg  2400
actatgatga caccatctct gtggagatga agaaggagga ctttgacatc tacgacgagg  2460
acgagaacca gagccccagg agcttccaga agaagaccag gcactacttc attgctgctg  2520
tggagaggct gtgggactat ggcatgagca gcagccccca tgtgctgagg aacagggccc  2580
agtctggctc tgtgccccag ttcaagaagg tggtgttcca ggagttcact gatggcagct  2640
tcacccagcc cctgtacaga ggggagctga atgagcacct gggcctgctg ggcccctaca  2700
tcagggctga ggtggaggac aacatcatgg tgaccttcag gaaccaggcc agcaggccct  2760
acagcttcta cagcagcctg atcagctatg aggaggacca gaggcagggg gctgagccca  2820
```

```
ggaagaactt tgtgaagccc aatgaaacca agacctactt ctggaaggtg cagcaccaca  2880
tggcccccac caaggatgag tttgactgca aggcctgggc ctacttctct gatgtggacc  2940
tggagaagga tgtgcactct ggcctgattg gcccccctgct ggtgtgccac accaacaccc  3000
tgaaccctgc ccatggcagg caggtgactg tgcaggagtt tgccctgttc ttcaccatct  3060
ttgatgaaac caagagctgg tacttcactg agaacatgga gaggaactgc agggcccccct  3120
gcaacatcca gatggaggac ccccaccttca aggagaacta caggttccat gccatcaatg  3180
gctacatcat ggacaccctg cctggcctgg tgatggccca ggaccagagg atcaggtggt  3240
acctgctgag catgggcagc aatgagaaca tccacagcat ccacttctct ggccatgtgt  3300
tcactgtgag gaagaaggag gagtacaaga tggccctgta caacctgtac cctggggtgt  3360
ttgagactgt ggagatgctg cccagcaagg ctggcatctg gagggtggag tgcctgattg  3420
gggagcacct gcatgctggc atgagcaccc tgttcctggt gtacagcaac aagtgccaga  3480
ccccccctggg catggcctct ggccacatca gggacttcca gatcactgcc tctggccagt  3540
atggccagtg ggcccccaag ctggccaggc tgcactactc tggcagcatc aatgcctgga  3600
gcaccaagga gcccttcagc tggatcaagg tggacctgct ggccccccatg atcatccatg  3660
gcatcaagac ccagggggcc aggcagaagt tcagcagcct gtacatcagc cagttcatca  3720
tcatgtacag cctggatggc aagaagtggc agacctacag gggcaacagc actggcaccc  3780
tgatggtgtt ctttggcaat gtggacagct ctggcatcaa gcacaacatc ttcaaccccc  3840
ccatcattgc cagatacatc aggctgcacc ccacccacta cagcatcagg agcaccctga  3900
ggatggagct gatgggctgt gacctgaaca gctgcagcat gcccctgggc atggagagca  3960
aggccatctc tgatgcccag atcactgcca gcagctactt caccaacatg tttgccacct  4020
ggagccccag caaggccagg ctgcacctgc agggcaggag caatgcctgg aggccccagg  4080
tcaacaaccc caaggagtgg ctgcaggtgg acttccagaa gaccatgaag gtgactgggg  4140
tgaccaccca gggggtgaag agcctgctga ccagcatgta tgtgaaggag ttcctgatca  4200
gcagcagcca ggatggccac cagtggaccc tgttcttcca gaatggcaag gtgaaggtgt  4260
tccagggcaa ccaggacagc ttcacccctg tggtgaacag cctggacccc cccctgctga  4320
ccagatacct gaggattcac ccccagagct gggtgcacca gattgccctg aggatggagg  4380
tgctgggctg tgaggcccag gacctgtact gatcgcgaat aaaagatctt tattttcatt  4440
agatctgtgt gttggttttt tgtgtg                                      4466
```

```
SEQ ID NO: 332          moltype = DNA  length = 4484
FEATURE                 Location/Qualifiers
misc_feature            1..4484
                        note = Synthetic polynucleotide
misc_feature            1..4484
                        note = pCB1019
source                  1..4484
                        mol_type = other DNA
                        organism = synthetic construct
SEQUENCE: 332
tgccagttcc cgatcgttac aggcggtact cctcaaagcg tactaaagaa ttattctttt  60
acatttcagt ggccaccaga aggtactacc tgggagctgt ggaactgagc tgggactaca  120
tgcagtctga cctgggagag ctgcctgtgg atgctagatt tcctccaaga gtgcccaaga  180
gcttcccctt caacacctct gtggtgtaca agaaaaccct gtttgtggaa ttcacagacc  240
acctgttcaa tattgccaag cctagacctc cttggatggg cctgctgggc cctacaattc  300
aggctgaggt gtatgacaca gtggtcatca ccctgaagaa catggccagc catcctgtgt  360
ctctgcatgc tgtgggagtg tcttactgga aggcttctga gggggctgag tatgatgacc  420
agacaagcca gagagagaaa gaggatgaca aggttttccc tgggggcagc cacacctatg  480
tctggcaggt cctgaaagaa aatggcccta tggcctctga tcctctgtgc ctgacataca  540
gctacctgag ccatgtggac ctggtcaagg acctgaactc tggcctgatt ggggctctgc  600
tggtgtgtag agaaggcagc ctggccaaag aaaagaccca gacactgcac aagttcatcc  660
tgctgtttgc tgtgtttgat gagggcaaga gctggcactc tgagacaaag aacagcctga  720
tgcaggacag agatgctgcc tctgctagag cttggcccaa gatgcacaca gtgaatggct  780
atgtgaacag aagcctgcct ggactgattg gatgccacag aaagtctgtg tactggcatg  840
tgattggcat gggcaccaca cctgaggtgc acagcatctt tctggaagga cacaccttcc  900
tggtgaggaa ccacagacag gccagcctgg aaatcagccc tatcaccttc ctgacagctc  960
agaccctgct gatggatctg ggccagtttc tgctgttctg ccacatcagc agccaccagc  1020
atgatggcat ggaagcctat gtgaaggtgg acagctgccc tgaagaaccc cagctgagaa  1080
tgaagaacaa tgaggaagct gaggactatg atgatgacct gacagactct gagatggatg  1140
tggtcagatt tgatgatgat aacagcccca gcttcatcca gatcagatct gtggccaaga  1200
agcaccccaa gacctgggtg cactatattg ctgctgagga agaggactgg gattatgctc  1260
ctctggtgct ggcccctgat gacagaagct acaagagcca gtacctgaac aatggccctc  1320
agagaattgg caggaagtat aagaaagtga ggttcatggc ctacacagat gagacattca  1380
agaccagaga ggctatccag catgagtctg gcattctggg acctctgctg tatggggaag  1440
tgggggacac actgctgatc atcttcaaga accaggccag cagaccctac aacatctacc  1500
ctcatggcat cacagatgtg aggcctctgt actctagaag gctgcccaag gggtgaagc   1560
acctgaagga cttccctatc ctgcctgggg agatcttcaa gtacaagtgg acagtgacag  1620
tggaggatgg ccctaccaag tctgatccta gatgcctgac aaggtactac agcagctttg  1680
tgaacatgga aagggacctg gcctctggcc tgattggtcc tctgctgatc tgctacaaag  1740
aatctgtgga ccagaggggc aaccagatca tgagtgacaa gagaaatgtg atcctgttct  1800
ctgtctttga tgagaacagg tcctggtatc tgacagagaa catccagagg tttctgccca  1860
atcctgctgg ggtgcagctg gaagatcctg agttccaggc ctccaacatc atgcactcca  1920
tcaatggcta tgtgtttgac agcctgcagc tgtctgtgtg cctgcatgaa gtggcctact  1980
ggtacatcct gtctattggg gcccagacag acttcctgtc tgtgttcttt tctggctaca  2040
ccttcaagca caagatggtg tatgaggata ccctgacact gttcccattc tctggggaga  2100
cagtgttcat gagcatggaa aaccctggcc tgtggatcct gggctgtcac aacagtgact  2160
tcagaaacag aggcatgaca gccctgctga aggtgtccag ctgtgacaag aacactgggg  2220
actactatga ggactcttat gaggacatct ctgcctacct gctgagcaag aacaatgcca  2280
ttgagcctag gagcttctct cagaacgcca ctaatgtgtc taacaacagc aacaccagca  2340
atgacagccc tcctgtgctg aagagacacc agagggagat caccagaacc acactgcagt  2400
```

```
ctgaccaaga ggaaattgat tatgatgaca ccatctctgt ggagatgaag aaagaagatt  2460
ttgacatcta tgatgaggat gagaatcaga gccccagatc tttccagaag aaaacaaggc  2520
actacttcat tgctgctgtg gaaagactgt gggactatgg catgagcagc agcccccatg  2580
tgctgagaaa cagggcccag tctggaagtg tgccccagtt caagaaagtg gtgttccaag  2640
agttcacaga tggcagcttc acccagcctc tgtatagagg ggagctgaat gagcacctgg  2700
gactgctggg accttacatc agagctgagg tggaggataa catcatggtc acctttagaa  2760
accaggcctc taggccctac tccttctaca gctccctgat cagctatgaa gaggaccaga  2820
gacagggggc tgagcccaga aagaactttg tgaagcccaa tgagactaag acctactttt  2880
ggaaggtgca gcaccacatg gcccctacaa aggatgagtt tgactgcaag gcctgggcct  2940
acttctctga tgtggacctg gagaaggatg tgcactctgg actcattgga cccctgcttg  3000
tgtgccacac caacacactg aatcctgctc atggcaggca agtgacagtg caagagtttg  3060
ccctgttctt caccatcttt gatgagacaa agtcctggta cttcacagaa aacatggaaa  3120
gaaactgcag ggccccttgc aacatccaga tggaagatcc caccttcaaa gagaactaca  3180
ggttccatgc catcaatggc tacatcatgg acactctgcc tggcctggtt atggcacagg  3240
atcagaggat cagatggtat ctgctgtcca tgggctccaa tgagaatatc cacagcatcc  3300
acttctctgg ccatgtgttc acagtgagga aaaaagaaga gtacaagatg gccctgtaca  3360
atctgtaccc tggggtgttt gagactgtgg aaatgctgcc tagcaaggct ggaatctgga  3420
gggtggaatg tctgattgga gagcatctgc atgctggaat gtctaccctg ttcctggtgt  3480
acagcaacaa gtgtcagacc cctctgggca tggcctctgg acacatcaga gacttccaga  3540
tcacagcctc tggccagtat ggacagtggg ctcctaaact ggctagactg cactactctg  3600
gcagcatcaa tgcctggtcc accaaagagc ccttcagctg gatcaaggtg gacctgctgg  3660
ctcccatgat catccatgga atcaagaccc agggggccag acagaagttc agcagcctgt  3720
acatcagcca gttcatcatc atgtacagcc tggatggcaa gaagtggcag acctacagag  3780
gcaacagcac aggcacactc atggtgttct ttggcaatgt ggactcttct ggcattaagc  3840
acaacatctt caaccctcca atcattgcca ggtacatcag gctgcacccc acacactaca  3900
gcatcagatc taccctgagg atggaactga tgggctgtga cctgaacagc tgctctatgc  3960
ccctgggaat ggaaagcaag gccatctctg atgcccagat cacagccagc agctacttca  4020
ccaacatgtt tgccacatgg tccccatcta aggccaggct gcatctgcag ggcagatcta  4080
atgcttggag gccccaagtg aacaacccca aagagtggct gcaggtggac tttcagaaaa  4140
ccatgaaagt gacaggagtg accacacagg gggtcaagtc tctgctgacc tctatgtatg  4200
tgaaagagtt cctgatctcc agcagccagg atggccacca gtggaccctg tttttccaga  4260
atggcaaagt caaggtgttc cagggaaacc aggacagctt cacacctgtg gtcaactccc  4320
tggatcctcc actgctgacc agatacctga gaattcaccc tcagtcttgg gtgcaccaga  4380
ttgctctgag aatggaagtg ctgggatgtg aagctcagga cctctactaa tcgcgaataa  4440
aagatcttta ttttcattag atctgtgtgt tggttttttg tgtg                  4484

SEQ ID NO: 333          moltype = DNA  length = 4484
FEATURE                 Location/Qualifiers
misc_feature            1..4484
                        note = Synthetic polynucleotide
misc_feature            1..4484
                        note = pCB1020
source                  1..4484
                        mol_type = other DNA
                        organism = synthetic construct
SEQUENCE: 333
tgccagttcc cgatcgttac aggcggtact cctcaaagcg tactaaagaa ttattctttt  60
acatttcagt ggctaccaga agatactacc tgggagctgt ggaactgagc tgggattaca  120
tgcagtctga cctgggagag ctgcctgtgg atgctagatt cccacctaga gtccctaagt  180
ccttcccctt caacacctct gtggtctaca agaaaaccct gtttgtggag tttacagacc  240
acctgttcaa cattgctaag cctagaccac catggatggg actgctggga ccaaccatcc  300
aggcagaggt gtatgacaca gtggtcatca ccctgaaaaa catggcttct caccctgtgt  360
ccctgcatgc tgtgggagtc tcctactgga aggcctctga aggggctgag tatgatgatc  420
agaccagcca gaggggaaaa gaggatgata aggtgttccc tggagggtcc catacctatg  480
tgtggcaggt cctgaaggag aatggaccaa tggcttctga ccctctgtgc ctgacctact  540
cttatctgtc ccatgtggac ctggtcaagg atctgaactc tggcctgatt ggggctctgc  600
tggtgtgtag ggaagggtcc ctggccaagg agaaaaccca gaccctgcat aagttcatcc  660
tgctgtttgc tgtgtttgat gaaggaaaaa gctggcactc tgagaccaag aactctctga  720
tgcaggacag ggatgctgct tctgccagag cttggcccaa gatgcacaca gtgaatggct  780
atgtcaatag gagcctgcct ggactgattg gctgccacag aaagtctgtg tattggcatg  840
tcattggaat gggcaccacc cctgaagtgc acagcatctt cctggagggg catacctttc  900
tggtcaggaa ccacaggcag gctagcctgg agatctctcc aatcaccttc ctgacagccc  960
agaccctgct gatggacctg ggacagttcc tgctgttttg ccacatctcc agccaccagc  1020
atgatggcat ggaggcttat gtgaaagtgg actcctgtcc tgaggaacct cagctgagga  1080
tgaagaacaa tgaggaagct gaagactatg atgatgacct gacagactct gagatggatg  1140
tggtcaggtt tgatgatgat aactctccct cctttatcca gatcaggtct gtggccaaga  1200
aacaccctaa gacctgggtc cattacattg ctgctgagga agaggactgg gattatgctc  1260
cactggtgct ggcccctgat gatagatcct acaaaagcca gtatctgaac aatggacccc  1320
agaggattgg cagaaagtac aagaaagtga ggttcatggc ttatacagat gagaccttta  1380
agaccagaga agccatccag catgagtctg ggatcctggg acctctgctg tatggggaag  1440
tgggggacac cctgctgatc atcttcaaga accaggccag caggccttac aatatctatc  1500
cacatggcat cacagatgtg agacctctgt actccaggag gctgccaaag gggtgaaac  1560
acctgaagga cttcccaatc ctgcctgggg aaatctttaa gtataaatgg acagtcacag  1620
tggaggatgg gcccaccaag tctgacccta ggtgcctgac cagatactat tcttcctttg  1680
tgaatatgga gagagacctg gcttctggac tgattggacc cctgctgatc tgttacaaag  1740
agtctgtgga tcagaggggc aaccagatca tgtctgacaa gaggaatgtg atcctgttct  1800
ctgtctttga tgaaaacagg tcttggtacc tgacagagaa catccagagg ttcctgccta  1860
atccagctgg agtgcagctg gaagatcctg agttccaggc ctctaacatc atgcattcca  1920
tcaatggcta tgtgtttgac tccctgcagc tgtctgtgtg cctgcatgag gtggcttact  1980
```

```
ggtatatcct gagcattgga gcccagacag atttcctgtc tgtgttcttt tctggctaca  2040
cctttaagca taaaatggtg tatgaggaca ccctgaccct gttcccattt tctggagaaa  2100
ctgtgttcat gagcatggag aatcctgggc tgtggatcct gggatgccac aactctgatt  2160
tcaggaatag agggatgaca gccctgctga aagtgagctc ttgtgacaag aacacaggag  2220
actactatga agatagctat gaggacatct ctgcttatct gctgtccaaa aacaatgcca  2280
ttgagcccag gagcttctct cagaacgcca ctaatgtgtc taacaacagc aacaccagca  2340
atgacagccc tccagtgctg aagaggcacc agagggagat caccagaacc accctgcagt  2400
ctgatcagga agagattgac tatgatgata ccatctctgt ggaaatgaag aaagaggact  2460
ttgatatcta tgatgaagat gagaaccagt ctcccaggtc cttccagaag aaaaccagac  2520
attactttat tgctgctgtg gagaggctgt gggactatgg catgtccagc tctcctcatg  2580
tgctgagaaa tagagctcag tctggatctg tcccacagtt caagaaagtg gtcttccagg  2640
agtttacaga tggaagcttt acccagccac tgtacagggg agaactgaat gagcacctgg  2700
ggctgctggg accctatatc agggctgaag tggaggataa catcatggtc accttcagga  2760
atcaggccag cagaccctac tctttttatt ccagcctgat ctcctatgaa gaggaccaga  2820
gacagggagc tgaaccaaga aaaaactttg tgaagcctaa tgagaccaaa acctactttt  2880
ggaaggtgca gcaccatatg gcccctacca aagatgagtt tgattgcaag gcctgggctt  2940
atttttctga tgtggatctg gagaaggatg tccactctgg cctgattggg ccactgctgg  3000
tgtgtcatac caacaccctg aatccagctc atggaaggca ggtgacagtc caggaatttg  3060
ccctgttctt taccatcttt gatgagacca agagctggta cttcacagaa aacatggaga  3120
ggaattgcag agccccatgt aacatccaga tggaagaccc caccttcaag gagaactaca  3180
gatttcatgc tatcaatggg tatatcatgg ataccctgcc aggactggtc atggctcagg  3240
accagaggat cagatggtac ctgctgagca tggggtctaa tgagaatatc cactccatcc  3300
atttctctgg acatgtgttt acagtaagga agaaagaaga gtacaagatg gccctgtaca  3360
acctgtatcc tggggtgttt gaaacagtgg agatgctgcc ttccaaggct gggatctgga  3420
gggtggaatg cctgattggg gagcacctgc atgctggaat gtctaccctg ttcctggtgt  3480
actccaataa gtgtcagacc cccctgggga tggcttctgg acatatcagg gacttccaga  3540
tcacagcttc tggacagtat ggacagtggg ctcctaagct ggctagactg cactattctg  3600
gctccatcaa tgcttggtct accaaagagc ctttctcctg gatcaaggtg gacctgctgg  3660
ctccaatgat catccatggc atcaaaaccc agggggccag gcagaagttc tcttccctgt  3720
acatcagcca gtttatcatc atgtattctc tggatgggaa gaaatggcag acctacagag  3780
gcaattccac agggaccctg atggtgttct ttggcaatgt ggacagctct gggatcaagc  3840
acaacatctt caatcccccct atcattgcca ggtacatcag actgcaccca acccattatt  3900
ccatcaggag caccctgaga atggagctga tggggtgtga tctgaacagc tgttctatgc  3960
cccctgggaat ggagtctaag gccatctctg atgctcagat cacagcctcc agctacttca  4020
ccaatatgtt tgctacctgg tccccaagca aggctagact gcatctgcag ggaagaagca  4080
atgcttggag accacaggtg aacaatccca aggagtggct gcaggtggac ttccagaaaa  4140
ccatgaaggt gacaggagtc accacccagg gagtgaaaag cctgctgacc tctatgtatg  4200
tcaaggagtt cctgatctct tccagccagg atgggcacca gtggaccctg ttctttcaga  4260
atggaaaggt gaaagtcttc cagggcaatc aggattcctt taccccctgtg gtcaacagcc  4320
tggacccacc cctgctgacc aggtacctga gaatccaccc acagtcctgg gtgcatcaga  4380
ttgctctgag gatggaagtc ctgggctgtg aggcccagga cctgtattga tcgcgaataa  4440
aagatcttta ttttcattag atctgtgtgt tggttttttg tgtg                  4484
```

SEQ ID NO: 334 moltype = DNA length = 4484
FEATURE Location/Qualifiers
misc_feature 1..4484
note = Synthetic polynucleotide
misc_feature 1..4484
note = pCB1025
source 1..4484
mol_type = other DNA
organism = synthetic construct

SEQUENCE: 334

```
tgccagttcc cgatcgttac aggcggtact cctcaaagcg tactaaagaa ttattctttt  60
acatttcagt ggccaccaga aggtactacc tgggagctgt ggaactgagc tgggactaca  120
tgcagtctga cctgggagag ctgcctgtgg atgctagatt tcctccaaga gtgcccaaga  180
gcttcccctt caacacctct gtggtgtaca agaaaaccct gtttgtggaa ttcacagacc  240
acctgttcaa tattgccaag cctagacctc cttggatggg cctgctgggc cctacaattc  300
aggctgaggt gtatgacaca gtggtcatca ccctgaagaa catggccagc catcctgtgt  360
ctctgcatgc tgtgggagtg tcttactgga aggcttctga gggggctgag tatgatgacc  420
agacaagcca gagagagaaa gaggatgaca aggttttccc tgggggcagc cacacctatg  480
tctggcaggt cctgaaagaa aatggcccta tggcctctga tcctctgtgc ctgacataca  540
gctacctgag ccatgtggac ctggtcaagg acctgaactc tggcctgatt ggggctctgc  600
tggtgtgtag agaaggcagc ctggccaaag aaaagaccca gacactgcac aagttcatcc  660
tgctgtttgc tgtgtttgat gagggcaaga gctggcactc tgagacaaag aacagcctga  720
tgcaggacag agatgctgcc tctgctagag cttggcccaa gatgcacaca gtgaatggct  780
atgtgaacag aagcctgcct ggactgattg gatgccacag aaagtctgtg tactggcatg  840
tgattggcat gggcaccaca cctgaggtgc acagcatctt tctggaagga cacaccttcc  900
tggtgaggaa ccacagacag gccagcctgg aaatcagccc tatcaccttc ctgacagctc  960
agaccctgct gatggatctg ggccagtttc tgctggcctg ccacatcagc agccaccagc  1020
atgatggcat ggaagcctat gtgaaggtgg acagctgccc tgaagaaccc cagctgagaa  1080
tgaagaacaa tgaggaagct gaggactatg atgatgacct gacagactct gagatggatg  1140
tggtcagatt tgatgatgat aacagcccca gcttcatcca gatcagatct gtggccaaga  1200
agcaccccaa gacctgggtg cactatattg ctgctgagga agaggactgg gattatgctc  1260
ctctggtgct ggcccctgat gacagaagct acaagagcca gtacctgaac aatggccctc  1320
agagaattgg caggaagtat aagaaagtga ggttcatggc ctacacagat gagacattca  1380
agaccagaga ggctatccag catgagtctg gcattctggg acctctgctg tatggggaag  1440
tgggggacac actgctgatc atcttcaaga accaggccag cagaccctac aacatctacc  1500
ctcatggcat cacagatgtg aggcctctgt actctagaag gctgcccaag ggggtgaagc  1560
```

-continued

```
acctgaagga cttccctatc ctgcctgggg agatcttcaa gtacaagtgg acagtgacag  1620
tggaggatgg ccctaccaag tctgatccta gatgcctgac aaggtactac agcagctttg  1680
tgaacatgga aagggacctg gcctctggcc tgattggtcc tctgctgatc tgctacaaag  1740
aatctgtgga ccagaggggc aaccagatca tgagtgacaa gagaaatgtg atcctgttct  1800
ctgtctttga tgagaacagg tcctggtatc tgacagagaa catccagagg tttctgccca  1860
atcctgctgg ggtgcagctg gaagatcctg agttccaggc ctccaacatc atgcactcca  1920
tcaatggcta tgtgtttgac agcctgcagc tgtctgtgtg cctgcatgaa gtggcctact  1980
ggtacatcct gtctattggg gcccagacag acttcctgtc tgtgttcttt tctggctaca  2040
ccttcaagca caagatggtg tatgaggata ccctgacact gttcccattc tctggggaga  2100
cagtgttcat gagcatggaa aaccctggcc tgtggatcct gggctgtcac aacagtgact  2160
tcagaaacag aggcatgaca gccctgctga aggtgtccag ctgtgacaag aacactgggg  2220
actactatga ggactcttat gaggacatct ctgcctacct gctgagcaag aacaatgcca  2280
ttgagcctag gagcttctct cagaacgcca ctaatgtgtc taacaacagc aacaccagca  2340
atgacagccc tcctgtgctg aagagacacc agagggagat caccagaacc acactgcagt  2400
ctgaccaaga ggaaattgat tatgatgaca ccatctctgt ggagatgaag aaagaagatt  2460
ttgacatcta tgatgaggat gagaatcaga gccccagatc tttccagaag aaaacaaggc  2520
actacttcat tgctgctgtg gaaagactgt gggactatgg catgagcagc agcccccatg  2580
tgctgagaaa cagggcccag tctggaagtg tgccccagtt caagaaagtg gtgttccaag  2640
agttcacaga tggcagcttc acccagcctc tgtatagagg ggagctgaat gagcacctgg  2700
gactgctggg accttacatc agagctgagg tggaggataa catcatggtc acctttagaa  2760
accaggcctc taggccctac tccttctaca gctccctgat cagctatgaa gaggaccaga  2820
gacagggggc tgagcccaga aagaactttg tgaagcccaa tgagactaag acctactttt  2880
ggaaggtgca gcaccacatg gcccctacaa aggatgagtt tgactgcaag gcctgggcct  2940
acttctctga tgtggacctg gagaaggatg tgcactctgg actcattgga cccctgcttg  3000
tgtgccacac caacacactg aatcctgctc atggcaggca agtgacagtg caagagtttg  3060
ccctgttctt caccatcttt gatgagacaa agtcctggta cttcacagaa aacatggaaa  3120
gaaactgcag ggccccttgc aacatccaga tggaagatcc caccttcaaa gagaactaca  3180
ggttccatgc catcaatggc tacatcatgg acactctgcc tggcctggtt atggcacagg  3240
atcagaggat cagatggtat ctgctgtcca tgggctccaa tgagaatatc cacagcatcc  3300
acttctctgg ccatgtgttc acagtgagga aaaaagaaga gtacaagatg gccctgtaca  3360
atctgtaccc tggggtgttt gagactgtgg aaatgctgcc tagcaaggct ggaatctgga  3420
gggtggaatg tctgattgga gagcatctgc atgctggaat gtctaccctg ttcctggtgt  3480
acagcaacaa gtgtcagacc cctctgggca tggcctctgg acacatcaga gacttccaga  3540
tcacagcctc tggccagtat ggacagtggg ctcctaaact ggctagactg cactactctg  3600
gcagcatcaa tgcctggtcc accaaagagc ccttcagctg gatcaaggtg gacctgctgg  3660
ctcccatgat catccatgga atcaagaccc agggggccag acagaagttc agcagcctgt  3720
acatcagcca gttcatcatc atgtacagcc tggatggcaa gaagtggcag acctacagag  3780
gcaacagcac aggcacactc atggtgttct ttggcaatgt ggactcttct ggcattaagc  3840
acaacatctt caaccctcca atcattgcca ggtacatcag gctgcacccc acacactaca  3900
gcatcagatc taccctgagg atggaactga tgggctgtga cctgaacagc tgctctatgc  3960
ccctgggaat ggaaagcaag gccatctctg atgcccagat cacagccagc agctacttca  4020
ccaacatgtt tgccacatgg tccccatcta aggccaggct gcatctgcag ggcagatcta  4080
atgcttggag gccccaagtg aacaacccca aagagtggct gcaggtggac tttcagaaaa  4140
ccatgaaagt gacaggagtg accacacagg gggtcaagtc tctgctgacc tctatgtatg  4200
tgaaagagtt cctgatctcc agcagccagg atggccacca gtggaccctg tttttccaga  4260
atggcaaagt caaggtgttc cagggaaacc aggacagctt cacacctgtg gtcaactccc  4320
tggatcctcc actgctgacc agatacctga gaattcaccc tcagtcttgg gtgcaccaga  4380
ttgctctgag aatggaagtg ctgggatgtg aagctcagga cctctactaa tcgcgaataa  4440
aagatcttta ttttcattag atctgtgtgt tggttttttg tgtg                  4484

SEQ ID NO: 335          moltype = DNA  length = 4484
FEATURE                 Location/Qualifiers
misc_feature            1..4484
                        note = Synthetic polynucleotide
misc_feature            1..4484
                        note = pCB1026
source                  1..4484
                        mol_type = other DNA
                        organism = synthetic construct
SEQUENCE: 335
tgccagttcc cgatcgttac aggcggtact cctcaaagcg tactaaagaa ttattctttt  60
acatttcagt ggccaccaga aggtactacc tgggagctgt ggaactgagc tgggactaca  120
tgcagtctga cctgggagag ctgcctgtgg atgctagatt tcctccaaga gtgcccaaga  180
gcttcccctt caacacctct gtggtgtaca agaaaaccct gtttgtggaa ttcacagacc  240
acctgttcaa tattgccaag cctagacctc cttggatggg cctgctgggc cctacaattc  300
aggctgaggt gtatgacaca gtggtcatca ccctgaagaa catggccagc catcctgtgt  360
ctctgcatgc tgtgggagtg tcttactgga aggcttctga gggggctgag tatgatgacc  420
agacaagcca gagagagaaa gaggatgaca aggttttccc tgggggcagc cacacctatg  480
tctggcaggt cctgaaagaa aatggcccta tggcctctga tcctctgtgc ctgacataca  540
gctacctgag ccatgtggac ctggtcaagg acctgaactc tggcctgatt ggggctctgc  600
tggtgtgtag agaaggcagc ctggccaaag aaaagaccca gacactgcac aagttcatcc  660
tgctgtttgc tgtgtttgat gagggcaaga gctggcactc tgagacaaag aacagcctga  720
tgcaggacag agatgctgcc tctgctagag cttggcccaa gatgcacaca gtgaatggct  780
atgtgaacag aagcctgcct ggactgattg gatgccacag aaagtctgtg tactggcatg  840
tgattggcat gggcaccaca cctgaggtgc acagcatctt tctggaagga cacaccttcc  900
tggtgaggaa ccacagacag gccagcctgg aaatcagccc tatcaccttc ctgacagctc  960
agaccctgct gatggatctg ggccagtttc tgctgagctg ccacatcagc agccaccagc  1020
atgatggcat ggaagcctat gtgaaggtgg acagctgccc tgaagaaccc cagctgagaa  1080
tgaagaacaa tgaggaagct gaggactatg atgatgacct gacagactct gagatggatg  1140
```

```
tggtcagatt tgatgatgat aacagcccca gcttcatcca gatcagatct gtggccaaga  1200
agcaccccaa gacctgggtg cactatattg ctgctgagga agaggactgg gattatgctc  1260
ctctggtgct ggcccctgat gacagaagct acaagagcca gtacctgaac aatggccctc  1320
agagaattgg caggaagtat aagaaagtga ggttcatggc ctacacagat gagacattca  1380
agaccagaga ggctatccag catgagtctg gcattctggg acctctgctg tatggggaag  1440
tgggggacac actgctgatc atcttcaaga accaggccag cagaccctac aacatctacc  1500
ctcatggcat cacagatgtg aggcctctgt actctagaag gctgcccaag gggtgaagc  1560
acctgaagga cttccctatc ctgcctgggg agatcttcaa gtacaagtgg acagtgacag  1620
tggaggatgg ccctaccaag tctgatccta gatgcctgac aaggtactac agcagctttg  1680
tgaacatgga aagggacctg gcctctggcc tgattggtcc tctgctgatc tgctacaaag  1740
aatctgtgga ccagaggggc aaccagatca tgagtgacaa gagaaatgtg atcctgttct  1800
ctgtctttga tgagaacagg tcctggtatc tgacagagaa catccagagg tttctgccca  1860
atcctgctgg ggtgcagctg gaagatcctg agttccaggc ctccaacatc atgcactcca  1920
tcaatggcta tgtgtttgac agcctgcagc tgtctgtgtg cctgcatgaa gtggcctact  1980
ggtacatcct gtctattggg gcccagacag acttcctgtc tgtgttcttt tctggctaca  2040
ccttcaagca caagatggtg tatgaggata ccctgacact gttcccattc tctggggaga  2100
cagtgttcat gagcatggaa aaccctggcc tgtggatcct gggctgtcac aacagtgact  2160
tcagaaacag aggcatgaca gccctgctga aggtgtccag ctgtgacaag aacactgggg  2220
actactatga ggactcttat gaggacatct ctgcctacct gctgagcaag aacaatgcca  2280
ttgagcctag gagcttctct cagaacgcca ctaatgtgtc taacaacagc aacaccagca  2340
atgacagccc tcctgtgctg aagagacacc agagggagat caccagaacc acactgcagt  2400
ctgaccaaga ggaaattgat tatgatgaca ccatctctgt ggagatgaag aaagaagatt  2460
ttgacatcta tgatgaggat gagaatcaga gccccagatc tttccagaag aaaacaaggc  2520
actacttcat tgctgctgtg gaaagactgt gggactatgg catgagcagc agcccccatg  2580
tgctgagaaa cagggcccag tctggaagtg tgccccagtt caagaaagtg gtgttccaag  2640
agttcacaga tggcagcttc acccagcctc tgtatagagg ggagctgaat gagcacctgg  2700
gactgctggg accttacatc agagctgagg tggaggataa catcatggtc acctttagaa  2760
accaggcctc taggccctac tccttctaca gctccctgat cagctatgaa gaggaccaga  2820
gacagggggc tgagcccaga aagaactttg tgaagcccaa tgagactaag acctactttt  2880
ggaaggtgca gcaccacatg gcccctacaa aggatgagtt tgactgcaag gcctgggcct  2940
acttctctga tgtggacctg gagaaggatg tgcactctgg actcattgga cccctgcttg  3000
tgtgccacac caacacactg aatcctgctc atggcaggca agtgacagtg caagagtttg  3060
ccctgttctt caccatcttt gatgagacaa agtcctggta cttcacagaa aacatggaaa  3120
gaaactgcag ggccccttgc aacatccaga tggaagatcc caccttcaaa gagaactaca  3180
ggttccatgc catcaatggc tacatcatgg acactctgcc tggcctggtt atggcacagg  3240
atcagaggat cagatggtat ctgctgtcca tgggctccaa tgagaatatc cacagcatcc  3300
acttctctgg ccatgtgttc acagtgagga aaaaagaaga gtacaagatg gccctgtaca  3360
atctgtaccc tggggtgttt gagactgtgg aaatgctgcc tagcaaggct ggaatctgga  3420
gggtggaatg tctgattgga gagcatctgc atgctggaat gtctaccctg ttcctggtgt  3480
acagcaacaa gtgtcagacc cctctgggca tggcctctgg acacatcaga gacttccaga  3540
tcacagcctc tggccagtat ggacagtggg ctcctaaact ggctagactg cactactctg  3600
gcagcatcaa tgcctggtcc accaaagagc ccttcagctg gatcaaggtg gacctgctgg  3660
ctcccatgat catccatgga atcaagaccc agggggccag acagaagttc agcagcctgt  3720
acatcagcca gttcatcatc atgtacagcc tggatggcaa gaagtggcag acctacagag  3780
gcaacagcac aggcacactc atggtgttct ttggcaatgt ggactcttct ggcattaagc  3840
acaacatctt caaccctcca atcattgcca ggtacatcag gctgcacccc acacactaca  3900
gcatcagatc taccctgagg atggaactga tgggctgtga cctgaacagc tgctctatgc  3960
ccctgggaat ggaaagcaag gccatctctg atgcccagat cacagccagc agctacttca  4020
ccaacatgtt tgccacatgg tccccatcta aggccaggct gcatctgcag ggcagatcta  4080
atgcttggag gccccaagtg aacaacccca aagagtggct gcaggtggac tttcagaaaa  4140
ccatgaaagt gacaggagtg accacacagg gggtcaagtc tctgctgacc tctatgtatg  4200
tgaaagagtt cctgatctcc agcagccagg atggccacca gtggaccctg tttttccaga  4260
atggcaaagt caaggtgttc cagggaaacc aggacagctt cacacctgtg gtcaactccc  4320
tggatcctcc actgctgacc agatacctga gaattcaccc tcagtcttgg gtgcaccaga  4380
ttgctctgag aatggaagtg ctgggatgtg aagctcagga cctctactaa tcgcgaataa  4440
aagatcttta ttttcattag atctgtgtgt tggttttttg tgtg                 4484
```

```
SEQ ID NO: 336          moltype = DNA  length = 4775
FEATURE                 Location/Qualifiers
misc_feature            1..4775
                        note = Synthetic polynucleotide
misc_feature            1..4775
                        note = pCB103
source                  1..4775
                        mol_type = other DNA
                        organism = synthetic construct
SEQUENCE: 336
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcccgc ggtgccagtt cccgatcgtt acaggcggta  180
ctcctcaaag cgtactaaag aattattctt ttacatttca gtggctacca gaagatacta  240
cctgggagct gtggaactga gctgggatta catgcagtct gacctgggag agctgcctgt  300
ggatgctaga ttcccaccta gagtccctaa gtccttcccc ttcaacacct ctgtggtcta  360
caagaaaacc ctgtttgtgg agtttacaga ccacctgttc aacattgcta agcctagacc  420
accatggatg ggactgctgg gaccaaccat ccaggcagag gtgtatgaca cagtggtcat  480
caccctgaaa aacatggctt ctcaccctgt gtccctgcat gctgtgggag tctcctactg  540
gaaggcctct gaaggggctg agtatgatga tcagaccagc cagagggaaa aagaggatga  600
taaggtgttc cctggagggt cccataccta tgtgtggcag gtcctgaagg agaatggacc  660
aatggcttct gaccctctgt gcctgaccta ctcttatctg tcccatgtgg acctggtcaa  720
```

-continued

```
ggatctgaac tctggcctga ttggggctct gctggtgtgt agggaagggt ccctggccaa  780
ggagaaaacc cagaccctgc ataagttcat cctgctgttt gctgtgtttg atgaaggaaa  840
aagctggcac tctgagacca agaactctct gatgcaggac agggatgctg cttctgccag  900
agcttggccc aagatgcaca cagtgaatgg ctatgtcaat aggagcctgc ctggactgat  960
tggctgccac agaaagtctg tgtattggca tgtcattgga atgggcacca cccctgaagt  1020
gcacagcatc ttcctggagg ggcatacctt tctggtcagg aaccacaggc aggctagcct  1080
ggagatctct ccaatcacct tcctgacagc ccagaccctg ctgatggacc tgggacagtt  1140
cctgctgttt tgccacatct ccagccacca gcatgatggc atggaggctt atgtgaaagt  1200
ggactcctgt cctgaggaac ctcagctgag gatgaagaac aatgaggaag ctgaagacta  1260
tgatgatgac ctgacagact ctgagatgga tgtggtcagg tttgatgatg ataactctcc  1320
ctcctttatc cagatcaggt ctgtggccaa gaaacaccct aagacctggg tccattacat  1380
tgctgctgag gaagaggact gggattatgc tccactggtg ctggcccctg atgatagatc  1440
ctacaaaagc cagtatctga acaatggacc ccagaggatt ggcagaaagt acaagaaagt  1500
gaggttcatg gcttatacag atgagacctt taagaccaga gaagccatcc agcatgagtc  1560
tgggatcctg ggacctctgc tgtatgggga agtgggggac accctgctga tcatcttcaa  1620
gaaccaggcc agcaggcctt acaatatcta tccacatggc atcacagatg tgagacctct  1680
gtactccagg aggctgccaa agggggtgaa acacctgaag gacttcccaa tcctgcctgg  1740
ggaaatcttt aagtataaat ggacagtcac agtggaggat gggcccacca agtctgaccc  1800
taggtgcctg accagatact attcttcctt tgtgaatatg gagagagacc tggcttctgg  1860
actgattgga cccctgctga tctgttacaa agagtctgtg gatcagaggg gcaaccagat  1920
catgtctgac aagaggaatg tgatcctgtt ctctgtcttt gatgaaaaca ggtcttggta  1980
cctgacagag aacatccaga ggttcctgcc taatccagct ggagtgcagc tggaagatcc  2040
tgagttccag gcctctaaca tcatgcattc catcaatggc tatgtgtttg actccctgca  2100
gctgtctgtg tgcctgcatg aggtggctta ctggtatatc ctgagcattg gagcccagac  2160
agatttcctg tctgtgttct ttctggcta caccttttaag cataaaatgg tgtatgagga  2220
caccctgacc ctgttcccat tttctggaga aactgtgttc atgagcatgg agaatcctgg  2280
gctgtggatc ctgggatgcc acaactctga tttcaggaat agagggatga cagccctgct  2340
gaaagtgagc tcttgtgaca agaacacagg agactactat gaagatagct atgaggacat  2400
ctctgcttat ctgctgtcca aaaacaatgc cattgagccc aggagcttct ctcagaaccc  2460
tccagtgctg aagaggcacc agagggagat caccagaacc accctgcagt ctgatcagga  2520
agagattgac tatgatgata ccatctctgt ggaaatgaag aaagaggact ttgatatcta  2580
tgatgaagat gagaaccagt ctcccaggtc cttccagaag aaaaccagac attactttat  2640
tgctgctgtg gagaggctgt gggactatgg catgtccagc tctcctcatg tgctgagaaa  2700
tagagctcag tctggatctg tcccacagtt caagaaagtg gtcttccagg agtttacaga  2760
tggaagcttt acccagccac tgtacagggg agaactgaat gagcacctgg ggctgctggg  2820
accctatatc agggctgaag tggaggataa catcatggtc accttcagga atcaggccag  2880
cagaccctac tctttttatt ccagcctgat ctcctatgaa gaggaccaga gacagggagc  2940
tgaaccaaga aaaaactttg tgaagcctaa tgagaccaaa acctactttt ggaaggtgca  3000
gcaccatatg gcccctacca aagatgagtt tgattgcaag gcctgggctt atttttctga  3060
tgtggatctg gagaaggatg tccactctgg cctgattggg ccactgctgg tgtgtcatac  3120
caacaccctg aatccagctc atggaaggca ggtgacagtc caggaatttg ccctgttctt  3180
taccatcttt gatgagacca agagctggta cttcacagaa aacatggaga ggaattgcag  3240
agccccatgt aacatccaga tggaagaccc caccttcaag gagaactaca gatttcatgc  3300
tatcaatggg tatatcatgg ataccctgcc aggactggtc atggctcagg accagaggat  3360
cagatggtac ctgctgagca tggggtctaa tgagaatatc cactccatcc atttctctgg  3420
acatgtgttt acagtaagga agaaagaaga gtacaagatg gccctgtaca acctgtatcc  3480
tggggtgttt gaaacagtgg agatgctgcc ttccaaggct gggatctgga gggtggaatg  3540
cctgattggg gagcacctgc atgctggaat gtctaccctg ttcctggtgt actccaataa  3600
gtgtcagacc cccctgggga tggcttctgg acatatcagg gacttccaga tcacagcttc  3660
tggacagtat ggacagtggg ctcctaagct ggctagactg cactattctg gctccatcaa  3720
tgcttggtct accaaagagc ctttctcctg gatcaaggtg gacctgctgg ctccaatgat  3780
catccatggc atcaaaaccc agggggccag gcagaagttc tcttccctgt acatcagcca  3840
gtttatcatc atgtattctc tggatgggaa gaaatggcag acctacagag gcaattccac  3900
agggaccctg atggtgttct ttggcaatgt ggacagctct gggatcaagc acaacatctt  3960
caatcccccct atcattgcca ggtacatcag actgcaccca acccattatt ccatcaggag  4020
caccctgaga atggagctga tggggtgtga tctgaacagc tgttctatgc cctgggaat  4080
ggagtctaag gccatctctg atgctcagat cacagcctcc agctacttca ccaatatgtt  4140
tgctacctgg tccccaagca aggctagact gcatctgcag ggaagaagca atgcttggag  4200
accacaggtg aacaatccca aggagtggct gcaggtggac ttccagaaaa ccatgaaggt  4260
gacaggagtc accacccagg gagtgaaaag cctgctgacc tctatgtatg tcaaggagtt  4320
cctgatctct tccagccagg atgggcacca gtggaccctg ttctttcaga atggaaaggt  4380
gaaagtcttc cagggcaatc aggattcctt tacccctgtg gtcaacagcc tggacccacc  4440
cctgctgacc aggtacctga gaatccaccc acagtcctgg gtgcatcaga ttgctctgag  4500
gatggaagtc ctgggctgtg aggcccagga cctgtattga tcgcgaataa aagatcttta  4560
ttttcattag atctgtgtgt tggtttttttg tgtgtgccag ttcccgatcg ttacaggcaa  4620
ttgccttagg ccgcaggaac ccctagtgat ggagttggcc actccctctc tgcgcgctcg  4680
ctcgctcact gaggccgggc gaccaaaggt cgcccgacgc ccgggctttg cccgggcggc  4740
ctcagtgagc gagcgagcgc gcagctgcct gcagg                              4775
```

```
SEQ ID NO: 337          moltype = AA  length = 14
FEATURE                 Location/Qualifiers
REGION                  1..14
                        note = Synthetic polypeptide
REGION                  1..14
                        note = MISC_FEATURE - "SQ linker"
source                  1..14
                        mol_type = protein
                        organism = synthetic construct
SEQUENCE: 337
```

```
SFSQNPPVLK RHQR                                                 14

SEQ ID NO: 338         moltype = DNA  length = 20
FEATURE                Location/Qualifiers
misc_feature           1..20
                       note = Synthetic polynucleotide
misc_feature           1..20
                       note = gRNA mALbT1
source                 1..20
                       mol_type = other DNA
                       organism = synthetic construct
SEQUENCE: 338
tgccagttcc cgatcgttac                                           20

SEQ ID NO: 339         moltype = RNA  length = 100
FEATURE                Location/Qualifiers
misc_feature           1..100
                       note = Synthetic polynucleotide
misc_feature           1..100
                       note = gRNA
misc_feature           1..2
                       note = phosphorothioate backbone
misc_feature           1..3
                       note = 2'-O-methyl nucleotides
misc_feature           2..3
                       note = phosphorothioate backbone
misc_feature           3..4
                       note = phosphorothioate backbone
misc_feature           29..32
                       note = 2'-O-methyl nucleotides
misc_feature           37..40
                       note = 2'-O-methyl nucleotides
misc_feature           68..72
                       note = 2'-O-methyl nucleotides
misc_feature           77..99
                       note = 2'-O-methyl nucleotides
misc_feature           97..98
                       note = phosphorothioate backbone
misc_feature           98..99
                       note = phosphorothioate backbone
misc_feature           99..100
                       note = phosphorothioate backbone
source                 1..100
                       mol_type = other RNA
                       organism = synthetic construct
SEQUENCE: 339
tgccagttcc cgatcgttac gttttagagc tagaaatagc aagttaaaat aaggctagtc  60
cgttatcaac ttgaaaaagt ggcaccgagt cggtgctttt                       100

SEQ ID NO: 340         moltype = DNA  length = 4438
FEATURE                Location/Qualifiers
misc_feature           1..4438
                       note = Synthetic polynucleotide
misc_feature           1..4438
                       note = spCas9 mRNA with NLS sequences
source                 1..4438
                       mol_type = other DNA
                       organism = synthetic construct
SEQUENCE: 340
ggaaataaga gagaaaagaa gagtaagaag aaatataaga gccaccatgg ccccaaagaa  60
gaagcggaag gtcggtatcc acggagtccc agcagccgac aagaagtaca gcatcggcct  120
ggacatcggc accaactctg tgggctgggc cgtgatcacc gacgagtaca aggtgcccag  180
caagaaattc aaggtgctgg gcaacaccga ccggcacagc atcaagaaga acctgatcgg  240
agccctgctg ttcgacagcg gcgaaacagc cgaggccacc cggctgaaga gaaccgccag  300
aagaagatac accagacgga agaaccggat ctgctatctg caagagatct tcagcaacga  360
gatggccaag gtggacgaca gcttcttcca cagactggaa gagtccttcc tggtggaaga  420
ggacaagaag cacgagagac accccatctt cggcaacatc gtggacgagg tggcctacca  480
cgagaagtac cccaccatct accacctgag aaagaaactg gtggacagca ccgacaaggc  540
cgacctgaga ctgatctacc tggccctggc ccacatgatc aagttcagag gccacttcct  600
gatcgagggc gacctgaacc ccgacaacag cgacgtggac aagctgttca tccagctggt  660
gcagacctac aaccagctgt tcgaggaaaa ccccatcaac gccagcggcg tggacgccaa  720
ggctatcctg tctgccagac tgagcaagag cagaaggctg gaaaatctga tcgcccagct  780
gcccggcgag aagaagaacg gcctgttcgg caacctgatt gccctgagcc tgggcctgac  840
ccccaacttc aagagcaact tcgacctggc cgaggatgcc aaactgcagc tgagcaagga  900
cacctacgac gacgacctgg acaacctgct ggcccagatc ggcgaccagt acgccgacct  960
gttcctggcc gccaagaacc tgtctgacgc catcctgctg agcgacatcc tgagagtgaa  1020
caccgagatc accaaggccc ccctgagcgc ctctatgatc aagagatacg acgagcacca  1080
ccaggacctg accctgctga aagctctcgt gcggcagcag ctgcctgaga agtacaaaga  1140
aatcttcttc gaccagagca agaacggcta cgccggctac atcgatggcg gcgctagcca  1200
```

```
ggaagagttc tacaagttca tcaagcccat cctggaaaag atggacggca ccgaggaact  1260
gctcgtgaag ctgaacagag aggacctgct gagaaagcag agaaccttcg acaacggcag  1320
catcccccac cagatccacc tgggagagct gcacgctatc ctgagaaggc aggaagattt  1380
ttacccattc ctgaaggaca accgggaaaa gatcgagaag atcctgacct tcaggatccc  1440
ctactacgtg ggcccctgg ccagaggcaa cagcagattc gcctggatga ccagaaagag  1500
cgaggaaacc atcacccct ggaacttcga ggaagtggtg gacaagggcg ccagcgccca  1560
gagcttcatc gagagaatga caaacttcga taagaacctg cccaacgaga aggtgctgcc  1620
caagcacagc ctgctgtacg agtacttcac cgtgtacaac gagctgacca aagtgaaata  1680
cgtgaccgag ggaatgagaa agcccgcctt cctgagcggc gagcagaaaa aggccatcgt  1740
ggacctgctg ttcaagacca acagaaaagt gaccgtgaag cagctgaaag aggactactt  1800
caagaaaatc gagtgcttcg actccgtgga aatctccggc gtggaagata gattcaacgc  1860
ctccctgggc acataccacg atctgctgaa aattatcaag gacaaggact tcctggataa  1920
cgaagagaac gaggacattc tggaagatat cgtgctgacc ctgacactgt ttgaggaccg  1980
cgagatgatc gaggaaaggc tgaaaaccta cgctcacctg ttcgacgaca aagtgatgaa  2040
gcagctgaag agaaggcggt acaccggctg gggcaggctg agcagaaagc tgatcaacgg  2100
catcagagac aagcagagcg gcaagacaat cctggatttc ctgaagtccg acggcttcgc  2160
caaccggaac ttcatgcagc tgatccacga cgacagcctg acattcaaag aggacatcca  2220
gaaagcccag gtgtccggcc agggcgactc tctgcacgag catatcgcta acctggccgg  2280
cagccccgct atcaagaagg gcatcctgca gacagtgaag gtggtggacg agctcgtgaa  2340
agtgatgggc agacacaagc ccgagaacat cgtgatcgag atggctagag agaaccagac  2400
cacccagaag ggacagaaga actcccgcga gaggatgaag agaatcgaag agggcatcaa  2460
agagctgggc agccagatcc tgaaagaaca ccccgtggaa aacacccagc tgcagaacga  2520
gaagctgtac ctgtactacc tgcagaatgg ccgggatatg tacgtggacc aggaactgga  2580
catcaacaga ctgtccgact acgatgtgga ccatatcgtg cctcagagct ttctgaagga  2640
cgactccatc gataacaaag tgctgactcg gagcgacaag aacagaggca agagcgacaa  2700
cgtgccctcc gaagaggtcg tgaagaagat gaagaactac tggcgacagc tgctgaacgc  2760
caagctgatt acccagagga agttcgataa cctgaccaag gccgagagag gcggcctgag  2820
cgagctggat aaggccggct tcatcaagag gcagctggtg gaaaccagac agatcacaaa  2880
gcacgtggca cagatcctgg actcccggat gaacactaag tacgacgaaa acgataagct  2940
gatccgggaa gtgaaagtga tcaccctgaa gtccaagctg gtgtccgatt tccggaagga  3000
tttccagttt tacaaagtgc gcgagatcaa caactaccac cacgcccacg acgcctacct  3060
gaacgccgtc gtgggaaccg ccctgatcaa aaagtaccct aagctggaaa gcgagttcgt  3120
gtacggcgac tacaaggtgt acgacgtgcg gaagatgatc gccaagagcg agcaggaaat  3180
cggcaaggct accgccaagt acttcttcta cagcaacatc atgaactttt tcaagaccga  3240
aatcaccctg gccaacggcg agatcagaaa gcgccctctg atcgagacaa acggcgaaac  3300
cggggagatc gtgtgggata agggcagaga cttcgccaca gtgcgaaagg tgctgagcat  3360
gccccaagtg aatatcgtga aaaagaccga ggtgcagaca ggcggcttca gcaaagagtc  3420
tatcctgccc aagaggaaca gcgacaagct gatcgccaga aagaaggact gggaccccaa  3480
gaagtacggc ggcttcgaca gccctaccgt ggcctactct gtgctggtgg tggctaaggt  3540
ggaaaagggc aagtccaaga aactgaagag tgtgaaagag ctgctgggga tcaccatcat  3600
ggaaagaagc agctttgaga agaaccctat cgactttctg gaagccaagg gctacaaaga  3660
agtgaaaaag gacctgatca tcaagctgcc taagtactcc ctgttcgagc tggaaaacgg  3720
cagaaagaga atgctggcct ctgccggcga actgcagaag ggaaacgagc tggccctgcc  3780
tagcaaatat gtgaacttcc tgtacctggc ctcccactat gagaagctga agggcagccc  3840
tgaggacaac gaacagaaac agctgtttgt ggaacagcat aagcactacc tggacgagat  3900
catcgagcag atcagcgagt tctccaagag agtgatcctg gccgacgcca atctggacaa  3960
ggtgctgtct gcctacaaca agcacaggga caagcctatc agagagcagg ccgagaatat  4020
catccacctg ttcaccctga caaacctggg cgctcctgcc gccttcaagt actttgacac  4080
caccatcgac cggaagaggt acaccagcac caaagaggtg ctggacgcca ccctgatcca  4140
ccagagcatc accggcctgt acgagacaag aatcgacctg tctcagctgg gaggcgacaa  4200
gagacctgcc gccactaaga aggccggaca ggccaaaaag aagaagtgag cggccgctta  4260
attaagctgc cttctgcggg gcttgccttc tggccatgcc cttcttctct cccttgcacc  4320
tgtacctctt ggtctttgaa taaagcctga gtaggaagaa aaaaaaaaaa aaaaaaaaaa  4380
aaaaaaaaaa aaaaaaaaaa aaaaaaaaaa aaaaaaaaaa aaaaaaaaaa aaaaaaaa    4438

SEQ ID NO: 341         moltype = DNA  length = 4779
FEATURE                Location/Qualifiers
misc_feature           1..4779
                       note = Synthetic polynucleotide
misc_feature           1..4779
                       note = pCB102
source                 1..4779
                       mol_type = other DNA
                       organism = synthetic construct
SEQUENCE: 341
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcccgc ggtgccagtt cccgatcgtt acaggcggta  180
ctcctcaaag cgtactaaag aattattctt ttacatttca gtggccacca ggagatacta  240
cctgggggct gtggagctga gctgggacta catgcagtct gacctggggg agctgcctgt  300
ggatgccagg ttcccccca gagtgcccaa gagcttcccc ttcaacacct ctgtggtgta  360
caagaagacc ctgtttgtgg agttcactga ccacctgttc aacattgcca agcccaggcc  420
cccctggatg ggcctgctgg gccccaccat ccaggctgag gtgtatgaca ctgtggtgat  480
caccctgaag aacatggcca gccaccctgt gagcctgcat gctgtggggg tgagctactg  540
gaaggcctct gagggggctg agtatgatga ccagaccagc cagagggaga aggaggatga  600
caaggtgttc cctgggggca gccacaccta tgtgtggcag gtgctgaagg agaatggccc  660
catggcctct gacccccctgt gcctgaccta cagctacctg agccatgtgg acctggtgaa  720
ggacctgaac tctggcctga ttggggccct gctggtgtgc agggagggca gcctggccaa  780
ggagaagacc cagaccctgc acaagttcat cctgctgttt gctgtgtttg atgagggcaa  840
```

```
gagctggcac tctgaaacca agaacagcct gatgcaggac agggatgctg cctctgccag  900
ggcctggccc aagatgcaca ctgtgaatgg ctatgtgaac aggagcctgc ctggcctgat  960
tggctgccac aggaagtctg tgtactggca tgtgattggc atgggcacca cccctgaggt  1020
gcacagcatc ttcctggagg gccacacctt cctggtcagg aaccacaggc aggccagcct  1080
ggagatcagc cccatcacct tcctgactgc ccagaccctg ctgatggacc tgggccagtt  1140
cctgctgttc tgccacatca gcagccacca gcatgatggc atggaggcct atgtgaaggt  1200
ggacagctgc cctgaggagc cccagctgag gatgaagaac aatgaggagg ctgaggacta  1260
tgatgatgac ctgactgact ctgagatgga tgtggtgagg tttgatgatg acaacagccc  1320
cagcttcatc cagatcaggt ctgtggccaa gaagcacccc aagacctggg tgcactacat  1380
tgctgctgag gaggaggact gggactatgc ccccctggtg ctggcccctg atgacaggag  1440
ctacaagagc cagtacctga acaatggccc ccagaggatt ggcaggaagt acaagaaggt  1500
caggttcatg gcctacactg atgaaacctt caagaccagg gaggccatcc agcatgagtc  1560
tggcatcctg ggcccccctgc tgtatgggga ggtgggggac accctgctga tcatcttcaa  1620
gaaccaggcc agcaggccct acaacatcta cccccatggc atcactgatg tgaggcccct  1680
gtacagcagg aggctgccca agggggtgaa gcacctgaag gacttcccca tcctgcctgg  1740
ggagatcttc aagtacaagt ggactgtgac tgtggaggat ggccccacca agtctgaccc  1800
caggtgcctg accagatact acagcagctt tgtgaacatg gagagggacc tggcctctgg  1860
cctgattggc cccctgctga tctgctacaa ggagtctgtg gaccagaggg gcaaccagat  1920
catgtctgac aagaggaatg tgatcctgtt ctctgtgttt gatgagaaca ggagctggta  1980
cctgactgag aacatccaga ggttcctgcc caaccctgct ggggtgcagc tggaggaccc  2040
tgagttccag gccagcaaca tcatgcacag catcaatggc tatgtgtttg acagcctgca  2100
gctgtctgtg tgcctgcatg aggtggccta ctggtacatc ctgagcattg ggcccagac  2160
tgacttcctg tctgtgttct tctctggcta caccttcaag cacaagatgg tgtatgagga  2220
caccctgacc ctgttcccct tctctgggga gactgtgttc atgagcatgg agaaccctgg  2280
cctgtggatt ctgggctgcc acaactctga cttcaggaac aggggcatga ctgccctgct  2340
gaaagtctcc agctgtgaca agaacactgg ggactactat gaggacagct atgaggacat  2400
ctctgcctac ctgctgagca agaacaatgc cattgagccc aggagcttca gccagaatcc  2460
cccagtgctg aagaggcacc agagggagat caccaggacc accctgcagt ctgaccagga  2520
ggagattgac tatgatgaca ccatctctgt ggagatgaag aaggaggact ttgacatcta  2580
cgacgaggac gagaaccaga gccccaggag cttccagaag aagaccaggc actacttcat  2640
tgctgctgtg gagaggctgt gggactatgg catgagcagc agcccccatg tgctgaggaa  2700
cagggcccag tctggctctg tgccccagtt caagaaggtg gtgttccagg agttcactga  2760
tggcagcttc acccagcccc tgtacagagg ggagctgaat gagcacctgg gcctgctggg  2820
cccctacatc agggctgagg tggaggacaa catcatggtg accttcagga accaggccag  2880
caggccctac agcttctaca gcagcctgat cagctatgag gaggaccaga ggcagggggc  2940
tgagcccagg aagaactttg tgaagcccaa tgaaaccaag acctacttct ggaaggtgca  3000
gcaccacatg gcccccacca aggatgagtt tgactgcaag gcctgggcct acttctctga  3060
tgtggacctg gagaaggatg tgcactctgg cctgattggc cccctgctgg tgtgccacac  3120
caacaccctg aaccctgccc atggcaggca ggtgactgtg caggagtttg ccctgttctt  3180
caccatcttt gatgaaacca agagctggta cttcactgag aacatggaga ggaactgcag  3240
ggcccccctgc aacatccaga tggaggaccc caccttcaag gagaactaca ggttccatgc  3300
catcaatggc tacatcatgg acaccctgcc tggcctggtg atggcccagg accagaggat  3360
caggtggtac ctgctgagca tgggcagcaa tgagaacatc cacagcatcc acttctctgg  3420
ccatgtgttc actgtgagga agaaggagga gtacaagatg gccctgtaca acctgtaccc  3480
tggggtgttt gagactgtgg agatgctgcc cagcaaggct ggcatctgga gggtggagtg  3540
cctgattggg gagcacctgc atgctggcat gagcaccctg ttcctggtgt acagcaacaa  3600
gtgccagacc cccctgggca tggcctctgg ccacatcagg gacttccaga tcactgcctc  3660
tggccagtat ggccagtggg cccccaagct ggccaggctg cactactctg gcagcatcaa  3720
tgcctggagc accaaggagc ccttcagctg gatcaaggtg gacctgctgg cccccatgat  3780
catccatggc atcaagaccc agggggccag gcagaagttc agcagcctgt acatcagcca  3840
gttcatcatc atgtacagcc tggatggcaa gaagtggcag acctacaggg gcaacagcac  3900
tggcaccctg atggtgttct ttggcaatgt ggacagctct ggcatcaagc acaacatctt  3960
caaccccccc atcattgcca gatacatcag gctgcacccc acccactaca gcatcaggag  4020
caccctgagg atggagctga tgggctgtga cctgaacagc tgcagcatgc ccctgggcat  4080
ggagagcaag gccatctctg atgcccagat cactgccagc agctacttca ccaacatgtt  4140
tgccacctgg agccccagca aggccaggct gcacctgcag ggcaggagca atgcctggag  4200
gccccaggtc aacaacccca aggagtggct gcaggtggac ttccagaaga ccatgaaggt  4260
gactggggtg accacccagg gggtgaagag cctgctgacc agcatgtatg tgaaggagtt  4320
cctgatcagc agcagccagg atggccacca gtggaccctg ttcttccaga atggcaaggt  4380
gaaggtgttc cagggcaacc aggacagctt caccccctgtg gtgaacagcc tggacccccc  4440
cctgctgacc agatacctga ggattcaccc ccagagctgg gtgcaccaga ttgccctgag  4500
gatggaggtg ctgggctgtg aggcccagga cctgtactga tcgcgaataa aagatcttta  4560
ttttcattag atctgtgtgt tggttttttg tgtggatctg ccagttcccg atcgttacag  4620
gcaattgcct taggccgcag gaacccctag tgatggagtt ggccactccc tctctgcgcg  4680
ctcgctcgct cactgaggcc gggcgaccaa aggtcgcccg acgcccgggc tttgcccggg  4740
cggcctcagt gagcgagcga gcgcgcagct gcctgcagg                         4779
```

```
SEQ ID NO: 342          moltype = AA  length = 30
FEATURE                 Location/Qualifiers
REGION                  1..30
                        note = Synthetic polypeptide
REGION                  1..30
                        note = MISC_FEATURE - modified B domain linker
source                  1..30
                        mol_type = protein
                        organism = synthetic construct
SEQUENCE: 342
FNATTIQNVS SNNSLSDNTS SNDSKNVSSP                                   30
```

-continued

```
SEQ ID NO: 343          moltype = AA  length = 14
FEATURE                 Location/Qualifiers
REGION                  1..14
                        note = Synthetic polypeptide
REGION                  1..14
                        note = MISC_FEATURE - B domain substitute
source                  1..14
                        mol_type = protein
                        organism = synthetic construct
SEQUENCE: 343
ATNVSNNSNT SNDS                                                   14

SEQ ID NO: 344          moltype = DNA  length = 14
FEATURE                 Location/Qualifiers
misc_feature            1..14
                        note = Synthetic polynucleotide
misc_feature            1..14
                        note = Terminal portion of sequence encoding signal peptide
                         from Transferrin Exon 2
source                  1..14
                        mol_type = other DNA
                        organism = synthetic construct
SEQUENCE: 344
ggctgtgtct ggct                                                   14

SEQ ID NO: 345          moltype = AA  length = 31
FEATURE                 Location/Qualifiers
REGION                  1..31
                        note = Synthetic polypeptide
REGION                  1..31
                        note = MISC_FEATURE - Variant FVIII B domain
source                  1..31
                        mol_type = protein
                        organism = synthetic construct
SEQUENCE: 345
SFSQNATNVS NNSNTSNDSN VSPPVLKRHQ R                                31

SEQ ID NO: 346          moltype = DNA  length = 21
FEATURE                 Location/Qualifiers
misc_feature            1..21
                        note = Synthetic polynucleotide
misc_feature            1..21
                        note = FGA2(DD) forward primer, mouse FGA intron
source                  1..21
                        mol_type = other DNA
                        organism = synthetic construct
SEQUENCE: 346
ctggagtttc tgacacattc t                                           21

SEQ ID NO: 347          moltype = DNA  length = 20
FEATURE                 Location/Qualifiers
misc_feature            1..20
                        note = Synthetic polynucleotide
misc_feature            1..20
                        note = RSA56.R reverse primer
source                  1..20
                        mol_type = other DNA
                        organism = synthetic construct
SEQUENCE: 347
gtgaactcca caaacagggt                                             20

SEQ ID NO: 348          moltype = DNA  length = 20
FEATURE                 Location/Qualifiers
misc_feature            1..20
                        note = Synthetic polynucleotide
misc_feature            1..20
                        note = TFR1(DD) reverse primer
source                  1..20
                        mol_type = other DNA
                        organism = synthetic construct
SEQUENCE: 348
agtgaactcc acaaacaggg                                             20

SEQ ID NO: 349          moltype = DNA  length = 20
FEATURE                 Location/Qualifiers
misc_feature            1..20
                        note = Synthetic polynucleotide
misc_feature            1..20
                        note = FGAP2(DD) donor probe
```

```
source                  1..20
                        mol_type = other DNA
                        organism = synthetic construct
SEQUENCE: 349
ccacagcccc caggtagtat                                                20

SEQ ID NO: 350          moltype = DNA  length = 20
FEATURE                 Location/Qualifiers
misc_feature            1..20
                        note = Synthetic polynucleotide
misc_feature            1..20
                        note = FGARefF2 (DD) forward primer
source                  1..20
                        mol_type = other DNA
                        organism = synthetic construct
SEQUENCE: 350
gttgctgggg attgatccag                                                20

SEQ ID NO: 351          moltype = DNA  length = 20
FEATURE                 Location/Qualifiers
misc_feature            1..20
                        note = Synthetic polynucleotide
misc_feature            1..20
                        note = FGARefR2 (DD) reverse primer
source                  1..20
                        mol_type = other DNA
                        organism = synthetic construct
SEQUENCE: 351
gttctcaacc tgtgggtcac                                                20

SEQ ID NO: 352          moltype = DNA  length = 20
FEATURE                 Location/Qualifiers
misc_feature            1..20
                        note = Synthetic polynucleotide
misc_feature            1..20
                        note = FGARefP2 (DD) probe
source                  1..20
                        mol_type = other DNA
                        organism = synthetic construct
SEQUENCE: 352
tgttgtgatg acccgcaact                                                20

SEQ ID NO: 353          moltype = DNA  length = 23
FEATURE                 Location/Qualifiers
misc_feature            1..23
                        note = Synthetic polynucleotide
misc_feature            1..23
                        note = AlbF forward primer
source                  1..23
                        mol_type = other DNA
                        organism = synthetic construct
SEQUENCE: 353
ccctccgttt gtcctagctt ttc                                            23

SEQ ID NO: 354          moltype = DNA  length = 30
FEATURE                 Location/Qualifiers
misc_feature            1..30
                        note = Synthetic polynucleotide
misc_feature            1..30
                        note = AlbR reverse primer
source                  1..30
                        mol_type = other DNA
                        organism = synthetic construct
SEQUENCE: 354
ccagatacag aatatcttcc tcaacgcaga                                     30

SEQ ID NO: 355          moltype = DNA  length = 20
FEATURE                 Location/Qualifiers
misc_feature            1..20
                        note = Synthetic polynucleotide
misc_feature            1..20
                        note = forward primer
source                  1..20
                        mol_type = other DNA
                        organism = synthetic construct
SEQUENCE: 355
cctttggcac aatgaagtgg                                                20

SEQ ID NO: 356          moltype = DNA  length = 22
```

```
FEATURE                 Location/Qualifiers
misc_feature            1..22
                        note = Synthetic polynucleotide
misc_feature            1..22
                        note = reverse primer
source                  1..22
                        mol_type = other DNA
                        organism = synthetic construct
SEQUENCE: 356
gaatctgaac cctgatgaca ag                                          22

SEQ ID NO: 357          moltype = DNA  length = 23
FEATURE                 Location/Qualifiers
misc_feature            1..23
                        note = Synthetic polynucleotide
misc_feature            1..23
                        note = T4
source                  1..23
                        mol_type = other DNA
                        organism = synthetic construct
SEQUENCE: 357
taaagcatag tgcaatggat agg                                         23

SEQ ID NO: 358          moltype = DNA  length = 23
FEATURE                 Location/Qualifiers
misc_feature            1..23
                        note = Synthetic polynucleotide
misc_feature            1..23
                        note = T5
source                  1..23
                        mol_type = other DNA
                        organism = synthetic construct
SEQUENCE: 358
atttatgaga tcaacagcac agg                                         23

SEQ ID NO: 359          moltype = DNA  length = 23
FEATURE                 Location/Qualifiers
misc_feature            1..23
                        note = Synthetic polynucleotide
misc_feature            1..23
                        note = T11
source                  1..23
                        mol_type = other DNA
                        organism = synthetic construct
SEQUENCE: 359
ttaaataaag catagtgcaa tgg                                         23

SEQ ID NO: 360          moltype = DNA  length = 23
FEATURE                 Location/Qualifiers
misc_feature            1..23
                        note = Synthetic polynucleotide
misc_feature            1..23
                        note = T13
source                  1..23
                        mol_type = other DNA
                        organism = synthetic construct
SEQUENCE: 360
taataaaatt caaacatcct agg                                         23

SEQ ID NO: 361          moltype = DNA  length = 4827
FEATURE                 Location/Qualifiers
misc_feature            1..4827
                        note = Synthetic polynucleotide
misc_feature            1..4827
                        note = AAV8-pCB1010
source                  1..4827
                        mol_type = other DNA
                        organism = synthetic construct
SEQUENCE: 361
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcccgc ggcctgggta actaattagg atgtccggta  180
ctcctcaaag cgtactaaag aattattctt ttacatttca gaccgccacc aggagatact  240
acctgggggc tgtggagctg agctgggact acatgcagtc tgacctgggg gagctgcctg  300
tggatgccag gttccccccc agagtgccca agagcttccc cttcaacacc tctgtggtgt  360
acaagaagac cctgtttgtg gagttcactg accacctgtt caacattgcc aagcccaggc  420
ccccctggat gggcctgctg ggccccacca tccaggctga ggtgtatgac actgtggtga  480
tcaccctgaa gaacatggcc agccaccctg tgagcctgca tgctgtgggg gtgagctact  540
ggaaggcctc tgagggggct gagtatgatg accagaccag ccagagggag aaggaggatg  600
```

```
acaaggtgtt ccctgggggc agccacacct atgtgtggca ggtgctgaag gagaatggcc  660
ccatggcctc tgacccccctg tgcctgacct acagctacct gagccatgtg gacctggtga  720
aggacctgaa ctctggcctg attggggccc tgctggtgtg cagggagggc agcctggcca  780
aggagaagac ccagaccctg cacaagttca tcctgctgtt tgctgtgttt gatgagggca  840
agagctggca ctctgaaacc aagaacagcc tgatgcagga cagggatgct gcctctgcca  900
gggcctggcc caagatgcac actgtgaatg gctatgtgaa caggagcctg cctggcctga  960
ttggctgcca caggaagtct gtgtactggc atgtgattgg catgggcacc acccctgagg  1020
tgcacagcat cttcctggag ggccacacct tcctggtcag gaaccacagg caggccagcc  1080
tggagatcag ccccatcacc ttcctgactg cccagaccct gctgatggac ctgggccagt  1140
tcctgctgtt ctgccacatc agcagccacc agcatgatgg catggaggcc tatgtgaagg  1200
tggacagctg ccctgaggag ccccagctga ggatgaagaa caatgaggag gctgaggact  1260
atgatgatga cctgactgac tctgagatgg atgtggtgag gtttgatgat gacaacagcc  1320
ccagcttcat ccagatcagg tctgtggcca agaagcaccc caagacctgg gtgcactaca  1380
ttgctgctga ggaggaggac tggactatgg cccccctggt gctggcccct gatgacagga  1440
gctacaagag ccagtacctg aacaatggcc cccagaggat tggcaggaag tacaagaagg  1500
tcaggttcat ggcctacact gatgaaacct tcaagaccag ggaggccatc cagcatgagt  1560
ctggcatcct gggccccctg ctgtatgggg aggtgggga caccctgctg atcatcttca  1620
agaaccaggc cagcaggccc tacaacatct acccccatgg catcactgat gtgaggcccc  1680
tgtacagcag gaggctgccc aagggggtga agcacctgaa ggacttcccc atcctgcctg  1740
gggagatctt caagtacaag tggactgtga ctgtggagga tggccccacc aagtctgacc  1800
ccaggtgcct gaccagatac tacagcagct ttgtgaacat ggagagggac ctggcctctg  1860
gcctgattgg cccccctgctg atctgctaca aggagtctgt ggaccagagg ggcaaccaga  1920
tcatgtctga caagaggaat gtgatcctgt tctctgtgtt tgatgagaac aggagctggt  1980
acctgactga gaacatccag aggttcctgc ccaaccctgc tggggtgcag ctggaggacc  2040
ctgagttcca ggccagcaac atcatgcaca gcatcaatgg ctatgtgttt gacagcctgc  2100
agctgtctgt gtgcctgcat gaggtggcct actggtacat cctgagcatt ggggcccaga  2160
ctgacttcct gtctgtgttc ttctctggct acaccttcaa gcacaagatg gtgtatgagg  2220
acaccctgac cctgttcccc ttctctgggg agactgtgtt catgagcatg gagaaccctg  2280
gcctgtggat tctgggctgc cacaactctg acttcaggaa caggggcatg actgccctgc  2340
tgaaagtctc cagctgtgac aagaacactg gggactacta tgaggacagc tatgaggaca  2400
tctctgccta cctgctgagc aagaacaatg ccattgagcc caggagcttc agccagaatg  2460
ccactaatgt gtctaacaac agcaacacca gcaatgacag caatgtgtct cccccagtgc  2520
tgaagaggca ccagagggag atcaccagga ccaccctgca gtctgaccag gaggagattg  2580
actatgatga caccatctct gtggagatga agaaggagga ctttgacatc tacgacgagg  2640
acgagaacca gagccccagg agcttccaga agaagaccag gcactacttc attgctgctg  2700
tggagaggct gtgggactat ggcatgagca gcagccccca tgtgctgagg aacagggccc  2760
agtctggctc tgtgccccag ttcaagaagg tggtgttcca ggagttcact gatggcagct  2820
tcacccagcc cctgtacaga ggggagctga atgagcacct gggcctgctg ggcccctaca  2880
tcagggctga ggtggaggac aacatcatgg tgaccttcag gaaccaggcc agcaggccct  2940
acagcttcta cagcagcctg atcagctatg aggaggacca gaggcagggg gctgagccca  3000
ggaagaactt tgtgaagccc aatgaaacca agacctactt ctggaaggtg cagcaccaca  3060
tggcccccac caaggatgag tttgactgca aggcctgggc ctacttctct gatgtggacc  3120
tggagaagga tgtgcactct ggcctgattg gccccctgct ggtgtgccac accaacaccc  3180
tgaaccctgc ccatggcagg caggtgactg tgcaggagtt tgccctgttc ttcaccatct  3240
ttgatgaaac caagagctgg tacttcactg agaacatgga gaggaactgc agggccccct  3300
gcaacatcca gatggaggac cccaccttca aggagaacta caggttccat gccatcaatg  3360
gctacatcat ggacaccctg cctggcctgg tgatggccca ggaccagagg atcaggtggt  3420
acctgctgag catgggcagc aatgagaaca tccacagcat ccacttctct ggccatgtgt  3480
tcactgtgag gaagaaggag gagtacaaga tggccctgta caacctgtac cctggggtgt  3540
ttgagactgt ggagatgctg cccagcaagg ctggcatctg gagggtggag tgcctgattg  3600
gggagcacct gcatgctggc atgagcaccc tgttcctggt gtacagcaac aagtgccaga  3660
ccccccctggg catggcctct ggccacatca gggacttcca gatcactgcc tctggccagt  3720
atggccagtg ggcccccaag ctggccaggc tgcactactc tggcagcatc aatgcctgga  3780
gcaccaagga gcccttcagc tggatcaagg tggacctgct ggcccccatg atcatccatg  3840
gcatcaagac ccagggggcc aggcagaagt tcagcagcct gtacatcagc cagttcatca  3900
tcatgtacag cctggatggc aagaagtggc agacctacag gggcaacagc actggcaccc  3960
tgatggtgtt ctttggcaat gtggacagct ctggcatcaa gcacaacatc ttcaaccccc  4020
ccatcattgc cagatacatc aggctgcacc ccacccacta cagcatcagg agcaccctga  4080
ggatggagct gatgggctgt gacctgaaca gctgcagcat gcccctgggc atggagagca  4140
aggccatctc tgatgcccag atcactgcca gcagctactt caccaacatg tttgccacct  4200
ggagccccag caaggccagg ctgcacctgc agggcaggag caatgcctgg aggccccagg  4260
tcaacaaccc caaggagtgg ctgcaggtgg acttccagaa gaccatgaag gtgactgggg  4320
tgaccaccca gggggtgaag agcctgctga ccagcatgta tgtgaaggag ttcctgatca  4380
gcagcagcca ggatggccac cagtggaccc tgttcttcca gaatggcaag gtgaaggtgt  4440
tccagggcaa ccaggacagc ttcacccctg tggtgaacag cctggacccc cccctgctga  4500
ccagatacct gaggattcac ccccagagct gggtgcacca gattgccctg aggatggagg  4560
tgctgggctg tgaggcccag gacctgtact gatcgcgaat aaaagatctt tattttcatt  4620
agatctgtgt gttggttttt tgtgtgcctg ggtaactaat taggatgtcc aattgcctta  4680
ggccgcagga acccctagtg atggagttgg ccactccctc tctgcgcgct cgctcgctca  4740
ctgaggccgg gcgaccaaag gtcgcccgac gcccgggctt tgcccgggcg gcctcagtga  4800
gcgagcgagc gcgcagctgc ctgcagg                                     4827
```

```
SEQ ID NO: 362          moltype = AA  length = 22
FEATURE                 Location/Qualifiers
REGION                  1..22
                        note = Synthetic polypeptide
REGION                  1..22
                        note = MISC_FEATURE - 3 glycan B domain substitute
source                  1..22
```

```
                        mol_type = protein
                        organism = synthetic construct
SEQUENCE: 362
SFSQNATNVS NNSPPVLKRH QR                                            22

SEQ ID NO: 363          moltype = AA  length = 25
FEATURE                 Location/Qualifiers
REGION                  1..25
                        note = Synthetic polypeptide
REGION                  1..25
                        note = MISC_FEATURE - 4 glycan B domain substitute
source                  1..25
                        mol_type = protein
                        organism = synthetic construct
SEQUENCE: 363
SFSQNATNVS NNSNTSPPVL KRHQR                                         25

SEQ ID NO: 364          moltype = AA  length = 28
FEATURE                 Location/Qualifiers
REGION                  1..28
                        note = Synthetic polypeptide
REGION                  1..28
                        note = MISC_FEATURE - 5 glycan B domain substitute
source                  1..28
                        mol_type = protein
                        organism = synthetic construct
SEQUENCE: 364
SFSQNATNVS NNSNTSNDSP PVLKRHQR                                      28

SEQ ID NO: 365          moltype = AA  length = 31
FEATURE                 Location/Qualifiers
REGION                  1..31
                        note = Synthetic polypeptide
REGION                  1..31
                        note = MISC_FEATURE - 6 glycan B domain substitute
source                  1..31
                        mol_type = protein
                        organism = synthetic construct
SEQUENCE: 365
SFSQNATNVS NNSNTSNDSN VSPPVLKRHQ R                                  31

SEQ ID NO: 366          moltype = AA  length = 31
FEATURE                 Location/Qualifiers
REGION                  1..31
                        note = Synthetic polypeptide
REGION                  1..31
                        note = MISC_FEATURE - 6 glycan B domain substitute (S-T)
source                  1..31
                        mol_type = protein
                        organism = synthetic construct
SEQUENCE: 366
SFSQNATNVS NNSNTSNDSN VTPPVLKRHQ R                                  31

SEQ ID NO: 367          moltype = AA  length = 34
FEATURE                 Location/Qualifiers
REGION                  1..34
                        note = Synthetic polypeptide
REGION                  1..34
                        note = MISC_FEATURE - 7 glycan B domain substitute
source                  1..34
                        mol_type = protein
                        organism = synthetic construct
SEQUENCE: 367
SFSQNATNVS NNSNTSNDSN VSNKTPPVLK RHQR                               34

SEQ ID NO: 368          moltype = AA  length = 37
FEATURE                 Location/Qualifiers
REGION                  1..37
                        note = Synthetic polypeptide
REGION                  1..37
                        note = MISC_FEATURE - 8 glycan B domain substitute
source                  1..37
                        mol_type = protein
                        organism = synthetic construct
SEQUENCE: 368
SFSQNATNVS NNSNTSNDSN VSNKTNNSPP VLKRHQR                            37

SEQ ID NO: 369          moltype = AA  length = 40
FEATURE                 Location/Qualifiers
```

```
REGION                  1..40
                        note = Synthetic polypeptide
REGION                  1..40
                        note = MISC_FEATURE - 9 glycan B domain substitute
source                  1..40
                        mol_type = protein
                        organism = synthetic construct
SEQUENCE: 369
SFSQNATNVS NNSNTSNDSN VSNKTNNSNA TPPVLKRHQR                        40

SEQ ID NO: 370          moltype = DNA  length = 4448
FEATURE                 Location/Qualifiers
misc_feature            1..4448
                        note = Synthetic polynucleotide
misc_feature            1..4448
                        note = pCB1030
source                  1..4448
                        mol_type = other DNA
                        organism = synthetic construct
SEQUENCE: 370
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga ccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctcccccagt gctgaagagg caccagaggg  2340
agatcaccag gaccaccctg cagtctgacc aggaggagat tgactatgat gacaccatct  2400
ctgtggagat gaagaaggag gactttgaca tctacgacga ggacgagaac cagagcccca  2460
ggagcttcca gaagaagacc aggcactact tcattgctgc tgtggagagg ctgtgggact  2520
atggcatgag cagcagcccc catgtgctga ggaacagggc ccagtctggc tctgtgcccc  2580
agttcaagaa ggtggtgttc caggagttca ctgatggcag cttcacccag cccctgtaca  2640
gaggggagct gaatgagcac ctgggcctgc tgggccccta catcagggct gaggtggagg  2700
acaacatcat ggtgaccttc aggaaccagg ccagcaggcc ctacagcttc tacagcagcc  2760
tgatcagcta tgaggaggac cagaggcagg gggctgagcc caggaagaac tttgtgaagc  2820
ccaatgaaac caagacctac ttctggaagg tgcagcacca catggccccc accaaggatg  2880
agtttgactg caaggcctgg gcctacttct ctgatgtgga cctggagaag gatgtgcact  2940
ctggcctgat tggccccctg ctggtgtgcc acaccaacac cctgaaccct gcccatggca  3000
ggcaggtgac tgtgcaggag tttgccctgt tcttcaccat ctttgatgaa accaagagct  3060
ggtacttcac tgagaacatg gagaggaact gcagggcccc ctgcaacatc cagatggagg  3120
accccacctt caaggagaac tacaggttcc atgccatcaa tggctacatc atggacaccc  3180
tgcctggcct ggtgatggcc caggaccaga ggatcaggtg gtacctgctg agcatgggca  3240
gcaatgagaa catccacagc atccacttct ctggccatgt gttcactgtg aggaagaagg  3300
aggagtacaa gatggccctg tacaacctgt accctggggt gtttgagact gtggagatgc  3360
tgcccagcaa ggctggcatc tggagggtgg agtgcctgat tggggagcac ctgcatgctg  3420
gcatgagcac cctgttcctg gtgtacagca acaagtgcca gacccccctg ggcatggcct  3480
ctggccacat cagggacttc cagatcactg cctctggcca gtatggccag tgggccccca  3540
```

```
agctggccag gctgcactac tctggcagca tcaatgcctg gagcaccaag gagcccttca  3600
gctggatcaa ggtggacctg ctggccccca tgatcatcca tggcatcaag acccaggggg  3660
ccaggcagaa gttcagcagc ctgtacatca gccagttcat catcatgtac agcctggatg  3720
gcaagaagtg gcagacctac aggggcaaca gcactggcac cctgatggtg ttctttggca  3780
atgtggacag ctctggcatc aagcacaaca tcttcaaccc ccccatcatt gccagataca  3840
tcaggctgca ccccacccac tacagcatca ggagcaccct gaggatggag ctgatgggct  3900
gtgacctgaa cagctgcagc atgcccctgg gcatggagag caaggccatc tctgatgccc  3960
agatcactgc cagcagctac ttcaccaaca tgtttgccac ctggagcccc agcaaggcca  4020
ggctgcacct gcagggcagg agcaatgcct ggaggcccca ggtcaacaac cccaaggagt  4080
ggctgcaggt ggacttccag aagaccatga aggtgactgg ggtgaccacc caggggggtga  4140
agagcctgct gaccagcatg tatgtgaagg agttcctgat cagcagcagc caggatggcc  4200
accagtggac cctgttcttc cagaatggca aggtgaaggt gttccagggc aaccaggaca  4260
gcttcacccc tgtggtgaac agcctggacc ccccccctgct gaccagatac ctgaggattc  4320
acccccagag ctgggtgcac cagattgccc tgaggatgga ggtgctgggc tgtgaggccc  4380
aggacctgta ctgatcgcga ataaaagatc tttattttca ttagatctgt gtgttggttt  4440
tttgtgtg                                                            4448
```

```
SEQ ID NO: 371         moltype = AA  length = 16
FEATURE                Location/Qualifiers
REGION                 1..16
                       note = Synthetic polypeptide
REGION                 1..16
                       note = MISC_FEATURE - 1-glycan B domain substitute
source                 1..16
                       mol_type = protein
                       organism = synthetic construct
SEQUENCE: 371
SFSQNATPPV LKRHQR                                                   16
```

```
SEQ ID NO: 372         moltype = DNA  length = 4457
FEATURE                Location/Qualifiers
misc_feature           1..4457
                       note = Synthetic polynucleotide
misc_feature           1..4457
                       note = pCB1029
source                 1..4457
                       mol_type = other DNA
                       organism = synthetic construct
SEQUENCE: 372
tgccagttcc cgatcgttac aggcggtact cctcaaagcg tactaaagaa ttattctttt  60
acatttcagt ggccaccagg agatactacc tgggggctgt ggagctgagc tgggactaca  120
tgcagtctga cctgggggag ctgcctgtgg atgccaggtt cccccccaga gtgcccaaga  180
gcttcccctt caacacctct gtggtgtaca agaagaccct gtttgtggag ttcactgacc  240
acctgttcaa cattgccaag cccaggcccc cctggatggg cctgctgggc cccaccatcc  300
aggctgaggt gtatgacact gtggtgatca ccctgaagaa catggccagc caccctgtga  360
gcctgcatgc tgtgggggtg agctactgga aggcctctga gggggctgag tatgatgacc  420
agaccagcca gagggagaag gaggatgaca aggtgttccc tgggggcagc cacacctatg  480
tgtggcaggt gctgaaggag aatggcccca tggcctctga ccccctgtgc ctgacctaca  540
gctacctgag ccatgtggac ctggtgaagg acctgaactc tggcctgatt ggggccctgc  600
tggtgtgcag ggagggcagc ctggccaagg agaagaccca gaccctgcac aagttcatcc  660
tgctgtttgc tgtgtttgat gagggcaaga gctggcactc tgaaaccaag aacagcctga  720
tgcaggacag ggatgctgcc tctgccaggg cctggcccaa gatgcacact gtgaatggct  780
atgtgaacag gagcctgcct ggcctgattg gctgccacag gaagtctgtg tactggcatg  840
tgattggcat gggcaccacc cctgaggtgc acagcatctt cctggagggc cacaccttcc  900
tggtcaggaa ccacaggcag gccagcctgg agatcagccc catcaccttc ctgactgccc  960
agaccctgct gatggacctg ggccagttcc tgctgttctg ccacatcagc agccaccagc  1020
atgatggcat ggaggcctat gtgaaggtgg acagctgccc tgaggagccc cagctgagga  1080
tgaagaacaa tgaggaggct gaggactatg atgatgacct gactgactct gagatggatg  1140
tggtgaggtt tgatgatgac aacagcccca gcttcatcca gatcaggtct gtggccaaga  1200
agcaccccaa gacctgggtg cactacattg ctgctgagga ggaggactgg gactatgccc  1260
ccctggtgct ggcccctgat gacaggagct acaagagcca gtacctgaac aatggccccc  1320
agaggattgg caggaagtac aagaaggtca ggttcatggc ctacactgat gaaaccttca  1380
agaccaggga ggccatccag catgagtctg gcatcctggg cccccctgctg tatggggagg  1440
tgggggacac cctgctgatc atcttcaaga accaggccag caggccctac aacatctacc  1500
cccatggcat cactgatgtg aggcccctgt acagcaggag gctgcccaag gggtgaagc  1560
acctgaagga cttccccatc ctgcctgggg agatcttcaa gtacaagtgg actgtgactg  1620
tggaggatgg ccccaccaag tctgacccca ggtgcctgac cagatactac agcagctttg  1680
tgaacatgga gagggacctg gcctctggcc tgattggccc cctgctgatc tgctacaagg  1740
agtctgtgga ccagaggggc aaccagatca tgtctgacaa gaggaatgtg atcctgttct  1800
ctgtgtttga tgagaacagg agctggtacc tgactgagaa catccagagg ttcctgccca  1860
accctgctgg ggtgcagctg gaggaccctg agttccaggc cagcaacatc atgcacagca  1920
tcaatggcta tgtgtttgac agcctgcagc tgtctgtgtg cctgcatgag gtggcctact  1980
ggtacatcct gagcattggg gcccagactg acttcctgtc tgtgttcttc tctggctaca  2040
ccttcaagca caagatggtg tatgaggaca ccctgaccct gttccccttc tctggggaga  2100
ctgtgttcat gagcatggag aaccctggcc tgtggattct gggctgccac aactctgact  2160
tcaggaacag gggcatgact gccctgctga aagtctccag ctgtgacaag aacactgggg  2220
actactatga ggacagctat gaggacatct ctgcctacct gctgagcaag aacaatgcca  2280
ttgagcccag gagcttcagc cagaatgcca ctaatgtgtc tcccccagtg ctgaagaggc  2340
accagaggga gatcaccagg accaccctgc agtctgacca ggaggagatt gactatgatg  2400
```

-continued

```
acaccatctc tgtggagatg aagaaggagg actttgacat ctacgacgag gacgagaacc  2460
agagccccag gagcttccag aagaagacca ggcactactt cattgctgct gtggagaggc  2520
tgtgggacta tggcatgagc agcagccccc atgtgctgag gaacagggcc cagtctggct  2580
ctgtgcccca gttcaagaag gtggtgttcc aggagttcac tgatggcagc ttcacccagc  2640
ccctgtacag aggggagctg aatgagcacc tgggcctgct gggcccctac atcagggctg  2700
aggtggagga caacatcatg gtgaccttca ggaaccaggc cagcaggccc tacagcttct  2760
acagcagcct gatcagctat gaggaggacc agaggcaggg ggctgagccc aggaagaact  2820
ttgtgaagcc caatgaaacc aagacctact tctggaaggt gcagcaccac atggccccca  2880
ccaaggatga gtttgactgc aaggcctggg cctacttctc tgatgtggac ctggagaagg  2940
atgtgcactc tggcctgatt ggccccctgc tggtgtgcca caccaacacc ctgaaccctg  3000
cccatggcag gcaggtgact gtgcaggagt ttgccctgtt cttcaccatc tttgatgaaa  3060
ccaagagctg gtacttcact gagaacatgg agaggaactg cagggccccc tgcaacatcc  3120
agatggagga ccccaccttc aaggagaact acaggttcca tgccatcaat ggctacatca  3180
tggacaccct gcctggcctg gtgatggccc aggaccagag gatcaggtgg tacctgctga  3240
gcatgggcag caatgagaac atccacagca tccacttctc tggccatgtg ttcactgtga  3300
ggaagaagga ggagtacaag atggccctgt acaacctgta ccctggggtg tttgagactg  3360
tggagatgct gcccagcaag gctggcatct ggagggtgga gtgcctgatt ggggagcacc  3420
tgcatgctgg catgagcacc ctgttcctgg tgtacagcaa caagtgccag acccccctgg  3480
gcatggcctc tggccacatc aggacttcc  agatcactgc ctctggccag tatggccagt  3540
gggcccccaa gctggccagg ctgcactact ctggcagcat caatgcctgg agcaccaagg  3600
agcccttcag ctggatcaag gtggacctgc tggcccccat gatcatccat ggcatcaaga  3660
cccagggggc caggcagaag ttcagcagcc tgtacatcag ccagttcatc atcatgtaca  3720
gcctggatgg caagaagtgg cagacctaca ggggcaacag cactggcacc ctgatggtgt  3780
tctttggcaa tgtggacagc tctggcatca agcacaacat cttcaacccc cccatcattg  3840
ccagatacat caggctgcac ccccacccact acagcatcag gagcaccctg aggatggagc  3900
tgatgggctg tgacctgaac agctgcagca tgcccctggg catggagagc aaggccatct  3960
ctgatgccca gatcactgcc agcagctact tcaccaacat gtttgccacc tggagcccca  4020
gcaaggccag gctgcacctg cagggcagga gcaatgcctg gaggccccag gtcaacaacc  4080
ccaaggagtg gctgcaggtg gacttccaga agaccatgaa ggtgactggg gtgaccaccc  4140
agggggtgaa gagcctgctg accagcatgt atgtgaagga gttcctgatc agcagcagcc  4200
aggatggcca ccagtggacc ctgttcttcc agaatggcaa ggtgaaggtg ttccagggca  4260
accaggacag cttcacccct gtggtgaaca gcctggaccc ccccctgctg accagatacc  4320
tgaggattca cccccagagc tgggtgcacc agattgccct gaggatggag gtgctgggct  4380
gtgaggccca ggacctgtac tgatcgcgaa taaaagatct ttattttcat tagatctgtg  4440
tgttggtttt ttgtgtg                                                 4457

SEQ ID NO: 373          moltype = AA  length = 19
FEATURE                 Location/Qualifiers
REGION                  1..19
                        note = Synthetic polypeptide
REGION                  1..19
                        note = MISC_FEATURE - 2-glycan B domain substitute
source                  1..19
                        mol_type = protein
                        organism = synthetic construct
SEQUENCE: 373
SFSQNATNVS PPVLKRHQR                                               19
```

GENE EDITING FOR HEMOPHILIA A WITH IMPROVED FACTOR VIII EXPRESSION

CROSS REFERENCE TO RELATED APPLICATIONS

This application is a continuation of U.S. application Ser. No. 16/849,796, filed Apr. 15, 2020, which claims the benefit of the filing dates of U.S. Provisional Application No. 62/806,702, filed Feb. 15, 2019, and U.S. Provisional Application No. 62/857,782, filed Jun. 5, 2019. The entire contents of each of the prior applications are incorporated by reference herein.

REFERENCE TO SEQUENCE LISTING

The application contains a Sequence Listing that has been filed electronically in in XML format, created Nov. 15, 2022, and named "095136-0728-021US2 SEQ.xml" (759,455 bytes), the contents of which are incorporated by reference herein in their entirety.

FIELD

The disclosures provided herein relate to materials and methods for treating hemophilia A, both ex vivo and in vivo. In addition, materials and methods are provided for gene editing to modulate the expression, function, or activity of a blood-clotting protein such as Factor VIII (FVIII).

BACKGROUND

Hemophilia A (HemA) is caused by a genetic defect in the FVIII gene (F8) that results in low or undetectable levels of FVIII protein in the blood. This results in ineffective clot formation at sites of tissue injury leading to uncontrolled bleeding that can be fatal if not treated. Replacement of the missing or nonfunctional FVIII protein is an effective treatment for HemA subjects and is the current standard of care. However, protein replacement therapy requires frequent intravenous administration of FVIII protein which is inconvenient in adults, problematic in children, cost prohibitive (>$200,000/year), and can result in break through bleeding events if the treatment regimen is not closely followed.

A permanent cure for hemophilia A is highly desirable. While virus-based gene therapy using Adeno Associated Virus (AAV) has shown some promise in preclinical animal models and in human subjects, it has a number of disadvantages. For example, reported AAV based gene therapy uses a FVIII coding sequence driven by a liver-specific promoter that is encapsulated inside an AAV virus capsid (generally using the serotypes AAV5, AAV8 or AAV9 or AAVrh10, among others). In general, AAV viruses used for gene therapy deliver the packaged coding sequence cassette into the nucleus of the transduced cells, where the cassette remains almost exclusively episomal, and it is the episomal copies of the therapeutic coding sequence that give rise to the therapeutic protein. AAV does not have a mechanism to integrate the encapsulated DNA into the genome of the host cells. Because the therapeutic coding sequence is maintained as an episome, it is not coordinately replicated when the host cell divides so can be lost from daughter cells. It has been demonstrated that when liver cells containing AAV episomes are induced to divide, the AAV genome is not replicated but is instead diluted. Accordingly, AAV based gene therapy is not expected to be effective in children whose livers have not yet achieved adult size. Because current therapies are inadequate, there is a critical need for new effective and permanent or long-lasting treatments for HemA for adults and children.

FVIII is initially expressed as a protein having the domain structure A1-A2-B-A3-C1-C2. The protein is activated by proteolytic cleavage of the bulky, heavily glycosylated B domain, leaving a heavy chain (A1-A2) and light chain (A3-C1-C2) heterodimer. The B domain of the FVIII protein is not required for biological activity. Removal of the large B domain from the FVIII coding sequence is essential to enable reliable packaging into AAV vectors used for in vivo delivery. However, removal of the B domain, which contains up to 18 N-linked glycosylation sites, results in impaired secretion of FVIII protein. Thus, there is a critical need for improved forms of FVIII which can be efficiently and effectively expressed.

SUMMARY

Applicants have discovered compositions and methods of gene editing that can be used to supplement a defective F8 gene, resulting in expression of a functional FVIII protein. Accordingly, inventions provided herein include systems and compositions for altering a host cell DNA sequence, methods for altering a host cell genome, methods and systems for inserting a synthetic Factor VIII coding sequence that provides for improved expression, a cell having a synthetic Factor VIII coding sequence that provides for improved expression that can be administered to a subject, methods for treating hemophilia A, and kits that embody any of the foregoing.

In one aspect, provided herein is a system for altering a host cell DNA sequence, having: a DNA endonuclease or a nucleic acid encoding the DNA endonuclease; a guide RNA (gRNA) having a spacer sequence complementary to a host cell locus or a nucleic acid encoding the gRNA; and a donor template having a nucleic acid sequence encoding a synthetic FVIII protein, where the synthetic FVIII protein comprises a B domain substitute, where the B domain substitute has from zero to nine N-linked glycosylation sites and from three to about 40 amino acids in length.

In another aspect, provided is a method of editing a genome in a host cell, which includes providing to the cell: a gRNA having a spacer sequence complementary to a host cell locus or a nucleic acid encoding the gRNA; a DNA endonuclease or a nucleic acid encoding the DNA endonuclease; and a donor template having a nucleic acid sequence encoding a synthetic FVIII protein, where the synthetic FVIII protein has a B domain substitute, the B domain substitute having from zero to nine N-linked glycosylation sites and from three to about 40 amino acids in length.

In another aspect, provided is a cell, where the genome of the cell includes DNA encoding a synthetic FVIII protein, the synthetic FVIII protein having a B domain substitute, where the B domain substitute has from zero to nine N-linked glycosylation sites and from three to about 40 amino acids in length.

In another aspect, provided is a method of treating hemophilia A in a subject, by administering a cell having DNA encoding a synthetic FVIII protein as described above to the subject.

In another aspect, provided is a method of treating hemophilia A in a subject, by providing the following to a cell in the subject: a gRNA having a spacer sequence complementary to a host cell locus or a nucleic acid encoding the gRNA; a DNA endonuclease or a nucleic acid encoding the DNA endonuclease; and a donor template having a nucleic acid sequence encoding a synthetic FVIII protein, where the synthetic FVIII protein has a B domain substitute, the B domain substitute having from zero to nine N-linked glycosylation sites and from three to about 40 amino acids in length.

In another aspect, provided herein is a kit comprising one or more elements of a system described above, and further comprising instructions for use.

In another aspect, provided herein is a nucleic acid having a polynucleotide sequence encoding a synthetic FVIII protein, where the synthetic FVIII protein has a B domain substitute, the B domain substitute having from zero to nine N-linked glycosylation sites and from three to about 40 amino acids in length.

In another aspect, provided herein is a method of increasing the amount of FVIII in a subject, by providing the following to a cell in the subject, where the subject has a first serum level of FVIII: a gRNA having a spacer sequence complementary to a host cell locus or a nucleic acid encoding the gRNA; a DNA endonuclease or a nucleic acid encoding the DNA endonuclease; and a donor template having a nucleic acid sequence encoding a synthetic FVIII protein, where the synthetic FVIII protein has a B domain substitute, the B domain substitute having from zero to nine N-linked glycosylation sites and from three to about 40 amino acids in length.

BRIEF DESCRIPTION OF THE DRAWINGS

An understanding of certain features and advantages of the present disclosure will be obtained by reference to the following detailed description that sets forth illustrative embodiments, in which the principles of the disclosure are utilized, and the accompanying drawings of which.

DETAILED DESCRIPTION

Figure 1:
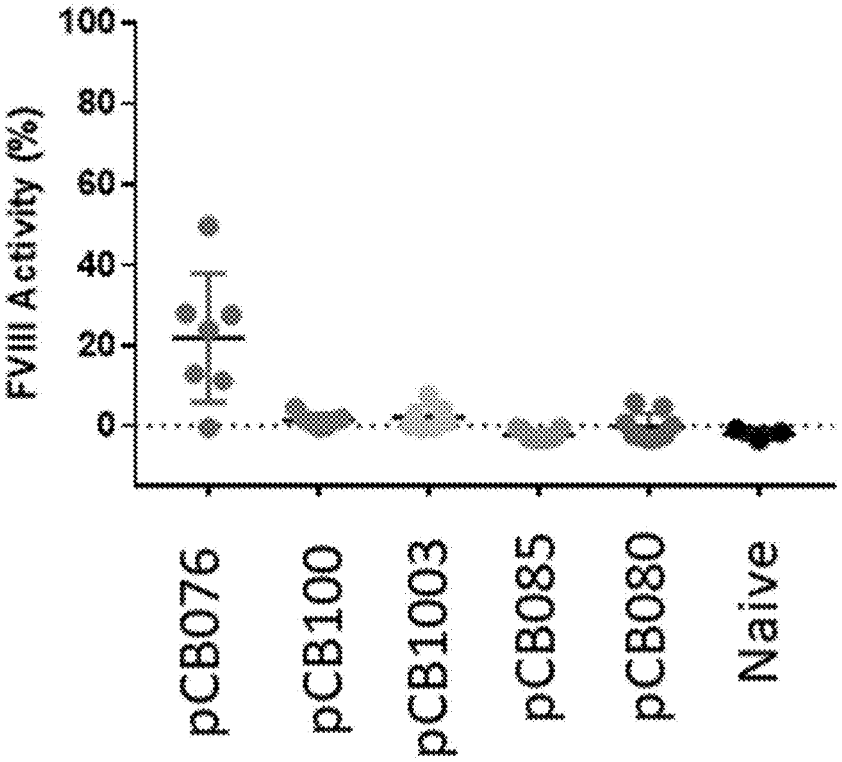
FIG. 1 depicts FVIII levels in the blood of mice after hydrodynamic injection of five plasmids encoding FVIII donor templates followed by LNP delivery of Cas9 mRNA and an sgRNA.

RNA guided endonuclease editing provides advantages over, e.g., lentiviral methods of gene therapy. However, insertion of large sequences in editing protocols can be problematic, for example, because large sequences may be difficult to package for delivery or, compared to short sequences, can be difficult to manufacture. Some proteins require the presence of N-linked glycosylation sites to be correctly secreted from the cell in which they are expressed. The consensus amino sequence of an N-glycosylation site is N-X-T/S, where X is any residue except proline. Glycans are added to the N (asparagine) residue (K. F. Medzihradszky, *Meth Mol Biol* (2008) 446:293-316). Applicants have discovered that the number of N-linked glycosylation sites in such proteins can be greatly reduced or even eliminated, thereby reducing the size of a protein coding sequence, without adversely affecting transcription, translation, or secretion. For example, applicants have discovered that engineering the B domain of a FVIII coding sequence to reduce or to eliminate the number of glycosylation sites can reduce the size of the FVIII sequence to be used in gene editing, without significantly affecting transcription, translation, or secretion of the resulting engineered (synthetic) FVIII, while producing an engineered FVIII protein that has FVIII function. Furthermore, minimizing the number of N-glycan sites that are added to B domain deleted FVIII will minimize the risk of creating a novel epitope for antibodies or T-cells and thereby reduce the risk that the novel FVIII protein may induce an immune response in subjects. The disclosures provide, inter alia, compositions and methods for gene editing to modulate the expression, function, or activity of a blood-clotting protein such as FVIII in a cell by genome editing. The disclosures also provide, inter alia, compositions and methods for treating a subject with hemophilia A, both ex vivo and in vivo. In particular, the invention provides genome editing methods and systems that provide improved integration and improved expression, and synthetic FVIII coding sequences and proteins capable of ameliorating hemophilia A.

Definitions

Unless defined otherwise, all technical and scientific terms used herein have the same meaning as is commonly understood by one of skill in the art to which the claimed subject matter belongs. It is to be understood that the detailed descriptions are exemplary and explanatory only and are not restrictive of any subject matter claimed. In this application, the use of the singular includes the plural unless specifically stated otherwise. As used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although features of the disclosures may be described in the context of a single embodiment, the features may also be provided separately or in any suitable combination. Conversely, although the disclosures may be described herein in the context of separate embodiments for clarity, the disclosures may also be implemented in a single embodiment. Any published patent applications and any other published references, documents, manuscripts, and scientific literature cited herein are incorporated herein by reference for any purpose. In the case of conflict, the present specification, including definitions, will control. In addition, the materials, methods, and examples are illustrative only and not intended to be limiting.

As used herein, ranges and amounts can be expressed as "about" a particular value or range. "About" also includes the exact amount. Hence "about 5 μL" means "about 5 μL" and also "5 μL." Generally, the term "about" includes an amount that would be expected to be within experimental error such as ±1%, ±2%, ±3%, ±5%, or ±10%.

When a range of numerical values is presented herein, it is contemplated that each intervening value between the lower and upper limit of the range, the values that are the upper and lower limits of the range, and all stated values with the range are encompassed within the disclosure. All the possible sub-ranges within the lower and upper limits of the range are also contemplated by the disclosure.

The terms "polypeptide," "peptide," and "protein," are used interchangeably herein to designate a linear series of amino acid residues connected one to the other by peptide bonds, which series may include proteins, polypeptides, oligopeptides, peptides, and fragments thereof. The protein may be made up of naturally occurring amino acids and/or synthetic (e.g., modified or non-naturally occurring) amino acids. The terms "amino acid", or "peptide residue", as used herein can refer to both naturally occurring and synthetic amino acids. The terms "polypeptide", "peptide", and "protein" include fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, a β-galactosidase, a luciferase, and the like. Furthermore, it should be noted that a dash at the beginning or end of an amino acid sequence indicates either a peptide bond to a further sequence of one or more amino acid residues, or a covalent bond to a carboxyl or hydroxyl end group. However, the absence of a dash should not be taken to mean that such peptide bond or covalent bond to a carboxyl or hydroxyl end group is not present, as it is conventional in representation of amino acid sequences to omit such.

The term "polynucleotide," "oligonucleotide," "oligomer," "oligo," "coding sequence", and "nucleic acid" refer to a polymeric form of nucleotides of different lengths, either ribonucleotides or deoxyribonucleotides. Thus, these terms include, without limitation, single-, double-, or multi-stranded DNA or RNA, genomic DNA, cDNA, DNA-RNA hybrids, or a polymer having purine and pyrimidine bases or other natural, chemically or biochemically modified, non-natural, or derivatized nucleotide bases.

The terms "functionally equivalent" or as "functional equivalent" refer without limitation to any molecule such as nucleic acid or protein that has a structure or sequence derived from the compounds disclosed herein and whose structure or sequence is sufficiently similar to those disclosed herein such that it has the same or similar activities and utilities or, based upon such similarity, would be expected by one skilled in the art to exhibit the same or similar activities and utilities as the referenced compounds. Modifications to obtain functional equivalents, "derivatives" or "variants" may include, for example, addition, deletion and/or substitution of one or more of the nucleic acids or amino acid residues.

The functional equivalent or fragment of the functional equivalent of a protein may have one or more conservative amino acid substitutions. The term "conservative amino acid substitution" refers to substitution of an amino acid for another amino acid that has similar properties as the original amino acid, i.e., substitution of an amino acid with another from the same group. The groups of conservative amino acids are as follows:

| Group | Amino acid name |
|---|---|
| Aliphatic | Gly, Ala, Val, Leu, Ile |
| Hydroxyl or Sulfhydryl/Selenium-containing | Ser, Cys, Thr, Met |
| Cyclic | Pro |
| Aromatic | Phe, Tyr, Trp |
| Basic | His, Lys, Arg |
| Acidic and their Amide | Asp, Glu, Asn, Gln |

Conservative substitutions may be introduced in any position of a predetermined peptide or fragment thereof. It may however also be desirable to introduce non-conservative substitutions, particularly, but not limited to, a non-conservative substitution in any one or more positions. A non-conservative substitution leading to the formation of a functionally equivalent fragment of the peptide would for example differ in polarity, in electric charge, in steric bulk, and/or in binding to other proteins or nucleic acids, while maintaining the anticoagulant functionality of the functional equivalent or variant fragment.

"Percentage of sequence identity" is determined by comparing two optimally aligned sequences over a comparison window, wherein the portion of the polynucleotide or polypeptide sequence in the comparison window may have additions or deletions (i.e., gaps) as compared to the reference sequence (which does not have additions or deletions) for optimal alignment of the two sequences. In some cases, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Sequence identity can be determined using, for example, AlignX (included in Vectro NTI, based on ClustalW (http://www.clustal.org/clutal2/), using standard parameters (for example: gap opening penalty=15; gap extension penalty=6.6; gap separation penalty range=8).

The terms "identical" or percent "identity" in the context of two or more nucleic acid or polypeptide sequences, refer to two or more sequences or subsequences that are the same or have a specified percentage of amino acid residues or nucleotides that are the same (e.g., 60%, 65%, 70%, 75%, 80%, 85%, 90%, 95%, 98%, or 99% identity over a specified region, e.g., the entire polypeptide sequences or individual domains of the polypeptides), when compared and aligned for maximum correspondence over a comparison window or designated region as measured using one of the following sequence comparison algorithms or by manual alignment and visual inspection. Such sequences are then said to be "substantially identical." This definition also refers to the complement of a test sequence.

The term "complementary" or "substantially complementary," interchangeably used herein, means that a nucleic acid (e.g., DNA or RNA) has a sequence of nucleotides that enables it to non-covalently bind, i.e., form Watson-Crick base pairs and/or G/U base pairs to another nucleic acid in a sequence-specific, antiparallel, manner (i.e., a nucleic acid specifically binds to a complementary nucleic acid). As is known in the art, standard Watson-Crick base-pairing includes: adenine (A) pairing with thymidine (T), adenine (A) pairing with uracil (U), and guanine (G) pairing with cytosine (C).

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g., tRNA, rRNA, or a guide RNA; also called "non-coding" RNA or "ncRNA"). A "protein coding sequence or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences.

As used herein, "codon" refers to a sequence of three nucleotides that together form a unit of genetic code in a DNA or RNA molecule. As used herein the term "codon degeneracy" refers to the nature in the genetic code permitting variation of the nucleotide sequence without affecting the amino acid sequence of an encoded polypeptide.

The term "codon-optimized" or "codon optimization" refers to genes or coding regions of nucleic acid molecules for transformation of suitable hosts, refers to the alteration of codons in the gene or coding regions of the nucleic acid molecules to reflect the codon usage of the host organism without altering the polypeptide encoded by the DNA. Such optimization includes replacing at least one, or more than one, or a significant number, of codons with one or more codons that are more frequently used in the genes of that organism. Codon usage tables are readily available, for example, at the "Codon Usage Database" available at www kazusa.or.jp/codon/ (visited Jan. 30, 2019). By utilizing the knowledge on codon usage or codon preference in each organism, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions are designed by methods known to those skilled in the art.

The term "recombinant" or "engineered" when used with reference, for example, to a cell, a nucleic acid, a protein, or a vector, indicates that the cell, nucleic acid, protein or vector has been modified by or is the result of laboratory methods. Thus, for example, recombinant or engineered proteins include proteins produced by laboratory methods. Recombinant or engineered proteins can include amino acid residues not found within the native (non-recombinant or wild type) form of the protein, and can include amino acid residues that have been modified, e.g., labeled. The term can include any modifications to the peptide, protein, or nucleic acid sequence. Such modifications include: any chemical modifications of the peptide, protein or nucleic acid sequence; addition, deletion, and/or substitution of one or more of amino acids in the peptide or protein; and addition, deletion, and/or substitution of one or more of nucleic acids in the nucleic acid sequence.

The term "genomic DNA" or "genomic sequence" refers to the DNA of a genome of an organism including, but not limited to, the DNA of the genome of a bacterium, fungus, archaeon, plant or animal.

As used herein, "transgene," "exogenous gene", and "exogenous sequence" refers to a nucleic acid sequence or gene that was not present in the genome of a cell, but is artificially introduced into the genome, for example by genome-edition.

As used herein, "endogenous gene" or "endogenous sequence" refers to a nucleic acid sequence or gene that is naturally present in the genome of a cell, without being introduced via any artificial means.

The term "vector" or "expression vector" means a replicon, such as plasmid, phage, virus, or cosmid, to which another DNA segment, e.g., an "insert", may be attached so as to bring about the replication of the attached segment in a cell.

The term "expression cassette" refers to a vector having a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression. The terms "recombinant expression vector," and "DNA construct" are used interchangeably herein to refer to a DNA molecule having a vector and at least one insert. Recombinant expression vectors are usually generated for the purpose of expressing and/or propagating the insert(s), or for the construction of other recombinant nucleotide sequences. The nucleic acid(s) may or may not be operably linked to a promoter sequence and may or may not be operably linked to DNA regulatory sequences.

The term "regulatory sequence" includes promoters, enhancers and other expression control elements (e.g., polyadenylation signals). Such regulatory sequences are known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells, and those that direct expression of the nucleotide sequence only in certain host cells (e.g., tissue-specific regulatory sequences).

A cell has been "genetically modified" or "transformed" or "transfected" by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell. The genetically modified (or transformed or transfected) cells that have therapeutic activity, e.g., treating hemophilia A, can be used and referred to as "therapeutic cells."

The term "concentration" used in the context of a molecule such as peptide fragment refers to an amount of molecule, e.g., the number of moles of the molecule, present in a given volume of solution.

The term “acute phase protein” refers to a protein that varies in expression or serum concentration in response to inflammation. Examples of acute phase proteins include albumin, transferrin, transthyretin, fibrinogen, antithrombin, and the like.

The terms “individual,” “subject”, and “host” refer to any subject for whom diagnosis, treatment or therapy is desired. In some aspects, the subject is a mammal. In some aspects, the subject is a human being. In some aspects, the subject is a human patient. In some aspects, the subject has or is suspected of having hemophilia A, and/or has one or more symptoms of hemophilia A. In some aspects, the subject is a human who is diagnosed with a risk of hemophilia A at the time of diagnosis or later. In some cases, the diagnosis with a risk of hemophilia A can be determined based on the presence of one or more mutations in the endogenous FVIII gene or genomic sequence near the FVIII gene in the genome that may affect the expression of FVIII gene.

The term “treatment” used in reference to a disease or condition means that at least an amelioration of the symptoms associated with the condition afflicting an individual is achieved, where amelioration is used in a broad sense to refer to at least a reduction in the magnitude of a parameter, e.g., a symptom, associated with the condition (e.g., hemophilia A) being treated. Treatment also includes situations where the pathological condition, or at least symptoms associated therewith, are completely inhibited, e.g., prevented from happening, or eliminated entirely such that the host no longer suffers from the condition, or at least the symptoms that characterize the condition. Thus, treatment includes: (i) prevention (i.e., reducing the risk of development of clinical symptoms, including causing the clinical symptoms not to develop, e.g., preventing disease progression), and (ii) inhibition (i.e., arresting the development or further development of clinical symptoms, e.g., mitigating or completely inhibiting an active disease).

The terms “effective amount,” “pharmaceutically effective amount,” and “therapeutically effective amount” mean a sufficient amount of the composition to provide the desired utility when administered to a subject having a particular condition. In the context of ex vivo treatment of hemophilia A, the term “effective amount” refers to the amount of a population of therapeutic cells or their progeny needed to prevent or alleviate at least one or more signs or symptoms of hemophilia A, and relates to a sufficient amount of a composition having the therapeutic cells or their progeny to provide the desired effect, e.g., to treat symptoms of hemophilia A of a subject. The term “therapeutically effective amount” therefore refers to an amount or number of therapeutic cells or a composition having therapeutic cells that is sufficient to promote a particular effect when administered to a subject in need of treatment, such as one who has or is at risk for hemophilia A. An effective amount also includes an amount or number sufficient to prevent or delay the development of a symptom of the disease, alter the course of a symptom of the disease (for example but not limited to, slowing the progression of a symptom of the disease), or reversing a symptom of the disease. In the context of in vivo treatment of hemophilia A in a subject (e.g., patient) or genome edition done in a cell cultured in vitro, an effective amount refers to an amount of components used for genome edition such as gRNA, donor template and/or a site-directed polypeptide (such as a DNA endonuclease) needed to edit the genome of the cell in the subject or the cell cultured in vitro. It is understood that for any given case, an appropriate “effective amount” can be determined by one of ordinary skill in the art.

The terms “pharmaceutical composition” and “medicament” as used herein refer to a pharmaceutically acceptable excipient, combined with a cell of the invention (expressing a synthetic FVIII protein) and/or one or more components of the system of the invention (i.e., a gRNA or nucleic acid encoding a gRNA, a DNA endonuclease or a nucleic acid encoding a DNA endonuclease, and/or a donor template encoding a synthetic Factor VIII protein).

The term “pharmaceutically acceptable excipient” as used herein refers to any suitable substance that provides a pharmaceutically acceptable carrier, additive or diluent for administration of a compound(s) of interest to a subject. “Pharmaceutically acceptable excipient” can encompass substances referred to as pharmaceutically acceptable diluents, pharmaceutically acceptable additives, and pharmaceutically acceptable carriers.

The term “synthetic FVIII” refers to a protein having substantial sequence identity to the A and C domains of wild type human Factor VIII (GenBank: CAD97566.1; G. A. Vehar et al., *Nature* (1984) 312:337-42), but having a B domain substitute instead of the wild type B domain. In an embodiment of the invention, the sequences of the A and C domains of synthetic FVIII protein are 80, 90, 95, 98, or 99% identical to the wild type sequences of the A and C domains. In some embodiments, the B domain substitute is a polypeptide of any sequence, having about 10 to about 200 amino acids. In some embodiments, the B domain substitute has about 20 to about 100 amino acids. In some embodiments, the B domain substitute can have having less than 40 amino acids (e.g., having any number of amino acids from three to 40 amino acids), and 1-9 N-linked glycosylation sites that provide for glycosylation of the B domain substitute when expressed. The B domain substitute can further include a protease cleavage site, so that the synthetic FVIII protein can be cleaved into heavy and light chains in the same manner as the wild type protein. In one embodiment, the B domain substitute protein sequence includes 1-10 amino acids from the N- and C-terminals of the wild type B domain, in addition to 1-9 N-linked glycosylation (“glycan”) sites. In one embodiment, the B domain substitute protein sequence has 1-6 glycan sites. In one embodiment, the B domain substitute protein sequence has 1-5 glycan sites. In one embodiment, the B domain substitute protein sequence has 1-4 glycan sites. In one embodiment, the B domain substitute protein sequence has 2-4 glycan sites. In an embodiment, the B domain substitute protein sequence has a sequence of any of SEQ ID NO: 362-369, 371, and 373, or a sequence that is at least 80%, 90%, 95%, 98%, or 99% identical to the sequence of any of SEQ ID NO: 362-369, 371, and 373. In one embodiment, the B domain substitute protein sequence has a sequence of any of SEQ ID NO: 362-366, 371, and 373, or a sequence that is at least 80%, 90%, 95%, 98%, or 99% identical to the sequence of any of SEQ ID NO: 362-366, 371, and 373. In one embodiment, the B domain substitute protein sequence has a sequence of any of SEQ ID NO: 362-364, 371, and 373, or a sequence that is at least 80%, 90%, 95%, 98%, or 99% identical to the sequence of any of any of SEQ ID NO: 362-364, 371, and 373. In one embodiment, the B domain substitute protein sequence has a sequence of any of SEQ ID NO: 362-363, or a sequence that is at least 80%, 90%, 95%, 98%, or 99% identical to the sequence of any of SEQ ID NO: 362-363. In one embodiment, the B domain substitute protein sequence has a sequence of any of SEQ ID NO: 362-369. In one embodiment, the B domain substitute protein sequence has a sequence of any of SEQ ID NO: 362-366. In one embodiment, the B domain substitute protein sequence has a sequence of any of SEQ ID NO: 362-364. In one embodiment, the B domain substitute protein sequence has a sequence of any of SEQ ID NO: 362-363, 371, and 373. In one embodiment, the B domain substitute protein sequence has a sequence of any of SEQ ID NO: 371 or 373.

The term "safe harbor locus" refers to a locus within a host cell genome that can be modified (for example, by cleaving, or by inserting a donor sequence) without disrupting the metabolism or regulation of the cell (for example, by causing apoptosis, proliferation, etc.), and/or without causing risk or adverse effects to other cells (non-edited cells) or the host organism as a whole (for example, by inadvertently causing the overexpression of growth factors, etc.). In some embodiments, the safe harbor locus is a locus that is expressed in the host cell. In some embodiments, the safe harbor locus is an albumin locus, a fibrinogen locus, an AAVS1 locus, or a transferrin locus.

Nucleic Acids

Genome-Targeting Nucleic Acid or Guide RNA

The present disclosure provides a genome-targeting nucleic acid that can direct the activities of an associated polypeptide (e.g., a site-directed polypeptide, such as a DNA endonuclease) to a specific target sequence within a target nucleic acid. In some embodiments, the genome-targeting nucleic acid is an RNA. A genome-targeting RNA is referred to as a "guide RNA" or "gRNA" herein. A guide RNA has at least a spacer sequence that can hybridize to a target nucleic acid sequence of interest and a CRISPR repeat sequence. In Type II systems, the gRNA also has a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide such that the gRNA and the site-directed polypeptide form a complex. The genome-targeting nucleic acid provides target specificity to the complex by virtue of its association with the site-directed polypeptide. The genome-targeting nucleic acid thus directs the activity of the site-directed polypeptide.

In some embodiments, the genome-targeting nucleic acid is a double-molecule gRNA. A double-molecule gRNA has two strands of RNA. The first strand has, in the 5' to 3' direction, an optional spacer extension sequence, a spacer sequence and a minimum CRISPR repeat sequence. The second strand has a minimum tracrRNA sequence (complementary to the minimum CRISPR repeat sequence), a 3' tracrRNA sequence and an optional tracrRNA extension sequence. In some embodiments, the genome-targeting nucleic acid is a single-molecule gRNA. A single-molecule gRNA (sgRNA) in a Type II system has, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may have elements that contribute additional functionality (e.g., stability) to the gRNA. The single-molecule guide linker links the minimum CRISPR repeat and the minimum tracrRNA sequence to form a hairpin structure. The optional tracrRNA extension has one or more hairpins. An sgRNA in a Type V system has, in the 5' to 3' direction, a minimum CRISPR repeat sequence and a spacer sequence.

By way of illustration, gRNAs used in the CRISPR/Cas/Cpf1 system, or other smaller RNAs can be readily synthesized by chemical means as illustrated below and described in the art. While chemical synthesis procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some embodiments of genome-targeting nucleic acids, a spacer extension sequence can modify activity, provide stability and/or provide a location for modifications of a genome-targeting nucleic acid. A spacer extension sequence can modify on- or off-target activity or specificity. In some embodiments, a spacer extension sequence is provided. A spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of about 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. In some embodiments, a spacer extension sequence is less than 10 nucleotides in length. In some embodiments, a spacer extension sequence is between 10-30 nucleotides in length. In some embodiments, a spacer extension sequence is between 30-70 nucleotides in length.

In some embodiments, the spacer extension sequence has another moiety (e.g., a stability control sequence, an endoribonuclease binding sequence, a ribozyme). In some embodiments, the moiety decreases or increases the stability of a nucleic acid targeting nucleic acid. In some embodiments, the moiety is a transcriptional terminator segment (i.e., a transcription termination sequence). In some embodiments, the moiety functions in a eukaryotic cell. In some embodiments, the moiety functions in a prokaryotic cell. In some embodiments, the moiety functions in both eukaryotic and prokaryotic cells. Non-limiting examples of suitable moieties include: a 5' cap (e.g., a 7-methylguanylate cap (m7G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence can hybridize to a sequence in a target nucleic acid of interest. The spacer of a genome-targeting nucleic acid interacts with a target nucleic acid in a sequence-specific manner via hybridization (i.e., base pairing). The nucleotide sequence of the spacer thus varies depending on the sequence of the target nucleic acid of interest.

In a CRISPR/Cas system herein, the spacer sequence is designed to hybridize to a target nucleic acid that is located 5' of a PAM of the Cas9 enzyme used in the system. The spacer can perfectly match the target sequence or can have mismatches. Each Cas9 enzyme has a particular PAM sequence that it recognizes in a target DNA. For example, *S. pyogenes* recognizes in a target nucleic acid a PAM that has the sequence 5'-NRG-3', where R has either A or G, where N is any nucleotide and N is immediately 3' of the target nucleic acid sequence targeted by the spacer sequence.

In some embodiments, the target nucleic acid sequence has 20 nucleotides. In some embodiments, the target nucleic acid has less than 20 nucleotides. In some embodiments, the target nucleic acid has more than 20 nucleotides. In some embodiments, the target nucleic acid has at least: 5, 10, 15, 16, 17, 18, 19, 20, 21, 22, 23, 24, 25, 30 or more nucleotides. In some embodiments, the target nucleic acid has at most: 5, 10, 15, 16, 17, 18, 19, 20, 21, 22, 23, 24, 25, 30 or more nucleotides. In some embodiments, the target nucleic acid sequence has 20 bases immediately 5' of the first nucleotide of the PAM. For example, in a sequence having 5'-NNNNNNNNNNNNNNNNNNNNNRG-3' (SEQ ID NO: 191), the target nucleic acid has the sequence that corresponds to the Ns, wherein N is any nucleotide, and the underlined NRG sequence (R is G or A) is the *Streptococcus pyogenes* Cas9 PAM. In some embodiments, the PAM sequence used in the compositions and methods of the present disclosure as a sequence recognized by S.p. Cas9 is NGG.

In some embodiments, the spacer sequence that hybridizes to the target nucleic acid has a length of at least about 6 nucleotides (nt). The spacer sequence can be at least about 6 nt, about 10 nt, about 15 nt, about 18 nt, about 19 nt, about 20 nt, about 25 nt, about 30 nt, about 35 nt or about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some embodiments, the spacer sequence has 20 nucleotides. In some embodiments, the spacer has 19 nucleotides. In some embodiments, the spacer has 18 nucleotides. In some embodiments, the spacer has 17 nucleotides. In some embodiments, the spacer has 16 nucleotides. In some embodiments, the spacer has 15 nucleotides.

In some embodiments, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some embodiments, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over about 20 contiguous nucleotides. In some embodiments, the length of the spacer sequence and the target nucleic acid can differ by one to 6 nucleotides, which can be thought of as a bulge or bulges.

In some embodiments, the spacer sequence is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

In some embodiments, a minimum CRISPR repeat sequence is a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from *S. pyogenes*; see, e.g., J. J. Ferretti et al., *Proc Natl Acad Sci USA* (2001) 98(8):4658-63).

In some embodiments, a minimum CRISPR repeat sequence has nucleotides that can hybridize to a minimum tracrRNA sequence in a cell. The minimum CRISPR repeat sequence and a minimum tracrRNA sequence form a duplex. Together, the minimum CRISPR repeat sequence and the minimum tracrRNA sequence bind to the site-directed polypeptide. At least a part of the minimum CRISPR repeat sequence hybridizes to the minimum tracrRNA sequence. In some embodiments, at least a part of the minimum CRISPR repeat sequence has at least about 30%, about 40%, about 50%, about 60%, about 65%, about 70%, about 75%, about 80%, about 85%, about 90%, about 95%, or 100% complementary to the minimum tracrRNA sequence. In some embodiments, at least a part of the minimum CRISPR repeat sequence has at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about seven nucleotides to about 100 nucleotides. For example, the length of the minimum CRISPR repeat sequence is from about 7 nt to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the minimum CRISPR repeat sequence is approximately nine nucleotides in length. In some embodiments, the minimum CRISPR repeat sequence is approximately 12 nucleotides in length.

In some embodiments, the minimum CRISPR repeat sequence is at least about 60% identical to a reference minimum CRISPR repeat sequence (e.g., wild type crRNA from *S. pyogenes*; see, e.g., J. J. Ferretti et al., supra) over a stretch of at least 6, 7, or 8 contiguous nucleotides. For example, the minimum CRISPR repeat sequence is at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

In some embodiments, a minimum tracrRNA sequence is a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*; see, e.g., J. J. Ferretti et al., supra).

In some embodiments, a minimum tracrRNA sequence has nucleotides that hybridize to a minimum CRISPR repeat sequence in a cell. A minimum tracrRNA sequence and a minimum CRISPR repeat sequence form a duplex. Together, the minimum tracrRNA sequence and the minimum CRISPR repeat bind to a site-directed polypeptide. At least a part of the minimum tracrRNA sequence can hybridize to the minimum CRISPR repeat sequence. In some embodiments, the minimum tracrRNA sequence is at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about seven nucleotides to about 100 nucleotides. For example, the minimum tracrRNA sequence can be from about 7 nt to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. In some embodiments, the minimum tracrRNA sequence is approximately nine nucleotides in length. In some embodiments, the minimum tracrRNA sequence is approximately 12 nucleotides. In some embodiments, the minimum tracrRNA consists of tracrRNA nt 23-48 described in M. Jinek et al., *Science* (2012) 337(6096):816-21.

In some embodiments, the minimum tracrRNA sequence is at least about 60% identical to a reference minimum tracrRNA (e.g., wild type, tracrRNA from *S. pyogenes*; see, e.g., J. J. Ferretti et al., supra) sequence over a stretch of at least 6, 7, or 8 contiguous nucleotides. For example, the minimum tracrRNA sequence is at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

In some embodiments, the duplex between the minimum CRISPR RNA and the minimum tracrRNA has a double helix. In some embodiments, the duplex between the minimum CRISPR RNA and the minimum tracrRNA has at least about 1, 2, 3, 4, 5, 6, 7, 8, 9, or 10 or more nucleotides. In some embodiments, the duplex between the minimum CRISPR RNA and the minimum tracrRNA has at most about 1, 2, 3, 4, 5, 6, 7, 8, 9, or 10 or more nucleotides.

In some embodiments, the duplex has a mismatch (i.e., the two strands of the duplex are not 100% complementary). In some embodiments, the duplex has at least about 1, 2, 3, 4, or 5 or mismatches. In some embodiments, the duplex has at most about 1, 2, 3, 4, or 5 or mismatches. In some embodiments, the duplex has no more than two mismatches.

Bulges

In some embodiments, there is a "bulge" in the duplex between the minimum CRISPR RNA and the minimum tracrRNA. The bulge is an unpaired region of nucleotides within the duplex. In some embodiments, the bulge contributes to the binding of the duplex to the site-directed polypeptide. A bulge has, on one side of the duplex, an unpaired 5'-XXXY-3' where X is any purine and Y has a nucleotide that can form a wobble pair with a nucleotide on the opposite strand, and an unpaired nucleotide region on the other side of the duplex. The number of unpaired nucleotides on the two sides of the duplex can be different.

In one example, the bulge has an unpaired purine (e.g., adenine) on the minimum CRISPR repeat strand of the bulge. In some embodiments, a bulge has an unpaired 5'-AAGY-3' of the minimum tracrRNA sequence strand of the bulge, where Y has a nucleotide that can form a wobble pairing with a nucleotide on the minimum CRISPR repeat strand.

In some embodiments, a bulge on the minimum CRISPR repeat side of the duplex has at least 1, 2, 3, 4, or 5 or more unpaired nucleotides. In some embodiments, a bulge on the minimum CRISPR repeat side of the duplex has at most 1, 2, 3, 4, or 5 or more unpaired nucleotides. In some embodiments, a bulge on the minimum CRISPR repeat side of the duplex has one unpaired nucleotide.

In some embodiments, a bulge on the minimum tracrRNA sequence side of the duplex has at least 1, 2, 3, 4, 5, 6, 7, 8, 9, or 10 or more unpaired nucleotides. In some embodiments, a bulge on the minimum tracrRNA sequence side of the duplex has at most 1, 2, 3, 4, 5, 6, 7, 8, 9, or 10 or more unpaired nucleotides. In some embodiments, a bulge on a second side of the duplex (e.g., the minimum tracrRNA sequence side of the duplex) has four unpaired nucleotides.

In some embodiments, a bulge has at least one wobble pairing. In some embodiments, a bulge has at most one wobble pairing. In some embodiments, a bulge has at least one purine nucleotide. In some embodiments, a bulge has at least three purine nucleotides. In some embodiments, a bulge sequence has at least five purine nucleotides. In some embodiments, a bulge sequence has at least one guanine nucleotide. In some embodiments, a bulge sequence has at least one adenine nucleotide.

Hairpins

In some embodiments, one or more hairpins are located 3' to the minimum tracrRNA in the 3' tracrRNA sequence.

In some embodiments, the hairpin starts at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. In some embodiments, the hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

In some embodiments, a hairpin has at least about 1, 2, 3, 4, 5, 6, 7, 8, 9, 10, 15, or 20 or more consecutive nucleotides. In some embodiments, a hairpin has at most about 1, 2, 3, 4, 5, 6, 7, 8, 9, 10, 15, or more consecutive nucleotides.

In some embodiments, a hairpin has a CC dinucleotide (i.e., two consecutive cytosine nucleotides).

In some embodiments, a hairpin has duplexed nucleotides (i.e., nucleotides in a hairpin, hybridized together). For example, a hairpin has a CC dinucleotide that is hybridized to a GG dinucleotide in a hairpin duplex of the 3' tracrRNA sequence.

One or more of the hairpins can interact with guide RNA-interacting regions of a site-directed polypeptide. In some embodiments, there are two or more hairpins, and in some embodiments there are three or more hairpins.

3' tracrRNA Sequence

In some embodiments, a 3' tracrRNA sequence has a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

In some embodiments, the 3' tracrRNA sequence has a length from about six nucleotides to about 100 nucleotides. For example, the 3' tracrRNA sequence can have a length from about 6 nt to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the 3' tracrRNA sequence has a length of approximately 14 nucleotides.

In some embodiments, the 3' tracrRNA sequence is at least about 60% identical to a reference 3' tracrRNA sequence over a stretch of at least 6, 7, or 8 contiguous nucleotides. For example, the 3' tracrRNA sequence is at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence over a stretch of at least 6, 7, or 8 contiguous nucleotides.

In some embodiments, a 3' tracrRNA sequence has more than one duplexed region. In some embodiments, a 3' tracrRNA sequence has two duplexed regions.

In some embodiments, the 3' tracrRNA sequence has a stem loop structure. In some embodiments, a stem loop structure in the 3' tracrRNA has at least 1, 2, 3, 4, 5, 6, 7, 8, 9, 10, 15 or 20 or more nucleotides. In some embodiments, the stem loop structure in the 3' tracrRNA has at most 1, 2, 3, 4, 5, 6, 7, 8, 9 or 10 or more nucleotides. In some embodiments, the stem loop structure has a functional moiety. For example, the stem loop structure can have an aptamer, a ribozyme, a protein-interacting hairpin, a CRISPR array, an intron, or an exon. In some embodiments, the stem loop structure has at least about 1, 2, 3, 4, or 5 or more functional moieties. In some embodiments, the stem loop structure has at most about 1, 2, 3, 4, or 5 or more functional moieties.

In some embodiments, the hairpin in the 3' tracrRNA sequence has a P-domain. In some embodiments, the P-domain has a double-stranded region in the hairpin.

tracrRNA Extension Sequence

In some embodiments, a tracrRNA extension sequence can be provided whether the tracrRNA is in the context of single-molecule guides or double-molecule guides. In some embodiments, a tracrRNA extension sequence has a length from about one nucleotide to about 400 nucleotides. In some embodiments, a tracrRNA extension sequence has a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. In some embodiments, a tracrRNA extension sequence has a length from about 20 to about 5000 or more nucleotides. In some embodiments, a tracrRNA extension sequence has a length of more than 1000 nucleotides. In some embodiments, a tracrRNA extension sequence has a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. In some embodiments, a tracrRNA extension sequence can have a length of less than 1000 nucleotides. In some embodiments, a tracrRNA extension sequence has less than 10 nucleotides in length. In some embodiments, a tracrRNA extension sequence is 10-30 nucleotides in length. In some embodiments, tracrRNA extension sequence is 30-70 nucleotides in length.

In some embodiments, the tracrRNA extension sequence has a functional moiety (e.g., a stability control sequence, ribozyme, endoribonuclease binding sequence). In some embodiments, the functional moiety has a transcriptional terminator segment. In some embodiments, the functional moiety has a total length from about 10 nt to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the functional moiety functions in a eukaryotic cell. In some embodiments, the functional moiety functions in a prokaryotic cell. In some embodiments, the functional moiety functions in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex, a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). In some embodiments, a tracrRNA extension sequence has a primer binding site or a molecular index (e.g., barcode sequence). In some embodiments, the tracrRNA extension sequence has one or more affinity tags.

Single-Molecule Guide Linker Sequence

In some embodiments, the linker sequence of a single-molecule guide nucleic acid has a length from about three nucleotides to about 100 nucleotides. An illustrative linker has a length from about 3 nt to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single-molecule guide nucleic acid is between 4 and 40 nucleotides. In some embodiments, a linker is at least about 100, 500, 1000, 1500, 2000, 2500, 3000, 3500, 4000, 4500, 5000, 5500, 6000, 6500, or 7000 or more nucleotides. In some embodiments, a linker is at most about 100, 500, 1000, 1500, 2000, 2500, 3000, 3500, 4000, 4500, 5000, 5500, 6000, 6500, or 7000 or more nucleotides.

Linkers can have any of a variety of sequences, although in some embodiments, the linker will not have sequences that have extensive regions of homology with other portions of the gRNA, which might cause intramolecular binding that could interfere with other functional regions of the gRNA. In M. Jinek et al., supra, a simple four nucleotide sequence -GAAA- was used, but numerous other sequences, including longer sequences, can likewise be used.

In some embodiments, the linker sequence has a functional moiety. For example, the linker sequence can have one or more features, including an aptamer, a ribozyme, a protein-interacting hairpin, a protein binding site, a CRISPR array, an intron, or an exon. In some embodiments, the linker sequence has at least about 1, 2, 3, 4, or 5 or more functional moieties. In some embodiments, the linker sequence has at most about 1, 2, 3, 4, or 5 or more functional moieties.

In some embodiments, a genomic location targeted by gRNAs in accordance with the present disclosure can be at, within or near a suitable endogenous locus in a genome, e.g., human genome. The endogenous locus may be selected on the basis of including a gene that is highly expressed, or alternatively a gene that is very selectively expressed (for example, a gene expressed only in certain tissues, or under certain conditions). Exemplary loci for expression in the liver include, for example, an albumin locus, a transferrin locus, and a fibrinogen locus.

In some embodiments, provided herein is a gRNA comprising a spacer sequence that is complementary to a genomic sequence within or near an endogenous transferrin locus in a cell. In some embodiments, the gRNA comprises a spacer sequence that is complementary to a sequence within intron 1 of an endogenous transferrin gene in the cell. In some embodiments, the gRNA comprises a spacer sequence from any one of SEQ ID NOs: 1-190 or a variant thereof having no more than three mismatches compared to any one of SEQ ID NOs: 1-190. In some embodiments, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than three mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than three mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than three mismatches compared to any one of SEQ ID NOs: 17, 18, 29, 76, 50, 54, 81, 96, 64, and 51. In some embodiments, the spacer sequence is 19 nucleotides in length and does not include the nucleotide at position 1 of the sequence from which it is selected.

In some embodiments, a genomic location targeted by gRNAs in accordance with the preset disclosure can be at, within or near an endogenous fibrinogen-alpha chain (fibrinogen-α) locus in a genome, e.g., human genome. Exemplary guide RNAs targeting such locations include the spacer sequences listed in any of SEQ ID NO: 192-270 and the associated Cas9 or Cpf1 cut site. As is understood by the person of ordinary skill in the art, each guide RNA is designed to include a spacer sequence complementary to its genomic target sequence. For example, each of the spacer sequences listed in any of SEQ ID NO: 192-270 can be put into a single RNA chimera or a crRNA (along with a corresponding tracrRNA). See M. Jinek et al., supra, and E. Deltcheva et al., *Nature* (2011) 471:602-07.

Exemplary guide RNAs targeting albumin locations include the spacer sequences from any one of SEQ ID NOs: 271-298 and the associated Cas9 or Cpf1 cut site. For example, a gRNA including a spacer sequence from SEQ ID NO: 271 can include the spacer sequence UAAUUUUC-UUUUGCGCACUA (SEQ ID NO: 299). As is understood by the person of ordinary skill in the art, each guide RNA is designed to include a spacer sequence complementary to its genomic target sequence. For example, each of the spacer sequences from any one of SEQ ID NOs: 271-298 can be put into a single RNA chimera or a crRNA (along with a corresponding tracrRNA).

Donor Template

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair (HDR), non-homologous end joining or alternative non-homologous end joining (A-NHEJ), or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR, which is also known as homologous recombination (HR) can occur when a homologous repair template, or donor, is available.

The homologous donor template has sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide, double-stranded oligonucleotide, or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few base pairs flanking the cleavage site to drive a favored end-joining DNA repair outcome. In some instances, it can be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor template (or donor, or donor sequence, or donor DNA template) herein. In some embodiments, the donor template, a portion of the donor template, a copy of the donor template, or a portion of a copy of the donor template is inserted into the target nucleic acid cleavage site. In some embodiments, the donor template is a sequence that does not naturally occur at the target nucleic acid cleavage site.

When an exogenous DNA molecule is supplied in sufficient concentration inside the nucleus of a cell in which the double-strand break occurs, the exogenous DNA can be inserted at the double-strand break during the NHEJ repair process and thus become a permanent addition to the genome. If the donor template contains a coding sequence for a gene of interest such as a FVIII gene, optionally together with relevant regulatory sequences such as promoters, enhancers, polyA sequences, and/or splice acceptor sequences (also referred to herein as a "donor cassette"), the coding sequence can be expressed from the integrated copy in the genome, resulting in permanent expression for the life of the cell. Moreover, the integrated copy of the donor template can be transmitted to the daughter cells when the cell divides.

In the presence of sufficient concentrations of a donor template that contains flanking DNA sequences with homology to the DNA sequence either side of the double-strand break (referred to as homology arms), the donor template can be integrated via the HDR pathway. The homology arms act as substrates for homologous recombination between the donor template and the sequences either side of the double-strand break. This can result in an error-free insertion of the donor template in which the sequences either side of the double-strand break are not altered from that in the unmodified genome.

Supplied donors for editing by HDR vary markedly, but generally contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors can be used. These oligonucleotides range in size from less than 100 nt to over many kb, though longer ssDNA can also be generated and used. Double-stranded donors are often used, including PCR amplicons, plasmids, and mini-circles. In general, it has been found that an AAV vector is a very effective means of delivery of a donor template, though the packaging limits for individual donors is <5 kb. Active transcription of the donor increased HDR three-fold, indicating the inclusion of promoter can increase conversion. Conversely, CpG methylation of the donor can decrease gene expression and HDR.

In some embodiments, the donor DNA can be supplied with the nuclease or independently by a variety of different methods, for example by transfection, nanoparticle, micro-injection, or viral transduction. A range of tethering options can be used to increase the availability of the donors for HDR in some embodiments. Examples include attaching the donor to the nuclease, attaching to DNA binding proteins that bind nearby, or attaching to proteins that are involved in DNA end binding or repair.

In addition to genome editing by NHEJ or HDR, site-specific gene insertions can be conducted that use both the NHEJ pathway and HR. A combination approach can be applicable in certain settings, possibly including intron/exon borders. NHEJ can prove effective for ligation in the intron, while the error-free HDR can be better suited in the coding region.

In embodiments, an exogenous sequence to be inserted into a genome is a synthetic FVIII coding sequence, encoding a synthetic FVIII protein having a B domain substitute in the position where the wild type B domain would be otherwise. The synthetic FVIII coding sequence can include a nucleic acid sequence encoding a synthetic FVIII protein that has a substantial activity of a wild type FVIII protein such as procoagulation activity. The synthetic FVIII protein can have a degree of activity of at least about 30%, about 40%, about 50%, about 60%, about 70%, about 80%, about 85%, about 90%, about 95% or about 100% of the activity that the wild type FVIII protein exhibits. In some embodiments, the synthetic FVIII protein can have at least about 30%, about 40%, about 50%, about 60%, about 70%, about 80%, about 85%, about 90%, about 95%, about 96%, about 97%, about 98% or about 99% amino acid sequence identity to the FVIII protein, e.g., the wild type FVIII protein. In some embodiments, the synthetic FVIII protein can have at least about 30%, about 40%, about 50%, about 60%, about 70%, about 80%, about 85%, about 90%, about 95%, about 96%, about 97%, about 98% or about 99% amino acid sequence identity to the FVIII protein not including the B domain, e.g., the wild type FVIII protein after cleavage of the B domain. In some embodiments, one having ordinary skill in the art can use a number of methods known in the field to test the functionality or activity of a compound, e.g., peptide or protein. The synthetic FVIII protein can also include any fragment of the wild type FVIII protein or fragment of a modified FVIII protein that has conservative modification on one or more of amino acid residues in the full length, wild type FVIII protein. Thus, in some embodiments, the synthetic FVIII coding sequence can have at least about 30%, about 40%, about 50%, about 60%, about 70%, about 80%, about 85%, about 90%, about 95%, about 96%, about 97%, about 98% or about 99% nucleic acid sequence identity to the FVIII coding sequence, e.g., the wild type FVIII coding sequence.

In embodiments of the invention, the synthetic FVIII contains one or more conservative or non-conservative amino acid substitutions that improve aspects of the protein without adversely affecting the anticoagulant properties of the protein. In one embodiment, the phenylalanine at position 309 is (non-conservatively) replaced with serine or alanine to provide F309S and F309A muteins, respectively. These substitutions are suggested to disrupt a potential binding site for chaperone immunoglobulin binding protein (BiP) in the A1 domain, thereby improving expression and secretion of the protein (M. Swaroop et al., *J Biol Chem* (1997) 272:24121-24).

The B domain substitute of the invention replaces the B domain of the wild type FVIII with a much smaller peptide chain, while still providing a protease cleavage site and one or more sites for N-linked glycosylation. The B domain substitute can have about 10 to about 200 amino acids. In some embodiments, the B domain substitute has about 20 to about 100 amino acids. In some embodiments, the B domain substitute has about 1 to about 40 amino acids, about 1 to about 35 amino acids, about 1 to about 30 amino acids, about 1 to about 25 amino acids, about 1 to about 20 amino acids, about 1 to about 15 amino acids, about 1 to about 10 amino acids, or about 1 to about 5 amino acids. In some embodiments, the B domain substitute has about 5 to about 40 amino acids, about 10 to about 40 amino acids, about 15 to about 40 amino acids, about 20 to about 40 amino acids, about 25 to about 40 amino acids, about 30 to about 40 amino acids, or about 35 to about 40 amino acids. In some embodiments, the B domain substitute has 1 amino acid, 2 amino acids, 3 amino acids, 4 amino acids, 5 amino acids, 6 amino acids, 7 amino acids, 8 amino acids, 9 amino acids, 10 amino acids, 11 amino acid, 12 amino acids, 13 amino acids, 14 amino acids, 15 amino acids, 16 amino acids, 17 amino acids, 18 amino acids, 19 amino acids, 20 amino acids, 21 amino acid, 22 amino acids, 23 amino acids, 24 amino acids, 25 amino acids, 26 amino acids, 27 amino acids, 28 amino acids, 29 amino acids, 30 amino acids, 31 amino acid, 32 amino acids, 33 amino acids, 34 amino acids, 35 amino acids, 36 amino acids, 37 amino acids, 38 amino acids, 39 amino acids, or 40 amino acids. In some embodiments, the nucleic acid encoding the B domain substitute is codon optimized. In some embodiments, the B domain substitute comprises a protease cleavage site, for example, RHQR.

In some embodiments where the insertion of a synthetic FVIII coding sequence thereof is concerned, a cDNA of synthetic FVIII coding sequence can be inserted into a genome of a subject having defective FVIII gene or its regulatory sequences. In such a case, a donor DNA or donor template can be an expression cassette or vector construct having the sequence encoding synthetic FVIII. In some embodiments, the expression vector contains a sequence encoding a synthetic FVIII, which is described elsewhere in the specification, can be used.

In some embodiments, according to any of the donor templates described herein comprising a donor cassette, the donor cassette is flanked on one or both sides by a gRNA target site. For example, such a donor template may comprise a donor cassette with a gRNA target site 5' of the donor cassette and/or a gRNA target site 3' of the donor cassette. In some embodiments, the donor template comprises a donor cassette with a gRNA target site 5' of the donor cassette. In some embodiments, the donor template comprises a donor cassette with a gRNA target site 3' of the donor cassette. In some embodiments, the donor template comprises a donor cassette with a gRNA target site 5' of the donor cassette and a gRNA target site 3' of the donor cassette. In some embodiments, the donor template comprises a donor cassette with a gRNA target site 5' of the donor cassette and a gRNA target site 3' of the donor cassette, and the two gRNA target sites comprise the same sequence. In some embodiments, the donor template comprises at least one gRNA target site, and the at least one gRNA target site in the donor template comprises the same sequence as a gRNA target site in a target locus into which the donor cassette of the donor template is to be integrated. In some embodiments, the donor template comprises at least one gRNA target site, and the at least one gRNA target site in the donor template comprises the reverse complement of a gRNA target site in a target locus into which the donor cassette of the donor template is to be integrated. In some embodiments, the donor template comprises a donor cassette with a gRNA target site 5' of the donor cassette and a gRNA target site 3' of the donor cassette, and the two gRNA target sites in the donor template comprises the same sequence as a gRNA target site in a target locus into which the donor cassette of the donor template is to be integrated. In some embodiments, the donor template comprises a donor cassette with a gRNA target site 5' of the donor cassette and a gRNA target site 3' of the donor cassette, and the two gRNA target sites in the donor template comprises the reverse complement of a gRNA target site in a target locus into which the donor cassette of the donor template is to be integrated.

Nucleic Acid Encoding a Site-Directed Polypeptide or DNA Endonuclease

In some embodiments, the methods of genome editing and compositions therefore can use a nucleic acid (or oligonucleotide) encoding a site-directed polypeptide, such as a DNA endonuclease. The nucleic acid sequence encoding the site-directed polypeptide can be DNA or RNA. If the nucleic acid sequence encoding the site-directed polypeptide is RNA, it can be covalently linked to a gRNA sequence or exist as a separate sequence. In some embodiments, a site-directed polypeptide (such as a DNA endonuclease) is used directly, instead of a nucleic acid sequence that encodes it.

Vectors

In another aspect, the present disclosure provides a nucleic acid having a nucleotide sequence encoding a genome-targeting nucleic acid of the disclosure, a site-directed polypeptide of the disclosure, and/or any nucleic acid or proteinaceous molecule necessary to carry out the embodiments of the methods of the disclosure. In some embodiments, such a nucleic acid is a vector (e.g., a recombinant expression vector).

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some embodiments, a vector has one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. In some embodiments, the vector is a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including gRNAs, promoters such as RNA polymerase III promoters, including for example U6 and H1, can be advantageous. Descriptions of and parameters for enhancing the use of such promoters are known in art, and additional information and approaches are regularly being described; see, e.g., H. Ma et al., *Mol Ther Nuc Acids* 3, e161 (2014) doi:10.1038/mtna.2014.12.

The expression vector can also contain a ribosome binding site for translation initiation and a transcription terminator. The expression vector can also include appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

In some embodiments, a promoter is an inducible promoter (e.g., a heat shock promoter, tetracycline-regulated promoter, steroid-regulated promoter, metal-regulated promoter, estrogen receptor-regulated promoter, etc.). In some embodiments, a promoter is a constitutive promoter (e.g., CMV promoter, UBC promoter). In some embodiments, the promoter is a spatially restricted and/or temporally restricted promoter (e.g., a tissue specific promoter, a cell type specific promoter, etc.). In some embodiments, a vector does not have a promoter for at least one gene to be expressed in a host cell if the gene is going to be expressed, after it is inserted into a genome, under an endogenous promoter present in the genome.

Site-Directed Polypeptide or DNA Endonuclease

Modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The process of integrating non-native nucleic acid into genomic DNA is an example of genome editing.

A site-directed polypeptide is a nuclease used in genome editing to cleave DNA. The site-directed polypeptide can be administered to a cell or a subject as either one or more polypeptides, or one or more mRNAs encoding the polypeptide(s).

In the context of a CRISPR/Cas or CRISPR/Cpf1 system, the site-directed polypeptide can bind to a gRNA that, in turn, specifies the site in the target DNA to which the polypeptide is directed. In embodiments of CRISPR/Cas or CRISPR/Cpf1 systems herein, the site-directed polypeptide is an endonuclease, such as a DNA endonuclease.

In some embodiments, a site-directed polypeptide has a plurality of nucleic acid-cleaving (i.e., nuclease) domains. Two or more nucleic acid-cleaving domains can be linked together via a linker. In some embodiments, the linker is a flexible linker. Linkers can have 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild type Cas9 enzymes have two nuclease domains, an HNH nuclease domain and a RuvC domain. Herein, the "Cas9" refers to both naturally-occurring and recombinant Cas9s. Cas9 enzymes contemplated herein have an HNH or HNH-like nuclease domain, and/or a RuvC or RuvC-like nuclease domain.

HNH and HNH-like domains have a McrA-like fold. HNH and HNH-like domains have two antiparallel β-strands and an α-helix, and have a metal binding site (e.g., a divalent cation binding site). HNH and HNH-like domains can cleave one strand of a target nucleic acid (e.g., the complementary strand of a crRNA targeted strand).

RuvC and RuvC-like domains have an RNaseH or RNaseH-like fold. RuvC/RNaseH domains are involved in a diverse set of nucleic acid-based functions, and act on both RNA and DNA. The RNaseH domain has five β-strands surrounded by a plurality of α-helices. RuvC/RNaseH and RuvC/RNaseH-like domains have a metal binding site (e.g., a divalent cation binding site), and can cleave one strand of a target nucleic acid (e.g., the non-complementary strand of a double-stranded target DNA).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild type exemplary site-directed polypeptide (e.g., Cas9 from *S. pyogenes*, US2014/0068797 Sequence ID No. 8, or R. Sapranauskas et al., *Nuc Acids Res* (2011) 39(21):9275-82), and other site-directed polypeptides).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to the nuclease domain of a wild type exemplary site-directed polypeptide (e.g., Cas9 from *S. pyogenes*).

In some embodiments, a site-directed polypeptide is a DNA endonuclease having at least 70, 75, 80, 85, 90, 95, 97, 99, or 100% identity to a wild type site-directed polypeptide (e.g., Cas9 from *S. pyogenes*) over 10 contiguous amino acids. In some embodiments, a site-directed polypeptide has at most: 70, 75, 80, 85, 90, 95, 97, 99, or 100% identity to a wild type site-directed polypeptide over 10 contiguous amino acids. In some embodiments, a site-directed polypeptide has at least: 70, 75, 80, 85, 90, 95, 97, 99, or 100% identity to a wild type site-directed polypeptide over 10 contiguous amino acids in an HNH nuclease domain of the site-directed polypeptide. In some embodiments, a site-directed polypeptide has at most: 70, 75, 80, 85, 90, 95, 97, 99, or 100% identity to a wild type site-directed polypeptide over 10 contiguous amino acids in an HNH nuclease domain of the site-directed polypeptide. In some embodiments, a site-directed polypeptide has at least: 70, 75, 80, 85, 90, 95, 97, 99, or 100% identity to a wild type site-directed polypeptide over 10 contiguous amino acids in a RuvC nuclease domain of the site-directed polypeptide. In some embodiments, a site-directed polypeptide has at most: 70, 75, 80, 85, 90, 95, 97, 99, or 100% identity to a wild type site-directed polypeptide over 10 contiguous amino acids in a RuvC nuclease domain of the site-directed polypeptide.

In some embodiments, the site-directed polypeptide has a modified form of a wild type exemplary site-directed polypeptide. The modified form of the wild-type exemplary site-directed polypeptide has a mutation that reduces the nucleic acid-cleaving activity of the site-directed polypeptide. In some embodiments, the modified form of the wild type exemplary site-directed polypeptide has less than 90%, less than 80%, less than 70%, less than 60%, less than 50%, less than 40%, less than 30%, less than 20%, less than 10%, less than 5%, or less than 1% of the nucleic acid-cleaving activity of the wild type exemplary site-directed polypeptide. The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

In some embodiments, the modified form of the site-directed polypeptide has a mutation such that it can induce a single-strand break (SSB) on a target nucleic acid (e.g., by cutting only one of the sugar-phosphate backbones of a double-strand target nucleic acid). In some embodiments, the mutation results in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild type site directed polypeptide (e.g., Cas9 from *S. pyogenes*). In some embodiments, the mutation results in one or more of the plurality of nucleic acid-cleaving domains retaining the ability to cleave the complementary strand of the target nucleic acid, but reducing its ability to cleave the non-complementary strand of the target nucleic acid. In some embodiments, the mutation results in one or more of the plurality of nucleic acid-cleaving domains retaining the ability to cleave the non-complementary strand of the target nucleic acid, but reducing its ability to cleave the complementary strand of the target nucleic acid. For example, residues in the wild type exemplary *S. pyogenes* Cas9 polypeptide, such as Asp10, His840, Asn854 and Asn856, are mutated to inactivate one or more of the plurality of nucleic acid-cleaving domains (e.g., nuclease domains). In some embodiments, the residues to be mutated correspond to residues Asp10, His840, Asn854 and Asn856 in the wild type exemplary *S. pyogenes* Cas9 polypeptide (e.g., as determined by sequence and/or structural alignment). Non-limiting examples of mutations include D10A, H840A, N854A and N856A. One skilled in the art will recognize that mutations other than alanine substitutions are suitable.

In some embodiments, a D10A mutation is combined with one or more of H840A, N854A, or N856A mutations to produce a site-directed polypeptide substantially lacking DNA cleavage activity. In some embodiments, a H840A mutation is combined with one or more of D10A, N854A, or N856A mutations to produce a site-directed polypeptide substantially lacking DNA cleavage activity. In some embodiments, a N854A mutation is combined with one or more of H840A, D10A, or N856A mutations to produce a site-directed polypeptide substantially lacking DNA cleavage activity. In some embodiments, a N856A mutation is combined with one or more of H840A, N854A, or D10A mutations to produce a site-directed polypeptide substantially lacking DNA cleavage activity. Site-directed polypeptides that have one substantially inactive nuclease domain are referred to as "nickases".

In some embodiments, variants of RNA-guided endonucleases, for example Cas9, can be used to increase the specificity of CRISPR-mediated genome editing. Wild type Cas9 is generally guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate gRNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two gRNA sites—if they exist—are unlikely to be sufficiently close to each other to enable the double-strand break to occur. As described in the art, nickases can also be used to promote HDR versus NHEJ. HDR can be used to introduce selected changes into target sites in the genome through the use of specific donor sequences that effectively mediate the desired changes. Descriptions of CRISPR/Cas systems for use in gene editing can be found, e.g., in international patent application publication number WO2013/176772, and in J. D. Sander et al., *Nature Biotech* (2014) 32:347-55, and references cited therein.

In some embodiments, the site-directed polypeptide (e.g., variant, mutated, enzymatically inactive and/or conditionally enzymatically inactive site-directed polypeptide) targets nucleic acid. In some embodiments, the site-directed polypeptide targets DNA. In some embodiments, the site-directed polypeptide targets RNA.

In some embodiments, the site-directed polypeptide has one or more non-native sequences (e.g., the site-directed polypeptide is a fusion protein).

In some embodiments, the site-directed polypeptide has an amino acid sequence having at least 15% amino acid identity to a Cas9 from a bacterium (e.g., *S. pyogenes*), a nucleic acid binding domain, and two nucleic acid cleaving domains (e.g., an HNH domain and a RuvC domain).

In some embodiments, the site-directed polypeptide has an amino acid sequence having at least 15% amino acid identity to a Cas9 from a bacterium, and two nucleic acid cleaving domains (i.e., an HNH domain and a RuvC domain).

In some embodiments, the site-directed polypeptide has an amino acid sequence having at least 15% amino acid identity to a Cas9 from a bacterium, and two nucleic acid cleaving domains, wherein one or both of the nucleic acid cleaving domains have at least 50% amino acid identity to a nuclease domain from Cas9 from a bacterium.

In some embodiments, the site-directed polypeptide has an amino acid sequence having at least 15% amino acid identity to a Cas9 from a bacterium, two nucleic acid cleaving domains (e.g., an HNH domain and a RuvC domain), and a non-native sequence (for example, a nuclear localization signal) or a linker linking the site-directed polypeptide to a non-native sequence.

In some embodiments, the site-directed polypeptide has an amino acid sequence having at least 15% amino acid identity to a Cas9 from a bacterium, and two nucleic acid cleaving domains (e.g., an HNH domain and a RuvC domain), wherein the site-directed polypeptide has a mutation in one or both of the nucleic acid cleaving domains that reduces the cleaving activity of the nuclease domains by at least 50%.

In some embodiments, the site-directed polypeptide has an amino acid sequence having at least 15% amino acid identity to a Cas9 from a bacterium, and two nucleic acid cleaving domains (e.g., an HNH domain and a RuvC domain), wherein one of the nuclease domains has mutation of aspartic acid 10, and/or wherein one of the nuclease domains has mutation of histidine 840, and wherein the mutation reduces the cleaving activity of the nuclease domain(s) by at least 50%.

In some embodiments, the one or more site-directed polypeptides, such as DNA endonucleases, include two nickases that together effect one double-strand break at a specific locus in the genome, or four nickases that together effect two double-strand breaks at specific loci in the genome. Alternatively, one site-directed polypeptide affects one double-strand break at a specific locus in the genome.

In some embodiments, a polynucleotide encoding a site-directed polypeptide can be used to edit a genome. In some of such embodiments, the polynucleotide encoding a site-directed polypeptide is codon-optimized according to methods known in the art for expression in the cell containing the target DNA of interest. For example, if the intended target nucleic acid is in a human cell, a human codon-optimized polynucleotide encoding Cas9 can be used to produce the Cas9 polypeptide.

The following provides some examples of site-directed polypeptides that can be used in embodiments of the disclosures.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary hairpin structures (e.g., hairpins) and/or have unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crRNA, which is processed into a mature form of the spacer-repeat unit. A crRNA has a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also has polynucleotide sequences encoding CRISPR Associated (Cas) genes. Cas genes encode endonucleases involved in the biogenesis and the interference stages of crRNA function in prokaryotes. Some Cas genes have homologous secondary and/or tertiary structures.

Type II CRISPR Systems crRNA biogenesis in a Type II CRISPR system in nature requires a trans-activating CRISPR RNA (tracrRNA). The tracrRNA is modified by endogenous RNaselll, and then hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA remains hybridized to the crRNA, and the tracrRNA and the crRNA associate with a site-directed polypeptide (e.g., Cas9). The crRNA of the crRNA-tracrRNA-Cas9 complex guides the complex to a target nucleic acid to which the crRNA can hybridize. Hybridization of the crRNA to the target nucleic acid activates Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). M. Jinek et al., supra, reported that the CRISPR/Cas9 system is useful for RNA-programmable genome editing, and international patent application publication number WO 2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays are processed into mature crRNAS without the requirement of an additional trans-activating tracrRNA. The Type V CRISPR array is processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems start with 20-24 nucleotides of spacer sequence followed by about 22 nucleotides of direct repeat. Also, Cpf1 utilizes a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a four or five nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Figure 5:
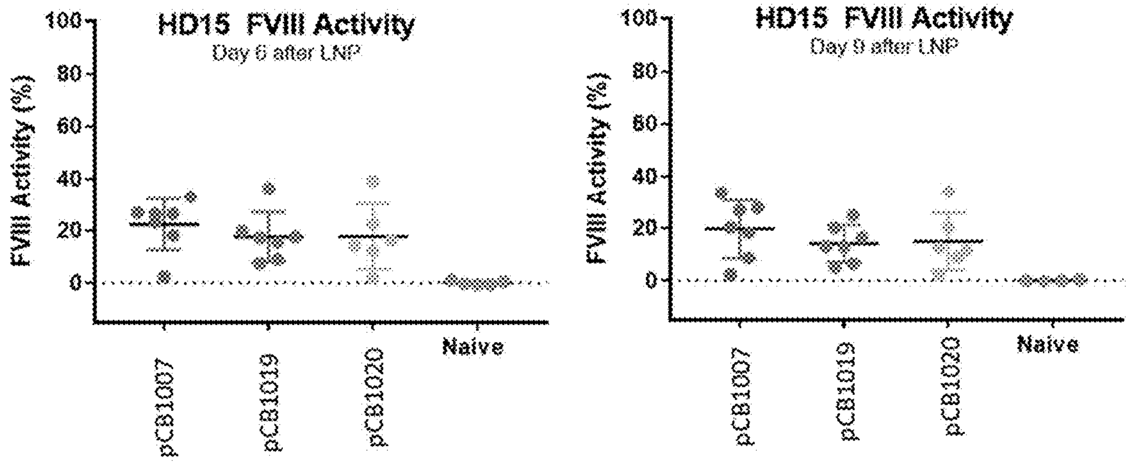
FIG. 5 depicts FVIII activity in the blood of mice that were hydrodynamically injected with plasmids pCB1007 (n=7 mice), pCB1019 (n=7) and pCB1020 (n=6), and retro-orbitally injected with LNP encapsulating mALbT1 gRNA and Cas9 mRNA. FVIII was measured on day six and day nine after LNP dosing.

Exemplary CRISPR/Cas polypeptides include the Cas9 polypeptides in FIG. 1 of I. Fonfara et al., *Nucleic Acids Res.* (2014) 42:2577-90. The CRISPR/Cas gene naming system has undergone extensive rewriting since the Cas genes were discovered. FIG. 5 of Fonfara, supra, provides PAM sequences for the Cas9 polypeptides from different species.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid (e.g., gRNA) guides the site-directed polypeptide to a target nucleic acid.

As stated previously, in some embodiments the site-directed polypeptide and genome-targeting nucleic acid can each be administered separately to a cell or a subject. In some embodiments, the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

Systems for Genome Editing

Provided herein are systems for genome editing, in particular, for inserting a synthetic FVIII coding sequence into the genome of a cell. These systems can be used in methods described herein, such as for editing the genome of a cell and for treating a subject, e.g., a subject having hemophilia A.

In some embodiments, provided herein is a system comprising (a) a DNA endonuclease or nucleic acid encoding the DNA endonuclease; (b) a gRNA targeting an albumin locus in the genome of a cell; and (c) a donor template comprising a nucleic acid sequence encoding a synthetic FVIII protein. In some embodiments, the gRNA targets intron 1 of an albumin gene. In some embodiments, the gRNA comprises a spacer sequence from any one of SEQ ID NOs: 271-298.

In some embodiments, provided herein is a system comprising (a) a deoxyribonucleic acid (DNA) endonuclease or nucleic acid encoding the DNA endonuclease; (b) a guide RNA (gRNA) comprising a spacer sequence from any one of SEQ ID NOs: 271-298; and (c) a donor template comprising a nucleic acid sequence encoding a synthetic FVIII protein. In some embodiments, the gRNA comprises a spacer sequence from any one of SEQ ID NOs: 274, 275, 281 and 283. In some embodiments, the gRNA comprises a spacer sequence from SEQ ID NO: 274. In some embodiments, the gRNA comprises a spacer sequence from SEQ ID NO: 275. In some embodiments, the gRNA comprises a spacer sequence from SEQ ID NO: 281. In some embodiments, the gRNA comprises a spacer sequence from SEQ ID NO: 283.

In some embodiments, according to any of the systems described herein, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional equivalent thereof. In some embodiments, the DNA endonuclease is Cas9. In some embodiments, the Cas9 is from *Streptococcus pyogenes* (spCas9). In some embodiments, the Cas9 is from *Staphylococcus lugdunensis* (SluCas9).

In some embodiments, according to any of the systems described herein, the nucleic acid sequence encoding a synthetic FVIII protein is codon optimized for expression in a host cell. In some embodiments, the nucleic acid sequence encoding a synthetic FVIII protein is codon optimized for expression in a human cell.

In some embodiments, according to any of the systems described herein, the system comprises a nucleic acid encoding a DNA endonuclease. In some embodiments, the nucleic acid encoding the DNA endonuclease is codon optimized for expression in a host cell. In some embodiments, the nucleic acid encoding the DNA endonuclease is codon optimized for expression in a human cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the systems described herein, the donor template is encoded in an AAV vector. In some embodiments, the donor template comprises a donor cassette comprising a synthetic FVIII coding sequence, and the donor cassette is flanked on one or both sides by a gRNA target site. In some embodiments, the donor cassette is flanked on both sides by a gRNA target site. In some embodiments, the gRNA target site is a target site for a gRNA in the system. In some embodiments, the gRNA target site of the donor template is the reverse complement of a cell genome gRNA target site for a gRNA in the system.

In some embodiments, according to any of the systems described herein, the DNA endonuclease or nucleic acid encoding the DNA endonuclease is formulated in a liposome or lipid nanoparticle. In some embodiments, the liposome or lipid nanoparticle also comprises the gRNA. In some embodiments, the liposome or lipid nanoparticle is a lipid nanoparticle. In some embodiments, the system comprises a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the systems described herein, the DNA endonuclease is complexed with the gRNA, forming an RNP complex.

Methods of Genome Edition

Provided herein is a method of genome editing, in particular, inserting a synthetic FVIII protein thereof into the genome of a cell. This method can be used to treat a subject, e.g., a patient having hemophilia A and in such a case, a cell can be isolated from the subject or a separate donor. Then, the chromosomal DNA of the cell is edited using the materials and methods described herein.

Provided herein are methods to knock-in a synthetic FVIII coding sequence into a genome. In one aspect, the present disclosure provides insertion of a nucleic acid sequence of a synthetic FVIII coding sequence, i.e., a nucleic acid sequence encoding a synthetic FVIII protein into a genome of a cell. The synthetic FVIII protein can include a peptide that has a substantial activity of the wild type FVIII protein, e.g., at least about 30%, about 40%, about 50%, about 60%, about 70%, about 80%, about 90%, about 95% or about 100% of the activity that the wild type FVIII protein exhibits. In some embodiments, one having ordinary skill in the art can use a number of methods known in the field to test the functionality or activity of a compound, e.g., peptide or protein. In some embodiments, the synthetic FVIII protein can also include any fragment of the wild type FVIII protein or fragment of a modified FVIII protein that has conservative modification on one or more of amino acid residues in the full length, wild type FVIII protein. In some embodiments, the synthetic FVIII protein can also include any modification(s), e.g., deletion, insertion and/or mutation of one or more amino acids that do not substantially negatively affect the functionality of the wild type FVIII protein. Thus, in some embodiments, the nucleic acid sequence of a synthetic FVIII coding sequence can have at least about 30%, about 40%, about 50%, about 60%, about 70%, about 80%, about 85%, about 90%, about 95%, about 96%, about 97%, about 98% or about 99% nucleic acid sequence identity to the FVIII coding sequence.

In some embodiments, a synthetic FVIII coding sequence is inserted into a genomic sequence in a cell. In some embodiments, the insertion site is at or within an albumin locus, a transferrin locus, or a fibrinogen alpha locus, in the genome of the cell. In some embodiments, the insertion site is an albumin locus. The insertion method uses one or more gRNAs targeting the first intron (or intron 1) of an albumin gene. In some embodiments, the donor DNA is single or double-stranded DNA having a synthetic FVIII coding sequence.

In some embodiments, the genome editing methods utilize a DNA endonuclease such as a CRISPR/Cas system to genetically introduce (knock-in) a synthetic FVIII coding sequence. In some embodiments, the DNA endonuclease is a Cas1, Cas1B, Cas2, Cas3, Cas4, Cas5, Cas6, Cas7, Cas8, Cas9 (also known as Csn1 and Csx12), Cas100, Csyl, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, a homolog thereof, recombination of the naturally occurring molecule, codon-optimized, or modified version thereof, and combinations of any of the foregoing. In some embodiments, the DNA endonuclease is Cas9. In some embodiments, the Cas9 is from *Streptococcus pyogenes* (spCas9). In some embodiments, the Cas9 is from *Staphylococcus lugdunensis* (SluCas9).

In some embodiments, the cell subject to the genome-edition has one or more mutation(s) in the genome which results in reduction of the expression of endogenous FVIII gene as compared to the expression in a normal that does not have such mutation(s). The normal cell can be a healthy or control cell that is originated (or isolated) from a different subject who does not have FVIII gene defects. In some embodiments, the cell subject to the genome-edition can be originated (or isolated) from a subject who is in need of treatment of FVIII gene-related condition or disorder, e.g., hemophilia A. Therefore, in some embodiments the expression of the endogenous FVIII gene in such cell is about 10%, about 20%, about 30%, about 40%, about 50%, about 60%, about 70%, about 80%, about 90% or about 100% reduced as compared to the expression of endogenous FVIII gene expression in the normal cell.

In some embodiments, the genome editing methods conducts targeted integration (at a non-coding region of the genome) of a functional FVIII coding sequence, e.g., a FVIII coding sequence that is operably linked to a supplied promoter so as to stably generate FVIII protein in vivo. In some embodiments, the targeted integration of a FVIII coding sequence occurs in an intron of an albumin gene that is highly expressed in the cell type of interest, e.g., hepatocytes or sinusoidal endothelial cells.

In one aspect, the nucleic acid sequence of a synthetic FVIII coding sequence is inserted into a genome of a cell. In embodiments, the synthetic FVIII coding sequence to be inserted is a modified FVIII coding sequence. In some embodiments, in the modified FVIII coding sequence the B domain of the wild type FVIII coding sequence is deleted and replaced with a B domain substitute. In some embodiments, a synthetic FVIII is superior to a full length wild type FVIII because of its smaller size (4371 bp vs 7053 bp). Thus, in some embodiments the synthetic FVIII coding sequence lacking the FVIII signal peptide and containing a splice acceptor sequence at its 5' end (N-terminus of the FVIII coding sequence) is integrated specifically into intron 1 of a gene locus in the hepatocytes of mammals, including humans. In an embodiment, the gene locus is an albumin locus. In another embodiment, the gene locus is a transferrin locus. In another embodiment, the gene locus is a fibrinogen alpha locus.

The transcription of the synthetic FVIII coding sequence from a transferrin promoter can result in a pre-mRNA that contains exon 1 of transferrin, part of intron 1 and the integrated synthetic FVIII coding sequence. When this pre-mRNA undergoes the natural splicing process to remove the introns, the splicing machinery can join the splice donor at the 3' side of transferrin exon 1 to the next available splice acceptor which will be the splice acceptor at the 5' end of the synthetic FVIII coding sequence of the inserted DNA donor. This can result in a mature mRNA containing transferrin exon 1 fused to the mature coding sequence for the synthetic FVIII.

The transcription of this synthetic FVIII coding sequence from an albumin promoter can result in a pre-mRNA that contains exon 1 of albumin, part of intron 1 and the integrated synthetic FVIII coding sequence. When this pre-mRNA undergoes the natural splicing process to remove the introns, the splicing machinery can join the splice donor at the 3' side of albumin exon 1 to the next available splice acceptor which will be the splice acceptor at the 5' end of the synthetic FVIII coding sequence of the inserted DNA donor. This can result in a mature mRNA containing albumin exon 1 fused to the mature coding sequence for synthetic FVIII. Exon 1 of albumin encodes the signal peptide plus two additional amino acids and one third of a codon that in humans normally encodes the protein sequence DAH at the N-terminus of albumin. Therefore, in some embodiments after the predicted cleavage of an albumin signal peptide during secretion from the cell a synthetic FVIII protein can be generated that has three additional amino acid residues added to the N-terminus resulting in the amino acid sequence -DAHATRRYY (SEQ ID NO: 300)- at the N-terminus of the synthetic FVIII protein. Because the third of these three amino acids (underlined) is encoded partly by the end of exon 1 and partly by the synthetic FVIII DNA donor template, it is possible to select the identity of the third additional amino acid residue to be either Leu, Pro, His, Gln or Arg. Among these options Leu is used in some embodiments since Leu is the least molecularly complex and thus least likely to form a new T-cell epitope, resulting in the amino acid sequence -DALATRRYY- at the N-terminus of the synthetic FVIII protein. Alternatively, the DNA donor template can be designed to delete the third residue resulting in the amino acid sequence DALTRRYY at the N-terminus of the synthetic FVIII protein. In some cases, adding additional amino acids to the sequence of a native protein can increase the immunogenicity risk. Therefore in some embodiments where an in silico analysis to predict the potential immunogenicity of the two potential options for the N-terminus of synthetic FVIII demonstrates that the deletion of one residue (DALTRRYY) has a lower immunogenicity score, this can be a design at least in some embodiments.

In some embodiments, a DNA sequence encoding synthetic FVIII in which the codon usage has been optimized can be used to improve the expression in mammalian cells (so-called "codon optimization"). Different computer algorithms are also available in the field for performing codon optimization and these generate distinct DNA sequences (V. P. Mauro et al., *Trends Mol Med* (2014) 20:604-13). Examples of commercially available codon optimization algorithms are those employed by companies ATUM and GeneArt (part of Thermo Fisher Scientific). Codon optimization of the FVIII coding sequence was demonstrated to significantly improve the expression of FVIII after gene based delivery to mice (A. C. Nathwani et al., *Blood* (2006) 107(7):2653-61.; N. J. Ward et al., *Blood* (2011) 117(3):798-807; P. A. Radcliffe et al., *Gene Ther.* (2008) 15(4):289-97). Codon optimization is an established approach for improving the expression of a coding sequence of interest, and is based primarily on the substitution of less frequently used codons for more frequently used codons, without alteration of the encoded amino acid sequence. Since the initial recognition that codon bias can influence protein expression, the methodology for codon optimization has evolved and algorithms are commercially available including those provided by DNA synthesis companies such as GeneArt and ATUM. These commercially available algorithms are available free to users as part of the DNA synthesis service, and are designed to also remove cryptic splicing signals and even out the G/C content across the coding sequence. Delivery of exogenous nucleic acids to cells in vivo can induce an innate immune response that is driven at least in part by the recognition of CG dinucleotides (also called CpG sequences) by the Toll receptor system, and reduction of the CG dinucleotide content is proposed as a way to reduce the innate immune response to these nucleic acids, particularly when plasmid DNA is the delivery vector. See also P. Colella et al., *Mol Ther Methods Clin Dev* (2018) 8:87-104. When the naturally occurring (native) coding sequence for a gene is optimized for expression in mammalian species, the number of CG dinucleotides is generally increased because the more frequently used codons contain a higher frequency of G and C nucleotides at the 3$^{rd}$ (wobble) position of the codon. Thus, the increase in the overall content of G and C nucleotides in the coding sequence will result in higher content of GC dinucleotides.

In some embodiments, the sequence homology or identity between a synthetic FVIII coding sequence that was codon optimized by different algorithms and the native FVIII sequence (as present in the human genome) can range from about 30%, about 40%, about 50%, about 60%, about 65%, about 70%, about 75%, about 80%, about 85%, about 90%, about 95%, or 100%. In some embodiments, the codon-optimized synthetic FVIII coding sequence has between about 75% to about 79% of sequence homology or identity to the native FVIII sequence. In some embodiments, the codon-optimized synthetic FVIII coding sequence has about 70%, about 71%, about 72%, about 73%, about 74%, about 75%, about 76%, about 77%, about 78%, about 79% or about 80% of sequence homology or identity to the native FVIII sequence.

In some embodiments, a donor template or donor construct is prepared to contain a DNA sequence encoding synthetic FVIII. In some embodiments, a DNA donor template is designed to contain a codon optimized human synthetic FVIII coding sequence. In some embodiments, the codon-optimization is done in such a way that the sequence at the 5' end encoding the signal peptide of FVIII has been deleted and replaced with a splice acceptor sequence, and in addition a polyadenylation signal is added to the 3' end after the FVIII stop codon (MAB8A—SEQ ID NO: 301). The splice acceptor sequence can be selected from among known splice acceptor sequences from known genes or a consensus splice acceptor sequence can be used that is derived from an alignment of many splice acceptor sequences known in the field. In some embodiments, a splice acceptor sequence from highly expressed genes is used since such sequences are thought to provide optimal splicing efficiency. In some embodiments, the consensus splicing acceptor sequence is composed of a Branch site with the consensus sequence T/CNC/TT/CA/GAC/T (SEQ ID NO: 302) followed within 20 bp with a polypyrimidine tract (C or T) of 10 to 12 bases followed by AG>G/A in which the > is the location of the intron/exon boundary. In one embodiment, a synthetic splice acceptor sequence (ctgacctcttctcttcctcccacag—SEQ ID NO: 303) is used. In another embodiment, the native splice acceptor sequence from an albumin gene intron 1/exon 2 boundary of human (TTAACAATCCTTTTTTTTCTTCCCTTGCCCAG—SEQ ID NO: 304) or mouse (ttaaatatgttgtgtggtttttctctccctgtttccacag—SEQ ID NO: 305) is used.

The polyadenylation sequence provides a signal for the cell to add a polyA tail which is essential for the stability of the mRNA within the cell. In some embodiments that the DNA-donor template is going to be packaged into AAV particles, embodiments of the invention keep the size of the packaged DNA within the packaging limits for AAV which can be less than about 5 Kb, or not more than about 4.7 Kb. Thus, in some embodiments a polyA sequence as short as possible is used, e.g., about 10-mer, about 20-mer, about 30-mer, about 40-mer, about 50-mer or about 60-mer or any intervening number of nucleotides of the foregoing. A consensus synthetic poly A signal sequence has been described in the literature (N. Levitt et al., *Genes Dev* (1989) 3(7):1019-25) with the sequence AATAAAAGATCTTTATTTTCATTAGATCTGTGTGTTGGTTTTTTGTGTG (SEQ ID NO: 306) and is commonly used in numerous expression vectors.

In some embodiments, additional sequence elements can be added to the DNA donor template to improve the integration frequency. One such element is homology arms. A sequence from the left side of the double-strand break (LHA) is appended to the 5' (N-terminal to the FVIII coding sequence) end of the DNA donor template and a sequence from the right side of the double-strand break (RHA) is appended to the 3' (C-terminal of the FVIII coding sequence) end of the DNA donor template for example MAB8B (SEQ ID NO: 308).

An alternative DNA donor template design that is provided in some embodiments has a sequence complementary to the recognition sequence for the sgRNA that will be used to cleave the genomic site. MAB8C (SEQ ID NO: 309) represents an example of this type of DNA donor templates. By including the sgRNA recognition site the DNA donor template will be cleaved by the sgRNA/Cas9 complex inside the nucleus of the cell to which the DNA donor template and the sgRNA/Cas9 have been delivered. Cleavage of the donor template into linear fragments can increase the frequency of integration at a double-strand break by the non-homologous end joining mechanism or by the HDR mechanism. This can be particularly beneficial in the case of delivery of donor templates packaged in AAV because after delivery to the nucleus the AAV genomes are known to concatemerize to form larger circular double-stranded DNA molecules (H. Nakai et al., *J Virol* (2001) 75:6969-76). Therefore, in some cases the circular concatemers can be less efficient donors for integration at double-strand breaks, particularly by the NHEJ mechanism. It was reported previously that the efficiency of targeted integration using circular plasmid DNA donor templates could be increased by including zinc finger nuclease cut sites in the plasmid (S. Cristea et al., *Biotechnol. Bioeng.* (2013) 110:871-80). More recently this approach was also applied using the CRISPR/Cas9 nuclease (K. Suzuki et al., *Nature* (2017) 540:144-49). While a sgRNA recognition sequence is active when present on either strand of a double-stranded DNA donor template, use of the reverse complement of the sgRNA recognition sequence that is present in the genome is predicted to favor stable integration because integration in the reverse orientation re-creates the sgRNA recognition sequence which can be recut thereby releasing the inserted donor template. Integration of such a donor template in the genome in the forward orientation by NHEJ is predicted to not re-create the sgRNA recognition sequence such that the integrated donor template cannot be excised out of the genome. The benefit of including sgRNA recognition sequences in the donor with or without homology arms upon the efficiency of integration of FVIII donor template can be tested and determined, e.g., in mice using AAV for delivery of the donor and LNP (lipid nanoparticle) for delivery of the CRISPR/CAS9 components.

In some embodiments, the donor template comprises the synthetic FVIII coding sequence in a donor cassette according to any of the embodiments described herein flanked on one or both sides by a gRNA target site. In some embodiments, the donor template comprises a gRNA target site 5' of the donor cassette and/or a gRNA target site 3' of the donor cassette. In some embodiments, the donor template comprises two flanking gRNA target sites, and the two gRNA target sites comprise the same sequence. In some embodiments, the donor template comprises at least one gRNA target site, and the at least one gRNA target site in the donor template is a target site for at least one of the one or more gRNAs targeting the first intron of an albumin gene. In some embodiments, the donor template comprises at least one gRNA target site, and the at least one gRNA target site in the donor template is the reverse complement of a target site for at least one of the one or more gRNAs in the first intron of an albumin gene. In some embodiments, the donor template comprises a gRNA target site 5' of the donor cassette and a gRNA target site 3' of the donor cassette, and the two gRNA target sites in the donor template are targeted by the one or more gRNAs targeting the first intron of an albumin gene. In some embodiments, the donor template comprises a gRNA target site 5' of the donor cassette and a gRNA target site 3' of the donor cassette, and the two gRNA target sites in the donor template are the reverse complement of a target site for at least one of the one or more gRNAs in the first intron of an albumin gene.

Insertion of a FVIII coding sequence into a target site, i.e., a genomic location where the FVIII coding sequence is inserted, can be in an endogenous albumin gene locus or neighboring sequences thereof. In some embodiments, the FVIII coding sequence is inserted in a manner that the expression of the inserted coding sequence is controlled by the endogenous promoter of an albumin gene. In some embodiments, the FVIII coding sequence in inserted in one of introns of an albumin gene. In some embodiments, the FVIII coding sequence is inserted in one of exons of an albumin gene. In some embodiments, the FVIII coding sequence is inserted at a junction of intron:exon (or vice versa). In some embodiments, the insertion of the FVIII coding sequence is in the first intron (or intron 1) of an albumin locus. In some embodiments, the insertion of the FVIII coding sequence does not significantly affect, e.g., upregulate or downregulate the expression of an albumin gene.

In embodiments, the target site for the insertion of a FVIII coding sequence is at, within, or near an endogenous albumin gene. In some embodiments, the target site is in an intergenic region that is upstream of the promoter of an albumin gene locus in the genome. In some embodiments, the target site is within an albumin gene locus. In some embodiments, the target site in one of the introns of an albumin gene locus. In some embodiments, the target site in one of the exons of an albumin gene locus. In some embodiments, the target site is in one of the junctions between an intron and exon (or vice versa) of an albumin gene locus. In some embodiments, the target site is in the first intron (or intron 1) of an albumin gene locus. In certain embodiments, the target site is at least, about or at most 0, 1, 5, 10, 20, 30, 40, 50, 100, 150, 200, 250, 300, 350, 400, 450 or 500 or 550 or 600 or 650 bp downstream of the first exon (i.e., from the last nucleic acid of the first exon) of an albumin gene. In some embodiments, the target site is at least, about or at most 0.1 kb, about 0.2 kb, about 0.3 kb, about 0.4 kb, about 0.5 kb, about 1 kb, about 1.5 kb, about 2 kb, about 2.5 kb, about 3 kb, about 3.5 kb, about 4 kb, about 4.5 kb or about 5 kb upstream of the first intron of an albumin gene. In some embodiments, the target site is anywhere within about 0 bp to about 100 bp upstream, about 101 bp to about 200 bp upstream, about 201 bp to about 300 bp upstream, about 301 bp to about 400 bp upstream, about 401 bp to about 500 bp upstream, about 501 bp to about 600 bp upstream, about 601 bp to about 700 bp upstream, about 701 bp to about 800 bp upstream, about 801 bp to about 900 bp upstream, about 901 bp to about 1000 bp upstream, about 1001 bp to about 1500 bp upstream, about 1501 bp to about 2000 bp upstream, about 2001 bp to about 2500 bp upstream, about 2501 bp to about 3000 bp upstream, about 3001 bp to about 3500 bp upstream, about 3501 bp to about 4000 bp upstream, about 4001 bp to about 4500 bp upstream or about 4501 bp to about 5000 bp upstream of the second exon of an albumin gene. In some embodiments, the target site is at least 37 bp downstream of the end (i.e., the 3' end) of the first exon of the human albumin gene in the genome. In some embodiments, the target site is at least 330 bp upstream of the start (i.e., the 5' start) of the second exon of the human albumin gene in the genome.

In some embodiments, provided herein is a method of editing a genome in a cell, the method comprising providing the following to the cell: (a) a guide RNA (gRNA) targeting an albumin locus in the cell genome; (b) a DNA endonuclease or nucleic acid encoding the DNA endonuclease; and (c) a donor template comprising a nucleic acid sequence encoding a synthetic FVIII protein. In some embodiments, the gRNA targets intron 1 of an albumin gene. In some embodiments, the gRNA comprises a spacer sequence from any one of SEQ ID NOs: 271-298.

In some embodiments, provided herein is a method of editing a genome in a cell, the method comprising providing the following to the cell: (a) a gRNA comprising a spacer sequence from any one of SEQ ID NOs: 271-298; (b) a DNA endonuclease or nucleic acid encoding the DNA endonuclease; and (c) a donor template comprising a nucleic acid sequence encoding a synthetic FVIII protein. In some embodiments, the gRNA comprises a spacer sequence from any one of SEQ ID NOs: 274, 275, 281, and 283. In some embodiments, the gRNA comprises a spacer sequence from SEQ ID NO: 274. In some embodiments, the gRNA comprises a spacer sequence from SEQ ID NO: 275. In some embodiments, the gRNA comprises a spacer sequence from SEQ ID NO: 281. In some embodiments, the gRNA comprises a spacer sequence from SEQ ID NO: 283. In some embodiments, the cell is a human cell, e.g., a human hepatocyte cell.

In some embodiments, according to any of the methods of editing a genome in a cell described herein, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csyl, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional equivalent thereof. In some embodiments, the DNA endonuclease is Cas9. In some embodiments, the Cas9 is spCas9. In some embodiments, the Cas9 is SluCas9.

In some embodiments, according to any of the methods of editing a genome in a cell described herein, the nucleic acid sequence encoding a synthetic FVIII protein is codon optimized for expression in the cell. In some embodiments, the cell is a human cell.

In some embodiments, according to any of the methods of editing a genome in a cell described herein, the method employs a nucleic acid encoding the DNA endonuclease. In some embodiments, the nucleic acid encoding the DNA endonuclease is codon optimized for expression in the cell. In some embodiments, the cell is a human cell, e.g., a human hepatocyte cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the methods of editing a genome in a cell described herein, the donor template is encoded in an AAV vector. In some embodiments, the donor template comprises a donor cassette comprising the nucleic acid sequence encoding a synthetic FVIII protein, and the donor cassette is flanked on one or both sides by a gRNA target site. In some embodiments, the donor cassette is flanked on both sides by a gRNA target site. In some embodiments, the gRNA target site is a target site for the gRNA that is administered. In some embodiments, the gRNA target site of the donor template is the reverse complement of a cell genome gRNA target site for the gRNA.

In some embodiments, according to any of the methods of editing a genome in a cell described herein, the DNA endonuclease or nucleic acid encoding the DNA endonuclease is formulated in a liposome or lipid nanoparticle. In some embodiments, the liposome or lipid nanoparticle also comprises the gRNA. In some embodiments, the liposome or lipid nanoparticle is a lipid nanoparticle. In some embodiments, the method employs a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the methods of editing a genome in a cell described herein, the DNA endonuclease is pre-complexed with the gRNA, forming an RNP complex.

In some embodiments, according to any of the methods of editing a genome in a cell described herein, the gRNA and the DNA endonuclease or nucleic acid encoding the DNA endonuclease are provided to the cell after the donor template is provided to the cell. In some embodiments, the gRNA and the DNA endonuclease or nucleic acid encoding the DNA endonuclease are provided to the cell more than four days after the donor template is provided to the cell. In some embodiments, the gRNA and the DNA endonuclease or nucleic acid encoding the DNA endonuclease are provided to the cell at least 14 days after the donor template is provided to the cell. In some embodiments, the gRNA and the DNA endonuclease or nucleic acid encoding the DNA endonuclease are provided to the cell at least 17 days after the donor template is provided to the cell. In some embodiments, (a) and (b) are provided to the cell as a lipid nanoparticle comprising nucleic acid encoding the DNA endonuclease and the gRNA. In some embodiments, the nucleic acid encoding the DNA endonuclease is an mRNA encoding the DNA endonuclease. In some embodiments, (c) is provided to the cell as an AAV vector encoding the donor template.

In some embodiments, according to any of the methods of editing a genome in a cell described herein, one or more additional doses of the gRNA and the DNA endonuclease or nucleic acid encoding the DNA endonuclease are provided to the cell following the first dose of the gRNA and the DNA endonuclease or nucleic acid encoding the DNA endonuclease. In some embodiments, one or more additional doses of the gRNA and the DNA endonuclease or nucleic acid encoding the DNA endonuclease are provided to the cell following the first dose of the gRNA and the DNA endonuclease or nucleic acid encoding the DNA endonuclease until a target level of targeted integration of the nucleic acid sequence encoding a synthetic FVIII protein and/or a target level of expression of the nucleic acid sequence encoding a synthetic FVIII protein is achieved.

In some embodiments, according to any of the methods of editing a genome in a cell described herein, the nucleic acid sequence encoding a synthetic FVIII protein is expressed under the control of the endogenous albumin promoter.

In some embodiments, provided herein is a method of inserting a synthetic FVIII coding sequence into an albumin locus of a cell genome, comprising introducing into the cell (a) a Cas DNA endonuclease (e.g., Cas9) or nucleic acid encoding the Cas DNA endonuclease, (b) a gRNA or nucleic acid encoding the gRNA, wherein the gRNA is capable of guiding the Cas DNA endonuclease to cleave a target polynucleotide sequence in an albumin locus, and (c) a donor template according to any of the embodiments described herein comprising the synthetic FVIII coding sequence. In some embodiments, the method comprises introducing into the cell an mRNA encoding the Cas DNA endonuclease. In some embodiments, the method comprises introducing into the cell an LNP according to any of the embodiments described herein comprising i) an mRNA encoding the Cas DNA endonuclease and ii) the gRNA. In some embodiments, the donor template is an AAV donor template. In some embodiments, the donor template comprises a donor cassette comprising the synthetic FVIII coding sequence, wherein the donor cassette is flanked on one or both sides by a target site of the gRNA. In some embodiments, the gRNA target sites flanking the donor cassette are the reverse complement of the gRNA target site in an albumin locus. In some embodiments, the Cas DNA endonuclease or nucleic acid encoding the Cas DNA endonuclease and the gRNA or nucleic acid encoding the gRNA are introduced into the cell following introduction of the donor template into the cell. In some embodiments, the Cas DNA endonuclease or nucleic acid encoding the Cas DNA endonuclease and the gRNA or nucleic acid encoding the gRNA are introduced into the cell a sufficient time following introduction of the donor template into the cell to allow for the donor template to enter the cell nucleus. In some embodiments, the Cas DNA endonuclease or nucleic acid encoding the Cas DNA endonuclease and the gRNA or nucleic acid encoding the gRNA are introduced into the cell a sufficient time following introduction of the donor template into the cell to allow for the donor template to be converted from a single-stranded AAV genome to a double-stranded DNA molecule in the cell nucleus. In some embodiments, the Cas DNA endonuclease is Cas9.

In some embodiments, according to any of the methods of inserting a synthetic FVIII coding sequence into an albumin locus of a cell genome described herein, the target polynucleotide sequence is in intron 1 of an albumin gene. In some embodiments, the gRNA comprises a spacer sequence of any of SEQ ID NOs: 271-298. In some embodiments, the gRNA comprises a spacer sequence from any one of SEQ ID NOs: 274, 275, 281, and 283. In some embodiments, the gRNA comprises a spacer sequence from SEQ ID NO: 274. In some embodiments, the gRNA comprises a spacer sequence from SEQ ID NO: 275. In some embodiments, the gRNA comprises a spacer sequence from SEQ ID NO: 281. In some embodiments, the gRNA comprises a spacer sequence from SEQ ID NO: 283.

In some embodiments, provided herein is a method of inserting a synthetic FVIII coding sequence into an albumin locus of a cell genome, comprising introducing into the cell (a) an LNP according to any of the embodiments described herein comprising i) an mRNA encoding a Cas9 DNA endonuclease and ii) a gRNA, wherein the gRNA is capable of guiding the Cas9 DNA endonuclease to cleave a target polynucleotide sequence in an albumin locus, and (b) an AAV donor template according to any of the embodiments described herein comprising the synthetic FVIII coding sequence. In some embodiments, the donor template comprises a donor cassette comprising the synthetic FVIII coding sequence, wherein the donor cassette is flanked on one or both sides by a target site of the gRNA. In some embodiments, the gRNA target sites flanking the donor cassette are the reverse complement of the gRNA target site in an albumin locus. In some embodiments, the LNP is introduced into the cell following introduction of the AAV donor template into the cell. In some embodiments, the LNP is introduced into the cell a sufficient time following introduction of the AAV donor template into the cell to allow for the donor template to enter the cell nucleus. In some embodiments, the LNP is introduced into the cell a sufficient time following introduction of the AAV donor template into the cell to allow for the donor template to be converted from a single-stranded AAV genome to a double-stranded DNA molecule in the cell nucleus. In some embodiments, one or more (such as 2, 3, 4, 5, or more) additional introductions of the LNP into the cell are performed following the first introduction of the LNP into the cell. In some embodiments, the gRNA comprises a spacer sequence from any one of SEQ ID NOs: 271-298. In some embodiments, the gRNA comprises a spacer sequence from any one of SEQ ID NOs: 274, 275, 281, and 283. In some embodiments, the gRNA comprises a spacer sequence from SEQ ID NO: 274. In some embodiments, the gRNA comprises a spacer sequence from SEQ ID NO: 275. In some embodiments, the gRNA comprises a spacer sequence from SEQ ID NO: 281. In some embodiments, the gRNA comprises a spacer sequence from SEQ ID NO: 283.

Insertion of a FVIII coding sequence into a target site can be in the endogenous fibrinogen-α gene locus or neighboring sequences thereof. In some embodiments, the FVIII coding sequence is inserted in a manner that the expression of the inserted coding sequence is controlled by the endogenous promoter of a fibrinogen-α gene. In some embodiments, the FVIII coding sequence in inserted in one of introns of a fibrinogen-α gene. In some embodiments, the FVIII coding sequence is inserted in one of exons of a fibrinogen-α gene. In some embodiments, the FVIII coding sequence is inserted at a junction of intron:exon (or vice versa). In some embodiments, the insertion of the FVIII coding sequence is in the first intron (or intron 1) of a fibrinogen-α locus. In some embodiments, the insertion of the FVIII coding sequence does not significantly affect, e.g., upregulate or downregulate, the expression of a fibrinogen-α gene.

In certain embodiments, the target site is at least, about or at most 0, 1, 5, 10, 20, 30, 40, 50, 100, 150, 200, 250, 300, 350, 400, 450, 500, 550, 600, 650, 700, 750, 800, 850, 900, 950, 1000, 1050, 1071 bp or any intervening length of the nucleic acids downstream of the first exon (i.e., from the last base pair or 3' end of the first exon) of a fibrinogen-α gene. In some embodiments, the target site is at least, about or at most 0.1 kb, about 0.2 kb, about 0.3 kb, about 0.4 kb, about 0.5 kb, about 1 kb, or any intervening length of the nucleic acids upstream of the second exon of a fibrinogen-α gene (i.e., from the first nucleic acid or 5' end of the second exon). In some embodiments, the target site is anywhere within about 0 bp to about 100 bp, about 101 bp to about 200 bp, about 201 bp to about 300 bp, about 301 bp to about 400 bp, about 401 bp to about 500 bp, about 501 bp to about 600 bp, about 601 bp to about 700 bp, about 701 bp to about 800 bp, about 801 bp to about 900 bp, about 901 bp to about 1000 bp, about 1001 bp to about 1071 bp upstream of the second exon of a fibrinogen-α gene (i.e., from the first nucleic acid or 5' end of the second exon).

In some embodiments, the target site for the insertion of a FVIII coding sequence is at least 40 bp downstream of the end of the first exon of the human fibrinogen-α gene in the genome and at least 60 bp upstream of the start of the second exon of the human fibrinogen-α gene in the genome.

In some embodiments, the target site for the insertion of a FVIII coding sequence is at least 42 bp downstream of the end of the first exon of the human fibrinogen-α gene in the genome and at least 65 bp upstream of the start of the second exon of the human fibrinogen-α gene in the genome.

In some embodiments, the insertion is at least 12 bp downstream of the end of the first exon of the human fibrinogen-α gene in the genome and at least 52 bp upstream of the start of the second exon of the human fibrinogen-α gene in the genome.

In some embodiments, the insertion is at least 94 bp downstream of the end of the first exon of the human fibrinogen-α gene in the genome and at least 86 bp upstream of the start of the second exon of the human fibrinogen-α gene in the genome.

In some embodiments, according to any of the systems described herein, the donor template comprises a nucleic acid sequence encoding a synthetic FVIII for targeted integration into intron 1 of a transferrin gene, wherein the donor template comprises, from 5' to 3', i) a first gRNA target site; ii) a splice acceptor; iii) the nucleotide sequence encoding a synthetic FVIII; and iv) a polyadenylation signal. In some embodiments, the donor template further comprises a second gRNA target site downstream of the iv) polyadenylation signal. In some embodiments, the first gRNA target site and the second gRNA target site are the same. In some embodiments, the donor template further comprises a sequence encoding the terminal portion of a transferrin signal peptide encoded on exon 2 of a transferrin gene or a variant thereof that retains at least some of the activity of the endogenous sequence between the ii) splice acceptor and iii) nucleotide sequence encoding a synthetic FVIII protein. In some embodiments, the donor template further comprises a polynucleotide spacer between the i) first gRNA target site and the ii) splice acceptor. In some embodiments, the polynucleotide spacer is 18 nucleotides in length. In some embodiments, the donor template is flanked on one side by a first AAV ITR (inverted terminal repeat) and/or flanked on the other side by a second AAV ITR. In some embodiments, the first AAV ITR is an AAV2 ITR and/or the second AAV ITR is an AAV2 ITR. In some embodiments, the iii) nucleotide sequence encoding a synthetic FVIII having a B domain substitute that comprises 3, 4, 5, or six N-linked glycosylation sites. Exemplary sequences for the donor template components can be found in the donor template sequences of SEQ ID NO: 310 and/or 311.

Target Sequence Selection

In some embodiments, shifts in the location of the 5' boundary and/or the 3' boundary relative to particular reference loci are used to facilitate or enhance particular applications of gene editing, which depend in part on the endonuclease system selected for the editing, as further described and illustrated herein.

In a first, non-limiting aspect of such target sequence selection, many endonuclease systems have rules or criteria that guide the initial selection of potential target sites for cleavage, such as the requirement of a PAM sequence motif in a particular position adjacent to the DNA cleavage sites in the case of CRISPR Type II or Type V endonucleases.

In another, non-limiting aspect of target sequence selection or optimization, the frequency of "off-target" activity for a particular combination of target sequence and DNA endonuclease (i.e., the frequency of double-strand breaks occurring at sites other than the selected target sequence) is assessed relative to the frequency of on-target activity. In some cases, cells that have been correctly edited at the desired locus can have a selective advantage relative to other cells. Illustrative, but non-limiting, examples of a selective advantage include the acquisition of attributes such as enhanced rates of replication, persistence, resistance to certain conditions, enhanced rates of successful engraftment or persistence in vivo following introduction into a subject, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some embodiments, cells can be edited two or more times to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

In embodiments, whether any selective advantage is applicable or any directed selection is to be applied in a particular case, target sequence selection is also guided by consideration of off-target frequencies to enhance the effectiveness of the application and/or reduce the potential for undesired alterations at sites other than the desired target. As described further and illustrated herein and in the art, the occurrence of off-target activity is influenced by a number of factors, including similarities and dissimilarities between the target site and off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also when DNA sequences are being synthesized, such as in the case of repairs of double-strand breaks (DSBs). DSBs occur on a regular basis during the normal cell replication cycle, but can also be enhanced by factors such as UV light and other inducers of DNA breakage, or the presence of agents such as chemical inducers. Many such inducers cause DSBs to occur indiscriminately in the genome, and DSBs are regularly induced and repaired in normal cells. During repair, the original sequence can be reconstructed with complete fidelity, however, in some cases, small indels are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a donor template, into a desired chromosomal location.

Regions of homology between particular sequences, which can be small regions of "microhomology" that can have as few as ten base pairs or less, can also be used to bring about desired deletions. For example, a single DSB is introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which can or cannot be desired given the particular circumstances.

The examples provided herein further illustrate the selection of target regions for the creation of DSBs designed to insert a FVIII coding sequence, as well as the selection of specific target sequences within such regions that are designed to minimize off-target events relative to on-target events.

Targeted Integration

In some embodiments, the method provided herein is to integrate a synthetic FVIII coding sequence at a specific location in the genome of the hepatocytes which is referred to as "targeted integration". In some embodiments, targeted integration is enabled by using a sequence-specific nuclease to generate a double-strand break in the genomic DNA.

The CRISPR/CAS system used in some embodiments has the advantage that a large number of genomic targets can be rapidly screened to identify an optimal CRISPR/CAS design. sgRNA molecules that target any region of the genome can be designed in silico by locating the 20 bp sequence adjacent to all PAM motifs. PAM motifs occur on average every 15 bp in the genome of eukaryotes. However, sgRNA designed by in silico methods will generate double-strand breaks in cells with differing efficiencies, and it is not presently possible to predict the cutting efficiencies of a series of sgRNA molecule using in silico methods. Because sgRNA can be rapidly synthesized in vitro, this enables the rapid screening of all potential sgRNA sequences in a given genomic region to identify the sgRNA that results in the most efficient cutting. Generally, when a series of sgRNA within a given genomic region are tested in cells a range of cleavage efficiencies between 0 and 90% is observed. In silico algorithms as well as laboratory experiments can also be used to determine the off-target potential of any given sgRNA. While a perfect match to the 20 bp recognition sequence of a sgRNA will primarily occur only once in most eukaryotic genomes there will be a number of additional sites in the genome with one or more base pair mismatches to the sgRNA. These sites can be cleaved at variable frequencies which are often not predictable based on the number or location of the mismatches. Cleavage at additional off-target sites that were not identified by the in silico analysis can also occur. Thus, screening a number of sgRNA in a relevant cell type to identify sgRNA that have the most favorable off-target profile is a critical component of selecting an optimal sgRNA for therapeutic use. A favorable off-target profile takes into account not only the number of actual off-target sites and the frequency of cutting at these sites, but also the location of these sites in the genome. For example, off-target sites close to or within functionally important genes, particularly oncogenes or anti-oncogenes are considered less favorable than sites in intergenic regions with no known function. Thus, the identification of an optimal sgRNA cannot be predicted simply by in silico analysis of the genomic sequence of an organism but requires experimental testing. While in silico analysis can be helpful in narrowing down the number of guides to test, it cannot predict guides that have high on-target cutting, or predict guides with low desirable off-target cutting. Experimental data indicates that the cutting efficiency of sgRNA that each has a perfect match to the genome in a region of interest (such as an albumin intron 1) varies from no cutting to >90% cutting, and is not predictable by any known algorithm. The ability of a given sgRNA to promote cleavage by a Cas enzyme can relate to the accessibility of that specific site in the genomic DNA, which can be determined by the chromatin structure in that region. While the majority of the genomic DNA in a quiescent differentiated cell, such as a hepatocyte, exists in highly condensed heterochromatin, regions that are actively transcribed exist in more open chromatin states that are known to be more accessible to large molecules such as proteins like the Cas protein. Even within actively transcribed genes, some specific regions of the DNA are more accessible than others due to the presence or absence of bound transcription factors or other regulatory proteins. Predicting sites in the genome or within a specific genomic locus or region of a genomic locus such as an intron, and such as albumin intron 1 is not possible and therefore would need to be determined experimentally in a relevant cell type. Once some sites are selected as potential sites for insertion, it can be possible to add some variations to such a site, e.g., by moving a few nucleotides upstream or downstream from the selected sites, with or without experimental tests.

In some embodiments, gRNAs that can be used in the methods disclosed herein are one or more of SEQ ID NOs: 271-298, or any functional equivalents thereof having at least about 85% nucleotide sequence identity to those of SEQ ID NOs: 271-298.

Nucleic Acid Modifications

In some embodiments, polynucleotides introduced into cells have one or more modifications that can be used individually or in combination, for example, to enhance activity, stability or specificity, alter delivery, reduce innate immune responses in host cells, or for other enhancements, as further described herein and known in the art.

In certain embodiments, modified polynucleotides are used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of non-limiting illustrations of such uses, modifications of guide RNAs can be used to enhance the formation or stability of the CRISPR/Cas9/Cpf1 genome editing complex having gRNAs, which can be single-molecule guides or double-molecule, and a Cas or Cpf1 endonuclease. Modifications of gRNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in embodiments in which a Cas or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e., the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding a Cas9 endonuclease, are more readily generated enzymatically. While fewer types of modifications are generally available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of types of modifications, especially those used frequently with smaller chemically synthesized RNAs, modifications can have one or more nucleotides modified at the 2' position of the sugar, in some embodiments a 2'-O-alkyl, 2'-O-alkyl-O-alkyl, or 2'-fluoro-modified nucleotide. In some embodiments, RNA modifications include 2'-fluoro, 2'-amino or 2'-O-methyl modifications on the ribose of pyrimidines, abasic residues, or an inverted base at the 3' end of the RNA. Such modifications have been incorporated into oligonucleotides, and these oligonucleotides have been reported to have a higher $T_m$ (i.e., higher target binding affinity) than 2'-deoxyoligonucleotides against a given target.

A number of nucleotide and nucleoside modifications have been reported to make the oligonucleotide into which they are incorporated more resistant to nuclease digestion than the native oligonucleotide; these modified oligos survive intact for a longer time than unmodified oligonucleotides. Specific examples of modified oligonucleotides include those having modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, $CH_2$—N($CH_3$)—O—$CH_2$ (known as a methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH,); amide backbones (see A. De Mesmaeker et al., *Ace Chem Res* (1995) 28:366-374); morpholino backbone structures (see Summerton and Weller, U.S. Pat. No. 5,034,506); and the peptide nucleic acid (PNA) backbone (described below). Phosphorus-containing linkages include, but are not limited to, phosphorothioates, chiral phosphorothioates, phosphorodithioates, phosphotriesters, aminoalkylphosphotriesters, methyl and other alkyl phosphonates having 3'alkylene phosphonates and chiral phosphonates, phosphinates, phosphoramidates having 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in D. A. Braasch et al., *Biochem* (2002) 41(14):4503-10; S. C. Ekker et al., *Genesis* (2001) 30(3):89-93 (and other papers in this issue); J. Heasman, *Dev Biol* (2002) 243:209-14; A. Nasevicius et al., *Nat Genet* (2000) 26:216-20; G. Lacerra et al., *Proc Natl Acad Sci USA* (2000) 97:9591-96; and U.S. Pat. No. 5,034,506.

Cyclohexenyl nucleic acid oligonucleotide mimetics are described in J. Wang et al., *J Arn Chem. Soc* (2000) 122:8595-602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These have those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)_nCH_3$, $O(CH_2)_nNH_2$, or $O(CH_2)_nCH_3$, where n is from one to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some embodiments, a modification includes 2'-methoxyethoxy (2'-O—$CH_2CH_2OCH_3$, also known as 2'-O-(2-methoxyethyl)) (P. Martin et al., *Helv Chim Acta* (1995) 78:486). Other modifications include 2'-methoxy (2'-O—$CH_3$), 2'-propoxy (2'-$OCH_2CH_2CH_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been reported to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds have, but are not limited to, U.S. Pat. Nos. 5,539,082; 5,714,331; and 5,719,262. Further teaching of PNA compounds can be found in P. E. Nielsen et al., *Science* (1991) 254:1497-500.

In some embodiments, guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2'-deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine.; G. Gebeyehu et al., *Nucl Acids Res* (1997) 15:4513. A "universal" base known in the art, e.g., inosine, can also be included. 5-Me-C substitutions have been reported to increase nucleic acid duplex stability by 0.6-1.2° C. (Y. S. Sanghvi et al., "Antisense Research and Applications", CRC Press, Boca Raton, 1993, pp. 276-278) and are embodiments of base substitutions.

In some embodiments, modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further nucleobases include those disclosed in U.S. Pat. No. 3,687,808, those disclosed in "The Concise Encyclopedia of Polymer Science and Engineering, pages 858-859, Kroschwitz, J. I., ed. John Wiley & Sons, 1990, those disclosed by Englisch et al., *Ange. Chemie, Int'l Ed*, (1991) 30:613, and those disclosed by Y. S. Sanghvi, Chapter 15, "Antisense Research and Applications", pp 289-302, Crooke, S. T. and Lebleu, B. ed., CRC Press, 1993. Certain of these nucleobases are particularly useful for increasing the binding affinity of the oligomeric compounds of the disclosure. These include 5-substituted pyrimidines, 6-azapyrimidines and N-2, N-6 and 0-6 substituted purines, having 2-aminopropyladenine, 5-propynyluracil and 5-propynylcytosine. 5-methylcytosine substitutions have been reported to increase nucleic acid duplex stability by 0.6-1.2° C. (Y. S. Sanghvi, supra, pp. 276-78) and are embodiments of base substitutions, even more particularly when combined with 2'-O-methoxyethyl sugar modifications. Modified nucleobases are described in U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

In some embodiments, the guide RNAs and/or mRNA (or DNA) encoding an endonuclease are chemically linked to one or more moieties or conjugates that enhance the activity, cellular distribution, or cellular uptake of the oligonucleotide. Such moieties include, but are not limited to, lipid moieties such as a cholesterol moiety (Letsinger et al., *Proc Natl Acad Sci USA*, (1989) 86:6553-56); cholic acid (Manoharan et al., *Bioorg Med Chem Let* (1994) 4:1053-60); a thioether, e.g., hexyl-S-tritylthiol (Manoharan et al., *Ann N Y Acad Sci* (1992) 660:306-09) and Manoharan et al., *Bioorg Med Chem Let*, (1993) 3:2765-70); a thiocholesterol (Oberhauser et al., *Nucl Acids Res* (1992) 20:533-538); an aliphatic chain, e.g., dodecandiol or undecyl residues (Kabanov et al., *FEBS Lett*. (1990) 259:327-330 and Svinarchuk et al., *Biochimie* (1993) 75:49-54); a phospholipid, e.g., di-hexadecyl-rac-glycerol or triethylammonium 1,2-di-O-hexadecyl-rac-glycero-3-H-phosphonate (Manoharan et al., *Tetrahedron Lett* (1995) 36:3651-54 and Shea et al., *Nucl Acids Res* (1990) 18:3777-83); a polyamine or a polyethylene glycol chain (Mancharan et al., *Nucleosides & Nucleotides* (1995) 14:969-73); adamantane acetic acid (Manoharan et al., *Tetrahedron Lett* (1995) 36:3651-54); a palmityl moiety (Mishra et al., *Biochim Biophys Acta* (1995) 1264: 229-37); or an octadecylamine or hexylamino-carbonyl-t-oxycholesterol moiety (Crooke et al., *J Pharrnacol Exp Ther* (1996) 277:923-37). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941.

In some embodiments, sugars and other moieties can be used to target proteins and complexes having nucleotides, such as cationic polysomes and liposomes, to particular sites. For example, hepatic cell-directed transfer can be mediated via asialoglycoprotein receptors (ASGPRs); see, e.g., Hu et al., *Protein Pept Lett* (2014) 21(10):1025-30. Other systems known in the art can be used to target biomolecules of use in the present case, and/or complexes thereof, to particular target cells of interest.

In some embodiments, these targeting moieties or conjugates can include conjugate groups covalently bound to functional groups, such as primary or secondary hydroxyl groups. Conjugate groups of the disclosure include intercalators, reporter molecules, polyamines, polyamides, polyethylene glycols, polyethers, groups that enhance the pharmacodynamic properties of oligomers, and groups that enhance the pharmacokinetic properties of oligomers. Exemplary conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this disclosure, include groups that improve uptake, distribution, metabolism or excretion of the compounds of the present disclosure. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol, or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737;

5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are generally produced by enzymatic synthesis can also be modified. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation within a cell), or to reduce the tendency of the RNA to elicit the innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as pseudo-UTP, 2-thio-UTP, 5-methylcytidine-5'-triphosphate (5-methyl-CTP) or N6-methyl-ATP), or treatment with phosphatase to remove 5' terminal phosphates. These and other modifications are known in the art, and new modifications of RNAs are regularly being developed.

It has been reported that chemically modified mRNA delivered in vivo can be used to achieve improved therapeutic effects; see, e.g., Kormann et al., *Nature Biotechnol* (2011) 29:154-57. Such modifications can be used, for example, to increase the stability of the RNA molecule and/or reduce its immunogenicity. Using chemical modifications such as pseudo-U, N6-methyl-A, 2-thio-U and 5-methyl-C, it was found that substituting just one quarter of the uridine and cytidine residues with 2-thio-U and 5-methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been reported that repeated administration of synthetic messenger RNAs incorporating modifications designed to bypass innate anti-viral responses can reprogram differentiated human cells to pluripotency. See, e.g., Warren et al., *Cell Stem Cell* (2010) 7(5):618-30. Such modified mRNAs that act as primary reprogramming proteins can be an efficient means of reprogramming multiple human cell types. Such cells are referred to as induced pluripotent stem cells (iPSCs), and it was found that enzymatically synthesized RNA incorporating 5-methyl-CTP, pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), and treatment with phosphatase to remove 5' terminal phosphates.

A number of compositions and techniques applicable to the generation of modified RNAs for use herein have been developed in connection with the modification of RNAi, including siRNAs. siRNAs present particular challenges in vivo because their effects on gene silencing via mRNA interference are generally transient, which can require repeated administration. In addition, siRNAs are double-stranded RNAs (dsRNA), and mammalian immune responses have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., *Pharmaceuticals* (*Basel*) (2013) 6(4):440-68; Kanasty et al., *Mol Ther* (2012) 20(3):513-24; Burnett et al., *Biotechnol J* (2011) 6(9):1130-46; Judge and MacLachlan, *Hum Gene Ther* (2008) 19(2):111-24; and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by K. A. Whitehead et al., *Ann Rev Chem Biomol Eng* (2011) 2:77-96; Gaglione and Messere, *Mini Rev Med Chem* (2010) 10(7):578-95; Chernolovskaya et al., *Curr Opin Mol Ther* (2010) 12(2):158-67; Deleavey et al., *Curr Protoc Nuc Acid Chem*, Chapter 16: Unit 16.3 (2009); *Behlke, Oligonucleotides* (2008) 18(4):305-19; Fucini et al., *Nucleic Acid Ther* (2012) 22(3): 205-210; Bremsen et al., *Front Genet* (2012) 3:154.

A number of commercial suppliers of modified RNAs, many of which have specialized in modifications designed to improve the effectiveness of siRNAs. A variety of approaches are offered based on findings reported in the literature. For example, Dharmacon notes that replacement of a non-bridging oxygen with sulfur (phosphorothioate, PS) has been used to improve nuclease resistance of siRNAs, as reported by Kole, *Nature Rev Drug Disc* (2012) 11:125-40. Modifications of the ribose 2'-position have been reported to improve nuclease resistance of the internucleotide phosphate bond while increasing duplex stability (T m), which has also been reported to provide protection from immune activation. A combination of moderate PS backbone modifications with small, well-tolerated 2'-substitutions (2'-O-methyl, 2'-fluoro, 2'-hydro) have been associated with highly stable siRNAs for applications in vivo, as reported by Soutschek et al., *Nature* (2004) 432:173-78; and 2'-O-methyl modifications have been reported to be effective in improving stability as reported by Volkov, *Oligonucleotides* (2009) 19:191-202. With respect to decreasing the induction of innate immune responses, modifying specific sequences with 2'-O-methyl, 2'-fluoro, 2'-hydro have been reported to reduce TLR7/TLR8 interaction while generally preserving silencing activity; see, e.g., Judge et al., *Mol Ther* (2006) 13:494-505; and Cekaite et al., *J Mol Biol* (2007) 365:90-108. Additional modifications, such as 2-thiouracil, pseudouracil, 5-methylcytosine, 5-methyluracil, and $N^6$-methyladenosine have also been reported to minimize the immune effects mediated by TLR3, TLR7, and TLR8; see, e.g., K. Kariko et al., *Immunity* (2005) 23:165-75.

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., Winkler, Ther. Deliv. (2013) 4:791-809, and references cited therein.

Delivery

In some embodiments, any nucleic acid molecules used in the methods provided herein, e.g., a nucleic acid encoding a genome-targeting nucleic acid of the disclosure and/or a site-directed polypeptide are packaged into or on the surface of delivery vehicles for delivery to cells. Delivery vehicles include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

The complexes, polypeptides, and nucleic acids of the disclosure into cells can be introduced by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

In embodiments, guide RNA polynucleotides (RNA or DNA) and/or endonuclease polynucleotide(s) (RNA or DNA) are delivered by viral or non-viral delivery vehicles known in the art. Alternatively, site-directed polypeptide(s) can be delivered by viral or non-viral delivery vehicles known in the art, such as electroporation or lipid nanoparticles. In some embodiments, a DNA endonuclease is delivered as one or more polypeptides, either alone or pre-complexed with one or more gRNAs, or one or more crRNA together with a tracrRNA.

In embodiments, polynucleotides are delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, *Gene Ther* (2011) 18:1127-33 (which focuses on non-viral delivery vehicles for siRNA that are also useful for delivery of other polynucleotides).

In embodiments, polynucleotides, such as guide RNA, sgRNA, and mRNA encoding an endonuclease, are delivered to a cell or a subject by a lipid nanoparticle (LNP).

While several non-viral delivery methods for nucleic acids have been tested both in animal models and in humans, the most developed system is lipid nanoparticles. LNP are generally composed of an ionizable cationic lipid and three or more additional components, generally cholesterol, DOPE and a polyethylene glycol (PEG) containing lipid (see, e.g., Example 1). The cationic lipid can bind to the positively charged nucleic acid, forming a dense complex that protects the nucleic acid from degradation. During passage through a microfluidics system, the components self-assemble to form particles in the size range of 50 to 150 nM, in which the nucleic acid is encapsulated in the core, complexed with the cationic lipid and surrounded by a lipid bilayer-like structure. After injection into the circulation of a subject, these particles can bind to apolipoprotein E (apoE). ApoE is a ligand for the LDL receptor and mediates uptake into the hepatocytes of the liver via receptor-mediated endocytosis. LNP of this type have been reported to efficiently deliver mRNA and siRNA to the hepatocytes of the livers of rodents, primates, and humans. After endocytosis, the LNP are present in endosomes. The encapsulated nucleic acid undergoes a process of endosomal escape mediated by the ionizable nature of the cationic lipid. This delivers the nucleic acid into the cytoplasm where mRNA can be translated into the encoded protein. Thus, in some embodiments encapsulation of gRNA and mRNA encoding Cas9 into an LNP is used to efficiently deliver both components to the hepatocytes after i.v. injection. After endosomal escape, the Cas9 mRNA is translated into Cas9 protein and forms a complex with the gRNA. In some embodiments, inclusion of a nuclear localization signal into the Cas9 protein sequence promotes translocation of the Cas9 protein/gRNA complex to the nucleus. Alternatively, the small gRNA crosses the nuclear pore complex and forms complexes with Cas9 protein in the nucleus. Once in the nucleus, the gRNA/Cas9 complex scans the genome for homologous target sites and generates double-strand breaks preferentially at the desired target site in the genome. The half-life of RNA molecules in vivo is short, on the order of hours to days. Similarly, the half-life of proteins tends to be short, on the order of hours to days. Thus, in some embodiments, delivery of the gRNA and Cas9 mRNA using an LNP can result in only transient expression and activity of the gRNA/Cas9 complex. This can provide the advantage of reducing the frequency of off-target cleavage, thus minimizing the risk of genotoxicity in some embodiments. LNP are generally less immunogenic than viral particles. While many humans have preexisting immunity to AAV, there is no pre-existing immunity to LNP. An additional and adaptive immune response against LNP is unlikely to occur, which enables repeat dosing of LNP.

When administering to a subject a gene editing based gene therapy in which a therapeutic coding sequence is integrated into a host genomic locus, such as a safe harbor locus, it would be advantageous to achieve a level of gene expression that provides the optimal therapeutic benefit to the subject. For example, in hemophilia A the most desirable level of FVIII protein in the blood would be in the range of 20% to 100%, 30% to 100%, 40% to 100%, or 50% to 100% of the normal level. Standard AAV based gene therapies that use a strong promoter to drive expression of the therapeutic coding sequence from episomal copies of the AAV genome do not enable control of the level of expression that is achieved, because the AAV virus can only be dosed once and the levels of expression that are achieved vary significantly between subjects (S. Rangarajan et al., *N Engl J Med* (2017) 377:2519-30). After the subject is dosed with an AAV virus, he or she develops high titer antibodies against the virus capsid proteins that, based upon preclinical models, are expected to prevent effective re-administration of the virus (H. Petry et al., *Gene Ther* (2008) 15:54-60). One approach, where the therapeutic gene delivered by an AAV virus is integrated into the genome at a safe harbor locus, such as albumin intron 1, and this targeted integration occurs via the creation of a double-strand break in the genome, provides an opportunity to control the level of targeted integration and thus the levels of the therapeutic coding sequence product. After the liver is transduced by an AAV encapsulating an AAV genome containing a donor DNA cassette encoding the synthetic FVIII, the AAV genome is maintained episomally within the nucleus of the transduced cells. These episomal AAV genomes are relatively stable over time, and therefore provide a pool of donor template for targeted integration at double-strand breaks created by CRISPR/Cas9.

Several different ionizable cationic lipids have been developed for use in LNP. These include C12-200 (K. T. Love et al., *Proc Natl Acad Sci USA* (2010) 107:1864-69), MC3 (M. Jayaraman et al., *Angew Chem Int Ed Engl* (2012)

51:8529-33), LN16, and MD1 (Fougerolles et al., U.S. Pat. No. 8,754,062), among others. C12-200 is 1,1'-((2-(4-(2-((2-(bis(2-hydroxydodecyl)amino)ethyl) (2-hydroxydodecyl) amino)ethyl)piperazin-1-yl)ethyl)azanediyl)bis(dodecan-2-431). In one type of LNP, a GalNac moiety is attached to the outside of the LNP and acts as a ligand for uptake into the liver via the asialoglycoprotein receptor. Any of these cationic lipids are used to formulate LNP for delivery of gRNA and Cas9 mRNA to the liver.

In some embodiments, the LNP has a diameter of less than about 1000 nm, 500 nm, 250 nm, 200 nm, 150 nm, 100 nm, 75 nm, 50 nm, or 25 nm. Alternatively, a nanoparticle can range in size from about 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as “helper lipids” to enhance transfection activity and nanoparticle stability. Limitations of cationic lipids can include low efficacy owing to poor stability and rapid clearance, as well as the generation of inflammatory or anti-inflammatory responses. LNPs can also have hydrophobic lipids, hydrophilic lipids, or both hydrophobic and hydrophilic lipids.

Any lipid or combination of lipids known in the art can be used to produce an LNP. Examples of lipids used to produce LNPs include: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids include 98N12-5, C12-200, DLin-KC2-DMA (KC2), DLin-MC3-DMA (MC3), XTC, MD1, and 7C1. Examples of neutral lipids include DPSC, DPPC, POPC, DOPE, and SM. Examples of PEG-modified lipids include PEG-DMG, PEG-CerC14, and PEG-CerC20.

In embodiments, the lipids can be combined in any number of molar ratios to produce an LNP. In addition, the polynucleotide(s) can be combined with lipid(s) in a wide range of molar ratios to produce an LNP.

In embodiments, the site-directed polypeptide and genome-targeting nucleic acid can each be administered separately to a cell or a subject. The site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is to form ribonucleoprotein particles (RNPs), in which the RNA is pre-complexed with an endonuclease. Another benefit of the RNP is that the RNA is protected from degradation.

In some embodiments, the endonuclease in the RNP is modified or unmodified. Likewise, the gRNA, crRNA, tracrRNA, or sgRNA can be modified or unmodified. Numerous modifications are known in the art and can be used.

The endonuclease and sgRNA are generally combined in about a 1:1 molar ratio. Alternatively, the endonuclease, crRNA and tracrRNA can be combined in about a 1:1:1 molar ratio. However, a wide range of molar ratios can be used to produce an RNP.

In some embodiments, a recombinant AAV vector is used for delivery. Techniques to produce rAAV particles, in which an AAV genome to be packaged that includes the polynucleotide to be delivered, rep and cap genes, and helper virus functions are provided to a cell are standard in the art. Production of rAAV requires that the following components are present within a single cell (denoted herein as a packaging cell): an rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including without limitation, AAV serotypes AAV-1, AAV-2, AAV-3, AAV-4, AAV-5, AAV-6, AAV-7, AAV-8, AAV-9, AAV-10, AAV-11, AAV-12, AAV-13, and AAV rh.74. Production of pseudotyped rAAV is disclosed in, for example, international patent application WO01/83692. See Table 1.

TABLE 1

AAV serotype and Genbank Accession No. of selected AAVs.

| AAV Serotype | Genbank Accession No. |
|---|---|
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

In some embodiments, a method of generating a packaging cell involves creating a cell line that stably expresses the necessary components for AAV particle production. For example, a plasmid (or multiple plasmids) having a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (R. J. Samulski et al., *Proc Natl Acad Sci USA* (1982) 79:2077-81), addition of synthetic linkers containing restriction endonuclease cleavage sites (C. A. Laughlin et al., *Gene* (1983) 23:65-73), and by direct, blunt-end ligation (P. Senapathy et al., *J Biol Chem* (1984) 259:4661-66). The packaging cell line is then infected with a helper virus, such as adenovirus. The advantages of this method are that the cells are selectable and are suitable for large-scale production of rAAV. Other suitable methods employ adenovirus or baculovirus, rather than plasmids, to introduce rAAV genomes and/or rep and cap genes into packaging cells.

General principles of rAAV production are reviewed in, for example, B. J. Carter, Cur Op *Biotechnol* (1992) 3(5): 533-39; and N. Muzyczka, *Curr Topics Microbiol Immunol* (1992) 158:97-129). Some approaches are described in J. D. Tratschin et al., *Mol Cell Biol* (1984) 4:2072-81; P. L. Hermonat et al., *Proc Natl Acad Sci USA* (1984) 81:6466-70; J. D. Tratschin et al., *Mol Cell Biol* (1985) 5:3251-60; S. K. McLaughlin et al., *J Virol* (1988) 62:1963-73; J. S. Lebkowski et al., *Mol Cell Biol* (1988) 8:3988-96; R. J. Samulski et al., *J Virol* (1989) 63:3822-28); U.S. Pat. No. 5,173,414; WO95/13365 and corresponding U.S. Pat. No. 5,658,776; WO95/13392; WO96/17947; PCT/US98/18600; WO97/09441 (PCT/US96/14423); WO97/08298 (PCT/

US96/13872); WO97/21825 (PCT/US96/20777); WO97/06243 (PCT/FR96/01064); WO99/11764; P. Perrin et al., *Vaccine* (1995) 13:1244-50; R. W. Paul et al., *Human Gene Ther* (1993) 4:609-15; Clark et al., *Gene Ther* (1996) 3:1124-32; U.S. Pat. Nos. 5,786,211; 5,871,982; and 6,258,595.

AAV vector serotypes can be matched to target cell types. For example, the following exemplary cell types can be transduced by the indicated AAV serotypes among others. For example, the serotypes of AAV vectors suitable to liver tissue/cell type include, without limitation, AAV3, AAV5, AAV8 and AAV9.

In addition to adeno-associated viral vectors, other viral vectors can be used. Such viral vectors include, without limitation, lentivirus, alphavirus, enterovirus, pestivirus, baculovirus, herpesvirus, Epstein Barr virus, papovavirus, poxvirus, vaccinia virus, and herpes simplex virus.

In some embodiments, Cas9 mRNA, sgRNA targeting one or two loci in albumin genes, and donor DNA, are each separately formulated into lipid nanoparticles, or are all co-formulated into one lipid nanoparticle, or co-formulated into two or more lipid nanoparticles.

In some embodiments, Cas9 mRNA is formulated in a lipid nanoparticle, while sgRNA and donor DNA are delivered in an AAV vector. In some embodiments, Cas9 mRNA and sgRNA are co-formulated in a lipid nanoparticle, while donor DNA is delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery: split versions of Cas9 and smaller orthologs of Cas9 can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA.

In some embodiments that are related to delivering genome-editing components for therapeutic treatments, at least two components are delivered into the nucleus of a cell to be transformed, e.g., hepatocytes: a sequence-specific nuclease and a DNA donor template. In some embodiments, the donor template is packaged into an AAV with tropism for the liver. In some embodiments, the AAV is selected from the serotypes AAV8, AAV9, AAVrh10, AAV5, AAV6 or AAV-DJ. In some embodiments, the AAV packaged DNA donor template is administered to a subject, e.g., a subject first by peripheral i.v. injection, followed by the sequence-specific nuclease. The advantage of delivering an AAV-packaged donor template first is that the delivered donor template will be stably maintained in the nucleus of the transduced hepatocytes, which allows for the subsequent administration of the sequence-specific nuclease. This creates a double-strand break in the genome, with subsequent integration of the donor template by HDR or NHEJ. It is desirable in some embodiments that the sequence-specific nuclease remain active in the target cell only for the time required to promote targeted integration of the transgene at sufficient levels for the desired therapeutic effect. If the sequence-specific nuclease remains active in the cell for an extended duration, this will result in an increased frequency of double-strand breaks at off-target sites. Specifically, the frequency of off-target cleavage is a function of the off-target cutting efficiency multiplied by the time over which the nuclease is active. Delivery of a sequence-specific nuclease in the form of an mRNA results in a short duration of nuclease activity, in the range of hours to a few days, because the mRNA and the translated protein are short-lived in the cell. Thus, delivery of the sequence-specific nuclease into cells that already contain the donor template is expected to result in a better ratio of targeted integration relative to off-target integration. In addition, AAV-mediated delivery of a donor template to the nucleus of hepatocytes after peripheral i.v. injection takes time, generally on the order of one to 14 days, due to the time required for the virus to infect the cell, escape the endosomes and transit to the nucleus, and conversion of the single-stranded AAV genome to a double-stranded DNA molecule by host components. Thus, in some embodiments the delivery of the donor template to the nucleus is completed before supplying the CRISPR/Cas9 components, since these nuclease components are active for about one to three days.

In some embodiments, the DNA endonuclease is CRISPR/Cas9, which is composed of a sgRNA directed to a DNA sequence within intron 1 of an albumin gene together with a Cas9 nuclease. In some embodiments, the Cas9 endonuclease is delivered as an mRNA encoding the Cas9 protein operably fused to one or more nuclear localization signals (NLS). In some embodiments, the sgRNA and the Cas9 mRNA are delivered to the hepatocytes packaged in a lipid nanoparticle. In some embodiments, the lipid nanoparticle contains the lipid C12-200 (K. T. Love et al., *Proc Natl Acad Sci USA* (2010) 107:1864-69). In some embodiments, the ratio of the sgRNA to the Cas9 mRNA that is packaged in the LNP is 1:1 (mass ratio), to result in maximal DNA cleavage in vivo in mice. In alternative embodiments, different mass ratios of the sgRNA to the Cas9 mRNA that is packaged in the LNP can be used, for example, 10:1, 9:1, 8:1, 7:1, 6:1, 5:1, 4:1, 3:1 or 2:1, or reverse ratios. In some embodiments, the Cas9 mRNA and the sgRNA are packaged into separate LNP formulations and the Cas9 mRNA containing LNP is delivered to the subject about one to about 8 hours before the LNP containing the sgRNA, to allow optimal time for the Cas9 mRNA to be translated prior to delivery of the sgRNA.

In some embodiments, an LNP formulation encapsulating a gRNA and a Cas9 mRNA ("LNP-nuclease formulation") is administered to a subject, e.g., a subject that previously was administered a DNA donor template packaged into an AAV. In some embodiments, the LNP-nuclease formulation is administered to the subject within one day to 28 days, or within seven days to 28 days, or within seven days to 14 days after administration of the AAV donor template. The optimal timing of delivery of the LNP-nuclease formulation relative to the AAV-donor template can be determined using techniques known in the art, e.g., studies done in animal models including mice and monkeys.

In some embodiments, a DNA-donor template is delivered to the hepatocytes of a subject, e.g., a subject, using a non-viral delivery method. While some subjects (generally 30%) have pre-existing neutralizing antibodies directed to most commonly used AAV serotypes that prevents the efficacious gene delivery by the AAV, all subjects are treatable with a non-viral delivery method. Several non-viral delivery methodologies are known in the field. In particular, LNP are known to efficiently deliver their encapsulated cargo to the cytoplasm of hepatocytes after intravenous injection in animals and humans. These LNP are actively taken up by the liver through a process of receptor-mediated endocytosis, resulting in preferential uptake into the liver.

In some embodiments, to promote nuclear localization of a donor template, a DNA sequence that can promote nuclear localization of plasmids, e.g., a 366 bp region of the simian virus 40 (SV40) origin of replication and early promoter, can be added to the donor template. Other DNA sequences that bind to cellular proteins can also be used to improve nuclear entry of DNA.

In some embodiments, a level of expression or activity of introduced FVIII is measured in the blood of a subject, e.g., a subject, following the first administration of an LNP-nuclease formulation, e.g., containing gRNA and Cas9 nuclease or mRNA encoding Cas9 nuclease, after the AAV donor template. If the FVIII level is not sufficient to treat the disease, for example a level of 5% of normal levels, then a second or third administration of the LNP-nuclease formulation can be given to promote additional targeted integration into a genome safe harbor locus. The feasibility of using multiple doses of the LNP-nuclease formulation to obtain the desired therapeutic levels of FVIII can be tested and optimized using the techniques known in the field, e.g., tests using animal models including the mouse and the monkey.

In some embodiments, according to any of the methods described herein comprising administration of i) an AAV donor template comprising a donor cassette and ii) an LNP-nuclease formulation to a subject, an initial dose of the LNP-nuclease formulation is administered to the subject within about one day to about 28 days after administration of the AAV donor template to the subject. In some embodiments, the initial dose of the LNP-nuclease formulation is administered to the subject after a sufficient time to allow delivery of the donor template to the nucleus of a target cell. In some embodiments, the initial dose of the LNP-nuclease formulation is administered to the subject after a sufficient time to allow conversion of the single-stranded AAV genome to a double-stranded DNA molecule in the nucleus of a target cell. In some embodiments, one or more (such as two, three, four, five, or more) additional doses of the LNP-nuclease formulation are administered to the subject following administration of the initial dose. In some embodiments, one or more doses of the LNP-nuclease formulation are administered to the subject until a target level of targeted integration of the donor cassette and/or a target level of expression of the donor cassette is achieved. In some embodiments, the method further comprises measuring the level of targeted integration of the donor cassette and/or the level of expression of the donor cassette following each administration of the LNP-nuclease formulation, and administering an additional dose of the LNP-nuclease formulation if the target level of targeted integration of the donor cassette and/or the target level of expression of the donor cassette is not achieved. In some embodiments, the amount of at least one of the additional doses of the LNP-nuclease formulation is the same as the initial dose. In some embodiments, the amount of at least one of the additional doses of the LNP-nuclease formulation is less than the initial dose. In some embodiments, the amount of at least one of the additional doses of the LNP-nuclease formulation is more than the initial dose.

Genetically Modified Cells and Cell Populations

In one aspect, the disclosures herewith provide a method of editing a genome in a cell, thereby creating a genetically modified cell. In some aspects, a population of genetically modified cells is provided. "Genetically modified cell" therefore refers to a cell that has at least one genetic modification introduced by genome editing (e.g., using a CRISPR/Cas9/Cpf1 system). In some embodiments, the genetically modified cell is a genetically modified hepatocyte cell. A genetically modified cell having an exogenous genome-targeting nucleic acid and/or an exogenous nucleic acid encoding a genome-targeting nucleic acid is contemplated herein.

In some embodiments, the genome of a cell can be edited by inserting a nucleic acid sequence of a synthetic FVIII coding sequence into a genomic sequence of the cell. In some embodiments, the cell subject to the genome-edition has one or more mutation(s) in the genome which results in reduced expression of an endogenous FVIII gene, as compared to the expression in a normal that does not have such a mutation(s). The normal cell can be a healthy or control cell that originated (or is isolated) from a different subject who does not have FVIII gene defects. In some embodiments, the cell subject to the genome-edition can be originated (or isolated) from a subject who is in need of treatment of FVIII gene-related condition or disorder. Therefore, in some embodiments the expression of endogenous FVIII gene in such cell is about 10%, about 20%, about 30%, about 40%, about 50%, about 60%, about 70%, about 80%, about 90%, or about 100% reduced as compared to the expression of endogenous FVIII gene expression in the normal cell.

Upon successful insertion of the transgene, e.g., a nucleic acid encoding a synthetic FVIII coding sequence, the expression of the introduced synthetic FVIII coding sequence in the cell can be at least about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1,000%, about 2,000%, about 3,000%, about 5,000%, about 10,000%, or more as compared to the expression of endogenous FVIII gene of the cell. In some embodiments, the activity of introduced FVIII coding sequence products, including synthetic FVIII coding sequence in the genome-edited cell can be at least about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1,000%, about 2,000%, about 3,000%, about 5,000%, about 10,000%, or more as compared to the expression of endogenous FVIII gene of the cell. In some embodiments, the expression of the introduced synthetic FVIII coding sequence in the cell is at least about 2 fold, about 3 fold, about 4 fold, about 5 fold, about 6 fold, about 7 fold, about 8 fold, about 9 fold, about 10 fold, about 15 fold, about 20 fold, about 30 fold, about 50 fold, about 100 fold, about 1000 fold, or more of the expression of endogenous FVIII gene of the cell. Also, in some embodiments, the activity of an introduced synthetic FVIII coding sequence in the genome-edited cell can be comparable to or greater than the activity of FVIII gene products in a normal, healthy cell.

In embodiments for treating or ameliorating hemophilia A, the principal targets for gene editing are human cells. In some embodiments, in the ex vivo and in vivo methods, the human cells are hepatocytes. In some embodiments, by performing gene editing in autologous cells that are derived from the subject in need (and are therefore already completely matched with the subject), it is possible to generate cells that can be safely re-introduced into the subject, and effectively give rise to a population of cells that will be effective in ameliorating one or more clinical conditions associated with the subject's disease. In some embodiments for such treatments, hepatocyte cells are isolated according to any method known in the art and used to create genetically modified, therapeutically effective cells. In one embodiment, liver stem cells are genetically modified ex vivo and then re-introduced into the subject, where they give rise to genetically modified hepatocytes or sinusoidal endothelial cells that express the inserted FVIII coding sequence.

Therapeutic Approach

Hemophilia is classified as "mild" (FVIII protein serum concentrations of 0.40 to 0.05 IU/mL), "moderate" (0.05 to 0.01 IU/mL), or "severe" (<0.01 IU/mL, less than 1% of normal) (G. C. White et al., *Thromb Haemost* (2001) 85(3): 560-75). An analysis of hemophilia A patients taking FVIII replacement protein therapy reported that at predicted FVIII trough levels of 3%, 5%, 10%, 15%, and 20% of normal, the frequency at which no bleeds occurred was 71%, 79%, 91%, 97%, and 100%, respectively (G. Spotts et al., *Blood* (2014) 124:689). This suggests that when FVIII levels are maintained above a minimum level of 15 to 20% the rate of bleeding events is reduced to close to zero. While a precise FVIII level required to cure hemophilia A has not been defined, and likely varies between subjects, levels of between about 5% and about 30% are expected to provide a significant reduction in bleeding events.

In one aspect, provided herein is a gene therapy approach for treating hemophilia A in a subject by editing the genome of the subject. In some embodiments, the gene therapy approach integrates a functional synthetic FVIII coding sequence into the genome of a relevant cell type in the subject, and provides a permanent cure for hemophilia A. In some embodiments, a synthetic FVIII coding sequence is integrated into a hepatocyte, because these cells efficiently express and secrete many proteins into the blood. In addition, this integration approach using hepatocytes can be considered for pediatric subjects whose livers are not fully grown, because the integrated coding sequence is transmitted to the daughter cells as the hepatocytes divide.

In another aspect, provided herein are cellular ex vivo and in vivo methods for using genome engineering tools to create permanent changes to the genome by knocking-in a synthetic FVIII coding sequence into a gene locus and restoring FVIII protein activity. Such methods use endonucleases, such as CRISPR-associated (CRISPR/Cas9, Cpf1 and the like) nucleases, to permanently delete, insert, edit, correct, or replace any sequences from a genome, or insert an exogenous sequence, e.g., a synthetic FVIII coding sequence, in a genomic locus. In this way, the examples set forth in the present disclosure restore the activity of FVIII gene with a single treatment (rather than deliver potential therapies for the lifetime of the subject).

In some embodiments, an ex vivo cell-based therapy uses hepatocytes isolated from a subject. The chromosomal DNA of these cells is edited using the materials and methods described herein. Finally, the edited cells and/or their progeny are administered or implanted into the subject.

One advantage of an ex vivo cell therapy approach is the ability to conduct a comprehensive analysis of the therapeutic prior to administration. Nuclease-based therapeutics have some level of off-target effects. Performing gene correction ex vivo allows one to characterize the corrected cell population prior to administration. Aspects of the disclosure include sequencing the genome of the corrected cells to ensure that any off-target cuts are in genomic locations associated with minimal risk to the subject. Further, populations of specific cells, including clonal populations, can be screened or isolated prior to administration or implantation.

Another embodiment is in vivo based therapy. In this method, the chromosomal DNA of the cells in the subject is corrected using the materials and methods described herein. In some embodiments, the cells are hepatocytes.

An advantage of in vivo gene therapy is the ease of therapeutic production and administration. The same therapeutic approach and therapy can be used to treat more than one subject, for example a number of subjects who share the same or similar genotype or allele. In contrast, ex vivo cell therapy generally uses a subject's own cells, which are isolated, manipulated and returned to the same subject.

In some embodiments, the subject has symptoms of hemophilia A. In some embodiments, the subject is a human suspected of having hemophilia A. Alternatively, the subject is a human diagnosed with a risk of hemophilia A. In some embodiments, the subject who is in need of the treatment has one or more genetic defects (e.g., deletion, insertion, and/or mutation) in the endogenous FVIII gene or its regulatory sequences, such that the activity (including the expression level or functionality) of the FVIII protein is substantially reduced as compared to a normal, healthy subject.

In some embodiments, provided herein is a method of treating hemophilia A in a subject, the method comprising providing the following to a cell in the subject: (a) a gRNA targeting an albumin locus in the cell genome; (b) a DNA endonuclease or nucleic acid encoding the DNA endonuclease; and (c) a donor template comprising a nucleic acid sequence encoding a synthetic FVIII protein. In some embodiments, the gRNA targets intron 1 of an albumin gene. In some embodiments, the gRNA comprises a spacer sequence from any one of SEQ ID NOs: 271-298.

In some embodiments, provided herein is a method of treating hemophilia A in a subject, the method comprising providing the following to a cell in the subject: (a) a gRNA comprising a spacer sequence from any one of SEQ ID NOs: 271-298; (b) a DNA endonuclease or nucleic acid encoding the DNA endonuclease; and (c) a donor template comprising a nucleic acid sequence encoding a synthetic FVIII protein. In some embodiments, the gRNA comprises a spacer sequence from any one of SEQ ID NOs: 274, 275, 281, and 283. In some embodiments, the gRNA comprises a spacer sequence from SEQ ID NO: 274. In some embodiments, the gRNA comprises a spacer sequence from SEQ ID NO: 275. In some embodiments, the gRNA comprises a spacer sequence from SEQ ID NO: 281. In some embodiments, the gRNA comprises a spacer sequence from SEQ ID NO: 283. In some embodiments, the cell is a human cell, e.g., a human hepatocyte cell. In some embodiments, the subject is a subject having or is suspected of having hemophilia A. In some embodiments, the subject is diagnosed with a risk of hemophilia A.

In some embodiments, according to any of the methods of treating hemophilia A described herein, the DNA endonuclease is selected from the group consisting of Cas1, Cas1B, Cas2, Cas3, Cas4, Cas5, Cas6, Cas7, Cas8, Cas9 (also known as Csn1 and Csx12), Cas100, Csyl, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease, and functional equivalents thereof. In some embodiments, the DNA endonuclease is Cas9. In some embodiments, the Cas9 is spCas9. In some embodiments, the Cas9 is SluCas9.

In some embodiments, according to any of the methods of treating hemophilia A described herein, the nucleic acid sequence encoding a synthetic FVIII coding sequence is codon-optimized for expression in the cell. In some embodiments, the cell is a human cell.

In some embodiments, according to any of the methods of treating hemophilia A described herein, the method employs a nucleic acid encoding the DNA endonuclease. In some embodiments, the nucleic acid encoding the DNA endonuclease is codon-optimized for expression in the cell. In some embodiments, the cell is a human cell, e.g., a human hepatocyte cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the methods of treating hemophilia A described herein, the donor template is encoded in an AAV vector. In some embodiments, the donor template comprises a donor cassette comprising the nucleic acid sequence encoding a synthetic FVIII protein, and the donor cassette is flanked on one or both sides by a gRNA target site. In some embodiments, the donor cassette is flanked on both sides by a gRNA target site. In some embodiments, the gRNA target site is a target site for the gRNA that is administered. In some embodiments, the gRNA target site of the donor template is the reverse complement of a cell genome gRNA target site for the gRNA that is administered. In some embodiments, providing the donor template to the cell comprises administering the donor template to the subject. In some embodiments, the administration is intravenous.

In some embodiments, according to any of the methods of treating hemophilia A described herein, the DNA endonuclease or nucleic acid encoding the DNA endonuclease is formulated in a liposome or an LNP. In some embodiments, the liposome or LNP also comprises the gRNA. In some embodiments, providing the gRNA and the DNA endonuclease or nucleic acid encoding the DNA endonuclease to the cell comprises administering the liposome or LNP to the subject. In some embodiments, the administration is intravenous. In some embodiments, the liposome or LNP is an LNP. In some embodiments, the method employs an LNP comprising nucleic acid encoding the DNA endonuclease and the gRNA. In some embodiments, the nucleic acid encoding the DNA endonuclease is an mRNA encoding the DNA endonuclease.

In some embodiments, according to any of the methods of treating hemophilia A described herein, the DNA endonuclease is pre-complexed with the gRNA, forming an RNP complex.

The process by which AAV infects cells, including cells of the liver, involves escape from the endosome, virus uncoating and the transport of the AAV genome to the nucleus. In the case of the AAV used in these studies in which single-stranded genomes are packaged in the virus, the single-stranded genomes undergo a process of second strand DNA synthesis to form double-stranded DNA genomes. The time required for complete conversion of single-stranded genomes to double-stranded genomes is not well established, but it is considered to be a rate limiting step (Ferrari et al., *J Virol* (1996) 70:3227-34). The double-stranded linear genomes then become concatemerized into multimeric circular forms composed of monomers joined head to tail and tail to head (Sun et al., *Human Gene Ther*. (2010) 21:750-62).

In some embodiments, according to any of the methods of treating hemophilia A described herein, the gRNA that is administered and the DNA endonuclease or nucleic acid encoding the DNA endonuclease that is administered are provided to the cell after the donor template is provided to the cell. In some embodiments, the gRNA that is administered and the DNA endonuclease or nucleic acid encoding the DNA endonuclease that is administered are provided to the cell more than four days after the donor template is provided to the cell. In some embodiments, the gRNA and the DNA endonuclease or nucleic acid encoding the DNA endonuclease are provided to the cell at least 14 days after the donor template is provided to the cell. In some embodiments, the gRNA and the DNA endonuclease or nucleic acid encoding the DNA endonuclease are provided to the cell at least 17 days after the donor template is provided to the cell. In some embodiments, providing the gRNA and the DNA endonuclease to the cell comprises administering (such as by an intravenous route) to the subject an LNP comprising nucleic acid encoding the DNA endonuclease and the gRNA. In some embodiments, the nucleic acid encoding the DNA endonuclease is an mRNA encoding the DNA endonuclease. In some embodiments, providing the donor template to the cell comprises administering (such as by an intravenous route) to the subject the donor template encoded in an AAV vector.

In some embodiments, according to any of the methods of treating hemophilia A described herein, one or more additional doses of the gRNA and the DNA endonuclease or nucleic acid encoding the DNA endonuclease are provided to the cell following the first dose of the gRNA and the DNA endonuclease or nucleic acid encoding the DNA endonuclease. In some embodiments, one or more additional doses of the gRNA and the DNA endonuclease or nucleic acid encoding the DNA endonuclease are provided to the cell following the first dose of the gRNA and the DNA endonuclease or nucleic acid encoding the DNA endonuclease until a target level of targeted integration of the nucleic acid sequence encoding a synthetic FVIII protein and/or a target level of expression of the nucleic acid sequence encoding a synthetic FVIII protein is achieved. In some embodiments, providing the gRNA and the DNA endonuclease to the cell comprises administering (such as by an intravenous route) to the subject a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the methods of treating hemophilia A described herein, the nucleic acid sequence encoding a synthetic FVIII protein is expressed under the control of an endogenous albumin promoter. In some embodiments, the nucleic acid sequence encoding a synthetic FVIII protein is expressed under the control of an endogenous transferrin promoter. In some embodiments, the nucleic acid sequence encoding a synthetic FVIII protein is expressed under the control of an endogenous fibrinogen-alpha chain promoter.

In some embodiments, according to any of the methods of treating hemophilia A described herein, the nucleic acid sequence encoding a synthetic FVIII protein is expressed in the liver of the subject.

Delivering Cells to a Subject

In some embodiments, the ex vivo methods of the disclosure involve administering the genome-edited cells into a subject in need thereof. This can be accomplished using any method of parenteral administration known in the art. For example, the genetically modified cells can be injected directly in the subject's blood, injected directly into or near the liver (implanted), or otherwise administered to the subject.

In some embodiments, the methods disclosed herein include implanting or "transplanting" genetically-modified therapeutic cells into a subject, by a method or route that results in at least partial localization of the introduced cells at a desired site such that a desired effect(s) is produced. The therapeutic cells or their differentiated progeny can be introduced by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the lifetime of the subject, i.e., long-term engraftment.

When provided prophylactically, the therapeutic cells described herein are administered to a subject in advance of any symptom of hemophilia A. Accordingly, in some embodiments, the prophylactic administration of a genetically modified hepatocyte cell population serves to prevent the occurrence of hemophilia A symptoms.

When provided therapeutically in some embodiments, genetically modified hepatocyte cells are provided at (or after) the onset of a symptom or indication of hemophilia A, e.g., upon the onset of disease.

In some embodiments, the therapeutic hepatocyte cell population being administered according to the methods described herein has allogeneic hepatocyte cells obtained from one or more donors. "Allogeneic" refers to a hepatocyte cell or biological samples having hepatocyte cells obtained from one or more different donors of the same species, where the genes at one or more loci are not identical. For example, a hepatocyte cell population being administered to a subject can be derived from one more unrelated donor subjects, or from one or more non-identical siblings. In some embodiments, syngeneic hepatocyte cell populations can be used, such as those obtained from genetically identical animals, or from identical twins. In other embodiments, the hepatocyte cells are autologous cells; that is, the hepatocyte cells are obtained or isolated from a subject and administered to the same subject, i.e., the donor and recipient are the same.

In one embodiment, an effective amount refers to the amount of a population of therapeutic cells needed to prevent or alleviate at least one or more signs or symptoms of hemophilia A, and relates to a sufficient amount of a composition to provide the desired effect, e.g., to treat a subject having hemophilia A. In embodiments, a therapeutically effective amount therefore refers to an amount of therapeutic cells or a composition having therapeutic cells that is sufficient to promote a particular effect when administered to a subject, such as one who has or is at risk for hemophilia A. An effective amount also includes an amount sufficient to prevent or delay the development of a symptom of the disease, alter the course of a symptom of the disease (for example, without limitation, to slow the progression of a symptom of the disease), or reverse a symptom of the disease. It is understood that for any given case, an appropriate effective amount can be determined by one of ordinary skill in the art.

For use in the embodiments described herein, an effective amount of therapeutic cells, e.g., genome-edited hepatocyte cells can be at least about $10^2$ cells, at least about $5\times10^2$ cells, at least about $10^3$ cells, at least about $5\times10^3$ cells, at least about $10^4$ cells, at least about $5\times10^4$ cells, at least about $10^5$ cells, at least about $2\times10^5$ cells, at least about $3\times10^5$ cells, at least about $4\times10^5$ cells, at least about $5\times10^5$ cells, at least about $6\times10^5$ cells, at least about $7\times10^5$ cells, at least about $8\times10^5$ cells, at least about $9\times10^5$ cells, at least about $1\times10^6$ cells, at least about $2\times10^6$ cells, at least about $3\times10^6$ cells, at least about $4\times10^6$ cells, at least about $5\times10^6$ cells, at least about $6\times10^6$ cells, at least about $7\times10^6$ cells, at least about $8\times10^6$ cells, at least about $9\times10^6$ cells, or multiples thereof. The therapeutic cells are derived from one or more donors, or are obtained from an autologous source. In some embodiments described herein, the therapeutic cells are expanded in culture prior to administration to a subject in need thereof.

In some embodiments, modest and incremental increases in the levels of functional FVIII expressed in cells of subjects having hemophilia A are beneficial for ameliorating one or more symptoms of the disease, for increasing long-term survival, and/or for reducing side effects associated with other treatments. Upon administration of such cells to human subjects, the presence of therapeutic cells that are producing increased levels of functional FVIII is beneficial. In some embodiments, effective treatment of a subject gives rise to at least about 1%, 3%, 5% or 7% functional FVIII relative to total FVIII in the treated subject. In some embodiments, functional FVIII is at least about 10% of total FVIII. In some embodiments, functional FVIII is at least, about, or at most 20%, 30%, 40%, 50%, 60%, 70%, 80%, 90% or 100% of total FVIII. Similarly, the introduction of even relatively limited subpopulations of cells having significantly elevated levels of functional FVIII is beneficial in subjects because in some situations normalized cells have a selective advantage relative to diseased cells. However, even modest levels of therapeutic cells with elevated levels of functional FVIII are beneficial for ameliorating one or more aspects of hemophilia A in subjects. In some embodiments, about 10%, about 20%, about 30%, about 40%, about 50%, about 60%, about 70%, about 80%, about 90% or more of the therapeutic in subjects to whom such cells are administered are producing increased levels of functional FVIII.

In embodiments, the delivery of a therapeutic cell composition into a subject by a method or route results in at least partial localization of the cell composition at a desired site. A cell composition can be administered by any appropriate route that results in effective treatment in the subject, i.e., administration results in delivery to a desired location in the subject where at least a portion of the composition delivered, i.e., at least about $1\times10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In some embodiments, the route is intravenous. For the delivery of cells, administration can be by injection or infusion.

In one embodiment, the cells are administered systemically, in other words a population of therapeutic cells are administered other than directly into a target site, tissue, or organ, such that it enters, instead, the subject's circulatory system, and thus is subject to metabolism and other like processes.

The efficacy of a treatment having a composition for the treatment of hemophilia A can be determined by the skilled clinician. However, a treatment is considered effective treatment if any one or more of the signs or symptoms of, as but one example, levels of functional FVIII are altered in a beneficial manner (e.g., increased by at least 10%), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art, and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

Composition

In one aspect, the present disclosure provides compositions for carrying out the methods disclosed herein. A composition can include one or more of the following: a genome-targeting nucleic acid (e.g., gRNA); a site-directed polypeptide (e.g., DNA endonuclease) or a nucleotide sequence encoding the site-directed polypeptide; and a polynucleotide to be inserted (e.g., a donor template) to effect the desired genetic modification of the methods disclosed herein.

In some embodiments, a composition has a nucleotide sequence encoding a genome-targeting nucleic acid (e.g., gRNA).

In some embodiments, a composition has a site-directed polypeptide (e.g., DNA endonuclease). In some embodiments, a composition has a nucleotide sequence encoding the site-directed polypeptide.

In some embodiments, a composition has a polynucleotide (e.g., a donor template) to be inserted into a genome.

In some embodiments, a composition has (i) a nucleotide sequence encoding a genome-targeting nucleic acid (e.g., gRNA) and (ii) a site-directed polypeptide (e.g., DNA endonuclease) or a nucleotide sequence encoding the site-directed polypeptide.

In some embodiments, a composition has (i) a nucleotide sequence encoding a genome-targeting nucleic acid (e.g., gRNA) and (ii) a polynucleotide (e.g., a donor template) to be inserted into a genome.

In some embodiments, a composition has (i) a site-directed polypeptide (e.g., DNA endonuclease) or a nucleotide sequence encoding the site-directed polypeptide and (ii) a polynucleotide (e.g., a donor template) to be inserted into a genome.

In some embodiments, a composition has (i) a nucleotide sequence encoding a genome-targeting nucleic acid, (ii) a site-directed polypeptide or a nucleotide sequence encoding the site-directed polypeptide and (iii) a polynucleotide (e.g., a donor template) to be inserted into a genome.

In some embodiments of any of the above compositions, the composition has a single-molecule guide genome-targeting nucleic acid. In some embodiments of any of the above compositions, the composition has a double-molecule genome-targeting nucleic acid. In some embodiments of any of the above compositions, the composition has two or more double-molecule guides or single-molecule guides. In some embodiments, the composition has a vector that encodes the nucleic acid targeting nucleic acid. In some embodiments, the genome-targeting nucleic acid is a DNA endonuclease, in particular, Cas9.

In some embodiments, a composition contains one or more gRNA suitable for genome-edition, in particular, insertion of a synthetic FVIII coding sequence into a genome of a cell. The gRNA for the composition can target a genomic site at, within, or near an endogenous albumin gene. In some embodiments, the gRNA has a spacer sequence complementary to a genomic sequence at, within, or near an albumin gene.

In some embodiments, a gRNA for a composition is a sequence selected from any of SEQ ID NOs: 271-298 and variants thereof, having at least about 50%, about 55%, about 60%, about 65%, about 70%, about 75%, about 80%, about 85%, about 90% or about 95% identity or homology to any of SEQ ID NOs: 271-298. In some embodiments, the variants of gRNA have at least about 85% homology to any of any of SEQ ID NOs: 271-298.

In some embodiments, a gRNA for a composition has a spacer sequence that is complementary to a target site in the genome. In some embodiments, the spacer sequence is 15 bases to 20 bases in length. In some embodiments, a complementarity between the spacer sequence and the genomic sequence is at least about 80%, at least about 85%, at least about 90%, at least about 95%, at least about 96%, at least about 97%, at least about 98%, at least about 99% or about 100%.

In some embodiments, a composition has a DNA endonuclease or a nucleic acid encoding the DNA endonuclease and/or a donor template having a nucleic acid sequence of a synthetic FVIII coding sequence. In some embodiments, the DNA endonuclease is Cas9. In some embodiments, the nucleic acid encoding the DNA endonuclease is DNA or RNA.

In some embodiments, one or more of any oligonucleotides or nucleic acid sequences is encoded in an AAV vector. Therefore, in some embodiments, a gRNA is encoded in an AAV vector. In some embodiments, a nucleic acid encoding a DNA endonuclease is encoded in an AAV vector. In some embodiments, a donor template is encoded in an AAV vector. In some embodiments, two or more oligonucleotides or nucleic acid sequences are encoded in a single AAV vector. Thus, in some embodiments, a gRNA sequence and a DNA endonuclease-encoding nucleic acid are encoded in a single AAV vector.

In some embodiments, a composition has a liposome or a lipid nanoparticle. Therefore, in some embodiments, any compounds (e.g., a DNA endonuclease or a nucleic acid encoding thereof, gRNA, and donor template) of the composition can be formulated in a liposome or LNP. In some embodiments, one or more such compounds are associated with a liposome or LNP via a covalent bond or non-covalent bond. In some embodiments, any of the compounds are separately or together contained in a liposome or LNP. Therefore, in some embodiments, each of a DNA endonuclease or a nucleic acid encoding thereof, gRNA and donor template is separately formulated in a liposome or LNP. In some embodiments, a DNA endonuclease is formulated in a liposome or LNP with gRNA. In some embodiments, a DNA endonuclease or a nucleic acid encoding thereof, gRNA, and donor template are formulated in a liposome or LNP together.

In some embodiments, a composition described above further has one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing, and the like. A buffer can be a stabilization buffer, a reconstituting buffer, a diluting buffer, or the like. In some embodiments, a composition also includes one or more components that can be used to facilitate or enhance the on-target binding or the cleavage of DNA by the endonuclease, or improve the specificity of targeting.

In some embodiments, any components of a composition are formulated with pharmaceutically acceptable excipients such as carriers, solvents, stabilizers, adjuvants, diluents, etc., depending upon the particular mode of administration and dosage form. In embodiments, guide RNA compositions are generally formulated to achieve a physiologically compatible pH, and range from a pH of about 3 to a pH of about 11, about pH 3 to about pH 7, depending on the formulation and route of administration. In some embodiments, the pH is adjusted to a range from about pH 5.0 to about pH 8.0. In some embodiments, the composition has a therapeutically effective amount of at least one compound as described herein, together with one or more pharmaceutically acceptable excipients. Optionally, the composition can have a combination of the compounds described herein, can include a second active ingredient useful in the treatment or prevention of bacterial growth (for example and without limitation, anti-bacterial or anti-microbial agents), and can include a combination of reagents of the disclosure. In some embodiments, gRNAs are formulated with one or more other oligonucleotides, e.g., a nucleic acid encoding a DNA endonuclease, and/or a donor template. Alternatively, a nucleic acid encoding DNA endonuclease and a donor template, separately or in combination with other oligonucleotides, is formulated with the method described above for gRNA formulation.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example, without limitation, ascorbic acid), chelating agents (for example, without limitation, EDTA), carbohydrates (for example, without limitation, dextrin, hydroxyalkylcellulose, and hydroxyalkylmethylcellulose), stearic acid, liquids (for example, without limitation, oils, water, saline, glycerol and ethanol), wetting or emulsifying agents, pH buffering substances, and the like.

In some embodiments, any compounds (e.g., a DNA endonuclease or a nucleic acid encoding thereof, gRNA, and donor template) of a composition are delivered via transfection such as electroporation. In some exemplary embodiments, a DNA endonuclease is precomplexed with a gRNA, forming an RNP complex, prior to the provision to the cell, and the RNP complex is electroporated. In such embodiments, the donor template can be delivered via electroporation.

In some embodiments, "composition" refers to a therapeutic composition having therapeutic cells that are used in an ex vivo treatment method.

In embodiments, therapeutic compositions contain a physiologically tolerable carrier together with the cell composition, and optionally at least one additional bioactive agent as described herein, dissolved or dispersed therein as an active ingredient. In some embodiments, the therapeutic composition is not substantially immunogenic when administered to a mammal or human subject for therapeutic purposes.

In general, the genetically-modified, therapeutic cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation having cells can include, e.g., osmotic buffers that permit cell membrane integrity to be maintained, and optionally, nutrients to maintain cell viability or enhance engraftment upon administration. Such formulations and suspensions are known to those of skill in the art, and/or can be adapted for use with the cells, as described herein.

In some embodiments, a cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and organic bases such as isopropylamine, trimethylamine, 2-ethylamino ethanol, histidine, procaine, and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol, and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition will depend on the nature of the disorder or condition, and can be determined by standard clinical techniques.

Kit

Some embodiments provide a kit that contains any of the above-described compositions, e.g., a composition for genome editing, or a therapeutic cell composition and one or more additional components.

In some embodiments, a kit can have one or more additional therapeutic agents that can be administered simultaneously or in sequence with the composition for a desired purpose, e.g., genome editing or cell therapy.

In some embodiments, a kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g., CD-ROM, diskette, flash drive, etc. In some instances, the actual instructions are not present in the kit, but means for obtaining the instructions from a remote source (e.g., via the Internet) are provided. An example of this embodiment is a kit that includes a web address where the instructions can be viewed and/or from which the instructions can be downloaded. As with the instructions, the method for obtaining the instructions can be recorded on a suitable substrate.

Additional Therapeutic Approaches

Gene editing can be conducted using site-directed polypeptides engineered to target specific sequences. To date there are four major types of such nucleases: meganucleases and their functional equivalents, zinc finger nucleases (ZFNs), transcription activator-like effector nucleases (TALENs), and CRISPR/CAS nuclease systems. The nuclease platforms vary in difficulty of design, targeting density and mode of action, particularly as the specificity of ZFNs and TALENs is through protein-DNA interactions, while RNA-DNA interactions primarily guide Cas proteins. Cas9 cleavage also requires an adjacent motif, the PAM, which differs between different CRISPR systems. Cas9 from *Streptococcus pyogenes* cleaves using an NRG PAM, while CRISPR from *Neisseria meningitidis* can cleave at sites with PAMs including NNNNGATT (SEQ ID NO: 312), NNNNNGTTT (SEQ ID NO: 313) and NNNNGCTT (SEQ ID NO: 314). A number of other Cas9 orthologs target protospacers adjacent to alternative PAMs.

CRISPR endonucleases, such as Cas9, can be used in embodiments of the methods of the disclosure. Further, the teachings described herein, such as therapeutic target sites, can be applied to other forms of endonucleases, such as ZFNs, TALENs, HEs, or MegaTALs, or using combinations of nucleases. However, to apply the teachings of the present disclosure to such endonucleases, one would need to, among other things, engineer proteins directed to the specific target sites.

Additional binding domains can be fused to the Cas9 protein to increase specificity. The target sites of these constructs map to the identified gRNA specified site, but require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or "dead" Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site.

In some embodiments, the compositions and methods of editing genome in accordance with the present disclosures (e.g., insertion of a FVIII coding sequence into an albumin locus) use any of the following approaches.

Zinc Finger Nucleases

Zinc finger nucleases (ZFNs) are modular proteins having an engineered zinc finger DNA binding domain, linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN generally has 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will generally recognize a combined target sequence of 24-36 bp, not including the 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity, so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., *Proc Natl Acad Sci USA* (1999) 96(6):2758-63; B. Dreier et al., *J Mol Biol.* (2000) 303(4):489-502; Q. Liu et al., *J Biol Chem.* (2002) 277(6):3850-6; Dreier et al., *J Biol Chem* (2005) 280(42):35588-97; and Dreier et al., *J Biol Chem.* (2001) 276(31):29466-78.

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major differences from ZFNs are the nature of the DNA binding domain, and the associated target DNA sequence recognition properties. The TALEN DNA binding domain derives from TALE proteins, which were originally described in the plant bacterial pathogen *Xanthomonas* sp. TALEs have tandem arrays of 33-35 amino acid repeats, with each repeat recognizing a single base pair in the target DNA sequence that is generally up to 20 bp in length, giving a total target sequence length of up to 40 bp. Nucleotide specificity of each repeat is determined by the repeat variable di-residue (RVD), which includes just two amino acids at positions 12 and 13. The bases guanine, adenine, cytosine, and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs also benefit from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9/Cpf1 "nickase"

mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported: see, e.g., Boch, *Science* (2009) 326(5959):1509-12; Mak et al., *Science* (2012) 335(6069):716-9; and Moscou et al., *Science* (2009) 326(5959):1501. The use of TALENs based on the "Golden Gate" platform, or cloning scheme, has been described by multiple groups: see, e.g., T. Cermak et al., *Nucleic Acids Res.* (2011) 39(12):e82; Li et al., *Nucleic Acids Res.* (2011) 39(14):6315-25; Weber et al., *PLoS One* (2011) 6(2):e16765; Wang et al., *J Genet Genomics* (2014) 41(6):339-47, Epub 2014 Can 17; and T. Cermak et al., *Methods Mol Biol.* (2015) 1239:133-59.

Homing Endonucleases

Homing endonucleases (HEs) are site-specific endonucleases that have long recognition sequences (14-44 base pairs) and cleave DNA with high specificity—often at sites unique in the genome. There are at least six known families of HEs as classified by their structure, including LAGLIDADG (SEQ ID NO: 6), GIY-YIG, His-Cis box, H-N-H, PD-(D/E)xK, and Vsr-like, that are derived from a broad range of hosts, including eukarya, protists, bacteria, archaea, cyanobacteria, and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported: see, e.g., the reviews by Steentoft et al., *Glycobiology* (2014) 24(8):663-80; Belfort and Bonocora, *Methods Mol Biol.* (2014) 1123:1-26; Hafez and Hausner, Genome (2012) 55(8):553-69; and references cited therein.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE: see, e.g., Boissel et al., *Nuc. Acids Res.* (2014) 42: 2591-601; Kleinstiver et al., G3 (2014) 4:1155-65; and Boissel and Scharenberg, *Methods Mol. Biol.* (2015) 1239: 171-96.

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., *Nuc. Acids Res.* (2014) 42:8816-29. It is anticipated that other combinations of existing nuclease-based approaches will evolve and be useful in achieving the targeted genome modifications described herein.

dCas9-FokI or dCpf1-FokI and Other Nucleases

Combining the structural and functional properties of the nuclease platforms described above offers a further approach to genome editing that can potentially overcome some of the inherent deficiencies. As an example, the CRISPR genome editing system generally uses a single Cas9 endonuclease to create a DSB. The specificity of targeting is driven by a 20 or 22 nucleotide sequence in the guide RNA that undergoes Watson-Crick base-pairing with the target DNA (plus an additional two bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., *Nature Biotech* (2014) 32:569-76; and Guilinger et al., *Nature Biotech.* (2014) 32:577-82. Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

The details of one or more embodiments of the disclosure are set forth in the accompanying description below. Other features, objects and advantages of the disclosure will be apparent from the description. In the description, the singular forms also include the plural unless the context clearly dictates otherwise. Unless defined otherwise, technical and scientific terms used herein have the same meaning as commonly understood by one of ordinary skill in the art to which this disclosure belongs. In the case of conflict, the present description will control.

It is understood that the examples and embodiments described herein are for illustrative purposes only and that modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Some embodiments of the disclosures provided herewith are further illustrated by the following non-limiting examples.

Exemplary Embodiments

Embodiment 1. A system comprising: a deoxyribonucleic acid (DNA) endonuclease or a nucleic acid encoding the DNA endonuclease; a guide RNA (gRNA) comprising a spacer sequence complementary to a host cell locus or a nucleic acid encoding the gRNA; and a donor template comprising a nucleic acid sequence encoding a synthetic FVIII protein, wherein the synthetic FVIII protein comprises a B domain substitute, wherein the B domain substitute comprises from zero to nine N-linked glycosylation sites and from three to about 40 amino acids in length.

Embodiment 2. The system of embodiment 1, wherein the B domain substitute comprises from zero to six N-linked glycosylation sites.

Embodiment 3. The system of embodiment 2, wherein the B domain substitute comprises from zero to three N-linked glycosylation sites.

Embodiment 4. The system of embodiment 1, wherein the B domain substitute comprises the amino acid sequence of any one of SEQ ID NOs: 362-369, 371, and 373.

Embodiment 5. The system of embodiment 4, wherein the B domain substitute comprises the amino acid sequence of any one of SEQ ID NOs: 362-366, 371, and 373 or a variant thereof having at least 80% identity to any one of SEQ ID NOs: 362-366, 371, and 373.

Embodiment 6. The system of embodiment 5, wherein the B domain substitute comprises the amino acid sequence of any one of SEQ ID NOs: 362-364, 371, and 373.

Embodiment 7. The system of any one of embodiments 1-6, wherein the host cell locus is the locus of a gene expressed in the liver.

Embodiment 8. The system of any one of embodiments 1-7, wherein the host cell locus is the locus of a gene encoding an acute-phase protein.

Embodiment 9. The system of embodiment 8, wherein the acute phase protein is an albumin, a transferrin, or a fibrinogen.

Embodiment 10. The system of any one of embodiments 1-7, wherein the host cell locus is a safe harbor locus.

Embodiment 11. The system of any one of embodiments 1-10, wherein the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csyl, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, and a functional derivative thereof.

Embodiment 12. The system of embodiment 11, wherein the DNA endonuclease is a Cas9.

Embodiment 13. The system of any one of embodiments 1-11, wherein the nucleic acid encoding the DNA endonuclease is codon-optimized for expression in the host cell.

Embodiment 14. The system of any one of embodiments 1-13, wherein the nucleic acid encoding the DNA endonuclease is a deoxyribonucleic acid (DNA).

Embodiment 15. The system of any one of embodiments 1-13, wherein the nucleic acid encoding the DNA endonuclease is a ribonucleic acid (RNA).

Embodiment 16. The system of embodiment 15, wherein the RNA encoding the DNA endonuclease is an mRNA.

Embodiment 17. The system of any one of embodiments 1-16, wherein the donor template nucleic acid sequence is codon optimized for expression in the host cell.

Embodiment 18. The system of any one of embodiments 1-17, wherein the donor template nucleic acid sequence comprises a reduced content of CpG di-nucleotides as compared to a wild type nucleic acid sequence encoding a FVIII protein.

Embodiment 19. The system of embodiment 18, wherein the donor template nucleic acid sequence does not comprise CpG di-nucleotides.

Embodiment 20. The system of any one of embodiments 1-19, wherein the donor template is encoded in an AAV vector.

Embodiment 21. The system of any one of embodiments 1-20, wherein the donor template comprises a donor cassette comprising the nucleic acid sequence encoding a synthetic FVIII protein, and wherein the donor cassette is flanked on one or both sides by a gRNA target site.

Embodiment 22. The system of embodiment 21, wherein the donor cassette is flanked on both sides by a gRNA target site.

Embodiment 23. The system of embodiment 21, wherein the donor cassette is flanked on its 5' side by a gRNA target site.

Embodiment 24. The system of any one of embodiments 21-23, wherein the gRNA target site is a target site for a gRNA in the system.

Embodiment 25. The system of embodiment 24, wherein the gRNA target site of the donor template is the reverse complement of a genomic gRNA target site for a gRNA in the system.

Embodiment 26. The system of any one of embodiments 1-25, wherein the DNA endonuclease or nucleic acid encoding the DNA endonuclease is contained in a liposome or lipid nanoparticle.

Embodiment 27. The system of embodiment 26, wherein the liposome or lipid nanoparticle also comprises the gRNA.

Embodiment 28. The system of any one of embodiments 1-27, wherein the DNA endonuclease is complexed with the gRNA, thereby providing a Ribonucleoprotein (RNP) complex.

Embodiment 29. A method of editing a genome in a host cell, the method comprising providing to the cell: (a) a gRNA comprising a spacer sequence complementary to a host cell locus or a nucleic acid encoding the gRNA; (b) a DNA endonuclease or a nucleic acid encoding the DNA endonuclease; and (c) a donor template comprising a nucleic acid sequence encoding a synthetic FVIII protein, wherein the synthetic FVIII protein comprises a B domain substitute, wherein the B domain substitute comprises from zero to nine N-linked glycosylation sites and from three to about 40 amino acids in length.

Embodiment 30. The method of embodiment 29, wherein the B domain substitute comprises from zero to six N-linked glycosylation sites.

Embodiment 31. The method of embodiment 30, wherein the B domain substitute comprises from zero to three N-linked glycosylation sites.

Embodiment 32. The method of embodiment 29, wherein the B domain substitute comprises the amino acid sequence of any one of SEQ ID NOs: 362-369, 371, and 373.

Embodiment 33. The method of embodiment 32, wherein the B domain substitute comprises the amino acid sequence of any one of SEQ ID NOs: 362-366, 371, and 373 or a variant thereof having at least 80% identity to any one of SEQ ID NOs: 362-366, 371, and 373.

Embodiment 34. The method of embodiment 33, wherein the B domain substitute comprises the amino acid sequence of any one of SEQ ID NOs: 362-364, 371, and 373.

Embodiment 35. The method of any one of embodiments 29-34, wherein the host cell endogenous locus is the locus of a gene expressed in the liver.

Embodiment 36. The method of any one of embodiments 29-35, wherein the host cell endogenous locus is the locus of a gene encoding an acute-phase protein.

Embodiment 37. The method of embodiment 36, wherein the acute phase protein is albumin, transferrin, or fibrinogen.

Embodiment 38. The method of any one of embodiments 29-34, wherein the host cell endogenous locus is a safe harbor locus.

Embodiment 39. The method of any one of embodiments 29-38, wherein the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csyl, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; or a functional derivative thereof.

Embodiment 40. The method of embodiment 39, wherein the DNA endonuclease is Cas9.

Embodiment 41. The method of any one of embodiments 29-40, wherein the nucleic acid encoding the DNA endonuclease is codon-optimized for expression in the host cell.

Embodiment 42. The method of any one of embodiments 29-41, wherein the nucleic acid encoding the DNA endonuclease is a deoxyribonucleic acid (DNA).

Embodiment 43. The method of any one of embodiments 29-41, wherein the nucleic acid encoding the DNA endonuclease is a ribonucleic acid (RNA).

Embodiment 44. The method of embodiment 43, wherein the RNA encoding the DNA endonuclease is an mRNA.

Embodiment 45. The method of embodiment 29, wherein the donor template is encoded in an AAV vector.

Embodiment 46. The method of any one of embodiments 29-45, wherein the donor template nucleic acid sequence is codon optimized for expression in the host cell.

Embodiment 47. The method of any one of embodiments 29-46, wherein the donor template nucleic acid sequence comprises a reduced content of CpG di-nucleotides as compared to a wild type nucleic acid sequence encoding FVIII.

Embodiment 48. The method of embodiment 47, wherein the donor template nucleic acid sequence does not comprise CpG di-nucleotides.

Embodiment 49. The method of any one of embodiments 29-48, wherein the donor template comprises a donor cassette comprising the nucleic acid sequence encoding a synthetic FVIII protein, and wherein the donor cassette is flanked on one or both sides by a gRNA target site.

Embodiment 50. The method of embodiment 49, wherein the donor cassette is flanked on both sides by a gRNA target site.

Embodiment 51. The method of embodiment 49, wherein the donor cassette is flanked on its 5' side by a gRNA target site.

Embodiment 52. The method of any one of embodiments 49-51, wherein the gRNA target site is a target site for the gRNA that is administered.

Embodiment 53. The method of embodiment 52, wherein the gRNA target site of the donor template is the reverse complement of a gRNA target site in the cell genome for the gRNA that is administered.

Embodiment 54. The method of any one of embodiments 29-53, wherein the DNA endonuclease or nucleic acid encoding the DNA endonuclease is formulated in a liposome or lipid nanoparticle.

Embodiment 55. The method of embodiment 54, wherein the liposome or lipid nanoparticle also comprises the gRNA.

Embodiment 56. The method of any one of embodiments 29-55, wherein the DNA endonuclease and the gRNA are provided to the host cell as a Ribonucleoprotein (RNP) complex, which comprises the DNA endonuclease precomplexed with the gRNA.

Embodiment 57. The method of any one of embodiments 29-56, wherein the gRNA or nucleic encoding the gRNA and the DNA endonuclease or nucleic acid encoding the DNA endonuclease are provided to the cell more than four days after the donor template is provided to the cell.

Embodiment 58. The method of any one of embodiments 29-57, wherein the gRNA or nucleic acid encoding the gRNA and the DNA endonuclease or nucleic acid encoding the DNA endonuclease are provided to the cell at least 14 days after the donor template is provided to the cell.

Embodiment 59. The method of embodiment 57 or 58, wherein one or more additional doses of the gRNA or nucleic acid encoding the gRNA and the DNA endonuclease or nucleic acid encoding the DNA endonuclease are provided to the cell following the first dose of the gRNA or nucleic acid encoding the gRNA and the DNA endonuclease or nucleic acid encoding the DNA endonuclease.

Embodiment 60. The method of embodiment 59, wherein one or more additional doses of the gRNA or nucleic acid encoding the gRNA and the DNA endonuclease or nucleic acid encoding the DNA endonuclease are provided to the cell following the first dose of the gRNA or nucleic acid encoding the gRNA and the DNA endonuclease or nucleic acid encoding the DNA endonuclease until a target level of targeted integration of the nucleic acid sequence encoding a synthetic FVIII protein is achieved, or a target level of expression of the nucleic acid sequence encoding a synthetic FVIII protein is achieved.

Embodiment 61. The method of any one of embodiments 29-60, wherein the cell is a liver cell.

Embodiment 62. The method of embodiment 61, wherein the cell is a human hepatocyte or human sinusoidal epithelial cell.

Embodiment 63. A cell, wherein the genome of the cell comprises DNA encoding a synthetic FVIII protein, wherein the synthetic FVIII protein comprises a B domain substitute, wherein the B domain substitute comprises from zero to nine N-linked glycosylation sites and from three to about 40 amino acids in length.

Embodiment 64. The cell of embodiment 63, wherein the synthetic FVIII protein is operably linked to an endogenous albumin promoter, an endogenous transferrin promoter, or an endogenous fibrinogen alpha promoter.

Embodiment 65. The cell of embodiment 63, wherein the nucleic acid sequence encoding the synthetic FVIII protein is codon-optimized for expression in the cell.

Embodiment 66. The cell of embodiment 63, wherein the cell is a human liver cell.

Embodiment 67. The cell of embodiment 66, wherein the cell is a human hepatocyte or a human sinusoid epithelial cell.

Embodiment 68. The cell of embodiment 67, wherein the cell is prepared by the method of any one of embodiments 29-62.

Embodiment 69. A method of treating hemophilia A in a subject, the method comprising: providing the following to a cell in the subject: (a) a gRNA comprising a spacer sequence complementary to a host cell locus or a nucleic acid encoding the gRNA; (b) a DNA endonuclease or a nucleic acid encoding the DNA endonuclease; and (c) a donor template comprising a nucleic acid sequence encoding a synthetic FVIII protein, wherein the synthetic FVIII protein comprises a B domain substitute, wherein the B domain substitute comprises from zero to nine N-linked glycosylation sites and from three to about 40 amino acids in length.

Embodiment 70. The method of embodiment 69, wherein the B domain substitute comprises from zero to six N-linked glycosylation sites.

Embodiment 71. The method of embodiment 70, wherein the B domain substitute comprises from zero to three N-linked glycosylation sites.

Embodiment 72. The method of embodiment 29, wherein the B domain substitute comprises the amino acid sequence of any one of SEQ ID NOs: 362-369, 371, and 373.

Embodiment 73. The method of embodiment 72, wherein the B domain substitute comprises the amino acid sequence of any one of SEQ ID NOs: 362-366, 371, and 373 or a variant thereof having at least 80% identity to any one of SEQ ID NOs: 362-366, 371, and 373.

Embodiment 74. The method of embodiment 73, wherein the B domain substitute comprises the amino acid sequence of any one of SEQ ID NOs: 362-364, 371, and 373.

Embodiment 75. The method of any one of embodiments 69-74, wherein the host cell locus is the locus of a gene expressed in the liver.

Embodiment 76. The method of any one of embodiments 69-75, wherein the host cell locus is the locus of a gene encoding an acute-phase protein.

Embodiment 77. The method of embodiment 76, wherein the acute phase protein is albumin, transferrin, or fibrinogen.

Embodiment 78. The method of any one of embodiments 69-74, wherein the host cell locus is a safe harbor locus.

Embodiment 79. The method of any one of embodiments 69-78, wherein the DNA endonuclease is selected from the group consisting of Cas1, Cas1B, Cas2, Cas3, Cas4, Cas5, Cas6, Cas7, Cas8, Cas9 (also known as Csn1 and Csx12), Cas100, Csyl, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease; or a functional derivative thereof.

Embodiment 80. The method of embodiment 79, wherein the DNA endonuclease is Cas9.

Embodiment 81. The method of embodiment 80, wherein the Cas9 is spCas9 or SluCas9.

Embodiment 82. The method of any one of embodiments 69-81, wherein the nucleic acid encoding the DNA endonuclease is codon-optimized for expression in the cell.

Embodiment 83. The method of any one of embodiments 69-82, wherein the nucleic acid encoding the DNA endonuclease is a deoxyribonucleic acid (DNA).

Embodiment 84. The method of any one of embodiments 69-82, wherein the nucleic acid encoding the DNA endonuclease is a ribonucleic acid (RNA).

Embodiment 85. The method of embodiment 84, wherein the RNA encoding the DNA endonuclease is an mRNA.

Embodiment 86. The method of any one of embodiments 69-85, wherein one or more of the gRNA or nucleic acid encoding the gRNA, the DNA endonuclease or nucleic acid encoding the DNA endonuclease, and the donor template are formulated in a liposome or lipid nanoparticle.

Embodiment 87. The method of any one of embodiments 69-86, wherein the donor template is encoded in an AAV vector.

Embodiment 88. The method of any one of embodiments 69-87, wherein the donor template nucleic acid sequence is codon optimized for expression in the host cell.

Embodiment 89. The method of any one of embodiments 69-88, wherein the donor template nucleic acid sequence comprises a reduced content of CpG di-nucleotides as compared to a wild type nucleic acid sequence encoding FVIII.

Embodiment 90. The method of embodiment 89, wherein the donor template nucleic acid sequence does not comprise CpG di-nucleotides.

Embodiment 91. The method of any one of embodiments 69-90, wherein the donor template comprises a donor cassette comprising the nucleic acid sequence encoding a synthetic FVIII protein, and wherein the donor cassette is flanked on one or both sides by a gRNA target site.

Embodiment 92. The method of embodiment 91, wherein the donor cassette is flanked on both sides by a gRNA target site.

Embodiment 93. The method of embodiment 91, wherein the donor cassette is flanked on its 5' side by a gRNA target site.

Embodiment 94. The method of any one of embodiments 91-93, wherein the gRNA target site is a target site for the gRNA.

Embodiment 95. The method of embodiment 94, wherein the gRNA target site of the donor template is the reverse complement of the gRNA target site in the cell genome for the gRNA.

Embodiment 96. The method of any one of embodiments 69-95, wherein providing the donor template to the cell comprises administering the donor template to the subject intravenously.

Embodiment 97. The method of any one of embodiments 69-96, wherein the DNA endonuclease or nucleic acid encoding the DNA endonuclease is formulated in a liposome or lipid nanoparticle.

Embodiment 98. The method of embodiment 97, wherein the liposome or lipid nanoparticle also comprises the gRNA.

Embodiment 99. The method of embodiment 98, wherein providing the gRNA or nucleic acid encoding the gRNA and the DNA endonuclease or nucleic acid encoding the DNA endonuclease to the cell comprises administering the liposome or lipid nanoparticle to the subject intravenously.

Embodiment 100. The method of any one of embodiments 69-99, wherein the DNA endonuclease and the gRNA are provided to the host cell as a Ribonucleoprotein (RNP) complex, which RNP complex comprises the DNA endonuclease complexed with the gRNA.

Embodiment 101. The method of any one of embodiments 69-100, wherein the gRNA or nucleic acid encoding the gRNA and the DNA endonuclease or nucleic acid encoding the DNA endonuclease are provided to the cell more than four days after the donor template is provided to the cell.

Embodiment 102. The method of any one of embodiments 69-101, wherein the gRNA or nucleic acid encoding the gRNA and the DNA endonuclease or nucleic acid encoding the DNA endonuclease are provided to the cell at least 14 days after the donor template is provided to the cell.

Embodiment 103. The method of embodiment 101 or 102, wherein one or more additional doses of the gRNA or nucleic acid encoding the gRNA and the DNA endonuclease or nucleic acid encoding the DNA endonuclease are provided to the cell following the first dose of the gRNA or nucleic acid encoding the gRNA and the DNA endonuclease or nucleic acid encoding the DNA endonuclease.

Embodiment 104. The method of embodiment 103, wherein one or more additional doses of the gRNA or nucleic acid encoding the gRNA and the DNA endonuclease or nucleic acid encoding the DNA endonuclease are provided to the cell following the first dose of the gRNA or nucleic acid encoding the gRNA and the DNA endonuclease or nucleic acid encoding the DNA endonuclease until a target level of targeted integration of the nucleic acid sequence encoding a synthetic FVIII protein and/or a target level of expression of the nucleic acid sequence encoding a synthetic FVIII protein is achieved.

Embodiment 105. The method of any one of embodiments 101-104, wherein providing the gRNA and the DNA endonuclease or nucleic acid encoding the DNA endonuclease to the cell comprises administering to the subject a lipid nanoparticle comprising nucleic acid encoding the DNA endonuclease and the gRNA.

Embodiment 106. The method of any one of embodiments 101-105, wherein providing the donor template to the cell comprises administering to the subject the donor template encoded in an AAV vector.

Embodiment 107. The method of any one of embodiments 69-106, wherein the cell is a hepatocyte.

Embodiment 108. The method of any one of embodiments 69-107, wherein the nucleic acid sequence encoding a synthetic FVIII protein is expressed in the liver of the subject.

Embodiment 109. A method of treating hemophilia A in a subject, comprising administering the cell of any one of embodiments 63-68 to the subject.

Embodiment 110. The method of embodiment 109, wherein the cell is autologous to the subject.

Embodiment 111. The method of embodiment 110, further comprising obtaining a biological sample from the subject, wherein the biological sample comprises a liver cell, and wherein the cell is prepared from the liver cell.

Embodiment 112. A kit comprising one or more elements of the system of any one of embodiments 1-28, further comprising instructions for use.

Embodiment 113. A nucleic acid comprising a polynucleotide sequence encoding a synthetic FVIII protein, wherein the synthetic FVIII protein comprises a B domain substitute, wherein the B domain substitute comprises from zero to nine N-linked glycosylation sites and from three to about 40 amino acids in length.

Embodiment 114. The nucleic acid of embodiment 113, wherein the B domain substitute comprises from zero to six N-linked glycosylation sites.

Embodiment 115. The nucleic acid of embodiment 113 wherein the B domain substitute comprises from zero to three N-linked glycosylation sites.

Embodiment 116. The nucleic acid of embodiment 113, wherein the B domain substitute comprises the amino acid sequence of any one of SEQ ID NOs: 362-369, 371, and 373.

Embodiment 117. The nucleic acid of embodiment 116, wherein the B domain substitute comprises the amino acid sequence of any one of SEQ ID NOs: 362-364, 371, and 373 or a variant thereof having at least 80% identity to any one of SEQ ID NOs: 362-364, 371, and 373.

Embodiment 118. The nucleic acid of embodiment 116, wherein the B domain substitute comprises the amino acid sequence of any one of SEQ ID NOs: 362-363, 371, and 373.

Embodiment 119. The nucleic acid of any one of embodiments 113-118, wherein the polynucleotide sequence encoding a synthetic FVIII protein is codon optimized for expression in a host cell.

Embodiment 120. The nucleic acid of any one of embodiments 113-119, wherein the polynucleotide sequence encoding a synthetic FVIII protein comprises a reduced content of CpG di-nucleotides as compared to a wild type nucleic acid sequence encoding FVIII.

Embodiment 121. The nucleic acid of embodiment 120, wherein the polynucleotide sequence encoding a synthetic FVIII protein does not comprise CpG di-nucleotides.

Embodiment 122. The nucleic acid of any one of embodiments 113-121, wherein the nucleic acid is a viral vector.

Embodiment 123. The nucleic acid of embodiment 122, wherein the viral vector is an AAV vector.

Embodiment 124. A method of increasing the amount of FVIII in a subject, the method comprising: providing the following to a cell in the subject, wherein the subject has a first serum level of FVIII: (a) a gRNA comprising a spacer sequence complementary to a host cell locus or a nucleic acid encoding the gRNA; (b) a DNA endonuclease or a nucleic acid encoding the DNA endonuclease; and (c) a donor template comprising a nucleic acid sequence encoding a synthetic FVIII protein, wherein the synthetic FVIII protein comprises a B domain substitute, wherein the B domain substitute comprises from zero to nine N-linked glycosylation sites and from three to about 40 amino acids in length.

Embodiment 125. The method of embodiment 124, wherein the first serum level of FVIII is less than about 0.40 IU/mL.

Embodiment 126. The method of embodiment 125, wherein the first serum level of FVIII is less than about 0.05 IU/mL.

Embodiment 127. The method of embodiment 125, wherein the first serum level of FVIII is less than about 0.01 IU/mL.

Embodiment 128. The use of the system of any one of embodiments 1-28 for the treatment of hemophilia A.

Embodiment 129. The use of the system of any one of embodiments 1-28 for the manufacture of a medicament for the treatment of hemophilia A.

Embodiment 130. The use of the cell of any one of embodiments 63-68 for the treatment of hemophilia A.

Embodiment 131. The use of the cell of any one of embodiments 63-68 for the manufacture of a medicament for the treatment of hemophilia A.

Embodiment 132. The use of the kit of embodiment 112 for the treatment of hemophilia A.

Embodiment 133. The use of the kit of embodiment 112 for the manufacture of a medicament for the treatment of hemophilia A.

Embodiment 134. The use of the nucleic acid of any one of embodiments 113-123 for the treatment of hemophilia A.

Embodiment 135. The use of the nucleic acid of any one of embodiments 113-123 for the manufacture of a medicament for the treatment of hemophilia A.

Embodiment 136. A synthetic FVIII protein, wherein the synthetic FVIII protein comprises a B domain substitute, wherein the B domain substitute comprises from zero to nine N-linked glycosylation sites and is no more than about 40 amino acids in length.

EXAMPLES

Example 1: An Amino Acid Sequence Containing N-Glycosylation Motifs Improves Expression of FVIII after Targeted Integration into Mouse Albumin Intron 1 Mediated by CRISPR/Cas9 Cleavage Construct Design A challenge to inserting an FVIII encoding nucleic acid sequence into a genome is that the natural FVIII coding sequence is 7053 bp, making it, among other things, difficult to package in adeno associated virus (AAV has a packaging limit in the range of 4800 to 5000 bp for in vivo delivery as a template for integration at a double-strand break created by a sequence-specific nuclease such as Cas9). To solve the problem, applicants designed a set of FVIII coding sequences with an altered B domain. Although the B domain of FVIII is not required for function, it improves the secretion of FVIII. These FVIII coding sequences were designed to express a synthetic FVIII having a short B domain (substitute B domain). To evaluate synthetic FVIII coding sequences having an substitute B domain for their ability to make and secrete FVIII protein after integration into the genome, constructs were designed to target integration of FVIII coding sequences into intron 1 of a mouse albumin gene. The albumin locus provides a strong promoter that is active in liver cells, so that a suitable FVIII coding sequence inserted at this locus can be expressed when operably linked to an albumin promoter.

A series of plasmids referred to herein as pCB076 (SEQ ID NO: 316), pCB100 (SEQ ID NO: 320), pCB1003 (SEQ ID NO: 324), pCB085 (SEQ ID NO: 3319), or pCB080 (SEQ ID NO: 318) were constructed using known molecular biology techniques. The same pUC19-based bacterial plasmid backbone (containing a bacterial origin of replication and a kanamycin resistance gene) was used for all five plasmids. The plasmids were constructed with the following elements (in order): gRNA target site (for gRNA mAlbT1, SEQ ID NO: 338, targeting exon 1 of a mouse albumin gene)|18 bp spacer|splice acceptor site ("SA") FVIII coding sequence|polyadenylation signal ("sPA"). The plasmids differed only in the codon optimization of the human FVIII coding sequence, and the presence (pCB076) or absence (pCB100, pCB1003, pCB085, and pCB080) of a sequence encoding a B domain substitute. The B domain substitute used in this example consisted of the first six N-glycosylation motifs from the N-terminus of the human FVIII B domain.

Plasmids pCB100, pCB1003, pCB085 and pCB080 all contain the coding sequence for B domain deleted human FVIII in which the B domain is replaced with the "SQ linker" (which encodes amino acids SFSQNPPVLKRHQR, SEQ ID NO: 337) The SQ linker includes a protease cleavage site (RHQR), but lacks an N-linked glycosylation site. Plasmid pCB076 (SEQ ID NO: 316) contains the same codon-optimized B domain deleted human FVIII coding sequence ("co1", see Example 4 below) as pCB100, and an additional DNA sequence encoding 17 amino acids corresponding to the first six N-glycosylation motifs from the N-terminus of the human FVIII B domain inserted into the SQ linker (thus forming a B domain substitute), in place of the B domain. The other plasmids have the following codon optimization: pCB100—co1 (SEQ ID NO: 320), pCB1003—co2 (SEQ ID NO: 324), pCB085—co3 (SEQ ID NO: 319), and pCB080—co4 (SEQ ID NO: 318) (see Example 4 below). The plasmids were designed to be donors for targeted integration into a double-strand break that is generated in intron 1 of a mouse albumin gene using a CRISPR/Cas9 system utilizing the gRNA mALbT1 (tgccagttcccgatcgttac, SEQ ID 338). The liver is the target organ for this targeted integration, specifically hepatocytes. Hepatocytes in vivo are mostly quiescent, and it is known that the dominant cellular mechanism that repairs double-strand breaks in DNA in non-dividing cells is non-homologous end joining (NHEJ) (Z. Mao et al., *Cell Cycle* (2008) 7:2902-06). In the presence of a linear double-stranded DNA molecule (the donor), and a double-strand break in the genome, the donor DNA can be inserted at the double-strand break by the NHEJ machinery.

Alternatively, the ends of the double-strand break in the genome can be re-joined to each other by the same NHEJ machinery, an event that is generally more frequent than insertion of the donor template. Repair by NHEJ is an error-prone process, and this leads to the introduction of insertions or deletions at the site of the double-strand break. Targeted integration of a donor template delivered as a plasmid at a double-strand break in the genome of a cell can be enhanced by including cut sites for a nuclease in the donor plasmid. Because plasmids are circular molecules, they are not templates for integration at a double-strand break. Including a single guide RNA cut site in the plasmid results in linearization of the plasmid in the presence of a Cas9/gRNA complex. Therefore, a single guide RNA cut site for the mALbT1 guide was inserted at the 5' end of the FVIII cassette in the reverse complement of the sequence present in the mouse genome.

Use of the reverse complement of the guide sequence in the genome theoretically favors integration in the forward orientation when two guide sites flanking the cassette are used. However, this advantage is unlikely to be maintained when only one guide cut site is used. The inclusion of guide cut sites flanking the coding sequence generates two linear fragments composed of the coding sequence cassette and the bacterial plasmid backbone (encoding the antibiotic resistance gene and origin of replication), in which case the bacterial backbone fragment competes for integration at the double-strand break in the genome. For this reason, applicants designed the plasmid so that a single guide cut site was used. The synthetic FVIII coding sequence cassette was composed of the following elements in order, starting at the 5' end; mAlbT1 gRNA target site, an 18 bp spacer sequence, a splice acceptor sequence (ACTAAAGAATTATTCTTT- TACATTTCAG, SEQ ID NO: 307), the B domain-deleted human FVIII coding sequence in which the signal peptide was replaced by the dinucleotide TG, and a polyadenylation signal (aataaaagatctttattttcattagatctgtgtgttggttttttgtgtg, SEQ ID NO: 306).

The constructs were designed so that after integration into intron 1 of albumin, a hybrid pre-mRNA was generated containing exon 1 of albumin, part of intron 1 of albumin, and the FVIII coding sequence cassette. After integration into albumin intron 1, it is expected that at some frequency the splicing machinery of the cell splices out intron 1, thereby creating a mature mRNA in which albumin exon 1 is fused in-frame to the coding sequence for mature FVIII. The TG dinucleotide is included in the construct to maintain the translational reading frame. Translation of this mRNA was predicted to produce a protein in which the signal peptide and pro-peptide of albumin is fused to the mature coding sequence of FVIII. Upon passage through the secretory machinery of the cell, the signal peptide and pro-peptide were predicted to be cleaved off, leaving three amino acids (Glu-Ala-Leu) added to the natural N-terminus of mature FVIII. The FVIII protein produced using this method was active in mice despite the presence of these additional three amino acids.

gRNAs

The gRNAs used in these experiments were chemically synthesized, incorporating chemically modified nucleotides to improve resistance to nucleases. The gRNA in one example is composed of the following structure: 5' usgscsCAGUUCCCGAUCGUUACGU-UUUAGAgcua-GAAAuagcAAGUUAAAAUAAGGCUAGUCCGUUAU-CaacuuGAAAa-aguggcaccgagucggugcusususU-3' (SEQ ID NO: 339), where “A, G, U, C” are native RNA nucleotides, “a, g, u, c” are 2'-O-methyl nucleotides, and “s” represents a phosphorothioate backbone. The mouse albumin targeting sequence of the gRNA is underlined, and the remainder of the gRNA sequence is the common scaffold sequence.

mRNA

The mRNA can be produced by methods known in the art. One such method used herein was in vitro transcription using T7 polymerase, in which the sequence of the mRNA is encoded in a plasmid that contains a T7 polymerase promoter. Briefly, upon incubation of the plasmid in an appropriate buffer containing T7 polymerase and ribonucleotides, an RNA molecule was produced that encoded the amino acid sequence of the desired protein. Either natural ribonucleotides or chemically modified ribonucleotides can be used in the reaction mixture to generate mRNA molecules with either the natural chemical structure of native mRNA, or with modified chemical structures. In the studies described herein, natural (unmodified) ribonucleotides were used. In addition, capping components were included in the transcription reaction so that the 5' end of the mRNA was capped The spCas9 mRNA was designed to encode the spCas9 protein fused to a nuclear localization domain (NLS), which is required to transport the spCas9 protein into the nuclear compartment where cleavage of genomic DNA can occur. Additional components of the Cas9 mRNA are a KOZAK sequence at the 5' end prior to the first codon to promote ribosome binding, and a polyA tail at the 3' end composed of a series of A residues. An example spCas9 mRNA with NLS sequences is set forth in SEQ ID NO: 340. In addition, the sequence of the spCas9 coding sequence was optimized for codon usage by utilizing the most frequently used codon for each amino acid. Additionally, to promote efficient translation of the mRNA into spCas9 protein, the coding sequence was optimized to remove cryptic ribosome binding sites and upstream open reading frames.

LNPs

A primary component of the LNP used in these studies is the lipid C12-200 (Love et al., 2010 supra). C12-200 forms a complex with the negatively-charged RNA molecules. In general, C12-200 was combined with 1,2-dioleoyl-sn-glycero-3-phosphoethanolamine (DOPE), DMPE-mPEG2000, and cholesterol. When mixed under controlled conditions, for example, in a NanoAssemblr® device (Precision NanoSystems, Vancouver, BC) with nucleic acids such as gRNA and mRNA, self-assembly of LNPs occurred in which the nucleic acids were encapsulated inside the LNP. To assemble the gRNA and the Cas9 mRNA in the LNP, ethanol and lipid stocks were pipetted into glass vials as appropriate. An exemplary ratio was composed of C12-200, DOPE, cholesterol and mPEG2000-DMG at a molar ratio of 50:10:38.5:1.5. The gRNA and mRNA were diluted in 100 mM Na citrate (pH 3.0) and 300 mM NaCl in RNase-free tubes. The NanoAssemblr® cartridge (Precision NanoSystems) was washed with ethanol on the lipid side and with water on the RNA side. The working stock of lipids was pulled into a syringe, air removed from the syringe, and the syringe inserted in the cartridge. The same procedure was used for loading a syringe with the mixture of gRNA and Cas9 mRNA. The NanoAssemblr® run was then performed under the manufacturer's recommended conditions. The LNP suspension was dialyzed using a 10K molecular weight cut-off (MWCO) dialysis cartridge in 4 liters of PBS for four hours, then concentrated by centrifugation through a 100K MWCO spin cartridge (Amicon), including washing three times in PBS during centrifugation. Finally, the LNP suspension was sterile filtered through a 0.2 μm syringe filter. Endotoxin levels were determined using a commercial endotoxin kit (a Limulus amebocyte lysate (LAL) assay), and the particle size distribution was determined by dynamic light scattering.

The concentration of encapsulated RNA was determined using a RiboGreen® assay (Thermo Fisher). Alternatively, the gRNA and the Cas9 mRNA were formulated separately into LNPs, and then mixed together prior to treatment of cells in culture or injection into animals. Using separately formulated gRNA and Cas9 mRNA allowed specific ratios of gRNA and Cas9 mRNA to be tested.

Alternative LNP formulations that utilize alternate cationic lipid molecules are also used for in vivo delivery of the gRNA and Cas9 mRNA.

In Vivo Testing of Constructs

A murine model was used to test the ability of the designed constructs to produce FVIII. Mouse models of hemophilia A are known in the art (for example, L. Bi et al., *Nat Genet*. (1995) 10:119-21, doi: 10.1038/ng0595-119). The plasmids pCB076, pCB100, pCB1003, pCB085, and pCB080 were purified using Qiagen EndoFree® plasmid maxi prep kits (cat #12362), and then diluted in 0.9% saline to a final concentration of 15 μg/mL. Hemophilia A mice (strain B6; 129S-F8$^{tm1Kaz}$/J), a strain of mice that lacks mouse FVIII protein, were obtained from The Jackson Laboratory (Bar Harbor, ME). Cohorts of Hemophilia A mice were injected via the tail vein with 2 mL of the diluted plasmid DNA per mouse over a period of five to six seconds, by hydrodynamic injection (“HDI”). The HDI process has been reported to result in the delivery of plasmid DNA into the nucleus of liver cells, including hepatocytes (see, e.g., F. Niola et al., *Meth Mol Biol* (2019) 1961:329-41). One day after injection, the mice were given retro-orbital (“RO”) injections of an LNP formulation encapsulating spCas9 mRNA and the guide RNA mAlbT1. The dose of LNP administered to mice was 1 mg/kg of body weight of spCas9 mRNA plus 1 mg/kg per kg of body weight of gRNA.

A group of mice dosed with the LNP alone was sacrificed after three days, and DNA was extracted from the whole livers and assayed using TIDE analysis (E. K. Brinkman et al., *Nuc Acid Res* (2014) 42:e168) for indels at the expected cut site for the mAlbT1 gRNA. In TIDE analysis, the genomic region of the expected CRISPR/Cas9 cut site is amplified from the genomic DNA of the treated cells by PCR, and then subjected to Sanger sequencing. The sequencing chromatograms were analyzed using the TIDE software program, which determines the frequency of insertions and deletions in the region around the predicted cut site.

In these experiments, the frequency of indels at the on-target site was determined to be 25.4%. Six days after the mice injected with plasmid were dosed with LNP, blood samples were taken by RO bleed into sodium citrate (1:9 ratio of sodium citrate to blood), and the plasma was collected by centrifugation. The FVIII activity in the plasma was measured using a FVIII activity assay (Diapharma, Chromogenix Coatest® SP Factor FVIII, cat #K824086). Kogenate® (Bayer), a recombinant human FVIII, was used for the standards, and the units per mL of FVIII activity in the blood was converted to percent of normal activity (1 U/mL=100%). The results are summarized in FIG. 1. Mice that were injected with plasmid pCB076, which contains the six N-glycan B domain substitute sequence in place of the B domain, had mean synthetic FVIII levels of equivalent to 20% of normal human FVIII levels. In contrast, mice that were injected with the pCB100 plasmid, which is identical to pCB076 except for the absence of the six N-glycan B domain substitute sequence, did not have detectable FVIII levels in their blood. The mice injected with plasmids pCB1003, pCB085, or pCB080, that contain differently codon-optimized B domain deleted FVIII coding sequences lacking the six N-glycan B domain substitute sequence, had low or unmeasurable FVIII activity in their blood when compared to non-gene edited (naïve) Hemophilia A mice. Some of the mice injected with pCB1003 and pCB080 had detectable FVIII in their blood, in the range of 1 to 3% of normal, indicating that codon optimizations co2 (pCB1003) and co4 (pCB080) may be more active than codon optimizations co1 (pCB100) and co3 (pCB085).

The level of FVIII produced in the blood of the mice in this study was dependent on both the frequency of targeted integration into albumin intron 1 in the forward orientation (orientation capable of producing FVIII protein), and the intrinsic expression efficiency of the FVIII coding sequence. The intrinsic expression efficiency of the FVIII coding sequence is a function of the transcriptional efficiency, the translation efficiency (which varies with the type of codon optimization employed), and the efficiency of the secretion process. In the case of the FVIII protein, it has been reported that secretion of the protein can be a rate limiting step, and is associated with the unfolded protein response that can be induced when FVIII is expressed at high levels in cells. (M. Swaroop et al., *J Biol Chem* (1997) 272:24121-24; R. J. Kaufman, *Blood* (2009) 114:SCI-19).

To distinguish between targeted integration frequency, which may vary between mice due to variability in the efficiency of delivery of the donor by HDI or other factors, and the intrinsic expression efficiency of the synthetic FVIII coding sequence, targeted integration frequency was quantified using droplet digital PCR (DD-PCR). DD-PCR is a method for quantitation of the absolute copy number of a nucleic acid sequence in a sample. To quantify only the forward orientation of the synthetic FVIII coding sequence cassette inserted into albumin intron 1, a pair of PCR primers was designed with the forward primer located in albumin intron 1 at a site 5' of the gRNA mALbT1 cut site and the reverse primer located at the 5' end of the FVIII coding sequence. A fluorogenic probe was designed that is complementary to the sequence between the two primers. A reference primer/probe set was designed against the native mouse albumin gene sequence at a site distant from the mALbT1 gRNA site. The reference primer probe was used to normalize for the amount of input mouse genomic DNA in each assay.

To carry out this analysis, mice from the experiments described above were sacrificed eight days after the mice were dosed with LNP. Whole livers were homogenized and total genomic DNA was purified using the Qiagen DNeasy® Tissue kit. Equal mass amounts of genomic DNA were then assayed for targeted integration frequency using the DD-PCR assay described above. The results for each mouse are summarized in Table 2. The targeted integration frequency in the forward orientation ranged from 0.09% to 0.95% (0.09 to 0.95 copies per 100 haploid genomes). Peak FVIII levels in the blood were positively correlated to the integration frequency, indicating that the level of FVIII was dependent on the number of copies of the FVIII cassette that were integrated into albumin intron 1. The mean targeted integration frequency in the mice injected with pCB076 was 0.47±0.26, compared to 0.28±0.15 in the mice injected with pCB100, indicating a trend to higher integration frequency in mice injected with pCB076 that contains the B domain substitute in place of the SQ linker, although this difference was not statistically significant.

TABLE 2

Targeted integration frequency in the livers of mice compared to the peak FVIII level in the blood

| Plasmid injected | Sample | % TI (copies per 100 haploid genomes) | Peak FVIII activity (% of normal) | FVIII/TI Ratio | Average FVIII/TI Ratio (SDev) |
|---|---|---|---|---|---|
| pCB076 | HD12A 1-2 | 0.57 | 27.66 | 48.40 | 42.0 (18.8) |
| | HD12A 1-4 | 0.27 | 12.98 | 48.02 | |
| | HD12A 1-5 | 0.44 | 24.07 | 54.10 | |
| | HD12A 2-2 | 0.24 | 11.32 | 47.34 | |
| | HD12A 2-3 | 0.15 | 0 | 0 | |
| | HD12A 2-5 | 0.95 | 49.7 | 52.20 | |
| | HD12A 3-3 | 0.64 | 28.08 | 43.86 | |
| pCB100 | HD12A 4-1 | 0.09 | 0 | 0 | 5.3 (1.5) |
| | HD12A 4-2 | 0.17 | 0 | 0 | |
| | HD12A 4-3 | 0.42 | 0.81 | 1.92 | |
| | HD12A 4-5 | 0.56 | 1.78 | 3.17 | |
| | HD12A 5-5 | 0.30 | 1.2 | 3.94 | |
| | HD12A 6-1 | 0.22 | 1.86 | 8.32 | |
| | HD12A 6-3 | 0.22 | 4.38 | 19.75 | |
| None (naïve mice) | HD1A N-1 | 0.00 | 0 | 0 | |

Normalizing the FVIII level in the blood of each mouse to the integration frequency provides a measure of the intrinsic expression efficiency of the FVIII coding sequence. The average of the ratio of FVIII level divided by targeted integration frequency was 42 for pCB076 and 5.3 for pCB100, and this difference was statistically significant (p=0.0004), as determined using a two-tailed Student's T-test. These results demonstrate that the intrinsic expression efficiency of the synthetic FVIII coding sequence in pCB076 is about eight fold greater than that of the coding sequence in pCB100. This demonstrates that including the sequence encoding the B domain substitute in place of the SQ linker improved the intrinsic expression efficiency of this codon-optimized FVIII coding sequence by about eight fold. The magnitude of this improvement is significantly greater than the two fold improvement reported for the same six glycan motif sequence when the FVIII coding sequence was delivered in a non-integrating AAV virus in which the FVIII coding sequence is driven by a strong liver specific promoter (J. McIntosh et al., *Blood* (2013) 121:3335-44).

Example 2: Replacing the SQ Linker with a B Domain Substitute Increases FVIII Expression from a FVIII Donor Cassette Delivered by an AAV and Integrated into Intron 1 of Albumin To determine whether the same beneficial effect of the B domain substitute peptide occurred when the synthetic FVIII coding sequence was delivered to the liver of mice using an AAV, the plasmids pCB099 (SEQ ID NO: 311) and pCB102 (SEQ ID NO: 341) were constructed and packaged in AAV8 (Vector Biolabs, Malvern, PA, or SabTech, Philadelphia, PA). The plasmids were constructed with the following elements (in order): ITR|gRNA target site (for mAlbT1)|18 bp spacer|splice acceptor site ("SA")|FVIII coding sequence|polyadenylation signal ("sPA")|gRNA target site|ITR. The FVIII coding sequence for pCB099 and pCB102 was identical to the FVIII coding sequence for pCB076 (having a B domain substitute) and pCB100 (having only the SQ linker), respectively. These FVIII cassettes lack a promoter, and so are unable to express FVIII as non-integrated AAV episomal genomes. Integration adjacent to an appropriate promoter is required for expression of FVIII delivered by these AAV viruses.

Figure 2:
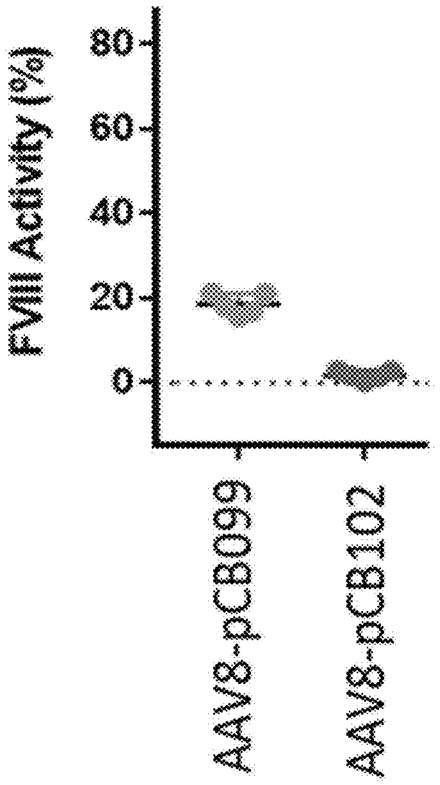
FIG. 2 depicts FVIII levels in the blood of mice injected with AAV8 virus encapsulating FVIII donor templates pCB099 and pCB102, followed four weeks later by administering LNP encapsulating spCas9 mRNA and gRNA mALbT1. FVIII levels were measured 10 days after the LNP was injected.

In these experiments, Hemophilia A mice were injected i.v. with $2\times10^{12}$ vector genomes ("vg") per kilogram of body weight, of AAV8-pCB099 or AAV8-pCB102. Four weeks later, the mice were injected i.v. with a 1:1 mixture of two LNP, one LNP encapsulating the mAlbT1 gRNA and the other LNP encapsulating spCas9 mRNA. The LNP were prepared as described in Example 1, and the total dose was 2 mg of RNA per kg of body weight. FVIII activity was measured in the blood of the mice 10 days after LNP dosing using the method set forth in Example 1. FVIII levels in the blood of the mice at 10 days after dosing the LNP (FIG. 2) were on average 20% of normal human FVIII levels for the mice that received AAV9-pCB099, but were at background levels in the mice that received AAV8-pCB102 (lacking the B domain substitute).

At day 24 after dosing the LNP, the mice were sacrificed, the whole livers were homogenized, and total genomic DNA was extracted from a portion of the liver lysate. The frequency of targeted integration into albumin intron 1 in the forward orientation was quantitated using the DD-PCR assay described in Example 1. The results for each mouse are summarized in Table 3.

The results show the mean targeted integration frequency (% per haploid genome) in the mice injected with AAV8-pCB099 was 1.86 (±0.25), while for mice injected with AAV8-pCB102 the mean targeted integration frequency was 0.46 (±0.2). This difference was statistically significant using a two-tailed Student's T-test ($p<0.01$). These results demonstrate that including the B domain substitute resulted in a 4-fold higher frequency of targeted integration, a result that would not have been predicted given that previously inclusion of glycans in place of the B domain of FVIII has only been shown to improve the expression level of FVIII. The mean FVIII level in the blood of mice injected with AAV8-pCB099 was 18.6 (±2.2) % of normal, while for mice injected with AAV8-pCB102 the mean FVIII level was 1.7 (±1.1) % of normal. This 11-fold difference was statistically significant ($p<0.01$) using a two-tailed Student's T-test. FVIII levels were normalized to the targeted integration frequency by dividing the FVIII level by the targeted integration frequency in individual mice (Table 3). The mean of the ratios of FVIII activity divided by targeted integration frequency was 10.2 (±1.7) for the AAV8-pCB099 injected mice and 3.1 (±1.7) for the AAV8-pCB102 injected mice. This difference was statistically significant ($p<0.01$) using a two-tailed Student's T-test.

These data demonstrate that the intrinsic expression efficiency of the FVIII coding sequence in AAV8-pCB099 is threefold higher than that of AAV8-pCB102. Because AAV8-pCB099 differs from AAV8-pCB102 only by the presence of the N-glycan motif containing sequence, these data demonstrate that the N-glycan motif in AAV8-pCB099 confers a three fold improvement in intrinsic expression efficiency. Therefore, the overall 11-fold improvement in FVIII levels in the blood of the mice is due to a combination of four fold higher targeted integration and three fold improved expression efficiency of the integrated FVIII coding sequence.

TABLE 3

Targeted integration frequency in the livers of mice compared to the peak FVIII level in the blood for mice injected with AAV8 viruses followed by LNP encapsulating Cas9 mRNA and mALbT1 gRNA

| AAV | Mouse ID# | Targeted Integration (% per haploid genome) | Average FVIII % of (normal) | Ratio FVIII divided by targeted integration |
|---|---|---|---|---|
| pAAV8-pCB099 | POC14 4-1 | 2.01 | 21.02 | 10.45 |
| | POC14 4-2 | 1.46 | 16.83 | 11.55 |
| | POC14 4-3 | 1.77 | 21.21 | 11.98 |
| | POC14 4-4 | 1.84 | 18.25 | 9.91 |
| | POC14 4-5 | 2.22 | 15.68 | 7.05 |
| pAAV8-pCB102 | POC14 5-1 | 0.72 | 2.80 | 3.88 |
| | POC14 5-2 | 0.57 | 2.88 | 5.05 |
| | POC14 5-3 | 0.11 | 0 | 0.00 |
| | POC14 5-4 | 0.48 | 1.26 | 2.65 |
| | POC14 5-5 | 0.43 | 1.61 | 3.79 |

Example 3: Optimization of the Number of N-Glycans in the B Domain Substitute The data from Examples 1 and 2 demonstrate that inserting a B domain substitute containing six N-linked glycan motifs improved expression of FVIII as well as the frequency of targeted integration. However, the dependence of this improvement on the number of N-glycan sequences in the B domain substitute was unknown. We therefore designed experiments to probe this aspect of FVIII expression. In particular, it was desirable to determine the minimum number of N-linked glycan motifs required for improvement in FVIII expression.

Plasmid Constructs

To explore the effect of different numbers of N-glycan motifs on expression, a series of donor plasmids were constructed containing between one and nine N-glycan motifs. These are summarized in Table 4. All plasmids were composed of the following sequence elements, in order from 5' to 3': target sequence for mAlbT1 gRNA|18 bp spacer-|splice acceptor|B domain deleted FVIII coding sequence in which the signal peptide is replaced by the TG dinucleotide-|polyadenylation signal sequence. In each of these plasmids, the FVIII coding sequence was based on the codon optimized sequence used in pCB076 (see Example 1) in which the signal peptide is replaced by the TG dinucleotide, but having from one to nine N-linked glycosylation sites in the B domain substitute. All plasmids contained the same pUC19-based bacterial plasmid backbone (containing the bacterial origin of replication and kanamycin resistance gene).

TABLE 4

FVIII donor plasmids containing different numbers of N-glycosylation site triplets in B domain substitute

| Plasmid ID | Number of N-glycan motifs | SEQ ID NO. | Protein SEQ ID: |
|---|---|---|---|
| pCB1030 | 1 | 370 | 371 |
| pCB1029 | 2 | 372 | 373 |
| pCB1018 | 3 | 331 | 362 |
| pCB1017 | 4 | 330 | 363 |
| pCB1007 | 5 | 326 | 364 |
| pCB077 | 6 | 317 | 365 |
| pCB1006 | 6 (with S to T change in C-terminal triplet) | 325 | 366 |
| pCB1008 | 7 | 327 | 367 |
| pCB1015 | 8 | 328 | 368 |
| pCB1016 | 9 | 329 | 369 |

In Vivo Testing of Constructs: 5, 6, and 7 Glycans

Figure 3:
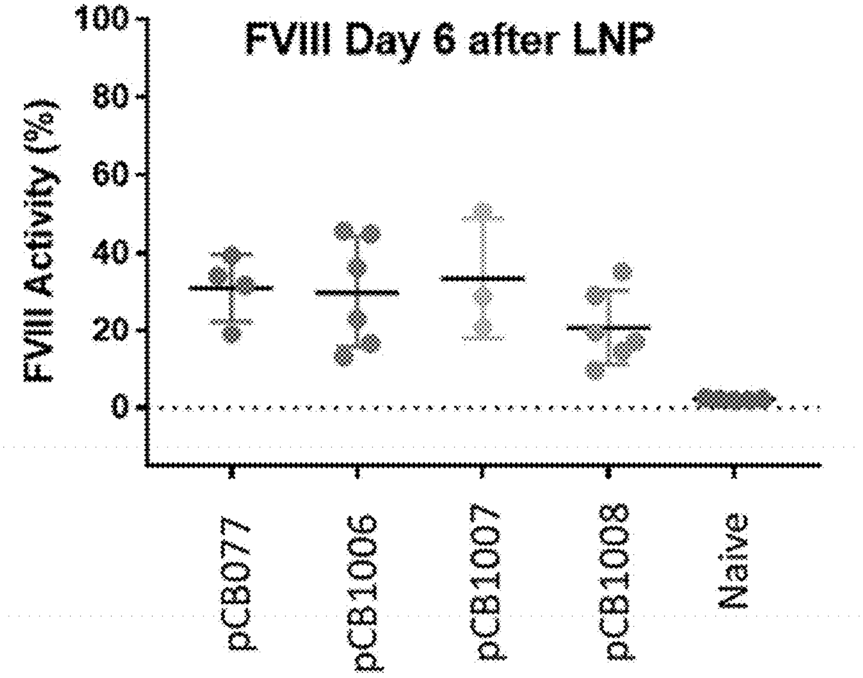
FIG. 3 depicts FVIII activity in the blood of Hemophilia A mice dosed with four different FVIII donor plasmids by HDI, followed by LNP encapsulating spCas9 and mALbT1 gRNA.

Hemophilia A mice were dosed with 30 μg per mouse of plasmids pCB077, pCB1006, pCB1007, or pCB1008 by hydrodynamic injection, using the method of Example 1. One day later, the same mice were injected retro-orbitally with a 1:1 mixture of LNP encapsulating spCas9 mRNA and mALbT1 gRNA, at a total RNA dose of 2 mg/kg body weight. The LNP were prepared as described in Example 1. FVIII activity was measured in the blood of the mice six days later using the method set forth in Example 1. The results are summarized in FIG. 3, and demonstrated that the level of FVIII produced by the four plasmid donors was similar.

The level of FVIII produced in the blood of the mice in this study depends on both the frequency of targeted integration into albumin intron 1 in the forward orientation (the orientation capable of producing FVIII protein) and the intrinsic expression efficiency of the FVIII coding sequence. The intrinsic expression efficiency of the FVIII coding sequence is a function of the transcription rate, the translation efficiency (which is impacted by the type of codon optimization that is used), and the efficiency of the secretion process. In the case of the FVIII protein it has been suggested that secretion of the protein can be a rate limiting step (M. Swaroop et al., supra) and is associated with the unfolded protein response (R. J. Kaufman, supra) that occurs when FVIII is expressed at high levels in cells. To distinguish between targeted integration frequency, which is expected to vary between individual mice, and the intrinsic expression efficiency of the integrated synthetic FVIII coding sequence, the targeted integration frequency was quantified using droplet digital PCR (DD-PCR) as described in Example 1.

Eight days after the mice were dosed with LNP, the mice were sacrificed, the whole liver was homogenized, and total genomic DNA was purified using the Qiagen DNeasy® Tissue kit. Equal mass amounts of genomic DNA were then assayed for targeted integration frequency using DD-PCR. The results for each mouse are summarized in Table 5. The targeted integration frequency in the forward orientation ranged from 0.17% to 0.70% in individual mice, but the average within each group of mice for the four plasmids was similar at 0.49%, 0.47%, 0.52%, and 0.38% for pCB077, pCB1006, pCB1007, and pCB1008 respectively. The mean of the ratio of FVIII activity to TI for the mice injected with pCB077, pCB1006, pCB1007, and pCB1008 was 51.33, 48.54, 48.9, and 38.9, respectively, and the differences between the plasmids were not statistically significant. These results demonstrate that synthetic FVIII coding sequences containing five N-glycan sites (pCB1007) or seven glycan sites (pCB1008), or in which one of the glycan tripeptide motifs was altered from NDS to NDT (pCB1006), have similar intrinsic expression efficiency compared to a synthetic FVIII coding sequence encoding six N-glycan sites (pCB077).

Identical mouse studies are performed with plasmids pCB1015 (SEQ ID NO: 328) and pCB1016 (SEQ ID NO: 329), in which the number of N-glycan motifs is changed to eight and nine, respectively. In addition, plasmids identical to pCB077 except having only one or two N-glycan motifs were constructed and tested for their ability to express FVIII after targeted integration into mouse albumin intron 1 using the same gRNA and spCas9 mRNA delivered in an LNP.

TABLE 5

Targeted integration frequency in the livers of mice compared to the peak FVIII level in the blood

| Plasmid injected | Sample | Targeted integration (% per haploid genome) | Peak FVIII activity (% of normal) | FVIII/TI Ratio | Average FVIII/TI Ratio (SDev) |
|---|---|---|---|---|---|
| pCB077 | HD14 1-1 | 0.24 | 13.13 | 55.19 | 51.33 (3.16) |
| | HD14 1-2 | 0.51 | 26.24 | 51.34 | |
| | HD14 1-3 | 0.7 | 36.72 | 52.37 | |
| | HD14 1-4 | 0.51 | 23.57 | 46.43 | |
| pCB1006 | HD14 2-2 | 0.67 | 34.17 | 50.84 | 48.54 (18.37) |
| | HD14 2-4 | 0.48 | 38.04 | 78.87 | |
| | HD14 5-4 | 0.35 | 10.89 | 30.87 | |
| | HD14 8-1 | 0.46 | 20.09 | 43.85 | |
| | HD14 8-2 | 0.47 | 29.16 | 62.3 | |
| | HD14 8-3 | 0.4 | 9.8 | 24.52 | |
| pCB1007 | HD14 9-1 | 0.61 | 35.69 | 58.77 | 48.9 (15.44) |
| | HD14 9-2 | 0.32 | 19.46 | 60.83 | |
| | HD14 9-3 | 0.64 | 17.43 | 27.1 | |
| pCB1008 | HD14 4-1 | 0.28 | 10.92 | 39.13 | 38.92 (11.21) |
| | HD14 4-2 | 0.17 | 8.47 | 48.87 | |
| | HD14 10-1 | 0.22 | 5.7 | 26.48 | |
| | HD14 10-2 | 0.6 | 18.86 | 31.63 | |
| | HD14 10-3 | 0.52 | 30.35 | 57.86 | |
| | HD14 10-5 | 0.51 | 15.18 | 29.52 | |
| none | HD14 N-1 | 0 | 1.97 | 0 | 0 |

In Vivo Testing of Constructs: 3, 4, and 5 Glycans

Plasmids pCB1007, pCB1017, and pCB1018 were purified and administered to Hemophilia A mice as described above. One day later, the mice were given retro-orbital (RO) injections of a C12-200 based LNP encapsulating spCas9 mRNA (1 mg/kg) and the guide RNA (gRNA) mAlbT1 (1 mg/kg). Blood samples were taken five days and seven days post LNP dosing by RO bleed into sodium citrate (1:9 ratio of sodium citrate to blood), and the plasma collected by centrifugation. The FVIII activity in the plasma was measured using the method set forth in Example 1.

The FVIII activity in the blood on day five averaged 8.1%, 5.0%, and 23.5% in mice injected with pCB1007, pCB1018, and pCB1018, respectively. On day 7, the FVIII activity averaged 7.9%, 3.0%, and 13.5% in mice injected with pCB1007, pCB1018 and pCB1018, respectively. Thus, the FVIII expression in mice that were injected with plasmids having four N-glycan motifs (pCB1017) or three N-glycan motifs (pCB1018) was similar to that of mice that received a plasmid containing five N-glycan motifs in the B domain substitute (pCB1007).

After the blood sample was taken on day seven post LNP administration, the mice were sacrificed and the whole livers were removed and stored in RNAlater™ buffer (Qiagen). The whole liver was homogenized using a bead-based homogenizer, and DNA was purified from an aliquot of the homogenate using a Qiagen DNA/RNA Mini Kit (cat #80204). The liver genomic DNA was analyzed by DD-PCR for the frequency of integration of the FVIII donor cassette in the forward orientation as described in Example 1. The average targeted integration frequency was 0.27%, 0.27%, and 0.55% for the mice injected with pCB1007, pCB1017, and pCB1018 respectively, and these values were not statistically different (two-tailed Student's T-test).

Normalizing the FVIII level in the blood of each mouse to the integration frequency provides a measure of the intrinsic expression efficiency of the FVIII coding sequence. The average of the ratio of FVIII level divided by targeted integration frequency was 23.6 for pCB1007 (five N-glycans) injected mice, 11.6 for pCB1017 (four N-glycans) injected mice, and 23.3 for pCB1018 (three N-glycans) injected mice. The FVIII divided by targeted integration ratios for pCB1017 and pCB1018 injected mice were not statistically different from that of the pCB1007 injected mice.

These data demonstrate that using a synthetic FVIII coding sequence containing a B domain substitute having either four N-glycan motifs or three N-glycan motifs results in similar expression to a FVIII coding sequence containing five N-glycan motifs when integrated into albumin intron 1. Therefore, synthetic FVIII constructs having B domain substitutes with three N-glycan motifs provide improved FVIII expression equivalent to that provided by B domain substitutes with five N-glycan motifs. By inference, because five N-glycan motif containing B domain substitutes were equivalent to six N-glycan motifs containing B domain substitutes, we infer that three N-glycan motifs are equivalently potent as six N-glycan motifs.

In Vivo Testing of Constructs: One and Two Glycans

Plasmids pCB1018 (comprising the FVIII donor with B domain substitute with three N-glycan motifs), pCB1029 (comprising the FVIII donor with B domain substitute with two N-glycan motifs), and pCB1030 (comprising the FVIII donor with B domain substitute with one N-glycan motif) were purified and administered to Hemophilia A mice by hydrodynamic injection as described above. One day later, the mice were given retro-orbital (RO) injections of a C12-200 based LNP encapsulating spCas9 mRNA (1 mg/kg) and the gRNA mAlbT1 (1 mg/kg). Blood samples were taken five days and eight days post LNP dosing by RO bleed into sodium citrate (1:9 sodium citrate to blood), and the plasma collected by centrifugation. The FVIII activity in the plasma was measured as described above, and expressed as percent of normal activity (1 U/mL=100%).

The FVIII activity in the blood on day five averaged 12.8%, 15.8%, and 13.4% in mice injected with pCB1018, pCB1029, and pCB1030, respectively. On day eight, the FVIII activity averaged 13.8%, 14.5%, and 16.0% in mice injected with pCB1018, pCB1029, and pCB1030, respectively. Thus, the FVIII expression in mice that were injected with plasmids containing B domain substitutes with three N-glycan motifs (pCB1018), two N-glycan motifs (pCB1029), or one N-glycan motif (pCB1030) were similar to each other.

After the blood sample was taken on day seven post LNP administration, the mice were sacrificed, and the whole liver was removed and stored in RNAlater™ buffer (Qiagen). The whole liver was homogenized, and the liver genomic DNA was analyzed by DD-PCR for the frequency of integration of the FVIII donor cassette in the forward orientation as described in Example 1. The average targeted integration frequency was 0.29%, 0.47%, and 0.36% for the mice injected with pCB1018, pCB1029, and pCB1030, respectively: these values were not statistically different (two-tailed Student's T-test).

Normalizing the FVIII level in the blood of each mouse to the integration frequency provides a measure of the intrinsic expression efficiency of the FVIII coding sequence. The average of the ratio of FVIII level divided by targeted integration frequency was 41.9 for pCB1018 (three N-glycans) injected mice, 31.4 for pCB1029 (two N-glycans) injected mice, and 40.2 for pCB1030 (one N-glycan) injected mice. The intrinsic expression efficiency for pCB1029 (three N-glycans) and pCB1030 (two N-glycans) injected mice were not statistically different from that of the pCB1018 (three N-glycans) injected mice. These data demonstrate that FVIII donor cassettes comprising B domain substitutes containing either two N-glycan motifs (amino acid sequence NATNVS) or one N-glycan motif (amino acid sequence NAT) are expressed with equal efficiency as a FVIII donor cassette containing B domain substitutes having three N-glycan motifs.

TABLE 6

FVIII activity, targeted integration frequencies, and FVIII activity normalized to integration frequency in mice injected with FVIII donors pCB1018, pCB1029 and

| Plasmid injected | Sample (Mouse ID) | Targeted integration (% per haploid genome) | Peak FVIII activity (d 5) (% of normal) | FVIII/TI Ratio | Average FVIII/TI Ratio (SDev) |
|---|---|---|---|---|---|
| pCB1018 (three N-glycans) | HD17 2-4 | 0.20 | | 12.0 | 40.1 (17.8) |
| | HD17 3-1 | 0.41 | 25.1 | 61.2 | |
| | HD17 3-2 | 0.22 | 11.2 | 50.9 | |
| | HD17 3-4 | 0.40 | 19.6 | 49.0 | |
| | HD17 3-5 | 0.20 | 5.5 | 27.5 | |
| pCB1029 (two N-glycans) | HD17 4-2 | 0.51 | 29.2 | 57.3 | 33.5 (12.9) |
| | HD17 4-3 | 0.38 | 13.5 | 35.5 | |
| | HD17 4-4 | 0.72 | 16.2 | 22.5 | |
| | HD17 5-4 | 0.28 | 6.2 | 22.1 | |
| | HD17 5-5 | 0.46 | 13.8 | 30.0 | |
| pCB1030 (one N-glycan) | HD17 7-1 | 0.59 | 19.6 | 33.2 | 35.6 (12.5) |
| | HD17 7-3 | 0.37 | 16.2 | 43.8 | |
| | HD17 7-4 | 0.16 | 5.9 | 36.9 | |
| | HD17 8-4 | 0.43 | 21.7 | 50.5 | |
| | HD17 8-5 | 0.25 | 3.4 | 13.6 | |

Figure 8:
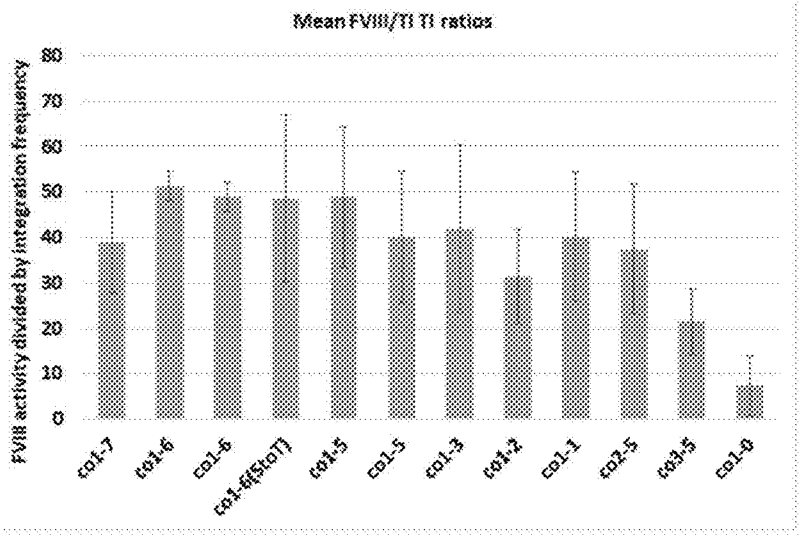
FIG. 8 depicts intrinsic expression efficiency (FVIII activity divided by targeted integration frequency) for FVIII donor cassettes having zero to seven N-linked glycan motifs and different codon optimizations.

Comparison of In Vivo FVIII Expression Results for FVIII Donor Cassettes Containing B Domain Substitutes Containing 0, 1, 2, 3, 4, 5, 6, or 7 N-Linked Glycan Motifs The intrinsic expression efficiencies of the different FVIII cassettes tested above were compared. The data sets described throughout Example 3 were generated in a total of five studies, using the same strain of mice (Hemophilia A mice) and the same experimental protocol. FVIII activity was measured on either day five or six, and again on day eight or nine. The targeted integration frequency was measured in DNA extracted from the whole liver of the mice which had been sacrificed on the day of the last FVIII activity measurement (day eight or nine). A compilation of the intrinsic expression efficiencies is shown in FIG. 8. Included in this comparison are FVIII cassettes with different codon optimizations. A comparison of the impact of different numbers of glycans upon normalized FVIII expression can be performed for donors with the codon optimization called "co1" which are the first nine bars in FIG. 8. These donors contain FVIII cassettes that differ only in the numbers of N-glycan motifs in the B domain substitute. The intrinsic expression efficiencies were not significantly different for glycan variants containing between one and seven N-glycan motifs. While the donor with two N-glycan motifs ("co1-2") showed a trend to lower normalized FVIII activity (a value of 30, compared to value of about 45 for the variants with five, six, or seven N-glycans), this difference was not statistically significant. The donor with no N-glycan motifs in place of the B domain ("co1-0") exhibited significantly lower normalized FVIII activity (a value of 7.4, compared to 40 to 50 for the variants with glycans and the same codon optimization). The FVIII donor with five glycans and codon optimization co2 was equivalent to co1 with five N-glycan motifs, while co3 with five N-glcyans was expressed at about 50% of the efficiency of co1 with five N-glycans. These data demonstrate that a FVIII coding sequence containing a B domain substitute comprising a single N-glycan motif was sufficient to confer FVIII expression levels equivalent to that achieved with B domain substitutes comprising between two and seven N-glycan motifs. The FVIII coding sequence containing the B domain substitute comprising a single N-glycan motif ("co1-1"/pCB1030 in FIG. 8) was expressed about 5.4-fold more efficiently (40.1/7.4) than the same FVIII coding sequence that lacked a B domain substitute ("co1-0"/pCB100). Therefore, a FVIIII coding sequence containing a B domain substitute with less than 6 N-glycans, for example 5 N-glycans, 4 N-glycans, 3-N-glycans, 2 N-glycans, or 1 N-glycan has advantages for use in gene editing approaches due to the reduction in the number of non-native amino acids added to the FVIII protein, as well as the reduction in size of the DNA donor.

Example 4: Identification of Optimal Codon Optimization of the FVIII Coding Sequence for Expression after Targeted Integration into a Safe Harbor Locus (e.g., Albumin Locus) in Mice Plasmid Constructs Experiments were performed to determine the effects of different forms of codon optimization on the expression of synthetic FVIII. The mature (lacking the signal peptide) B domain deleted human FVIII coding sequence containing the 14 amino acid SQ linker in place of the B domain (a total coding sequence of 1438 amino acids) was codon optimized by applying the commercially available algorithm available at GeneArt (co3), which increased the number of CG dinucleotides from the 54 that exist in the native sequence to 198. A variant of the co3 form of B domain deleted FVIII ("co4") was created by manually eliminating all 198 CG dinucleotides, by selecting an alternate codon that was either the next most frequent codon or a more frequently used codon according to a published *H. sapiens* codon usage table (H. C. Brown et al., *Mol Ther Meth & Clin Dev* (2018) 9:57-69 (doi: 10.1016/j.omtm.2018.01.004). B domain deleted FVIII ("FVIII-BDD") coding sequences were codon optimized using an algorithm based on the codon bias of genes highly expressed in the liver (H. C. Brown et al., supra) to generate FVIII-BDD co2, containing 176 CG dinucleotides. This construct that was further modified to remove all the CG dinucleotides, referred to here as FVIII-BDD co5, was also synthesized. The codon optimized FVIII-BDD coding sequence of J. McIntosh et al., *Blood* (2013) 121(17):3335-44 and U.S. Pat. No. 9,393,323 (SEQ ID NO: 1 therein) was also constructed, referred to herein as "co1." A further codon optimized variant of the B domain deleted FVIII coding sequence published in WO2011/005968 (SEQ ID NO: 5 therein) that contains 245 CG dinucleotides was synthesized ("FVIII-BDD cob" herein). Plasmids were constructed as follows: pUC19 plasmid backbone|ITR|target site for gRNA mALbT1|18 bp spacer|splice acceptor (SA)|TG dinucleotide|B domain deleted FVIII sequence|polyA (sPA)|target site for gRNA mALbT1|ITR, where the donor sequence codon optimizations were co2 (pCB1002, SEQ ID NO: 323), co3 (pCB1001, SEQ ID NO: 322), co4 (pCB1000, SEQ ID NO: 321), or co5 (pCB103, SEQ ID NO: 336).

The FVIII donor cassettes in each plasmid were flanked by the AAV2 ITR and used to package the cassettes into AAV8 using a HEK293-based packaging system, and purified using cesium chloride density centrifugation. The resulting AAV8 viruses (designated as AAV8-pCB103, AAV8-pCB1002, AAV8-pCB1001, and AAV8-pCB1000) were titered using Q-PCR or DD-PCR with primer/probe sets located within the coding sequence for the FVIII gene. These FVIII donor cassettes are designed to express FVIII only after targeted integration into albumin intron 1. The donor cassettes lack a promoter and thus are incapable of being transcribed into mRNA from non-integrated episomal viral genomes. In addition, all the FVIII donor cassettes lack a signal peptide sequence at the N-terminus of the FVIII coding sequence, and therefore any protein that might be expressed from non-integrated episomal viral copies cannot be secreted into the circulation. After integration into albumin intron 1, transcription from an albumin promoter in the genome produces a hybrid pre-mRNA comprising the mouse albumin exon 1, part of intron 1, and the synthetic FVIII coding sequence, terminating at the polyadenylation signal included at the 5' end of the FVIII donor cassette. Splicing of this pre-mRNA between the splice donor of albumin exon 1 and the splice acceptor included at the 5' end of the FVIII donor cassette generates an mRNA in which exon 1 of albumin encodes a signal peptide and pre-pro-peptide fused in-frame to the mature FVIII coding sequence. The protein encoded by this hybrid mRNA is processed through the secretion machinery of the cell, during which the signal peptide and pre-pro peptide of albumin should be cleaved off, resulting in a predicted two chain FVIII molecule in which three amino acids not normally present in FVIII are included at the N-terminus of the heavy chain.

In Vivo Testing of Constructs

Figure 4:
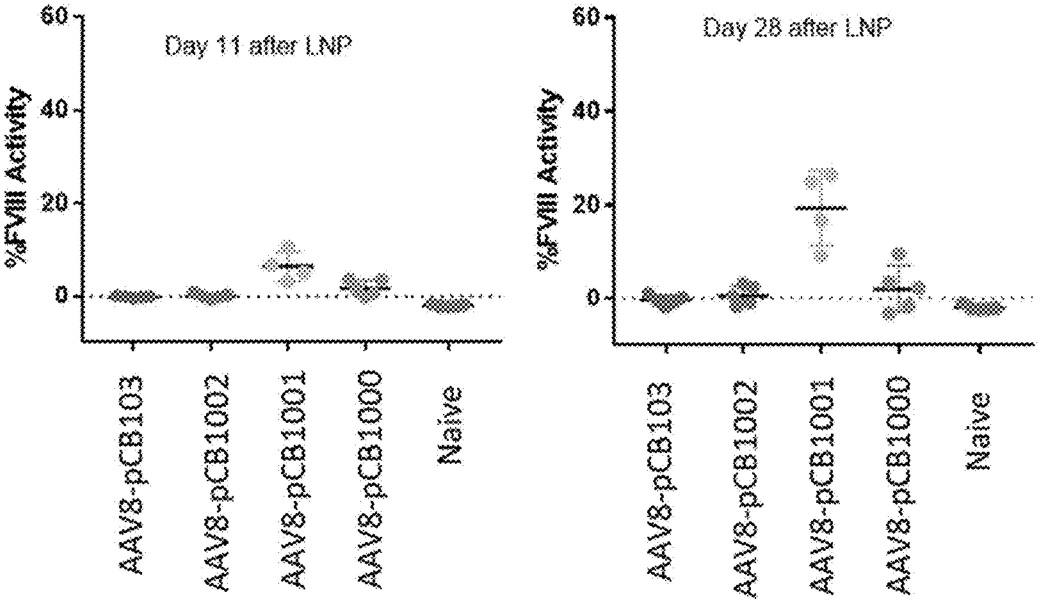
FIG. 4 depicts FVIII activity in the blood of Hemophilia A mice at 11 and 28 days after dosing with LNP. Mice received $2\times10^{12}$ vg/kg of AAV8 virus four weeks prior to the LNP dosing.

To test these formulations, cohorts of four or five Hemophilia A mice were injected via the tail vein with each of the AAV8 viruses (AAV8-pCB103, AAV8-pCB1002, AAV8-pCB1001, and AAV8-pCB1000) at a dose of $2\times10^{12}$ vg/kg. Four weeks later, all of the mice were injected i.v. with a 1:1 mixture of LNP encapsulating mAlbT1 gRNA and spCas9 mRNA at a total RNA dose of 2 mg/kg. The LNP was formulated according to the method described in Example 1. FVIII activity in the blood was measured using the method set forth in Example 1. The results are summarized in FIG. 4.

In these experiments, mice that received AAV8-pCB103 and AAV8-pCB1002 (containing FVIII-BDD with codon optimizations co5 and co2, respectively) did not have detectable FVIII activity in their blood. Mice that received virus pCB1001 (codon optimization co3) had on average 8% FVIII activity on day 11 and 20% FVIII activity on day 28 after LNP dosing. Three of the five mice that received virus AAV8-pCB1000 (codon optimization co4) had FVIII activity levels of 1% to 3% of normal. These data demonstrate that a FVIII-BDD DNA sequence that was codon optimized using the GeneArt algorithm (AAV8-pCB1001, co3) resulted in higher levels of FVIII expression than the FVIII-BDD codon optimized based on most frequent codons of genes highly expressed in the liver (AAV8-pCB103 and AAV8-pCB1002). Modification of the GeneArt codon-optimized FVIII-BDD sequence to remove CG dinucleotides (AAV8-pCB1000, co4) resulted in a reduction in FVIII expression compared with the same cassette in which the FVIII-BDD was codon optimized using the GeneArt algorithm that retained CG dinucleotides. The FVIII-BDD with the co4 codon optimization was able to generate measurable FVIII activity, unlike the co2 and co5 codon optimizations. Mice that received AAV8-pCB102 (co1 codon optimized FVIII-BDD DNA sequence, see Example 2) did not generate FVIII activity in Hemophilia A mice when delivered in AAV8 at the same dose of $2\times10^{12}$ vg/kg and the same dose of LNP was used (Example 2, FIG. 2, AAV8-pCB102). This demonstrates that co1 was inferior to the co3 and co4 codon optimized FVIII-BDD sequences for expression of FVIII after targeted integration into albumin intron 1 in mice.

Example 5: Expression of FVIII in Mice after Targeted Integration into Albumin Intron 1 of a Donor Template Encoding Synthetic FVIII with Five N-Glycans and Alternative Codon Optimizations Co4 and Co5

To test the effects of different codon optimizations using synthetic FVIII having a B domain substitute, FVIII-BDD coding sequences lacking the signal peptide were constructed using the three codon optimized DNA sequences designated co1, co4 and co5, and further containing B domain substitute in place of the B domain. The B domain substitute contained five N-glycan motifs (sequence: ATNVSNNSNTSNDS, SEQ ID NO: 343). These coding sequences were flanked on the 5' side by the target site for the mALbT1 gRNA, an 18 bp spacer, a splice acceptor, and two nucleotides (TG). The TG dinucleotide maintains the correct reading frame after splicing to mouse albumin exon 1. The short polyadenylation signal (sPA) was included at the 3' end of the coding sequence. The synthetic FVIII coding sequences in these three plasmids encode FVIII proteins with identical amino acid sequences, but the coding sequences are encoded by different DNA sequences due to the different codon optimizations. These plasmids designated as pCB1007 (co1, SEQ ID NO: 326), pCB1019 (co4, SEQ ID NO: 332), and pCB1020 (co5, SEQ ID NO: 333) were tested in Hemophilia A mice for their ability to express active FVIII protein after targeted integration into albumin intron 1 mediated by CRISPR/Cas9 cleavage at the target site for the mALbT1 gRNA.

The experimental protocol was identical to that in Example 1. The plasmid DNA of plasmids pCB1007, pCB1019, and pCB1029 was purified using Qiagen EndoFree® maxiprep kits (cat #12362) and then diluted in 0.9% saline to a final concentration of 15 μg/mL. Cohorts of Hemophilia A mice were injected with 2 mL of the diluted plasmid DNA per mouse by HDI. One day later the mice were given retro-orbital injections of a C12-200 based LNP encapsulating spCas9 mRNA (1 mg/kg of body weight) and gRNA mAlbT1 (1 mg/kg body weight). A cohort of five Hemophilia A mice that were injected with only the LNP encapsulating spCas9 mRNA and mALbT1 gRNA were sacrificed three days after dosing, and genomic DNA extracted from the whole liver was analyzed for indels at the on-target site in albumin intron 1. The mean indel frequency was 52.9%, indicating efficient cleavage at the on-target site in the liver.

Six days and nine days after the mice injected with plasmid were dosed with LNP, blood samples were taken by RO bleed into sodium citrate (1:9 ratio of sodium citrate to blood), and the plasma was collected by centrifugation. The FVIII activity in the plasma was measured using the method set forth in Example 1. The results are summarized in FIG. 5.

The mean FVIII activity in mice that received the plasmids pCB1007, pCB1019, or pCB1020 was 22.3%, 17.6%, and 17.8% of normal on day six post LNP dosing. The mean FVIII activity in mice that received the plasmids pCB1007, pCB1019, or pCB1020 was 19.7, 14.1, and 14.9% of normal on day nine post LNP dosing. The FVIII levels in mice dosed with the three plasmids were not statistically significantly different on either day six or day nine when evaluated using a homoscedastic (2 sample equal variance) two-tailed T-test (p values all >0.28).

These results demonstrate that in the context of a donor template encoding a synthetic FVIII having a B domain substitute containing five N-glycan motifs in place of the B domain, codon optimizations co1, co4 and co5 (all of which lack CG dinucleotides) produced similar levels of FVIII after targeted integration into albumin intron 1. Therefore, there is no apparent advantage to a specific codon optimization, and any CpG-free codon optimizations (e.g., co1, co4, and co5) provides similar levels of synthetic FVIII protein after targeted integration.

Example 6: Combination of B Domain Substitute and Mutation of F309 to S or A

It has been reported that a point mutation (F309S) within a potential binding site for the chaperone immunoglobulin binding protein (BiP) in the A1 domain improved secretion of B domain deleted FVIII about three fold in cells in culture (M. Swaroop et al., *J Biol Chem* (1997) 272:24121-24). The F309A mutein of FVIII had similarly improved secretion. The combination of F309S and the 226 amino acid N-terminal portion of the B domain was reported to improve FVIII levels in vivo in mice by 20 to 30-fold compared to B domain deleted FVIII while the addition of the 226 amino acid N-terminus of the B domain improved FVIII levels by only five fold (H. Z. Miao et al., *Blood* (2004) 103(9):3412-19).

To evaluate if a combination of a B domain substitute with substitution of the phenylalanine residue at 309 with serine or alanine results in a further improvement in FVIII expression after targeted integration, plasmids pCB1025 (SEQ ID NO: 334) and pCB1026 (SEQ ID NO: 335) were constructed. Both plasmids contained the co4 codon optimized FVIII DNA sequence having B domain substitute containing five N-linked glycosylation sites. The plasmids had the following elements: pUC19 plasmid backbone|target site for gRNA mALbT1|18 bp spacer|splice acceptor (SA)|TG dinucleotide|FVIII sequence (co4) with five site B domain substitute|polyA (sPA). Plasmid pCB1007 was identical to pCB1025 and pCB1026, except that pCB1025 had Ala instead of Phe at position 309, and pCB1026 had Ser instead of Phe at position 309. Plasmid pCB1007 was used as a comparator in the study.

The experimental protocol was identical to that in Example 1. Plasmids pCB1007, pCB1025, and pCB1026 were purified using Qiagen EndoFree® maxiprep kits (cat #12362), and then diluted in 0.9% saline to a final concentration of 15 μg/mL. Cohorts of hemophilia A mice were injected with 2 mL of the diluted plasmid DNA per mouse by HDI. One day later, the mice were given RO injections of a C12-200 based LNP encapsulating spCas9 mRNA (1 mg/kg) and the gRNA mAlbT1 (1 mg/kg). Five days post LNP dosing (pCB1025, pCB1026) or six days post LNP dosing (pCB1019) blood samples were taken by RO bleed into sodium citrate (1:9 ratio of sodium citrate to blood), and the plasma collected by centrifugation. FVIII activity in the plasma was measured using the method set forth in Example 1. FVIII activities were similar in the three groups of mice injected with pCB1019, pCB1025, or pCB1026 with average FVIII activities of 17.6%, 27.2%, and 24.5%, respectively.

FVIII activity in the blood of the same Hemophilia A mice was also assayed at day nine post LNP (pCB1019 injected mice) or seven days post LNP (pCB1025 and pCB1026 injected mice). The mice were then sacrificed, and whole livers were prepared and analyzed for integration frequency as described in Example 1 above. The targeted integration frequencies were similar between the three groups with average frequencies of 0.42 for pCB1019 injected mice, 0.47 for pCB1025 injected mice, and 0.36 for pCB1026 injected mice.

Normalizing the FVIII level in the blood of each mouse to the integration frequency provides a measure of the intrinsic expression efficiency of the FVIII coding sequence. The average of the ratio of FVIII level divided by targeted integration frequency was 37.4 for pCB1019 injected mice, 41.5 for pCB1025 injected mice, and 49.9 for pCB1026 injected mice. The difference in the FVIII activity normalized to targeted integration for pCB1025 and pCB1026 injected mice compared to the pCB1019 injected mice was not statistically significant (two-tailed Student's T-test), which demonstrates that changing amino acid F309 to serine or alanine (in the context of a FVIII-BDD cassette containing five N-glycan motifs in place of the B domain) did not improve FVIII expression. Thus, not all amino acid changes made to the FVIII protein have an effect on FVIII expression after targeted integration in to albumin intron 1.

Example 7: Targeted Integration of a Synthetic FVIII into Transferrin Intron 1 by a CRISPR/Cas Nuclease Results in Expression of Therapeutic Levels of Human FVIII DNA Constructs To examine integration into and expression from a transferrin locus, as an alternative to an albumin locus, a human FVIII donor cassette (SEQ ID NO: 224) was constructed with sequence elements in order from 5' to 3' as follows: the inverted terminal repeat of AAV2 (ITR)|the target site for gRNA mTF-T2|an 18 bp spacer|a splice acceptor|a sequence (ggctgtgtctggct, SEQ ID NO: 225) that encodes the last four amino acids of the signal peptide of mouse transferrin|a synthetic FVIII coding sequence|a polyadenylation signal (spA)|the target site for gRNA mTF-T2|and the inverted terminal repeat of AAV2 (ITR). The sequence of the target site for gRNA mTF-T2 was the reverse complement of the target sequence in the mouse genome, which may favor integration in the forward orientation. The polyadenylation signal is a short 49 bp sequence reported to effectively direct polyadenylation (N. Levitt et al., *Genes Dev* (1989) 3:1019-25). The synthetic FVIII coding sequence encoded a B domain substitute containing the amino acid sequence SFSQN-ATNVSNNSNTSNDSNVSPPVLKRHQR (SEQ ID NO: 226) in place of the B domain, and included a heterologous 31 amino acid sequence replacing the B domain. This sequence contains six tripeptides corresponding to N-linked glycosylation sites (represented in bold), and is indicated to improve the expression of FVIII (J. McIntosh et al., *Blood* (2013) 121:3335-44).

Packaging of the pCB1009 FVIII donor DNA into AAV8 was accomplished using established viral packaging methods in HEK293 cells that were transfected with three plasmids; one encoding the AAV packaging proteins, the second encoding adenovirus helper proteins, and the third containing the FVIII donor DNA sequence flanked by AAV ITR sequences. The transfected cells gave rise to AAV particles of the serotype specified by the composition of the AAV capsid proteins encoded on the first plasmid. These AAV particles were collected from the cell supernatant or the supernatant and the lysed cells, and purified over a CsCl gradient. The purified viral particles were quantified by measuring the number of genome copies of the donor DNA by digital droplet PCR (DD-PCR).

In Vivo Testing of Constructs

Figure 6:
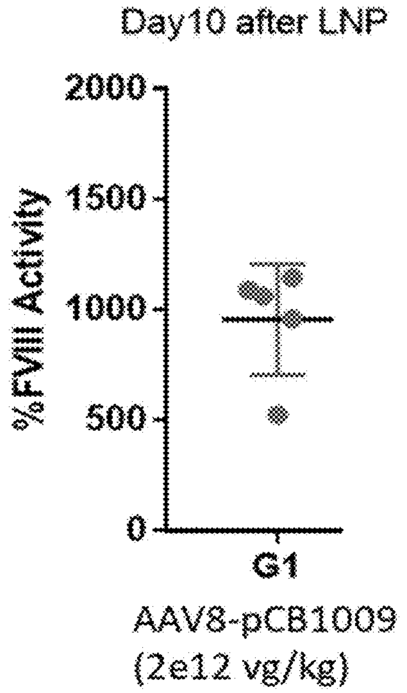
FIG. 6 depicts FVIII activity in the blood of mice that are hydrodynamically injected with plasmids pCB1007 (n=7 mice), pCB1025 (n=7) and pCB1026 (n=6), and retro-orbitally injected with LNP encapsulating mALbT1 gRNA and Cas9 mRNA. FVIII was measured on day six and day nine after LNP dosing.

A cohort of five Hemophilia A mice was injected intravenously (i.v.) into the tail vein with AAV8-pCB1009 at a dose of $2\times10^{12}$ vg/kg body weight. The AAV8 virus preferentially transduces hepatocytes. Four weeks later, the same mice were injected i.v. with a 1:1 (by mass of RNA) mixture of two LNPs, one encapsulating an spCas9 mRNA and one encapsulating the guide RNA mTF-T2, at a total RNA dose of 2 mg/kg of body weight. The LNPs are taken up primarily by hepatocytes. Ten days after dosing the LNP, blood samples were obtained and assayed as described above. FVIII activity averaged 954% (±251%) of normal human FVIII levels (FIG. 6), equivalent to 9.54 IU/mL or 9.5-fold greater than average levels in humans without hemophilia. Naïve Hemophilia A mice had undetectable FVIII activity (<0.5% of normal).

These data demonstrate that targeting integration of a FVIII coding sequence into intron 1 of transferrin can result in high levels of FVIII expression and activity, demonstrating the utility of this method for treating a condition having a defective FVIII such as hemophilia A.

Example 8: Additional Modes of Delivery

In another example, the donor template is delivered in vivo using a non-viral LNP delivery system. DNA molecules are encapsulated into LNP particles similar to those described above, and delivered to the liver by i.v. injection. While DNA escape from the endosome to the cytoplasm occurs relatively efficiently, translocation of large charged DNA molecules into the nucleus is not efficient. In one case, the delivery of DNA to the nucleus is improved by mimicking the AAV genome by incorporating AAV ITR sequences into the donor template. In this case, the ITR sequences stabilize the DNA or otherwise improve nuclear translocation. Removing CG di-nucleotides (CpG sequences) from the donor template sequence also improves nuclear delivery. DNA containing CG di-nucleotides is recognized by the innate immune system and eliminated. Removal of CpG sequences that are present in artificial DNA sequences improves the persistence of DNA delivered by non-viral and viral vectors. The process of codon optimization generally increases the content of CG di-nucleotides because the most frequent codons in many cases have a C residue in the 3rd position, which increases the chance of creating a CG when the next codon starts with a G. A combination of LNP delivery of the donor template followed one hour to five days later with an LNP containing the gRNA and Cas9 mRNA is evaluated in Hemophilia A mice.

In vivo delivery of the gRNA and the Cas9 mRNA can be accomplished by known methods. In one method, the gRNA and Cas9 protein are expressed from an AAV viral vector. In this case, the transcription of the gRNA is driven by a U6 promoter, and the Cas9 mRNA transcription is driven by either a ubiquitous promoter, e.g., EF1-alpha, or a liver-specific promoter/enhancer, such as the transthyretin promoter/enhancer. The size of the spCas9 coding sequence (4.4 Kb) precludes inclusion of the spCas9 and the gRNA cassettes in a single AAV, thereby requiring separate AAV to deliver the gRNA and spCas9. In a second case, an AAV vector that has sequence elements that promote self-inactivation of the viral genome is used. In this case, including cleavage sites for the gRNA in the vector DNA results in cleavage of the vector DNA in vivo. By including cleavage sites in locations that block expression of the Cas9 when cleaved, Cas9 expression is limited to a shorter time period. In a third, alternative approach to deliver gRNA and Cas9 to cells in vivo, a non-viral delivery method is used. In one example, LNP are used as a non-viral delivery method. Several different ionizable cationic lipids are available for use in LNP. These include C12-200, MC3, LN16, and MD1, among others. In one type of LNP, a GalNac moiety is attached to the outside of the LNP and acts as a ligand for uptake into the liver via the asialoglycoprotein receptor. Any of these cationic lipids are used to formulate LNP for delivery of gRNA and Cas9 mRNA to the liver.

Example 9: Targeted Integration of a Therapeutic Coding Sequence at Mouse Fibrinogen Alpha Intron 1

To examine integration into and expression from a fibrinogen alpha locus, as an alternative to an albumin or a transferrin locus, an AAV8 virus (AAV8-pCB1010, SEQ ID NO: 361) was constructed having a cassette with the following elements: a target site for the gRNA mFGA-T6, a 18 bp spacer, a FIX splice acceptor, the mature human FVIII coding sequence (with N-terminus modified so as to complete the FGA signal peptide after splicing to endogenous FGA exon 1) in which the B domain was replaced by six N-glycan motifs, a polyadenylation sequence and the target site for the gRNA mFGA-T6.

Hemophilia A mice were injected with AAV8-pCB1010, followed 28 days later with an LNP encapsulating the T6 gRNA (targeting mouse fibrinogen alpha intron 1) and a Cas9 mRNA. Ten days after dosing of the LNP, blood samples were taken by retro-orbital bleeds into capillary tubes containing sodium citrate (1:9 ratio of sodium citrate to blood), and the plasma was collected by centrifugation. The plasma samples were then assayed for FVIII as described above. Assay results were reported as percentage of normal human FVIII activity (normal defined as 1 IU/mL). FVIII activity averaged 1124% (±527%) of normal human FVIII levels, equivalent to 11.24 IU/mL or 11-fold greater than average levels in humans without hemophilia. Naïve Hemophilia A mice had undetectable FVIII activity (<0.5% of normal). Because the AAV8-pCB1010 virus contains a FVIII cassette in which the coding sequence lacks a signal peptide and also lacks a promoter, this virus alone is incapable of giving rise to secreted FVIII protein.

These data demonstrate the suitability of fibrinogen as a site for insertion of a coding sequence. Further, they demonstrate that a B domain substituted FVIII sequence can be used to express useful amounts of an FVIII. Accordingly, such constructs and methods can be used for treating disorders associated with defective FVIII.

Example 10: Identification and Selection of Guide RNAs that Cleave Efficiently at Human Albumin Intron 1 in Primary Human Hepatocytes in Culture To demonstrate operation of the system of the invention in human hepatocytes, four gRNA (T4—SEQ ID NO: 357, T5—SEQ ID NO: 358, T11—SEQ ID NO: 359, and T13—SEQ ID NO: 360) were prepared, based on having perfect identity between human and a non-human primate and the screening for cutting efficiency in HuH7 and HepG2 cells, for evaluation of cutting efficiency in primary human hepatocytes. Primary human hepatocytes (obtained from BioIVT) were thawed, transferred to Cryopreserved Hepatocyte Recovery Medium (CHRM) (Gibco), pelleted at low speed, then plated in InVitroGRO™ CP Medium (BioIVT) plus Torpedo™ Antibiotic Mix (BioIVT) at a density of $0.7\times10^6$ cells/mL in 24-well plates pre-coated with collagen IV (Corning). Plates were incubated in 5% CO 2 at 37° C. After the cells adhered (3-4 hours after plating), dead cells that had not adhered to the plate were washed out with fresh warm complete medium, additional medium was added, and cells were incubated in 5% CO 2 at 37° C. To transfect the cells, Cas9 mRNA (Trilink) and guide RNA were thawed on ice, then added to 30 μL Opti-Mem™ media (Gibco) at 0.6 μg mRNA and 0.2 μg guide RNA per well. MessengerMax™ (Thermo Fisher) diluted in 30 μL in Opti-Mem™ at a 2:1 volume to total nucleic acid weight was incubated with the Cas9 mRNA/gRNA Opti-Mem™ solution at room temperature for 20 minutes. This mixture was added dropwise to the 500 μL of hepatocyte plating medium per well of cultured hepatocytes in a 24-well plate, and the cells incubated in 5% CO 2 at 37° C. The cells were washed and re-fed the next morning. Cells were collected for genomic DNA extraction 48 hours post-transfection by adding 200 μL of warm 0.25% Trypsin-EDTA (Gibco) to each well and incubating 5 to 10 minutes at 37° C. Once cells were dislodged, 200 μL FBS (Gibco) was added to inactivate trypsin. After adding 1 mL PBS (Gibco) the cells were pelleted at 1200 rpm for three minutes, then resuspended in 50 μL PBS. Genomic DNA was extracted using the MagMAX™ DNA Multi-Sample Ultra 2.0 Kit (Applied Biosytems) following the kit instructions. The genomic DNA quality and concentration was analyzed using a spectrophotometer. For TIDE analysis, the genomic DNA was PCR amplified using primers flanking the predicted on-target cleavage site (AlbF: CCCTCCGTTTGTCCTAGCTTTTC, SEQ ID NO: 353, and AlbR: CCAGATACAGAATATCTTCCTCAACGCAGA, SEQ ID NO: 354) and Platinum® PCR SuperMix High Fidelity (Invitrogen™) using 35 cycles of PCR and an annealing temperature of 55° C. PCR products were analyzed by agarose gel electrophoresis to confirm that the right sized product (1053 bp) had been generated, then purified and sequenced using primers (forward: CCTTTGGCACAATGAAGTGG, SEQ ID NO: 355; reverse: GAATCTGAACCCTGATGACAAG, SEQ ID NO: 356). Sequence data were analyzed using a modified version of the TIDES algorithm (E. K. Brinkman et al., *Nuc Acids*

*Res* (2014) 42(22):e168) named Tsunami, that determines the frequency of indels present at the predicted cut site for the gRNA/Cas9 complex.

Figure 7:
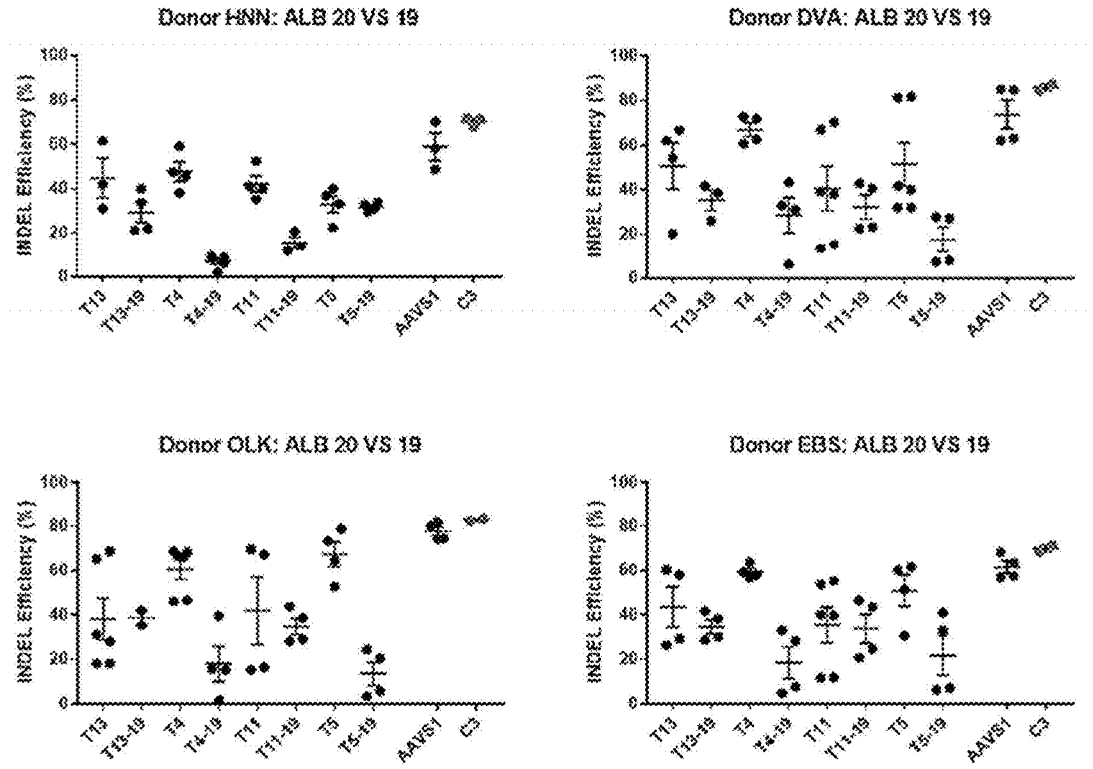
FIG. 7 depicts the results for cutting efficiency of guide RNAs T4, T5, T11, and T13 (targeting human albumin intron 1) in primary human hepatocytes from four donors, comparing 19 base vs. 20 base target sequences.

Guide RNA containing either a 20 nucleotide target sequence or a 19 nucleotide target sequence (1 bp shorter at the 5' end) of the T4 (SEQ ID NO: 357), T5 (SEQ ID NO: 358), T11 (SEQ ID NO: 359), and T13 (SEQ ID NO: 360) guides were tested. A 19 nucleotide gRNA may be more sequence specific, but a shorter guide may have lower potency (efficiency in double-strand cleavage, measured as indels). Control guides targeting human AAVS1 locus and human complement factor were included for comparison across donors. Indel frequency at the target site in albumin intron 1 was measured 48 hours after transfection using the TIDES method. FIG. 7 summarizes the results from transfections of primary hepatocyte from four different human donors.

The results demonstrate cutting efficiencies ranging from to 20% to 80% for the different guides. The 20 nucleotide version of each albumin gRNA was consistently more potent than the 19 nucleotide variant. The superior potency of the 20 nucleotide gRNAs may offset any potential benefit a 19 nucleotide gRNA may have in terms of less off-target cutting. Guide RNA T4 exhibited the most consistent cutting across the four cell donors with indel frequencies of about 60%.

Figure 9:
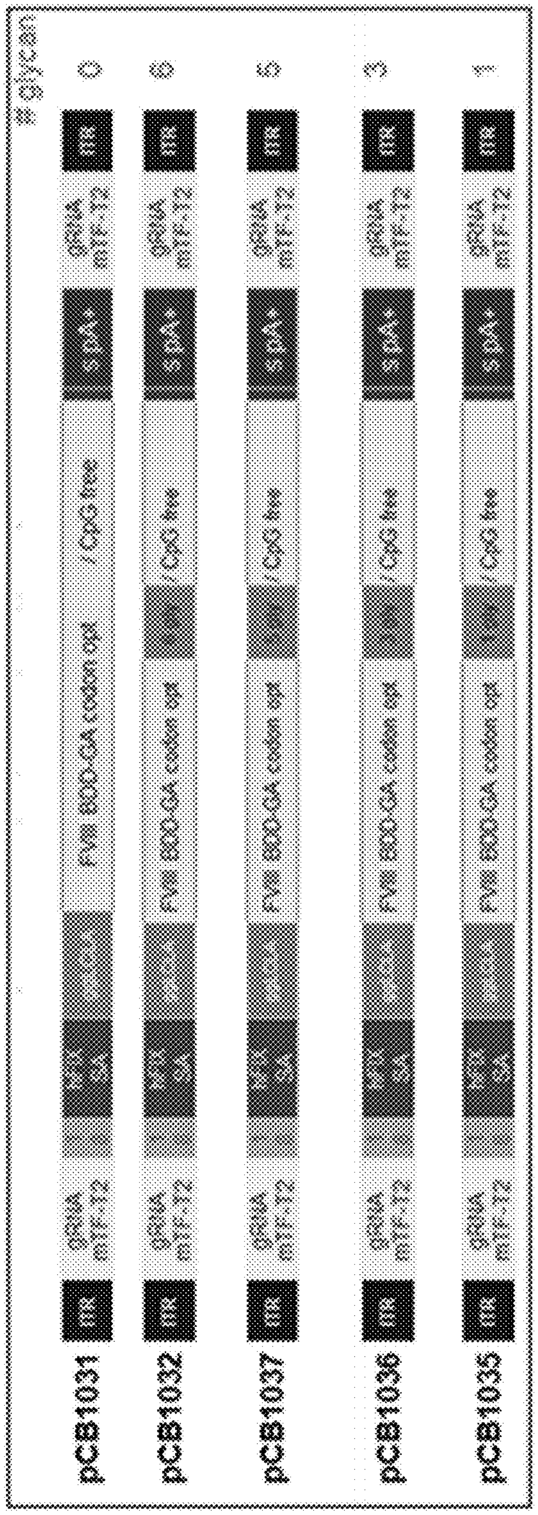
FIG. 9 depicts FVIII constructs in which the B domain substitute contains either 0, 1, 3, 5, or 6 glycans.

Example 11: Evaluation of FVIII Expression from an AAV8 Virus Encapsulating a Codon Optimized FVIII Coding Sequence (CpG Free) with B-Domain Substitutes Composed of Different Numbers of N-Glycans Followed by a Single LNP Dose with gRNA Targeting the Transferrin Locus This study evaluated FVIII expression from AAV8 virus encoding FVIII in which the B-domain substitutes contained either 0, 1, 3, 5, or 6 glycans. The FVIII coding sequece was codon optimized, and then CpG were eliminated manually. The constructs used in this study are shown in FIG. 9.

On Day 0, Hemophilia A mice (8-10 weeks old) were dosed with respective virus by tail vein injection. On Day 28, Hemophilia A mice were retro-orbital injected with lipid nano-particle (LNP) encapsulating Cas9 mRNA (411 μg/ml) and the guide RNA mTF-T2 (379 μg/ml). Study groups and dosage are shown in Table 7.

TABLE 7

Study groups and dosage.

| Group (n = 5/grp) | Mouse strain | AAV donor | AAV dose (TV) | Volume per mouse (μl) | LNP Dose Cas9 | LNP Dose gRNA | LNP Dose Total RNA dose |
|---|---|---|---|---|---|---|---|
| 1 | HemA | AAV8-CB1031 | 2E12 vg/kg | 100 μl | 0.125 mg/kg | 0.125 mg/kg | 0.25 mg/kg |
| 2 | HemA | AAV8-CB1032 | 2E12 vg/kg | 100 μl | 0.125 mg/kg | 0.125 mg/kg | 0.25 mg/kg |
| 3 | HemA | AAV8-CB1035 | 2E12 vg/kg | 100 μl | 0.125 mg/kg | 0.125 mg/kg | 0.25 mg/kg |
| 4 | HemA | AAV8-CB1036 | 2E12 vg/kg | 100 μl | 0.125 mg/kg | 0.125 mg/kg | 0.25 mg/kg |
| 5 | HemA | AAV8-CB1037 | 2E12 vg/kg | 100 μl | 0.125 mg/kg | 0.125 mg/kg | 0.25 mg/kg |
| 6 (Naïve) | HemA | — | — | — | — | — | — |

Eleven days after dosing the LNP, blood samples were obtained and assayed as described above. Then, 18 days after dosing the LNP, blood samples were obtained via terminal cardiac bleeds and assayed as described above.

Figure 10:
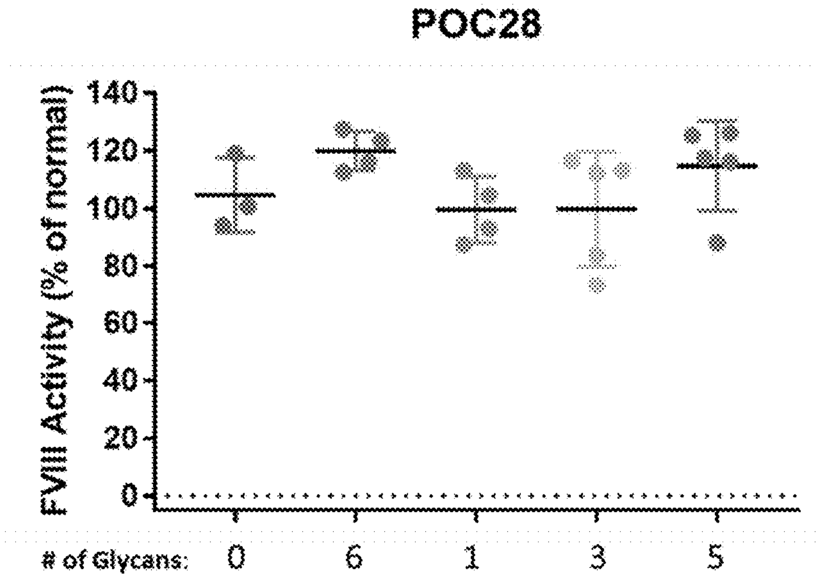
FIG. 10 depicts FVIII activity in the blood of Hemophilia A mice at 11 days after dosing with LNP.
Figure 11:
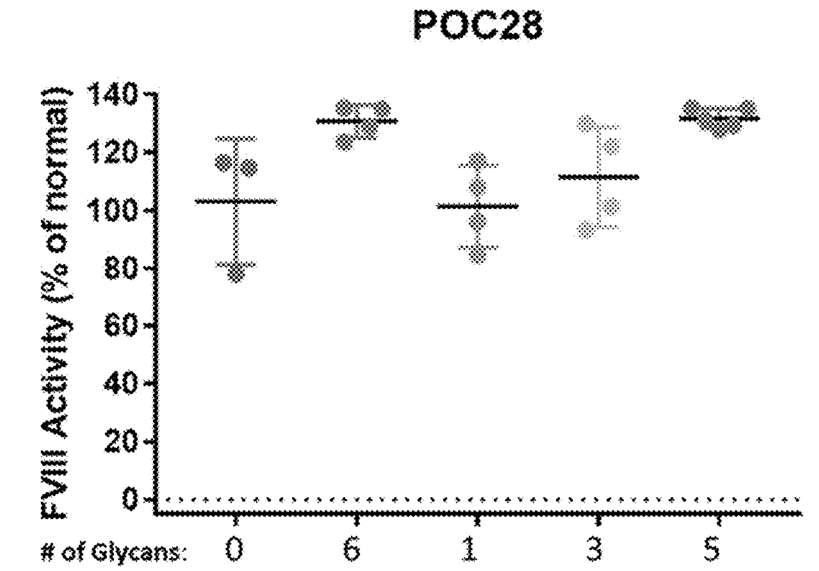
FIG. 11 depicts FVIII activity in the blood of Hemophilia A mice at 28 days after dosing with LNP.

FVIII activity levels measured on Day 11 are shown in FIG. 10. FVIII activity levels measured on Day 18 are shown in FIG. 11. FVIII activity levels are provided in Tables 8 and 9.

TABLE 8

FVIII activity levels on Day 11.

| Group (n) | AAV Donor | # of N-Glycans | % FVIII Day 10 | Avg % FVIII (+/− STD) |
|---|---|---|---|---|
| 1 (3) | AAV8-CB1031 | 0 | 94.1<br>119.0<br>100.8 | 104.7 (12.9) |
| 2 (4) | AAV8-CB1032 | 6 | 116.2<br>112.7<br>127.5<br>123.3 | 119.9 (6.7) |
| 3 (4) | AAV8-CB1035 | 1 | 87.5<br>104.6<br>113.1<br>93.1 | 99.6 (11.5) |
| 4 (5) | AAV8-CB1036 | 3 | 116.6<br>113.2<br>112.3<br>83.7<br>73.3 | 99.8 (19.9) |
| 5 (5) | AAV8-CB1037 | 5 | 126.2<br>116.2<br>117.6<br>88.1<br>125.4 | 114.7 (15.5) |

TABLE 9

FVIII activity levels on Day 18.

| Group (n) | AAV Donor | # of N-Glycans | % FVIII Day 18 | Avg % FVIII (+/− STD) |
|---|---|---|---|---|
| 1 (3) | AAV8-CB1031 | 0 | 114.7<br>78.0<br>116.4 | 103 (21.7) |
| 2 (4) | AAV8-CB1032 | 6 | 128.9<br>123.5 | 130.7 (5.7) |

TABLE 9-continued

| FVIII activity levels on Day 18. | | | | |
|---|---|---|---|---|
| Group (n) | AAV Donor | # of N-Glycans | % FVIII Day 18 | Avg % FVIII (+/− STD) |
| | | | 135.4 | |
| | | | 135.0 | |
| 3 (4) | AAV8- | 1 | 84.6 | 101.4 (14.2) |
| | CB1035 | | 96.0 | |
| | | | 117.2 | |
| | | | 107.9 | |
| 4 (5) | AAV8- | 3 | 129.9 | 111.6 (17.2) |
| | CB1036 | | 122.5 | |
| | | | CLOT | |
| | | | 101.3 | |
| | | | 93.2 | |
| 5 (5) | AAV8- | 5 | 135.2 | 131.7 (3.4) |
| | CB1037 | | 129.3 | |
| | | | 135.2 | |
| | | | 127.9 | |
| | | | 131.2 | |

Figure 12:
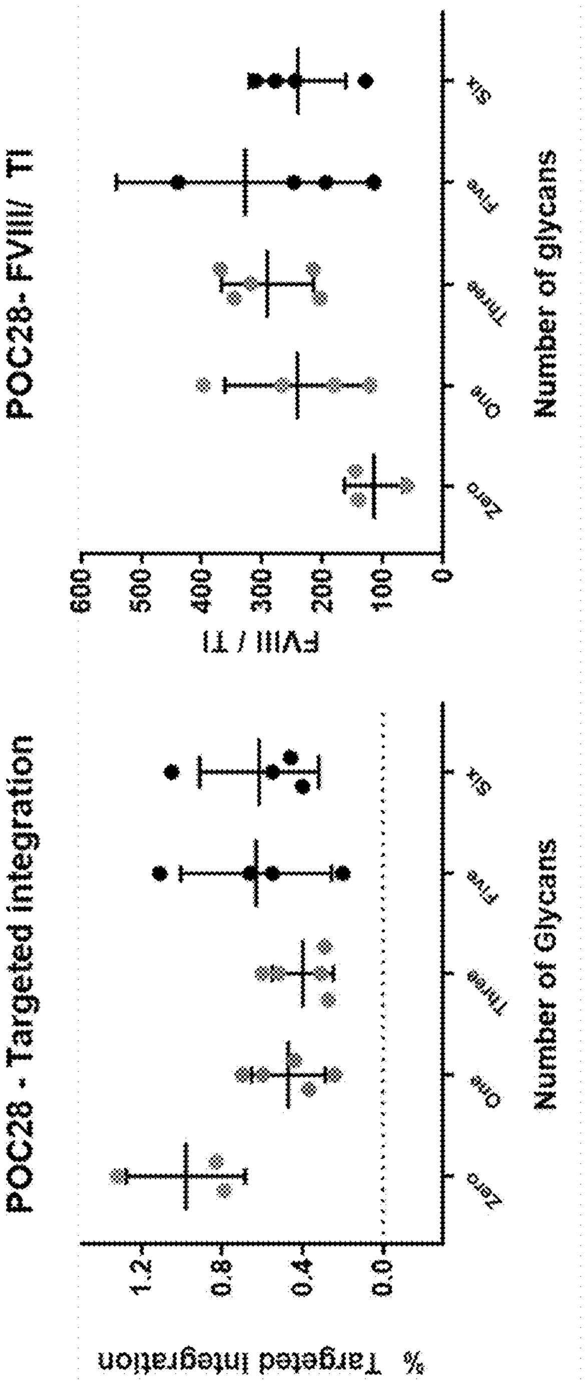
FIG. 12 depicts intrinsic expression efficiency (FVIII activity divided by targeted integration frequency) for FVIII donor cassettes having 0, 1, 3, 5, or 6 N-linked glycan motifs.

After the mice were sacrificed, the whole livers were homogenized, and total genomic DNA was extracted from a portion of the liver lysate. The frequency of targeted integration into albumin intron 1 in the forward orientation was quantitated using the DD-PCR assay described in Example 1. The results are shown in FIG. 12 and Table 10.

TABLE 10

| FVIII targeted integration frequency. | | | |
|---|---|---|---|
| POC28 Group # | Terminal % FVIII (Day 18) | Average % TI | Average FVIII/TI |
| G1 (Zero glycan) | 103.3 | 0.98 | 114.9 |
| G2 (Six glycan) | 130.7 | 0.62 | 240.8 |
| G3 (one glycan) | 101.42 | 0.49 | 241 |
| G4 (Three glycan) | 111.84 | 0.41 | 290 |
| G5 (Five glycan) | 131.3 | 0.57 | 328 |

These data demonstrate that a FVIII coding sequence containing either 0, 1, 3, 5 or 6 glycans can result in high levels of FVIII expression and activity, demonstrating the utility of this method for treating a condition having a defective FVIII such as hemophilia A.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

SEQUENCE LISTING

In addition to sequences disclosed elsewhere in the present disclosures, the following sequences are provided as they are mentioned or used in exemplary embodiments of the disclosures, which are provided for the purpose of illustration.

| SEQ ID | Sequence | Description |
|---|---|---|
| 1 | AAGGAAGCGGTGCCATCGAG | Transferrin_T12 gRNA spacer |
| 2 | AACTTCTGCCTGCCATTCAT | Transferrin_T168 gRNA spacer |
| 3 | AGCAAAGGGTTTTGATAACC | Transferrin_T73 gRNA spacer |
| 4 | TTGCCTGGGAGGGTCAAATG | Transferrin_T99 gRNA spacer |
| 5 | GGCTTGGCCAACGACAAGCA | Transferrin_T26 gRNA spacer |
| 6 | CCTTGTGGGCCACCACAGCA | Transferrin_T111 gRNA spacer |
| 7 | GGGCCCACTCCCTATGCTGA | Transferrin_T76 gRNA spacer |
| 8 | TCTGAGTCTGAGCCAATAGA | Transferrin_T128 gRNA spacer |
| 9 | CCTGCCTCCAGAGTTCCCAT | Transferrin_T188 gRNA spacer |
| 10 | ACAGCTCTCCAGGATGCATG | Transferrin_T151 gRNA spacer |
| 11 | GGCCCATGGGAAATCCTAGG | Transferrin_T67 gRNA spacer |
| 12 | AGGGTGGTCAGTAGGAAACT | Transferrin_T138 gRNA spacer |

-continued

| SEQ ID | Sequence | Description |
|---|---|---|
| 13 | CCTTGCTGTGGTGGCCCACA | Transferrin_T115 gRNA spacer |
| 14 | GGTAGCAAGCCAATGTGTTG | Transferrin_T45 gRNA spacer |
| 15 | GCAGATTGTCATCTCCAGCT | Transferrin_T180 gRNA spacer |
| 16 | CCACAGCAAGGCTGACTCAC | Transferrin_T148 gRNA spacer |
| 17 | ACTGAGGCTTATGTTCCATG | Transferrin_T100 gRNA spacer |
| 18 | GGGCAAAAGCTCATGTGATA | Transferrin_T66 gRNA spacer |
| 19 | ATACTGAGGCTTATGTTCCA | Transferrin_T162 gRNA spacer |
| 20 | CCAGTGAGTCAGCCTTGCTG | Transferrin_T175 gRNA spacer |
| 21 | GGATTTCCCATGGGCCAAGA | Transferrin_T172 gRNA spacer |
| 22 | GGGTCAAATGAGGGTCAGCG | Transferrin_T104 gRNA spacer |
| 23 | TCAACTATGGAAAACCAGCG | Transferrin_T19 gRNA spacer |
| 24 | CATAAGCCTCAGTATGCACA | Transferrin_T77 gRNA spacer |
| 25 | TATGTTCCATGGGGGGCCAG | Transferrin_T62 gRNA spacer |
| 26 | AGGGCCCACTCCCTATGCTG | Transferrin_T106 gRNA spacer |
| 27 | GCTGTGGGCCTCCTCTCCAC | Transferrin_T163 gRNA spacer |
| 28 | ACAAATGCCCCATGAATGGC | Transferrin_T134 gRNA spacer |
| 29 | GTGGCTGTCAAGGCCTTTCT | Transferrin_T167 gRNA spacer |
| 30 | TCCTGTCCATGAACACTACA | Transferrin_T61 gRNA spacer |
| 31 | AGACAGCATCGCCCCTAGAA | Transferrin_T6 gRNA spacer |
| 32 | CCTTCTTGGCCAGTAGTTGA | Transferrin_T44 gRNA spacer |
| 33 | AAGGTCACCCTGCTTGTCGT | Transferrin_T3 gRNA spacer |
| 34 | GAGGGAAAATGGGGGTCGCT | Transferrin_T68 gRNA spacer |
| 35 | TAGGAGGCAACATAAGCCTG | Transferrin_T103 gRNA spacer |
| 36 | AAAACGCCCTGTGCATACTG | Transferrin_T81 gRNA spacer |
| 37 | GTGAGTCAGCCTTGCTGTGG | Transferrin_T146 gRNA spacer |

-continued

| SEQ ID | Sequence | Description |
|---|---|---|
| 38 | GGCTGTCAAGGCCTTTCTAG | Transferrin_T63 gRNA spacer |
| 39 | AGGTAGCAAGCCAATGTGTT | Transferrin_T87 gRNA spacer |
| 40 | GATTGTCATCTCCAGCTGGG | Transferrin_T184 gRNA spacer |
| 41 | TCCTGGCCGGCTCCTCACCA | Transferrin_T116 gRNA spacer |
| 42 | ATTCTCGCCTATGGGAACTC | Transferrin_T24 gRNA spacer |
| 43 | TGGCTTGGCCAACGACAAGC | Transferrin_T21 gRNA spacer |
| 44 | TTGGCTTGCTACCTCAACTA | Transferrin_T41 gRNA spacer |
| 45 | GAGGTAGCAAGCCAATGTGT | Transferrin_T55 gRNA spacer |
| 46 | AGGAGACAAGGCGGATACAG | Transferrin_T90 gRNA spacer |
| 47 | GACTCTGGGTCTGCTACTCA | Transferrin_T101 gRNA spacer |
| 48 | CCGCTGGTTTTCCATAGTTG | Transferrin_T39 gRNA spacer |
| 49 | CCTCAACTATGGAAAACCAG | Transferrin_T150 gRNA spacer |
| 50 | TGGATTTTAATAGTTACCCA | Transferrin_T156 gRNA spacer |
| 51 | GGGGATAAAGGCAAGTAACG | Transferrin_T40 gRNA spacer |
| 52 | CCGGGTTGCAGGGAACGCGC | Transferrin_T8 gRNA spacer |
| 53 | CGCGCGGGCCAGCGACTCTG | Transferrin_T53 gRNA spacer |
| 54 | CTGAGGCTTATGTTCCATGG | Transferrin_T117 gRNA spacer |
| 55 | CGGAGTGCATGCAGGCTGCG | Transferrin_T49 gRNA spacer |
| 56 | ACAGGCTTATGTTGCCTCCT | Transferrin_T83 gRNA spacer |
| 57 | GGGCATTTGTCACACTGTTG | Transferrin_T64 gRNA spacer |
| 58 | TGGCCCCTCCTCATGCATCC | Transferrin_T120 gRNA spacer |
| 59 | AAAATGGAGGGATAGTTCAG | Transferrin_T161 gRNA spacer |
| 60 | TGTGACAAATGCCCCATGAA | Transferrin_T183 gRNA spacer |
| 61 | GTGGTCAGTAGGAAACTGGG | Transferrin_T182 gRNA spacer |
| 62 | TGAGGCTTATGTTCCATGGG | Transferrin_T119 gRNA spacer |

-continued

| SEQ ID | Sequence | Description |
|---|---|---|
| 63 | GGGATAAAGGCAAGTAACGT | Transferrin_T18 gRNA spacer |
| 64 | AGGGCAAAAGCTCATGTGAT | Transferrin_T107 gRNA spacer |
| 65 | GCCATCGAGCGGTCAGAGCA | Transferrin_T20 gRNA spacer |
| 66 | CCCTCAACTACTGGCCAAGA | Transferrin_T80 gRNA spacer |
| 67 | CCTCAACTACTGGCCAAGAA | Transferrin_T133 gRNA spacer |
| 68 | GAGGGTGGTCAGTAGGAAAC | Transferrin_T84 gRNA spacer |
| 69 | GTCGCTGGGGTGGCCATCCC | Transferrin_T85 gRNA spacer |
| 70 | TGGGGAGAGAAAACTAAACG | Transferrin_T143 gRNA spacer |
| 71 | CCTGAGCGCGGAGTGCATGC | Transferrin_T15 gRNA spacer |
| 72 | GCGACCCCCATTTTCCCTCT | Transferrin_T96 gRNA spacer |
| 73 | CTCAACTATGGAAAACCAGC | Transferrin_T118 gRNA spacer |
| 74 | GATCCACAAAGCCTGTGGAG | Transferrin_T152 gRNA spacer |
| 75 | CCCCGCACAGAGCACTTCAC | Transferrin_T38 gRNA spacer |
| 76 | TGCAAGGTAATGCTCCACTG | Transferrin_T132 gRNA spacer |
| 77 | AGGGGACGTCAGCCTCTGAA | Transferrin_T149 gRNA spacer |
| 78 | AGGGAAAATGGGGGTCGCTG | Transferrin_T171 gRNA spacer |
| 79 | TGAGGACACATTCTCGCCTA | Transferrin_T30 gRNA spacer |
| 80 | TGCCTCCTAGGATTTCCCAT | Transferrin_T71 gRNA spacer |
| 81 | CTTGGCCCATGGGAAATCCT | Transferrin_T158 gRNA spacer |
| 82 | AGGAGTTCGGACTTGACAAG | Transferrin_T36 gRNA spacer |
| 83 | ACATAAGCCTCAGTATGCAC | Transferrin_T27 gRNA spacer |
| 84 | CAGGACATCTACAGCTCCCA | Transferrin_T130 gRNA spacer |
| 85 | GGGCCCCACCTCAGGAGGTC | Transferrin_T124 gRNA spacer |
| 86 | AACGACAAGCAGGGTGACCT | Transferrin_T185 gRNA spacer |
| 87 | GCAGGACATCTACAGCTCCC | Transferrin_T79 gRNA spacer |

-continued

| SEQ ID | Sequence | Description |
|---|---|---|
| 88 | CCTGTGAAGTGCTCTGTGCG | Transferrin_T72 gRNA spacer |
| 89 | TGCCTGGGAGGGTCAAATGA | Transferrin_T179 gRNA spacer |
| 90 | TGGCCATGCCTGCACCCCTC | Transferrin_T170 gRNA spacer |
| 91 | GCCAGCAGAGGGTGGTCAGT | Transferrin_T181 gRNA spacer |
| 92 | CTCCTGTCCATGAACACTAC | Transferrin_T42 gRNA spacer |
| 93 | GGAGTGGGCCCTTCCACCTC | Transferrin_T114 gRNA spacer |
| 94 | CAACTATGGAAAACCAGCGG | Transferrin_T23 gRNA spacer |
| 95 | TACTGAGGCTTATGTTCCAT | Transferrin_T144 gRNA spacer |
| 96 | CCCATGCTCTGACCGCTCGA | Transferrin_T1 gRNA spacer |
| 97 | CTCCCCGACCTCCTGAGGTG | Transferrin_T186 gRNA spacer |
| 98 | GGGGAATGGTCAGACCCGGG | Transferrin_T58 gRNA spacer |
| 99 | CTTGTGCCCTGTAGTGTTCA | Transferrin_T113 gRNA spacer |
| 100 | CCCGCGCGTTCCCTGCAACC | Transferrin_T29 gRNA spacer |
| 101 | CCATCGAGCGGTCAGAGCAT | Transferrin_T2 gRNA spacer |
| 102 | GCCCTGTAGTGTTCATGGAC | Transferrin_T48 gRNA spacer |
| 103 | AAATCAGAGCACGTCTAACC | Transferrin_T17 gRNA spacer |
| 104 | GCCTGTGAAGTGCTCTGTGC | Transferrin_T153 gRNA spacer |
| 105 | CTCGCCTATGGGAACTCTGG | Transferrin_T60 gRNA spacer |
| 106 | GGCCCCACCTCAGGAGGTCG | Transferrin_T164 gRNA spacer |
| 107 | CCGCGCGTTCCCTGCAACCC | Transferrin_T47 gRNA spacer |
| 108 | TGGCTGTCAAGGCCTTTCTA | Transferrin_T110 gRNA spacer |
| 109 | TGGCAGATGCTGAGTACCAG | Transferrin_T177 gRNA spacer |
| 110 | GTTAATTTACCCTCAACTAC | Transferrin_T13 gRNA spacer |
| 111 | CCTGCATGCACTCCGCGCTC | Transferrin_T7 gRNA spacer |

-continued

| SEQ ID | Sequence | Description |
|---|---|---|
| 112 | GACCCTCATTTGACCCTCCC | Transferrin_T89 gRNA spacer |
| 113 | CCATTAGGGCAACCTTCTAT | Transferrin_T16 gRNA spacer |
| 114 | ATGCATGAGGAGGGGCCACC | Transferrin_T155 gRNA spacer |
| 115 | GTCAGCCACTGCCCCATAGC | Transferrin_T108 gRNA spacer |
| 116 | CCTATGGGAACTCTGGAGGC | Transferrin_T160 gRNA spacer |
| 117 | ACTTCTGCCTGCCATTCATG | Transferrin_T139 gRNA spacer |
| 118 | CGGTGGCCGCCCGGGTTGCA | Transferrin_T11 gRNA spacer |
| 119 | GGGGACGTCAGCCTCTGAAA | Transferrin_T169 gRNA spacer |
| 120 | GAGGACACATTCTCGCCTAT | Transferrin_T5 gRNA spacer |
| 121 | GCATGGCATTCAAGGCCTCC | Transferrin_T131 gRNA spacer |
| 122 | CATCGAGCGGTCAGAGCATG | Transferrin_T22 gRNA spacer |
| 123 | CTCAACTACTGGCCAAGAAG | Transferrin_T126 gRNA spacer |
| 124 | CTGTGGTGGCCCACAAGGAG | Transferrin_T145 gRNA spacer |
| 125 | TCTGCTGGCCAGAGGGGTGC | Transferrin_T187 gRNA spacer |
| 126 | AGGCGAGAATGTGTCCTCAG | Transferrin_T112 gRNA spacer |
| 127 | GCTCGATGGCACCGCTTCCT | Transferrin_T14 gRNA spacer |
| 128 | GTCCTGGCCGGCTCCTCACC | Transferrin_T70 gRNA spacer |
| 129 | TTTCAGCTACCCCAACACAT | Transferrin_T57 gRNA spacer |
| 130 | GGGTAGCACCGCAGAGTCGC | Transferrin_T4 gRNA spacer |
| 131 | CCCTTCTTGGCCAGTAGTTG | Transferrin_T92 gRNA spacer |
| 132 | AAAGGGGAATGGTCAGACCC | Transferrin_T102 gRNA spacer |
| 133 | AGCTAGCAATTCCTTGAGAG | Transferrin_T159 gRNA spacer |
| 134 | CATGCACTCCGCGCTCAGGC | Transferrin_T10 gRNA spacer |
| 135 | TTGCCTCCTAGGATTTCCCA | Transferrin_T157 gRNA spacer |
| 136 | CATCACAGCACTTGCCTGGG | Transferrin_T173 gRNA spacer |

-continued

| SEQ ID | Sequence | Description |
|---|---|---|
| 137 | TGATGACCCCCTCCCTGGTG | Transferrin_T121 gRNA spacer |
| 138 | AGCAGATTGTCATCTCCAGC | Transferrin_T137 gRNA spacer |
| 139 | TCAAATGAGGGTCAGCGAGG | Transferrin_T98 gRNA spacer |
| 140 | TGGCCGGCTCCTCACCAGGG | Transferrin_T141 gRNA spacer |
| 141 | GATGGCAATTCCTCCCCCGC | Transferrin_T50 gRNA spacer |
| 142 | CAAGGAATTGCTAGCTTATG | Transferrin_T94 gRNA spacer |
| 143 | TAACGTGGGGTCCTCTCTCA | Transferrin_T86 gRNA spacer |
| 144 | AGTGCTCTGTGCGGGGATAA | Transferrin_T35 gRNA spacer |
| 145 | CATTTTCCCTCTTGGCCCAT | Transferrin_T174 gRNA spacer |
| 146 | TTCACTGCTGCAAGATTTAC | Transferrin_T97 gRNA spacer |
| 147 | GTGAGGAGCCGGCCAGGACT | Transferrin_T127 gRNA spacer |
| 148 | ATGTTGCACACATCCTGCTA | Transferrin_T56 gRNA spacer |
| 149 | TCAAGGAATTGCTAGCTTAT | Transferrin_T65 gRNA spacer |
| 150 | TCTTGGATCCAAGTCCTGGC | Transferrin_T123 gRNA spacer |
| 151 | TTCTGAGTTACACCCCTTCT | Transferrin_T59 gRNA spacer |
| 152 | TTCAGAGGCTGACGTCCCCT | Transferrin_T129 gRNA spacer |
| 153 | CCAATAGAAGGTTGCCCTAA | Transferrin_T9 gRNA spacer |
| 154 | CACTCCCCGACCTCCTGAGG | Transferrin_T122 gRNA spacer |
| 155 | CGCGTTCCCTGCAACCCGGG | Transferrin_T31 gRNA spacer |
| 156 | GATGGCACCGCTTCCTTGGC | Transferrin_T28 gRNA spacer |
| 157 | TATGAAGGGGGCCCCACCTC | Transferrin_T43 gRNA spacer |
| 158 | TGCTGTGATGACCCCCTCCC | Transferrin_T125 gRNA spacer |

-continued

| SEQ ID | Sequence | Description |
|---|---|---|
| 159 | CACATCCTGCTATGGGGCAG | Transferrin_T165 gRNA spacer |
| 160 | AGGCTGCGCGGTGGCCGCCC | Transferrin_T82 gRNA spacer |
| 161 | TGGGGCATTTGTCACACTGT | Transferrin_T109 gRNA spacer |
| 162 | CTCAAGGAATTGCTAGCTTA | Transferrin_T52 gRNA spacer |
| 163 | CTATGGAAAACCAGCGGGGG | Transferrin_T34 gRNA spacer |
| 164 | TGTTGCACACATCCTGCTAT | Transferrin_T88 gRNA spacer |
| 165 | AGAGGGAAAATGGGGGTCGC | Transferrin_T51 gRNA spacer |
| 166 | CTTATGTTCCATGGGGGGCC | Transferrin_T46 gRNA spacer |
| 167 | TCTGACCATTCCCCTTTCAG | Transferrin_T178 gRNA spacer |
| 168 | GGGGCATTTGTCACACTGTT | Transferrin_T74 gRNA spacer |
| 169 | CCGCGCTCAGGCTGGAAGCC | Transferrin_T176 gRNA spacer |
| 170 | GCGGTGGCCGCCCGGGTTGC | Transferrin_T54 gRNA spacer |
| 171 | TGCTTGTCGTTGGCCAAGCC | Transferrin_T32 gRNA spacer |
| 172 | TCCCTGGTGAGGAGCCGGCC | Transferrin_T136 gRNA spacer |
| 173 | TTATGTTCCATGGGGGGCCA | Transferrin_T78 gRNA spacer |
| 174 | TTTTAATAGTTACCCATGGC | Transferrin_T154 gRNA spacer |
| 175 | CCAGGCTTCCAGCCTGAGCG | Transferrin_T140 gRNA spacer |
| 176 | CAGGCTGCGCGGTGGCCGCC | Transferrin_T93 gRNA spacer |
| 177 | ATGTGTGCAACATCTGCCAC | Transferrin_T95 gRNA spacer |
| 178 | AGTGCATGCAGGCTGCGCGG | Transferrin_T37 gRNA spacer |
| 179 | ACTCCCCGACCTCCTGAGGT | Transferrin_T91 gRNA spacer |
| 180 | GAAAGGGGAATGGTCAGACC | Transferrin_T166 gRNA spacer |
| 181 | CGCGCTCAGGCTGGAAGCCT | Transferrin_T105 gRNA spacer |
| 182 | GTGTCTAGAAGCCCAAGCAA | Transferrin_T142 gRNA spacer |
| 183 | CCCGGGTTGCAGGGAACGCG | Transferrin_T25 gRNA spacer |

-continued

| SEQ ID | Sequence | Description |
|---|---|---|
| 184 | TTTCAGAGGCTGACGTCCCC | Transferrin_T135 gRNA spacer |
| 185 | GAGCTGTAGATGTCCTGCCA | Transferrin_T69 gRNA spacer |
| 186 | GGGTCATCACAGCACTTGCC | Transferrin_T147 gRNA spacer |
| 187 | GGATAAAGGCAAGTAACGTG | Transferrin_T33 gRNA spacer |
| 188 | TCTCCCTCAGCATAGGGAGT | Transferrin_T75 gRNA spacer |
| 189 | TAACAAGCAAGACCCGTCGC | mTF-T1 gRNA spacer |
| 190 | GAGAACGCACCACTTTACGA | mTF-T2 gRNA spacer |
| 191 | NNNNNNNNNNNNNNNNNNNNNRG | Example target seq. with *S. pyogenes* Cas9 PAM |
| 192 | GATTAAGGAGAGCAGACACA | FGA Intron 1_T61 gRNA spacer |
| 193 | GAGAGTGTACAAACTCACAA | FGA Intron 1_T30 gRNA spacer |
| 194 | TATCTTCAAATGGAAATCCT | FGA Intron 1_T57 gRNA spacer |
| 195 | ACCAAGGCTTTATAGGTACA | FGA Intron 1_T11 gRNA spacer |
| 196 | GGCCTGGGAGGAAATTTCCT | FGA Intron 1_T26 gRNA spacer |
| 197 | TTATTCCACAAAGAGCCTGG | FGA Intron 1_T33 gRNA spacer |
| 198 | CTTGACACCTCAAGAATACA | FGA Intron 1_T20 gRNA spacer |
| 199 | ATCTCTTCCTGGGGACTTGT | FGA Intron 1_T24 gRNA spacer |
| 200 | CACCCAGGAAATTTCCTCCC | FGA Intron 1_T27 gRNA spacer |
| 201 | AGGCCTGGGAGGAAATTTCC | FGA Intron 1_T48 gRNA spacer |
| 202 | ACTAGCATTATAATGCACCA | FGA Intron 1_T8 gRNA spacer |
| 203 | TACAAGTCCCCAGGAAGAGA | FGA Intron 1_T56 gRNA spacer |
| 204 | TGGCACTCTCACAGAGATTA | FGA Intron 1_T19 gRNA spacer |
| 205 | TTAGCCAGAAGAGGAGACAG | FGA Intron 1_T67 gRNA spacer |
| 206 | GAGAGTGCCATCTCTTCCTG | FGA Intron 1_T41 gRNA spacer |
| 207 | GTGAGAGTGCCATCTCTTCC | FGA Intron 1_T18 gRNA spacer |
| 208 | AGATTAAGGAGAGCAGACAC | FGA Intron 1_T45 gRNA spacer |

-continued

| SEQ ID | Sequence | Description |
|---|---|---|
| 209 | GGAGTTGTTATGAGAATTAA | FGA Intron 1_T66 gRNA spacer |
| 210 | TGGCATGCCTACAAGTCCCC | FGA Intron 1_T4 gRNA spacer |
| 211 | TTGAGGTGTCAAGCCCACCC | FGA Intron 1_T5 gRNA spacer |
| 212 | TATGAGAATTAAAGGAGACA | FGA Intron 1_T69 gRNA spacer |
| 213 | GGAGAGCAGACACAGGGCTT | FGA Intron 1_T54 gRNA spacer |
| 214 | TCTGACCTCCAGGCTCTTTG | FGA Intron 1_T42 gRNA spacer |
| 215 | GCAGGTAGACTCTGACCTCC | FGA Intron 1_T23 gRNA spacer |
| 216 | ACCAAGAGGAAGATCTTAGA | FGA Intron 1_T29 gRNA spacer |
| 217 | TCTACTGAAGCAGCAATTAC | FGA Intron 1_T13 gRNA spacer |
| 218 | TGAGAGTGCCATCTCTTCCT | FGA Intron 1_T25 gRNA spacer |
| 219 | TCAGAAGAGATTAGTTAGTA | FGA Intron 1_T16 gRNA spacer |
| 220 | AGTGTGTCAGGACATAGAGC | FGA Intron 1_T22 gRNA spacer |
| 221 | ACAGCAATGTTAGCCAGAAG | FGA Intron 1_T44 gRNA spacer |
| 222 | AGGCTTTATAGGTACAAGGA | FGA Intron 1_T14 gRNA spacer |
| 223 | CAGGGTAATATGACACCAAG | FGA Intron 1_T28 gRNA spacer |
| 224 | ATAATGCACCAAGGCTTTAT | FGA Intron 1_T7 gRNA spacer |
| 225 | TCCATCTAAGATCTTCCTCT | FGA Intron 1_T40 gRNA spacer |
| 226 | AAATCCTAGGACCCATTTTA | FGA Intron 1_T36 gRNA spacer |
| 227 | ACATTCAGTTAAGATAGTCT | FGA Intron 1_T15 gRNA spacer |
| 228 | CATGCCACTGTCTCCTCTTC | FGA Intron 1_T58 gRNA spacer |
| 229 | TCATAACAACTCCATAAAAT | FGA Intron 1_T63 gRNA spacer |
| 230 | TTCTATGTAACCTTTAGAGA | FGA Intron 1_T55 gRNA spacer |
| 231 | TTAAAAGAATACCATTACTG | FGA Intron 1_T50 gRNA spacer |
| 232 | CATATTACCCTGTATTCTTG | FGA Intron 1_T21 gRNA spacer |
| 233 | GCTTGACACCTCAAGAATAC | FGA Intron 1_T2 gRNA spacer |
| 234 | AAGGTTACATAGAAACTTGA | FGA Intron 1_T60 gRNA spacer |

-continued

| SEQ ID | Sequence | Description |
|---|---|---|
| 235 | GCAAGAAGAAAAAATGAAAA | FGA Intron 1_T77 gRNA spacer |
| 236 | ACTCTTAGCTTTATGACCCC | FGA Intron 1_T10 gRNA spacer |
| 237 | CTCATAACAACTCCATAAAA | FGA Intron 1_T64 gRNA spacer |
| 238 | AATACGCTTTTCCGCAGTAA | FGA Intron 1_T3 gRNA spacer |
| 239 | GAAATTTCCTCCCAGGCCTG | FGA Intron 1_T49 gRNA spacer |
| 240 | CTGGGAGGAAATTTCCTGGG | FGA Intron 1_T46 gRNA spacer |
| 241 | ACAGGGCTTCGGCAAGCTTC | FGA Intron 1_T1 gRNA spacer |
| 242 | TCCTTGTACCTATAAAGCCT | FGA Intron 1_T6 gRNA spacer |
| 243 | TGGGAGGAAATTTCCTGGGT | FGA Intron 1_T37 gRNA spacer |
| 244 | ACTAAAAGTTCTGCTTATTA | FGA Intron 1_T52 gRNA spacer |
| 245 | ATAAGCATTTGATAAATATT | FGA Intron 1_T71 gRNA spacer |
| 246 | AACTCCATAAAATGGGTCCT | FGA Intron 1_T12 gRNA spacer |
| 247 | AATTATGAATCCATCTCTAA | FGA Intron 1_T47 gRNA spacer |
| 248 | GTTAGTACAGTTTTGCTGAA | FGA Intron 1_T43 gRNA spacer |
| 249 | TGAGAGTGTACAAACTCACA | FGA Intron 1_T39 gRNA spacer |
| 250 | AAACAAAACAAAACAAAATG | FGA Intron 1_T76 gRNA spacer |
| 251 | TAGCTTTATGACCCCAGGCC | FGA Intron 1_T17 gRNA spacer |
| 252 | TTTATGACCCCAGGCCTGGG | FGA Intron 1_T38 gRNA spacer |
| 253 | AAAAGCAAACGAATTATCTT | FGA Intron 1_T51 gRNA spacer |
| 254 | CATAAAGCTAAGAGTGTGTC | FGA Intron 1_T9 gRNA spacer |
| 255 | CATAGAAACTTGAAGGAGAG | FGA Intron 1_T62 gRNA spacer |
| 256 | ATTCAAATAATTTTCCTTTT | FGA Intron 1_T74 gRNA spacer |
| 257 | TGCATTATAATGCTAGTTAA | FGA Intron 1_T34 gRNA spacer |
| 258 | AGTCATTAGTAAAAATGAAA | FGA Intron 1_T70 gRNA spacer |
| 259 | TGTTTATTCCACAAAGAGCC | FGA Intron 1_T31 gRNA spacer |

-continued

| SEQ ID | Sequence | Description |
|---|---|---|
| 260 | TTTAAAGAATCCATCCTAAA | FGA Intron 1_T59 gRNA spacer |
| 261 | TAATGGAATAAAACATTTTA | FGA Intron 1_T72 gRNA spacer |
| 262 | AAATAATTTTCCTTTTAGGA | FGA Intron 1_T65 gRNA spacer |
| 263 | GTTTTGTTTTGTTTTAAAAA | FGA Intron 1_T79 gRNA spacer |
| 264 | AGCTTTATGACCCCAGGCCT | FGA Intron 1_T32 gRNA spacer |
| 265 | TCAGGTTTCTTATCTTCAAA | FGA Intron 1_T68 gRNA spacer |
| 266 | AGCAAGAAGAAAAAATGAAA | FGA Intron 1_T75 gRNA spacer |
| 267 | TGTTTTGTTTTGTTTTAAAA | FGA Intron 1_T78 gRNA spacer |
| 268 | GGAAATTTCCTCCCAGGCCT | FGA Intron 1_T35 gRNA spacer |
| 269 | AGGAAATTTCCTCCCAGGCC | FGA Intron 1_T53 gRNA spacer |
| 270 | TTTTCTTCTTGCTTTCTCTC | FGA Intron 1_T73 gRNA spacer |
| 271 | TAATTTTCTTTTGCGCACTAAGG | Human Albumin Intron-1_T1 |
| 272 | TAGTGCAATGGATAGGTCTTTGG | Human Albumin Intron-1_T2 |
| 273 | AGTGCAATGGATAGGTCTTTGGG | Human Albumin Intron-1_T3 |
| 274 | TAAAGCATAGTGCAATGGATAGG | Human Albumin Intron-1_T4 |
| 275 | ATTTATGAGATCAACAGCACAGG | Human Albumin Intron-1_T5 |
| 276 | TGATTCCTACAGAAAAACTCAGG | Human Albumin Intron-1_T6 |
| 277 | TGTATTTGTGAAGTCTTACAAGG | Human Albumin Intron-1_T7 |
| 278 | GACTGAAACTTCACAGAATAGGG | Human Albumin Intron-1_T8 |
| 279 | AATGCATAATCTAAGTCAAATGG | Human Albumin Intron-1_T9 |
| 280 | TGACTGAAACTTCACAGAATAGG | Human Albumin Intron-1_T10 |
| 281 | TTAAATAAAGCATAGTGCAATGG | Human Albumin Intron-1_T11 |
| 282 | GATCAACAGCACAGGTTTTGTGG | Human Albumin Intron-1_T12 |
| 283 | TAATAAAATTCAAACATCCTAGG | Human Albumin Intron-1_T13 |
| 284 | TTCATTTTAGTCTGTCTTCTTGG | Human Albumin Intron-1_T14 |

-continued

| SEQ ID | Sequence | Description |
|---|---|---|
| 285 | ATTATCTAAGTTTGAATATAAGG | Human Albumin Intron-1_T15 |
| 286 | ATCATCCTGAGTTTTTCTGTAGG | Human Albumin Intron-1_T16 |
| 287 | GCATCTTTAAAGAATTATTTTGG | Human Albumin Intron-1_T17 |
| 288 | TACTAAAACTTTATTTTACTGGG | Human Albumin Intron-1_T18 |
| 289 | TGAATTATTCTTCTGTTTAAAGG | Human Albumin Intron-1_T19 |
| 290 | AATTTTTAAAATAGTATTCTTGG | Human Albumin Intron-1_T20 |
| 291 | ATGCATTTGTTTCAAAATATTGG | Human Albumin Intron-1_T21 |
| 292 | TTTGGCATTTATTTCTAAAATGG | Human Albumin Intron-1_T22 |
| 293 | AAAGTTGAACAATAGAAAAATGG | Human Albumin Intron-1_T23 |
| 294 | TTACTAAAACTTTATTTTACTGG | Human Albumin Intron-1_T24 |
| 295 | TGCATTTGTTTCAAAATATTGGG | Human Albumin Intron-1_T26 |
| 296 | TGGGCAAGGGAAGAAAAAAAAGG | Human Albumin Intron-1_T27 |
| 297 | TCCTAGGTAAAAAAAAAAAAAGG | Human Albumin Intron-1_T28 |
| 298 | ACCTTTTTTTTTTTTTACCTAGG | Human Albumin Intron-1_T25 |
| 299 | UAAUUUUCUUUUGCGCACUA | Exemplary gRNA spacer |
| 300 | DAHATRRYY | N-terminal sequence |
| 301 | AATTGCTGACCTCTTCTCTTCCTCCCACAGTGGCCACCAGAAGATACTA CCTCGGAGCCGTCGAATTGAGCTGGGATTACATGCAATCCGACCTGGGA GAACTGCCCGTGGATGCCAGGTTTCCTCCTCGGGTCCCCAAGTCCTTCC CGTTCAACACCTCAGTCGTCTACAAGAAAACCCTCTTCGTGGAGTTCAC CGACCATCTGTTCAACATCGCCAAGCCAAGACCCCCGTGGATGGGACTC CTCGGTCCGACCATCCAAGCCGAAGTGTACGACACTGTGGTCATTACCC TGAAGAACATGGCCTCCCATCCTGTGTCCCTGCATGCAGTGGGCGTGTC CTACTGGAAGGCTTCCGAAGGGGCCGAGTACGACGATCAAACCAGCCAG CGGGAAAAGGAGGATGACAAAGTGTTCCCGGGTGGTTCGCACACCTACG TGTGGCAAGTGCTCAAGGAGAACGGTCCTATGGCCTCTGATCCCCTGTG TCTGACCTACTCCTACCTGTCCCATGTCGACCTCGTGAAGGATCTGAAC AGCGGGCTGATTGGCGCCCTGCTCGTGTGCCGGGAAGGCTCCCTGGCCA AGGAAAAGACCCAGACACTGCACAAGTTCATCTTGCTGTTCGCCGTGTT TGATGAGGGAAAGTCCTGGCATAGCGAGACTAAGAACTCCCTTATGCAA GACCGGGATGCTGCCTCCGCTAGGGCTTGGCCTAAGATGCATACTGTGA ACGGATACGTGAACAGATCCCTGCCTGGCCTTATCGGTTGCCACCGGAA GTCCGTGTATTGGCATGTGATCGGCATGGGAACCACTCCAGAGGTGCAC TCCATTTTCTTGGAGGGGCATACCTTCTTGGTGCGCAACCACAGACAGG CCTCCCTGGAAATTTCTCCGATCACTTTCCTGACTGCCCAGACCCTCCT TATGGACCTGGGTCAGTTCCTGCTGTTCTGCCACATTTCGTCCCACCAA CACGATGGCATGGAAGCCTACGTGAAAGTGGACTCGTGCCCGGAAGAAC CACAGCTGCGGATGAAGAACAACGAAGAGGCAGAGGACTACGATGATGA TCTTACCGATTCGGAAATGGATGTGGTCCGATTCGACGACGATAATAGC CCATCCTTCATCCAAATTAGGAGCGTGGCCAAGAAGCACCCCAAAACTT GGGTGCATTACATTGCGGCCGAGGAAGAGGATTGGGACTACGCACCCCT CGTGCTTGCACCCGATGATCGGTCCTACAAGTCCCAATACCTGAACAAC GGCCCGCAGAGGATCGGTCGGAAGTATAAGAAAGTGCGCTTCATGGCCT ACACCGACGAGACTTTCAAGACCAGAGAGGCCATTCAGCACGAAAGCGG CATTCTGGGGCCGCTGTTGTACGGGGAGGTCGGAGATACACTGCTCATC | MAB8A |

-continued

| SEQ ID | Sequence | Description |
|---|---|---|
| | ATTTTCAAGAACCAGGCGTCCAGACCCTACAACATCTACCCGCACGGAA<br>TCACTGACGTCCGCCCCCTGTACTCCCGGAGACTCCCGAAGGGAGTCAA<br>GCACTTGAAAGACTTCCCCATCCTGCCTGGGGAAATCTTCAAGTACAAG<br>TGGACCGTGACCGTCGAGGATGGGCCGACCAAGTCCGATCCAAGATGCC<br>TCACTAGATACTACTCATCCTTCGTCAACATGGAACGGGACCTGGCCTC<br>AGGACTGATTGGCCCCCTGCTCATCTGCTACAAGGAGTCCGTGGATCAG<br>CGCGGAAACCAGATCATGTCGGACAAACGCAACGTCATCCTCTTCTCCG<br>TCTTTGACGAGAACCGCTCATGGTACCTTACGGAGAACATCCAGCGGTT<br>CCTCCCCAACCCTGCCGGAGTGCAGCTCGAGGACCCGGAATTCCAGGCA<br>TCAAACATTATGCACTCCATCAACGGTTACGTGTTCGACAGCCTCCAGC<br>TTAGCGTGTGCCTCCATGAAGTCGCATATTGGTACATCCTGTCCATTGG<br>AGCACAAACCGACTTTCTCTCCGTGTTCTTCTCCGGATATACCTTCAAG<br>CACAAGATGGTGTACGAGGATACCCTGACCCTCTTCCCCTTCTCCGGAG<br>AGACTGTGTTTATGTCGATGGAAAACCCAGGCCTGTGGATTTTGGGGTG<br>CCACAACTCGGATTTCCGAAACCGGGGCATGACTGCCTTGCTCAAGGTG<br>TCCTCCTGTGACAAGAACACGGGAGACTACTACGAGGACTCCTACGAGG<br>ATATTTCCGCCTACCTCCTGTCCAAGAACAACGCCATCGAACCCAGGTC<br>CTTCAGCCAGAACCCTCCTGTCCTCAAGCGCCATCAGAGAGAAATCACC<br>CGCACGACCCTGCAGTCCGACCAGGAAGAGATCGATTACGACGACACTA<br>TCTCCGTCGAAATGAAGAAGGAGGACTTTGACATCTACGACGAAGATGA<br>AAATCAGTCCCCTCGCTCGTTCCAAAAGAAAACGAGACACTACTTCATC<br>GCTGCTGTGGAGCGGCTCTGGGACTACGGCATGTCCTCATCGCCCCACG<br>TGCTTAGGAACCGGGCTCAATCCGGGAGCGTCCCTCAGTTCAAGAAAGT<br>GGTGTTTCAAGAATTCACCGATGGAAGCTTCACGCAGCCGTTGTACAGG<br>GGCGAACTGAACGAGCACCTTGGCCTGCTGGGACCTTACATCAGAGCAG<br>AGGTCGAGGACAACATCATGGTGACCTTCCGGAACCAAGCCTCCCGGCC<br>ATATTCATTCTACTCGAGCCTTATCTCATACGAGGAGGATCAGAGACAG<br>GGGGCTGAACCTCGGAAGAACTTCGTCAAGCCGAACGAGACAAAGACCT<br>ACTTTTGGAAGGTGCAGCACCACATGGCCCCGACCAAGGATGAGTTCGA<br>CTGCAAGGCCTGGGCGTACTTCTCCGACGTGGATCTCGAAAAGGACGTG<br>CATTCCGGGCTGATCGGACCGCTGCTCGTCTGCCACACTAACACCCTCA<br>ATCCTGCTCACGGCAGACAAGTGACCGTGCAGGAGTTCGCCCTGTTCTT<br>CACCATCTTCGACGAAACTAAGTCATGGTACTTTACCGAGAACATGGAG<br>CGGAATTGTCGGGCCCCATGTAACATCCAGATGGAGGACCCGACATTCA<br>AGGAGAACTACCGGTTCCACGCCATTAACGGATACATTATGGACACTCT<br>TCCGGGACTCGTGATGGCACAGGACCAACGCATCAGATGGTATCTTCTG<br>TCGATGGGGAGCAACGAAAACATCCATTCGATCCACTTTAGCGGTCACG<br>TGTTCACAGTGCGCAAGAAGGAAGAGTACAAGATGGCGCTGTACAACCT<br>GTACCCTGGGGTGTTCGAGACTGTGGAAATGCTGCCGTCCAAGGCCGGA<br>ATTTGGCGCGTGGAATGTCTGATCGGTGAACATCTGCATGCCGGAATGT<br>CCACCCTGTTCCTGGTGTACTCCAACAAGTGCCAAACCCCACTGGGAAT<br>GGCATCAGGACACATTAGAGACTTCCAGATTACCGCGAGCGGACAGTAC<br>GGACAATGGGCCCCCAAGTTGGCCAGGCTGCACTACTCTGGAAGCATTA<br>ACGCCTGGAGCACCAAGGAGCCGTTCAGCTGGATCAAGGTGGACCTTCT<br>GGCGCCAATGATCATCCACGGAATTAAGACTCAGGGAGCCCGCCAGAAG<br>TTCTCATCGCTCTACATCTCCCAGTTTATCATCATGTACTCACTGGATG<br>GGAAGAAGTGGCAGACTTACCGGGGAAATTCCACCGGTACTCTGATGGT<br>GTTCTTCGGAAACGTGGACAGCTCCGGCATCAAGCACAATATCTTTAAC<br>CCGCCTATCATCGCCCGATACATCCGGCTCCACCCGACTCACTACTCCA<br>TCCGGTCGACTCTGCGGATGGAACTCATGGGTTGCGACCTCAACTCCTG<br>CTCAATGCCACTGGGCATGGAGTCCAAGGCTATCTCGGACGCTCAGATT<br>ACTGCATCGTCGTACTTTACCAACATGTTCGCTACCTGGTCCCCGTCCA<br>AAGCCCGGCTGCATCTCCAAGGCAGATCAAACGCGTGGAGGCCTCAGGT<br>CAACAACCCGAAGGAATGGCTTCAGGTCGACTTCCAAAAGACCATGAAA<br>GTCACCGGAGTGACCACCCAGGGCGTGAAATCGCTGCTGACCTCTATGT<br>ACGTGAAGGAATTCCTGATCTCATCAAGCCAGGACGGCCACCAGTGGAC<br>ACTGTTCTTCCAAAATGGAAAGGTCAAGGTCTTTCAGGGAAATCAAGAC<br>TCCTTCACCCCCGTGGTGAACTCCCTGGACCCCCCTCTGCTTACCCGCT<br>ACTTGCGCATTCATCCGCAATCCTGGGTGCACCAGATCGCCCTGCGAAT<br>GGAAGTGCTGGGCTGTGAAGCGCAGGACCTGTACTAAAATAAAAGATCT<br>TTATTTTCATTAGATCTGTGTGTTGGTTTTTTGTGTGCCGC | |
| 302 | T/CNC/TT/CA/GAC/T | Branch site consensus sequence |
| 303 | ctgacctcttctcttcctcccacag | synthetic splice acceptor |
| 304 | TTAACAATCCTTTTTTTTCTTCCCTTGCCCAG | native albumin intron 1/exon 2 splice acceptor, human |
| 305 | ttaaatatgttgtgtggtttttctctccctgtttccacag | native albumin intron 1/exon 2 splice acceptor, mouse |

-continued

| SEQ ID | Sequence | Description |
|---|---|---|
| 306 | AATAAAAGATCTTTATTTTCATTAGATCTGTGTGTTGGTTTTTTGTGTG | consensus synthetic poly A signal |
| 307 | ACTAAAGAATTATTCTTTTACATTTCAG | Native splice acceptor sequence from human Factor IX gene intron 1/exon 2 boundary |
| 308 | AATTGAACTTTGAGTGTAGCAGAGAGGAACCATTGCCACCTTCAGATTT<br>TAATGTCTGACCTCTTCTCTTCCTCCCACAGTGGCCACCAGAAGATACT<br>ACCTCGGAGCCGTCGAATTGAGCTGGGATTACATGCAATCCGACCTGGG<br>AGAACTGCCCGTGGATGCCAGGTTTCCTCCTCGGGTCCCCAAGTCCTTC<br>CCGTTCAACACCTCAGTCGTCTACAAGAAAACCCTCTTCGTGGAGTTCA<br>CCGACCATCTGTTCAACATCGCCAAGCCAAGACCCCCGTGGATGGGACT<br>CCTCGGTCCGACCATCCAAGCCGAAGTGTACGACACTGTGGTCATTACC<br>CTGAAGAACATGGCCTCCCATCCTGTGTCCCTGCATGCAGTGGGCGTGT<br>CCTACTGGAAGGCTTCCGAAGGGGCCGAGTACGACGATCAAACCAGCCA<br>GCGGGAAAAGGAGGATGACAAAGTGTTCCCGGGTGGTTCGCACACCTAC<br>GTGTGGCAAGTGCTCAAGGAGAACGGTCCTATGGCCTCTGATCCCCTGT<br>GTCTGACCTACTCCTACCTGTCCCATGTCGACCTCGTGAAGGATCTGAA<br>CAGCGGGCTGATTGGCGCCCTGCTCGTGTGCCGGGAAGGCTCCCTGGCC<br>AAGGAAAAGACCCAGACACTGCACAAGTTCATCTTGCTGTTCGCCGTGT<br>TTGATGAGGGAAAGTCCTGGCATAGCGAGACTAAGAACTCCCTTATGCA<br>AGACCGGGATGCTGCCTCCGCTAGGGCTTGGCCTAAGATGCATACTGTG<br>AACGGATACGTGAACAGATCCCTGCCTGGCCTTATCGGTTGCCACCGGA<br>AGTCCGTGTATTGGCATGTGATCGGCATGGGAACCACTCCAGAGGTGCA<br>CTCCATTTTCTTGGAGGGGCATACCTTCTTGGTGCGCAACCACAGACAG<br>GCCTCCCTGGAAATTTCTCCGATCACTTTCCTGACTGCCCAGACCCTCC<br>TTATGGACCTGGGTCAGTTCCTGCTGTTCTGCCACATTTCGTCCCACCA<br>ACACGATGGCATGGAAGCCTACGTGAAAGTGGACTCGTGCCCGGAAGAA<br>CCACAGCTGCGGATGAAGAACAACGAAGAGGCAGAGGACTACGATGATG<br>ATCTTACCGATTCGGAAATGGATGTGGTCCGATTCGACGACGATAATAG<br>CCCATCCTTCATCCAAATTAGGAGCGTGGCCAAGAAGCACCCCAAAACT<br>TGGGTGCATTACATTGCGGCCGAGGAAGAGGATTGGGACTACGCACCCC<br>TCGTGCTTGCACCCGATGATCGGTCCTACAAGTCCCAATACCTGAACAA<br>CGGCCCGCAGAGGATCGGTCGGAAGTATAAGAAAGTGCGCTTCATGGCC<br>TACACCGACGAGACTTTCAAGACCAGAGAGGCCATTCAGCACGAAAGCG<br>GCATTCTGGGGCCGCTGTTGTACGGGGAGGTCGGAGATACACTGCTCAT<br>CATTTTCAAGAACCAGGCGTCCAGACCCTACAACATCTACCCGCACGGA<br>ATCACTGACGTCCGCCCCCTGTACTCCCGGAGACTCCCGAAGGGAGTCA<br>AGCACTTGAAAGACTTCCCCATCCTGCCTGGGGAAATCTTCAAGTACAA<br>GTGGACCGTGACCGTCGAGGATGGGCCGACCAAGTCCGATCCAAGATGC<br>CTCACTAGATACTACTCATCCTTCGTCAACATGGAACGGGACCTGGCCT<br>CAGGACTGATTGGCCCCCTGCTCATCTGCTACAAGGAGTCCGTGGATCA<br>GCGCGGAAACCAGATCATGTCGGACAAACGCAACGTCATCCTCTTCTCC<br>GTCTTTGACGAGAACCGCTCATGGTACCTTACGGAGAACATCCAGCGGT<br>TCCTCCCCAACCCTGCCGGAGTGCAGCTCGAGGACCCGGAATTCCAGGC<br>ATCAAACATTATGCACTCCATCAACGGTTACGTGTTCGACAGCCTCCAG<br>CTTAGCGTGTGCCTCCATGAAGTCGCATATTGGTACATCCTGTCCATTG<br>GAGCACAAACCGACTTTCTCTCCGTGTTCTTCTCCGGATATACCTTCAA<br>GCACAAGATGGTGTACGAGGATACCCTGACCCTCTTCCCCTTCTCCGGA<br>GAGACTGTGTTTATGTCGATGGAAAACCCAGGCCTGTGGATTTTGGGGT<br>GCCACAACTCGGATTTCCGAAACCGGGGCATGACTGCCTTGCTCAAGGT<br>GTCCTCCTGTGACAAGAACACGGGAGACTACTACGAGGACTCCTACGAG<br>GATATTTCCGCCTACCTCCTGTCCAAGAACAACGCCATCGAACCCAGGT<br>CCTTCAGCCAGAACCCTCCTGTCCTCAAGCGCCATCAGAGAGAAATCAC<br>CCGCACGACCCTGCAGTCCGACCAGGAAGAGATCGATTACGACGACACT<br>ATCTCCGTCGAAATGAAGAAGGAGGACTTTGACATCTACGACGAAGATG<br>AAAATCAGTCCCCTCGCTCGTTCCAAAAGAAAACGAGACACTACTTCAT<br>CGCTGCTGTGGAGCGGCTCTGGGACTACGGCATGTCCTCATCGCCCCAC<br>GTGCTTAGGAACCGGGCTCAATCCGGGAGCGTCCCTCAGTTCAAGAAAG<br>TGGTGTTTCAAGAATTCACCGATGGAAGCTTCACGCAGCCGTTGTACAG<br>GGGCGAACTGAACGAGCACCTTGGCCTGCTGGGACCTTACATCAGAGCA<br>GAGGTCGAGGACAACATCATGGTGACCTTCCGGAACCAAGCCTCCCGGC<br>CATATTCATTCTACTCGAGCCTTATCTCATACGAGGAGGATCAGAGACA<br>GGGGGCTGAACCTCGGAAGAACTTCGTCAAGCCGAACGAGACAAAGACC<br>TACTTTTGGAAGGTGCAGCACCACATGGCCCCGACCAAGGATGAGTTCG<br>ACTGCAAGGCCTGGGCGTACTTCTCCGACGTGGATCTCGAAAAGGACGT<br>GCATTCCGGGCTGATCGGACCGCTGCTCGTCTGCCACACTAACACCCTC<br>AATCCTGCTCACGGCAGACAAGTGACCGTGCAGGAGTTCGCCCTGTTCT<br>TCACCATCTTCGACGAAACTAAGTCATGGTACTTTACCGAGAACATGGA<br>GCGGAATTGTCGGGCCCCATGTAACATCCAGATGGAGGACCCGACATTC<br>AAGGAGAACTACCGGTTCCACGCCATTAACGGATACATTATGGACACTC<br>TTCCGGGACTCGTGATGGCACAGGACCAACGCATCAGATGGTATCTTCT<br>GTCGATGGGGAGCAACGAAAACATCCATTCGATCCACTTTAGCGGTCAC | MAB8B |

-continued

| SEQ ID | Sequence | Description |
|---|---|---|
| | GTGTTCACAGTGCGCAAGAAGGAAGAGTACAAGATGGCGCTGTACAACC<br>TGTACCCTGGGGTGTTCGAGACTGTGGAAATGCTGCCGTCCAAGGCCGG<br>AATTTGGCGCGTGGAATGTCTGATCGGTGAACATCTGCATGCCGGAATG<br>TCCACCCTGTTCCTGGTGTACTCCAACAAGTGCCAAACCCCACTGGGAA<br>TGGCATCAGGACACATTAGAGACTTCCAGATTACCGCGAGCGGACAGTA<br>CGGACAATGGGCCCCCAAGTTGGCCAGGCTGCACTACTCTGGAAGCATT<br>AACGCCTGGAGCACCAAGGAGCCGTTCAGCTGGATCAAGGTGGACCTTC<br>TGGCGCCAATGATCATCCACGGAATTAAGACTCAGGGAGCCCGCCAGAA<br>GTTCTCATCGCTCTACATCTCCCAGTTTATCATCATGTACTCACTGGAT<br>GGGAAGAAGTGGCAGACTTACCGGGGAAATTCCACCGGTACTCTGATGG<br>TGTTCTTCGGAAACGTGGACAGCTCCGGCATCAAGCACAATATCTTTAA<br>CCCGCCTATCATCGCCCGATACATCCGGCTCCACCCGACTCACTACTCC<br>ATCCGGTCGACTCTGCGGATGGAACTCATGGGTTGCGACCTCAACTCCT<br>GCTCAATGCCACTGGGCATGGAGTCCAAGGCTATCTCGGACGCTCAGAT<br>TACTGCATCGTCGTACTTTACCAACATGTTCGCTACCTGGTCCCCGTCC<br>AAAGCCCGGCTGCATCTCCAAGGCAGATCAAACGCGTGGAGGCCTCAGG<br>TCAACAACCCGAAGGAATGGCTTCAGGTCGACTTCCAAAAGACCATGAA<br>AGTCACCGGAGTGACCACCCAGGGCGTGAAATCGCTGCTGACCTCTATG<br>TACGTGAAGGAATTCCTGATCTCATCAAGCCAGGACGGCCACCAGTGGA<br>CACTGTTCTTCCAAAATGGAAAGGTCAAGGTCTTTCAGGGAAATCAAGA<br>CTCCTTCACCCCCGTGGTGAACTCCCTGGACCCCCCTCTGCTTACCCGC<br>TACTTGCGCATTCATCCGCAATCCTGGGTGCACCAGATCGCCCTGCGAA<br>TGGAAGTGCTGGGCTGTGAAGCGCAGGACCTGTACTAAAATAAAAGATC<br>TTTATTTTCATTAGATCTGTGTGTTGGTTTTTTGTGTGCGATCGGGAAC<br>TGGCATCTTCAGGGAGTAGCTTAGGTCAGTGAAGAGAAGCCGC | |
| 309 | gcggcctaaggcAATTGTGCCAGTTCCCGATCGTTACAGGAACTTTGAG<br>TGTAGCAGAGAGGAACCATTGCCACCTTCAGATTTTAATGTCTGACCTC<br>TTCTCTTCCTCCCACAGTGGCCACCAGAAGATACTACCTCGGAGCCGTC<br>GAATTGAGCTGGGATTACATGCAATCCGACCTGGGAGAACTGCCCGTGG<br>ATGCCAGGTTTCCTCCTCGGGTCCCCAAGTCCTTCCCGTTCAACACCTC<br>AGTCGTCTACAAGAAAACCCTCTTCGTGGAGTTCACCGACCATCTGTTC<br>AACATCGCCAAGCCAAGACCCCCGTGGATGGGACTCCTCGGTCCGACCA<br>TCCAAGCCGAAGTGTACGACACTGTGGTCATTACCCTGAAGAACATGGC<br>CTCCCATCCTGTGTCCCTGCATGCAGTGGGCGTGTCCTACTGGAAGGCT<br>TCCGAAGGGGCCGAGTACGACGATCAAACCAGCCAGCGGGAAAAGGAGG<br>ATGACAAAGTGTTCCCGGGTGGTTCGCACACCTACGTGTGGCAAGTGCT<br>CAAGGAGAACGGTCCTATGGCCTCTGATCCCCTGTGTCTGACCTACTCC<br>TACCTGTCCCATGTCGACCTCGTGAAGGATCTGAACAGCGGGCTGATTG<br>GCGCCCTGCTCGTGTGCCGGGAAGGCTCCCTGGCCAAGGAAAAGACCCA<br>GACACTGCACAAGTTCATCTTGCTGTTCGCCGTGTTTGATGAGGGAAAG<br>TCCTGGCATAGCGAGACTAAGAACTCCCTTATGCAAGACCGGGATGCTG<br>CCTCCGCTAGGGCTTGGCCTAAGATGCATACTGTGAACGGATACGTGAA<br>CAGATCCCTGCCTGGCCTTATCGGTTGCCACCGGAAGTCCGTGTATTGG<br>CATGTGATCGGCATGGGAACCACTCCAGAGGTGCACTCCATTTTCTTGG<br>AGGGGCATACCTTCTTGGTGCGCAACCACAGACAGGCCTCCCTGGAAAT<br>TTCTCCGATCACTTTCCTGACTGCCCAGACCCTCCTTATGGACCTGGGT<br>CAGTTCCTGCTGTTCTGCCACATTTCGTCCCACCAACACGATGGCATGG<br>AAGCCTACGTGAAAGTGGACTCGTGCCCGGAAGAACCACAGCTGCGGAT<br>GAAGAACAACGAAGAGGCAGAGGACTACGATGATGATCTTACCGATTCG<br>GAAATGGATGTGGTCCGATTCGACGACGATAATAGCCCATCCTTCATCC<br>AAATTAGGAGCGTGGCCAAGAAGCACCCCAAAACTTGGGTGCATTACAT<br>TGCGGCCGAGGAAGAGGATTGGGACTACGCACCCCTCGTGCTTGCACCC<br>GATGATCGGTCCTACAAGTCCCAATACCTGAACAACGGCCCGCAGAGGA<br>TCGGTCGGAAGTATAAGAAAGTGCGCTTCATGGCCTACACCGACGAGAC<br>TTTCAAGACCAGAGAGGCCATTCAGCACGAAAGCGGCATTCTGGGGCCG<br>CTGTTGTACGGGGAGGTCGGAGATACACTGCTCATCATTTTCAAGAACC<br>AGGCGTCCAGACCCTACAACATCTACCCGCACGGAATCACTGACGTCCG<br>CCCCCTGTACTCCCGGAGACTCCCGAAGGGAGTCAAGCACTTGAAAGAC<br>TTCCCCATCCTGCCTGGGGAAATCTTCAAGTACAAGTGGACCGTGACCG<br>TCGAGGATGGGCCGACCAAGTCCGATCCAAGATGCCTCACTAGATACTA<br>CTCATCCTTCGTCAACATGGAACGGGACCTGGCCTCAGGACTGATTGGC<br>CCCCTGCTCATCTGCTACAAGGAGTCCGTGGATCAGCGCGGAAACCAGA<br>TCATGTCGGACAAACGCAACGTCATCCTCTTCTCCGTCTTTGACGAGAA<br>CCGCTCATGGTACCTTACGGAGAACATCCAGCGGTTCCTCCCCAACCCT<br>GCCGGAGTGCAGCTCGAGGACCCGGAATTCCAGGCATCAAACATTATGC<br>ACTCCATCAACGGTTACGTGTTCGACAGCCTCCAGCTTAGCGTGTGCCT<br>CCATGAAGTCGCATATTGGTACATCCTGTCCATTGGAGCACAAACCGAC<br>TTTCTCTCCGTGTTCTTCTCCGGATATACCTTCAAGCACAAGATGGTGT<br>ACGAGGATACCCTGACCCTCTTCCCCTTCTCCGGAGAGACTGTGTTTAT<br>GTCGATGGAAAACCCAGGCCTGTGGATTTTGGGGTGCCACAACTCGGAT<br>TTCCGAAACCGGGGCATGACTGCCTTGCTCAAGGTGTCCTCCTGTGACA<br>AGAACACGGGAGACTACTACGAGGACTCCTACGAGGATATTTCCGCCTA<br>CCTCCTGTCCAAGAACAACGCCATCGAACCCAGGTCCTTCAGCCAGAAC<br>CCTCCTGTCCTCAAGCGCCATCAGAGAGAAATCACCCGCACGACCCTGC<br>AGTCCGACCAGGAAGAGATCGATTACGACGACACTATCTCCGTCGAAAT<br>GAAGAAGGAGGACTTTGACATCTACGACGAAGATGAAAATCAGTCCCCT | MAB8C |

-continued

| SEQ ID | Sequence | Description |
|---|---|---|
| | CGCTCGTTCCAAAAGAAAACGAGACACTACTTCATCGCTGCTGTGGAGC<br>GGCTCTGGGACTACGGCATGTCCTCATCGCCCCACGTGCTTAGGAACCG<br>GGCTCAATCCGGGAGCGTCCCTCAGTTCAAGAAAGTGGTGTTTCAAGAA<br>TTCACCGATGGAAGCTTCACGCAGCCGTTGTACAGGGGCGAACTGAACG<br>AGCACCTTGGCCTGCTGGGACCTTACATCAGAGCAGAGGTCGAGGACAA<br>CATCATGGTGACCTTCCGGAACCAAGCCTCCCGGCCATATTCATTCTAC<br>TCGAGCCTTATCTCATACGAGGAGGATCAGAGACAGGGGGCTGAACCTC<br>GGAAGAACTTCGTCAAGCCGAACGAGACAAAGACCTACTTTTGGAAGGT<br>GCAGCACCACATGGCCCCGACCAAGGATGAGTTCGACTGCAAGGCCTGG<br>GCGTACTTCTCCGACGTGGATCTCGAAAAGGACGTGCATTCCGGGCTGA<br>TCGGACCGCTGCTCGTCTGCCACACTAACACCCTCAATCCTGCTCACGG<br>CAGACAAGTGACCGTGCAGGAGTTCGCCCTGTTCTTCACCATCTTCGAC<br>GAAACTAAGTCATGGTACTTTACCGAGAACATGGAGCGGAATTGTCGGG<br>CCCCATGTAACATCCAGATGGAGGACCCGACATTCAAGGAGAACTACCG<br>GTTCCACGCCATTAACGGATACATTATGGACACTCTTCCGGGACTCGTG<br>ATGGCACAGGACCAACGCATCAGATGGTATCTTCTGTCGATGGGGAGCA<br>ACGAAAACATCCATTCGATCCACTTTAGCGGTCACGTGTTCACAGTGCG<br>CAAGAAGGAAGAGTACAAGATGGCGCTGTACAACCTGTACCCTGGGGTG<br>TTCGAGACTGTGGAAATGCTGCCGTCCAAGGCCGGAATTTGGCGCGTGG<br>AATGTCTGATCGGTGAACATCTGCATGCCGGAATGTCCACCCTGTTCCT<br>GGTGTACTCCAACAAGTGCCAAACCCCACTGGGAATGGCATCAGGACAC<br>ATTAGAGACTTCCAGATTACCGCGAGCGGACAGTACGGACAATGGGCCC<br>CCAAGTTGGCCAGGCTGCACTACTCTGGAAGCATTAACGCCTGGAGCAC<br>CAAGGAGCCGTTCAGCTGGATCAAGGTGGACCTTCTGGCGCCAATGATC<br>ATCCACGGAATTAAGACTCAGGGAGCCCGCCAGAAGTTCTCATCGCTCT<br>ACATCTCCCAGTTTATCATCATGTACTCACTGGATGGGAAGAAGTGGCA<br>GACTTACCGGGGAAATTCCACCGGTACTCTGATGGTGTTCTTCGGAAAC<br>GTGGACAGCTCCGGCATCAAGCACAATATCTTTAACCCGCCTATCATCG<br>CCCGATACATCCGGCTCCACCCGACTCACTACTCCATCCGGTCGACTCT<br>GCGGATGGAACTCATGGGTTGCGACCTCAACTCCTGCTCAATGCCACTG<br>GGCATGGAGTCCAAGGCTATCTCGGACGCTCAGATTACTGCATCGTCGT<br>ACTTTACCAACATGTTCGCTACCTGGTCCCCGTCCAAAGCCCGGCTGCA<br>TCTCCAAGGCAGATCAAACGCGTGGAGGCCTCAGGTCAACAACCCGAAG<br>GAATGGCTTCAGGTCGACTTCCAAAAGACCATGAAAGTCACCGGAGTGA<br>CCACCCAGGGCGTGAAATCGCTGCTGACCTCTATGTACGTGAAGGAATT<br>CCTGATCTCATCAAGCCAGGACGGCCACCAGTGGACACTGTTCTTCCAA<br>AATGGAAAGGTCAAGGTCTTTCAGGGAAATCAAGACTCCTTCACCCCCG<br>TGGTGAACTCCCTGGACCCCCCTCTGCTTACCCGCTACTTGCGCATTCA<br>TCCGCAATCCTGGGTGCACCAGATCGCCCTGCGAATGGAAGTGCTGGGC<br>TGTGAAGCGCAGGACCTGTACTAAAATAAAAGATCTTTATTTTCATTAG<br>ATCTGTGTGTTGGTTTTTTGTGTGCGATCGGGAACTGGCATCTTCAGGG<br>AGTAGCTTAGGTCAGTGAAGAGAAGTGCCAGTTCCCGATCGTTACAGGC<br>CGCgggccgc | |
| 310 | cctgcaggcagctgcgcgctcgctcgctcactgaggccgcccgggcaaa<br>gcccgggcgtcgggcgacctttggtcgcccggcctcagtgagcgagcga<br>gcgcgcagagagggagtggccaactccatcactaggggttcctgcggcc<br>cGCGGgagaacgcaccactttacgaaggCGGTACTCCTCAAAGCGTACT<br>AAAGAATTATTCTTTTACATTTCAGggctgtgtctggctGCCACCAGGA<br>GATACTACCTGGGGGCTGTGGAGCTGAGCTGGGACTACATGCAGTCTGA<br>CCTGGGGGAGCTGCCTGTGGATGCCAGGTTCCCCCCCAGAGTGCCCAAG<br>AGCTTCCCCTTCAACACCTCTGTGGTGTACAAGAAGACCCTGTTTGTGG<br>AGTTCACTGACCACCTGTTCAACATTGCCAAGCCCAGGCCCCCCTGGAT<br>GGGCCTGCTGGGCCCCACCATCCAGGCTGAGGTGTATGACACTGTGGTG<br>ATCACCCTGAAGAACATGGCCAGCCACCCTGTGAGCCTGCATGCTGTGG<br>GGGTGAGCTACTGGAAGGCCTCTGAGGGGGCTGAGTATGATGACCAGAC<br>CAGCCAGAGGGAGAAGGAGGATGACAAGGTGTTCCCTGGGGGCAGCCAC<br>ACCTATGTGTGGCAGGTGCTGAAGGAGAATGGCCCCATGGCCTCTGACC<br>CCCTGTGCCTGACCTACAGCTACCTGAGCCATGTGGACCTGGTGAAGGA<br>CCTGAACTCTGGCCTGATTGGGGCCCTGCTGGTGTGCAGGGAGGGCAGC<br>CTGGCCAAGGAGAAGACCCAGACCCTGCACAAGTTCATCCTGCTGTTTG<br>CTGTGTTTGATGAGGGCAAGAGCTGGCACTCTGAAACCAAGAACAGCCT<br>GATGCAGGACAGGGATGCTGCCTCTGCCAGGGCCTGGCCCAAGATGCAC<br>ACTGTGAATGGCTATGTGAACAGGAGCCTGCCTGGCCTGATTGGCTGCC<br>ACAGGAAGTCTGTGTACTGGCATGTGATTGGCATGGGCACCACCCCTGA<br>GGTGCACAGCATCTTCCTGGAGGGCCACACCTTCCTGGTCAGGAACCAC<br>AGGCAGGCCAGCCTGGAGATCAGCCCCATCACCTTCCTGACTGCCCAGA<br>CCCTGCTGATGGACCTGGGCCAGTTCCTGCTGTTCTGCCACATCAGCAG<br>CCACCAGCATGATGGCATGGAGGCCTATGTGAAGGTGGACAGCTGCCCT<br>GAGGAGCCCCAGCTGAGGATGAAGAACAATGAGGAGGCTGAGGACTATG<br>ATGATGACCTGACTGACTCTGAGATGGATGTGGTGAGGTTTGATGATGA<br>CAACAGCCCCAGCTTCATCCAGATCAGGTCTGTGGCCAAGAAGCACCCC<br>AAGACCTGGGTGCACTACATTGCTGCTGAGGAGGAGGACTGGGACTATG<br>CCCCCCTGGTGCTGGCCCCTGATGACAGGAGCTACAAGAGCCAGTACCT<br>GAACAATGGCCCCCAGAGGATTGGCAGGAAGTACAAGAAGGTCAGGTTC<br>ATGGCCTACACTGATGAAACCTTCAAGACCAGGGAGGCCATCCAGCATG<br>AGTCTGGCATCCTGGGCCCCCTGCTGTATGGGGAGGTGGGGGACACCCT | pCB1009 (FVIII donor for integration intro Transferrin intron 1) |

-continued

| SEQ ID | Sequence | Description |
|---|---|---|
| | GCTGATCATCTTCAAGAACCAGGCCAGCAGGCCCTACAACATCTACCCC<br>CATGGCATCACTGATGTGAGGCCCCTGTACAGCAGGAGGCTGCCCAAGG<br>GGGTGAAGCACCTGAAGGACTTCCCCATCCTGCCTGGGGAGATCTTCAA<br>GTACAAGTGGACTGTGACTGTGGAGGATGGCCCCACCAAGTCTGACCCC<br>AGGTGCCTGACCAGATACTACAGCAGCTTTGTGAACATGGAGAGGGACC<br>TGGCCTCTGGCCTGATTGGCCCCCTGCTGATCTGCTACAAGGAGTCTGT<br>GGACCAGAGGGGCAACCAGATCATGTCTGACAAGAGGAATGTGATCCTG<br>TTCTCTGTGTTTGATGAGAACAGGAGCTGGTACCTGACTGAGAACATCC<br>AGAGGTTCCTGCCCAACCCTGCTGGGGTGCAGCTGGAGGACCCTGAGTT<br>CCAGGCCAGCAACATCATGCACAGCATCAATGGCTATGTGTTTGACAGC<br>CTGCAGCTGTCTGTGTGCCTGCATGAGGTGGCCTACTGGTACATCCTGA<br>GCATTGGGGCCCAGACTGACTTCCTGTCTGTGTTCTTCTCTGGCTACAC<br>CTTCAAGCACAAGATGGTGTATGAGGACACCCTGACCCTGTTCCCCTTC<br>TCTGGGGAGACTGTGTTCATGAGCATGGAGAACCCTGGCCTGTGGATTC<br>TGGGCTGCCACAACTCTGACTTCAGGAACAGGGGCATGACTGCCCTGCT<br>GAAAGTCTCCAGCTGTGACAAGAACACTGGGGACTACTATGAGGACAGC<br>TATGAGGACATCTCTGCCTACCTGCTGAGCAAGAACAATGCCATTGAGC<br>CCAGGAGCTTCAGCCAGAATGCCACTAATGTGTCTAACAACAGCAACAC<br>CAGCAATGACAGCAATGTGTCTCCCCCAGTGCTGAAGAGGCACCAGAGG<br>GAGATCACCAGGACCACCCTGCAGTCTGACCAGGAGGAGATTGACTATG<br>ATGACACCATCTCTGTGGAGATGAAGAAGGAGGACTTTGACATCTACGA<br>CGAGGACGAGAACCAGAGCCCCAGGAGCTTCCAGAAGAAGACCAGGCAC<br>TACTTCATTGCTGCTGTGGAGAGGCTGTGGGACTATGGCATGAGCAGCA<br>GCCCCCATGTGCTGAGGAACAGGGCCCAGTCTGGCTCTGTGCCCCAGTT<br>CAAGAAGGTGGTGTTCCAGGAGTTCACTGATGGCAGCTTCACCCAGCCC<br>CTGTACAGAGGGGAGCTGAATGAGCACCTGGGCCTGCTGGGCCCCTACA<br>TCAGGGCTGAGGTGGAGGACAACATCATGGTGACCTTCAGGAACCAGGC<br>CAGCAGGCCCTACAGCTTCTACAGCAGCCTGATCAGCTATGAGGAGGAC<br>CAGAGGCAGGGGGCTGAGCCCAGGAAGAACTTTGTGAAGCCCAATGAAA<br>CCAAGACCTACTTCTGGAAGGTGCAGCACCACATGGCCCCCACCAAGGA<br>TGAGTTTGACTGCAAGGCCTGGGCCTACTTCTCTGATGTGGACCTGGAG<br>AAGGATGTGCACTCTGGCCTGATTGGCCCCCTGCTGGTGTGCCACACCA<br>ACACCCTGAACCCTGCCCATGGCAGGCAGGTGACTGTGCAGGAGTTTGC<br>CCTGTTCTTCACCATCTTTGATGAAACCAAGAGCTGGTACTTCACTGAG<br>AACATGGAGAGGAACTGCAGGGCCCCCTGCAACATCCAGATGGAGGACC<br>CCACCTTCAAGGAGAACTACAGGTTCCATGCCATCAATGGCTACATCAT<br>GGACACCCTGCCTGGCCTGGTGATGGCCCAGGACCAGAGGATCAGGTGG<br>TACCTGCTGAGCATGGGCAGCAATGAGAACATCCACAGCATCCACTTCT<br>CTGGCCATGTGTTCACTGTGAGGAAGAAGGAGGAGTACAAGATGGCCCT<br>GTACAACCTGTACCCTGGGGTGTTTGAGACTGTGGAGATGCTGCCCAGC<br>AAGGCTGGCATCTGGAGGGTGGAGTGCCTGATTGGGGAGCACCTGCATG<br>CTGGCATGAGCACCCTGTTCCTGGTGTACAGCAACAAGTGCCAGACCCC<br>CCTGGGCATGGCCTCTGGCCACATCAGGGACTTCCAGATCACTGCCTCT<br>GGCCAGTATGGCCAGTGGGCCCCCAAGCTGGCCAGGCTGCACTACTCTG<br>GCAGCATCAATGCCTGGAGCACCAAGGAGCCCTTCAGCTGGATCAAGGT<br>GGACCTGCTGGCCCCCATGATCATCCATGGCATCAAGACCCAGGGGGCC<br>AGGCAGAAGTTCAGCAGCCTGTACATCAGCCAGTTCATCATCATGTACA<br>GCCTGGATGGCAAGAAGTGGCAGACCTACAGGGGCAACAGCACTGGCAC<br>CCTGATGGTGTTCTTTGGCAATGTGGACAGCTCTGGCATCAAGCACAAC<br>ATCTTCAACCCCCCCATCATTGCCAGATACATCAGGCTGCACCCCACCC<br>ACTACAGCATCAGGAGCACCCTGAGGATGGAGCTGATGGGCTGTGACCT<br>GAACAGCTGCAGCATGCCCCTGGGCATGGAGAGCAAGGCCATCTCTGAT<br>GCCCAGATCACTGCCAGCAGCTACTTCACCAACATGTTTGCCACCTGGA<br>GCCCCAGCAAGGCCAGGCTGCACCTGCAGGGCAGGAGCAATGCCTGGAG<br>GCCCCAGGTCAACAACCCCAAGGAGTGGCTGCAGGTGGACTTCCAGAAG<br>ACCATGAAGGTGACTGGGGTGACCACCCAGGGGGTGAAGAGCCTGCTGA<br>CCAGCATGTATGTGAAGGAGTTCCTGATCAGCAGCAGCCAGGATGGCCA<br>CCAGTGGACCCTGTTCTTCCAGAATGGCAAGGTGAAGGTGTTCCAGGGC<br>AACCAGGACAGCTTCACCCCTGTGGTGAACAGCCTGGACCCCCCCCTGC<br>TGACCAGATACCTGAGGATTCACCCCCAGAGCTGGGTGCACCAGATTGC<br>CCTGAGGATGGAGGTGCTGGGCTGTGAGGCCCAGGACCTGTACTGAtcg<br>cgaataaaagatctttattttcattagatctgtgtgttggttttttgtg<br>tggagaacgcaccactttacgaaggCAATTgccttaggccgcaggaacc<br>cctagtgatggagttggccactccctctctgcgcgctcgctcgctcact<br>gaggccgggcgaccaaaggtcgcccgacgcccgggctttgcccgggcgg<br>cctcagtgagcgagcgagcgcgcagctgcctgcagg | |
| 311 | cctgcaggcagctgcgcgctcgctcgctcactgaggccgcccgggcaaa<br>gcccgggcgtcgggcgacctttggtcgcccggcctcagtgagcgagcga<br>gcgcgcagagagggagtggccaactccatcactaggggttcctgcggcc<br>taaggcAATTGCCTGTAACGATCGGGAACTGGCAGATCcacacaaaaaa<br>ccaacacacagatctaatgaaaaaaagatcttttattcgcgaTCAGTA<br>CAGGTCCTGGGCCTCACAGCCCAGCACCTCCATCCTCAGGGCAATCTGG<br>TGCACCCAGCTCTGGGGGTGAATCCTCAGGTATCTGGTCAGCAGGGGGG<br>GGTCCAGGCTGTTCACCACAGGGGTGAAGCTGTCCTGGTTGCCCTGGAA<br>CACCTTCACCTTGCCATTCTGGAAGAACAGGGTCCACTGGTGGCCATCC<br>TGGCTGCTGCTGATCAGGAACTCCTTCACATACATGCTGGTCAGCAGGC | pCB099 (FVIII donor for integration into albumin intron 1) |

-continued

| SEQ ID | Sequence | Description |
|---|---|---|
| | TCTTCACCCCCTGGGTGGTCACCCCAGTCACCTTCATGGTCTTCTGGAA<br>GTCCACCTGCAGCCACTCCTTGGGGTTGTTGACCTGGGGCCTCCAGGCA<br>TTGCTCCTGCCCTGCAGGTGCAGCCTGGCCTTGCTGGGGCTCCAGGTGG<br>CAAACATGTTGGTGAAGTAGCTGCTGGCAGTGATCTGGGCATCAGAGAT<br>GGCCTTGCTCTCCATGCCCAGGGGCATGCTGCAGCTGTTCAGGTCACAG<br>CCCATCAGCTCCATCCTCAGGGTGCTCCTGATGCTGTAGTGGGTGGGGT<br>GCAGCCTGATGTATCTGGCAATGATGGGGGGGTTGAAGATGTTGTGCTT<br>GATGCCAGAGCTGTCCACATTGCCAAAGAACACCATCAGGGTGCCAGTG<br>CTGTTGCCCCTGTAGGTCTGCCACTTCTTGCCATCCAGGCTGTACATGA<br>TGATGAACTGGCTGATGTACAGGCTGCTGAACTTCTGCCTGGCCCCCTG<br>GGTCTTGATGCCATGGATGATCATGGGGGCCAGCAGGTCCACCTTGATC<br>CAGCTGAAGGGCTCCTTGGTGCTCCAGGCATTGATGCTGCCAGAGTAGT<br>GCAGCCTGGCCAGCTTGGGGGCCCACTGGCCATACTGGCCAGAGGCAGT<br>GATCTGGAAGTCCCTGATGTGGCCAGAGGCCATGCCCAGGGGGGTCTGG<br>CACTTGTTGCTGTACACCAGGAACAGGGTGCTCATGCCAGCATGCAGGT<br>GCTCCCCAATCAGGCACTCCACCCTCCAGATGCCAGCCTTGCTGGGCAG<br>CATCTCCACAGTCTCAAACACCCCAGGGTACAGGTTGTACAGGGCCATC<br>TTGTACTCCTCCTTCTTCCTCACAGTGAACACATGGCCAGAGAAGTGGA<br>TGCTGTGGATGTTCTCATTGCTGCCCATGCTCAGCAGGTACCACCTGAT<br>CCTCTGGTCCTGGGCCATCACCAGGCCAGGCAGGGTGTCCATGATGTAG<br>CCATTGATGGCATGGAACCTGTAGTTCTCCTTGAAGGTGGGGTCCTCCA<br>TCTGGATGTTGCAGGGGGCCCTGCAGTTCCTCTCCATGTTCTCAGTGAA<br>GTACCAGCTCTTGGTTTCATCAAAGATGGTGAAGAACAGGGCAAACTCC<br>TGCACAGTCACCTGCCTGCCATGGGCAGGGTTCAGGGTGTTGGTGTGGC<br>ACACCAGCAGGGGGCCAATCAGGCCAGAGTGCACATCCTTCTCCAGGTC<br>CACATCAGAGAAGTAGGCCCAGGCCTTGCAGTCAAACTCATCCTTGGTG<br>GGGGCCATGTGGTGCTGCACCTTCCAGAAGTAGGTCTTGGTTTCATTGG<br>GCTTCACAAAGTTCTTCCTGGGCTCAGCCCCCTGCCTCTGGTCCTCCTC<br>ATAGCTGATCAGGCTGCTGTAGAAGCTGTAGGGCCTGCTGGCCTGGTTC<br>CTGAAGGTCACCATGATGTTGTCCTCCACCTCAGCCCTGATGTAGGGGC<br>CCAGCAGGCCCAGGTGCTCATTCAGCTCCCCTCTGTACAGGGGCTGGGT<br>GAAGCTGCCATCAGTGAACTCCTGGAACACCACCTTCTTGAACTGGGGC<br>ACAGAGCCAGACTGGGCCCTGTTCCTCAGCACATGGGGGCTGCTGCTCA<br>TGCCATAGTCCCACAGCCTCTCCACAGCAGCAATGAAGTAGTGCCTGGT<br>CTTCTTCTGGAAGCTCCTGGGGCTCTGGTTCTCGTCCTCGTCGTAGATG<br>TCAAAGTCCTCCTTCTTCATCTCCACAGAGATGGTGTCATCATAGTCAA<br>TCTCCTCCTGGTCAGACTGCAGGGTGGTCCTGGTGATCTCCCTCTGGTG<br>CCTCTTCAGCACTGGGGGAGACACATTGCTGTCATTGCTGGTGTTGCTG<br>TTGTTAGACACATTAGTGGCATTCTGGCTGAAGCTCCTGGGCTCAATGG<br>CATTGTTCTTGCTCAGCAGGTAGGCAGAGATGTCCTCATAGCTGTCCTC<br>ATAGTAGTCCCCAGTGTTCTTGTCACAGCTGGAGACTTTCAGCAGGGCA<br>GTCATGCCCCTGTTCCTGAAGTCAGAGTTGTGGCAGCCCAGAATCCACA<br>GGCCAGGGTTCTCCATGCTCATGAACACAGTCTCCCCAGAGAAGGGGAA<br>CAGGGTCAGGGTGTCCTCATACACCATCTTGTGCTTGAAGGTGTAGCCA<br>GAGAAGAACACAGACAGGAAGTCAGTCTGGGCCCCAATGCTCAGGATGT<br>ACCAGTAGGCCACCTCATGCAGGCACACAGACAGCTGCAGGCTGTCAAA<br>CACATAGCCATTGATGCTGTGCATGATGTTGCTGGCCTGGAACTCAGGG<br>TCCTCCAGCTGCACCCCAGCAGGGTTGGGCAGGAACCTCTGGATGTTCT<br>CAGTCAGGTACCAGCTCCTGTTCTCATCAAACACAGAGAACAGGATCAC<br>ATTCCTCTTGTCAGACATGATCTGGTTGCCCCTCTGGTCCACAGACTCC<br>TTGTAGCAGATCAGCAGGGGGCCAATCAGGCCAGAGGCCAGGTCCCTCT<br>CCATGTTCACAAAGCTGCTGTAGTATCTGGTCAGGCACCTGGGGTCAGA<br>CTTGGTGGGGCCATCCTCCACAGTCACAGTCCACTTGTACTTGAAGATC<br>TCCCCAGGCAGGATGGGGAAGTCCTTCAGGTGCTTCACCCCCTTGGGCA<br>GCCTCCTGCTGTACAGGGGCCTCACATCAGTGATGCCATGGGGGTAGAT<br>GTTGTAGGGCCTGCTGGCCTGGTTCTTGAAGATGATCAGCAGGGTGTCC<br>CCCACCTCCCCATACAGCAGGGGGCCCAGGATGCCAGACTCATGCTGGA<br>TGGCCTCCCTGGTCTTGAAGGTTTCATCAGTGTAGGCCATGAACCTGAC<br>CTTCTTGTACTTCCTGCCAATCCTCTGGGGGCCATTGTTCAGGTACTGG<br>CTCTTGTAGCTCCTGTCATCAGGGGCCAGCACCAGGGGGGCATAGTCCC<br>AGTCCTCCTCCTCAGCAGCAATGTAGTGCACCCAGGTCTTGGGGTGCTT<br>CTTGGCCACAGACCTGATCTGGATGAAGCTGGGGCTGTTGTCATCATCA<br>AACCTCACCACATCCATCTCAGAGTCAGTCAGGTCATCATCATAGTCCT<br>CAGCCTCCTCATTGTTCTTCATCCTCAGCTGGGGCTCCTCAGGGCAGCT<br>GTCCACCTTCACATAGGCCTCCATGCCATCATGCTGGTGGCTGCTGATG<br>TGGCAGAACAGCAGGAACTGGCCCAGGTCCATCAGCAGGGTCTGGGCAG<br>TCAGGAAGGTGATGGGGCTGATCTCCAGGCTGGCCTGCCTGTGGTTCCT<br>GACCAGGAAGGTGTGGCCCTCCAGGAAGATGCTGTGCACCTCAGGGGTG<br>GTGCCCATGCCAATCACATGCCAGTACACAGACTTCCTGTGGCAGCCAA<br>TCAGGCCAGGCAGGCTCCTGTTCACATAGCCATTCACAGTGTGCATCTT<br>GGGCCAGGCCCTGGCAGAGGCAGCATCCCTGTCCTGCATCAGGCTGTTC<br>TTGGTTTCAGAGTGCCAGCTCTTGCCCTCATCAAACACAGCAAACAGCA<br>GGATGAACTTGTGCAGGGTCTGGGTCTTCTCCTTGGCCAGGCTGCCCTC<br>CCTGCACACCAGCAGGGCCCCAATCAGGCCAGAGTTCAGGTCCTTCACC<br>AGGTCCACATGGCTCAGGTAGCTGTAGGTCAGGCACAGGGGGTCAGAGG<br>CCATGGGGCCATTCTCCTTCAGCACCTGCCACACATAGGTGTGGCTGCC<br>CCCAGGGAACACCTTGTCATCCTCCTTCTCCCTCTGGCTGGTCTGGTCA | |

-continued

| SEQ ID | Sequence | Description |
|---|---|---|
| | TCATACTCAGCCCCCTCAGAGGCCTTCCAGTAGCTCACCCCCACAGCAT<br>GCAGGCTCACAGGGTGGCTGGCCATGTTCTTCAGGGTGATCACCACAGT<br>GTCATACACCTCAGCCTGGATGGTGGGGCCCAGCAGGCCCATCCAGGGG<br>GGCCTGGGCTTGGCAATGTTGAACAGGTGGTCAGTGAACTCCACAAACA<br>GGGTCTTCTTGTACACCACAGAGGTGTTGAAGGGGAAGCTCTTGGGCAC<br>TCTGGGGGGGAACCTGGCATCCACAGGCAGCTCCCCCAGGTCAGACTGC<br>ATGTAGTCCCAGCTCAGCTCCACAGCCCCCAGGTAGTATCTCCTGGTGG<br>CCACTGAAATGTAAAAGAATAATTCTTTAGTACGCTTTGAGGAGTACCG<br>CCTGTAACGATCGGGAACTGGCACCGCgggccgcaggaacccctagtga<br>tggagttggccactccctctctgcgcgctcgctcgctcactgaggccgg<br>gcgaccaaaggtcgcccgacgcccgggctttgcccgggcggcctcagtg<br>agcgagcgagcgcgcagctgcctgcagg | |
| 312 | NNNNGATT | *Neisseria meningitidis* PAM (N is any nucleotide) |
| 313 | NNNNNGTTT | *Neisseria meningitidis* PAM (N is any nucleotide) |
| 314 | NNNNGCTT | *Neisseria meningitidis* PAM (N is any nucleotide) |
| 315 | LAGLIDADG | Structural classification for homing endonuclease (HE) |
| 316 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG<br>GATGAAGAACAATGAGGAGGCTGAGGACTATGATGATGACCTGACTGAC<br>TCTGAGATGGATGTGGTGAGGTTTGATGATGACAACAGCCCCAGCTTCA<br>TCCAGATCAGGTCTGTGGCCAAGAAGCACCCCAAGACCTGGGTGCACTA<br>CATTGCTGCTGAGGAGGAGGACTGGGACTATGCCCCCCTGGTGCTGGCC<br>CCTGATGACAGGAGCTACAAGAGCCAGTACCTGAACAATGGCCCCCAGA<br>GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT<br>GAGGCCCCTGTACAGCAGGAGGCTGCCCAAGGGGGTGAAGCACCTGAAG<br>GACTTCCCCATCCTGCCTGGGGAGATCTTCAAGTACAAGTGGACTGTGA<br>CTGTGGAGGATGGCCCCACCAAGTCTGACCCCAGGTGCCTGACCAGATA<br>CTACAGCAGCTTTGTGAACATGGAGAGGGACCTGGCCTCTGGCCTGATT<br>GGCCCCCTGCTGATCTGCTACAAGGAGTCTGTGGACCAGAGGGGCAACC<br>AGATCATGTCTGACAAGAGGAATGTGATCCTGTTCTCTGTGTTTGATGA<br>GAACAGGAGCTGGTACCTGACTGAGAACATCCAGAGGTTCCTGCCCAAC<br>CCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTG<br>CCTGCATGAGGTGGCCTACTGGTACATCCTGAGCATTGGGGCCCAGACT<br>GACTTCCTGTCTGTGTTCTTCTCTGGCTACACCTTCAAGCACAAGATGG<br>TGTATGAGGACACCCTGACCCTGTTCCCCTTCTCTGGGGAGACTGTGTT<br>CATGAGCATGGAGAACCCTGGCCTGTGGATTCTGGGCTGCCACAACTCT<br>GACTTCAGGAACAGGGGCATGACTGCCCTGCTGAAAGTCTCCAGCTGTG<br>ACAAGAACACTGGGGACTACTATGAGGACAGCTATGAGGACATCTCTGC<br>CTACCTGCTGAGCAAGAACAATGCCATTGAGCCCAGGAGCTTCAGCCAG | pCB076 |

-continued

| SEQ ID | Sequence | Description |
|---|---|---|
| | AATGCCACTAATGTGTCTAACAACAGCAACACCAGCAATGACAGCAATG<br>TGTCTCCCCCAGTGCTGAAGAGGCACCAGAGGGAGATCACCAGGACCAC<br>CCTGCAGTCTGACCAGGAGGAGATTGACTATGATGACACCATCTCTGTG<br>GAGATGAAGAAGGAGGACTTTGACATCTACGACGAGGACGAGAACCAGA<br>GCCCCAGGAGCTTCCAGAAGAAGACCAGGCACTACTTCATTGCTGCTGT<br>GGAGAGGCTGTGGGACTATGGCATGAGCAGCAGCCCCCATGTGCTGAGG<br>AACAGGGCCCAGTCTGGCTCTGTGCCCCAGTTCAAGAAGGTGGTGTTCC<br>AGGAGTTCACTGATGGCAGCTTCACCCAGCCCCTGTACAGAGGGGAGCT<br>GAATGAGCACCTGGGCCTGCTGGGCCCCTACATCAGGGCTGAGGTGGAG<br>GACAACATCATGGTGACCTTCAGGAACCAGGCCAGCAGGCCCTACAGCT<br>TCTACAGCAGCCTGATCAGCTATGAGGAGGACCAGAGGCAGGGGGCTGA<br>GCCCAGGAAGAACTTTGTGAAGCCCAATGAAACCAAGACCTACTTCTGG<br>AAGGTGCAGCACCACATGGCCCCCACCAAGGATGAGTTTGACTGCAAGG<br>CCTGGGCCTACTTCTCTGATGTGGACCTGGAGAAGGATGTGCACTCTGG<br>CCTGATTGGCCCCCTGCTGGTGTGCCACACCAACACCCTGAACCCTGCC<br>CATGGCAGGCAGGTGACTGTGCAGGAGTTTGCCCTGTTCTTCACCATCT<br>TTGATGAAACCAAGAGCTGGTACTTCACTGAGAACATGGAGAGGAACTG<br>CAGGGCCCCCTGCAACATCCAGATGGAGGACCCCACCTTCAAGGAGAAC<br>TACAGGTTCCATGCCATCAATGGCTACATCATGGACACCCTGCCTGGCC<br>TGGTGATGGCCCAGGACCAGAGGATCAGGTGGTACCTGCTGAGCATGGG<br>CAGCAATGAGAACATCCACAGCATCCACTTCTCTGGCCATGTGTTCACT<br>GTGAGGAAGAAGGAGGAGTACAAGATGGCCCTGTACAACCTGTACCCTG<br>GGGTGTTTGAGACTGTGGAGATGCTGCCCAGCAAGGCTGGCATCTGGAG<br>GGTGGAGTGCCTGATTGGGGAGCACCTGCATGCTGGCATGAGCACCCTG<br>TTCCTGGTGTACAGCAACAAGTGCCAGACCCCCCTGGGCATGGCCTCTG<br>GCCACATCAGGGACTTCCAGATCACTGCCTCTGGCCAGTATGGCCAGTG<br>GGCCCCCAAGCTGGCCAGGCTGCACTACTCTGGCAGCATCAATGCCTGG<br>AGCACCAAGGAGCCCTTCAGCTGGATCAAGGTGGACCTGCTGGCCCCCA<br>TGATCATCCATGGCATCAAGACCCAGGGGGCCAGGCAGAAGTTCAGCAG<br>CCTGTACATCAGCCAGTTCATCATCATGTACAGCCTGGATGGCAAGAAG<br>TGGCAGACCTACAGGGGCAACAGCACTGGCACCCTGATGGTGTTCTTTG<br>GCAATGTGGACAGCTCTGGCATCAAGCACAACATCTTCAACCCCCCCAT<br>CATTGCCAGATACATCAGGCTGCACCCCACCCACTACAGCATCAGGAGC<br>ACCCTGAGGATGGAGCTGATGGGCTGTGACCTGAACAGCTGCAGCATGC<br>CCCTGGGCATGGAGAGCAAGGCCATCTCTGATGCCCAGATCACTGCCAG<br>CAGCTACTTCACCAACATGTTTGCCACCTGGAGCCCCAGCAAGGCCAGG<br>CTGCACCTGCAGGGCAGGAGCAATGCCTGGAGGCCCCAGGTCAACAACC<br>CCAAGGAGTGGCTGCAGGTGGACTTCCAGAAGACCATGAAGGTGACTGG<br>GGTGACCACCCAGGGGGTGAAGAGCCTGCTGACCAGCATGTATGTGAAG<br>GAGTTCCTGATCAGCAGCAGCCAGGATGGCCACCAGTGGACCCTGTTCT<br>TCCAGAATGGCAAGGTGAAGGTGTTCCAGGGCAACCAGGACAGCTTCAC<br>CCCTGTGGTGAACAGCCTGGACCCCCCCCTGCTGACCAGATACCTGAGG<br>ATTCACCCCCAGAGCTGGGTGCACCAGATTGCCCTGAGGATGGAGGTGC<br>TGGGCTGTGAGGCCCAGGACCTGTACTGAaataaaagatctttattttc<br>attagatctgtgtgttggtttttgtgtg | |
| 317 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG<br>GATGAAGAACAATGAGGAGGCTGAGGACTATGATGATGACCTGACTGAC<br>TCTGAGATGGATGTGGTGAGGTTTGATGATGACAACAGCCCCAGCTTCA<br>TCCAGATCAGGTCTGTGGCCAAGAAGCACCCCAAGACCTGGGTGCACTA<br>CATTGCTGCTGAGGAGGAGGACTGGGACTATGCCCCCCTGGTGCTGGCC<br>CCTGATGACAGGAGCTACAAGAGCCAGTACCTGAACAATGGCCCCCAGA<br>GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT | pCB077 |

-continued

| SEQ ID | Sequence | Description |
|---|---|---|
| | GAGGCCCCTGTACAGCAGGAGGCTGCCCAAGGGGGTGAAGCACCTGAAG | |
| | GACTTCCCCATCCTGCCTGGGGAGATCTTCAAGTACAAGTGGACTGTGA | |
| | CTGTGGAGGATGGCCCCACCAAGTCTGACCCCAGGTGCCTGACCAGATA | |
| | CTACAGCAGCTTTGTGAACATGGAGAGGGACCTGGCCTCTGGCCTGATT | |
| | GGCCCCCTGCTGATCTGCTACAAGGAGTCTGTGGACCAGAGGGGCAACC | |
| | AGATCATGTCTGACAAGAGGAATGTGATCCTGTTCTCTGTGTTTGATGA | |
| | GAACAGGAGCTGGTACCTGACTGAGAACATCCAGAGGTTCCTGCCCAAC | |
| | CCTGCTGGGGTGCAGCTGGAGGACCCTGAGTTCCAGGCCAGCAACATCA | |
| | TGCACAGCATCAATGGCTATGTGTTTGACAGCCTGCAGCTGTCTGTGTG | |
| | CCTGCATGAGGTGGCCTACTGGTACATCCTGAGCATTGGGGCCCAGACT | |
| | GACTTCCTGTCTGTGTTCTTCTCTGGCTACACCTTCAAGCACAAGATGG | |
| | TGTATGAGGACACCCTGACCCTGTTCCCCTTCTCTGGGGAGACTGTGTT | |
| | CATGAGCATGGAGAACCCTGGCCTGTGGATTCTGGGCTGCCACAACTCT | |
| | GACTTCAGGAACAGGGGCATGACTGCCCTGCTGAAAGTCTCCAGCTGTG | |
| | ACAAGAACACTGGGGACTACTATGAGGACAGCTATGAGGACATCTCTGC | |
| | CTACCTGCTGAGCAAGAACAATGCCATTGAGCCCAGGAGCTTCAGCCAG | |
| | AATGCCACTAATGTGTCTAACAACAGCAACACCAGCAATGACAGCAATG | |
| | TGTCTCCCCCAGTGCTGAAGAGGCACCAGAGGGAGATCACCAGGACCAC | |
| | CCTGCAGTCTGACCAGGAGGAGATTGACTATGATGACACCATCTCTGTG | |
| | GAGATGAAGAAGGAGGACTTTGACATCTACGACGAGGACGAGAACCAGA | |
| | GCCCCAGGAGCTTCCAGAAGAAGACCAGGCACTACTTCATTGCTGCTGT | |
| | GGAGAGGCTGTGGGACTATGGCATGAGCAGCAGCCCCCATGTGCTGAGG | |
| | AACAGGGCCCAGTCTGGCTCTGTGCCCCAGTTCAAGAAGGTGGTGTTCC | |
| | AGGAGTTCACTGATGGCAGCTTCACCCAGCCCCTGTACAGAGGGGAGCT | |
| | GAATGAGCACCTGGGCCTGCTGGGCCCCTACATCAGGGCTGAGGTGGAG | |
| | GACAACATCATGGTGACCTTCAGGAACCAGGCCAGCAGGCCCTACAGCT | |
| | TCTACAGCAGCCTGATCAGCTATGAGGAGGACCAGAGGCAGGGGGCTGA | |
| | GCCCAGGAAGAACTTTGTGAAGCCCAATGAAACCAAGACCTACTTCTGG | |
| | AAGGTGCAGCACCACATGGCCCCCACCAAGGATGAGTTTGACTGCAAGG | |
| | CCTGGGCCTACTTCTCTGATGTGGACCTGGAGAAGGATGTGCACTCTGG | |
| | CCTGATTGGCCCCCTGCTGGTGTGCCACACCAACACCCTGAACCCTGCC | |
| | CATGGCAGGCAGGTGACTGTGCAGGAGTTTGCCCTGTTCTTCACCATCT | |
| | TTGATGAAACCAAGAGCTGGTACTTCACTGAGAACATGGAGAGGAACTG | |
| | CAGGGCCCCCTGCAACATCCAGATGGAGGACCCCACCTTCAAGGAGAAC | |
| | TACAGGTTCCATGCCATCAATGGCTACATCATGGACACCCTGCCTGGCC | |
| | TGGTGATGGCCCAGGACCAGAGGATCAGGTGGTACCTGCTGAGCATGGG | |
| | CAGCAATGAGAACATCCACAGCATCCACTTCTCTGGCCATGTGTTCACT | |
| | GTGAGGAAGAAGGAGGAGTACAAGATGGCCCTGTACAACCTGTACCCTG | |
| | GGGTGTTTGAGACTGTGGAGATGCTGCCCAGCAAGGCTGGCATCTGGAG | |
| | GGTGGAGTGCCTGATTGGGGAGCACCTGCATGCTGGCATGAGCACCCTG | |
| | TTCCTGGTGTACAGCAACAAGTGCCAGACCCCCCTGGGCATGGCCTCTG | |
| | GCCACATCAGGGACTTCCAGATCACTGCCTCTGGCCAGTATGGCCAGTG | |
| | GGCCCCCAAGCTGGCCAGGCTGCACTACTCTGGCAGCATCAATGCCTGG | |
| | AGCACCAAGGAGCCCTTCAGCTGGATCAAGGTGGACCTGCTGGCCCCCA | |
| | TGATCATCCATGGCATCAAGACCCAGGGGGCCAGGCAGAAGTTCAGCAG | |
| | CCTGTACATCAGCCAGTTCATCATCATGTACAGCCTGGATGGCAAGAAG | |
| | TGGCAGACCTACAGGGGCAACAGCACTGGCACCCTGATGGTGTTCTTTG | |
| | GCAATGTGGACAGCTCTGGCATCAAGCACAACATCTTCAACCCCCCCAT | |
| | CATTGCCAGATACATCAGGCTGCACCCCACCCACTACAGCATCAGGAGC | |
| | ACCCTGAGGATGGAGCTGATGGGCTGTGACCTGAACAGCTGCAGCATGC | |
| | CCCTGGGCATGGAGAGCAAGGCCATCTCTGATGCCCAGATCACTGCCAG | |
| | CAGCTACTTCACCAACATGTTTGCCACCTGGAGCCCCAGCAAGGCCAGG | |
| | CTGCACCTGCAGGGCAGGAGCAATGCCTGGAGGCCCCAGGTCAACAACC | |
| | CCAAGGAGTGGCTGCAGGTGGACTTCCAGAAGACCATGAAGGTGACTGG | |
| | GGTGACCACCCAGGGGGTGAAGAGCCTGCTGACCAGCATGTATGTGAAG | |
| | GAGTTCCTGATCAGCAGCAGCCAGGATGGCCACCAGTGGACCCTGTTCT | |
| | TCCAGAATGGCAAGGTGAAGGTGTTCCAGGGCAACCAGGACAGCTTCAC | |
| | CCCTGTGGTGAACAGCCTGGACCCCCCCCTGCTGACCAGATACCTGAGG | |
| | ATTCACCCCCAGAGCTGGGTGCACCAGATTGCCCTGAGGATGGAGGTGC | |
| | TGGGCTGTGAGGCCCAGGACCTGTACTGAtcgcgaataaaagatcttta | |
| | ttttcattagatctgtgtgttggtttttttgtgtg | |
| 318 | TGCCAGTTCCCGATCGTTACAGGCGGTACTCCTCAAAGCGTACTAAAGA | pCB080 |
| | ATTATTCTTTTACATTTCAGTGGCCACCAGAAGGTACTACCTGGGAGCT | |
| | GTGGAACTGAGCTGGGACTACATGCAGTCTGACCTGGGAGAGCTGCCTG | |
| | TGGATGCTAGATTTCCTCCAAGAGTGCCCAAGAGCTTCCCCTTCAACAC | |
| | CTCTGTGGTGTACAAGAAAACCCTGTTTGTGGAATTCACAGACCACCTG | |
| | TTCAATATTGCCAAGCCTAGACCTCCTTGGATGGGCCTGCTGGGCCCTA | |
| | CAATTCAGGCTGAGGTGTATGACACAGTGGTCATCACCCTGAAGAACAT | |
| | GGCCAGCCATCCTGTGTCTCTGCATGCTGTGGGAGTGTCTTACTGGAAG | |
| | GCTTCTGAGGGGGCTGAGTATGATGACCAGACAAGCCAGAGAGAGAAAG | |
| | AGGATGACAAGGTTTTCCCTGGGGGCAGCCACACCTATGTCTGGCAGGT | |
| | CCTGAAAGAAAATGGCCCTATGGCCTCTGATCCTCTGTGCCTGACATAC | |
| | AGCTACCTGAGCCATGTGGACCTGGTCAAGGACCTGAACTCTGGCCTGA | |
| | TTGGGGCTCTGCTGGTGTGTAGAGAAGGCAGCCTGGCCAAAGAAAAGAC | |
| | CCAGACACTGCACAAGTTCATCCTGCTGTTTGCTGTGTTTGATGAGGGC | |
| | AAGAGCTGGCACTCTGAGACAAAGAACAGCCTGATGCAGGACAGAGATG | |

-continued

| SEQ ID | Sequence | Description |
|---|---|---|
| | CTGCCTCTGCTAGAGCTTGGCCCAAGATGCACACAGTGAATGGCTATGT<br>GAACAGAAGCCTGCCTGGACTGATTGGATGCCACAGAAAGTCTGTGTAC<br>TGGCATGTGATTGGCATGGGCACCACACCTGAGGTGCACAGCATCTTTC<br>TGGAAGGACACACCTTCCTGGTGAGGAACCACAGACAGGCCAGCCTGGA<br>AATCAGCCCTATCACCTTCCTGACAGCTCAGACCCTGCTGATGGATCTG<br>GGCCAGTTTCTGCTGTTCTGCCACATCAGCAGCCACCAGCATGATGGCA<br>TGGAAGCCTATGTGAAGGTGGACAGCTGCCCTGAAGAACCCCAGCTGAG<br>AATGAAGAACAATGAGGAAGCTGAGGACTATGATGATGACCTGACAGAC<br>TCTGAGATGGATGTGGTCAGATTTGATGATGATAACAGCCCCAGCTTCA<br>TCCAGATCAGATCTGTGGCCAAGAAGCACCCCAAGACCTGGGTGCACTA<br>TATTGCTGCTGAGGAAGAGGACTGGGATTATGCTCCTCTGGTGCTGGCC<br>CCTGATGACAGAAGCTACAAGAGCCAGTACCTGAACAATGGCCCTCAGA<br>GAATTGGCAGGAAGTATAAGAAAGTGAGGTTCATGGCCTACACAGATGA<br>GACATTCAAGACCAGAGAGGCTATCCAGCATGAGTCTGGCATTCTGGGA<br>CCTCTGCTGTATGGGGAAGTGGGGGACACACTGCTGATCATCTTCAAGA<br>ACCAGGCCAGCAGACCCTACAACATCTACCCTCATGGCATCACAGATGT<br>GAGGCCTCTGTACTCTAGAAGGCTGCCCAAGGGGGTGAAGCACCTGAAG<br>GACTTCCCTATCCTGCCTGGGGAGATCTTCAAGTACAAGTGGACAGTGA<br>CAGTGGAGGATGGCCCTACCAAGTCTGATCCTAGATGCCTGACAAGGTA<br>CTACAGCAGCTTTGTGAACATGGAAAGGGACCTGGCCTCTGGCCTGATT<br>GGTCCTCTGCTGATCTGCTACAAAGAATCTGTGGACCAGAGGGGCAACC<br>AGATCATGAGTGACAAGAGAAATGTGATCCTGTTCTCTGTCTTTGATGA<br>GAACAGGTCCTGGTATCTGACAGAGAACATCCAGAGGTTTCTGCCCAAT<br>CCTGCTGGGGTGCAGCTGGAAGATCCTGAGTTCCAGGCCTCCAACATCA<br>TGCACTCCATCAATGGCTATGTGTTTGACAGCCTGCAGCTGTCTGTGTG<br>CCTGCATGAAGTGGCCTACTGGTACATCCTGTCTATTGGGGCCCAGACA<br>GACTTCCTGTCTGTGTTCTTTTCTGGCTACACCTTCAAGCACAAGATGG<br>TGTATGAGGATACCCTGACACTGTTCCCATTCTCTGGGGAGACAGTGTT<br>CATGAGCATGGAAAACCCTGGCCTGTGGATCCTGGGCTGTCACAACAGT<br>GACTTCAGAAACAGAGGCATGACAGCCCTGCTGAAGGTGTCCAGCTGTG<br>ACAAGAACACTGGGGACTACTATGAGGACTCTTATGAGGACATCTCTGC<br>CTACCTGCTGAGCAAGAACAATGCCATTGAGCCTAGGAGCTTCTCTCAG<br>AACCCTCCTGTGCTGAAGAGACACCAGAGGGAGATCACCAGAACCACAC<br>TGCAGTCTGACCAAGAGGAAATTGATTATGATGACACCATCTCTGTGGA<br>GATGAAGAAAGAAGATTTTGACATCTATGATGAGGATGAGAATCAGAGC<br>CCCAGATCTTTCCAGAAGAAAACAAGGCACTACTTCATTGCTGCTGTGG<br>AAAGACTGTGGGACTATGGCATGAGCAGCAGCCCCCATGTGCTGAGAAA<br>CAGGGCCCAGTCTGGAAGTGTGCCCCAGTTCAAGAAAGTGGTGTTCCAA<br>GAGTTCACAGATGGCAGCTTCACCCAGCCTCTGTATAGAGGGGAGCTGA<br>ATGAGCACCTGGGACTGCTGGGACCTTACATCAGAGCTGAGGTGGAGGA<br>TAACATCATGGTCACCTTTAGAAACCAGGCCTCTAGGCCCTACTCCTTC<br>TACAGCTCCCTGATCAGCTATGAAGAGGACCAGAGACAGGGGGCTGAGC<br>CCAGAAAGAACTTTGTGAAGCCCAATGAGACTAAGACCTACTTTTGGAA<br>GGTGCAGCACCACATGGCCCCTACAAAGGATGAGTTTGACTGCAAGGCC<br>TGGGCCTACTTCTCTGATGTGGACCTGGAGAAGGATGTGCACTCTGGAC<br>TCATTGGACCCCTGCTTGTGTGCCACACCAACACACTGAATCCTGCTCA<br>TGGCAGGCAAGTGACAGTGCAAGAGTTTGCCCTGTTCTTCACCATCTTT<br>GATGAGACAAAGTCCTGGTACTTCACAGAAAACATGGAAAGAAACTGCA<br>GGGCCCCTTGCAACATCCAGATGGAAGATCCCACCTTCAAAGAGAACTA<br>CAGGTTCCATGCCATCAATGGCTACATCATGGACACTCTGCCTGGCCTG<br>GTTATGGCACAGGATCAGAGGATCAGATGGTATCTGCTGTCCATGGGCT<br>CCAATGAGAATATCCACAGCATCCACTTCTCTGGCCATGTGTTCACAGT<br>GAGGAAAAAAGAAGAGTACAAGATGGCCCTGTACAATCTGTACCCTGGG<br>GTGTTTGAGACTGTGGAAATGCTGCCTAGCAAGGCTGGAATCTGGAGGG<br>TGGAATGTCTGATTGGAGAGCATCTGCATGCTGGAATGTCTACCCTGTT<br>CCTGGTGTACAGCAACAAGTGTCAGACCCCTCTGGGCATGGCCTCTGGA<br>CACATCAGAGACTTCCAGATCACAGCCTCTGGCCAGTATGGACAGTGGG<br>CTCCTAAACTGGCTAGACTGCACTACTCTGGCAGCATCAATGCCTGGTC<br>CACCAAAGAGCCCTTCAGCTGGATCAAGGTGGACCTGCTGGCTCCCATG<br>ATCATCCATGGAATCAAGACCCAGGGGGCCAGACAGAAGTTCAGCAGCC<br>TGTACATCAGCCAGTTCATCATCATGTACAGCCTGGATGGCAAGAAGTG<br>GCAGACCTACAGAGGCAACAGCACAGGCACACTCATGGTGTTCTTTGGC<br>AATGTGGACTCTTCTGGCATTAAGCACAACATCTTCAACCCTCCAATCA<br>TTGCCAGGTACATCAGGCTGCACCCCACACACTACAGCATCAGATCTAC<br>CCTGAGGATGGAACTGATGGGCTGTGACCTGAACAGCTGCTCTATGCCC<br>CTGGGAATGGAAAGCAAGGCCATCTCTGATGCCCAGATCACAGCCAGCA<br>GCTACTTCACCAACATGTTTGCCACATGGTCCCCATCTAAGGCCAGGCT<br>GCATCTGCAGGGCAGATCTAATGCTTGGAGGCCCCAAGTGAACAACCCC<br>AAAGAGTGGCTGCAGGTGGACTTTCAGAAAACCATGAAAGTGACAGGAG<br>TGACCACACAGGGGGTCAAGTCTCTGCTGACCTCTATGTATGTGAAAGA<br>GTTCCTGATCTCCAGCAGCCAGGATGGCCACCAGTGGACCCTGTTTTTC<br>CAGAATGGCAAAGTCAAGGTGTTCCAGGGAAACCAGGACAGCTTCACAC<br>CTGTGGTCAACTCCCTGGATCCTCCACTGCTGACCAGATACCTGAGAAT<br>TCACCCTCAGTCTTGGGTGCACCAGATTGCTCTGAGAATGGAAGTGCTG<br>GGATGTGAAGCTCAGGACCTCTACTAAAATAAAAGATCTTTATTTTCAT<br>TAGATCTGTGTGTTGGTTTTTTGTGTG | |

-continued

| SEQ ID | Sequence | Description |
|---|---|---|
| 319 | TGCCAGTTCCCGATCGTTACAGGCGGTACTCCTCAAAGCGTACTAAAGA<br>ATTATTCTTTTACATTTCAGTGGCCACCAGAAGGTACTACCTAGGAGCC<br>GTGGAACTGAGCTGGGACTACATGCAGTCTGACCTGGGAGAGCTGCCCG<br>TGGACGCTAGATTTCCTCCAAGAGTGCCCAAGAGCTTCCCCTTCAACAC<br>CTCCGTGGTGTACAAGAAAACCCTGTTCGTGGAATTCACCGACCACCTG<br>TTCAATATCGCCAAGCCTAGACCTCCTTGGATGGGCCTGCTGGGCCCTA<br>CAATTCAGGCCGAGGTGTACGACACCGTGGTCATCACCCTGAAGAACAT<br>GGCCAGCCATCCTGTGTCTCTGCACGCCGTGGGAGTGTCTTACTGGAAG<br>GCTTCTGAGGGCGCCGAGTACGACGACCAGACAAGCCAGAGAGAGAAAG<br>AGGACGACAAGGTTTTCCCTGGCGGCAGCCACACCTATGTCTGGCAGGT<br>CCTGAAAGAAAACGGCCCTATGGCCTCCGATCCTCTGTGCCTGACATAC<br>AGCTACCTGAGCCATGTGGACCTGGTCAAGGACCTGAACTCTGGCCTGA<br>TCGGCGCTCTGCTCGTGTGTAGAGAAGGCAGCCTGGCCAAAGAAAAGAC<br>CCAGACACTGCACAAGTTCATCCTGCTGTTCGCCGTGTTCGACGAGGGC<br>AAGAGCTGGCACAGCGAGACAAAGAACAGCCTGATGCAGGACAGAGATG<br>CCGCCTCTGCTAGAGCTTGGCCCAAGATGCACACCGTGAACGGCTACGT<br>GAACAGAAGCCTGCCTGGACTGATCGGATGCCACAGAAAGTCCGTGTAC<br>TGGCATGTGATCGGCATGGGCACCACACCTGAGGTGCACAGCATCTTTC<br>TGGAAGGACACACCTTCCTCGTGCGGAACCACAGACAGGCCAGCCTGGA<br>AATCAGCCCTATCACCTTCCTGACCGCTCAGACCCTGCTGATGGATCTG<br>GGCCAGTTTCTGCTGTTCTGCCACATCAGCAGCCACCAGCACGATGGCA<br>TGGAAGCCTACGTGAAGGTGGACAGCTGCCCCGAAGAACCCCAGCTGAG<br>AATGAAGAACAACGAGGAAGCCGAGGACTACGACGACGACCTGACCGAC<br>TCTGAGATGGACGTCGTCAGATTCGACGACGATAACAGCCCCAGCTTCA<br>TCCAGATCAGAAGCGTGGCCAAGAAGCACCCCAAGACCTGGGTGCACTA<br>TATCGCCGCCGAGGAAGAGGACTGGGATTACGCTCCTCTGGTGCTGGCC<br>CCTGACGACAGAAGCTACAAGAGCCAGTACCTGAACAACGGCCCTCAGA<br>GAATCGGCCGGAAGTATAAGAAAGTGCGGTTCATGGCCTACACCGACGA<br>GACATTCAAGACCAGAGAGGCTATCCAGCACGAGAGCGGCATTCTGGGA<br>CCTCTGCTGTATGGCGAAGTGGGCGACACACTGCTGATCATCTTCAAGA<br>ACCAGGCCAGCAGACCCTACAACATCTACCCTCACGGCATCACCGATGT<br>GCGGCCTCTGTACTCTAGAAGGCTGCCCAAGGGCGTGAAGCACCTGAAG<br>GACTTCCCTATCCTGCCTGGCGAGATCTTCAAGTACAAGTGGACCGTGA<br>CCGTCGAGGACGGCCCTACCAAGAGCGATCCTAGATGCCTGACACGGTA<br>CTACAGCAGCTTCGTGAACATGGAACGCGACCTGGCCAGCGGCCTGATT<br>GGTCCTCTGCTGATCTGCTACAAAGAAAGCGTGGACCAGAGGGGCAACC<br>AGATCATGAGCGACAAGAGAAACGTGATCCTGTTCTCCGTCTTTGACGA<br>GAACAGGTCCTGGTATCTGACCGAGAACATCCAGCGGTTTCTGCCCAAT<br>CCTGCTGGCGTGCAGCTGGAAGATCCTGAGTTCCAGGCCTCCAACATCA<br>TGCACTCCATCAACGGCTATGTGTTCGACAGCCTGCAGCTGAGCGTGTG<br>CCTGCACGAAGTGGCCTACTGGTACATCCTGTCTATCGGCGCCCAGACC<br>GACTTCCTGTCCGTGTTCTTTAGCGGCTACACCTTCAAGCACAAGATGG<br>TGTACGAGGATACCCTGACACTGTTCCCATTCAGCGGCGAGACAGTGTT<br>CATGAGCATGGAAAACCCCGGCCTGTGGATCCTGGGCTGTCACAACAGC<br>GACTTCAGAAACAGAGGCATGACAGCCCTGCTGAAGGTGTCCAGCTGCG<br>ACAAGAACACCGGCGACTACTACGAGGACTCTTACGAGGACATCAGCGC<br>CTACCTGCTGAGCAAGAACAATGCCATCGAGCCTCGGAGCTTCTCTCAG<br>AACCCTCCTGTGCTGAAGAGACACCAGCGCGAGATCACCAGAACCACAC<br>TGCAGAGCGACCAAGAGGAAATCGATTACGACGACACCATCAGCGTCGA<br>GATGAAGAAAGAAGATTTCGACATCTACGACGAGGACGAGAATCAGAGC<br>CCCAGATCTTTCCAGAAGAAAACGCGGCACTACTTCATTGCCGCCGTGG<br>AAAGACTGTGGGACTACGGCATGAGCAGCAGCCCACATGTGCTGAGAAA<br>CAGGGCCCAGAGCGGAAGCGTGCCCCAGTTCAAGAAAGTGGTGTTCCAA<br>GAGTTCACCGACGGCAGCTTCACCCAGCCTCTGTATAGAGGCGAGCTGA<br>ACGAGCACCTGGGACTGCTGGGACCTTACATCAGAGCTGAGGTCGAGGA<br>TAACATCATGGTCACCTTTAGAAACCAGGCCTCTAGGCCCTACTCCTTC<br>TACAGCTCCCTGATCAGCTACGAAGAGGACCAGAGACAGGGCGCTGAGC<br>CCAGAAAGAACTTCGTGAAGCCCAACGAGACTAAGACCTACTTTTGGAA<br>GGTGCAGCACCACATGGCCCCTACAAAGGACGAGTTCGACTGCAAGGCC<br>TGGGCCTACTTCTCTGACGTGGACCTCGAGAAGGATGTGCACAGCGGAC<br>TCATCGGACCCCTGCTTGTGTGCCACACCAACACACTGAATCCCGCTCA<br>CGGCAGGCAAGTGACCGTGCAAGAGTTCGCCCTGTTCTTCACCATCTTC<br>GATGAGACAAAGTCCTGGTACTTCACCGAAAACATGGAAAGAAACTGCA<br>GGGCCCCTTGCAACATCCAGATGGAAGATCCCACCTTCAAAGAGAACTA<br>CCGGTTCCACGCCATCAATGGCTACATCATGGACACTCTGCCCGGCCTG<br>GTTATGGCACAGGATCAGAGGATCAGATGGTATCTGCTGTCCATGGGCT<br>CCAACGAGAATATCCACAGCATCCACTTCAGCGGCCATGTGTTCACCGT<br>GCGGAAAAAAGAAGAGTACAAGATGGCCCTGTACAATCTGTACCCCGGC<br>GTGTTCGAGACTGTGGAAATGCTGCCTAGCAAGGCCGGAATCTGGCGCG<br>TGGAATGTCTGATCGGAGAGCATCTGCATGCCGGAATGTCTACCCTGTT<br>CCTGGTGTACAGCAACAAGTGTCAGACCCCTCTCGGCATGGCCTCTGGA<br>CACATCAGAGACTTCCAGATCACCGCCTCTGGCCAGTACGGACAGTGGG<br>CTCCTAAACTGGCTAGACTGCACTACAGCGGCAGCATCAACGCCTGGTC<br>CACCAAAGAGCCCTTCAGCTGGATCAAGGTGGACCTGCTGGCTCCCATG<br>ATCATCCACGGAATCAAGACCCAGGGCGCCAGACAGAAGTTCAGCAGCC<br>TGTACATCAGCCAGTTCATCATCATGTACAGCCTGGACGGCAAGAAGTG<br>GCAGACCTACAGAGGCAACAGCACCGGCACACTCATGGTGTTCTTCGGC | pCB085 |

-continued

| SEQ ID | Sequence | Description |
|---|---|---|
| | AACGTGGACTCCAGCGGCATTAAGCACAACATCTTCAACCCTCCAATCA | |
| | TTGCCCGGTACATCCGGCTGCACCCCACACACTACAGCATCAGATCTAC | |
| | CCTGAGGATGGAACTGATGGGCTGCGACCTGAACAGCTGCTCTATGCCC | |
| | CTCGGAATGGAAAGCAAGGCCATCAGCGACGCCCAGATCACAGCCAGCA | |
| | GCTACTTCACCAACATGTTCGCCACATGGTCCCCATCTAAGGCCCGGCT | |
| | GCATCTGCAGGGCAGATCTAACGCTTGGAGGCCCCAAGTGAACAACCCC | |
| | AAAGAGTGGCTGCAGGTCGACTTTCAGAAAACCATGAAAGTGACCGGCG | |
| | TGACCACACAGGGCGTCAAGTCTCTGCTGACCTCTATGTACGTGAAAGA | |
| | GTTCCTGATCTCCAGCAGCCAGGACGGCCACCAGTGGACCCTGTTTTTC | |
| | CAGAACGGCAAAGTCAAGGTGTTCCAGGGAAACCAGGACAGCTTCACAC | |
| | CCGTGGTCAACTCCCTGGATCCTCCACTGCTGACCAGATACCTGAGAAT | |
| | TCACCCTCAGTCTTGGGTGCACCAGATCGCTCTGAGAATGGAAGTGCTG | |
| | GGATGTGAAGCTCAGGACCTCTACTAAAATAAAAGATCTTTATTTTCAT | |
| | TAGATCTGTGTGTTGGTTTTTTGTGTG | |
| 320 | TGCCAGTTCCCGATCGTTACAGGCGGTACTCCTCAAAGCGTACTAAAGA | pCB100 |
| | ATTATTCTTTTACATTTCAGTGGCCACCAGGAGATACTACCTGGGGGCT | |
| | GTGGAGCTGAGCTGGGACTACATGCAGTCTGACCTGGGGGAGCTGCCTG | |
| | TGGATGCCAGGTTCCCCCCCAGAGTGCCCAAGAGCTTCCCCTTCAACAC | |
| | CTCTGTGGTGTACAAGAAGACCCTGTTTGTGGAGTTCACTGACCACCTG | |
| | TTCAACATTGCCAAGCCCAGGCCCCCCTGGATGGGCCTGCTGGGCCCCA | |
| | CCATCCAGGCTGAGGTGTATGACACTGTGGTGATCACCCTGAAGAACAT | |
| | GGCCAGCCACCCTGTGAGCCTGCATGCTGTGGGGGTGAGCTACTGGAAG | |
| | GCCTCTGAGGGGGCTGAGTATGATGACCAGACCAGCCAGAGGGAGAAGG | |
| | AGGATGACAAGGTGTTCCCTGGGGGCAGCCACACCTATGTGTGGCAGGT | |
| | GCTGAAGGAGAATGGCCCCATGGCCTCTGACCCCCTGTGCCTGACCTAC | |
| | AGCTACCTGAGCCATGTGGACCTGGTGAAGGACCTGAACTCTGGCCTGA | |
| | TTGGGGCCCTGCTGGTGTGCAGGGAGGGCAGCCTGGCCAAGGAGAAGAC | |
| | CCAGACCCTGCACAAGTTCATCCTGCTGTTTGCTGTGTTTGATGAGGGC | |
| | AAGAGCTGGCACTCTGAAACCAAGAACAGCCTGATGCAGGACAGGGATG | |
| | CTGCCTCTGCCAGGGCCTGGCCCAAGATGCACACTGTGAATGGCTATGT | |
| | GAACAGGAGCCTGCCTGGCCTGATTGGCTGCCACAGGAAGTCTGTGTAC | |
| | TGGCATGTGATTGGCATGGGCACCACCCCTGAGGTGCACAGCATCTTCC | |
| | TGGAGGGCCACACCTTCCTGGTCAGGAACCACAGGCAGGCCAGCCTGGA | |
| | GATCAGCCCCATCACCTTCCTGACTGCCCAGACCCTGCTGATGGACCTG | |
| | GGCCAGTTCCTGCTGTTCTGCCACATCAGCAGCCACCAGCATGATGGCA | |
| | TGGAGGCCTATGTGAAGGTGGACAGCTGCCCTGAGGAGCCCCAGCTGAG | |
| | GATGAAGAACAATGAGGAGGCTGAGGACTATGATGATGACCTGACTGAC | |
| | TCTGAGATGGATGTGGTGAGGTTTGATGATGACAACAGCCCCAGCTTCA | |
| | TCCAGATCAGGTCTGTGGCCAAGAAGCACCCCAAGACCTGGGTGCACTA | |
| | CATTGCTGCTGAGGAGGAGGACTGGGACTATGCCCCCCTGGTGCTGGCC | |
| | CCTGATGACAGGAGCTACAAGAGCCAGTACCTGAACAATGGCCCCCAGA | |
| | GGATTGGCAGGAAGTACAAGAAGGTCAGGTTCATGGCCTACACTGATGA | |
| | AACCTTCAAGACCAGGGAGGCCATCCAGCATGAGTCTGGCATCCTGGGC | |
| | CCCCTGCTGTATGGGGAGGTGGGGGACACCCTGCTGATCATCTTCAAGA | |
| | ACCAGGCCAGCAGGCCCTACAACATCTACCCCCATGGCATCACTGATGT | |
| | GAGGCCCCTGTACAGCAGGAGGCTGCCCAAGGGGGTGAAGCACCTGAAG | |
| | GACTTCCCCATCCTGCCTGGGGAGATCTTCAAGTACAAGTGGACTGTGA | |
| | CTGTGGAGGATGGCCCCACCAAGTCTGACCCCAGGTGCCTGACCAGATA | |
| | CTACAGCAGCTTTGTGAACATGGAGAGGGACCTGGCCTCTGGCCTGATT | |
| | GGCCCCCTGCTGATCTGCTACAAGGAGTCTGTGGACCAGAGGGGCAACC | |
| | AGATCATGTCTGACAAGAGGAATGTGATCCTGTTCTCTGTGTTTGATGA | |
| | GAACAGGAGCTGGTACCTGACTGAGAACATCCAGAGGTTCCTGCCCAAC | |
| | CCTGCTGGGGTGCAGCTGGAGGACCCTGAGTTCCAGGCCAGCAACATCA | |
| | TGCACAGCATCAATGGCTATGTGTTTGACAGCCTGCAGCTGTCTGTGTG | |
| | CCTGCATGAGGTGGCCTACTGGTACATCCTGAGCATTGGGGCCCAGACT | |
| | GACTTCCTGTCTGTGTTCTTCTCTGGCTACACCTTCAAGCACAAGATGG | |
| | TGTATGAGGACACCCTGACCCTGTTCCCCTTCTCTGGGGAGACTGTGTT | |
| | CATGAGCATGGAGAACCCTGGCCTGTGGATTCTGGGCTGCCACAACTCT | |
| | GACTTCAGGAACAGGGGCATGACTGCCCTGCTGAAAGTCTCCAGCTGTG | |
| | ACAAGAACACTGGGGACTACTATGAGGACAGCTATGAGGACATCTCTGC | |
| | CTACCTGCTGAGCAAGAACAATGCCATTGAGCCCAGGAGCTTCAGCCAG | |
| | AATCCCCCAGTGCTGAAGAGGCACCAGAGGGAGATCACCAGGACCACCC | |
| | TGCAGTCTGACCAGGAGGAGATTGACTATGATGACACCATCTCTGTGGA | |
| | GATGAAGAAGGAGGACTTTGACATCTACGACGAGGACGAGAACCAGAGC | |
| | CCCAGGAGCTTCCAGAAGAAGACCAGGCACTACTTCATTGCTGCTGTGG | |
| | AGAGGCTGTGGGACTATGGCATGAGCAGCAGCCCCCATGTGCTGAGGAA | |
| | CAGGGCCCAGTCTGGCTCTGTGCCCCAGTTCAAGAAGGTGGTGTTCCAG | |
| | GAGTTCACTGATGGCAGCTTCACCCAGCCCCTGTACAGAGGGGAGCTGA | |
| | ATGAGCACCTGGGCCTGCTGGGCCCCTACATCAGGGCTGAGGTGGAGGA | |
| | CAACATCATGGTGACCTTCAGGAACCAGGCCAGCAGGCCCTACAGCTTC | |
| | TACAGCAGCCTGATCAGCTATGAGGAGGACCAGAGGCAGGGGGCTGAGC | |
| | CCAGGAAGAACTTTGTGAAGCCCAATGAAACCAAGACCTACTTCTGGAA | |
| | GGTGCAGCACCACATGGCCCCCACCAAGGATGAGTTTGACTGCAAGGCC | |
| | TGGGCCTACTTCTCTGATGTGGACCTGGAGAAGGATGTGCACTCTGGCC | |
| | TGATTGGCCCCCTGCTGGTGTGCCACACCAACACCCTGAACCCTGCCCA | |
| | TGGCAGGCAGGTGACTGTGCAGGAGTTTGCCCTGTTCTTCACCATCTTT | |

-continued

| SEQ ID | Sequence | Description |
|---|---|---|
| | GATGAAACCAAGAGCTGGTACTTCACTGAGAACATGGAGAGGAACTGCA<br>GGGCCCCCTGCAACATCCAGATGGAGGACCCCACCTTCAAGGAGAACTA<br>CAGGTTCCATGCCATCAATGGCTACATCATGGACACCCTGCCTGGCCTG<br>GTGATGGCCCAGGACCAGAGGATCAGGTGGTACCTGCTGAGCATGGGCA<br>GCAATGAGAACATCCACAGCATCCACTTCTCTGGCCATGTGTTCACTGT<br>GAGGAAGAAGGAGGAGTACAAGATGGCCCTGTACAACCTGTACCCTGGG<br>GTGTTTGAGACTGTGGAGATGCTGCCCAGCAAGGCTGGCATCTGGAGGG<br>TGGAGTGCCTGATTGGGGAGCACCTGCATGCTGGCATGAGCACCCTGTT<br>CCTGGTGTACAGCAACAAGTGCCAGACCCCCCTGGGCATGGCCTCTGGC<br>CACATCAGGGACTTCCAGATCACTGCCTCTGGCCAGTATGGCCAGTGGG<br>CCCCCAAGCTGGCCAGGCTGCACTACTCTGGCAGCATCAATGCCTGGAG<br>CACCAAGGAGCCCTTCAGCTGGATCAAGGTGGACCTGCTGGCCCCCATG<br>ATCATCCATGGCATCAAGACCCAGGGGGCCAGGCAGAAGTTCAGCAGCC<br>TGTACATCAGCCAGTTCATCATCATGTACAGCCTGGATGGCAAGAAGTG<br>GCAGACCTACAGGGGCAACAGCACTGGCACCCTGATGGTGTTCTTTGGC<br>AATGTGGACAGCTCTGGCATCAAGCACAACATCTTCAACCCCCCCATCA<br>TTGCCAGATACATCAGGCTGCACCCCACCCACTACAGCATCAGGAGCAC<br>CCTGAGGATGGAGCTGATGGGCTGTGACCTGAACAGCTGCAGCATGCCC<br>CTGGGCATGGAGAGCAAGGCCATCTCTGATGCCCAGATCACTGCCAGCA<br>GCTACTTCACCAACATGTTTGCCACCTGGAGCCCCAGCAAGGCCAGGCT<br>GCACCTGCAGGGCAGGAGCAATGCCTGGAGGCCCCAGGTCAACAACCCC<br>AAGGAGTGGCTGCAGGTGGACTTCCAGAAGACCATGAAGGTGACTGGGG<br>TGACCACCCAGGGGGTGAAGAGCCTGCTGACCAGCATGTATGTGAAGGA<br>GTTCCTGATCAGCAGCAGCCAGGATGGCCACCAGTGGACCCTGTTCTTC<br>CAGAATGGCAAGGTGAAGGTGTTCCAGGGCAACCAGGACAGCTTCACCC<br>CTGTGGTGAACAGCCTGGACCCCCCCCTGCTGACCAGATACCTGAGGAT<br>TCACCCCCAGAGCTGGGTGCACCAGATTGCCCTGAGGATGGAGGTGCTG<br>GGCTGTGAGGCCCAGGACCTGTACTGAaataaaagatctttattttcat<br>tagatctgtgtgttggtttttttgtgtg | |
| 321 | cctgcaggcagctgcgcgctcgctcgctcactgaggccgcccgggcaaa<br>gcccgggcgtcgggcgacctttggtcgcccggcctcagtgagcgagcga<br>gcgcgcagagagggagtggccaactccatcactaggggttcctgcggcc<br>taaggcAATTGTGCCAGTTCCCGATCGTTACAGGCGGTACTCCTCAAAG<br>CGTACTAAAGAATTATTCTTTTACATTTCAGTGGCCACCAGAAGGTACT<br>ACCTGGGAGCTGTGGAACTGAGCTGGGACTACATGCAGTCTGACCTGGG<br>AGAGCTGCCTGTGGATGCTAGATTTCCTCCAAGAGTGCCCAAGAGCTTC<br>CCCTTCAACACCTCTGTGGTGTACAAGAAAACCCTGTTTGTGGAATTCA<br>CAGACCACCTGTTCAATATTGCCAAGCCTAGACCTCCTTGGATGGGCCT<br>GCTGGGCCCTACAATTCAGGCTGAGGTGTATGACACAGTGGTCATCACC<br>CTGAAGAACATGGCCAGCCATCCTGTGTCTCTGCATGCTGTGGGAGTGT<br>CTTACTGGAAGGCTTCTGAGGGGGCTGAGTATGATGACCAGACAAGCCA<br>GAGAGAGAAAGAGGATGACAAGGTTTTCCCTGGGGGCAGCCACACCTAT<br>GTCTGGCAGGTCCTGAAAGAAAATGGCCCTATGGCCTCTGATCCTCTGT<br>GCCTGACATACAGCTACCTGAGCCATGTGGACCTGGTCAAGGACCTGAA<br>CTCTGGCCTGATTGGGGCTCTGCTGGTGTGTAGAGAAGGCAGCCTGGCC<br>AAAGAAAAGACCCAGACACTGCACAAGTTCATCCTGCTGTTTGCTGTGT<br>TTGATGAGGGCAAGAGCTGGCACTCTGAGACAAAGAACAGCCTGATGCA<br>GGACAGAGATGCTGCCTCTGCTAGAGCTTGGCCCAAGATGCACACAGTG<br>AATGGCTATGTGAACAGAAGCCTGCCTGGACTGATTGGATGCCACAGAA<br>AGTCTGTGTACTGGCATGTGATTGGCATGGGCACCACACCTGAGGTGCA<br>CAGCATCTTTCTGGAAGGACACACCTTCCTGGTGAGGAACCACAGACAG<br>GCCAGCCTGGAAATCAGCCCTATCACCTTCCTGACAGCTCAGACCCTGC<br>TGATGGATCTGGGCCAGTTTCTGCTGTTCTGCCACATCAGCAGCCACCA<br>GCATGATGGCATGGAAGCCTATGTGAAGGTGGACAGCTGCCCTGAAGAA<br>CCCCAGCTGAGAATGAAGAACAATGAGGAAGCTGAGGACTATGATGATG<br>ACCTGACAGACTCTGAGATGGATGTGGTCAGATTTGATGATGATAACAG<br>CCCCAGCTTCATCCAGATCAGATCTGTGGCCAAGAAGCACCCCAAGACC<br>TGGGTGCACTATATTGCTGCTGAGGAAGAGGACTGGGATTATGCTCCTC<br>TGGTGCTGGCCCCTGATGACAGAAGCTACAAGAGCCAGTACCTGAACAA<br>TGGCCCTCAGAGAATTGGCAGGAAGTATAAGAAAGTGAGGTTCATGGCC<br>TACACAGATGAGACATTCAAGACCAGAGAGGCTATCCAGCATGAGTCTG<br>GCATTCTGGGACCTCTGCTGTATGGGGAAGTGGGGGACACACTGCTGAT<br>CATCTTCAAGAACCAGGCCAGCAGACCCTACAACATCTACCCTCATGGC<br>ATCACAGATGTGAGGCCTCTGTACTCTAGAAGGCTGCCCAAGGGGGTGA<br>AGCACCTGAAGGACTTCCCTATCCTGCCTGGGGAGATCTTCAAGTACAA<br>GTGGACAGTGACAGTGGAGGATGGCCCTACCAAGTCTGATCCTAGATGC<br>CTGACAAGGTACTACAGCAGCTTTGTGAACATGGAAAGGGACCTGGCCT<br>CTGGCCTGATTGGTCCTCTGCTGATCTGCTACAAAGAATCTGTGGACCA<br>GAGGGGCAACCAGATCATGAGTGACAAGAGAAATGTGATCCTGTTCTCT<br>GTCTTTGATGAGAACAGGTCCTGGTATCTGACAGAGAACATCCAGAGGT<br>TTCTGCCCAATCCTGCTGGGGTGCAGCTGGAAGATCCTGAGTTCCAGGC<br>CTCCAACATCATGCACTCCATCAATGGCTATGTGTTTGACAGCCTGCAG<br>CTGTCTGTGTGCCTGCATGAAGTGGCCTACTGGTACATCCTGTCTATTG<br>GGGCCCAGACAGACTTCCTGTCTGTGTTCTTTTCTGGCTACACCTTCAA<br>GCACAAGATGGTGTATGAGGATACCCTGACACTGTTCCCATTCTCTGGG<br>GAGACAGTGTTCATGAGCATGGAAAACCCTGGCCTGTGGATCCTGGGCT | pCB1000 |

-continued

| SEQ ID | Sequence | Description |
|---|---|---|
| | GTCACAACAGTGACTTCAGAAACAGAGGCATGACAGCCCTGCTGAAGGT<br>GTCCAGCTGTGACAAGAACACTGGGGACTACTATGAGGACTCTTATGAG<br>GACATCTCTGCCTACCTGCTGAGCAAGAACAATGCCATTGAGCCTAGGA<br>GCTTCTCTCAGAACCCTCCTGTGCTGAAGAGACACCAGAGGGAGATCAC<br>CAGAACCACACTGCAGTCTGACCAAGAGGAAATTGATTATGATGACACC<br>ATCTCTGTGGAGATGAAGAAAGAAGATTTTGACATCTATGATGAGGATG<br>AGAATCAGAGCCCCAGATCTTTCCAGAAGAAAACAAGGCACTACTTCAT<br>TGCTGCTGTGGAAAGACTGTGGGACTATGGCATGAGCAGCAGCCCCCAT<br>GTGCTGAGAAACAGGGCCCAGTCTGGAAGTGTGCCCCAGTTCAAGAAAG<br>TGGTGTTCCAAGAGTTCACAGATGGCAGCTTCACCCAGCCTCTGTATAG<br>AGGGGAGCTGAATGAGCACCTGGGACTGCTGGGACCTTACATCAGAGCT<br>GAGGTGGAGGATAACATCATGGTCACCTTTAGAAACCAGGCCTCTAGGC<br>CCTACTCCTTCTACAGCTCCCTGATCAGCTATGAAGAGGACCAGAGACA<br>GGGGGCTGAGCCCAGAAAGAACTTTGTGAAGCCCAATGAGACTAAGACC<br>TACTTTTGGAAGGTGCAGCACCACATGGCCCCTACAAAGGATGAGTTTG<br>ACTGCAAGGCCTGGGCCTACTTCTCTGATGTGGACCTGGAGAAGGATGT<br>GCACTCTGGACTCATTGGACCCCTGCTTGTGTGCCACACCAACACACTG<br>AATCCTGCTCATGGCAGGCAAGTGACAGTGCAAGAGTTTGCCCTGTTCT<br>TCACCATCTTTGATGAGACAAAGTCCTGGTACTTCACAGAAAACATGGA<br>AAGAAACTGCAGGGCCCCTTGCAACATCCAGATGGAAGATCCCACCTTC<br>AAAGAGAACTACAGGTTCCATGCCATCAATGGCTACATCATGGACACTC<br>TGCCTGGCCTGGTTATGGCACAGGATCAGAGGATCAGATGGTATCTGCT<br>GTCCATGGGCTCCAATGAGAATATCCACAGCATCCACTTCTCTGGCCAT<br>GTGTTCACAGTGAGGAAAAAAGAAGAGTACAAGATGGCCCTGTACAATC<br>TGTACCCTGGGGTGTTTGAGACTGTGGAAATGCTGCCTAGCAAGGCTGG<br>AATCTGGAGGGTGGAATGTCTGATTGGAGAGCATCTGCATGCTGGAATG<br>TCTACCCTGTTCCTGGTGTACAGCAACAAGTGTCAGACCCCTCTGGGCA<br>TGGCCTCTGGACACATCAGAGACTTCCAGATCACAGCCTCTGGCCAGTA<br>TGGACAGTGGGCTCCTAAACTGGCTAGACTGCACTACTCTGGCAGCATC<br>AATGCCTGGTCCACCAAAGAGCCCTTCAGCTGGATCAAGGTGGACCTGC<br>TGGCTCCCATGATCATCCATGGAATCAAGACCCAGGGGGCCAGACAGAA<br>GTTCAGCAGCCTGTACATCAGCCAGTTCATCATCATGTACAGCCTGGAT<br>GGCAAGAAGTGGCAGACCTACAGAGGCAACAGCACAGGCACACTCATGG<br>TGTTCTTTGGCAATGTGGACTCTTCTGGCATTAAGCACAACATCTTCAA<br>CCCTCCAATCATTGCCAGGTACATCAGGCTGCACCCCACACACTACAGC<br>ATCAGATCTACCCTGAGGATGGAACTGATGGGCTGTGACCTGAACAGCT<br>GCTCTATGCCCCTGGGAATGGAAAGCAAGGCCATCTCTGATGCCCAGAT<br>CACAGCCAGCAGCTACTTCACCAACATGTTTGCCACATGGTCCCCATCT<br>AAGGCCAGGCTGCATCTGCAGGGCAGATCTAATGCTTGGAGGCCCCAAG<br>TGAACAACCCCAAAGAGTGGCTGCAGGTGGACTTTCAGAAAACCATGAA<br>AGTGACAGGAGTGACCACACAGGGGGTCAAGTCTCTGCTGACCTCTATG<br>TATGTGAAAGAGTTCCTGATCTCCAGCAGCCAGGATGGCCACCAGTGGA<br>CCCTGTTTTTCCAGAATGGCAAAGTCAAGGTGTTCCAGGGAAACCAGGA<br>CAGCTTCACACCTGTGGTCAACTCCCTGGATCCTCCACTGCTGACCAGA<br>TACCTGAGAATTCACCCTCAGTCTTGGGTGCACCAGATTGCTCTGAGAA<br>TGGAAGTGCTGGGATGTGAAGCTCAGGACCTCTACTGAtcgcgAATAAA<br>AGATCTTTATTTTCATTAGATCTGTGTGTTGGTTTTTTGTGTGTGCCAG<br>TTCCCGATCGTTACAGGCCGCgggccgcaggaacccctagtgatggagt<br>tggccactccctctctgcgcgctcgctcgctcactgaggccgggcgacc<br>aaaggtcgcccgacgcccgggctttgcccgggcggcctcagtgagcgag<br>cgagcgcgcagctgcctgcagg | |
| 322 | cctgcaggcagctgcgcgctcgctcgctcactgaggccgcccgggcaaa<br>gcccgggcgtcgggcgacctttggtcgcccggcctcagtgagcgagcga<br>gcgcgcagagagggagtggccaactccatcactaggggttcctgcggcc<br>taaggcAATTGTGCCAGTTCCCGATCGTTACAGGCGGTACTCCTCAAAG<br>CGTACTAAAGAATTATTCTTTTACATTTCAGTGGCCACCAGAAGGTACT<br>ACCTAGGAGCCGTGGAACTGAGCTGGGACTACATGCAGTCTGACCTGGG<br>AGAGCTGCCCGTGGACGCTAGATTTCCTCCAAGAGTGCCCAAGAGCTTC<br>CCCTTCAACACCTCCGTGGTGTACAAGAAAACCCTGTTCGTGGAATTCA<br>CCGACCACCTGTTCAATATCGCCAAGCCTAGACCTCCTTGGATGGGCCT<br>GCTGGGCCCTACAATTCAGGCCGAGGTGTACGACACCGTGGTCATCACC<br>CTGAAGAACATGGCCAGCCATCCTGTGTCTCTGCACGCCGTGGGAGTGT<br>CTTACTGGAAGGCTTCTGAGGGCGCCGAGTACGACGACCAGACAAGCCA<br>GAGAGAGAAAGAGGACGACAAGGTTTTCCCTGGCGGCAGCCACACCTAT<br>GTCTGGCAGGTCCTGAAAGAAAACGGCCCTATGGCCTCCGATCCTCTGT<br>GCCTGACATACAGCTACCTGAGCCATGTGGACCTGGTCAAGGACCTGAA<br>CTCTGGCCTGATCGGCGCTCTGCTCGTGTGTAGAGAAGGCAGCCTGGCC<br>AAAGAAAAGACCCAGACACTGCACAAGTTCATCCTGCTGTTCGCCGTGT<br>TCGACGAGGGCAAGAGCTGGCACAGCGAGACAAAGAACAGCCTGATGCA<br>GGACAGAGATGCCGCCTCTGCTAGAGCTTGGCCCAAGATGCACACCGTG<br>AACGGCTACGTGAACAGAAGCCTGCCTGGACTGATCGGATGCCACAGAA<br>AGTCCGTGTACTGGCATGTGATCGGCATGGGCACCACACCTGAGGTGCA<br>CAGCATCTTTCTGGAAGGACACACCTTCCTCGTGCGGAACCACAGACAG<br>GCCAGCCTGGAAATCAGCCCTATCACCTTCCTGACCGCTCAGACCCTGC<br>TGATGGATCTGGGCCAGTTTCTGCTGTTCTGCCACATCAGCAGCCACCA<br>GCACGATGGCATGGAAGCCTACGTGAAGGTGGACAGCTGCCCCGAAGAA | pCB1001 |

-continued

| SEQ ID | Sequence | Description |
|---|---|---|
| | CCCCAGCTGAGAATGAAGAACAACGAGGAAGCCGAGGACTACGACGACG<br>ACCTGACCGACTCTGAGATGGACGTCGTCAGATTCGACGACGATAACAG<br>CCCCAGCTTCATCCAGATCAGAAGCGTGGCCAAGAAGCACCCCAAGACC<br>TGGGTGCACTATATCGCCGCCGAGGAAGAGGACTGGGATTACGCTCCTC<br>TGGTGCTGGCCCCTGACGACAGAAGCTACAAGAGCCAGTACCTGAACAA<br>CGGCCCTCAGAGAATCGGCCGGAAGTATAAGAAAGTGCGGTTCATGGCC<br>TACACCGACGAGACATTCAAGACCAGAGAGGCTATCCAGCACGAGAGCG<br>GCATTCTGGGACCTCTGCTGTATGGCGAAGTGGGCGACACACTGCTGAT<br>CATCTTCAAGAACCAGGCCAGCAGACCCTACAACATCTACCCTCACGGC<br>ATCACCGATGTGCGGCCTCTGTACTCTAGAAGGCTGCCCAAGGGCGTGA<br>AGCACCTGAAGGACTTCCCTATCCTGCCTGGCGAGATCTTCAAGTACAA<br>GTGGACCGTGACCGTCGAGGACGGCCCTACCAAGAGCGATCCTAGATGC<br>CTGACACGGTACTACAGCAGCTTCGTGAACATGGAACGCGACCTGGCCA<br>GCGGCCTGATTGGTCCTCTGCTGATCTGCTACAAAGAAAGCGTGGACCA<br>GAGGGGCAACCAGATCATGAGCGACAAGAGAAACGTGATCCTGTTCTCC<br>GTCTTTGACGAGAACAGGTCCTGGTATCTGACCGAGAACATCCAGCGGT<br>TTCTGCCCAATCCTGCTGGCGTGCAGCTGGAAGATCCTGAGTTCCAGGC<br>CTCCAACATCATGCACTCCATCAACGGCTATGTGTTCGACAGCCTGCAG<br>CTGAGCGTGTGCCTGCACGAAGTGGCCTACTGGTACATCCTGTCTATCG<br>GCGCCCAGACCGACTTCCTGTCCGTGTTCTTTAGCGGCTACACCTTCAA<br>GCACAAGATGGTGTACGAGGATACCCTGACACTGTTCCCATTCAGCGGC<br>GAGACAGTGTTCATGAGCATGGAAAACCCCGGCCTGTGGATCCTGGGCT<br>GTCACAACAGCGACTTCAGAAACAGAGGCATGACAGCCCTGCTGAAGGT<br>GTCCAGCTGCGACAAGAACACCGGCGACTACTACGAGGACTCTTACGAG<br>GACATCAGCGCCTACCTGCTGAGCAAGAACAATGCCATCGAGCCTCGGA<br>GCTTCTCTCAGAACCCTCCTGTGCTGAAGAGACACCAGCGCGAGATCAC<br>CAGAACCACACTGCAGAGCGACCAAGAGGAAATCGATTACGACGACACC<br>ATCAGCGTCGAGATGAAGAAAGAAGATTTCGACATCTACGACGAGGACG<br>AGAATCAGAGCCCCAGATCTTTCCAGAAGAAAACGCGGCACTACTTCAT<br>TGCCGCCGTGGAAAGACTGTGGGACTACGGCATGAGCAGCAGCCCACAT<br>GTGCTGAGAAACAGGGCCCAGAGCGGAAGCGTGCCCCAGTTCAAGAAAG<br>TGGTGTTCCAAGAGTTCACCGACGGCAGCTTCACCCAGCCTCTGTATAG<br>AGGCGAGCTGAACGAGCACCTGGGACTGCTGGGACCTTACATCAGAGCT<br>GAGGTCGAGGATAACATCATGGTCACCTTTAGAAACCAGGCCTCTAGGC<br>CCTACTCCTTCTACAGCTCCCTGATCAGCTACGAAGAGGACCAGAGACA<br>GGGCGCTGAGCCCAGAAAGAACTTCGTGAAGCCCAACGAGACTAAGACC<br>TACTTTTGGAAGGTGCAGCACCACATGGCCCCTACAAAGGACGAGTTCG<br>ACTGCAAGGCCTGGGCCTACTTCTCTGACGTGGACCTCGAGAAGGATGT<br>GCACAGCGGACTCATCGGACCCCTGCTTGTGTGCCACACCAACACACTG<br>AATCCCGCTCACGGCAGGCAAGTGACCGTGCAAGAGTTCGCCCTGTTCT<br>TCACCATCTTCGATGAGACAAAGTCCTGGTACTTCACCGAAAACATGGA<br>AAGAAACTGCAGGGCCCCTTGCAACATCCAGATGGAAGATCCCACCTTC<br>AAAGAGAACTACCGGTTCCACGCCATCAATGGCTACATCATGGACACTC<br>TGCCCGGCCTGGTTATGGCACAGGATCAGAGGATCAGATGGTATCTGCT<br>GTCCATGGGCTCCAACGAGAATATCCACAGCATCCACTTCAGCGGCCAT<br>GTGTTCACCGTGCGGAAAAAAGAAGAGTACAAGATGGCCCTGTACAATC<br>TGTACCCCGGCGTGTTCGAGACTGTGGAAATGCTGCCTAGCAAGGCCGG<br>AATCTGGCGCGTGGAATGTCTGATCGGAGAGCATCTGCATGCCGGAATG<br>TCTACCCTGTTCCTGGTGTACAGCAACAAGTGTCAGACCCCTCTCGGCA<br>TGGCCTCTGGACACATCAGAGACTTCCAGATCACCGCCTCTGGCCAGTA<br>CGGACAGTGGGCTCCTAAACTGGCTAGACTGCACTACAGCGGCAGCATC<br>AACGCCTGGTCCACCAAAGAGCCCTTCAGCTGGATCAAGGTGGACCTGC<br>TGGCTCCCATGATCATCCACGGAATCAAGACCCAGGGCGCCAGACAGAA<br>GTTCAGCAGCCTGTACATCAGCCAGTTCATCATCATGTACAGCCTGGAC<br>GGCAAGAAGTGGCAGACCTACAGAGGCAACAGCACCGGCACACTCATGG<br>TGTTCTTCGGCAACGTGGACTCCAGCGGCATTAAGCACAACATCTTCAA<br>CCCTCCAATCATTGCCCGGTACATCCGGCTGCACCCCACACACTACAGC<br>ATCAGATCTACCCTGAGGATGGAACTGATGGGCTGCGACCTGAACAGCT<br>GCTCTATGCCCCTCGGAATGGAAAGCAAGGCCATCAGCGACGCCCAGAT<br>CACAGCCAGCAGCTACTTCACCAACATGTTCGCCACATGGTCCCCATCT<br>AAGGCCCGGCTGCATCTGCAGGGCAGATCTAACGCTTGGAGGCCCCAAG<br>TGAACAACCCCAAAGAGTGGCTGCAGGTCGACTTTCAGAAAACCATGAA<br>AGTGACCGGCGTGACCACACAGGGCGTCAAGTCTCTGCTGACCTCTATG<br>TACGTGAAAGAGTTCCTGATCTCCAGCAGCCAGGACGGCCACCAGTGGA<br>CCCTGTTTTTCCAGAACGGCAAAGTCAAGGTGTTCCAGGGAAACCAGGA<br>CAGCTTCACACCCGTGGTCAACTCCCTGGATCCTCCACTGCTGACCAGA<br>TACCTGAGAATTCACCCTCAGTCTTGGGTGCACCAGATCGCTCTGAGAA<br>TGGAAGTGCTGGGATGTGAAGCTCAGGACCTCTACTGAtcgcgAATAAA<br>AGATCTTTATTTTCATTAGATCTGTGTGTTGGTTTTTTGTGTGTGCCAG<br>TTCCCGATCGTTACAGGCCGCgggccgcaggaacccctagtgatggagt<br>tggccactccctctctgcgcgctcgctcgctcactgaggccgggcgacc<br>aaaggtcgcccgacgcccgggctttgcccgggcggcctcagtgagcgag<br>cgagcgcgcagctgcctgcagg | |
| 323 | cctgcaggcagctgcgcgctcgctcgctcactgaggccgcccgggcaaa<br>gcccgggcgtcgggcgacctttggtcgcccggcctcagtgagcgagcga<br>gcgcgcagagagggagtggccaactccatcactaggggttcctgcggcc | pCB1002 |

-continued

| SEQ ID | Sequence | Description |
|---|---|---|
| | CTCGAGTGCCAGTTCCCGATCGTTACAGGCGGTACTCCTCAAAGCGTAC<br>TAAAGAATTATTCTTTTACATTTCAGTGGCTACCAGAAGATACTACCTG<br>GGAGCCGTCGAACTGAGCTGGGATTACATGCAGTCTGACCTGGGAGAGC<br>TGCCCGTGGACGCTAGATTCCCACCTAGAGTCCCTAAGTCCTTCCCCTT<br>CAACACCAGCGTGGTCTACAAGAAAACCCTGTTCGTGGAGTTTACCGAC<br>CACCTGTTCAACATCGCTAAGCCTAGACCACCATGGATGGGACTGCTGG<br>GACCAACCATCCAGGCCGAGGTGTACGACACCGTGGTCATCACCCTGAA<br>AAACATGGCTTCTCACCCCGTGTCCCTGCATGCTGTGGGCGTCTCCTAC<br>TGGAAGGCCAGCGAAGGGGCTGAGTATGACGATCAGACCAGCCAGCGGG<br>AAAAAGAGGACGATAAGGTGTTCCCTGGCGGGTCCCATACCTACGTGTG<br>GCAGGTCCTGAAGGAGAATGGACCAATGGCTTCCGACCCTCTGTGCCTG<br>ACCTACTCTTATCTGTCCCACGTGGACCTGGTCAAGGATCTGAACAGCG<br>GCCTGATCGGGGCTCTGCTGGTGTGTCGCGAAGGGTCCCTGGCCAAGGA<br>GAAAACCCAGACCCTGCATAAGTTCATCCTGCTGTTCGCCGTGTTTGAC<br>GAAGGAAAAAGCTGGCACTCTGAGACCAAGAACTCTCTGATGCAGGACA<br>GGGATGCCGCTTCCGCCAGAGCTTGGCCCAAGATGCACACCGTGAACGG<br>CTACGTCAATAGGAGCCTGCCTGGACTGATCGGCTGCCACAGAAAGTCC<br>GTGTATTGGCATGTCATCGGAATGGGCACCACCCCTGAAGTGCACAGCA<br>TCTTCCTGGAGGGGCATACCTTTCTGGTCCGCAACCACCGGCAGGCTAG<br>CCTGGAGATCTCTCCAATCACCTTCCTGACCGCCCAGACCCTGCTGATG<br>GACCTGGGACAGTTCCTGCTGTTTTGCCACATCTCCAGCCACCAGCATG<br>ATGGCATGGAGGCTTACGTGAAAGTCGACTCCTGTCCCGAGGAACCTCA<br>GCTGAGGATGAAGAACAATGAGGAAGCCGAAGACTATGACGATGACCTG<br>ACCGACAGCGAGATGGATGTGGTCCGCTTCGATGACGATAACTCTCCCT<br>CCTTTATCCAGATCCGGTCCGTGGCCAAGAAACACCCTAAGACCTGGGT<br>CCATTACATCGCCGCTGAGGAAGAGGACTGGGATTATGCTCCACTGGTG<br>CTGGCCCCCGACGATAGATCCTACAAAAGCCAGTATCTGAACAATGGAC<br>CCCAGAGGATCGGCAGAAAGTACAAGAAAGTGAGGTTCATGGCTTATAC<br>CGATGAGACCTTTAAGACCAGAGAAGCCATCCAGCACGAGTCCGGGATC<br>CTGGGACCTCTGCTGTACGGCGAAGTGGGGGACACCCTGCTGATCATCT<br>TCAAGAACCAGGCCAGCAGGCCTTACAATATCTATCCACATGGCATCAC<br>CGATGTGAGACCTCTGTACTCCCGCCGGCTGCCAAAGGGCGTGAAACAC<br>CTGAAGGACTTCCCAATCCTGCCCGGGGAAATCTTTAAGTATAAATGGA<br>CCGTCACCGTCGAGGATGGGCCCACCAAGAGCGACCCTAGGTGCCTGAC<br>CAGATACTATTCTTCCTTCGTGAATATGGAGAGAGACCTGGCTTCCGGA<br>CTGATCGGACCCCTGCTGATCTGTTACAAAGAGAGCGTGGATCAGCGCG<br>GCAACCAGATCATGTCTGACAAGCGGAATGTGATCCTGTTCAGCGTCTT<br>TGACGAAAACCGCTCTTGGTACCTGACCGAGAACATCCAGCGGTTCCTG<br>CCTAATCCAGCTGGAGTGCAGCTGGAAGATCCCGAGTTCCAGGCCTCTA<br>ACATCATGCATTCCATCAATGGCTACGTGTTCGACTCCCTGCAGCTGAG<br>CGTGTGCCTGCACGAGGTCGCTTACTGGTATATCCTGAGCATCGGAGCC<br>CAGACCGATTTCCTGTCTGTGTTCTTTTCCGGCTACACCTTTAAGCATA<br>AAATGGTGTATGAGGACACCCTGACCCTGTTCCCATTTTCCGGCGAAAC<br>CGTGTTCATGAGCATGGAGAATCCCGGGCTGTGGATCCTGGGATGCCAC<br>AACTCCGATTTCAGGAATAGAGGGATGACCGCCCTGCTGAAAGTGAGCT<br>CTTGTGACAAGAACACCGGAGACTACTATGAAGATAGCTACGAGGACAT<br>CTCTGCTTATCTGCTGTCCAAAAACAATGCCATCGAGCCCAGGAGCTTC<br>TCTCAGAACCCTCCAGTGCTGAAGCGCCACCAGCGGGAGATCACCAGAA<br>CCACCCTGCAGAGCGATCAGGAAGAGATCGACTACGACGATACCATCTC<br>CGTGGAAATGAAGAAAGAGGACTTCGATATCTATGACGAAGATGAGAAC<br>CAGTCTCCCAGGTCCTTCCAGAAGAAAACCAGACATTACTTTATCGCCG<br>CTGTGGAGCGGCTGTGGGACTATGGCATGTCCAGCTCTCCTCACGTGCT<br>GAGAAATAGAGCTCAGTCCGGAAGCGTCCCACAGTTCAAGAAAGTGGTC<br>TTCCAGGAGTTTACCGACGGAAGCTTTACCCAGCCACTGTACCGCGGCG<br>AACTGAACGAGCACCTGGGGCTGCTGGGACCCTATATCCGGGCTGAAGT<br>GGAGGATAACATCATGGTCACCTTCAGGAATCAGGCCAGCAGACCCTAC<br>TCTTTTTATTCCAGCCTGATCTCCTACGAAGAGGACCAGAGACAGGGAG<br>CTGAACCAAGAAAAAACTTCGTGAAGCCTAATGAGACCAAAACCTACTT<br>TTGGAAGGTGCAGCACCATATGGCCCCTACCAAAGACGAGTTCGATTGC<br>AAGGCCTGGGCTTATTTTAGCGACGTGGATCTGGAGAAGGACGTCCACT<br>CCGGCCTGATCGGGCCACTGCTGGTGTGTCATACCAACACCCTGAATCC<br>AGCTCACGGAAGGCAGGTGACCGTCCAGGAATTCGCCCTGTTCTTTACC<br>ATCTTTGATGAGACCAAGAGCTGGTACTTCACCGAAAACATGGAGAGGA<br>ATTGCAGAGCCCCATGTAACATCCAGATGGAAGACCCCACCTTCAAGGA<br>GAACTACAGATTTCATGCTATCAATGGGTATATCATGGATACCCTGCCA<br>GGACTGGTCATGGCTCAGGACCAGAGGATCAGATGGTACCTGCTGAGCA<br>TGGGGTCTAACGAGAATATCCACTCCATCCATTTCAGCGGACACGTGTT<br>TACCGTCCGCAAGAAAGAAGAGTACAAGATGGCCCTGTACAACCTGTAT<br>CCCGGCGTGTTCGAAACCGTCGAGATGCTGCCTTCCAAGGCTGGGATCT<br>GGCGGGTGGAATGCCTGATCGGGGAGCACCTGCATGCCGGAATGTCTAC<br>CCTGTTCCTGGTGTACTCCAATAAGTGTCAGACCCCCCTGGGGATGGCT<br>AGCGGACATATCCGCGACTTCCAGATCACCGCTTCCGGACAGTACGGAC<br>AGTGGGCTCCTAAGCTGGCTAGACTGCACTATTCTGGCTCCATCAACGC<br>TTGGTCTACCAAAGAGCCTTTCTCCTGGATCAAGGTGGACCTGCTGGCT<br>CCAATGATCATCCATGGCATCAAAACCCAGGGGGCCAGGCAGAAGTTCT<br>CTTCCCTGTACATCAGCCAGTTTATCATCATGTATTCTCTGGATGGGAA<br>GAAATGGCAGACCTACAGAGGCAATTCCACCGGGACCCTGATGGTGTTC | |

-continued

| SEQ ID | Sequence | Description |
|---|---|---|
| | TTTGGCAACGTCGACAGCTCTGGGATCAAGCACAACATCTTCAATCCCC CTATCATCGCCCGCTACATCCGGCTGCACCCAACCCATTATTCCATCCG CAGCACCCTGCGGATGGAGCTGATGGGGTGCGATCTGAACAGCTGTTCT ATGCCCCTGGGAATGGAGTCTAAGGCCATCTCCGACGCTCAGATCACCG CCTCCAGCTACTTCACCAATATGTTTGCTACCTGGTCCCCAAGCAAGGC TAGACTGCATCTGCAGGGAAGAAGCAACGCTTGGAGACCACAGGTGAAC AATCCCAAGGAGTGGCTGCAGGTCGACTTCCAGAAAACCATGAAGGTGA CCGGAGTCACCACCCAGGGCGTGAAAAGCCTGCTGACCTCTATGTACGT CAAGGAGTTCCTGATCTCTTCCAGCCAGGACGGGCACCAGTGGACCCTG TTCTTTCAGAACGGAAAGGTGAAAGTCTTCCAGGGCAATCAGGATTCCT TTACCCCTGTGGTCAACAGCCTGGACCCACCCCTGCTGACCAGGTACCT GAGAATCCACCCACAGTCCTGGGTGCATCAGATCGCTCTGAGGATGGAA GTCCTGGGCTGCGAGGCCCAGGACCTGTATTGATCGCGAATAAAAGATC TTTATTTTCATTAGATCTGTGTGTTGGTTTTTTGTGTGGATCTGCCAGT TCCCGATCGTTACAGGCAATTgccttaggccgcaggaacccctagtgat ggagttggccactccctctctgcgcgctcgctcgctcactgaggccggg cgaccaaaggtcgcccgacgcccgggctttgcccgggcggcctcagtga gcgagcgagcgcgcagctgcctgcagg | |
| 324 | TGCCAGTTCCCGATCGTTACAGGCGGTACTCCTCAAAGCGTACTAAAGA ATTATTCTTTTACATTTCAGTGGCTACCAGAAGATACTACCTGGGAGCC GTCGAACTGAGCTGGGATTACATGCAGTCTGACCTGGGAGAGCTGCCCG TGGACGCTAGATTCCCACCTAGAGTCCCTAAGTCCTTCCCCTTCAACAC CAGCGTGGTCTACAAGAAAACCCTGTTCGTGGAGTTTACCGACCACCTG TTCAACATCGCTAAGCCTAGACCACCATGGATGGGACTGCTGGGACCAA CCATCCAGGCCGAGGTGTACGACACCGTGGTCATCACCCTGAAAAACAT GGCTTCTCACCCCGTGTCCCTGCATGCTGTGGGCGTCTCCTACTGGAAG GCCAGCGAAGGGGCTGAGTATGACGATCAGACCAGCCAGCGGGAAAAAG AGGACGATAAGGTGTTCCCTGGCGGGTCCCATACCTACGTGTGGCAGGT CCTGAAGGAGAATGGACCAATGGCTTCCGACCCTCTGTGCCTGACCTAC TCTTATCTGTCCCACGTGGACCTGGTCAAGGATCTGAACAGCGGCCTGA TCGGGGCTCTGCTGGTGTGTCGCGAAGGGTCCCTGGCCAAGGAGAAAAC CCAGACCCTGCATAAGTTCATCCTGCTGTTCGCCGTGTTTGACGAAGGA AAAAGCTGGCACTCTGAGACCAAGAACTCTCTGATGCAGGACAGGGATG CCGCTTCCGCCAGAGCTTGGCCCAAGATGCACACCGTGAACGGCTACGT CAATAGGAGCCTGCCTGGACTGATCGGCTGCCACAGAAAGTCCGTGTAT TGGCATGTCATCGGAATGGGCACCACCCCTGAAGTGCACAGCATCTTCC TGGAGGGGCATACCTTTCTGGTCCGCAACCACCGGCAGGCTAGCCTGGA GATCTCTCCAATCACCTTCCTGACCGCCCAGACCCTGCTGATGGACCTG GGACAGTTCCTGCTGTTTTGCCACATCTCCAGCCACCAGCATGATGGCA TGGAGGCTTACGTGAAAGTCGACTCCTGTCCCGAGGAACCTCAGCTGAG GATGAAGAACAATGAGGAAGCCGAAGACTATGACGATGACCTGACCGAC AGCGAGATGGATGTGGTCCGCTTCGATGACGATAACTCTCCCTCCTTTA TCCAGATCCGGTCCGTGGCCAAGAAACACCCTAAGACCTGGGTCCATTA CATCGCCGCTGAGGAAGAGGACTGGGATTATGCTCCACTGGTGCTGGCC CCCGACGATAGATCCTACAAAAGCCAGTATCTGAACAATGGACCCCAGA GGATCGGCAGAAAGTACAAGAAAGTGAGGTTCATGGCTTATACCGATGA GACCTTTAAGACCAGAGAAGCCATCCAGCACGAGTCCGGGATCCTGGGA CCTCTGCTGTACGGCGAAGTGGGGGACACCCTGCTGATCATCTTCAAGA ACCAGGCCAGCAGGCCTTACAATATCTATCCACATGGCATCACCGATGT GAGACCTCTGTACTCCCGCCGGCTGCCAAAGGGCGTGAAACACCTGAAG GACTTCCCAATCCTGCCCGGGGAAATCTTTAAGTATAAATGGACCGTCA CCGTCGAGGATGGGCCCACCAAGAGCGACCCTAGGTGCCTGACCAGATA CTATTCTTCCTTCGTGAATATGGAGAGAGACCTGGCTTCCGGACTGATC GGACCCCTGCTGATCTGTTACAAAGAGAGCGTGGATCAGCGCGGCAACC AGATCATGTCTGACAAGCGGAATGTGATCCTGTTCAGCGTCTTTGACGA AAACCGCTCTTGGTACCTGACCGAGAACATCCAGCGGTTCCTGCCTAAT CCAGCTGGAGTGCAGCTGGAAGATCCCGAGTTCCAGGCCTCTAACATCA TGCATTCCATCAATGGCTACGTGTTCGACTCCCTGCAGCTGAGCGTGTG CCTGCACGAGGTCGCTTACTGGTATATCCTGAGCATCGGAGCCCAGACC GATTTCCTGTCTGTGTTCTTTTCCGGCTACACCTTTAAGCATAAAATGG TGTATGAGGACACCCTGACCCTGTTCCCATTTTCCGGCGAAACCGTGTT CATGAGCATGGAGAATCCCGGGCTGTGGATCCTGGGATGCCACAACTCC GATTTCAGGAATAGAGGGATGACCGCCCTGCTGAAAGTGAGCTCTTGTG ACAAGAACACCGGAGACTACTATGAAGATAGCTACGAGGACATCTCTGC TTATCTGCTGTCCAAAAACAATGCCATCGAGCCCAGGAGCTTCTCTCAG AACCCTCCAGTGCTGAAGCGCCACCAGCGGGAGATCACCAGAACCACCC TGCAGAGCGATCAGGAAGAGATCGACTACGACGATACCATCTCCGTGGA AATGAAGAAAGAGGACTTCGATATCTATGACGAAGATGAGAACCAGTCT CCCAGGTCCTTCCAGAAGAAAACCAGACATTACTTTATCGCCGCTGTGG AGCGGCTGTGGGACTATGGCATGTCCAGCTCTCCTCACGTGCTGAGAAA TAGAGCTCAGTCCGGAAGCGTCCCACAGTTCAAGAAAGTGGTCTTCCAG GAGTTTACCGACGGAAGCTTTACCCAGCCACTGTACCGCGGCGAACTGA ACGAGCACCTGGGGCTGCTGGGACCCTATATCCGGGCTGAAGTGGAGGA TAACATCATGGTCACCTTCAGGAATCAGGCCAGCAGACCCTACTCTTTT TATTCCAGCCTGATCTCCTACGAAGAGGACCAGAGACAGGGAGCTGAAC CAAGAAAAAACTTCGTGAAGCCTAATGAGACCAAAACCTACTTTTGGAA | pCB1003 |

-continued

| SEQ ID | Sequence | Description |
|---|---|---|
| | GGTGCAGCACCATATGGCCCCTACCAAAGACGAGTTCGATTGCAAGGCC<br>TGGGCTTATTTTAGCGACGTGGATCTGGAGAAGGACGTCCACTCCGGCC<br>TGATCGGGCCACTGCTGGTGTGTCATACCAACACCCTGAATCCAGCTCA<br>CGGAAGGCAGGTGACCGTCCAGGAATTCGCCCTGTTCTTTACCATCTTT<br>GATGAGACCAAGAGCTGGTACTTCACCGAAAACATGGAGAGGAATTGCA<br>GAGCCCCATGTAACATCCAGATGGAAGACCCCACCTTCAAGGAGAACTA<br>CAGATTTCATGCTATCAATGGGTATATCATGGATACCCTGCCAGGACTG<br>GTCATGGCTCAGGACCAGAGGATCAGATGGTACCTGCTGAGCATGGGGT<br>CTAACGAGAATATCCACTCCATCCATTTCAGCGGACACGTGTTTACCGT<br>CCGCAAGAAAGAAGAGTACAAGATGGCCCTGTACAACCTGTATCCCGGC<br>GTGTTCGAAACCGTCGAGATGCTGCCTTCCAAGGCTGGGATCTGGCGGG<br>TGGAATGCCTGATCGGGGAGCACCTGCATGCCGGAATGTCTACCCTGTT<br>CCTGGTGTACTCCAATAAGTGTCAGACCCCCCTGGGGATGGCTAGCGGA<br>CATATCCGCGACTTCCAGATCACCGCTTCCGGACAGTACGGACAGTGGG<br>CTCCTAAGCTGGCTAGACTGCACTATTCTGGCTCCATCAACGCTTGGTC<br>TACCAAAGAGCCTTTCTCCTGGATCAAGGTGGACCTGCTGGCTCCAATG<br>ATCATCCATGGCATCAAAACCCAGGGGGCCAGGCAGAAGTTCTCTTCCC<br>TGTACATCAGCCAGTTTATCATCATGTATTCTCTGGATGGGAAGAAATG<br>GCAGACCTACAGAGGCAATTCCACCGGGACCCTGATGGTGTTCTTTGGC<br>AACGTCGACAGCTCTGGGATCAAGCACAACATCTTCAATCCCCCTATCA<br>TCGCCCGCTACATCCGGCTGCACCCAACCCATTATTCCATCCGCAGCAC<br>CCTGCGGATGGAGCTGATGGGGTGCGATCTGAACAGCTGTTCTATGCCC<br>CTGGGAATGGAGTCTAAGGCCATCTCCGACGCTCAGATCACCGCCTCCA<br>GCTACTTCACCAATATGTTTGCTACCTGGTCCCCAAGCAAGGCTAGACT<br>GCATCTGCAGGGAAGAAGCAACGCTTGGAGACCACAGGTGAACAATCCC<br>AAGGAGTGGCTGCAGGTCGACTTCCAGAAAACCATGAAGGTGACCGGAG<br>TCACCACCCAGGGCGTGAAAAGCCTGCTGACCTCTATGTACGTCAAGGA<br>GTTCCTGATCTCTTCCAGCCAGGACGGGCACCAGTGGACCCTGTTCTTT<br>CAGAACGGAAAGGTGAAAGTCTTCCAGGGCAATCAGGATTCCTTTACCC<br>CTGTGGTCAACAGCCTGGACCCACCCCTGCTGACCAGGTACCTGAGAAT<br>CCACCCACAGTCCTGGGTGCATCAGATCGCTCTGAGGATGGAAGTCCTG<br>GGCTGCGAGGCCCAGGACCTGTATTGATCGCGAATAAAAGATCTTTATT<br>TTCATTAGATCTGTGTGTTGGTTTTTTGTGTG | |
| 325 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG<br>GATGAAGAACAATGAGGAGGCTGAGGACTATGATGATGACCTGACTGAC<br>TCTGAGATGGATGTGGTGAGGTTTGATGATGACAACAGCCCCAGCTTCA<br>TCCAGATCAGGTCTGTGGCCAAGAAGCACCCCAAGACCTGGGTGCACTA<br>CATTGCTGCTGAGGAGGAGGACTGGGACTATGCCCCCCTGGTGCTGGCC<br>CCTGATGACAGGAGCTACAAGAGCCAGTACCTGAACAATGGCCCCCAGA<br>GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT<br>GAGGCCCCTGTACAGCAGGAGGCTGCCCAAGGGGGTGAAGCACCTGAAG<br>GACTTCCCCATCCTGCCTGGGGAGATCTTCAAGTACAAGTGGACTGTGA<br>CTGTGGAGGATGGCCCCACCAAGTCTGACCCCAGGTGCCTGACCAGATA<br>CTACAGCAGCTTTGTGAACATGGAGAGGGACCTGGCCTCTGGCCTGATT<br>GGCCCCCTGCTGATCTGCTACAAGGAGTCTGTGGACCAGAGGGGCAACC<br>AGATCATGTCTGACAAGAGGAATGTGATCCTGTTCTCTGTGTTTGATGA<br>GAACAGGAGCTGGTACCTGACTGAGAACATCCAGAGGTTCCTGCCCAAC<br>CCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTG<br>CCTGCATGAGGTGGCCTACTGGTACATCCTGAGCATTGGGGCCCAGACT<br>GACTTCCTGTCTGTGTTCTTCTCTGGCTACACCTTCAAGCACAAGATGG<br>TGTATGAGGACACCCTGACCCTGTTCCCCTTCTCTGGGGAGACTGTGTT | pCB1006 |

-continued

| SEQ ID | Sequence | Description |
|---|---|---|
| | CATGAGCATGGAGAACCCTGGCCTGTGGATTCTGGGCTGCCACAACTCT GACTTCAGGAACAGGGGCATGACTGCCCTGCTGAAAGTCTCCAGCTGTG ACAAGAACACTGGGGACTACTATGAGGACAGCTATGAGGACATCTCTGC CTACCTGCTGAGCAAGAACAATGCCATTGAGCCCAGGAGCTTCAGCCAG AATGCCACTAATGTGTCTAACAACAGCAACACCAGCAATGACACCAATG TGTCTCCCCCAGTGCTGAAGAGGCACCAGAGGGAGATCACCAGGACCAC CCTGCAGTCTGACCAGGAGGAGATTGACTATGATGACACCATCTCTGTG GAGATGAAGAAGGAGGACTTTGACATCTACGACGAGGACGAGAACCAGA GCCCCAGGAGCTTCCAGAAGAAGACCAGGCACTACTTCATTGCTGCTGT GGAGAGGCTGTGGGACTATGGCATGAGCAGCAGCCCCCATGTGCTGAGG AACAGGGCCCAGTCTGGCTCTGTGCCCCAGTTCAAGAAGGTGGTGTTCC AGGAGTTCACTGATGGCAGCTTCACCCAGCCCCTGTACAGAGGGGAGCT GAATGAGCACCTGGGCCTGCTGGGCCCCTACATCAGGGCTGAGGTGGAG GACAACATCATGGTGACCTTCAGGAACCAGGCCAGCAGGCCCTACAGCT TCTACAGCAGCCTGATCAGCTATGAGGAGGACCAGAGGCAGGGGGCTGA GCCCAGGAAGAACTTTGTGAAGCCCAATGAAACCAAGACCTACTTCTGG AAGGTGCAGCACCACATGGCCCCCACCAAGGATGAGTTTGACTGCAAGG CCTGGGCCTACTTCTCTGATGTGGACCTGGAGAAGGATGTGCACTCTGG CCTGATTGGCCCCCTGCTGGTGTGCCACACCAACACCCTGAACCCTGCC CATGGCAGGCAGGTGACTGTGCAGGAGTTTGCCCTGTTCTTCACCATCT TTGATGAAACCAAGAGCTGGTACTTCACTGAGAACATGGAGAGGAACTG CAGGGCCCCCTGCAACATCCAGATGGAGGACCCCACCTTCAAGGAGAAC TACAGGTTCCATGCCATCAATGGCTACATCATGGACACCCTGCCTGGCC TGGTGATGGCCCAGGACCAGAGGATCAGGTGGTACCTGCTGAGCATGGG CAGCAATGAGAACATCCACAGCATCCACTTCTCTGGCCATGTGTTCACT GTGAGGAAGAAGGAGGAGTACAAGATGGCCCTGTACAACCTGTACCCTG GGGTGTTTGAGACTGTGGAGATGCTGCCCAGCAAGGCTGGCATCTGGAG GGTGGAGTGCCTGATTGGGGAGCACCTGCATGCTGGCATGAGCACCCTG TTCCTGGTGTACAGCAACAAGTGCCAGACCCCCCTGGGCATGGCCTCTG GCCACATCAGGGACTTCCAGATCACTGCCTCTGGCCAGTATGGCCAGTG GGCCCCCAAGCTGGCCAGGCTGCACTACTCTGGCAGCATCAATGCCTGG AGCACCAAGGAGCCCTTCAGCTGGATCAAGGTGGACCTGCTGGCCCCCA TGATCATCCATGGCATCAAGACCCAGGGGGCCAGGCAGAAGTTCAGCAG CCTGTACATCAGCCAGTTCATCATCATGTACAGCCTGGATGGCAAGAAG TGGCAGACCTACAGGGGCAACAGCACTGGCACCCTGATGGTGTTCTTTG GCAATGTGGACAGCTCTGGCATCAAGCACAACATCTTCAACCCCCCCAT CATTGCCAGATACATCAGGCTGCACCCCACCCACTACAGCATCAGGAGC ACCCTGAGGATGGAGCTGATGGGCTGTGACCTGAACAGCTGCAGCATGC CCCTGGGCATGGAGAGCAAGGCCATCTCTGATGCCCAGATCACTGCCAG CAGCTACTTCACCAACATGTTTGCCACCTGGAGCCCCAGCAAGGCCAGG CTGCACCTGCAGGGCAGGAGCAATGCCTGGAGGCCCCAGGTCAACAACC CCAAGGAGTGGCTGCAGGTGGACTTCCAGAAGACCATGAAGGTGACTGG GGTGACCACCCAGGGGGTGAAGAGCCTGCTGACCAGCATGTATGTGAAG GAGTTCCTGATCAGCAGCAGCCAGGATGGCCACCAGTGGACCCTGTTCT TCCAGAATGGCAAGGTGAAGGTGTTCCAGGGCAACCAGGACAGCTTCAC CCCTGTGGTGAACAGCCTGGACCCCCCCCTGCTGACCAGATACCTGAGG ATTCACCCCCAGAGCTGGGTGCACCAGATTGCCCTGAGGATGGAGGTGC TGGGCTGTGAGGCCCAGGACCTGTACTGAtcgcgaataaaagatcttta ttttcattagatctgtgtgttggttttttgtgtg | |
| 326 | TGCCAGTTCCCGATCGTTACAGGCGGTACTCCTCAAAGCGTACTAAAGA ATTATTCTTTTACATTTCAGTGGCCACCAGGAGATACTACCTGGGGGCT GTGGAGCTGAGCTGGGACTACATGCAGTCTGACCTGGGGGAGCTGCCTG TGGATGCCAGGTTCCCCCCCAGAGTGCCCAAGAGCTTCCCCTTCAACAC CTCTGTGGTGTACAAGAAGACCCTGTTTGTGGAGTTCACTGACCACCTG TTCAACATTGCCAAGCCCAGGCCCCCCTGGATGGGCCTGCTGGGCCCCA CCATCCAGGCTGAGGTGTATGACACTGTGGTGATCACCCTGAAGAACAT GGCCAGCCACCCTGTGAGCCTGCATGCTGTGGGGGTGAGCTACTGGAAG GCCTCTGAGGGGGCTGAGTATGATGACCAGACCAGCCAGAGGGAGAAGG AGGATGACAAGGTGTTCCCTGGGGGCAGCCACACCTATGTGTGGCAGGT GCTGAAGGAGAATGGCCCCATGGCCTCTGACCCCCTGTGCCTGACCTAC AGCTACCTGAGCCATGTGGACCTGGTGAAGGACCTGAACTCTGGCCTGA TTGGGGCCCTGCTGGTGTGCAGGGAGGGCAGCCTGGCCAAGGAGAAGAC CCAGACCCTGCACAAGTTCATCCTGCTGTTTGCTGTGTTTGATGAGGGC AAGAGCTGGCACTCTGAAACCAAGAACAGCCTGATGCAGGACAGGGATG CTGCCTCTGCCAGGGCCTGGCCCAAGATGCACACTGTGAATGGCTATGT GAACAGGAGCCTGCCTGGCCTGATTGGCTGCCACAGGAAGTCTGTGTAC TGGCATGTGATTGGCATGGGCACCACCCCTGAGGTGCACAGCATCTTCC TGGAGGGCCACACCTTCCTGGTCAGGAACCACAGGCAGGCCAGCCTGGA GATCAGCCCCATCACCTTCCTGACTGCCCAGACCCTGCTGATGGACCTG GGCCAGTTCCTGCTGTTCTGCCACATCAGCAGCCACCAGCATGATGGCA TGGAGGCCTATGTGAAGGTGGACAGCTGCCCTGAGGAGCCCCAGCTGAG GATGAAGAACAATGAGGAGGCTGAGGACTATGATGATGACCTGACTGAC TCTGAGATGGATGTGGTGAGGTTTGATGATGACAACAGCCCCAGCTTCA TCCAGATCAGGTCTGTGGCCAAGAAGCACCCCAAGACCTGGGTGCACTA CATTGCTGCTGAGGAGGAGGACTGGGACTATGCCCCCCTGGTGCTGGCC CCTGATGACAGGAGCTACAAGAGCCAGTACCTGAACAATGGCCCCCAGA | pCB1007 |

-continued

| SEQ ID | Sequence | Description |
|---|---|---|
| | GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT<br>GAGGCCCCTGTACAGCAGGAGGCTGCCCAAGGGGGTGAAGCACCTGAAG<br>GACTTCCCCATCCTGCCTGGGGAGATCTTCAAGTACAAGTGGACTGTGA<br>CTGTGGAGGATGGCCCCACCAAGTCTGACCCCAGGTGCCTGACCAGATA<br>CTACAGCAGCTTTGTGAACATGGAGAGGGACCTGGCCTCTGGCCTGATT<br>GGCCCCCTGCTGATCTGCTACAAGGAGTCTGTGGACCAGAGGGGCAACC<br>AGATCATGTCTGACAAGAGGAATGTGATCCTGTTCTCTGTGTTTGATGA<br>GAACAGGAGCTGGTACCTGACTGAGAACATCCAGAGGTTCCTGCCCAAC<br>CCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTG<br>CCTGCATGAGGTGGCCTACTGGTACATCCTGAGCATTGGGGCCCAGACT<br>GACTTCCTGTCTGTGTTCTTCTCTGGCTACACCTTCAAGCACAAGATGG<br>TGTATGAGGACACCCTGACCCTGTTCCCCTTCTCTGGGGAGACTGTGTT<br>CATGAGCATGGAGAACCCTGGCCTGTGGATTCTGGGCTGCCACAACTCT<br>GACTTCAGGAACAGGGGCATGACTGCCCTGCTGAAAGTCTCCAGCTGTG<br>ACAAGAACACTGGGGACTACTATGAGGACAGCTATGAGGACATCTCTGC<br>CTACCTGCTGAGCAAGAACAATGCCATTGAGCCCAGGAGCTTCAGCCAG<br>AATGCCACTAATGTGTCTAACAACAGCAACACCAGCAATGACAGCCCCC<br>CAGTGCTGAAGAGGCACCAGAGGGAGATCACCAGGACCACCCTGCAGTC<br>TGACCAGGAGGAGATTGACTATGATGACACCATCTCTGTGGAGATGAAG<br>AAGGAGGACTTTGACATCTACGACGAGGACGAGAACCAGAGCCCCAGGA<br>GCTTCCAGAAGAAGACCAGGCACTACTTCATTGCTGCTGTGGAGAGGCT<br>GTGGGACTATGGCATGAGCAGCAGCCCCCATGTGCTGAGGAACAGGGCC<br>CAGTCTGGCTCTGTGCCCCAGTTCAAGAAGGTGGTGTTCCAGGAGTTCA<br>CTGATGGCAGCTTCACCCAGCCCCTGTACAGAGGGGAGCTGAATGAGCA<br>CCTGGGCCTGCTGGGCCCCTACATCAGGGCTGAGGTGGAGGACAACATC<br>ATGGTGACCTTCAGGAACCAGGCCAGCAGGCCCTACAGCTTCTACAGCA<br>GCCTGATCAGCTATGAGGAGGACCAGAGGCAGGGGGCTGAGCCCAGGAA<br>GAACTTTGTGAAGCCCAATGAAACCAAGACCTACTTCTGGAAGGTGCAG<br>CACCACATGGCCCCCACCAAGGATGAGTTTGACTGCAAGGCCTGGGCCT<br>ACTTCTCTGATGTGGACCTGGAGAAGGATGTGCACTCTGGCCTGATTGG<br>CCCCCTGCTGGTGTGCCACACCAACACCCTGAACCCTGCCCATGGCAGG<br>CAGGTGACTGTGCAGGAGTTTGCCCTGTTCTTCACCATCTTTGATGAAA<br>CCAAGAGCTGGTACTTCACTGAGAACATGGAGAGGAACTGCAGGGCCCC<br>CTGCAACATCCAGATGGAGGACCCCACCTTCAAGGAGAACTACAGGTTC<br>CATGCCATCAATGGCTACATCATGGACACCCTGCCTGGCCTGGTGATGG<br>CCCAGGACCAGAGGATCAGGTGGTACCTGCTGAGCATGGGCAGCAATGA<br>GAACATCCACAGCATCCACTTCTCTGGCCATGTGTTCACTGTGAGGAAG<br>AAGGAGGAGTACAAGATGGCCCTGTACAACCTGTACCCTGGGGTGTTTG<br>AGACTGTGGAGATGCTGCCCAGCAAGGCTGGCATCTGGAGGGTGGAGTG<br>CCTGATTGGGGAGCACCTGCATGCTGGCATGAGCACCCTGTTCCTGGTG<br>TACAGCAACAAGTGCCAGACCCCCCTGGGCATGGCCTCTGGCCACATCA<br>GGGACTTCCAGATCACTGCCTCTGGCCAGTATGGCCAGTGGGCCCCCAA<br>GCTGGCCAGGCTGCACTACTCTGGCAGCATCAATGCCTGGAGCACCAAG<br>GAGCCCTTCAGCTGGATCAAGGTGGACCTGCTGGCCCCCATGATCATCC<br>ATGGCATCAAGACCCAGGGGGCCAGGCAGAAGTTCAGCAGCCTGTACAT<br>CAGCCAGTTCATCATCATGTACAGCCTGGATGGCAAGAAGTGGCAGACC<br>TACAGGGGCAACAGCACTGGCACCCTGATGGTGTTCTTTGGCAATGTGG<br>ACAGCTCTGGCATCAAGCACAACATCTTCAACCCCCCCATCATTGCCAG<br>ATACATCAGGCTGCACCCCACCCACTACAGCATCAGGAGCACCCTGAGG<br>ATGGAGCTGATGGGCTGTGACCTGAACAGCTGCAGCATGCCCCTGGGCA<br>TGGAGAGCAAGGCCATCTCTGATGCCCAGATCACTGCCAGCAGCTACTT<br>CACCAACATGTTTGCCACCTGGAGCCCCAGCAAGGCCAGGCTGCACCTG<br>CAGGGCAGGAGCAATGCCTGGAGGCCCCAGGTCAACAACCCCAAGGAGT<br>GGCTGCAGGTGGACTTCCAGAAGACCATGAAGGTGACTGGGGTGACCAC<br>CCAGGGGGTGAAGAGCCTGCTGACCAGCATGTATGTGAAGGAGTTCCTG<br>ATCAGCAGCAGCCAGGATGGCCACCAGTGGACCCTGTTCTTCCAGAATG<br>GCAAGGTGAAGGTGTTCCAGGGCAACCAGGACAGCTTCACCCCTGTGGT<br>GAACAGCCTGGACCCCCCCCTGCTGACCAGATACCTGAGGATTCACCCC<br>CAGAGCTGGGTGCACCAGATTGCCCTGAGGATGGAGGTGCTGGGCTGTG<br>AGGCCCAGGACCTGTACTGAtcgcgaataaaagatctttattttcatta<br>gatctgtgtgttggttttttgtgtg | |
| 327 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC | pCB1008 |

-continued

| SEQ ID | Sequence | Description |
|---|---|---|
| | AGCTACCTGAGCCATGTGGACCTGGTGAAGGACCTGAACTCTGGCCTGA | |
| | TTGGGGCCCTGCTGGTGTGCAGGGAGGGCAGCCTGGCCAAGGAGAAGAC | |
| | CCAGACCCTGCACAAGTTCATCCTGCTGTTTGCTGTGTTTGATGAGGGC | |
| | AAGAGCTGGCACTCTGAAACCAAGAACAGCCTGATGCAGGACAGGGATG | |
| | CTGCCTCTGCCAGGGCCTGGCCCAAGATGCACACTGTGAATGGCTATGT | |
| | GAACAGGAGCCTGCCTGGCCTGATTGGCTGCCACAGGAAGTCTGTGTAC | |
| | TGGCATGTGATTGGCATGGGCACCACCCCTGAGGTGCACAGCATCTTCC | |
| | TGGAGGGCCACACCTTCCTGGTCAGGAACCACAGGCAGGCCAGCCTGGA | |
| | GATCAGCCCCATCACCTTCCTGACTGCCCAGACCCTGCTGATGGACCTG | |
| | GGCCAGTTCCTGCTGTTCTGCCACATCAGCAGCCACCAGCATGATGGCA | |
| | TGGAGGCCTATGTGAAGGTGGACAGCTGCCCTGAGGAGCCCCAGCTGAG | |
| | GATGAAGAACAATGAGGAGGCTGAGGACTATGATGATGACCTGACTGAC | |
| | TCTGAGATGGATGTGGTGAGGTTTGATGATGACAACAGCCCCAGCTTCA | |
| | TCCAGATCAGGTCTGTGGCCAAGAAGCACCCCAAGACCTGGGTGCACTA | |
| | CATTGCTGCTGAGGAGGAGGACTGGGACTATGCCCCCCTGGTGCTGGCC | |
| | CCTGATGACAGGAGCTACAAGAGCCAGTACCTGAACAATGGCCCCCAGA | |
| | GGATTGGCAGGAAGTACAAGAAGGTCAGGTTCATGGCCTACACTGATGA | |
| | AACCTTCAAGACCAGGGAGGCCATCCAGCATGAGTCTGGCATCCTGGGC | |
| | CCCCTGCTGTATGGGGAGGTGGGGGACACCCTGCTGATCATCTTCAAGA | |
| | ACCAGGCCAGCAGGCCCTACAACATCTACCCCCATGGCATCACTGATGT | |
| | GAGGCCCCTGTACAGCAGGAGGCTGCCCAAGGGGGTGAAGCACCTGAAG | |
| | GACTTCCCCATCCTGCCTGGGGAGATCTTCAAGTACAAGTGGACTGTGA | |
| | CTGTGGAGGATGGCCCCACCAAGTCTGACCCCAGGTGCCTGACCAGATA | |
| | CTACAGCAGCTTTGTGAACATGGAGAGGGACCTGGCCTCTGGCCTGATT | |
| | GGCCCCCTGCTGATCTGCTACAAGGAGTCTGTGGACCAGAGGGGCAACC | |
| | AGATCATGTCTGACAAGAGGAATGTGATCCTGTTCTCTGTGTTTGATGA | |
| | GAACAGGAGCTGGTACCTGACTGAGAACATCCAGAGGTTCCTGCCCAAC | |
| | CCTGCTGGGGTGCAGCTGGAGGACCCTGAGTTCCAGGCCAGCAACATCA | |
| | TGCACAGCATCAATGGCTATGTGTTTGACAGCCTGCAGCTGTCTGTGTG | |
| | CCTGCATGAGGTGGCCTACTGGTACATCCTGAGCATTGGGGCCCAGACT | |
| | GACTTCCTGTCTGTGTTCTTCTCTGGCTACACCTTCAAGCACAAGATGG | |
| | TGTATGAGGACACCCTGACCCTGTTCCCCTTCTCTGGGGAGACTGTGTT | |
| | CATGAGCATGGAGAACCCTGGCCTGTGGATTCTGGGCTGCCACAACTCT | |
| | GACTTCAGGAACAGGGGCATGACTGCCCTGCTGAAAGTCTCCAGCTGTG | |
| | ACAAGAACACTGGGGACTACTATGAGGACAGCTATGAGGACATCTCTGC | |
| | CTACCTGCTGAGCAAGAACAATGCCATTGAGCCCAGGAGCTTCAGCCAG | |
| | AATGCCACTAATGTGTCTAACAACAGCAACACCAGCAATGACAGCAATG | |
| | TGTCTAACAAGACTCCCCCAGTGCTGAAGAGGCACCAGAGGGAGATCAC | |
| | CAGGACCACCCTGCAGTCTGACCAGGAGGAGATTGACTATGATGACACC | |
| | ATCTCTGTGGAGATGAAGAAGGAGGACTTTGACATCTACGACGAGGACG | |
| | AGAACCAGAGCCCCAGGAGCTTCCAGAAGAAGACCAGGCACTACTTCAT | |
| | TGCTGCTGTGGAGAGGCTGTGGGACTATGGCATGAGCAGCAGCCCCCAT | |
| | GTGCTGAGGAACAGGGCCCAGTCTGGCTCTGTGCCCCAGTTCAAGAAGG | |
| | TGGTGTTCCAGGAGTTCACTGATGGCAGCTTCACCCAGCCCCTGTACAG | |
| | AGGGGAGCTGAATGAGCACCTGGGCCTGCTGGGCCCCTACATCAGGGCT | |
| | GAGGTGGAGGACAACATCATGGTGACCTTCAGGAACCAGGCCAGCAGGC | |
| | CCTACAGCTTCTACAGCAGCCTGATCAGCTATGAGGAGGACCAGAGGCA | |
| | GGGGGCTGAGCCCAGGAAGAACTTTGTGAAGCCCAATGAAACCAAGACC | |
| | TACTTCTGGAAGGTGCAGCACCACATGGCCCCCACCAAGGATGAGTTTG | |
| | ACTGCAAGGCCTGGGCCTACTTCTCTGATGTGGACCTGGAGAAGGATGT | |
| | GCACTCTGGCCTGATTGGCCCCCTGCTGGTGTGCCACACCAACACCCTG | |
| | AACCCTGCCCATGGCAGGCAGGTGACTGTGCAGGAGTTTGCCCTGTTCT | |
| | TCACCATCTTTGATGAAACCAAGAGCTGGTACTTCACTGAGAACATGGA | |
| | GAGGAACTGCAGGGCCCCCTGCAACATCCAGATGGAGGACCCCACCTTC | |
| | AAGGAGAACTACAGGTTCCATGCCATCAATGGCTACATCATGGACACCC | |
| | TGCCTGGCCTGGTGATGGCCCAGGACCAGAGGATCAGGTGGTACCTGCT | |
| | GAGCATGGGCAGCAATGAGAACATCCACAGCATCCACTTCTCTGGCCAT | |
| | GTGTTCACTGTGAGGAAGAAGGAGGAGTACAAGATGGCCCTGTACAACC | |
| | TGTACCCTGGGGTGTTTGAGACTGTGGAGATGCTGCCCAGCAAGGCTGG | |
| | CATCTGGAGGGTGGAGTGCCTGATTGGGGAGCACCTGCATGCTGGCATG | |
| | AGCACCCTGTTCCTGGTGTACAGCAACAAGTGCCAGACCCCCCTGGGCA | |
| | TGGCCTCTGGCCACATCAGGGACTTCCAGATCACTGCCTCTGGCCAGTA | |
| | TGGCCAGTGGGCCCCCAAGCTGGCCAGGCTGCACTACTCTGGCAGCATC | |
| | AATGCCTGGAGCACCAAGGAGCCCTTCAGCTGGATCAAGGTGGACCTGC | |
| | TGGCCCCCATGATCATCCATGGCATCAAGACCCAGGGGGCCAGGCAGAA | |
| | GTTCAGCAGCCTGTACATCAGCCAGTTCATCATCATGTACAGCCTGGAT | |
| | GGCAAGAAGTGGCAGACCTACAGGGGCAACAGCACTGGCACCCTGATGG | |
| | TGTTCTTTGGCAATGTGGACAGCTCTGGCATCAAGCACAACATCTTCAA | |
| | CCCCCCCATCATTGCCAGATACATCAGGCTGCACCCCACCCACTACAGC | |
| | ATCAGGAGCACCCTGAGGATGGAGCTGATGGGCTGTGACCTGAACAGCT | |
| | GCAGCATGCCCCTGGGCATGGAGAGCAAGGCCATCTCTGATGCCCAGAT | |
| | CACTGCCAGCAGCTACTTCACCAACATGTTTGCCACCTGGAGCCCCAGC | |
| | AAGGCCAGGCTGCACCTGCAGGGCAGGAGCAATGCCTGGAGGCCCCAGG | |
| | TCAACAACCCCAAGGAGTGGCTGCAGGTGGACTTCCAGAAGACCATGAA | |
| | GGTGACTGGGGTGACCACCCAGGGGGTGAAGAGCCTGCTGACCAGCATG | |
| | TATGTGAAGGAGTTCCTGATCAGCAGCAGCCAGGATGGCCACCAGTGGA | |
| | CCCTGTTCTTCCAGAATGGCAAGGTGAAGGTGTTCCAGGGCAACCAGGA | |

-continued

| SEQ ID | Sequence | Description |
|---|---|---|
| | CAGCTTCACCCCTGTGGTGAACAGCCTGGACCCCCCCCTGCTGACCAGA<br>TACCTGAGGATTCACCCCCAGAGCTGGGTGCACCAGATTGCCCTGAGGA<br>TGGAGGTGCTGGGCTGTGAGGCCCAGGACCTGTACTGAtcgcgaataaa<br>agatctttattttcattagatctgtgtgttggttttttgtgtg | |
| 328 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG<br>GATGAAGAACAATGAGGAGGCTGAGGACTATGATGATGACCTGACTGAC<br>TCTGAGATGGATGTGGTGAGGTTTGATGATGACAACAGCCCCAGCTTCA<br>TCCAGATCAGGTCTGTGGCCAAGAAGCACCCCAAGACCTGGGTGCACTA<br>CATTGCTGCTGAGGAGGAGGACTGGGACTATGCCCCCCTGGTGCTGGCC<br>CCTGATGACAGGAGCTACAAGAGCCAGTACCTGAACAATGGCCCCCAGA<br>GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT<br>GAGGCCCCTGTACAGCAGGAGGCTGCCCAAGGGGGTGAAGCACCTGAAG<br>GACTTCCCCATCCTGCCTGGGGAGATCTTCAAGTACAAGTGGACTGTGA<br>CTGTGGAGGATGGCCCCACCAAGTCTGACCCCAGGTGCCTGACCAGATA<br>CTACAGCAGCTTTGTGAACATGGAGAGGGACCTGGCCTCTGGCCTGATT<br>GGCCCCCTGCTGATCTGCTACAAGGAGTCTGTGGACCAGAGGGGCAACC<br>AGATCATGTCTGACAAGAGGAATGTGATCCTGTTCTCTGTGTTTGATGA<br>GAACAGGAGCTGGTACCTGACTGAGAACATCCAGAGGTTCCTGCCCAAC<br>CCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTG<br>CCTGCATGAGGTGGCCTACTGGTACATCCTGAGCATTGGGGCCCAGACT<br>GACTTCCTGTCTGTGTTCTTCTCTGGCTACACCTTCAAGCACAAGATGG<br>TGTATGAGGACACCCTGACCCTGTTCCCCTTCTCTGGGGAGACTGTGTT<br>CATGAGCATGGAGAACCCTGGCCTGTGGATTCTGGGCTGCCACAACTCT<br>GACTTCAGGAACAGGGGCATGACTGCCCTGCTGAAAGTCTCCAGCTGTG<br>ACAAGAACACTGGGGACTACTATGAGGACAGCTATGAGGACATCTCTGC<br>CTACCTGCTGAGCAAGAACAATGCCATTGAGCCCAGGAGCTTCAGCCAG<br>AATGCCACTAATGTGTCTAACAACAGCAACACCAGCAATGACAGCAATG<br>TGTCTAACAAGACTAACAATAGCCCCCCAGTGCTGAAGAGGCACCAGAG<br>GGAGATCACCAGGACCACCCTGCAGTCTGACCAGGAGGAGATTGACTAT<br>GATGACACCATCTCTGTGGAGATGAAGAAGGAGGACTTTGACATCTACG<br>ACGAGGACGAGAACCAGAGCCCCAGGAGCTTCCAGAAGAAGACCAGGCA<br>CTACTTCATTGCTGCTGTGGAGAGGCTGTGGGACTATGGCATGAGCAGC<br>AGCCCCCATGTGCTGAGGAACAGGGCCCAGTCTGGCTCTGTGCCCCAGT<br>TCAAGAAGGTGGTGTTCCAGGAGTTCACTGATGGCAGCTTCACCCAGCC<br>CCTGTACAGAGGGGAGCTGAATGAGCACCTGGGCCTGCTGGGCCCCTAC<br>ATCAGGGCTGAGGTGGAGGACAACATCATGGTGACCTTCAGGAACCAGG<br>CCAGCAGGCCCTACAGCTTCTACAGCAGCCTGATCAGCTATGAGGAGGA<br>CCAGAGGCAGGGGGCTGAGCCCAGGAAGAACTTTGTGAAGCCCAATGAA<br>ACCAAGACCTACTTCTGGAAGGTGCAGCACCACATGGCCCCCACCAAGG<br>ATGAGTTTGACTGCAAGGCCTGGGCCTACTTCTCTGATGTGGACCTGGA<br>GAAGGATGTGCACTCTGGCCTGATTGGCCCCCTGCTGGTGTGCCACACC<br>AACACCCTGAACCCTGCCCATGGCAGGCAGGTGACTGTGCAGGAGTTTG<br>CCCTGTTCTTCACCATCTTTGATGAAACCAAGAGCTGGTACTTCACTGA<br>GAACATGGAGAGGAACTGCAGGGCCCCCTGCAACATCCAGATGGAGGAC<br>CCCACCTTCAAGGAGAACTACAGGTTCCATGCCATCAATGGCTACATCA<br>TGGACACCCTGCCTGGCCTGGTGATGGCCCAGGACCAGAGGATCAGGTG<br>GTACCTGCTGAGCATGGGCAGCAATGAGAACATCCACAGCATCCACTTC<br>TCTGGCCATGTGTTCACTGTGAGGAAGAAGGAGGAGTACAAGATGGCCC<br>TGTACAACCTGTACCCTGGGGTGTTTGAGACTGTGGAGATGCTGCCCAG<br>CAAGGCTGGCATCTGGAGGGTGGAGTGCCTGATTGGGGAGCACCTGCAT<br>GCTGGCATGAGCACCCTGTTCCTGGTGTACAGCAACAAGTGCCAGACCC | pCB1015 |

-continued

| SEQ ID | Sequence | Description |
|---|---|---|
| | CCCTGGGCATGGCCTCTGGCCACATCAGGGACTTCCAGATCACTGCCTC<br>TGGCCAGTATGGCCAGTGGGCCCCCAAGCTGGCCAGGCTGCACTACTCT<br>GGCAGCATCAATGCCTGGAGCACCAAGGAGCCCTTCAGCTGGATCAAGG<br>TGGACCTGCTGGCCCCCATGATCATCCATGGCATCAAGACCCAGGGGGC<br>CAGGCAGAAGTTCAGCAGCCTGTACATCAGCCAGTTCATCATCATGTAC<br>AGCCTGGATGGCAAGAAGTGGCAGACCTACAGGGGCAACAGCACTGGCA<br>CCCTGATGGTGTTCTTTGGCAATGTGGACAGCTCTGGCATCAAGCACAA<br>CATCTTCAACCCCCCCATCATTGCCAGATACATCAGGCTGCACCCCACC<br>CACTACAGCATCAGGAGCACCCTGAGGATGGAGCTGATGGGCTGTGACC<br>TGAACAGCTGCAGCATGCCCCTGGGCATGGAGAGCAAGGCCATCTCTGA<br>TGCCCAGATCACTGCCAGCAGCTACTTCACCAACATGTTTGCCACCTGG<br>AGCCCCAGCAAGGCCAGGCTGCACCTGCAGGGCAGGAGCAATGCCTGGA<br>GGCCCCAGGTCAACAACCCCAAGGAGTGGCTGCAGGTGGACTTCCAGAA<br>GACCATGAAGGTGACTGGGGTGACCACCCAGGGGGTGAAGAGCCTGCTG<br>ACCAGCATGTATGTGAAGGAGTTCCTGATCAGCAGCAGCCAGGATGGCC<br>ACCAGTGGACCCTGTTCTTCCAGAATGGCAAGGTGAAGGTGTTCCAGGG<br>CAACCAGGACAGCTTCACCCCTGTGGTGAACAGCCTGGACCCCCCCCTG<br>CTGACCAGATACCTGAGGATTCACCCCCAGAGCTGGGTGCACCAGATTG<br>CCCTGAGGATGGAGGTGCTGGGCTGTGAGGCCCAGGACCTGTACTGAtc<br>gcgaataaaagatctttattttcattagatctgtgtgttggttttttgt<br>gtg | |
| 329 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG<br>GATGAAGAACAATGAGGAGGCTGAGGACTATGATGATGACCTGACTGAC<br>TCTGAGATGGATGTGGTGAGGTTTGATGATGACAACAGCCCCAGCTTCA<br>TCCAGATCAGGTCTGTGGCCAAGAAGCACCCCAAGACCTGGGTGCACTA<br>CATTGCTGCTGAGGAGGAGGACTGGGACTATGCCCCCCTGGTGCTGGCC<br>CCTGATGACAGGAGCTACAAGAGCCAGTACCTGAACAATGGCCCCCAGA<br>GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT<br>GAGGCCCCTGTACAGCAGGAGGCTGCCCAAGGGGGTGAAGCACCTGAAG<br>GACTTCCCCATCCTGCCTGGGGAGATCTTCAAGTACAAGTGGACTGTGA<br>CTGTGGAGGATGGCCCCACCAAGTCTGACCCCAGGTGCCTGACCAGATA<br>CTACAGCAGCTTTGTGAACATGGAGAGGGACCTGGCCTCTGGCCTGATT<br>GGCCCCCTGCTGATCTGCTACAAGGAGTCTGTGGACCAGAGGGGCAACC<br>AGATCATGTCTGACAAGAGGAATGTGATCCTGTTCTCTGTGTTTGATGA<br>GAACAGGAGCTGGTACCTGACTGAGAACATCCAGAGGTTCCTGCCCAAC<br>CCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTG<br>CCTGCATGAGGTGGCCTACTGGTACATCCTGAGCATTGGGGCCCAGACT<br>GACTTCCTGTCTGTGTTCTTCTCTGGCTACACCTTCAAGCACAAGATGG<br>TGTATGAGGACACCCTGACCCTGTTCCCCTTCTCTGGGGAGACTGTGTT<br>CATGAGCATGGAGAACCCTGGCCTGTGGATTCTGGGCTGCCACAACTCT<br>GACTTCAGGAACAGGGGCATGACTGCCCTGCTGAAAGTCTCCAGCTGTG<br>ACAAGAACACTGGGGACTACTATGAGGACAGCTATGAGGACATCTCTGC<br>CTACCTGCTGAGCAAGAACAATGCCATTGAGCCCAGGAGCTTCAGCCAG<br>AATGCCACTAATGTGTCTAACAACAGCAACACCAGCAATGACAGCAATG<br>TGTCTAACAAGACTAACAATAGCAATGCCACCCCCCCAGTGCTGAAGAG<br>GCACCAGAGGGAGATCACCAGGACCACCCTGCAGTCTGACCAGGAGGAG<br>ATTGACTATGATGACACCATCTCTGTGGAGATGAAGAAGGAGGACTTTG<br>ACATCTACGACGAGGACGAGAACCAGAGCCCCAGGAGCTTCCAGAAGAA<br>GACCAGGCACTACTTCATTGCTGCTGTGGAGAGGCTGTGGGACTATGGC<br>ATGAGCAGCAGCCCCCATGTGCTGAGGAACAGGGCCCAGTCTGGCTCTG<br>TGCCCCAGTTCAAGAAGGTGGTGTTCCAGGAGTTCACTGATGGCAGCTT | pCB1016 |

-continued

| SEQ ID | Sequence | Description |
|---|---|---|
| | CACCCAGCCCCTGTACAGAGGGGAGCTGAATGAGCACCTGGGCCTGCTG<br>GGCCCCTACATCAGGGCTGAGGTGGAGGACAACATCATGGTGACCTTCA<br>GGAACCAGGCCAGCAGGCCCTACAGCTTCTACAGCAGCCTGATCAGCTA<br>TGAGGAGGACCAGAGGCAGGGGGCTGAGCCCAGGAAGAACTTTGTGAAG<br>CCCAATGAAACCAAGACCTACTTCTGGAAGGTGCAGCACCACATGGCCC<br>CCACCAAGGATGAGTTTGACTGCAAGGCCTGGGCCTACTTCTCTGATGT<br>GGACCTGGAGAAGGATGTGCACTCTGGCCTGATTGGCCCCCTGCTGGTG<br>TGCCACACCAACACCCTGAACCCTGCCCATGGCAGGCAGGTGACTGTGC<br>AGGAGTTTGCCCTGTTCTTCACCATCTTTGATGAAACCAAGAGCTGGTA<br>CTTCACTGAGAACATGGAGAGGAACTGCAGGGCCCCCTGCAACATCCAG<br>ATGGAGGACCCCACCTTCAAGGAGAACTACAGGTTCCATGCCATCAATG<br>GCTACATCATGGACACCCTGCCTGGCCTGGTGATGGCCCAGGACCAGAG<br>GATCAGGTGGTACCTGCTGAGCATGGGCAGCAATGAGAACATCCACAGC<br>ATCCACTTCTCTGGCCATGTGTTCACTGTGAGGAAGAAGGAGGAGTACA<br>AGATGGCCCTGTACAACCTGTACCCTGGGGTGTTTGAGACTGTGGAGAT<br>GCTGCCCAGCAAGGCTGGCATCTGGAGGGTGGAGTGCCTGATTGGGGAG<br>CACCTGCATGCTGGCATGAGCACCCTGTTCCTGGTGTACAGCAACAAGT<br>GCCAGACCCCCCTGGGCATGGCCTCTGGCCACATCAGGGACTTCCAGAT<br>CACTGCCTCTGGCCAGTATGGCCAGTGGGCCCCCAAGCTGGCCAGGCTG<br>CACTACTCTGGCAGCATCAATGCCTGGAGCACCAAGGAGCCCTTCAGCT<br>GGATCAAGGTGGACCTGCTGGCCCCCATGATCATCCATGGCATCAAGAC<br>CCAGGGGGCCAGGCAGAAGTTCAGCAGCCTGTACATCAGCCAGTTCATC<br>ATCATGTACAGCCTGGATGGCAAGAAGTGGCAGACCTACAGGGGCAACA<br>GCACTGGCACCCTGATGGTGTTCTTTGGCAATGTGGACAGCTCTGGCAT<br>CAAGCACAACATCTTCAACCCCCCCATCATTGCCAGATACATCAGGCTG<br>CACCCCACCCACTACAGCATCAGGAGCACCCTGAGGATGGAGCTGATGG<br>GCTGTGACCTGAACAGCTGCAGCATGCCCCTGGGCATGGAGAGCAAGGC<br>CATCTCTGATGCCCAGATCACTGCCAGCAGCTACTTCACCAACATGTTT<br>GCCACCTGGAGCCCCAGCAAGGCCAGGCTGCACCTGCAGGGCAGGAGCA<br>ATGCCTGGAGGCCCCAGGTCAACAACCCCAAGGAGTGGCTGCAGGTGGA<br>CTTCCAGAAGACCATGAAGGTGACTGGGGTGACCACCCAGGGGGTGAAG<br>AGCCTGCTGACCAGCATGTATGTGAAGGAGTTCCTGATCAGCAGCAGCC<br>AGGATGGCCACCAGTGGACCCTGTTCTTCCAGAATGGCAAGGTGAAGGT<br>GTTCCAGGGCAACCAGGACAGCTTCACCCCTGTGGTGAACAGCCTGGAC<br>CCCCCCCTGCTGACCAGATACCTGAGGATTCACCCCCAGAGCTGGGTGC<br>ACCAGATTGCCCTGAGGATGGAGGTGCTGGGCTGTGAGGCCCAGGACCT<br>GTACTGAtcgcgaataaaagatctttattttcattagatctgtgtgttg<br>gtttttgtgtg | |
| 330 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG<br>GATGAAGAACAATGAGGAGGCTGAGGACTATGATGATGACCTGACTGAC<br>TCTGAGATGGATGTGGTGAGGTTTGATGATGACAACAGCCCCAGCTTCA<br>TCCAGATCAGGTCTGTGGCCAAGAAGCACCCCAAGACCTGGGTGCACTA<br>CATTGCTGCTGAGGAGGAGGACTGGGACTATGCCCCCCTGGTGCTGGCC<br>CCTGATGACAGGAGCTACAAGAGCCAGTACCTGAACAATGGCCCCCAGA<br>GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT<br>GAGGCCCCTGTACAGCAGGAGGCTGCCCAAGGGGGTGAAGCACCTGAAG<br>GACTTCCCCATCCTGCCTGGGGAGATCTTCAAGTACAAGTGGACTGTGA<br>CTGTGGAGGATGGCCCCACCAAGTCTGACCCCAGGTGCCTGACCAGATA<br>CTACAGCAGCTTTGTGAACATGGAGAGGGACCTGGCCTCTGGCCTGATT<br>GGCCCCCTGCTGATCTGCTACAAGGAGTCTGTGGACCAGAGGGGCAACC<br>AGATCATGTCTGACAAGAGGAATGTGATCCTGTTCTCTGTGTTTGATGA<br>GAACAGGAGCTGGTACCTGACTGAGAACATCCAGAGGTTCCTGCCCAAC | pCB1017 |

-continued

| SEQ ID | Sequence | Description |
|---|---|---|
| | CCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTG<br>CCTGCATGAGGTGGCCTACTGGTACATCCTGAGCATTGGGGCCCAGACT<br>GACTTCCTGTCTGTGTTCTTCTCTGGCTACACCTTCAAGCACAAGATGG<br>TGTATGAGGACACCCTGACCCTGTTCCCCTTCTCTGGGGAGACTGTGTT<br>CATGAGCATGGAGAACCCTGGCCTGTGGATTCTGGGCTGCCACAACTCT<br>GACTTCAGGAACAGGGGCATGACTGCCCTGCTGAAAGTCTCCAGCTGTG<br>ACAAGAACACTGGGGACTACTATGAGGACAGCTATGAGGACATCTCTGC<br>CTACCTGCTGAGCAAGAACAATGCCATTGAGCCCAGGAGCTTCAGCCAG<br>AATGCCACTAATGTGTCTAACAACAGCAACACCAGCCCCCCAGTGCTGA<br>AGAGGCACCAGAGGGAGATCACCAGGACCACCCTGCAGTCTGACCAGGA<br>GGAGATTGACTATGATGACACCATCTCTGTGGAGATGAAGAAGGAGGAC<br>TTTGACATCTACGACGAGGACGAGAACCAGAGCCCCAGGAGCTTCCAGA<br>AGAAGACCAGGCACTACTTCATTGCTGCTGTGGAGAGGCTGTGGGACTA<br>TGGCATGAGCAGCAGCCCCCATGTGCTGAGGAACAGGGCCCAGTCTGGC<br>TCTGTGCCCCAGTTCAAGAAGGTGGTGTTCCAGGAGTTCACTGATGGCA<br>GCTTCACCCAGCCCCTGTACAGAGGGGAGCTGAATGAGCACCTGGGCCT<br>GCTGGGCCCCTACATCAGGGCTGAGGTGGAGGACAACATCATGGTGACC<br>TTCAGGAACCAGGCCAGCAGGCCCTACAGCTTCTACAGCAGCCTGATCA<br>GCTATGAGGAGGACCAGAGGCAGGGGGCTGAGCCCAGGAAGAACTTTGT<br>GAAGCCCAATGAAACCAAGACCTACTTCTGGAAGGTGCAGCACCACATG<br>GCCCCCACCAAGGATGAGTTTGACTGCAAGGCCTGGGCCTACTTCTCTG<br>ATGTGGACCTGGAGAAGGATGTGCACTCTGGCCTGATTGGCCCCCTGCT<br>GGTGTGCCACACCAACACCCTGAACCCTGCCCATGGCAGGCAGGTGACT<br>GTGCAGGAGTTTGCCCTGTTCTTCACCATCTTTGATGAAACCAAGAGCT<br>GGTACTTCACTGAGAACATGGAGAGGAACTGCAGGGCCCCCTGCAACAT<br>CCAGATGGAGGACCCCACCTTCAAGGAGAACTACAGGTTCCATGCCATC<br>AATGGCTACATCATGGACACCCTGCCTGGCCTGGTGATGGCCCAGGACC<br>AGAGGATCAGGTGGTACCTGCTGAGCATGGGCAGCAATGAGAACATCCA<br>CAGCATCCACTTCTCTGGCCATGTGTTCACTGTGAGGAAGAAGGAGGAG<br>TACAAGATGGCCCTGTACAACCTGTACCCTGGGGTGTTTGAGACTGTGG<br>AGATGCTGCCCAGCAAGGCTGGCATCTGGAGGGTGGAGTGCCTGATTGG<br>GGAGCACCTGCATGCTGGCATGAGCACCCTGTTCCTGGTGTACAGCAAC<br>AAGTGCCAGACCCCCCTGGGCATGGCCTCTGGCCACATCAGGGACTTCC<br>AGATCACTGCCTCTGGCCAGTATGGCCAGTGGGCCCCCAAGCTGGCCAG<br>GCTGCACTACTCTGGCAGCATCAATGCCTGGAGCACCAAGGAGCCCTTC<br>AGCTGGATCAAGGTGGACCTGCTGGCCCCCATGATCATCCATGGCATCA<br>AGACCCAGGGGGCCAGGCAGAAGTTCAGCAGCCTGTACATCAGCCAGTT<br>CATCATCATGTACAGCCTGGATGGCAAGAAGTGGCAGACCTACAGGGGC<br>AACAGCACTGGCACCCTGATGGTGTTCTTTGGCAATGTGGACAGCTCTG<br>GCATCAAGCACAACATCTTCAACCCCCCCATCATTGCCAGATACATCAG<br>GCTGCACCCCACCCACTACAGCATCAGGAGCACCCTGAGGATGGAGCTG<br>ATGGGCTGTGACCTGAACAGCTGCAGCATGCCCCTGGGCATGGAGAGCA<br>AGGCCATCTCTGATGCCCAGATCACTGCCAGCAGCTACTTCACCAACAT<br>GTTTGCCACCTGGAGCCCCAGCAAGGCCAGGCTGCACCTGCAGGGCAGG<br>AGCAATGCCTGGAGGCCCCAGGTCAACAACCCCAAGGAGTGGCTGCAGG<br>TGGACTTCCAGAAGACCATGAAGGTGACTGGGGTGACCACCCAGGGGGT<br>GAAGAGCCTGCTGACCAGCATGTATGTGAAGGAGTTCCTGATCAGCAGC<br>AGCCAGGATGGCCACCAGTGGACCCTGTTCTTCCAGAATGGCAAGGTGA<br>AGGTGTTCCAGGGCAACCAGGACAGCTTCACCCCTGTGGTGAACAGCCT<br>GGACCCCCCCCTGCTGACCAGATACCTGAGGATTCACCCCCAGAGCTGG<br>GTGCACCAGATTGCCCTGAGGATGGAGGTGCTGGGCTGTGAGGCCCAGG<br>ACCTGTACTGAtcgcgaataaaagatctttattttcattagatctgtgt<br>gttggtttttgtgtg | |
| 331 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG | pCB1018 |

-continued

| SEQ ID | Sequence | Description |
|---|---|---|
| | GATGAAGAACAATGAGGAGGCTGAGGACTATGATGATGACCTGACTGAC TCTGAGATGGATGTGGTGAGGTTTGATGATGACAACAGCCCCAGCTTCA TCCAGATCAGGTCTGTGGCCAAGAAGCACCCCAAGACCTGGGTGCACTA CATTGCTGCTGAGGAGGAGGACTGGGACTATGCCCCCCTGGTGCTGGCC CCTGATGACAGGAGCTACAAGAGCCAGTACCTGAACAATGGCCCCCAGA GGATTGGCAGGAAGTACAAGAAGGTCAGGTTCATGGCCTACACTGATGA AACCTTCAAGACCAGGGAGGCCATCCAGCATGAGTCTGGCATCCTGGGC CCCCTGCTGTATGGGGAGGTGGGGGACACCCTGCTGATCATCTTCAAGA ACCAGGCCAGCAGGCCCTACAACATCTACCCCCATGGCATCACTGATGT GAGGCCCCTGTACAGCAGGAGGCTGCCCAAGGGGGTGAAGCACCTGAAG GACTTCCCCATCCTGCCTGGGGAGATCTTCAAGTACAAGTGGACTGTGA CTGTGGAGGATGGCCCCACCAAGTCTGACCCCAGGTGCCTGACCAGATA CTACAGCAGCTTTGTGAACATGGAGAGGGACCTGGCCTCTGGCCTGATT GGCCCCCTGCTGATCTGCTACAAGGAGTCTGTGGACCAGAGGGGCAACC AGATCATGTCTGACAAGAGGAATGTGATCCTGTTCTCTGTGTTTGATGA GAACAGGAGCTGGTACCTGACTGAGAACATCCAGAGGTTCCTGCCCAAC CCTGCTGGGGTGCAGCTGGAGGACCCTGAGTTCCAGGCCAGCAACATCA TGCACAGCATCAATGGCTATGTGTTTGACAGCCTGCAGCTGTCTGTGTG CCTGCATGAGGTGGCCTACTGGTACATCCTGAGCATTGGGGCCCAGACT GACTTCCTGTCTGTGTTCTTCTCTGGCTACACCTTCAAGCACAAGATGG TGTATGAGGACACCCTGACCCTGTTCCCCTTCTCTGGGGAGACTGTGTT CATGAGCATGGAGAACCCTGGCCTGTGGATTCTGGGCTGCCACAACTCT GACTTCAGGAACAGGGGCATGACTGCCCTGCTGAAAGTCTCCAGCTGTG ACAAGAACACTGGGGACTACTATGAGGACAGCTATGAGGACATCTCTGC CTACCTGCTGAGCAAGAACAATGCCATTGAGCCCAGGAGCTTCAGCCAG AATGCCACTAATGTGTCTAACAACAGCCCCCCAGTGCTGAAGAGGCACC AGAGGGAGATCACCAGGACCACCCTGCAGTCTGACCAGGAGGAGATTGA CTATGATGACACCATCTCTGTGGAGATGAAGAAGGAGGACTTTGACATC TACGACGAGGACGAGAACCAGAGCCCCAGGAGCTTCCAGAAGAAGACCA GGCACTACTTCATTGCTGCTGTGGAGAGGCTGTGGGACTATGGCATGAG CAGCAGCCCCCATGTGCTGAGGAACAGGGCCCAGTCTGGCTCTGTGCCC CAGTTCAAGAAGGTGGTGTTCCAGGAGTTCACTGATGGCAGCTTCACCC AGCCCCTGTACAGAGGGGAGCTGAATGAGCACCTGGGCCTGCTGGGCCC CTACATCAGGGCTGAGGTGGAGGACAACATCATGGTGACCTTCAGGAAC CAGGCCAGCAGGCCCTACAGCTTCTACAGCAGCCTGATCAGCTATGAGG AGGACCAGAGGCAGGGGGCTGAGCCCAGGAAGAACTTTGTGAAGCCCAA TGAAACCAAGACCTACTTCTGGAAGGTGCAGCACCACATGGCCCCCACC AAGGATGAGTTTGACTGCAAGGCCTGGGCCTACTTCTCTGATGTGGACC TGGAGAAGGATGTGCACTCTGGCCTGATTGGCCCCCTGCTGGTGTGCCA CACCAACACCCTGAACCCTGCCCATGGCAGGCAGGTGACTGTGCAGGAG TTTGCCCTGTTCTTCACCATCTTTGATGAAACCAAGAGCTGGTACTTCA CTGAGAACATGGAGAGGAACTGCAGGGCCCCCTGCAACATCCAGATGGA GGACCCCACCTTCAAGGAGAACTACAGGTTCCATGCCATCAATGGCTAC ATCATGGACACCCTGCCTGGCCTGGTGATGGCCCAGGACCAGAGGATCA GGTGGTACCTGCTGAGCATGGGCAGCAATGAGAACATCCACAGCATCCA CTTCTCTGGCCATGTGTTCACTGTGAGGAAGAAGGAGGAGTACAAGATG GCCCTGTACAACCTGTACCCTGGGGTGTTTGAGACTGTGGAGATGCTGC CCAGCAAGGCTGGCATCTGGAGGGTGGAGTGCCTGATTGGGGAGCACCT GCATGCTGGCATGAGCACCCTGTTCCTGGTGTACAGCAACAAGTGCCAG ACCCCCCTGGGCATGGCCTCTGGCCACATCAGGGACTTCCAGATCACTG CCTCTGGCCAGTATGGCCAGTGGGCCCCCAAGCTGGCCAGGCTGCACTA CTCTGGCAGCATCAATGCCTGGAGCACCAAGGAGCCCTTCAGCTGGATC AAGGTGGACCTGCTGGCCCCCATGATCATCCATGGCATCAAGACCCAGG GGGCCAGGCAGAAGTTCAGCAGCCTGTACATCAGCCAGTTCATCATCAT GTACAGCCTGGATGGCAAGAAGTGGCAGACCTACAGGGGCAACAGCACT GGCACCCTGATGGTGTTCTTTGGCAATGTGGACAGCTCTGGCATCAAGC ACAACATCTTCAACCCCCCCATCATTGCCAGATACATCAGGCTGCACCC CACCCACTACAGCATCAGGAGCACCCTGAGGATGGAGCTGATGGGCTGT GACCTGAACAGCTGCAGCATGCCCCTGGGCATGGAGAGCAAGGCCATCT CTGATGCCCAGATCACTGCCAGCAGCTACTTCACCAACATGTTTGCCAC CTGGAGCCCCAGCAAGGCCAGGCTGCACCTGCAGGGCAGGAGCAATGCC TGGAGGCCCCAGGTCAACAACCCCAAGGAGTGGCTGCAGGTGGACTTCC AGAAGACCATGAAGGTGACTGGGGTGACCACCCAGGGGGTGAAGAGCCT GCTGACCAGCATGTATGTGAAGGAGTTCCTGATCAGCAGCAGCCAGGAT GGCCACCAGTGGACCCTGTTCTTCCAGAATGGCAAGGTGAAGGTGTTCC AGGGCAACCAGGACAGCTTCACCCCTGTGGTGAACAGCCTGGACCCCCC CCTGCTGACCAGATACCTGAGGATTCACCCCCAGAGCTGGGTGCACCAG ATTGCCCTGAGGATGGAGGTGCTGGGCTGTGAGGCCCAGGACCTGTACT GAtcgcgaataaaagatctttattttcattagatctgtgtgttggtttt ttgtgtg | |
| 332 | TGCCAGTTCCCGATCGTTACAGGCGGTACTCCTCAAAGCGTACTAAAGA ATTATTCTTTTACATTTCAGTGGCCACCAGAAGGTACTACCTGGGAGCT GTGGAACTGAGCTGGGACTACATGCAGTCTGACCTGGGAGAGCTGCCTG TGGATGCTAGATTTCCTCCAAGAGTGCCCAAGAGCTTCCCCTTCAACAC CTCTGTGGTGTACAAGAAAACCCTGTTTGTGGAATTCACAGACCACCTG TTCAATATTGCCAAGCCTAGACCTCCTTGGATGGGCCTGCTGGGCCCTA | pCB1019 |

-continued

| SEQ ID | Sequence | Description |
|---|---|---|
| | CAATTCAGGCTGAGGTGTATGACACAGTGGTCATCACCCTGAAGAACAT<br>GGCCAGCCATCCTGTGTCTCTGCATGCTGTGGGAGTGTCTTACTGGAAG<br>GCTTCTGAGGGGGCTGAGTATGATGACCAGACAAGCCAGAGAGAGAAAG<br>AGGATGACAAGGTTTTCCCTGGGGGCAGCCACACCTATGTCTGGCAGGT<br>CCTGAAAGAAAATGGCCCTATGGCCTCTGATCCTCTGTGCCTGACATAC<br>AGCTACCTGAGCCATGTGGACCTGGTCAAGGACCTGAACTCTGGCCTGA<br>TTGGGGCTCTGCTGGTGTGTAGAGAAGGCAGCCTGGCCAAAGAAAAGAC<br>CCAGACACTGCACAAGTTCATCCTGCTGTTTGCTGTGTTTGATGAGGGC<br>AAGAGCTGGCACTCTGAGACAAAGAACAGCCTGATGCAGGACAGAGATG<br>CTGCCTCTGCTAGAGCTTGGCCCAAGATGCACACAGTGAATGGCTATGT<br>GAACAGAAGCCTGCCTGGACTGATTGGATGCCACAGAAAGTCTGTGTAC<br>TGGCATGTGATTGGCATGGGCACCACACCTGAGGTGCACAGCATCTTTC<br>TGGAAGGACACACCTTCCTGGTGAGGAACCACAGACAGGCCAGCCTGGA<br>AATCAGCCCTATCACCTTCCTGACAGCTCAGACCCTGCTGATGGATCTG<br>GGCCAGTTTCTGCTGTTCTGCCACATCAGCAGCCACCAGCATGATGGCA<br>TGGAAGCCTATGTGAAGGTGGACAGCTGCCCTGAAGAACCCCAGCTGAG<br>AATGAAGAACAATGAGGAAGCTGAGGACTATGATGATGACCTGACAGAC<br>TCTGAGATGGATGTGGTCAGATTTGATGATGATAACAGCCCCAGCTTCA<br>TCCAGATCAGATCTGTGGCCAAGAAGCACCCCAAGACCTGGGTGCACTA<br>TATTGCTGCTGAGGAAGAGGACTGGGATTATGCTCCTCTGGTGCTGGCC<br>CCTGATGACAGAAGCTACAAGAGCCAGTACCTGAACAATGGCCCTCAGA<br>GAATTGGCAGGAAGTATAAGAAAGTGAGGTTCATGGCCTACACAGATGA<br>GACATTCAAGACCAGAGAGGCTATCCAGCATGAGTCTGGCATTCTGGGA<br>CCTCTGCTGTATGGGGAAGTGGGGGACACACTGCTGATCATCTTCAAGA<br>ACCAGGCCAGCAGACCCTACAACATCTACCCTCATGGCATCACAGATGT<br>GAGGCCTCTGTACTCTAGAAGGCTGCCCAAGGGGGTGAAGCACCTGAAG<br>GACTTCCCTATCCTGCCTGGGGAGATCTTCAAGTACAAGTGGACAGTGA<br>CAGTGGAGGATGGCCCTACCAAGTCTGATCCTAGATGCCTGACAAGGTA<br>CTACAGCAGCTTTGTGAACATGGAAAGGGACCTGGCCTCTGGCCTGATT<br>GGTCCTCTGCTGATCTGCTACAAAGAATCTGTGGACCAGAGGGGCAACC<br>AGATCATGAGTGACAAGAGAAATGTGATCCTGTTCTCTGTCTTTGATGA<br>GAACAGGTCCTGGTATCTGACAGAGAACATCCAGAGGTTTCTGCCCAAT<br>CCTGCTGGGGTGCAGCTGGAAGATCCTGAGTTCCAGGCCTCCAACATCA<br>TGCACTCCATCAATGGCTATGTGTTTGACAGCCTGCAGCTGTCTGTGTG<br>CCTGCATGAAGTGGCCTACTGGTACATCCTGTCTATTGGGGCCCAGACA<br>GACTTCCTGTCTGTGTTCTTTTCTGGCTACACCTTCAAGCACAAGATGG<br>TGTATGAGGATACCCTGACACTGTTCCCATTCTCTGGGGAGACAGTGTT<br>CATGAGCATGGAAAACCCTGGCCTGTGGATCCTGGGCTGTCACAACAGT<br>GACTTCAGAAACAGAGGCATGACAGCCCTGCTGAAGGTGTCCAGCTGTG<br>ACAAGAACACTGGGGACTACTATGAGGACTCTTATGAGGACATCTCTGC<br>CTACCTGCTGAGCAAGAACAATGCCATTGAGCCTAGGAGCTTCTCTCAG<br>AACGCCACTAATGTGTCTAACAACAGCAACACCAGCAATGACAGCCCTC<br>CTGTGCTGAAGAGACACCAGAGGGAGATCACCAGAACCACACTGCAGTC<br>TGACCAAGAGGAAATTGATTATGATGACACCATCTCTGTGGAGATGAAG<br>AAAGAAGATTTTGACATCTATGATGAGGATGAGAATCAGAGCCCCAGAT<br>CTTTCCAGAAGAAAACAAGGCACTACTTCATTGCTGCTGTGGAAAGACT<br>GTGGGACTATGGCATGAGCAGCAGCCCCCATGTGCTGAGAAACAGGGCC<br>CAGTCTGGAAGTGTGCCCCAGTTCAAGAAAGTGGTGTTCCAAGAGTTCA<br>CAGATGGCAGCTTCACCCAGCCTCTGTATAGAGGGGAGCTGAATGAGCA<br>CCTGGGACTGCTGGGACCTTACATCAGAGCTGAGGTGGAGGATAACATC<br>ATGGTCACCTTTAGAAACCAGGCCTCTAGGCCCTACTCCTTCTACAGCT<br>CCCTGATCAGCTATGAAGAGGACCAGAGACAGGGGGCTGAGCCCAGAAA<br>GAACTTTGTGAAGCCCAATGAGACTAAGACCTACTTTTGGAAGGTGCAG<br>CACCACATGGCCCCTACAAAGGATGAGTTTGACTGCAAGGCCTGGGCCT<br>ACTTCTCTGATGTGGACCTGGAGAAGGATGTGCACTCTGGACTCATTGG<br>ACCCCTGCTTGTGTGCCACACCAACACACTGAATCCTGCTCATGGCAGG<br>CAAGTGACAGTGCAAGAGTTTGCCCTGTTCTTCACCATCTTTGATGAGA<br>CAAAGTCCTGGTACTTCACAGAAAACATGGAAAGAAACTGCAGGGCCCC<br>TTGCAACATCCAGATGGAAGATCCCACCTTCAAAGAGAACTACAGGTTC<br>CATGCCATCAATGGCTACATCATGGACACTCTGCCTGGCCTGGTTATGG<br>CACAGGATCAGAGGATCAGATGGTATCTGCTGTCCATGGGCTCCAATGA<br>GAATATCCACAGCATCCACTTCTCTGGCCATGTGTTCACAGTGAGGAAA<br>AAAGAAGAGTACAAGATGGCCCTGTACAATCTGTACCCTGGGGTGTTTG<br>AGACTGTGGAAATGCTGCCTAGCAAGGCTGGAATCTGGAGGGTGGAATG<br>TCTGATTGGAGAGCATCTGCATGCTGGAATGTCTACCCTGTTCCTGGTG<br>TACAGCAACAAGTGTCAGACCCCTCTGGGCATGGCCTCTGGACACATCA<br>GAGACTTCCAGATCACAGCCTCTGGCCAGTATGGACAGTGGGCTCCTAA<br>ACTGGCTAGACTGCACTACTCTGGCAGCATCAATGCCTGGTCCACCAAA<br>GAGCCCTTCAGCTGGATCAAGGTGGACCTGCTGGCTCCCATGATCATCC<br>ATGGAATCAAGACCCAGGGGGCCAGACAGAAGTTCAGCAGCCTGTACAT<br>CAGCCAGTTCATCATCATGTACAGCCTGGATGGCAAGAAGTGGCAGACC<br>TACAGAGGCAACAGCACAGGCACACTCATGGTGTTCTTTGGCAATGTGG<br>ACTCTTCTGGCATTAAGCACAACATCTTCAACCCTCCAATCATTGCCAG<br>GTACATCAGGCTGCACCCCACACACTACAGCATCAGATCTACCCTGAGG<br>ATGGAACTGATGGGCTGTGACCTGAACAGCTGCTCTATGCCCCTGGGAA<br>TGGAAAGCAAGGCCATCTCTGATGCCCAGATCACAGCCAGCAGCTACTT<br>CACCAACATGTTTGCCACATGGTCCCCATCTAAGGCCAGGCTGCATCTG | |

-continued

| SEQ ID | Sequence | Description |
|---|---|---|
| | CAGGGCAGATCTAATGCTTGGAGGCCCCAAGTGAACAACCCCAAAGAGT GGCTGCAGGTGGACTTTCAGAAAACCATGAAAGTGACAGGAGTGACCAC ACAGGGGGTCAAGTCTCTGCTGACCTCTATGTATGTGAAAGAGTTCCTG ATCTCCAGCAGCCAGGATGGCCACCAGTGGACCCTGTTTTTCCAGAATG GCAAAGTCAAGGTGTTCCAGGGAAACCAGGACAGCTTCACACCTGTGGT CAACTCCCTGGATCCTCCACTGCTGACCAGATACCTGAGAATTCACCCT CAGTCTTGGGTGCACCAGATTGCTCTGAGAATGGAAGTGCTGGGATGTG AAGCTCAGGACCTCTACTAAtcgcgaataaaagatctttattttcatta gatctgtgtgttggttttttgtgtg | |
| 333 | TGCCAGTTCCCGATCGTTACAGGCGGTACTCCTCAAAGCGTACTAAAGA ATTATTCTTTTACATTTCAGTGGCTACCAGAAGATACTACCTGGGAGCT GTGGAACTGAGCTGGGATTACATGCAGTCTGACCTGGGAGAGCTGCCTG TGGATGCTAGATTCCCACCTAGAGTCCCTAAGTCCTTCCCCTTCAACAC CTCTGTGGTCTACAAGAAAACCCTGTTTGTGGAGTTTACAGACCACCTG TTCAACATTGCTAAGCCTAGACCACCATGGATGGGACTGCTGGGACCAA CCATCCAGGCAGAGGTGTATGACACAGTGGTCATCACCCTGAAAAACAT GGCTTCTCACCCTGTGTCCCTGCATGCTGTGGGAGTCTCCTACTGGAAG GCCTCTGAAGGGGCTGAGTATGATGATCAGACCAGCCAGAGGGAAAAAG AGGATGATAAGGTGTTCCCTGGAGGGTCCCATACCTATGTGTGGCAGGT CCTGAAGGAGAATGGACCAATGGCTTCTGACCCTCTGTGCCTGACCTAC TCTTATCTGTCCCATGTGGACCTGGTCAAGGATCTGAACTCTGGCCTGA TTGGGGCTCTGCTGGTGTGTAGGGAAGGGTCCCTGGCCAAGGAGAAAAC CCAGACCCTGCATAAGTTCATCCTGCTGTTTGCTGTGTTTGATGAAGGA AAAAGCTGGCACTCTGAGACCAAGAACTCTCTGATGCAGGACAGGGATG CTGCTTCTGCCAGAGCTTGGCCCAAGATGCACACAGTGAATGGCTATGT CAATAGGAGCCTGCCTGGACTGATTGGCTGCCACAGAAAGTCTGTGTAT TGGCATGTCATTGGAATGGGCACCACCCCTGAAGTGCACAGCATCTTCC TGGAGGGGCATACCTTTCTGGTCAGGAACCACAGGCAGGCTAGCCTGGA GATCTCTCCAATCACCTTCCTGACAGCCCAGACCCTGCTGATGGACCTG GGACAGTTCCTGCTGTTTTGCCACATCTCCAGCCACCAGCATGATGGCA TGGAGGCTTATGTGAAAGTGGACTCCTGTCCTGAGGAACCTCAGCTGAG GATGAAGAACAATGAGGAAGCTGAAGACTATGATGATGATGACCTGACAGAC TCTGAGATGGATGTGGTCAGGTTTGATGATGATAACTCTCCCTCCTTTA TCCAGATCAGGTCTGTGGCCAAGAAACACCCTAAGACCTGGGTCCATTA CATTGCTGCTGAGGAAGAGGACTGGGATTATGCTCCACTGGTGCTGGCC CCTGATGATAGATCCTACAAAAGCCAGTATCTGAACAATGGACCCCAGA GGATTGGCAGAAAGTACAAGAAAGTGAGGTTCATGGCTTATACAGATGA GACCTTTAAGACCAGAGAAGCCATCCAGCATGAGTCTGGGATCCTGGGA CCTCTGCTGTATGGGGAAGTGGGGGACACCCTGCTGATCATCTTCAAGA ACCAGGCCAGCAGGCCTTACAATATCTATCCACATGGCATCACAGATGT GAGACCTCTGTACTCCAGGAGGCTGCCAAAGGGGGTGAAACACCTGAAG GACTTCCCAATCCTGCCTGGGGAAATCTTTAAGTATAAATGGACAGTCA CAGTGGAGGATGGGCCCACCAAGTCTGACCCTAGGTGCCTGACCAGATA CTATTCTTCCTTTGTGAATATGGAGAGAGACCTGGCTTCTGGACTGATT GGACCCCTGCTGATCTGTTACAAAGAGTCTGTGGATCAGAGGGGCAACC AGATCATGTCTGACAAGAGGAATGTGATCCTGTTCTCTGTCTTTGATGA AAACAGGTCTTGGTACCTGACAGAGAACATCCAGAGGTTCCTGCCTAAT CCAGCTGGAGTGCAGCTGGAAGATCCTGAGTTCCAGGCCTCTAACATCA TGCATTCCATCAATGGCTATGTGTTTGACTCCCTGCAGCTGTCTGTGTG CCTGCATGAGGTGGCTTACTGGTATATCCTGAGCATTGGAGCCCAGACA GATTTCCTGTCTGTGTTCTTTTCTGGCTACACCTTTAAGCATAAAATGG TGTATGAGGACACCCTGACCCTGTTCCCATTTTCTGGAGAAACTGTGTT CATGAGCATGGAGAATCCTGGGCTGTGGATCCTGGGATGCCACAACTCT GATTTCAGGAATAGAGGGATGACAGCCCTGCTGAAAGTGAGCTCTTGTG ACAAGAACACAGGAGACTACTATGAAGATAGCTATGAGGACATCTCTGC TTATCTGCTGTCCAAAAACAATGCCATTGAGCCCAGGAGCTTCTCTCAG AACGCCACTAATGTGTCTAACAACAGCAACACCAGCAATGACAGCCCTC CAGTGCTGAAGAGGCACCAGAGGGAGATCACCAGAACCACCCTGCAGTC TGATCAGGAAGAGATTGACTATGATGATACCATCTCTGTGGAAATGAAG AAAGAGGACTTTGATATCTATGATGAAGATGAGAACCAGTCTCCCAGGT CCTTCCAGAAGAAAACCAGACATTACTTTATTGCTGCTGTGGAGAGGCT GTGGGACTATGGCATGTCCAGCTCTCCTCATGTGCTGAGAAATAGAGCT CAGTCTGGATCTGTCCCACAGTTCAAGAAAGTGGTCTTCCAGGAGTTTA CAGATGGAAGCTTTACCCAGCCACTGTACAGGGGAGAACTGAATGAGCA CCTGGGGCTGCTGGGACCCTATATCAGGGCTGAAGTGGAGGATAACATC ATGGTCACCTTCAGGAATCAGGCCAGCAGACCCTACTCTTTTTATTCCA GCCTGATCTCCTATGAAGAGGACCAGAGACAGGGAGCTGAACCAAGAAA AAACTTTGTGAAGCCTAATGAGACCAAAACCTACTTTTGGAAGGTGCAG CACCATATGGCCCCTACCAAAGATGAGTTTGATTGCAAGGCCTGGGCTT ATTTTTCTGATGTGGATCTGGAGAAGGATGTCCACTCTGGCCTGATTGG GCCACTGCTGGTGTGTCATACCAACACCCTGAATCCAGCTCATGGAAGG CAGGTGACAGTCCAGGAATTTGCCCTGTTCTTTACCATCTTTGATGAGA CCAAGAGCTGGTACTTCACAGAAAACATGGAGAGGAATTGCAGAGCCCC ATGTAACATCCAGATGGAAGACCCCACCTTCAAGGAGAACTACAGATTT CATGCTATCAATGGGTATATCATGGATACCCTGCCAGGACTGGTCATGG CTCAGGACCAGAGGATCAGATGGTACCTGCTGAGCATGGGGTCTAATGA | pCB1020 |

-continued

| SEQ ID | Sequence | Description |
|---|---|---|
| | GAATATCCACTCCATCCATTTCTCTGGACATGTGTTTACAGTAAGGAAG<br>AAAGAAGAGTACAAGATGGCCCTGTACAACCTGTATCCTGGGGTGTTTG<br>AAACAGTGGAGATGCTGCCTTCCAAGGCTGGGATCTGGAGGGTGGAATG<br>CCTGATTGGGGAGCACCTGCATGCTGGAATGTCTACCCTGTTCCTGGTG<br>TACTCCAATAAGTGTCAGACCCCCCTGGGGATGGCTTCTGGACATATCA<br>GGGACTTCCAGATCACAGCTTCTGGACAGTATGGACAGTGGGCTCCTAA<br>GCTGGCTAGACTGCACTATTCTGGCTCCATCAATGCTTGGTCTACCAAA<br>GAGCCTTTCTCCTGGATCAAGGTGGACCTGCTGGCTCCAATGATCATCC<br>ATGGCATCAAAACCCAGGGGGCCAGGCAGAAGTTCTCTTCCCTGTACAT<br>CAGCCAGTTTATCATCATGTATTCTCTGGATGGGAAGAAATGGCAGACC<br>TACAGAGGCAATTCCACAGGGACCCTGATGGTGTTCTTTGGCAATGTGG<br>ACAGCTCTGGGATCAAGCACAACATCTTCAATCCCCCTATCATTGCCAG<br>GTACATCAGACTGCACCCAACCCATTATTCCATCAGGAGCACCCTGAGA<br>ATGGAGCTGATGGGGTGTGATCTGAACAGCTGTTCTATGCCCCTGGGAA<br>TGGAGTCTAAGGCCATCTCTGATGCTCAGATCACAGCCTCCAGCTACTT<br>CACCAATATGTTTGCTACCTGGTCCCCAAGCAAGGCTAGACTGCATCTG<br>CAGGGAAGAAGCAATGCTTGGAGACCACAGGTGAACAATCCCAAGGAGT<br>GGCTGCAGGTGGACTTCCAGAAAACCATGAAGGTGACAGGAGTCACCAC<br>CCAGGGAGTGAAAAGCCTGCTGACCTCTATGTATGTCAAGGAGTTCCTG<br>ATCTCTTCCAGCCAGGATGGGCACCAGTGGACCCTGTTCTTTCAGAATG<br>GAAAGGTGAAAGTCTTCCAGGGCAATCAGGATTCCTTTACCCCTGTGGT<br>CAACAGCCTGGACCCACCCCTGCTGACCAGGTACCTGAGAATCCACCCA<br>CAGTCCTGGGTGCATCAGATTGCTCTGAGGATGGAAGTCCTGGGCTGTG<br>AGGCCCAGGACCTGTATTGATCGCGAATAAAAGATCTTTATTTTCATTA<br>GATCTGTGTGTTGGTTTTTTGTGTG | |
| 334 | TGCCAGTTCCCGATCGTTACAGGCGGTACTCCTCAAAGCGTACTAAAGA<br>ATTATTCTTTTACATTTCAGTGGCCACCAGAAGGTACTACCTGGGAGCT<br>GTGGAACTGAGCTGGGACTACATGCAGTCTGACCTGGGAGAGCTGCCTG<br>TGGATGCTAGATTTCCTCCAAGAGTGCCCAAGAGCTTCCCCTTCAACAC<br>CTCTGTGGTGTACAAGAAAACCCTGTTTGTGGAATTCACAGACCACCTG<br>TTCAATATTGCCAAGCCTAGACCTCCTTGGATGGGCCTGCTGGGCCCTA<br>CAATTCAGGCTGAGGTGTATGACACAGTGGTCATCACCCTGAAGAACAT<br>GGCCAGCCATCCTGTGTCTCTGCATGCTGTGGGAGTGTCTTACTGGAAG<br>GCTTCTGAGGGGGCTGAGTATGATGACCAGACAAGCCAGAGAGAGAAAG<br>AGGATGACAAGGTTTTCCCTGGGGGCAGCCACACCTATGTCTGGCAGGT<br>CCTGAAAGAAAATGGCCCTATGGCCTCTGATCCTCTGTGCCTGACATAC<br>AGCTACCTGAGCCATGTGGACCTGGTCAAGGACCTGAACTCTGGCCTGA<br>TTGGGGCTCTGCTGGTGTGTAGAGAAGGCAGCCTGGCCAAAGAAAAGAC<br>CCAGACACTGCACAAGTTCATCCTGCTGTTTGCTGTGTTTGATGAGGGC<br>AAGAGCTGGCACTCTGAGACAAAGAACAGCCTGATGCAGGACAGAGATG<br>CTGCCTCTGCTAGAGCTTGGCCCAAGATGCACACAGTGAATGGCTATGT<br>GAACAGAAGCCTGCCTGGACTGATTGGATGCCACAGAAAGTCTGTGTAC<br>TGGCATGTGATTGGCATGGGCACCACACCTGAGGTGCACAGCATCTTTC<br>TGGAAGGACACACCTTCCTGGTGAGGAACCACAGACAGGCCAGCCTGGA<br>AATCAGCCCTATCACCTTCCTGACAGCTCAGACCCTGCTGATGGATCTG<br>GGCCAGTTTCTGCTGGCCTGCCACATCAGCAGCCACCAGCATGATGGCA<br>TGGAAGCCTATGTGAAGGTGGACAGCTGCCCTGAAGAACCCCAGCTGAG<br>AATGAAGAACAATGAGGAAGCTGAGGACTATGATGATGACCTGACAGAC<br>TCTGAGATGGATGTGGTCAGATTTGATGATGATAACAGCCCCAGCTTCA<br>TCCAGATCAGATCTGTGGCCAAGAAGCACCCCAAGACCTGGGTGCACTA<br>TATTGCTGCTGAGGAAGAGGACTGGGATTATGCTCCTCTGGTGCTGGCC<br>CCTGATGACAGAAGCTACAAGAGCCAGTACCTGAACAATGGCCCTCAGA<br>GAATTGGCAGGAAGTATAAGAAAGTGAGGTTCATGGCCTACACAGATGA<br>GACATTCAAGACCAGAGAGGCTATCCAGCATGAGTCTGGCATTCTGGGA<br>CCTCTGCTGTATGGGGAAGTGGGGGACACACTGCTGATCATCTTCAAGA<br>ACCAGGCCAGCAGACCCTACAACATCTACCCTCATGGCATCACAGATGT<br>GAGGCCTCTGTACTCTAGAAGGCTGCCCAAGGGGGTGAAGCACCTGAAG<br>GACTTCCCTATCCTGCCTGGGGAGATCTTCAAGTACAAGTGGACAGTGA<br>CAGTGGAGGATGGCCCTACCAAGTCTGATCCTAGATGCCTGACAAGGTA<br>CTACAGCAGCTTTGTGAACATGGAAAGGGACCTGGCCTCTGGCCTGATT<br>GGTCCTCTGCTGATCTGCTACAAAGAATCTGTGGACCAGAGGGGCAACC<br>AGATCATGAGTGACAAGAGAAATGTGATCCTGTTCTCTGTCTTTGATGA<br>GAACAGGTCCTGGTATCTGACAGAGAACATCCAGAGGTTTCTGCCCAAT<br>CCTGCTGGGGTGCAGCTGGAAGATCCTGAGTTCCAGGCCTCCAACATCA<br>TGCACTCCATCAATGGCTATGTGTTTGACAGCCTGCAGCTGTCTGTGTG<br>CCTGCATGAAGTGGCCTACTGGTACATCCTGTCTATTGGGGCCCAGACA<br>GACTTCCTGTCTGTGTTCTTTTCTGGCTACACCTTCAAGCACAAGATGG<br>TGTATGAGGATACCCTGACACTGTTCCCATTCTCTGGGGAGACAGTGTT<br>CATGAGCATGGAAAACCCTGGCCTGTGGATCCTGGGCTGTCACAACAGT<br>GACTTCAGAAACAGAGGCATGACAGCCCTGCTGAAGGTGTCCAGCTGTG<br>ACAAGAACACTGGGGACTACTATGAGGACTCTTATGAGGACATCTCTGC<br>CTACCTGCTGAGCAAGAACAATGCCATTGAGCCTAGGAGCTTCTCTCAG<br>AACGCCACTAATGTGTCTAACAACAGCAACACCAGCAATGACAGCCCTC<br>CTGTGCTGAAGAGACACCAGAGGGAGATCACCAGAACCACACTGCAGTC<br>TGACCAAGAGGAAATTGATTATGATGACACCATCTCTGTGGAGATGAAG<br>AAAGAAGATTTTGACATCTATGATGAGGATGAGAATCAGAGCCCCAGAT | pCB1025 |

-continued

| SEQ ID | Sequence | Description |
|---|---|---|
| | CTTTCCAGAAGAAAACAAGGCACTACTTCATTGCTGCTGTGGAAAGACT<br>GTGGGACTATGGCATGAGCAGCAGCCCCCATGTGCTGAGAAACAGGGCC<br>CAGTCTGGAAGTGTGCCCCAGTTCAAGAAAGTGGTGTTCCAAGAGTTCA<br>CAGATGGCAGCTTCACCCAGCCTCTGTATAGAGGGGAGCTGAATGAGCA<br>CCTGGGACTGCTGGGACCTTACATCAGAGCTGAGGTGGAGGATAACATC<br>ATGGTCACCTTTAGAAACCAGGCCTCTAGGCCCTACTCCTTCTACAGCT<br>CCCTGATCAGCTATGAAGAGGACCAGAGACAGGGGGCTGAGCCCAGAAA<br>GAACTTTGTGAAGCCCAATGAGACTAAGACCTACTTTTGGAAGGTGCAG<br>CACCACATGGCCCCTACAAAGGATGAGTTTGACTGCAAGGCCTGGGCCT<br>ACTTCTCTGATGTGGACCTGGAGAAGGATGTGCACTCTGGACTCATTGG<br>ACCCCTGCTTGTGTGCCACACCAACACACTGAATCCTGCTCATGGCAGG<br>CAAGTGACAGTGCAAGAGTTTGCCCTGTTCTTCACCATCTTTGATGAGA<br>CAAAGTCCTGGTACTTCACAGAAAACATGGAAAGAAACTGCAGGGCCCC<br>TTGCAACATCCAGATGGAAGATCCCACCTTCAAAGAGAACTACAGGTTC<br>CATGCCATCAATGGCTACATCATGGACACTCTGCCTGGCCTGGTTATGG<br>CACAGGATCAGAGGATCAGATGGTATCTGCTGTCCATGGGCTCCAATGA<br>GAATATCCACAGCATCCACTTCTCTGGCCATGTGTTCACAGTGAGGAAA<br>AAAGAAGAGTACAAGATGGCCCTGTACAATCTGTACCCTGGGGTGTTTG<br>AGACTGTGGAAATGCTGCCTAGCAAGGCTGGAATCTGGAGGGTGGAATG<br>TCTGATTGGAGAGCATCTGCATGCTGGAATGTCTACCCTGTTCCTGGTG<br>TACAGCAACAAGTGTCAGACCCCTCTGGGCATGGCCTCTGGACACATCA<br>GAGACTTCCAGATCACAGCCTCTGGCCAGTATGGACAGTGGGCTCCTAA<br>ACTGGCTAGACTGCACTACTCTGGCAGCATCAATGCCTGGTCCACCAAA<br>GAGCCCTTCAGCTGGATCAAGGTGGACCTGCTGGCTCCCATGATCATCC<br>ATGGAATCAAGACCCAGGGGGCCAGACAGAAGTTCAGCAGCCTGTACAT<br>CAGCCAGTTCATCATCATGTACAGCCTGGATGGCAAGAAGTGGCAGACC<br>TACAGAGGCAACAGCACAGGCACACTCATGGTGTTCTTTGGCAATGTGG<br>ACTCTTCTGGCATTAAGCACAACATCTTCAACCCTCCAATCATTGCCAG<br>GTACATCAGGCTGCACCCCACACACTACAGCATCAGATCTACCCTGAGG<br>ATGGAACTGATGGGCTGTGACCTGAACAGCTGCTCTATGCCCCTGGGAA<br>TGGAAAGCAAGGCCATCTCTGATGCCCAGATCACAGCCAGCAGCTACTT<br>CACCAACATGTTTGCCACATGGTCCCCATCTAAGGCCAGGCTGCATCTG<br>CAGGGCAGATCTAATGCTTGGAGGCCCCAAGTGAACAACCCCAAAGAGT<br>GGCTGCAGGTGGACTTTCAGAAAACCATGAAAGTGACAGGAGTGACCAC<br>ACAGGGGGTCAAGTCTCTGCTGACCTCTATGTATGTGAAAGAGTTCCTG<br>ATCTCCAGCAGCCAGGATGGCCACCAGTGGACCCTGTTTTTCCAGAATG<br>GCAAAGTCAAGGTGTTCCAGGGAAACCAGGACAGCTTCACACCTGTGGT<br>CAACTCCCTGGATCCTCCACTGCTGACCAGATACCTGAGAATTCACCCT<br>CAGTCTTGGGTGCACCAGATTGCTCTGAGAATGGAAGTGCTGGGATGTG<br>AAGCTCAGGACCTCTACTAAtcgcgaataaaagatctttattttcatta<br>gatctgtgtgttggtttttttgtgtg | |
| 335 | TGCCAGTTCCCGATCGTTACAGGCGGTACTCCTCAAAGCGTACTAAAGA<br>ATTATTCTTTTACATTTCAGTGGCCACCAGAAGGTACTACCTGGGAGCT<br>GTGGAACTGAGCTGGGACTACATGCAGTCTGACCTGGGAGAGCTGCCTG<br>TGGATGCTAGATTTCCTCCAAGAGTGCCCAAGAGCTTCCCCTTCAACAC<br>CTCTGTGGTGTACAAGAAAACCCTGTTTGTGGAATTCACAGACCACCTG<br>TTCAATATTGCCAAGCCTAGACCTCCTTGGATGGGCCTGCTGGGCCCTA<br>CAATTCAGGCTGAGGTGTATGACACAGTGGTCATCACCCTGAAGAACAT<br>GGCCAGCCATCCTGTGTCTCTGCATGCTGTGGGAGTGTCTTACTGGAAG<br>GCTTCTGAGGGGGCTGAGTATGATGACCAGACAAGCCAGAGAGAGAAAG<br>AGGATGACAAGGTTTTCCCTGGGGGCAGCCACACCTATGTCTGGCAGGT<br>CCTGAAAGAAAATGGCCCTATGGCCTCTGATCCTCTGTGCCTGACATAC<br>AGCTACCTGAGCCATGTGGACCTGGTCAAGGACCTGAACTCTGGCCTGA<br>TTGGGGCTCTGCTGGTGTGTAGAGAAGGCAGCCTGGCCAAAGAAAAGAC<br>CCAGACACTGCACAAGTTCATCCTGCTGTTTGCTGTGTTTGATGAGGGC<br>AAGAGCTGGCACTCTGAGACAAAGAACAGCCTGATGCAGGACAGAGATG<br>CTGCCTCTGCTAGAGCTTGGCCCAAGATGCACACAGTGAATGGCTATGT<br>GAACAGAAGCCTGCCTGGACTGATTGGATGCCACAGAAAGTCTGTGTAC<br>TGGCATGTGATTGGCATGGGCACCACACCTGAGGTGCACAGCATCTTTC<br>TGGAAGGACACACCTTCCTGGTGAGGAACCACAGACAGGCCAGCCTGGA<br>AATCAGCCCTATCACCTTCCTGACAGCTCAGACCCTGCTGATGGATCTG<br>GGCCAGTTTCTGCTGAGCTGCCACATCAGCAGCCACCAGCATGATGGCA<br>TGGAAGCCTATGTGAAGGTGGACAGCTGCCCTGAAGAACCCCAGCTGAG<br>AATGAAGAACAATGAGGAAGCTGAGGACTATGATGATGACCTGACAGAC<br>TCTGAGATGGATGTGGTCAGATTTGATGATGATAACAGCCCCAGCTTCA<br>TCCAGATCAGATCTGTGGCCAAGAAGCACCCCAAGACCTGGGTGCACTA<br>TATTGCTGCTGAGGAAGAGGACTGGGATTATGCTCCTCTGGTGCTGGCC<br>CCTGATGACAGAAGCTACAAGAGCCAGTACCTGAACAATGGCCCTCAGA<br>GAATTGGCAGGAAGTATAAGAAAGTGAGGTTCATGGCCTACACAGATGA<br>GACATTCAAGACCAGAGAGGCTATCCAGCATGAGTCTGGCATTCTGGGA<br>CCTCTGCTGTATGGGGAAGTGGGGGACACACTGCTGATCATCTTCAAGA<br>ACCAGGCCAGCAGACCCTACAACATCTACCCTCATGGCATCACAGATGT<br>GAGGCCTCTGTACTCTAGAAGGCTGCCCAAGGGGGTGAAGCACCTGAAG<br>GACTTCCCTATCCTGCCTGGGGAGATCTTCAAGTACAAGTGGACAGTGA<br>CAGTGGAGGATGGCCCTACCAAGTCTGATCCTAGATGCCTGACAAGGTA<br>CTACAGCAGCTTTGTGAACATGGAAAGGGACCTGGCCTCTGGCCTGATT | pCB1026 |

-continued

| SEQ ID | Sequence | Description |
|---|---|---|
| | GGTCCTCTGCTGATCTGCTACAAAGAATCTGTGGACCAGAGGGGCAACC<br>AGATCATGAGTGACAAGAGAAATGTGATCCTGTTCTCTGTCTTTGATGA<br>GAACAGGTCCTGGTATCTGACAGAGAACATCCAGAGGTTTCTGCCCAAT<br>CCTGCTGGGGTGCAGCTGGAAGATCCTGAGTTCCAGGCCTCCAACATCA<br>TGCACTCCATCAATGGCTATGTGTTTGACAGCCTGCAGCTGTCTGTGTG<br>CCTGCATGAAGTGGCCTACTGGTACATCCTGTCTATTGGGGCCCAGACA<br>GACTTCCTGTCTGTGTTCTTTTCTGGCTACACCTTCAAGCACAAGATGG<br>TGTATGAGGATACCCTGACACTGTTCCCATTCTCTGGGGAGACAGTGTT<br>CATGAGCATGGAAAACCCTGGCCTGTGGATCCTGGGCTGTCACAACAGT<br>GACTTCAGAAACAGAGGCATGACAGCCCTGCTGAAGGTGTCCAGCTGTG<br>ACAAGAACACTGGGGACTACTATGAGGACTCTTATGAGGACATCTCTGC<br>CTACCTGCTGAGCAAGAACAATGCCATTGAGCCTAGGAGCTTCTCTCAG<br>AACGCCACTAATGTGTCTAACAACAGCAACACCAGCAATGACAGCCCTC<br>CTGTGCTGAAGAGACACCAGAGGGAGATCACCAGAACCACACTGCAGTC<br>TGACCAAGAGGAAATTGATTATGATGACACCATCTCTGTGGAGATGAAG<br>AAAGAAGATTTTGACATCTATGATGAGGATGAGAATCAGAGCCCCAGAT<br>CTTTCCAGAAGAAAACAAGGCACTACTTCATTGCTGCTGTGGAAAGACT<br>GTGGGACTATGGCATGAGCAGCAGCCCCCATGTGCTGAGAAACAGGGCC<br>CAGTCTGGAAGTGTGCCCCAGTTCAAGAAAGTGGTGTTCCAAGAGTTCA<br>CAGATGGCAGCTTCACCCAGCCTCTGTATAGAGGGGAGCTGAATGAGCA<br>CCTGGGACTGCTGGGACCTTACATCAGAGCTGAGGTGGAGGATAACATC<br>ATGGTCACCTTTAGAAACCAGGCCTCTAGGCCCTACTCCTTCTACAGCT<br>CCCTGATCAGCTATGAAGAGGACCAGAGACAGGGGGCTGAGCCCAGAAA<br>GAACTTTGTGAAGCCCAATGAGACTAAGACCTACTTTTGGAAGGTGCAG<br>CACCACATGGCCCCTACAAAGGATGAGTTTGACTGCAAGGCCTGGGCCT<br>ACTTCTCTGATGTGGACCTGGAGAAGGATGTGCACTCTGGACTCATTGG<br>ACCCCTGCTTGTGTGCCACACCAACACACTGAATCCTGCTCATGGCAGG<br>CAAGTGACAGTGCAAGAGTTTGCCCTGTTCTTCACCATCTTTGATGAGA<br>CAAAGTCCTGGTACTTCACAGAAAACATGGAAAGAAACTGCAGGGCCCC<br>TTGCAACATCCAGATGGAAGATCCCACCTTCAAAGAGAACTACAGGTTC<br>CATGCCATCAATGGCTACATCATGGACACTCTGCCTGGCCTGGTTATGG<br>CACAGGATCAGAGGATCAGATGGTATCTGCTGTCCATGGGCTCCAATGA<br>GAATATCCACAGCATCCACTTCTCTGGCCATGTGTTCACAGTGAGGAAA<br>AAAGAAGAGTACAAGATGGCCCTGTACAATCTGTACCCTGGGGTGTTTG<br>AGACTGTGGAAATGCTGCCTAGCAAGGCTGGAATCTGGAGGGTGGAATG<br>TCTGATTGGAGAGCATCTGCATGCTGGAATGTCTACCCTGTTCCTGGTG<br>TACAGCAACAAGTGTCAGACCCCTCTGGGCATGGCCTCTGGACACATCA<br>GAGACTTCCAGATCACAGCCTCTGGCCAGTATGGACAGTGGGCTCCTAA<br>ACTGGCTAGACTGCACTACTCTGGCAGCATCAATGCCTGGTCCACCAAA<br>GAGCCCTTCAGCTGGATCAAGGTGGACCTGCTGGCTCCCATGATCATCC<br>ATGGAATCAAGACCCAGGGGGCCAGACAGAAGTTCAGCAGCCTGTACAT<br>CAGCCAGTTCATCATCATGTACAGCCTGGATGGCAAGAAGTGGCAGACC<br>TACAGAGGCAACAGCACAGGCACACTCATGGTGTTCTTTGGCAATGTGG<br>ACTCTTCTGGCATTAAGCACAACATCTTCAACCCTCCAATCATTGCCAG<br>GTACATCAGGCTGCACCCCACACACTACAGCATCAGATCTACCCTGAGG<br>ATGGAACTGATGGGCTGTGACCTGAACAGCTGCTCTATGCCCCTGGGAA<br>TGGAAAGCAAGGCCATCTCTGATGCCCAGATCACAGCCAGCAGCTACTT<br>CACCAACATGTTTGCCACATGGTCCCCATCTAAGGCCAGGCTGCATCTG<br>CAGGGCAGATCTAATGCTTGGAGGCCCCAAGTGAACAACCCCAAAGAGT<br>GGCTGCAGGTGGACTTTCAGAAAACCATGAAAGTGACAGGAGTGACCAC<br>ACAGGGGGTCAAGTCTCTGCTGACCTCTATGTATGTGAAAGAGTTCCTG<br>ATCTCCAGCAGCCAGGATGGCCACCAGTGGACCCTGTTTTTCCAGAATG<br>GCAAAGTCAAGGTGTTCCAGGGAAACCAGGACAGCTTCACACCTGTGGT<br>CAACTCCCTGGATCCTCCACTGCTGACCAGATACCTGAGAATTCACCCT<br>CAGTCTTGGGTGCACCAGATTGCTCTGAGAATGGAAGTGCTGGGATGTG<br>AAGCTCAGGACCTCTACTAAtcgcgaataaaagatctttattttcatta<br>gatctgtgtgttggtttttttgtgtg | |
| 336 | cctgcaggcagctgcgcgctcgctcgctcactgaggccgcccgggcaaa<br>gcccgggcgtcgggcgacctttggtcgcccggcctcagtgagcgagcga<br>gcgcgcagagagggagtggccaactccatcactaggggttcctgcggcc<br>CGCGGTGCCAGTTCCCGATCGTTACAGGCGGTACTCCTCAAAGCGTACT<br>AAAGAATTATTCTTTTACATTTCAGTGGCTACCAGAAGATACTACCTGG<br>GAGCTGTGGAACTGAGCTGGGATTACATGCAGTCTGACCTGGGAGAGCT<br>GCCTGTGGATGCTAGATTCCCACCTAGAGTCCCTAAGTCCTTCCCCTTC<br>AACACCTCTGTGGTCTACAAGAAAACCCTGTTTGTGGAGTTTACAGACC<br>ACCTGTTCAACATTGCTAAGCCTAGACCACCATGGATGGGACTGCTGGG<br>ACCAACCATCCAGGCAGAGGTGTATGACACAGTGGTCATCACCCTGAAA<br>AACATGGCTTCTCACCCTGTGTCCCTGCATGCTGTGGGAGTCTCCTACT<br>GGAAGGCCTCTGAAGGGGCTGAGTATGATGATCAGACCAGCCAGAGGGA<br>AAAAGAGGATGATAAGGTGTTCCCTGGAGGGTCCCATACCTATGTGTGG<br>CAGGTCCTGAAGGAGAATGGACCAATGGCTTCTGACCCTCTGTGCCTGA<br>CCTACTCTTATCTGTCCCATGTGGACCTGGTCAAGGATCTGAACTCTGG<br>CCTGATTGGGGCTCTGCTGGTGTGTAGGGAAGGGTCCCTGGCCAAGGAG<br>AAAACCCAGACCCTGCATAAGTTCATCCTGCTGTTTGCTGTGTTTGATG<br>AAGGAAAAAGCTGGCACTCTGAGACCAAGAACTCTCTGATGCAGGACAG<br>GGATGCTGCTTCTGCCAGAGCTTGGCCCAAGATGCACACAGTGAATGGC | pCB103 |

-continued

| SEQ ID | Sequence | Description |
|---|---|---|
| | TATGTCAATAGGAGCCTGCCTGGACTGATTGGCTGCCACAGAAAGTCTG<br>TGTATTGGCATGTCATTGGAATGGGCACCACCCCTGAAGTGCACAGCAT<br>CTTCCTGGAGGGGCATACCTTTCTGGTCAGGAACCACAGGCAGGCTAGC<br>CTGGAGATCTCTCCAATCACCTTCCTGACAGCCCAGACCCTGCTGATGG<br>ACCTGGGACAGTTCCTGCTGTTTTGCCACATCTCCAGCCACCAGCATGA<br>TGGCATGGAGGCTTATGTGAAAGTGGACTCCTGTCCTGAGGAACCTCAG<br>CTGAGGATGAAGAACAATGAGGAAGCTGAAGACTATGATGATGACCTGA<br>CAGACTCTGAGATGGATGTGGTCAGGTTTGATGATGATAACTCTCCCTC<br>CTTTATCCAGATCAGGTCTGTGGCCAAGAAACACCCTAAGACCTGGGTC<br>CATTACATTGCTGCTGAGGAAGAGGACTGGGATTATGCTCCACTGGTGC<br>TGGCCCCTGATGATAGATCCTACAAAAGCCAGTATCTGAACAATGGACC<br>CCAGAGGATTGGCAGAAAGTACAAGAAAGTGAGGTTCATGGCTTATACA<br>GATGAGACCTTTAAGACCAGAGAAGCCATCCAGCATGAGTCTGGGATCC<br>TGGGACCTCTGCTGTATGGGGAAGTGGGGGACACCCTGCTGATCATCTT<br>CAAGAACCAGGCCAGCAGGCCTTACAATATCTATCCACATGGCATCACA<br>GATGTGAGACCTCTGTACTCCAGGAGGCTGCCAAAGGGGGTGAAACACC<br>TGAAGGACTTCCCAATCCTGCCTGGGGAAATCTTTAAGTATAAATGGAC<br>AGTCACAGTGGAGGATGGGCCCACCAAGTCTGACCCTAGGTGCCTGACC<br>AGATACTATTCTTCCTTTGTGAATATGGAGAGAGACCTGGCTTCTGGAC<br>TGATTGGACCCCTGCTGATCTGTTACAAAGAGTCTGTGGATCAGAGGGG<br>CAACCAGATCATGTCTGACAAGAGGAATGTGATCCTGTTCTCTGTCTTT<br>GATGAAAACAGGTCTTGGTACCTGACAGAGAACATCCAGAGGTTCCTGC<br>CTAATCCAGCTGGAGTGCAGCTGGAAGATCCTGAGTTCCAGGCCTCTAA<br>CATCATGCATTCCATCAATGGCTATGTGTTTGACTCCCTGCAGCTGTCT<br>GTGTGCCTGCATGAGGTGGCTTACTGGTATATCCTGAGCATTGGAGCCC<br>AGACAGATTTCCTGTCTGTGTTCTTTTCTGGCTACACCTTTAAGCATAA<br>AATGGTGTATGAGGACACCCTGACCCTGTTCCCATTTTCTGGAGAAACT<br>GTGTTCATGAGCATGGAGAATCCTGGGCTGTGGATCCTGGGATGCCACA<br>ACTCTGATTTCAGGAATAGAGGGATGACAGCCCTGCTGAAAGTGAGCTC<br>TTGTGACAAGAACACAGGAGACTACTATGAAGATAGCTATGAGGACATC<br>TCTGCTTATCTGCTGTCCAAAAACAATGCCATTGAGCCCAGGAGCTTCT<br>CTCAGAACCCTCCAGTGCTGAAGAGGCACCAGAGGGAGATCACCAGAAC<br>CACCCTGCAGTCTGATCAGGAAGAGATTGACTATGATGATACCATCTCT<br>GTGGAAATGAAGAAAGAGGACTTTGATATCTATGATGAAGATGAGAACC<br>AGTCTCCCAGGTCCTTCCAGAAGAAAACCAGACATTACTTTATTGCTGC<br>TGTGGAGAGGCTGTGGGACTATGGCATGTCCAGCTCTCCTCATGTGCTG<br>AGAAATAGAGCTCAGTCTGGATCTGTCCCACAGTTCAAGAAAGTGGTCT<br>TCCAGGAGTTTACAGATGGAAGCTTTACCCAGCCACTGTACAGGGGAGA<br>ACTGAATGAGCACCTGGGGCTGCTGGGACCCTATATCAGGGCTGAAGTG<br>GAGGATAACATCATGGTCACCTTCAGGAATCAGGCCAGCAGACCCTACT<br>CTTTTTATTCCAGCCTGATCTCCTATGAAGAGGACCAGAGACAGGGAGC<br>TGAACCAAGAAAAAACTTTGTGAAGCCTAATGAGACCAAAACCTACTTT<br>TGGAAGGTGCAGCACCATATGGCCCCTACCAAAGATGAGTTTGATTGCA<br>AGGCCTGGGCTTATTTTTCTGATGTGGATCTGGAGAAGGATGTCCACTC<br>TGGCCTGATTGGGCCACTGCTGGTGTGTCATACCAACACCCTGAATCCA<br>GCTCATGGAAGGCAGGTGACAGTCCAGGAATTTGCCCTGTTCTTTACCA<br>TCTTTGATGAGACCAAGAGCTGGTACTTCACAGAAAACATGGAGAGGAA<br>TTGCAGAGCCCCATGTAACATCCAGATGGAAGACCCCACCTTCAAGGAG<br>AACTACAGATTTCATGCTATCAATGGGTATATCATGGATACCCTGCCAG<br>GACTGGTCATGGCTCAGGACCAGAGGATCAGATGGTACCTGCTGAGCAT<br>GGGGTCTAATGAGAATATCCACTCCATCCATTTCTCTGGACATGTGTTT<br>ACAGTAAGGAAGAAAGAAGAGTACAAGATGGCCCTGTACAACCTGTATC<br>CTGGGGTGTTTGAAACAGTGGAGATGCTGCCTTCCAAGGCTGGGATCTG<br>GAGGGTGGAATGCCTGATTGGGGAGCACCTGCATGCTGGAATGTCTACC<br>CTGTTCCTGGTGTACTCCAATAAGTGTCAGACCCCCCTGGGGATGGCTT<br>CTGGACATATCAGGGACTTCCAGATCACAGCTTCTGGACAGTATGGACA<br>GTGGGCTCCTAAGCTGGCTAGACTGCACTATTCTGGCTCCATCAATGCT<br>TGGTCTACCAAAGAGCCTTTCTCCTGGATCAAGGTGGACCTGCTGGCTC<br>CAATGATCATCCATGGCATCAAAACCCAGGGGGCCAGGCAGAAGTTCTC<br>TTCCCTGTACATCAGCCAGTTTATCATCATGTATTCTCTGGATGGGAAG<br>AAATGGCAGACCTACAGAGGCAATTCCACAGGGACCCTGATGGTGTTCT<br>TTGGCAATGTGGACAGCTCTGGGATCAAGCACAACATCTTCAATCCCCC<br>TATCATTGCCAGGTACATCAGACTGCACCCAACCCATTATTCCATCAGG<br>AGCACCCTGAGAATGGAGCTGATGGGGTGTGATCTGAACAGCTGTTCTA<br>TGCCCCTGGGAATGGAGTCTAAGGCCATCTCTGATGCTCAGATCACAGC<br>CTCCAGCTACTTCACCAATATGTTTGCTACCTGGTCCCCAAGCAAGGCT<br>AGACTGCATCTGCAGGGAAGAAGCAATGCTTGGAGACCACAGGTGAACA<br>ATCCCAAGGAGTGGCTGCAGGTGGACTTCCAGAAAACCATGAAGGTGAC<br>AGGAGTCACCACCCAGGGAGTGAAAAGCCTGCTGACCTCTATGTATGTC<br>AAGGAGTTCCTGATCTCTTCCAGCCAGGATGGGCACCAGTGGACCCTGT<br>TCTTTCAGAATGGAAAGGTGAAAGTCTTCCAGGGCAATCAGGATTCCTT<br>TACCCCTGTGGTCAACAGCCTGGACCCACCCCTGCTGACCAGGTACCTG<br>AGAATCCACCCACAGTCCTGGGTGCATCAGATTGCTCTGAGGATGGAAG<br>TCCTGGGCTGTGAGGCCCAGGACCTGTATTGAtcgcgaataaaagatct<br>ttattttcattagatctgtgtgttggttttttgtgtgTGCCAGTTCCCG<br>ATCGTTACAGGCAATTgccttaggccgcaggaacccctagtgatggagt<br>tggccactccctctctgcgcgctcgctcgctcactgaggccgggcgacc | |

-continued

| SEQ ID | Sequence | Description |
|---|---|---|
| | aaaggtcgcccgacgcccgggctttgcccgggcggcctcagtgagcgag<br>cgagcgcgcagctgcctgcagg | |
| 337 | SFSQNPPVLKRHQR | "SQ linker" |
| 338 | tgccagttcccgatcgttac | gRNA mALbT1 |
| 339 | usgscsCAGUUCCCGAUCGUUACGU-<br>UUUAGAgcuaGAAAuagcAAGUUAAAAUAAGGCUA-<br>GUCCGUUAUCaacuuGAAAaaguggcaccgagucggugcusususU<br>**("A, G, U, C" are native RNA nucleotides, "a, g, u, c" are 2'-O-methyl nucleotides, and "s" represents a phosphorothioate backbone)** | gRNA |
| 340 | GGAAATAAGAGAGAAAAGAAGAGTAAGAAGAAATATAAGAGCCACCATG<br>GCCCCAAAGAAGAAGCGGAAGGTCGGTATCCACGGAGTCCCAGCAGCCG<br>ACAAGAAGTACAGCATCGGCCTGGACATCGGCACCAACTCTGTGGGCTG<br>GGCCGTGATCACCGACGAGTACAAGGTGCCCAGCAAGAAATTCAAGGTG<br>CTGGGCAACACCGACCGGCACAGCATCAAGAAGAACCTGATCGGAGCCC<br>TGCTGTTCGACAGCGGCGAAACAGCCGAGGCCACCCGGCTGAAGAGAAC<br>CGCCAGAAGAAGATACACCAGACGGAAGAACCGGATCTGCTATCTGCAA<br>GAGATCTTCAGCAACGAGATGGCCAAGGTGGACGACAGCTTCTTCCACA<br>GACTGGAAGAGTCCTTCCTGGTGGAAGAGGACAAGAAGCACGAGAGACA<br>CCCCATCTTCGGCAACATCGTGGACGAGGTGGCCTACCACGAGAAGTAC<br>CCCACCATCTACCACCTGAGAAAGAAACTGGTGGACAGCACCGACAAGG<br>CCGACCTGAGACTGATCTACCTGGCCCTGGCCCACATGATCAAGTTCAG<br>AGGCCACTTCCTGATCGAGGGCGACCTGAACCCCGACAACAGCGACGTG<br>GACAAGCTGTTCATCCAGCTGGTGCAGACCTACAACCAGCTGTTCGAGG<br>AAAACCCCATCAACGCCAGCGGCGTGGACGCCAAGGCTATCCTGTCTGC<br>CAGACTGAGCAAGAGCAGAAGGCTGGAAAATCTGATCGCCCAGCTGCCC<br>GGCGAGAAGAAGAACGGCCTGTTCGGCAACCTGATTGCCCTGAGCCTGG<br>GCCTGACCCCCAACTTCAAGAGCAACTTCGACCTGGCCGAGGATGCCAA<br>ACTGCAGCTGAGCAAGGACACCTACGACGACGACCTGGACAACCTGCTG<br>GCCCAGATCGGCGACCAGTACGCCGACCTGTTCCTGGCCGCCAAGAACC<br>TGTCTGACGCCATCCTGCTGAGCGACATCCTGAGAGTGAACACCGAGAT<br>CACCAAGGCCCCCCTGAGCGCCTCTATGATCAAGAGATACGACGAGCAC<br>CACCAGGACCTGACCCTGCTGAAAGCTCTCGTGCGGCAGCAGCTGCCTG<br>AGAAGTACAAAGAAATCTTCTTCGACCAGAGCAAGAACGGCTACGCCGG<br>CTACATCGATGGCGGCGCTAGCCAGGAAGAGTTCTACAAGTTCATCAAG<br>CCCATCCTGGAAAAGATGGACGGCACCGAGGAACTGCTCGTGAAGCTGA<br>ACAGAGAGGACCTGCTGAGAAAGCAGAGAACCTTCGACAACGGCAGCAT<br>CCCCCACCAGATCCACCTGGGAGAGCTGCACGCTATCCTGAGAAGGCAG<br>GAAGATTTTTACCCATTCCTGAAGGACAACCGGGAAAAGATCGAGAAGA<br>TCCTGACCTTCAGGATCCCCTACTACGTGGGCCCCCTGGCCAGAGGCAA<br>CAGCAGATTCGCCTGGATGACCAGAAAGAGCGAGGAAACCATCACCCCC<br>TGGAACTTCGAGGAAGTGGTGGACAAGGGCGCCAGCGCCCAGAGCTTCA<br>TCGAGAGAATGACAAACTTCGATAAGAACCTGCCCAACGAGAAGGTGCT<br>GCCCAAGCACAGCCTGCTGTACGAGTACTTCACCGTGTACAACGAGCTG<br>ACCAAAGTGAAATACGTGACCGAGGGAATGAGAAAGCCCGCCTTCCTGA<br>GCGGCGAGCAGAAAAAGGCCATCGTGGACCTGCTGTTCAAGACCAACAG<br>AAAAGTGACCGTGAAGCAGCTGAAAGAGGACTACTTCAAGAAAATCGAG<br>TGCTTCGACTCCGTGGAAATCTCCGGCGTGGAAGATAGATTCAACGCCT<br>CCCTGGGCACATACCACGATCTGCTGAAAATTATCAAGGACAAGGACTT<br>CCTGGATAACGAAGAGAACGAGGACATTCTGGAAGATATCGTGCTGACC<br>CTGACACTGTTTGAGGACCGCGAGATGATCGAGGAAAGGCTGAAAACCT<br>ACGCTCACCTGTTCGACGACAAAGTGATGAAGCAGCTGAAGAGAAGGCG<br>GTACACCGGCTGGGGCAGGCTGAGCAGAAAGCTGATCAACGGCATCAGA<br>GACAAGCAGAGCGGCAAGACAATCCTGGATTTCCTGAAGTCCGACGGCT<br>TCGCCAACCGGAACTTCATGCAGCTGATCCACGACGACAGCCTGACATT<br>CAAAGAGGACATCCAGAAAGCCCAGGTGTCCGGCCAGGGCGACTCTCTG<br>CACGAGCATATCGCTAACCTGGCCGGCAGCCCCGCTATCAAGAAGGGCA<br>TCCTGCAGACAGTGAAGGTGGTGGACGAGCTCGTGAAAGTGATGGGCAG<br>ACACAAGCCCGAGAACATCGTGATCGAGATGGCTAGAGAGAACCAGACC<br>ACCCAGAAGGGACAGAAGAACTCCCGCGAGAGGATGAAGAGAATCGAAG<br>AGGGCATCAAAGAGCTGGGCAGCCAGATCCTGAAAGAACACCCCGTGGA<br>AAACACCCAGCTGCAGAACGAGAAGCTGTACCTGTACTACCTGCAGAAT<br>GGCCGGGATATGTACGTGGACCAGGAACTGGACATCAACAGACTGTCCG<br>ACTACGATGTGGACCATATCGTGCCTCAGAGCTTTCTGAAGGACGACTC<br>CATCGATAACAAAGTGCTGACTCGGAGCGACAAGAACAGAGGCAAGAGC<br>GACAACGTGCCCTCCGAAGAGGTCGTGAAGAAGATGAAGAACTACTGGC<br>GACAGCTGCTGAACGCCAAGCTGATTACCCAGAGGAAGTTCGATAACCT<br>GACCAAGGCCGAGAGAGGCGGCCTGAGCGAGCTGGATAAGGCCGGCTTC<br>ATCAAGAGGCAGCTGGTGGAAACCAGACAGATCACAAAGCACGTGGCAC<br>AGATCCTGGACTCCCGGATGAACACTAAGTACGACGAAAACGATAAGCT<br>GATCCGGGAAGTGAAAGTGATCACCCTGAAGTCCAAGCTGGTGTCCGAT<br>TTCCGGAAGGATTTCCAGTTTTACAAAGTGCGCGAGATCAACAACTACC<br>ACCACGCCCACGACGCCTACCTGAACGCCGTCGTGGGAACCGCCCTGAT | spCas9 mRNA with NLS sequences |

-continued

| SEQ ID | Sequence | Description |
|---|---|---|
| | CAAAAAGTACCCTAAGCTGGAAAGCGAGTTCGTGTACGGCGACTACAAG<br>GTGTACGACGTGCGGAAGATGATCGCCAAGAGCGAGCAGGAAATCGGCA<br>AGGCTACCGCCAAGTACTTCTTCTACAGCAACATCATGAACTTTTTCAA<br>GACCGAAATCACCCTGGCCAACGGCGAGATCAGAAAGCGCCCTCTGATC<br>GAGACAAACGGCGAAACCGGGGAGATCGTGTGGGATAAGGGCAGAGACT<br>TCGCCACAGTGCGAAAGGTGCTGAGCATGCCCCAAGTGAATATCGTGAA<br>AAAGACCGAGGTGCAGACAGGCGGCTTCAGCAAAGAGTCTATCCTGCCC<br>AAGAGGAACAGCGACAAGCTGATCGCCAGAAAGAAGGACTGGGACCCCA<br>AGAAGTACGGCGGCTTCGACAGCCCTACCGTGGCCTACTCTGTGCTGGT<br>GGTGGCTAAGGTGGAAAAGGGCAAGTCCAAGAAACTGAAGAGTGTGAAA<br>GAGCTGCTGGGGATCACCATCATGGAAAGAAGCAGCTTTGAGAAGAACC<br>CTATCGACTTTCTGGAAGCCAAGGGCTACAAAGAAGTGAAAAAGGACCT<br>GATCATCAAGCTGCCTAAGTACTCCCTGTTCGAGCTGGAAAACGGCAGA<br>AAGAGAATGCTGGCCTCTGCCGGCGAACTGCAGAAGGGAAACGAGCTGG<br>CCCTGCCTAGCAAATATGTGAACTTCCTGTACCTGGCCTCCCACTATGA<br>GAAGCTGAAGGGCAGCCCTGAGGACAACGAACAGAAACAGCTGTTTGTG<br>GAACAGCATAAGCACTACCTGGACGAGATCATCGAGCAGATCAGCGAGT<br>TCTCCAAGAGAGTGATCCTGGCCGACGCCAATCTGGACAAGGTGCTGTC<br>TGCCTACAACAAGCACAGGGACAAGCCTATCAGAGAGCAGGCCGAGAAT<br>ATCATCCACCTGTTCACCCTGACAAACCTGGGCGCTCCTGCCGCCTTCA<br>AGTACTTTGACACCACCATCGACCGGAAGAGGTACACCAGCACCAAAGA<br>GGTGCTGGACGCCACCCTGATCCACCAGAGCATCACCGGCCTGTACGAG<br>ACAAGAATCGACCTGTCTCAGCTGGGAGGCGACAAGAGACCTGCCGCCA<br>CTAAGAAGGCCGGACAGGCCAAAAAGAAGAAGTGAGCGGCCGCTTAATT<br>AAGCTGCCTTCTGCGGGGCTTGCCTTCTGGCCATGCCCTTCTTCTCTCC<br>CTTGCACCTGTACCTCTTGGTCTTTGAATAAAGCCTGAGTAGGAAGAAA<br>AAAAAAAAAAAAAAAAAAAAAAAAAAAAAAAAAAAAAAAAAAAAAAAAA<br>AAAAAAAAAAAAAAAAAAAAAAAAAAAA | |
| 341 | cctgcaggcagctgcgcgctcgctcgctcactgaggccgcccgggcaaa<br>gcccgggcgtcgggcgacctttggtcgcccggcctcagtgagcgagcga<br>gcgcgcagagagggagtggccaactccatcactaggggttcctgcggcc<br>cGCGGTGCCAGTTCCCGATCGTTACAGGCGGTACTCCTCAAAGCGTACT<br>AAAGAATTATTCTTTTACATTTCAGTGGCCACCAGGAGATACTACCTGG<br>GGGCTGTGGAGCTGAGCTGGGACTACATGCAGTCTGACCTGGGGGAGCT<br>GCCTGTGGATGCCAGGTTCCCCCCCAGAGTGCCCAAGAGCTTCCCCTTC<br>AACACCTCTGTGGTGTACAAGAAGACCCTGTTTGTGGAGTTCACTGACC<br>ACCTGTTCAACATTGCCAAGCCCAGGCCCCCCTGGATGGGCCTGCTGGG<br>CCCCACCATCCAGGCTGAGGTGTATGACACTGTGGTGATCACCCTGAAG<br>AACATGGCCAGCCACCCTGTGAGCCTGCATGCTGTGGGGGTGAGCTACT<br>GGAAGGCCTCTGAGGGGGCTGAGTATGATGACCAGACCAGCCAGAGGGA<br>GAAGGAGGATGACAAGGTGTTCCCTGGGGGCAGCCACACCTATGTGTGG<br>CAGGTGCTGAAGGAGAATGGCCCCATGGCCTCTGACCCCCTGTGCCTGA<br>CCTACAGCTACCTGAGCCATGTGGACCTGGTGAAGGACCTGAACTCTGG<br>CCTGATTGGGGCCCTGCTGGTGTGCAGGGAGGGCAGCCTGGCCAAGGAG<br>AAGACCCAGACCCTGCACAAGTTCATCCTGCTGTTTGCTGTGTTTGATG<br>AGGGCAAGAGCTGGCACTCTGAAACCAAGAACAGCCTGATGCAGGACAG<br>GGATGCTGCCTCTGCCAGGGCCTGGCCCAAGATGCACACTGTGAATGGC<br>TATGTGAACAGGAGCCTGCCTGGCCTGATTGGCTGCCACAGGAAGTCTG<br>TGTACTGGCATGTGATTGGCATGGGCACCACCCCTGAGGTGCACAGCAT<br>CTTCCTGGAGGGCCACACCTTCCTGGTCAGGAACCACAGGCAGGCCAGC<br>CTGGAGATCAGCCCCATCACCTTCCTGACTGCCCAGACCCTGCTGATGG<br>ACCTGGGCCAGTTCCTGCTGTTCTGCCACATCAGCAGCCACCAGCATGA<br>TGGCATGGAGGCCTATGTGAAGGTGGACAGCTGCCCTGAGGAGCCCCAG<br>CTGAGGATGAAGAACAATGAGGAGGCTGAGGACTATGATGATGACCTGA<br>CTGACTCTGAGATGGATGTGGTGAGGTTTGATGATGACAACAGCCCCAG<br>CTTCATCCAGATCAGGTCTGTGGCCAAGAAGCACCCCAAGACCTGGGTG<br>CACTACATTGCTGCTGAGGAGGAGGACTGGGACTATGCCCCCCTGGTGC<br>TGGCCCCTGATGACAGGAGCTACAAGAGCCAGTACCTGAACAATGGCCC<br>CCAGAGGATTGGCAGGAAGTACAAGAAGGTCAGGTTCATGGCCTACACT<br>GATGAAACCTTCAAGACCAGGGAGGCCATCCAGCATGAGTCTGGCATCC<br>TGGGCCCCCTGCTGTATGGGGAGGTGGGGGACACCCTGCTGATCATCTT<br>CAAGAACCAGGCCAGCAGGCCCTACAACATCTACCCCCATGGCATCACT<br>GATGTGAGGCCCCTGTACAGCAGGAGGCTGCCCAAGGGGGTGAAGCACC<br>TGAAGGACTTCCCCATCCTGCCTGGGGAGATCTTCAAGTACAAGTGGAC<br>TGTGACTGTGGAGGATGGCCCCACCAAGTCTGACCCCAGGTGCCTGACC<br>AGATACTACAGCAGCTTTGTGAACATGGAGAGGGACCTGGCCTCTGGCC<br>TGATTGGCCCCCTGCTGATCTGCTACAAGGAGTCTGTGGACCAGAGGGG<br>CAACCAGATCATGTCTGACAAGAGGAATGTGATCCTGTTCTCTGTGTTT<br>GATGAGAACAGGAGCTGGTACCTGACTGAGAACATCCAGAGGTTCCTGC<br>CCAACCCTGCTGGGGTGCAGCTGGAGGACCCTGAGTTCCAGGCCAGCAA<br>CATCATGCACAGCATCAATGGCTATGTGTTTGACAGCCTGCAGCTGTCT<br>GTGTGCCTGCATGAGGTGGCCTACTGGTACATCCTGAGCATTGGGGCCC<br>AGACTGACTTCCTGTCTGTGTTCTTCTCTGGCTACACCTTCAAGCACAA<br>GATGGTGTATGAGGACACCCTGACCCTGTTCCCCTTCTCTGGGGAGACT<br>GTGTTCATGAGCATGGAGAACCCTGGCCTGTGGATTCTGGGCTGCCACA<br>ACTCTGACTTCAGGAACAGGGGCATGACTGCCCTGCTGAAAGTCTCCAG | pCB102 |

-continued

| SEQ ID | Sequence | Description |
|---|---|---|
| | CTGTGACAAGAACACTGGGGACTACTATGAGGACAGCTATGAGGACATC<br>TCTGCCTACCTGCTGAGCAAGAACAATGCCATTGAGCCCAGGAGCTTCA<br>GCCAGAATCCCCCAGTGCTGAAGAGGCACCAGAGGGAGATCACCAGGAC<br>CACCCTGCAGTCTGACCAGGAGGAGATTGACTATGATGACACCATCTCT<br>GTGGAGATGAAGAAGGAGGACTTTGACATCTACGACGAGGACGAGAACC<br>AGAGCCCCAGGAGCTTCCAGAAGAAGACCAGGCACTACTTCATTGCTGC<br>TGTGGAGAGGCTGTGGGACTATGGCATGAGCAGCAGCCCCCATGTGCTG<br>AGGAACAGGGCCCAGTCTGGCTCTGTGCCCCAGTTCAAGAAGGTGGTGT<br>TCCAGGAGTTCACTGATGGCAGCTTCACCCAGCCCCTGTACAGAGGGGA<br>GCTGAATGAGCACCTGGGCCTGCTGGGCCCCTACATCAGGGCTGAGGTG<br>GAGGACAACATCATGGTGACCTTCAGGAACCAGGCCAGCAGGCCCTACA<br>GCTTCTACAGCAGCCTGATCAGCTATGAGGAGGACCAGAGGCAGGGGGC<br>TGAGCCCAGGAAGAACTTTGTGAAGCCCAATGAAACCAAGACCTACTTC<br>TGGAAGGTGCAGCACCACATGGCCCCCACCAAGGATGAGTTTGACTGCA<br>AGGCCTGGGCCTACTTCTCTGATGTGGACCTGGAGAAGGATGTGCACTC<br>TGGCCTGATTGGCCCCCTGCTGGTGTGCCACACCAACACCCTGAACCCT<br>GCCCATGGCAGGCAGGTGACTGTGCAGGAGTTTGCCCTGTTCTTCACCA<br>TCTTTGATGAAACCAAGAGCTGGTACTTCACTGAGAACATGGAGAGGAA<br>CTGCAGGGCCCCCTGCAACATCCAGATGGAGGACCCCACCTTCAAGGAG<br>AACTACAGGTTCCATGCCATCAATGGCTACATCATGGACACCCTGCCTG<br>GCCTGGTGATGGCCCAGGACCAGAGGATCAGGTGGTACCTGCTGAGCAT<br>GGGCAGCAATGAGAACATCCACAGCATCCACTTCTCTGGCCATGTGTTC<br>ACTGTGAGGAAGAAGGAGGAGTACAAGATGGCCCTGTACAACCTGTACC<br>CTGGGGTGTTTGAGACTGTGGAGATGCTGCCCAGCAAGGCTGGCATCTG<br>GAGGGTGGAGTGCCTGATTGGGGAGCACCTGCATGCTGGCATGAGCACC<br>CTGTTCCTGGTGTACAGCAACAAGTGCCAGACCCCCCTGGGCATGGCCT<br>CTGGCCACATCAGGGACTTCCAGATCACTGCCTCTGGCCAGTATGGCCA<br>GTGGGCCCCCAAGCTGGCCAGGCTGCACTACTCTGGCAGCATCAATGCC<br>TGGAGCACCAAGGAGCCCTTCAGCTGGATCAAGGTGGACCTGCTGGCCC<br>CCATGATCATCCATGGCATCAAGACCCAGGGGGCCAGGCAGAAGTTCAG<br>CAGCCTGTACATCAGCCAGTTCATCATCATGTACAGCCTGGATGGCAAG<br>AAGTGGCAGACCTACAGGGGCAACAGCACTGGCACCCTGATGGTGTTCT<br>TTGGCAATGTGGACAGCTCTGGCATCAAGCACAACATCTTCAACCCCCC<br>CATCATTGCCAGATACATCAGGCTGCACCCCACCCACTACAGCATCAGG<br>AGCACCCTGAGGATGGAGCTGATGGGCTGTGACCTGAACAGCTGCAGCA<br>TGCCCCTGGGCATGGAGAGCAAGGCCATCTCTGATGCCCAGATCACTGC<br>CAGCAGCTACTTCACCAACATGTTTGCCACCTGGAGCCCCAGCAAGGCC<br>AGGCTGCACCTGCAGGGCAGGAGCAATGCCTGGAGGCCCCAGGTCAACA<br>ACCCCAAGGAGTGGCTGCAGGTGGACTTCCAGAAGACCATGAAGGTGAC<br>TGGGGTGACCACCCAGGGGGTGAAGAGCCTGCTGACCAGCATGTATGTG<br>AAGGAGTTCCTGATCAGCAGCAGCCAGGATGGCCACCAGTGGACCCTGT<br>TCTTCCAGAATGGCAAGGTGAAGGTGTTCCAGGGCAACCAGGACAGCTT<br>CACCCCTGTGGTGAACAGCCTGGACCCCCCCCTGCTGACCAGATACCTG<br>AGGATTCACCCCCAGAGCTGGGTGCACCAGATTGCCCTGAGGATGGAGG<br>TGCTGGGCTGTGAGGCCCAGGACCTGTACTGAtcgcgaataaaagatct<br>ttattttcattagatctgtgtgttggttttttgtgtgGATCTGCCAGTT<br>CCCGATCGTTACAGGCAATTgccttaggccgcaggaacccctagtgatg<br>gagttggccactccctctctgcgcgctcgctcgctcactgaggccgggc<br>gaccaaaggtcgcccgacgcccgggctttgcccgggcggcctcagtgag<br>cgagcgagcgcgcagctgcctgcagg | |
| 342 | FNATTIQNVSSNNSLSDNTSSNDSKNVSSP | modified B domain linker |
| 343 | ATNVSNNSNTSNDS | B domain substitute |
| 344 | ggctgtgtctggct | Terminal portion of sequence encoding signal peptide from Transferrin Exon 2 |
| 345 | SFSQN**ATNVSNNSNTSNDSNVS**PPVLKRHQR | Variant FVIII B domain |
| 346 | CTGGAGTTTCTGACACATTCT | FGA2(DD) forward primer, mouse FGA intron |
| 347 | GTGAACTCCACAAACAGGGT | RSA56.R reverse primer |
| 348 | AGTGAACTCCACAAACAGGG | TFR1(DD) reverse primer |
| 349 | CCACAGCCCCCAGGTAGTAT | FGAP2(DD) donor probe |

-continued

| SEQ ID | Sequence | Description |
|---|---|---|
| 350 | GTTGCTGGGGATTGATCCAG | FGARefF2 (DD) forward primer |
| 351 | GTTCTCAACCTGTGGGTCAC | FGARefR2 (DD) reverse primer |
| 352 | TGTTGTGATGACCCGCAACT | FGARefP2 (DD) probe |
| 353 | CCCTCCGTTTGTCCTAGCTTTTC | AlbF forward primer |
| 354 | CCAGATACAGAATATCTTCCTCAACGCAGA | AlbR reverse primer |
| 355 | CCTTTGGCACAATGAAGTGG | forward primer |
| 356 | GAATCTGAACCCTGATGACAAG | reverse primer |
| 357 | TAAAGCATAGTGCAATGGATAGG | T4 |
| 358 | ATTTATGAGATCAACAGCACAGG | T5 |
| 359 | TTAAATAAAGCATAGTGCAATGG | T11 |
| 360 | TAATAAAATTCAAACATCCTAGG | T13 |
| 361 | **cctgcaggcagctgcgcgctcgctcgctcactgaggccgcccgggcaaa**<br>**gcccgggcgtcgggcgacctttggtcgcccggcctcagtgagcgagcga**<br>**gcgcgcagagagggagtggccaactccatcactaggggttcct**gcggcc<br>cGCGGcctgggtaactaattaggatgtcCGGTACTCCTCAAAGCGTACT<br>AAAGAATTATTCTTTTACATTTCAGACCGCCACCAGGAGATACTACCTG<br>GGGGCTGTGGAGCTGAGCTGGGACTACATGCAGTCTGACCTGGGGGAGC<br>TGCCTGTGGATGCCAGGTTCCCCCCCAGAGTGCCCAAGAGCTTCCCCTT<br>CAACACCTCTGTGGTGTACAAGAAGACCCTGTTTGTGGAGTTCACTGAC<br>CACCTGTTCAACATTGCCAAGCCCAGGCCCCCCTGGATGGGCCTGCTGG<br>GCCCCACCATCCAGGCTGAGGTGTATGACACTGTGGTGATCACCCTGAA<br>GAACATGGCCAGCCACCCTGTGAGCCTGCATGCTGTGGGGGTGAGCTAC<br>TGGAAGGCCTCTGAGGGGGCTGAGTATGATGACCAGACCAGCCAGAGGG<br>AGAAGGAGGATGACAAGGTGTTCCCTGGGGGCAGCCACACCTATGTGTG<br>GCAGGTGCTGAAGGAGAATGGCCCCATGGCCTCTGACCCCCTGTGCCTG<br>ACCTACAGCTACCTGAGCCATGTGGACCTGGTGAAGGACCTGAACTCTG<br>GCCTGATTGGGGCCCTGCTGGTGTGCAGGGAGGGCAGCCTGGCCAAGGA<br>GAAGACCCAGACCCTGCACAAGTTCATCCTGCTGTTTGCTGTGTTTGAT<br>GAGGGCAAGAGCTGGCACTCTGAAACCAAGAACAGCCTGATGCAGGACA<br>GGGATGCTGCCTCTGCCAGGGCCTGGCCCAAGATGCACACTGTGAATGG<br>CTATGTGAACAGGAGCCTGCCTGGCCTGATTGGCTGCCACAGGAAGTCT<br>GTGTACTGGCATGTGATTGGCATGGGCACCACCCCTGAGGTGCACAGCA<br>TCTTCCTGGAGGGCCACACCTTCCTGGTCAGGAACCACAGGCAGGCCAG<br>CCTGGAGATCAGCCCCATCACCTTCCTGACTGCCCAGACCCTGCTGATG<br>GACCTGGGCCAGTTCCTGCTGTTCTGCCACATCAGCAGCCACCAGCATG<br>ATGGCATGGAGGCCTATGTGAAGGTGGACAGCTGCCCTGAGGAGCCCCA<br>GCTGAGGATGAAGAACAATGAGGAGGCTGAGGACTATGATGATGACCTG<br>ACTGACTCTGAGATGGATGTGGTGAGGTTTGATGATGACAACAGCCCCA<br>GCTTCATCCAGATCAGGTCTGTGGCCAAGAAGCACCCCAAGACCTGGGT<br>GCACTACATTGCTGCTGAGGAGGAGGACTGGGACTATGCCCCCCTGGTG<br>CTGGCCCCTGATGACAGGAGCTACAAGAGCCAGTACCTGAACAATGGCC<br>CCCAGAGGATTGGCAGGAAGTACAAGAAGGTCAGGTTCATGGCCTACAC<br>TGATGAAACCTTCAAGACCAGGGAGGCCATCCAGCATGAGTCTGGCATC<br>CTGGGCCCCCTGCTGTATGGGGAGGTGGGGGACACCCTGCTGATCATCT<br>TCAAGAACCAGGCCAGCAGGCCCTACAACATCTACCCCCATGGCATCAC<br>TGATGTGAGGCCCCTGTACAGCAGGAGGCTGCCCAAGGGGGTGAAGCAC<br>CTGAAGGACTTCCCCATCCTGCCTGGGGAGATCTTCAAGTACAAGTGGA<br>CTGTGACTGTGGAGGATGGCCCCACCAAGTCTGACCCCAGGTGCCTGAC<br>CAGATACTACAGCAGCTTTGTGAACATGGAGAGGGACCTGGCCTCTGGC<br>CTGATTGGCCCCCTGCTGATCTGCTACAAGGAGTCTGTGGACCAGAGGG<br>GCAACCAGATCATGTCTGACAAGAGGAATGTGATCCTGTTCTCTGTGTT<br>TGATGAGAACAGGAGCTGGTACCTGACTGAGAACATCCAGAGGTTCCTG<br>CCCAACCCTGCTGGGGTGCAGCTGGAGGACCCTGAGTTCCAGGCCAGCA<br>ACATCATGCACAGCATCAATGGCTATGTGTTTGACAGCCTGCAGCTGTC<br>TGTGTGCCTGCATGAGGTGGCCTACTGGTACATCCTGAGCATTGGGGCC<br>CAGACTGACTTCCTGTCTGTGTTCTTCTCTGGCTACACCTTCAAGCACA<br>AGATGGTGTATGAGGACACCCTGACCCTGTTCCCCTTCTCTGGGGAGAC<br>TGTGTTCATGAGCATGGAGAACCCTGGCCTGTGGATTCTGGGCTGCCAC<br>AACTCTGACTTCAGGAACAGGGGCATGACTGCCCTGCTGAAAGTCTCCA<br>GCTGTGACAAGAACACTGGGGACTACTATGAGGACAGCTATGAGGACAT<br>CTCTGCCTACCTGCTGAGCAAGAACAATGCCATTGAGCCCAGGAGCTTC<br>AGCCAGAATGCCACTAATGTGTCTAACAACAGCAACACCAGCAATGACA<br>GCAATGTGTCTCCCCCAGTGCTGAAGAGGCACCAGAGGGAGATCACCAG | AAV8-pCB1010 |

-continued

| SEQ ID | Sequence | Description |
|---|---|---|
| | GACCACCCTGCAGTCTGACCAGGAGGAGATTGACTATGATGACACCATC<br>TCTGTGGAGATGAAGAAGGAGGACTTTGACATCTACGACGAGGACGAGA<br>ACCAGAGCCCCAGGAGCTTCCAGAAGAAGACCAGGCACTACTTCATTGC<br>TGCTGTGGAGAGGCTGTGGGACTATGGCATGAGCAGCAGCCCCCATGTG<br>CTGAGGAACAGGGCCCAGTCTGGCTCTGTGCCCCAGTTCAAGAAGGTGG<br>TGTTCCAGGAGTTCACTGATGGCAGCTTCACCCAGCCCCTGTACAGAGG<br>GGAGCTGAATGAGCACCTGGGCCTGCTGGGCCCCTACATCAGGGCTGAG<br>GTGGAGGACAACATCATGGTGACCTTCAGGAACCAGGCCAGCAGGCCCT<br>ACAGCTTCTACAGCAGCCTGATCAGCTATGAGGAGGACCAGAGGCAGGG<br>GGCTGAGCCCAGGAAGAACTTTGTGAAGCCCAATGAAACCAAGACCTAC<br>TTCTGGAAGGTGCAGCACCACATGGCCCCCACCAAGGATGAGTTTGACT<br>GCAAGGCCTGGGCCTACTTCTCTGATGTGGACCTGGAGAAGGATGTGCA<br>CTCTGGCCTGATTGGCCCCCTGCTGGTGTGCCACACCAACACCCTGAAC<br>CCTGCCCATGGCAGGCAGGTGACTGTGCAGGAGTTTGCCCTGTTCTTCA<br>CCATCTTTGATGAAACCAAGAGCTGGTACTTCACTGAGAACATGGAGAG<br>GAACTGCAGGGCCCCCTGCAACATCCAGATGGAGGACCCCACCTTCAAG<br>GAGAACTACAGGTTCCATGCCATCAATGGCTACATCATGGACACCCTGC<br>CTGGCCTGGTGATGGCCCAGGACCAGAGGATCAGGTGGTACCTGCTGAG<br>CATGGGCAGCAATGAGAACATCCACAGCATCCACTTCTCTGGCCATGTG<br>TTCACTGTGAGGAAGAAGGAGGAGTACAAGATGGCCCTGTACAACCTGT<br>ACCCTGGGGTGTTTGAGACTGTGGAGATGCTGCCCAGCAAGGCTGGCAT<br>CTGGAGGGTGGAGTGCCTGATTGGGGAGCACCTGCATGCTGGCATGAGC<br>ACCCTGTTCCTGGTGTACAGCAACAAGTGCCAGACCCCCCTGGGCATGG<br>CCTCTGGCCACATCAGGGACTTCCAGATCACTGCCTCTGGCCAGTATGG<br>CCAGTGGGCCCCCAAGCTGGCCAGGCTGCACTACTCTGGCAGCATCAAT<br>GCCTGGAGCACCAAGGAGCCCTTCAGCTGGATCAAGGTGGACCTGCTGG<br>CCCCCATGATCATCCATGGCATCAAGACCCAGGGGGCCAGGCAGAAGTT<br>CAGCAGCCTGTACATCAGCCAGTTCATCATCATGTACAGCCTGGATGGC<br>AAGAAGTGGCAGACCTACAGGGGCAACAGCACTGGCACCCTGATGGTGT<br>TCTTTGGCAATGTGGACAGCTCTGGCATCAAGCACAACATCTTCAACCC<br>CCCCATCATTGCCAGATACATCAGGCTGCACCCCACCCACTACAGCATC<br>AGGAGCACCCTGAGGATGGAGCTGATGGGCTGTGACCTGAACAGCTGCA<br>GCATGCCCCTGGGCATGGAGAGCAAGGCCATCTCTGATGCCCAGATCAC<br>TGCCAGCAGCTACTTCACCAACATGTTTGCCACCTGGAGCCCCAGCAAG<br>GCCAGGCTGCACCTGCAGGGCAGGAGCAATGCCTGGAGGCCCCAGGTCA<br>ACAACCCCAAGGAGTGGCTGCAGGTGGACTTCCAGAAGACCATGAAGGT<br>GACTGGGGTGACCACCCAGGGGGTGAAGAGCCTGCTGACCAGCATGTAT<br>GTGAAGGAGTTCCTGATCAGCAGCAGCCAGGATGGCCACCAGTGGACCC<br>TGTTCTTCCAGAATGGCAAGGTGAAGGTGTTCCAGGGCAACCAGGACAG<br>CTTCACCCCTGTGGTGAACAGCCTGGACCCCCCCCTGCTGACCAGATAC<br>CTGAGGATTCACCCCCAGAGCTGGGTGCACCAGATTGCCCTGAGGATGG<br>AGGTGCTGGGCTGTGAGGCCCAGGACCTGTACTGAtcgcgaataaaaga<br>tctttattttcattagatctgtgtgttggttttttgtgtgcctgggtaa<br>ctaattaggatgtcCAATTgccttaggccgc**aggaacccctagtgatgg**<br>**agttggccactccctctctgcgcgctcgctcgctcactgaggccgggcg**<br>**accaaaggtcgcccgacgcccgggctttgcccgggcggcctcagtgagc**<br>**gagcgagcgcgcagctgcctgcagg** | |
| 362 | SFSQNATNVSNNSPPVLKRHQR | 3 glycan B domain substitute |
| 363 | SFSQNATNVSNNSNTSPPVLKRHQR | 4 glycan B domain substitute |
| 364 | SFSQNATNVSNNSNTSNDSPPVLKRHQR | 5 glycan B domain substitute |
| 365 | SFSQNATNVSNNSNTSNDSNVSPPVLKRHQR | 6 glycan B domain substitute |
| 366 | SFSQNATNVSNNSNTSNDSNVTPPVLKRHQR | 6 glycan B domain substitute (S->T) |
| 367 | SFSQNATNVSNNSNTSNDSNVSNKTPPVLKRHQR | 7 glycan B domain substitute |
| 368 | SFSQNATNVSNNSNTSNDSNVSNKTNNSPPVLKRHQR | 8 glycan B domain substitute |
| 369 | SFSQNATNVSNNSNTSNDSNVSNKTNNSNATPPVLKRHQR | 9 glycan B domain substitute |
| 370 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG | pCB1030 |

-continued

| SEQ ID | Sequence | Description |
|---|---|---|
| | TTCAACATTGCCAAGCCCAGGCCCCCCTGGATGGGCCTGCTGGGCCCCA | |
| | CCATCCAGGCTGAGGTGTATGACACTGTGGTGATCACCCTGAAGAACAT | |
| | GGCCAGCCACCCTGTGAGCCTGCATGCTGTGGGGGTGAGCTACTGGAAG | |
| | GCCTCTGAGGGGGCTGAGTATGATGACCAGACCAGCCAGAGGGAGAAGG | |
| | AGGATGACAAGGTGTTCCCTGGGGGCAGCCACACCTATGTGTGGCAGGT | |
| | GCTGAAGGAGAATGGCCCCATGGCCTCTGACCCCCTGTGCCTGACCTAC | |
| | AGCTACCTGAGCCATGTGGACCTGGTGAAGGACCTGAACTCTGGCCTGA | |
| | TTGGGGCCCTGCTGGTGTGCAGGGAGGGCAGCCTGGCCAAGGAGAAGAC | |
| | CCAGACCCTGCACAAGTTCATCCTGCTGTTTGCTGTGTTTGATGAGGGC | |
| | AAGAGCTGGCACTCTGAAACCAAGAACAGCCTGATGCAGGACAGGGATG | |
| | CTGCCTCTGCCAGGGCCTGGCCCAAGATGCACACTGTGAATGGCTATGT | |
| | GAACAGGAGCCTGCCTGGCCTGATTGGCTGCCACAGGAAGTCTGTGTAC | |
| | TGGCATGTGATTGGCATGGGCACCACCCCTGAGGTGCACAGCATCTTCC | |
| | TGGAGGGCCACACCTTCCTGGTCAGGAACCACAGGCAGGCCAGCCTGGA | |
| | GATCAGCCCCATCACCTTCCTGACTGCCCAGACCCTGCTGATGGACCTG | |
| | GGCCAGTTCCTGCTGTTCTGCCACATCAGCAGCCACCAGCATGATGGCA | |
| | TGGAGGCCTATGTGAAGGTGGACAGCTGCCCTGAGGAGCCCCAGCTGAG | |
| | GATGAAGAACAATGAGGAGGCTGAGGACTATGATGATGACCTGACTGAC | |
| | TCTGAGATGGATGTGGTGAGGTTTGATGATGACAACAGCCCCAGCTTCA | |
| | TCCAGATCAGGTCTGTGGCCAAGAAGCACCCCAAGACCTGGGTGCACTA | |
| | CATTGCTGCTGAGGAGGAGGACTGGGACTATGCCCCCCTGGTGCTGGCC | |
| | CCTGATGACAGGAGCTACAAGAGCCAGTACCTGAACAATGGCCCCCAGA | |
| | GGATTGGCAGGAAGTACAAGAAGGTCAGGTTCATGGCCTACACTGATGA | |
| | AACCTTCAAGACCAGGGAGGCCATCCAGCATGAGTCTGGCATCCTGGGC | |
| | CCCCTGCTGTATGGGGAGGTGGGGGACACCCTGCTGATCATCTTCAAGA | |
| | ACCAGGCCAGCAGGCCCTACAACATCTACCCCCATGGCATCACTGATGT | |
| | GAGGCCCCTGTACAGCAGGAGGCTGCCCAAGGGGGTGAAGCACCTGAAG | |
| | GACTTCCCCATCCTGCCTGGGGAGATCTTCAAGTACAAGTGGACTGTGA | |
| | CTGTGGAGGATGGCCCCACCAAGTCTGACCCCAGGTGCCTGACCAGATA | |
| | CTACAGCAGCTTTGTGAACATGGAGAGGGACCTGGCCTCTGGCCTGATT | |
| | GGCCCCCTGCTGATCTGCTACAAGGAGTCTGTGGACCAGAGGGGCAACC | |
| | AGATCATGTCTGACAAGAGGAATGTGATCCTGTTCTCTGTGTTTGATGA | |
| | GAACAGGAGCTGGTACCTGACTGAGAACATCCAGAGGTTCCTGCCCAAC | |
| | CCTGCTGGGGTGCAGCTGGAGGACCCTGAGTTCCAGGCCAGCAACATCA | |
| | TGCACAGCATCAATGGCTATGTGTTTGACAGCCTGCAGCTGTCTGTGTG | |
| | CCTGCATGAGGTGGCCTACTGGTACATCCTGAGCATTGGGGCCCAGACT | |
| | GACTTCCTGTCTGTGTTCTTCTCTGGCTACACCTTCAAGCACAAGATGG | |
| | TGTATGAGGACACCCTGACCCTGTTCCCCTTCTCTGGGGAGACTGTGTT | |
| | CATGAGCATGGAGAACCCTGGCCTGTGGATTCTGGGCTGCCACAACTCT | |
| | GACTTCAGGAACAGGGGCATGACTGCCCTGCTGAAAGTCTCCAGCTGTG | |
| | ACAAGAACACTGGGGACTACTATGAGGACAGCTATGAGGACATCTCTGC | |
| | CTACCTGCTGAGCAAGAACAATGCCATTGAGCCCAGGAGCTTCAGCCAG | |
| | AATGCCACTCCCCCAGTGCTGAAGAGGCACCAGAGGGAGATCACCAGGA | |
| | CCACCCTGCAGTCTGACCAGGAGGAGATTGACTATGATGACACCATCTC | |
| | TGTGGAGATGAAGAAGGAGGACTTTGACATCTACGACGAGGACGAGAAC | |
| | CAGAGCCCCAGGAGCTTCCAGAAGAAGACCAGGCACTACTTCATTGCTG | |
| | CTGTGGAGAGGCTGTGGGACTATGGCATGAGCAGCAGCCCCCATGTGCT | |
| | GAGGAACAGGGCCCAGTCTGGCTCTGTGCCCCAGTTCAAGAAGGTGGTG | |
| | TTCCAGGAGTTCACTGATGGCAGCTTCACCCAGCCCCTGTACAGAGGGG | |
| | AGCTGAATGAGCACCTGGGCCTGCTGGGCCCCTACATCAGGGCTGAGGT | |
| | GGAGGACAACATCATGGTGACCTTCAGGAACCAGGCCAGCAGGCCCTAC | |
| | AGCTTCTACAGCAGCCTGATCAGCTATGAGGAGGACCAGAGGCAGGGGG | |
| | CTGAGCCCAGGAAGAACTTTGTGAAGCCCAATGAAACCAAGACCTACTT | |
| | CTGGAAGGTGCAGCACCACATGGCCCCCACCAAGGATGAGTTTGACTGC | |
| | AAGGCCTGGGCCTACTTCTCTGATGTGGACCTGGAGAAGGATGTGCACT | |
| | CTGGCCTGATTGGCCCCCTGCTGGTGTGCCACACCAACACCCTGAACCC | |
| | TGCCCATGGCAGGCAGGTGACTGTGCAGGAGTTTGCCCTGTTCTTCACC | |
| | ATCTTTGATGAAACCAAGAGCTGGTACTTCACTGAGAACATGGAGAGGA | |
| | ACTGCAGGGCCCCCTGCAACATCCAGATGGAGGACCCCACCTTCAAGGA | |
| | GAACTACAGGTTCCATGCCATCAATGGCTACATCATGGACACCCTGCCT | |
| | GGCCTGGTGATGGCCCAGGACCAGAGGATCAGGTGGTACCTGCTGAGCA | |
| | TGGGCAGCAATGAGAACATCCACAGCATCCACTTCTCTGGCCATGTGTT | |
| | CACTGTGAGGAAGAAGGAGGAGTACAAGATGGCCCTGTACAACCTGTAC | |
| | CCTGGGGTGTTTGAGACTGTGGAGATGCTGCCCAGCAAGGCTGGCATCT | |
| | GGAGGGTGGAGTGCCTGATTGGGGAGCACCTGCATGCTGGCATGAGCAC | |
| | CCTGTTCCTGGTGTACAGCAACAAGTGCCAGACCCCCCTGGGCATGGCC | |
| | TCTGGCCACATCAGGGACTTCCAGATCACTGCCTCTGGCCAGTATGGCC | |
| | AGTGGGCCCCCAAGCTGGCCAGGCTGCACTACTCTGGCAGCATCAATGC | |
| | CTGGAGCACCAAGGAGCCCTTCAGCTGGATCAAGGTGGACCTGCTGGCC | |
| | CCCATGATCATCCATGGCATCAAGACCCAGGGGGCCAGGCAGAAGTTCA | |
| | GCAGCCTGTACATCAGCCAGTTCATCATCATGTACAGCCTGGATGGCAA | |
| | GAAGTGGCAGACCTACAGGGGCAACAGCACTGGCACCCTGATGGTGTTC | |
| | TTTGGCAATGTGGACAGCTCTGGCATCAAGCACAACATCTTCAACCCCC | |
| | CCATCATTGCCAGATACATCAGGCTGCACCCCACCCACTACAGCATCAG | |
| | GAGCACCCTGAGGATGGAGCTGATGGGCTGTGACCTGAACAGCTGCAGC | |
| | ATGCCCCTGGGCATGGAGAGCAAGGCCATCTCTGATGCCCAGATCACTG | |
| | CCAGCAGCTACTTCACCAACATGTTTGCCACCTGGAGCCCCAGCAAGGC | |

-continued

| SEQ ID | Sequence | Description |
|---|---|---|
| | CAGGCTGCACCTGCAGGGCAGGAGCAATGCCTGGAGGCCCCAGGTCAAC<br>AACCCCAAGGAGTGGCTGCAGGTGGACTTCCAGAAGACCATGAAGGTGA<br>CTGGGGTGACCACCCAGGGGGTGAAGAGCCTGCTGACCAGCATGTATGT<br>GAAGGAGTTCCTGATCAGCAGCAGCCAGGATGGCCACCAGTGGACCCTG<br>TTCTTCCAGAATGGCAAGGTGAAGGTGTTCCAGGGCAACCAGGACAGCT<br>TCACCCCTGTGGTGAACAGCCTGGACCCCCCCCTGCTGACCAGATACCT<br>GAGGATTCACCCCCAGAGCTGGGTGCACCAGATTGCCCTGAGGATGGAG<br>GTGCTGGGCTGTGAGGCCCAGGACCTGTACTGAtcgcgaataaaagatc<br>tttattttcattagatctgtgtgttggttttttgtgtg | |
| 371 | SFSQNATPPVLKRHQR | 1-glycan B domain substitute |
| 372 | TGCCAGTTCCCGATCGTTACAGGCGGTACTCCTCAAAGCGTACTAAAGA<br>ATTATTCTTTTACATTTCAGTGGCCACCAGGAGATACTACCTGGGGGCT<br>GTGGAGCTGAGCTGGGACTACATGCAGTCTGACCTGGGGGAGCTGCCTG<br>TGGATGCCAGGTTCCCCCCCAGAGTGCCCAAGAGCTTCCCCTTCAACAC<br>CTCTGTGGTGTACAAGAAGACCCTGTTTGTGGAGTTCACTGACCACCTG<br>TTCAACATTGCCAAGCCCAGGCCCCCCTGGATGGGCCTGCTGGGCCCCA<br>CCATCCAGGCTGAGGTGTATGACACTGTGGTGATCACCCTGAAGAACAT<br>GGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGG<br>AGGATGACAAGGTGTTCCCTGGGGGCAGCCACACCTATGTGTGGCAGGT<br>GCTGAAGGAGAATGGCCCCATGGCCTCTGACCCCCTGTGCCTGACCTAC<br>AGCTACCTGAGCCATGTGGACCTGGTGAAGGACCTGAACTCTGGCCTGA<br>TTGGGGCCCTGCTGGTGTGCAGGGAGGGCAGCCTGGCCAAGGAGAAGAC<br>CCAGACCCTGCACAAGTTCATCCTGCTGTTTGCTGTGTTTGATGAGGGC<br>AAGAGCTGGCACTCTGAAACCAAGAACAGCCTGATGCAGGACAGGGATG<br>CTGCCTCTGCCAGGGCCTGGCCCAAGATGCACACTGTGAATGGCTATGT<br>GAACAGGAGCCTGCCTGGCCTGATTGGCTGCCACAGGAAGTCTGTGTAC<br>TGGCATGTGATTGGCATGGGCACCACCCCTGAGGTGCACAGCATCTTCC<br>TGGAGGGCCACACCTTCCTGGTCAGGAACCACAGGCAGGCCAGCCTGGA<br>GATCAGCCCCATCACCTTCCTGACTGCCCAGACCCTGCTGATGGACCTG<br>GGCCAGTTCCTGCTGTTCTGCCACATCAGCAGCCACCAGCATGATGGCA<br>TGGAGGCCTATGTGAAGGTGGACAGCTGCCCTGAGGAGCCCCAGCTGAG<br>GATGAAGAACAATGAGGAGGCTGAGGACTATGATGATGACCTGACTGAC<br>TCTGAGATGGATGTGGTGAGGTTTGATGATGACAACAGCCCCAGCTTCA<br>TCCAGATCAGGTCTGTGGCCAAGAAGCACCCCAAGACCTGGGTGCACTA<br>CATTGCTGCTGAGGAGGAGGACTGGGACTATGCCCCCCTGGTGCTGGCC<br>CCTGATGACAGGAGCTACAAGAGCCAGTACCTGAACAATGGCCCCCAGA<br>GGATTGGCAGGAAGTACAAGAAGGTCAGGTTCATGGCCTACACTGATGA<br>AACCTTCAAGACCAGGGAGGCCATCCAGCATGAGTCTGGCATCCTGGGC<br>CCCCTGCTGTATGGGGAGGTGGGGGACACCCTGCTGATCATCTTCAAGA<br>ACCAGGCCAGCAGGCCCTACAACATCTACCCCCATGGCATCACTGATGT<br>GAGGCCCCTGTACAGCAGGAGGCTGCCCAAGGGGGTGAAGCACCTGAAG<br>GACTTCCCCATCCTGCCTGGGGAGATCTTCAAGTACAAGTGGACTGTGA<br>CTGTGGAGGATGGCCCCACCAAGTCTGACCCCAGGTGCCTGACCAGATA<br>CTACAGCAGCTTTGTGAACATGGAGAGGGACCTGGCCTCTGGCCTGATT<br>GGCCCCCTGCTGATCTGCTACAAGGAGTCTGTGGACCAGAGGGGCAACC<br>AGATCATGTCTGACAAGAGGAATGTGATCCTGTTCTCTGTGTTTGATGA<br>GAACAGGAGCTGGTACCTGACTGAGAACATCCAGAGGTTCCTGCCCAAC<br>CCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTG<br>CCTGCATGAGGTGGCCTACTGGTACATCCTGAGCATTGGGGCCCAGACT<br>GACTTCCTGTCTGTGTTCTTCTCTGGCTACACCTTCAAGCACAAGATGG<br>TGTATGAGGACACCCTGACCCTGTTCCCCTTCTCTGGGGAGACTGTGTT<br>CATGAGCATGGAGAACCCTGGCCTGTGGATTCTGGGCTGCCACAACTCT<br>GACTTCAGGAACAGGGGCATGACTGCCCTGCTGAAAGTCTCCAGCTGTG<br>ACAAGAACACTGGGGACTACTATGAGGACAGCTATGAGGACATCTCTGC<br>CTACCTGCTGAGCAAGAACAATGCCATTGAGCCCAGGAGCTTCAGCCAG<br>AATGCCACTAATGTGTCTCCCCCAGTGCTGAAGAGGCACCAGAGGGAGA<br>TCACCAGGACCACCCTGCAGTCTGACCAGGAGGAGATTGACTATGATGA<br>CACCATCTCTGTGGAGATGAAGAAGGAGGACTTTGACATCTACGACGAG<br>GACGAGAACCAGAGCCCCAGGAGCTTCCAGAAGAAGACCAGGCACTACT<br>TCATTGCTGCTGTGGAGAGGCTGTGGGACTATGGCATGAGCAGCAGCCC<br>CCATGTGCTGAGGAACAGGGCCCAGTCTGGCTCTGTGCCCCAGTTCAAG<br>AAGGTGGTGTTCCAGGAGTTCACTGATGGCAGCTTCACCCAGCCCCTGT<br>ACAGAGGGGAGCTGAATGAGCACCTGGGCCTGCTGGGCCCCTACATCAG<br>GGCTGAGGTGGAGGACAACATCATGGTGACCTTCAGGAACCAGGCCAGC<br>AGGCCCTACAGCTTCTACAGCAGCCTGATCAGCTATGAGGAGGACCAGA<br>GGCAGGGGGCTGAGCCCAGGAAGAACTTTGTGAAGCCCAATGAAACCAA<br>GACCTACTTCTGGAAGGTGCAGCACCACATGGCCCCCACCAAGGATGAG<br>TTTGACTGCAAGGCCTGGGCCTACTTCTCTGATGTGGACCTGGAGAAGG<br>ATGTGCACTCTGGCCTGATTGGCCCCCTGCTGGTGTGCCACACCAACAC<br>CCTGAACCCTGCCCATGGCAGGCAGGTGACTGTGCAGGAGTTTGCCCTG<br>TTCTTCACCATCTTTGATGAAACCAAGAGCTGGTACTTCACTGAGAACA<br>TGGAGAGGAACTGCAGGGCCCCCTGCAACATCCAGATGGAGGACCCCAC | pCB1029 |

-continued

| SEQ ID | Sequence | Description |
| --- | --- | --- |
| | CTTCAAGGAGAACTACAGGTTCCATGCCATCAATGGCTACATCATGGAC ACCCTGCCTGGCCTGGTGATGGCCCAGGACCAGAGGATCAGGTGGTACC TGCTGAGCATGGGCAGCAATGAGAACATCCACAGCATCCACTTCTCTGG CCATGTGTTCACTGTGAGGAAGAAGGAGGAGTACAAGATGGCCCTGTAC AACCTGTACCCTGGGGTGTTTGAGACTGTGGAGATGCTGCCCAGCAAGG CTGGCATCTGGAGGGTGGAGTGCCTGATTGGGGAGCACCTGCATGCTGG CATGAGCACCCTGTTCCTGGTGTACAGCAACAAGTGCCAGACCCCCCTG GGCATGGCCTCTGGCCACATCAGGGACTTCCAGATCACTGCCTCTGGCC AGTATGGCCAGTGGGCCCCCAAGCTGGCCAGGCTGCACTACTCTGGCAG CATCAATGCCTGGAGCACCAAGGAGCCCTTCAGCTGGATCAAGGTGGAC CTGCTGGCCCCCATGATCATCCATGGCATCAAGACCCAGGGGGCCAGGC AGAAGTTCAGCAGCCTGTACATCAGCCAGTTCATCATCATGTACAGCCT GGATGGCAAGAAGTGGCAGACCTACAGGGGCAACAGCACTGGCACCCTG ATGGTGTTCTTTGGCAATGTGGACAGCTCTGGCATCAAGCACAACATCT TCAACCCCCCCATCATTGCCAGATACATCAGGCTGCACCCCACCCACTA CAGCATCAGGAGCACCCTGAGGATGGAGCTGATGGGCTGTGACCTGAAC AGCTGCAGCATGCCCCTGGGCATGGAGAGCAAGGCCATCTCTGATGCCC AGATCACTGCCAGCAGCTACTTCACCAACATGTTTGCCACCTGGAGCCC CAGCAAGGCCAGGCTGCACCTGCAGGGCAGGAGCAATGCCTGGAGGCCC CAGGTCAACAACCCCAAGGAGTGGCTGCAGGTGGACTTCCAGAAGACCA TGAAGGTGACTGGGGTGACCACCCAGGGGGTGAAGAGCCTGCTGACCAG CATGTATGTGAAGGAGTTCCTGATCAGCAGCAGCCAGGATGGCCACCAG TGGACCCTGTTCTTCCAGAATGGCAAGGTGAAGGTGTTCCAGGGCAACC AGGACAGCTTCACCCCTGTGGTGAACAGCCTGGACCCCCCCCTGCTGAC CAGATACCTGAGGATTCACCCCCAGAGCTGGGTGCACCAGATTGCCCTG AGGATGGAGGTGCTGGGCTGTGAGGCCCAGGACCTGTACTGAtcgcgaa taaaagatctttattttcattagatctgtgtgttggttttttgtgtg | |
| 373 | SFSQNATNVSPPVLKRHQR | 2-glycan B domain substitute |

What is claimed is:

1. A nucleic acid, comprising a nucleotide sequence encoding a synthetic FVIII protein, wherein the synthetic FVIII protein comprises a B domain substitute, and wherein the B domain substitute comprises the amino acid sequence of any one of SEQ ID NOs: 362-364, 366-369, 371, and 373.

2. The nucleic acid of claim 1, wherein the B domain substitute comprises the amino acid sequence of SEQ ID NO: 364.

3. The nucleic acid of claim 1, wherein the nucleotide sequence encoding the synthetic FVIII protein is codon optimized for expression in a host cell.

4. The nucleic acid of claim 1, wherein the nucleotide sequence encoding the synthetic FVIII protein comprises a reduced content of CpG di-nucleotides as compared to a wild-type nucleic acid sequence encoding FVIII.

5. The nucleic acid of claim 1, wherein the nucleotide sequence encoding the synthetic FVIII does not comprise CpG di-nucleotides.

6. The nucleic acid of claim 1, wherein the nucleic acid is a donor template.

7. The nucleic acid of claim 6, wherein the donor template comprises a donor cassette comprising the nucleotide sequence encoding the synthetic FVIII protein, and wherein the donor cassette is flanked on one or both sides by a gRNA target site.

8. The nucleic acid of claim 1, wherein the nucleic acid is located in a viral vector.

9. The nucleic acid of claim 8, wherein the viral vector is an adeno-associated virus (AAV) vector.

10. A cell, wherein the genome of the cell comprises the nucleic acid of claim 1.

11. The cell of claim 10, wherein the nucleotide sequence encoding the synthetic FVIII protein is operably linked to an endogenous albumin promoter, an endogenous transferrin promoter, or an endogenous fibrinogen alpha promoter in the genome of the cell.

12. The cell of claim 10, wherein the cell is a human liver cell, a human hepatocyte, or a human sinusoid epithelial cell.

13. A synthetic FVIII protein, wherein the synthetic FVIII protein comprises a B domain substitute, and wherein the B domain substitute comprises the amino acid sequence of any one of SEQ ID NOs: 362-364, 366-369, 371, and 373.

* * * * *